US008440810B2

(12) United States Patent
Breaker et al.

(10) Patent No.: US 8,440,810 B2
(45) Date of Patent: May 14, 2013

(54) RIBOSWITCHES, METHODS FOR THEIR USE, AND COMPOSITIONS FOR USE WITH RIBOSWITCHES

(75) Inventors: Ronald R. Breaker, Guilford, CT (US); Ali Nahvi, New Haven, CT (US); Narasimhan Sudarsan, New Haven, CT (US); Margaret S. Ebert, Hopewell, NJ (US); Wade Winkler, Dallas, TX (US); Jeffrey E. Barrick, Lansing, MI (US); John K. Wickiser, Cornwall on Hudson, NY (US)

(73) Assignee: Yale University, New Haven, CT (US)

( * ) Notice: Subject to any disclaimer, the term of this patent is extended or adjusted under 35 U.S.C. 154(b) by 0 days.

(21) Appl. No.: 13/033,174

(22) Filed: Feb. 23, 2011

(65) Prior Publication Data

US 2011/0152213 A1 Jun. 23, 2011

Related U.S. Application Data

(62) Division of application No. 12/492,866, filed on Jun. 26, 2009, which is a division of application No. 10/669,162, filed on Sep. 22, 2003, now Pat. No. 7,794,931.

(60) Provisional application No. 60/412,468, filed on Sep. 20, 2002.

(51) Int. Cl.

| | |
|---|---|
| ***C12Q 1/68*** | (2006.01) |
| ***C12P 19/34*** | (2006.01) |
| ***C12N 15/63*** | (2006.01) |
| ***C07H 21/02*** | (2006.01) |
| ***C07H 21/04*** | (2006.01) |

(52) U.S. Cl.
USPC ............ 536/24.5; 435/6; 435/92.1; 435/455; 536/23.1; 536/24.3; 536/45

(58) Field of Classification Search ............ 435/6, 91.1, 435/91.31, 455; 514/44; 536/23.1, 24.5, 536/24.3, 45
See application file for complete search history.

(56) References Cited

U.S. PATENT DOCUMENTS

| | | | |
|---|---|---|---|
| 3,687,808 | A | 8/1972 | Merigan |
| 4,469,863 | A | 9/1984 | Tso |
| 4,476,301 | A | 10/1984 | Imbach |
| 4,683,195 | A | 7/1987 | Mullis |
| 4,683,202 | A | 7/1987 | Mullis |
| 4,800,159 | A | 1/1989 | Mullis |
| 4,845,205 | A | 7/1989 | HuynhDinh |
| 4,868,116 | A | 9/1989 | Morgan |
| 4,883,750 | A | 11/1989 | Whiteley |
| 4,980,286 | A | 12/1990 | Morgan |
| 4,981,957 | A | 1/1991 | Lebleu |
| 4,987,071 | A | 1/1991 | Cech |
| 5,023,243 | A | 6/1991 | Tullis |
| 5,034,506 | A | 7/1991 | Summerton |
| 5,118,800 | A | 6/1992 | Smith |
| 5,130,302 | A | 7/1992 | Spielvogel |
| 5,134,066 | A | 7/1992 | Rogers |
| 5,166,315 | A | 11/1992 | Summerton |
| 5,175,273 | A | 12/1992 | Bischofberger |
| 5,177,196 | A | 1/1993 | Meyer, Jr. |
| 5,185,444 | A | 2/1993 | Summerton |
| 5,188,897 | A | 2/1993 | Suhadolnik |
| 5,214,134 | A | 5/1993 | Weis |
| 5,216,141 | A | 6/1993 | Benner |
| 5,235,033 | A | 8/1993 | Summerton |
| 5,264,423 | A | 11/1993 | Cohen |
| 5,264,562 | A | 11/1993 | Matteucci |
| 5,264,564 | A | 11/1993 | Matteucci |
| 5,276,019 | A | 1/1994 | Cohen |
| 5,278,302 | A | 1/1994 | Caruthers |
| 5,286,717 | A | 2/1994 | Cohen |
| 5,297,721 | A | 3/1994 | Schneider |

(Continued)

FOREIGN PATENT DOCUMENTS

| | | |
|---|---|---|
| EP | 0070685 | 1/1983 |
| EP | 0320308 | 6/1989 |

(Continued)

OTHER PUBLICATIONS

Breaker, R.R., Curr. Opin. Biotech., vol. 13, pp. 31-39 (2002).*

(Continued)

*Primary Examiner* — Jane Zara
(74) *Attorney, Agent, or Firm* — Pabst Patent Group LLP

(57) ABSTRACT

It has been discovered that certain natural mRNAs serve as metabolite-sensitive genetic switches wherein the RNA directly binds a small organic molecule. This binding process changes the conformation of the mRNA, which causes a change in gene expression by a variety of different mechanisms. Modified versions of these natural "riboswitches" (created by using various nucleic acid engineering strategies) can be employed as designer genetic switches that are controlled by specific effector compounds. Such effector compounds that activate a riboswitch are referred to herein as trigger molecules. The natural switches are targets for antibiotics and other small molecule therapies. In addition, the architecture of riboswitches allows actual pieces of the natural switches to be used to construct new non-immunogenic genetic control elements, for example the aptamer (molecular recognition) domain can be swapped with other non-natural aptamers (or otherwise modified) such that the new recognition domain causes genetic modulation with user-defined effector compounds. The changed switches become part of a therapy regimen—turning on, or off, or regulating protein synthesis. Newly constructed genetic regulation networks can be applied in such areas as living biosensors, metabolic engineering of organisms, and in advanced forms of gene therapy treatments.

16 Claims, 143 Drawing Sheets

U.S. PATENT DOCUMENTS

| | | | |
|---|---|---|---|
| 5,319,080 | A | 6/1994 | Leumann |
| 5,321,131 | A | 6/1994 | Agrawal |
| 5,334,711 | A | 8/1994 | Sproat |
| 5,354,855 | A | 10/1994 | Cech |
| 5,359,044 | A | 10/1994 | Cook |
| 5,367,066 | A | 11/1994 | Urdea |
| 5,393,878 | A | 2/1995 | Leumann |
| 5,399,676 | A | 3/1995 | Froehler |
| 5,405,938 | A | 4/1995 | Summerton |
| 5,405,939 | A | 4/1995 | Suhadolnik |
| 5,432,272 | A | 7/1995 | Benner |
| 5,434,257 | A | 7/1995 | Matteucci |
| 5,446,137 | A | 8/1995 | Maag |
| 5,453,496 | A | 9/1995 | Caruthers |
| 5,455,233 | A | 10/1995 | Spielvogel |
| 5,457,187 | A | 10/1995 | Gmeiner |
| 5,459,255 | A | 10/1995 | Cook |
| 5,466,677 | A | 11/1995 | Baxter |
| 5,466,786 | A | 11/1995 | Buhr |
| 5,470,967 | A | 11/1995 | Huie |
| 5,475,096 | A | 12/1995 | Gold |
| 5,476,925 | A | 12/1995 | Letsinger |
| 5,484,908 | A | 1/1996 | Froehler |
| 5,489,677 | A | 2/1996 | Sanghvi |
| 5,502,177 | A | 3/1996 | Matteucci |
| 5,514,785 | A | 5/1996 | VanNess |
| 5,519,126 | A | 5/1996 | Hecht |
| 5,519,134 | A | 5/1996 | Acevedo |
| 5,525,711 | A | 6/1996 | Hawkins |
| 5,536,821 | A | 7/1996 | Agrawal |
| 5,539,082 | A | 7/1996 | Nielsen |
| 5,541,306 | A | 7/1996 | Agrawal |
| 5,541,307 | A | 7/1996 | Cook |
| 5,550,111 | A | 8/1996 | Suhadolnik |
| 5,552,540 | A | 9/1996 | Haralambidis |
| 5,561,225 | A | 10/1996 | Maddry |
| 5,563,037 | A | 10/1996 | Sutherland |
| 5,563,253 | A | 10/1996 | Agrawal |
| 5,567,811 | A | 10/1996 | Misiura |
| 5,571,799 | A | 11/1996 | Tkachuk |
| 5,576,427 | A | 11/1996 | Cook |
| 5,587,361 | A | 12/1996 | Cook |
| 5,587,469 | A | 12/1996 | Cook |
| 5,591,722 | A | 1/1997 | Montgomery |
| 5,594,121 | A | 1/1997 | Froehler |
| 5,596,086 | A | 1/1997 | Matteucci |
| 5,596,091 | A | 1/1997 | Switzer |
| 5,597,909 | A | 1/1997 | Urdea |
| 5,602,240 | A | 2/1997 | Mesmaeker |
| 5,608,046 | A | 3/1997 | Cook |
| 5,610,289 | A | 3/1997 | Cook |
| 5,610,300 | A | 3/1997 | Altmann |
| 5,614,617 | A | 3/1997 | Cook |
| 5,618,704 | A | 4/1997 | Sanghvi |
| 5,623,070 | A | 4/1997 | Cook |
| 5,624,803 | A | 4/1997 | Noonberg |
| 5,625,050 | A | 4/1997 | Beaton |
| 5,627,053 | A | 5/1997 | Usman |
| 5,631,359 | A | 5/1997 | Chowrira |
| 5,633,360 | A | 5/1997 | Bischofberger |
| 5,639,873 | A | 6/1997 | Barascut |
| 5,646,265 | A | 7/1997 | McGee |
| 5,648,211 | A | 7/1997 | Fraiser |
| 5,658,873 | A | 8/1997 | Bertsch-Frank |
| 5,663,312 | A | 9/1997 | Chaturvedula |
| 5,670,633 | A | 9/1997 | Cook |
| 5,677,437 | A | 10/1997 | Teng |
| 5,677,439 | A | 10/1997 | Weis |
| 5,681,941 | A | 10/1997 | Cook |
| 5,700,920 | A | 12/1997 | Altmann |
| 5,712,124 | A | 1/1998 | Walker |
| 5,714,331 | A | 2/1998 | Buchardt |
| 5,719,262 | A | 2/1998 | Buchardt |
| 5,744,311 | A | 4/1998 | Fraiser |
| 5,807,718 | A | 9/1998 | Joyce |
| 5,834,186 | A | 11/1998 | George |
| 5,854,038 | A | 12/1998 | Sullenger |
| 5,861,288 | A | 1/1999 | Usman |
| 6,001,411 | A | 12/1999 | Kester |
| 6,518,252 | B2 | 2/2003 | Wooley |
| 6,831,171 | B2 | 12/2004 | Breaker |
| 2003/0108949 | A1 | 6/2003 | Bao |
| 2004/0072783 | A1 | 4/2004 | Breaker |
| 2004/0219523 | A1 | 11/2004 | Stanton |
| 2005/0053951 | A1 | 3/2005 | Breaker |
| 2007/0016983 | A1 | 1/2007 | Muhlbauer |

FOREIGN PATENT DOCUMENTS

| | | |
|---|---|---|
| EP | 0329822 | 8/1989 |
| EP | 0360257 | 3/1990 |
| GB | 981458 | 1/1965 |
| JP | 2007259787 | 10/2007 |
| WO | 8706270 | 10/1987 |
| WO | 8801315 | 2/1988 |
| WO | 8902439 | 3/1989 |
| WO | 8906700 | 7/1989 |
| WO | 8907136 | 8/1989 |
| WO | 8909284 | 10/1989 |
| WO | 9002806 | 3/1990 |
| WO | 9007641 | 7/1990 |
| WO | 9103162 | 3/1991 |
| WO | 9207065 | 4/1992 |
| WO | 9315187 | 8/1993 |
| WO | 9323569 | 11/1993 |
| WO | 9402595 | 2/1994 |
| WO | 9413688 | 6/1994 |
| WO | 9506731 | 3/1995 |
| WO | 9511910 | 5/1995 |
| WO | 9610390 | 4/1996 |
| WO | 9610391 | 4/1996 |
| WO | 9610392 | 4/1996 |
| WO | 9610395 | 4/1996 |
| WO | 9619836 | 6/1996 |
| WO | 9717076 | 5/1997 |
| WO | 9717471 | 5/1997 |
| WO | 9726270 | 7/1997 |
| WO | 9827104 | 6/1998 |
| WO | 9843993 | 10/1998 |
| WO | 9916871 | 4/1999 |
| WO | 9954459 | 10/1999 |
| WO | 0020040 | 4/2000 |
| WO | 0026226 | 5/2000 |
| WO | 2004027035 | 4/2004 |
| WO | 2008033866 | 3/2008 |
| WO | 2008076156 | 6/2008 |

OTHER PUBLICATIONS

Nahvi et al., Chem. & Biology, vol. 9, pp. 1043-1049 (2002).*

Werstuck et al., Science, vol. 282, pp. 296-298 (1998).*

Viswanathan et al., J. Biol. Chem., vol. 273, No. 33, pp. 21276-21281 (1998).*

24519.6.8402, Prosecution History for Eu application 03781294 up to May 12, 2008.

24519.6.8402 Prosecution History for U.S. Appl. No. 12/492,866.

24519.6.8403 Prosecution History for U.S. Patent 7,794,931.

24519.6.8404 Prosecution History for U.S. Appl. No. 12/709,072.

24519.6.8406 Prosecution History for U.S. Appl. No. 13/033,258.

24519.6.8407 Prosecution History for U.S. Appl. No. 13/033,319.

24519.6.8408 Prosecution History for U.S. Appl. No. 13/033,352.

24519.6.9031, Prosecution History for EP application 03781294.8.

24519.6.9032, Prosecution History for EP application 1003657.3.

24519.6.9033, Prosecution History for EP application 10195258.8.

Abrue-Gooder and Merino, "Ribex: a web server for locating riboswitches and other conserved bacterial regulatory elements", Nucleic Acids Res., 33:W690-92 (2005).

Agrawal, et al., Antisense oligonucleotides: toward clinical trials, TIBTECH. 14: 376-380 (1996).

Ahn, et al., Vitamin B1 functions as n activator of plant disease resistance, Plant Physiol., 138:1505-15 (2005).

Akimoto, et al., "Queuine analogues, their synthesis and inhibition of growth of mouse L5178Y cells in citro", J. Med. Chem., 29:1749-53 (1986).

Akimoto, et al., "Synthesis of queuine, the base of naturally occurring hypermodified nucleoside (queuosine), and its analogues", J. Chem. Soc. Perkin Trans., 1:1637-44 (1988).

Altschul, et al., Gapped BLAST and PSI-BLAST, a new generation of protein database search programs, Nucleic Acids Res., 25:3389-3402 (1997).
Anagnostopoulos, et al., "Requirements for transformation in *Bacillus subtilis*", J. Bacteriol., 81:741-746 (1961).
Anderson, et al., "ModE-dependant molybdate regulation of the molybdenum cofactor operon moa in *Escherichia coli*", J. Bacteriol., 182:7035-43 (2000).
Antson, et al, "The structure of trp RNA-binding attenuation protein", Nature, 374:693 (1995).
Auger, et al., "The metIC operon involved in methionine biosynthesis in *Bacillus subtilis* is controlled by transcription antitermination", Microbiol., 148:507-518 (2002).
Axmann, et al., "Identification of cyanobacteria) non-coding RNAs by comparative genome analysis", Genome Biology, 6:R73 (2005).
Babitzke and Gollnick, "Posttranscription initiation control of tryptophan metabolism in *Bacillus subtilis* by th trp Rna-binding attenuation protein (TRAP), anti-TRAP, and RNA structure", J. Bacteriol., 183:5795-5802 (2001).
Bader, et al., "Structure of the molybdenum-cofactor biosynthesis protein MoaB of *Escherichia coli*", Acta Cryst., D60:1068-75 (2004).
Badet-Denisot, et al., "Mechanistic investigations on glucosamine-6-phosphate synthase", Bull. Soc. Chim. Fr., 130:249-255 (1993).
Baker and Boxer, "Regulation of the chIA locus of *Escherichia coli* K12: involvement of molybdenum cofactor", Mol Microbiol., 5:901-907 (1991).
Banerji, et al., "A lymphcyte specific cellular enhancer is located downstream of the joining region in immunoglobulin heavy chain genes", Cell, 33:729 (1983).
Barker, et al, "Superfamily classification in PIR-International protein sequence database", Methods Enzymol, 266:59-71 (1996).
Barrick, et al., "New RNA motifs suggest an expanded scope for riboswitches in bacterial genetic control", PNAS USA, 101:6421-26 (2004).
Barrick and Breaker, "The distributions, mechanisms, and structures of metabolite-binding riboswitches", Genome Biol., 8:R239 (2007).
Bartel and Szostak, "Isolation of new ribzymes from a large pool of random sequences", Science, 261:1411-1418 (1993).
Bassler and Losick, "Bacterially Speaking", Cell, 125:237-46 (2006).
Bateman, et al., "The Pfam Protein Families Database", Nucleic Acid Res., 30:276-280 (2002).
Batey, et al., "Structure of a natural guanine-responsive ribswitch complexed with the metabolite hypoxanthine", Nature, 432:411-415 (2004).
Batey, "Structures of regulatory elements in mRNAs", Current Opin. Struct. Biol., 16:299-306 (2006).
Baugh, et al., Molybdenum metalloenzymes, Comprehensice Biol. Catalysis, vol. III:377-4010 (1998).
Baugh, et al., "2.8 A cyrstal sturcture of the malachite green aptamer", J. Mol. Biol. 301:117-128 (2000).
Bayer, et al."Programmable ligand-controlled riboregulators of eukaryotic gene expression", Nat. Biotechnol. 23:337-343 (2005).
Bayly, et al., "A well-behaved electrostatic potential based method using charge restraints for deriving atomic charges—the RESP model", J. Phys. Chem., 97:10269-80 (1993).
Beaucage and Leyer, "The functionalization of oligonucleotides via phosphramidte derivatives", Tetrahedron, 49:1925-1963 (1993).
Beaudry and Joyce, "Directed evolution of an RNA enzyme", Science, 257: 635-641 (1992).
Beaudry and Joyce, "Minimum secondary structure requirements fro catalytic activity of a self-splicing group I intron", Biochemistry, 29:6534-6539 (1990).
Been, et al., "Secondary structure of the self-cleaving RNA of hepatitis delta virus: Applications to catalytic RNa design", Biochemistry, 31:11843-11852 (1992).
Beigelman, et al., "Chemical modification of hammerhead ribozymes", J. Biol. Chem., 270:25702-08 (1995).
Beigelman, et al., "Synthesis of 1-Deoxy-D-Ribofuranose Phosphoramidite & the incorporation of abasic nucleotides in stem-loop II of a hammerhead ribozyme", Biorganiz & Medical Chem. Lttrs., 4:1715-20 (1994).
Bellon, et al., "Post-synthetically ligated ribozymes: an alternative approach to iterative solid phase synthesis", Bioconjugated Chem., 8:204-212 (1997).
Bellon, et al. "Amino linked ribozymes: post-synthetic conjugation of half-ribozyme", Nucleasides & Nucleotides, 6:951-954 (1997).
Benner, et al., "Modern mertabolism as a palimpsest of the RNA world", PNAS, 86: 7054-7058 (1989).
Benseler, et al., "Hammerhead-like molecules containig non-nucleoside linkers are active RRNA catalysts". J. Am. Chem. Soc., 115: 8483-8484 (1993).
Berkner, et al., "Abundant expression of polyomavirus middle T antigen and dihydrofolate reductase in an adenovirus recombinant". J. Virology, 61:1213-220 (1987).
Bevers, et al., "Tungsten transport protein A (WtpA) in pyrococcus furiosus: the first member of a new class of tungstate and molybdate transporters", J. Bacteriol., 188:6498-6505 (2006).
Beyhan and Yildiz, "Smooth to rugose phase variation in Vibrio cholerae can be mediated by a single nucleotide change that targets c-di-GMP signalling pathway", Mol. Microbiol., 63:995-1007 (2007).
Bienz and Kubli, "Wild-type tRNA TyrG reads the TMV RNA stop codon, but Q bas-modified tRNA TyrQ does not", Nature, 294:188-190 (1981).
Birikh,et al.,"The structure, function and application of the hammerhead ribozyme," Eur. J. Biochem., 245:1-16 1997.
Black, "Protein diversity from alternative splicing: a challenge for bioinformatics and post-genome biology", Cell, 103:367-70 (2000).
Blaise, et al., "A minimalist glutamyl-tRNA synthetase dedicated to aminaocyltion of the tRNA aspQUC anticodon", Nucleic Acids Res., 32:2768-75 (2004).
Blencrowe, "Alternative splicing, new insights for global analyses", Cell, 126:37-47 (2006).
Blount, et al., "Antibacterial lysine analogs that target lysine riboswitches", Nature Chem. Biol., 1:44-49 (2007).
Blount, et al., "Development and application of a high-throughput assay for Glms riboswitch activators". RNA Biology, 3(2):77-81 (2006).
Bock, et al., "Photoaptamer arrays applied to multiplexed proteomic analysis", Proteomics, 4:609-618 (2004).
Bocobza, et al., "Ribswitch-dependent gene regulation and its evolution in the plant kingdom", Genes Dev., 21:2874-79 (2007).
Bonhoeffer, et al. "RNA multi-structure landscapes: aA study based on temperature dependent partition functions", Eur. Biophys. J., 22 13-24 (1993).
Borchardt,et al., "Potential inhibitor of S-adenosylmethionine-dependent methlytransferase 1. Modification of the amino acid portion of S-adenosylhomocysteine". J. Med. Chem., 17:862-868 (1974).
Borsuk, et al., "L-Arginine influences the structure and function of arginase mRNA in *Aspergillus nidulans*", Biol. Chem., 388:135-144 (2007).
Bout, "Lung gene therapy: in vivo adenovirus-mediated gene transfer to rhesus monkey airway epithelium", Human Gene Therapy, 5:3-10 (1994).
Boy, et al., "Isolation and identification of mutants constitutive for aspartokinase III synthesis in *Escherichia coli* K 12". Biochimie, 61:1151-1160 (1979).
Braasch and Corey, "Novel antisense and peptide nucleic acid strategies for controlling gene expression". Biochem., 41(14):4503-4510 (2002).
Branch, "A good antisense molecule is hard to find", Trends Biochem. Sci., 23 (2): 45-50 (1998).
Breaker, "Are engineered proteins getting competition for RNA", Current Opinion in Biotechnology, 7:442-448 (1996).
Breaker, "Catalytic DNA: in training and seeking employment". Nature Biotech., 17: 422-423 (1999).
Breaker, "Engineered Allosteric Ribozymes as Biosensor Components", Curr Opin. Biotechnol., 13:31-39 (2002).
Breaker, "In vitro selection of catalytic polynucleotides", Chem. Rev, 97:371-390 (1997).
Breaker, "Natural and engineered nucleic acids as tools to explore biology", Nature Biotechnol., 432:838-845 (2004).

Breaker., "In vitro Selection of Self-cleaving Ribozymes and Deoxyribozymes". In: Intracellular Ribozyme Applications: Principles and Protocols. L. Couture, J. Rossie eds. Horizon Scientific Press, Norfolk, England (1999).
Breaker and Joyce, "A DNA enzyme that cleaves RNA". Chem. Bio., 1:223-229 (1994).
Breaker and Joyce, "Inventing and improving ribzyme function: rational design versus iterative selection methods", TIBTECH., 12:265-275 (1994).
Breaker et al., "A DNA enzyme with Mg2+ dependent RNa phophoresterase activity", Chem Biol., 2(10): 655-660 (1995).
Brennan, et al., "Two-deminsional parallel array technology as a new apporach to automated combinatorial solid phase organic sythesis", Biotech. Bioeng., 61:33-45 (1998).
Brown, et al, "Conformational studies of 5'=deoxyandenosyl-13-epicobalamin, a coenzymatically active structural analog of coenzyme B12", Polyhedron, 17:2213 (1998).
Brown and Burlington, "Penetration of host cell membranes by adenovirus 2", J. Virology, 12:386-396 (1973).
Brown and Zou, "Thermolysis of coenzymes B12 at physiological temperatures: activation parameters for cobalt-carbon bond homolysis and a quantitative analysis of the perturbation of the homolysis equilibrium by the ribonucleoside triphosphate reductase from *Lactobacillus leichmannii*", J. Inorg. Biochem 77:185.195 (1999).
Brunger, et al., "Cyrstallography and NMR system: a new software suite for macromolecular structure determination". Acta Crystallogr., D 54:905-921 (1998).
Buc, et al., "Enzymatic and physiological properties of the tungsten-substituted molybdenum TMAO reductase from *Escherichia coli*", Mol. Microbiol., 32:159-68 (1999).
Bugg, et al., "From peptidoglycan to glycoproteins: common features of lipd-linked oligosaccharide biosynthesis", FEMS Microbiol. Lett., 119:255-262 (1994).
Bunka and Stockley, "Aptamers come of age-at last", Nat. Rev. aMicrobiol., 4:588-96 (2006).
Buratowski, "Connections between mRNA 3\ end processinf and transcription termination", Curr. Opin. Cell Biol., 17:257-61 (2005).
Burgin,et al., "Chemically modified hammerhead ribozymes with imporved catalytic rates". Biochemistry, 35:14090-14097 (1996).
Burke, et al. "Allosteric hammerhead ribozyme TRAPs", Biochemistry, 41:6588-6594 (2002).
Cadwell and Joyce, "Mutagenic PCR", PCR methods Appl., 3(6): S136-140 (1994).
Caillaud, "Adenoviral vector as a gene delivery system into cultured rat neuronal and glial cells", Eur. J. Neuroscience, 5:1287-1291 (1993).
Cameron, et al., "RNA secondary structure regulates the translation of sxy and competence development in *Haemophilus influenzae*", Nucleic Acids Res., 36:10-20 (2008).
Canny, et al., "Fast cleavage kinetics of a natural hammerhead ribozyme", J. Am. Chem. Soc., 126:10848-10849 (2004).
Caruthers, et al., "Chemical synthesis of deooxyoligonucleotides and deoxyoligonucleotide analogs", Methods Enzymol., 2111:3-19 (1992).
Castanotto, et al., "Intracellular expression and function of antisense catalytic RNAs", Methods Enzymol., 313:401-20 (2000).
Cate, et al, "RNA tertiary structure mediation by adenosine platforms", Science, 273: 1696-1699 (1996).
Cazzonelli and Velten, "Construction and testing of an intron-containing luciferase reporter gene from *Renilla reniformis*", Plant Mol. Biol. Rep., 21:271-80 (2003).
Cech, et al., "In vitro splicing of the ribosomal RNA precursor of Tetrahymena: involvement of a guanosine nucleotide in the excision of the intervening sequence", Cell, 3 (Pt2):487-96 (1981).
Cech, "Ribozyme engineering", Current Opinion in Structural Biology, 2:605-609 (1992).
Cech, "Ribozymes and their medical implications", JAMA, 260:3030-34 (1988).
Cech and Golden, "Building a catalytic active site using only RNA", In: The RNA World, Second Edition, 321-350 (1999).
Chan, et al., "Structural basis of activity and allosteric control of diguanylate cyclase", PNAS, 101:17084-9 (2004).
Chan, et al., "Structure of a hyperthermophilic tungstopterin enzyme, aldehyde ferredoxin oxidoreductase", Science, 267:1463-69 (1995).
Chardonnet and Dales, "Early events in the interaction of adenoviruses with HeLa cells. I. Penetration of type 5 and intracellular release of the DNA genome", Virology, 40(3): 462-477 (1970).
Chartrand, et al., "An oligodeoxyribonucleotide that supoprts catalytic activity in the hammerhead ribozyme domain", Nucleic Acid Res., 23(20):4092-4096 (1995).
Cheah, et al., "Control of alternative RNA splicing and gene expression by eukaryotic riboswitches", Nature, 447(7143:497-500 (2007).
Chee,et al., "Accessing genetic information with high-density DNA arrays," Science, 274:610-614, 1996.
Chen, et al., "Multitarget-ribozyme directed to cleave at up to nine highly conserved HIV-1 env RNA regions inhibits HIV-1 replication-potential effectiveness against most presently sequenced HIV-1 isolates", Nucleic Acids Res., 20:4581-4589 (1992).
Chen, et al., "Structure-based discovery of ligands targeted to the RNA double Helix", Biochemistry, 36:11402-407 (1997).
Choi and Zalkin, "Sturctural characterization and corepressor binding of the *Escherichia coli* purine repressor", J. Bacterial., 174:6207-6214 (1992).
Chowira, et al., "In vitro and in vivo comparison of hammerhead, hairpin and hapatitis delta virus self-processing ribozyme cassettes", J. Biol. Chem., 269:25856-25864 (1994).
Chowira and Burke, "Extensive phophorothioate sustitution yields highly active and nuclease-resitant hairpin ribozymes", Nucleic Acids Res., ,20:2835-2840 (1994).
Christiansen, et al., "Xanthine metabolism in *Bacillus subtilis*: characterization of the xpt-pbuX operon and evidence for purine—and nitrogen- controlled expression of genes involved in the xanthine salvage and catabolism", J. Bacterial, 179:2540-2550 (1997).
Christoffersaen and Marr, "Riobzymes as human therapeutic agents", J. Med. Chem, 38:2023-2037 (1995).
Clarke, et al, The structure of the ferric siderophore binding protein FhuD complexed with galiichrome, Nat. Struct. Biol., 7:287-91 (2000).
Claverie, Fewer genes, more encoding RNA, Science, 309:1529-30 (2005).
Cload and Schepartz, "Polyether tethered olignucleotide probes", J. Amer. Chem. Soc., 113: 6324-6326 (1991).
Clough and Bent, "Floral did, a simplified method for agrobacterium-mediated transformation of *Arabidopsis thaliana*", Plant J., 16:735-43 (1998).
Cochrane, et al., "Structural investigation of the GlmS ribozyme bound to Its catalytic cofactor", Chem Biol., 14:97-105 (2007).
Collins, et al., "The cell cycle and cancer," Proc. Natl. Acad. Sci. USA, 94(7);2776-2778 (1997).
Collins and Olive, "Reaction conditions and kinetics of self-cleavage of a ribozyme derived from Neurospora VS RNA", Biochem., 32(11):2795-2799 (1993).
Connelly and Manley, "A functional mRNA polyadenylation signal is required for transcription termination y RNA polymerase II", Genes Dev., 2:440-52 (1988).
Coppins, et al., "The intricate world of riboswitches", Curr. Opin. Microbiol., 10:176-181 (2007).
Corbino, et al. Evidence for a second class of S-adenosylmethiothine riboswitches and other regulatory RNA motifs in alpha-proteobacteria, Genome Biol., 6A:R70 (2005).
Cornell, et al., "A 2nd generation force0-field for the simulation of proteins, nucleic acids, and organic molecules", J. Am. Chem. Soc., 117:5179-5195 (1995).
Correll, et al., "The common and the disticntive features of the bulged-G motif based on a 1.04 ú resolution RNA structure", Nucleic Acids Res., 31:6806-6818 (2003).
Costa and Michel, "Frequent use of the same tertiary motif by srlf-folding RNAs", EMBRO J., 14:1276-85 (1995).
Costa and Michel, "Rules for RNA recognition of GNRA tetraloops deduced by in vitro selection: comparison with in vivo evolution", EMBRO J., 16:3289-3302 (1997).
Couture and Stinchcomb, "Anti-gene therapy: the use of ribozymes to prohibit gene function", Trends in Genetics, 12:510-515 (1996).

Coventry, et al., "MSARI: multiple sequence alignments for statistical detection of RNA secondary structure", Proceedings of the Nat. Aca. of Science, 101:12102-07 (2004).
Cromie, et al., "An RNA sensor for intracellular Mg(2+)", Cell, 125:71-84 (2006).
Cuenoud and Szostak, "A DNA metalloenzyme with DNA ligase activity" , Nature, 375: 611-614 (1995).
Czechoeski, et al., "Genome-wide identification and testing of superior reference genes for transcript normalization in *Arabidopsis*" , Plant Physiol., 139:5-17 (2005).
Dai, et al., "Cleavage of an amide bond by a ribozyme" , Science, 267(5195): 237-40 (1995).
Daiger, http://www.sph.uth.tmc.edu/retnet/help.htm.
Das, et al., "SAFA: Semi-automated footprinting and analysis software for high-thoughput quanitification of nucleic acid footprinting experiments" , RNA-a publication of the RNA Soc., 11:344-54 (2005).
Dauter, et al., "Jolly SAD" , Acta Crystallogr Biol Crystallogr, 58:494-506 (2002).
Davidson, et al., "Overproduction of polyomavirus middle T antigen in mammalian cells through the use of an adenovirus vector", J. Virology, 61:1226-1239 (1987).
Dayhoff, et al., "Protin superfamilies", Atlas of Protein Sequence and Structure, 5:2 (1976).
De La Pena, et al., "Peripheral regions of natural hammerhead ribozymes greatly increase their self-cleavage activity", EMBO J., 22:5561-5570 (2003).
Della Ragione, et al., "*Escherichia coli* S-adenosylhomocysteine/5\-methylthiaoadenosine nucleosidase, purification, substrate specificity and mechanism of action", Biochem. J., 232:335-41 (1985).
Desai et al., "Genetic screens and selections for small molecules based on a synthetic riboswitch that activates protein translation". J. Am. Chem. Soc., 126:13247-13254 (2004).
Dewey and Kiddler, "Partial purification and properties of as nucleoside hydrolase from crithidia", Arch. Biochem. Biophys., 157:380-87 (1973).
Dillon and Rosen, "A rapid method for the construction of synthetic genes using the polymerase chain-reaction", Biotechniques, 9:298-300 (1990).
Dock-Bregeon and Moras, "Conformation changes and dynamics of tRNAs: evidience from hydolysis patterns", Cold Spring Harbor Symp. Quant. Biol., 52: 113-121 (1987).
Doherty, et al., "A universal mode of helix packing in RNA" , Nature Struct. Biol., 8: 339-343 (2001).
Dong, "An efficient asymmetric synthesis of L-a,É-diaminoalkanoic acids", Tetrahedron Lett., 33:7725-7726 (1992).
Douce, et al., "The glycine decarboxylase system: a fascinating complex", Trends Plant Sci, 6:167 (2001).
Doudna, "Preparation of homogeneous ribozyme RNA for crystallization", Methods Mol Biol., 74:365-70 (1997).
Drenser,et al.,"Ribozyme-targeted destruction of RNAs associated with ADRP," Inv. Ophth. Vis. Sci., 39:681-689 (1998).
Dropulic, et al., "Functional characterization of a U5 Ribozyme: intracellular suppression of human immunodeficiency virus type 1 expression", J. Virol., 66:1432-41 (1992).
Durand, et al., "Circular dichrosim studies of an oligdeoxyribonucleotide containing a hairpin loop made of a hexaethylene glycol chain: conformation and stability", Nucleic Acids Res., 18:6353-6359 (1990).
Durand, et al., "vacC, a virulence-associated chromosomal locus of shigella flexneri, is homologous to tgt, a gene encoding tRNA-guanime transglycosylase Tgt) of *Escherrichia coli* K-12", J. Bacteriol, 176:4627-34 (1994).
Dye and Proudfoot, "Multiple transcript cleavage precedes polymerase release in termination by RNA polymerase II", Cell, 105:669-81 (2001).
Ebbole and Sachs, "A rapid and simple method for isolation of neurospora crassa homokaryons using microconidia", Fungal Genet. Newsl., 37:17-18 (1990).
Ebbole and Zalkin, "Cloning and characterization of a 12-gene cluster from *Bacillus subtilis* encoding nine enzymes for de novo purine nucleotide synthesis", J. Biol. Chem., 262: 8274-8287 (1987).
Eddy, Infernal User†s Guide, (2005).
Eddy, "Infernal, version 0.55", Dept of Genetics, Washington Univ School of Medicine St. Louis Mo. (2003).
Eddy and Durbin, "RNA sequence analysis using covariance models", Nucleic Acids Res., 22:2079-88 (1994).
Edelstein, "Cooperative interactions of hemoglobin", Annu Rev Biochem., 44:209 (1975).
Edwards and Ferrè-D Amarè, "Crystal structures of the thi-box riboswitch bound to thiamine pyrophosphate analogs reveal adaptive RNA-small molecule recognition", Structure, 14:1459-68 (2006).
Egli, et al., "Atomic-resolution structure of the cellulose synthase regulator cyclic diguanylic acid", PNAS, 87:3235 (1990).
Eisen, et al., "Cluster analysis and display of genome-wide expression patterns," Proc. Nat'l Acad. Sci. USA, 95:14863-14868 (1998).
Eldridge, et al., "Empirical scoring functions: I. The development of a fast empirical scoring function to estimate the binding affinity of ligands in receptor complexes", J. Comput-Aided Mol. Des., 11:425-445 (1997).
Elroy-Stein and Moss, "Cytoplasmic expression system based on constitutive sythesis of bacteriophage T7 RNA polymerase in mammalian cells", PNAS, 87:6743-6747 (1990).
Emilsson and Breaker, "Deoxyribozymes. New Activitiies an dNew Applications", Cell. Mol. Life Sci., 59:596-607 (2002).
Englisch, et al., "Chemically Modified Oligonucleotides as Probes and Inhibitors", Angewandte Chemie International Edition, 30:613-629 (1991).
Epshtein, et al., "The riboswitch-mediated control of sulfur metabolism in bacteria",. PNAS, 100:5052-5056 (2003).
Famulok, "Molecular biology. RNAs turn on in tandem", Science, 306:233-34 (2004).
Famulok, "Oligonucleotide aptamers that recognize small molecules". Current Opinion in Sturctural Biologoy, 9:324 (1999).
Fan, et al., "Molecular recognition in the FMN-RNA aptamer complex", J. Mol, Biol. 258:480-500 (1996).
Faou and Tropschug, "A novel binding protein for a member of CyP40-type Cyclophilins, *N crassa* CyPBP37 a growth and thiamine regulated protein homolog to yeast Thi-4p", J. Mol. Biol., 33:831-844 (2003).
Faou and Tropschug, "*Neurospora crassa* CyPBP37, a cytosolic stress protein that is able to replace yeast Thi-4p function in the synthesis of vitamin b1", J. Mol. Biol., 344:1147-57 (2004).
Fasken and Corbett, "Process or perish, quality control in mRNA biogenesis", Nat Struct Mol Biol., 12:482-488 (2005).
Fedor and Uhlenbeck, "Substrate sequence effects on 'hammerhead' RNA catalytic efficiency," Proc. Nat'l Acad. Sci. USA, 87:1668-1672 (1990).
Fedor and Uhlenbeck, "Kinetics of intermolecular cleavage by hammerhead ribozymes", Biochemisty, 31:12042-12054 (1992).
Feig and Brooks, "Recent advances in the development and application of implicit solvent models in biomolecule simulations.", Curr. Opin. Sturct. Biol., 14:217-224 (2004).
Ferentz and Verdine, "Disulfide cross-linked oligonucleotides", J. Am. Chem. Soc., 113:4000-4002 (1991).
Ferguson, et al., "A novel strategy for selection of allosteric ribozymes yields RiboReporter sensors for caffeine and aspartame", Nucleic Acids Res., 32:1756-1766 (2004).
Fiers, et al., "Complete nucleotide sequence of SV40 DNA", Nature, 273:113 (1978).
Finn, et al., "Pfam:clans, webtools and services", Nucleic Acids Res., 24:247-51 (2006).
Flamm, et al., "Design of multi-stable RNA molecules", RNA, 7:254-265 (2001).
Flamm, et al., "RNA folding kinetics at elementary step resolution", RNA, 6:325-338 (2000).
Forster and Symons, "Self cleavage of plus and minus RNAs of a virusoid and structural moldel for the active sites", Cell, 49:211-220 (1987).
Foulkes and Sassone-Corsi, "More is better: activators and repressors from the same gene", Cell, 68:411 (1992).
Freier, et al., "Improved free-energy parameters for predictions of RNA duplex stability", PNAS, 83:9373-9377 (1986).
Frey, et al., "Mutations in the *Escherichia coli* fnr and tgt genes: control molybdate reductase activity and the cytochrome d complex by fnr", J. Bacteriol., 171:1524-30 (1989).

Frey, et al., "New function of vitamin B12 cobamide-dependent reduction of epoxyqueuosine to queuosine in tRNAs of *Escherichia coli* and *Salmonella typhimurium*", J. Bacteria, 170:2078-82 (1988).
Froehlich, et al., "Rhythmic binding of a white collar-containing complex to the frequency promoter is inhibited by frequency", PNAS, 100:5914-19 (2003).
Fuchs, et al., The S(MK) box is a new SAM-binding RNA for translational regulation of SAM synthesis, Nat Struct. Mol. Biol., 13:226-233 (2006).
Galagan, et al., "Sequencing of *Aspergillus nidulans* and comparative analysis with A fumigatus and A oryzae", Nature, 438:1105-15 (2005).
Galperin, et al., "Novel domains of the prokaryotic two-component signal transduction systems", FEMS Microbiol. Lett, 203:11 (2001).
Gao and Huang, "Cytoplasmic expression of a reporter gene by co-delivery of T7 RNA polymerase and T7 promoter sequence with cationic liposomes", Nucleic Acids Res., 21: 2867-2872 (1993).
Garcia Martin, et al., "Metagenomic analysis of two enhanced biological phosphorus removal (EBPR) sludge communities", Natl. Biotechnol., 24:1263-69 (2006).
Gaur and Varshney, "Genetic analysis identifies a function for the queC(ybaX) gene product at an initial step in the queuosine iosynthetic pathway in *Eschrichia coli*", J. Bacteriol., 187:6893-6901 (2005).
Gelford, et al., "A conserved RNA structure element involved in the regulation of bacterial riboflavin synthesis genes", Trends Gen., 15:439-442 (1999).
Gerstein, et al. "Volume changes in protein evolution", J. Mol. Biol., 236:1067-78 (1994).
Gewirtz, et al., "Facilitating oligonucleotide delivery: helping antisense deliver on its promise", PNAS, 93:3161-3163 (1996).
Geyer and Sen, "Evidence for the metal cofactor independence of an RNA phophodiester cleaving DNA enzyme", Chem. Biol., 4:579-593 (1997).
Gilbert, et al., "Thermodynamic and kinetic characterization of ligand binding to the purine riboswitch aptamer domain", J. Mol. Biol., 359:754-68 (2006).
Gill, et al., "Metagenomic analysis of the human distal gut microbiome", Science, 312:1355 (2006).
Gohlke, et al., "Knowledge based scoring function to predict protein-ligand interactions", J. Mol. Biol., 295:337-356 (2000).
Gohlkeand Klebe, "Apporaches to the description and prediction of the biding affinity of small-molecule ligands to macromolecular receptors", Angew. Chem. Int. Ed., 41: 2644-4647 (2002).
Gold, et al, "From oligonucleotide shapes to genomic SELEX: novel biological regulatory loops", PNAS, 94:59-64 (1997).
Gold, et al., "Diversity of oligonucleotide functions", Annual Review of Biochemistry, 64:763-797 (1995).
Gold, et al., "SELEX and the evolution of genomes", Curr. Opin. Gen. Dev., 7:848-851 (1997).
Gomez-Foix, et al., "Adenovirus mediated transfer of the muscle glycogen phosphorylase gene into hepatocytes confers altered regulation of glycogen metabolism", J. Biol. Chem., 267:25129-25134 (1992).
Gooch, et al., "Fully codon-optimized luciferase uncovers novel temperature characteristics of the neurospora clock", Eularyotic Cell, 7(1):28-37 (2008).
Good, et al, "Expression of small, therapeutic RNAs in human nuclei", Gene Therapy, 4:45-54 (1997).
Gottesman, "Stealth regulation: biological circuits with small RNA switches", Genes Dev., 16:2829-2842 (2002).
Grate, et al., "Inducible regulation of the *S. Cerevisiae* cell cycle mediated by an RNA aptamer-ligand complex", Bioorg. Med. Chem., 9:2565-2570 (2001).
Graveley, "Alternative splicing: increasing diversity in the proteomic world", Trends Genet., 17:100 (2001).
Greenway, et al., "Human cytomegalovirus DNA: BamHI, EcoRI and Pstl restriction endonuclease cleavage maps", Gene, 18:355-360 (1982).
Griffiths-Jones, et al., "Rfam:annotating non-coding RNAs in complete genomes", Nucleic Acids Res., 33:121-24 (2005a).
Griffiths-Jones, "RALEE-RNA alignment editor in ermacs", Bioinformatics, 21:257-59 (2005).
Gruden and Shanmugam, "Molybdate transport and regulation in bacteria", Arch. Microbiol., 168:345-54 (1997).
Grunden, et al., "An analysis of the binding of repressor proten ModE to modABCD (molybdate transport) operator/promoter DN of *Escherichia coli*", J. Biol. Chem., 274:24305-15 (1999).
Grundy, et al., tRNA-mediated transcription antitermination in vitro: codon-anticodon pairing independent of the ribosome. PNAS, 99, 11121 (2002).
Grundy, et al., "The L box regulon: Lysine sensing by leader RNAs of bacterial lysine biosynthesis genes", Nucleic Acids Res., 100:12057-12062 (2003).
Grundy and Henkin, "The S box regulon: a new global transcription termination control sytem for methionine and cysteine biosynthesis genes in Gram-positive bacteria", Molecular Microbiology, 30:737 (1998).
Grundy and Henkin, "The T box and S box transcription termination control systems", Frontiers Biosci., 8:D20 (2003).
Guerout-Fleury, et al., "Plasmids for ectopic integration into *Bacillus subtilis*", Gene, 180:57-61 (1996).
Guerrier-Takada, et al. "The RNA Moiety of ribonuclease P is the catalytic subunit of the enzyme", Cell, 35:849 (1983).
Guo and Collins, "Efficient trans-cleavage of a stem-loop RNA substrate by a ribozyme derived from Neuorspora VS RNA", EMBO J., 14:368-376 (1995).
Guo et al., "Direct fluorescence analysis of genetic polymorphisms by hybridization with oligonucleotide arrays on glass supports", Nucleic Acids Res., 22: 5456-5465 (1994).
Gusarov and Nudler, "The mechanism of intrinsic transcription termination", Molecular Cell, 3:495-504 (1999).
Guzman, et al., "Efficient gene trasnfer into myocardium by direct injection of adenovirus vectors", Circulation Research, 73:1201-1207 (1993).
Guzman, et al., "Tight regulation modulation and high-expression by vectors containing the arabinose Pbad promoter", J. Bacteriol., 177:4121-30 (1995).
Gündüz and Katze, "Salvage of the nucleic acid base queuine from queuine-containing tRNA by animal cells", Biochem. Biophys. Res. Commun., 109:159-67 (1982).
Gündüz and Katze, "Queuine salvage in mammalian cells, evidence that queuine is generated from qwueuosine 5\-phosphate", J. Biol. Chem., 259:1110-13 (1984).
Haj-Ahmad, et al., "Development of a helper-independent human adenovirus vector and its use in the transfer of the herpes simplex virus thymidine kinase gene", J. Virology, 57: 267-274 (1986).
Hamaguchi, et al. "Aptamer beacons for the detection of proteins", Anal. Biochem., 294:126-131 (2001).
Hammann, et al., "Length variation of helix II in a hammerhead ribozyme and its influence on cleavage activity", Antisense and Nucleic Acid Drug Dev., 9:25-31 (1999).
Hampel, et al. "Hairpin catalytic RNA model: evidence for helices and sequence requirement for substrate", RNA Nucl. Acids Res., 18:299 (1990).
Hampel, et al. "RNA catalytic properties of the minimum (−)s TRSV sequence", Biochem., 28:4929 (1989).
Hannon, "RNA Interference", Nature, 418:244-251 (2002).
Harada and Nishimura, "Possible anticodon sequences of tRNA his, tRNA asn and tRN asp from *Escherichia coli* B auniversat presence of nucleoside Q in the first position of the anticodons of these transfer ribonucleic acids", Biochemistry, 11:301-08 (1972).
Harvey, et al., "Inhibition of translation by RNA-small molecule interactions", RNA, 8:452-463 (2002).
He and Hannon, "microRNAs: small RNAs with a big role in gene regulation", Nature Reviews Genetics, 5:522-31 (2004).
Hendrix, et al., "RNA structural motifs :building blocks of a modular biomolecule", Q Rev. Biophys., 38:221-43 (2005).
Hendry, et al., "Using linkers to investigate the spatial separation of the conserved nucleotides A9 and G12 in the hammerhead ribozyme", Biochimica at Biophysica acta, 1219: 405-412 (1994).
Henegariu, et al., "Custom fluorescent nucleotide synthesis as an alternative method for nucleic acid labeling", Nature Biotechnology, 18:345-348 (2000).
Henkin, "Transcription termination control in bacteria", Current Opinion in Microbiology, 3:149 (2000).

Henkin, "tRNA directed transcription antitermination", Mol. Microbiol. 3:381-387 (1994).
Henkin and Yanofsky, "Regulation by transcription attenuation in bacteria: how RNA provides instructions for transcription termination/antitermination decisions", Bioessays, 24:700 (2002).
Hermann and Patel, "Adaptive recognition by nucleic acid aptamers", Science, 287:820-825 (2000).
Hermes, et al, "Influence of an altered methylation potential on mRNAS methylation and gene expression in HepG2 cells", Experimental Cell Res., 294:325-34 (2004).
Hertel, et al., "Numbering system for the hammerhead", Nucleic Acids. Res., 20: 3252 (1992).
Hesselberth, et al., "Simultaneous detection of diverse analytes with an aptazyme ligase array", Anal. Biochem., 312:106-112 (2003).
Hesselberth and Ellington, "A (ribo) switch in the paradigms of genetic regulation", Nature Struct. Biol., 9:891-893 (2002).
Heus and Pardi, "Structural features that give rise to the unusual stability of RNA hairpins containing GNRA loops", Science, 253:191-94 (1991).
Higgins, et al., "Peptide transport in bacteria", Methods Enzymol, 125:365-77 (1986).
Hirsch, et al., "Identification of positive and negative regulatory elements governing cell-type-specific expression of the neural-cell-adhesion-molecule gene," Mol. Cell. Biol., 10:1959 (1990).
Hofacker, et al. "Fast folding and comparison of RNA secondary structures", Monatsh. Chem., 125:167-188 (1994).
Hofacker, "Vienna RNA secondary structure server", Nucleic Acids Res., 31:3429-3431 (2003).
Hourman, et al., "Transcriptional antitermination in the bgl operon of *E. coli* is modulation by a specific RNA binding protein", Cell, 62:1153-63 (1990).
Hoy, et al., "Bromodeoxyuridine/DNA analysis of replication in CHO cells after exposure to UV light", Mutation Research, 290:217-230 (1993).
Hunziker, et al., Nucleic Acid analogues: synthesis and properties, in Modern synthetic methods, VCH, 331-417 (1995).
Hurt, et al., "Site-specific modification of shigella flexneir virF mRNA by tRNA-guanine guanine transglycosylase in vitro", Nucleic Acids Res., 35:4905-13 (2007).
Hutton, et al., "Inhibitors of lysine biosynthesis as antibacterial agents", Mini. Rev. Med. Chem, 3:115-127 (2003).
Höfgen and Willmitzer, "Transgenic potato plants depleted for the major tuber protein patatin via expression o antisense RNA", Plant Sci., 87:45-54 (1992).
Iobbi-Nivol, et al., "The mob locus of *Escherichia coli* K 12 reuired for molybdenum cofactor biosynthesis is expressed at very low levels", Microbiology, 141:1663-71 (1995).
Isaacs, et al. "Engineered riboregulators enable post-transcriptional control of gene expression", Nat. Biotechnol., 22:841-847 (2004).
Ishiwata, et al., "Physical-chemistry characteristics and biodistribution of poly(ethylene glycol) coated liposmes using poly (oxyethylene) coholesteryl ether", Chem. Pharm. Bull., 43:1005-1011 (1995).
Iwata-Reuyl, "Biosynthesis of the 7-deazaguanosine hypermodified nucleosides of transfer RNA", Bioorg. Chem., 31:24-43 (2003).
Iyer, et al., "The prokaryotic antecedents of the ubiquitin-signaling system and the early evolution of ubiquitin-like-$^2$-grasp domains", Genome Biol., 7a;R60 (2006).
Izant and Weintraub, "Constitutive and conditional suppression of exogenous and endogenous genes by anti-sense RNA", Science, 229:345-352 (1985).
Jadhav and Yarus, "Coenzymes as coribozymes", Biochimie, 84:877-888 (2002).
Jaeger, et al., "Predicting optimal and suboptimal secondary structure for RNA", Methods Enzymol., 183:281-306 (1990).
Jaeger,et al., "Improved predictions of secondary structures for RNA", PNAS, 86: 7706-7710 (1989).
Jansen, et al., "Backbone and nucleobase contacts to glucosamine-6-phosphate in the glmS ribozyme", Nat. Struct. Mol. Biol., 13:517-523 (2006).
Jarmer, et al., "Transcriptome analysis documents induced competence of *Bacillus subtilis* during nitrogen limiting conditions", FEMS Microbiol. Lett., 206:197 (2002).
Jaschke, et al., "Automated incorporation of polyethylene gycol into synthetic oligonucleotides", Tetrahedron Letters, 34:301-304 (1993).
Jeffares, et al., "Relics from the RNA world", J. Mol. Evol., 46:18-36 (1998).
Jefferies and Symons, "A catalytic 13-mer ribozyme", Nucleic Acids Res., 17: 1371-1377 (1989).
Jenal, "Mechanisms of cyclic-di-GMP signaling in bacteria", Annu Rev. Genet, 40;385-407 (2006).
Jenison, et al., "High resolution molecular dicrimination by RNA", Science, 263: 1425-1429 (1994).
Jenne, et al., "A novel ribozyme with ester transferase activity", Chem Biol., 5 (1) 23-34 (1998).
Jiang and Wu, "Alternative splicing and programmed cell death", Prod. Soc. Exp. Biol. Med., 220:64 (1999).
Johansen, et al., "Definition of a second *Bacillus subtilis* pur regulon comprins the pur and xpt-pbuX operons plus pbuG, nupG (yxjA), and pbuE (ydhL)", J. Bacterial., 185:5200-5209 (2003).
Johnson, et al., "Identification of molybdopterin as the organic component of the tungsten cofactor in four enzymes from hyperthermophilic archaea", J. Bio. Chem., 268:4848-52 (1993).
Johnson, et al., "Molybdenum cofactor biosynthesis in *Escherichia coli*, requiremenr of the chiB gene product for the formation of molybdopterin guanine dinucleotide", J. Biol. Chem., 266:12140-45 (1991).
Jones, et al., "Improved methods for building protein models in electorn density maps and the location of errors in these models", Acta Crystallogr, A 47 (pt 2):110-9 (1991).
Jones, et al., "Moleuclar recongition of recpetor sites using a genetic algorithem with a description of desolvation", J. Mol. Biol., 245:43-53 (1995).
Jose, et al., "Cooperative binding of effectors by an allosteric ribozyme", Nucleic Acids Res., 29:1631-1637 (2001).
Joseph, et al., "Rapid orientated cloning in a shuttle vector allowing modulated gene expression in *Bacillus subtilis*", FEMS Microbiol. Lett., 205:91 (2001).
Joseph and Burke, "Optimization of an anti-HIV hairpin ribozyme by in vitro selection", J. Biol. Chem., 268:24515-24518 (1993).
Joyce, et al., "Amplification, mutation and selection of catalytic RNA", Gene, 82:83-87 (1989).
Joyce, et al., "Directed molecular evolution", Scientific American, 267:90-97 (1992).
Joyce, "RNA evolution and the origins of life", Nature, 338:217-244 (1989).
Joyce, "The antiquity of RNA-based evolution", Nature, 418:214-221 (2002).
Kanehisa, et al., "From genomics to chemical genomics: new developments in KEGG", Nucleic Acids Res., 34:D354-57 (2006).
Kasjani-Sabet, et al., "Reversal of the malignant phenotype by an anti-ras ribozyme", Antisense Research & Development, 2:3-15 (1992).
Kawasaki et al., "Thiamine regulatory mutants in *Escherichia coli*", J. Biochem. (Tokyo), 65:417-25 (1969).
Kerkhof, "A comparison of substrates for quantifying the signal from a nonradiolabeled DNA probe", Anal. Biochem., 205:359-364 (1992).
Kertèsz, et al., "Both introns and long 3\-UTRs operate as cis-acting elements to trigger nonsense-mediated decay in plants", Nucleic Acids Res., 34:6147-57 (2006).
Khrapko, et al., "Hybridization of Dna with oligonucleotides immobilized in a gel: a convenient method for recording single base replacements", Mol Biol (Mosk) (USSR), 25:718-730 (1991).
Khvorova, et al., "Sequence elements outside the hammerhead ribozyme catalytic core enable intracellular activity", Nature Struct. Biol., 10:708-712 (2003).
Kief and Warner, "Coordinate control of syntheses of ribosomal ribonucleic acid and ribosomal proteins during nutritional shift-up in *Saccharomyces cerevisiae*," Mol. Cell Biol., 1:1007-1015, 1981.
Kieft and Batey, "Ageneral method for rapid and nondenatureing purification of RNAs", RNA, 10:988-995 (2004).
Kieser, et al., Practical streptomyces genetics, The John Innes Foundation, Norwich UK (2000).

Kiga, et al., “An RNA aptamer to the xanthine/guanine base with a distinctive mode of purine recognition”, Nucleic Acids Res., 26: 1755-1760 (1998).
Kikuchi, “The glycine cleavage system: composition, reaction mechanism, and physiological significance”, Mol Cell Biochem., 1:169 (1973).
Kil, et al., “Riboflavin operon of *Bacillus subtilis*: unusual symmetric arrangement of the regulatory region”, Molecular & General Genetics, 233:483 (1992).
Kim, et al., “Accumulation of S-adenosyl-L-methionine enhances production of actinorhodin but inhibits sporulaton in streptomyces licidans TK23”, J. Bacteriol., 185:592-600 (2003).
Kim, et al., “An artificial riboswitch for controlling pre-mRNA splicing”, RNA, 11 (11):1667-77 (2005).
Kim, et al., “Two putative c-type multiheme cytochromes required for the expression of OmcB, an outer membrane protein essential for optimal Fe(III) reduction in geobacter sulfurreducens”, J. Bacteriol., 188:3138-42 (2006).
Kim and Cech, “Three-dimensional model of the active site of the self-splicing rRNA precursor of Tetrahymena”, PNAS, 84:8788-92 (1987).
Kima and Nam, “Genomics of microRNA”, Trends Genet., 22:165-73 (2006).
Kim, et al., “A colonization factor links vibrio cholerae environmental survival and human infection”, Nature, 438:863-66 (2005).
Kirschenbaum, et al., “Highly efficient gene transfer into adult ventricular myocytes by recombinant adenovirus”, J. Clin. Invest., 92:381-387 (1993).
Klein, et al., “Structural basis of blmS ribozyme activation by glucosamine-6-phosphate”, Science, 313:1752-1756 (2006).
Klein and Eddy, “Research: finding homologs of single structured RNA sequences”, BMC Bioinfotmatics, 4:44 (2003).
Kletzin and Adams, “Tungsten in biological systems”, FEMS Microbiol. Rev., 18:5-63 (1996).
Kobayashi, et al., “Essential *Bacillus subtilis* genes”, Proc. Natl, Acad. Sci. USA, 100: 4678-4683 (2003).
Kochhar and Paulus, “Lysine-induced premature transcription termination in the lysC operon of *Bacillus subtilis*”, Microbiol., 142:1635-1639 (1996).
Koizumi, et al, “Allosteric selection of ribozymes that repond to the second messengers cGMP and cAMP”, Nature Struct. Biol., 6:1062-1071 (1999).
Komatsu, et al., “Construction of new ribozymes requiring short regulator oligonucleotides as a cofactor”, J. Mol. Biol., 299:1231-1243 (2000).
Krasilinkov, et al., Basis for structural diversity in homologous RNAs, Science, 306:104-07 (2004).
Kreneva, et al., “Inactivation of the ypaA gene in *Bacillus subtilis*; analysis of the resulting phenotypic expression”, Gentika, 36: 972-74 (2000).
Kreneva, et al. “Study of the phenotypic occurrence of ura gene inactivation in *Bacillus subtilis*”, Genetika, 36(8):116-68 (2000) (Abstract only).
Kubodera, et al., “Thiamine-regulated gene expression of *Aspergillus oryzae* thiA requires splicing of the intron containing a riboswitch-like domain in the 51'UTR”, FEBS Lett, 555:516-520 (2003).
Kuchino, et al., “Biosynthesis of the modified nucleoside Q in transfer RNA”, Nucleic Acids Res., 3:393-98 (1976).
Kumar and Ellington, “Artificial evolution and natural ribozymes”, FASEB J, 9:1183-1195 (1995).
Kunkel, et al., Rapid and effcient site-specific mutagenesis without phenotypic selection. Methods Enzymol., 154: 367-82 (1987).
L'Huillier., et al., “Cytoplasmic delivery of ribozymes leads to efficient redution in alpha-latalbumin mRNA levels in C1271 mouse”, EMBO J., 11:4411-4418 (1992).
Laimins, et al., Osmotic control of kdp operon expression in *Escherichia coli*. PNAS, 78: 464-8 (1981).
Lake, et al, “The crystal structure of the *Escherichia coli* MobA protein provides insight into molybdopterin guanine dinucleotide biosynthesis”, J. Biol. Chem., 275:40211-17 (2000).
Landick, et al., “Quantitative analysis of transcriptional pausing by *Escherichia coli* RNA polymerase: his leader pause site as paradigm”, Methods Enzymol., 274:334-353 (1996).
Langer, et al., “Enzymatic synthesis of biotin-labeled polynucleotides: novel nucleic acid affinity probes”, PNAS, 78:6633 (1981).
Lasic and Needham, “The stealth liposome: a protypcial biomaterial”, Chem. Rev., 95:2601-2627 (1995).
Lasic and Paphajopoulos, “Liposomes revisited”, Science, 267:1275-76 (1995).
Lauhon and Szostak, “RNA aptamers that bind flavin and nicotinamide redox cofactors”, Journal of the American Chemical Society, 117: 1246 (1995).
Lazazzera et al., “An exported peptide functions intracellularly to contribute to cell density signalling in *B. subtilis*”, Cell, 89:917-925 (1997).
Le Gal La Salle, et al., “An adenovirus vector for gene transfer into neurons and glia in the brain”, Science, 259:988-990 (1993).
Lea, et al., “Turning on\ riboswitches to their antibacterial potential”, Nature, 3:16-17 (2007).
Leavitt and Freire, “Direct measurement of protein biding energitics by isothermal titration calorimetry”, Curr Opin Struct Biol, 11:560-6 (2001).
Lee, et al., “A cyclic-di-GMP receptor required for bacterial exopolysaccharide production”, Mol. Microbiol., 65:1474-84 (2007).
Lee, et al., “RNA expression analysis using an antisense *Bacillus subtilis* genome array”, J. of Bacteriology, 183:7371 (2001).
Lemay, et al., “Folding of the adenine riboswitch”, Chem. Biol., 13:857-68 (2006).
Leontis and Westhof, “A common motif organizes the structure of multi-helix loops in 16S and 23S ribosomal RNAs”, Mol. Biol. 283:571-583 (1998).
Leulliot and Varani, “Current topics in RNA-protein recognition: control of specificity and biological function through induced fit and conformational capture”, Biochemistry, 40:7947-7956 (2001).
Lewin, et al., “Ribozyme gene therapy: applications for molecular medicine”, Trends Mol. Med., 7 221-228 (2001).
Li and Breaker, “Deoxyribozymes: new players in the ancient game of biocatalysts”, Curr. Opin. Struct. Biol., 9:315-323 (1999).
Li and Breaker, “Kinetics of RNA degradation by specific base catalysts of transesterification involivng the 2'-hydroxyl group”, J. Am. chem. Soc., 121:5364-5372 (1999).
Li and Breaker, “In vitro Selection of Kinase and Ligase Deoxyribozymes”, Methods, 23:179-190 (2001).
Li and Sen, “A catalytic DNA for porphyrin metallation”, Nat. Struct. Biol., 3:743-747 (1996).
Liang and Pardee, “Differential display. A general protocol,” Methods Mol. Biol., 10:261-67 (1998).
Liao and Hsen, “Analysis of the regulatory region of the lysC gene of *Escherichia coil*”, FEMS Microbiol Lett., 168:31-36 (1998).
Lieber, et al., “A mutant T7 phage promoter is specifically transcribed by T7-RNA polymerase in mammalian cells”, Eur J Biochem, 217:387-94 (1993).
Lieber, et al. “Stable high level gene expression in mammalian cells by T7 phage RNA polymerase”, Methods Enzymol., 217: 47-66 (1993).
Lillo, et al., “Comparative genomics study of inverted repeats in bacteria”. Bioinformatics, 18:971 (2002).
Lim, et al., “Characteristics of ligand recognition by a glmS self-cleaving ribozyme”, Angew. Chem. Int., 45:6689-93 (2006a).
Lim, et al., “Cyclic-diGMP signal transduction systems in Vibrio cholerae: modulation of rugosity and biofilm formation”, Mol. Microbiol., 60:331-48 (2006c).
Lim, et al., “Molecular-recognition characteristics of SAM-binding riboswitches”, Angewandte Chem. Int. Ed., 45: 964-968 (2006b).
Limbach, et al., “Summary: the modified nucleosides of RNA”, Nucleic Acids Res., 22(12):2183-2196 (1994).
Lisziewicz, et al, “Inhibition of human immunodeficiency virus type-1 replication by regulated expression of a polymeric tat activation response RNA decoy as a strategy for gene therapy in AIDS”, PNAS, 90:8000-8004 (1993).
Lisziewicz, et al., Long-term treatment of human immunodeficiency virus-infected cells with antisense oligonucleotide phosphorothioates PNAS, 90:3860-64 (1993).

Liu, et al., "The RNA molecule CsrB binds to the global regulatory protein CsrA and antagonizes its activity in *Escherichia coli*", J. Biol. Chem., 272:17502-510 (1997).
Liu et al., Cationic liposome mediated intravenous gene delivery. J. Biol. Chem. 270(42): 24864-24870 (1995).
Logan, et al., "A poly(A) addition site and a downstream termination region are required for efficient cessation of transcription by RNA polymerase II in the mouse beta maj-globin gene", PNAS, 84:8306-10 (1987).
Lohse, et al. "Ribozyme-catalysed amino-acid transfer reactions", Nature, 30:381(6581):442-4 (1996).
Long and Uhlenback, "Kinetic characterization of intramolecular and intermolecular hammerhead RNAs with stem II deletions", PNAS, 91:6977-6981 (1994).
Loros and Dunlap, "*Neurospora crassa* clock-controlled genes are regulated at the level of transcription", Mol. Cell Biol., 11:558-563 (1991).
Lu, et al., "Fine-structure mapping of cis-acting control sites in the lysC operon of *Bacillus subtilis*", FEMS Microbiol Lett., 92:23-27 (1992).
Lu, et al., "Identification of aecA mutations in *Bacillus sbutilis* as nucleotide substitutions in the untranslated leader region of the aspartokinase II operon", J. Gen. Microbiol., 137:1135-1141 (1991).
Lundrigan, et al., "Transcribed sequences of the *Escherichia coli* btuB gene control its expressiona nd regulation by vitamin B12", PNAS, 88:1479-1483 (1991).
Lundrigan and Kadner, "Altered cobalamin metabolism in *Escherichia coli* btuR mutants affects btuB gene regulation", J. Bacterial., 171:154-161 (1989).
Lusky, et al., "*Bovine pailloma* virus contains an activator of gene expression at the distal end of the early transcription unit", Mol. Cell Bio., 3:1108 (1983).
Ma, et al, "Design and synthesis of RNA miniduplexes via a sythetic linker approach", Biochemistry, 32:1751-1758 (1993).
Ma, et al., "Design and sythesis of RNA miniduplexes via a synthetic linker approach. 2. Generation of covalently closed, double stranded cyclic HIV-1 TAR RNA analogs with high tat-binding affinity", Nucleic Acids. Res., 21:2585-2589 (1993).
MacKerell,et al., "All-atom empirical potential for molecular modeling and dynamics studies of proteins", J. Phys. Chem. B., 102:3586-3616 (1998).
Mader, et al, "Transcriptome and proteome analysis of *Bacillus subtilis* gene expression modulated by amino acid availability", J. Bacteriol., 184:4288-4295 (2002).
Mager and Planta, "Coordinate expression of ribosomal protein genes in yeast as a function of cellular growth rate," Mol. Cell Biochem., 104:181-187 (1991).
Makdessi, et al., "Tungstate uptake by a highly specific ABC transporter in eubacterium acidaminophilum", J. Biol. Chem., 276:24557-64 (2001).
Makela, "Alternative forms of Max as enhancers or suppressors of Myc-ras cotransformation", Science, 256:373-77 (1992).
Mandal, et al., "Riboswitches control fundamental biochemical pathways in *Bacillus subtilis* and other bacteria", Cell, 113:577-86 (2003).
Mandal and Breaker, "Adenine riboswitches and gene activation by disruption of a transcription terminator", Nature Struct Mol Biol., 11:29-35 (2004).
Mandel, et al., "Gene regulation by riboswitches", Nature Rev Mol Cell Biol., 5:451-463, 2004.
Mandel, et al. "A Glycine-Dependent Riboswitch That Uses Cooperative Binding to Control Gene Expression", Science, 306:275-279 (2004).
Manoharan, "2'-carbohydrate modifications in antisense oligonucleotide therapy: importance of conformation, configuration, and conjunction", Beiochem Biophys. Acta, 1489(1): 117-130 (1999).
Mansilla, et al., "Transcriptional control of the sulfur-regulated cysH operon, containing genes involved in L-cysteine biosynthesis in *Bacillus subtilis*", J. Bacteriol., 182: 5885 (2000).
Marchler-Bauer, et al., "CDD: a consrrved domain database for protein classification", Nucleic Acids Res., 33:192-96 (2005).
Massie, et al, "Construction of a helper-free recombinant adenovirus that expresses polyomavirus large T antigen", Mol. Cell. Biol., 6:2872-2883 (1986).
Mathews, et al., "Expnaded sequence dependence of thermodynamic parameters imporves prediction of RNA secondary structure", J Mol. Biol., 288:911-940 (1999).
Matlin, et al., "Understanding alternative splicing: Towards a cellular code", Nature, 6:386-398 (2005).
Matthews and Nichols, "Lactose repressor protein: functional properties and structure", Prog. Nucleic Acids Res. Mol. Biol., 58:127-164 (1998).
Maundrell, "nmtl of fission yeast, a highly expressed gene completely repressed by thiamine", J. Biol Chem., 265:10857-64 (1989).
Maupin-Furlow, et al., "Genetic analysis of the modABCD (molybdate transport) operon of *Escherichia coli*", J. Bacteriol., 177:4851-56 (1995).
Mayer, et al., "High-throughput-compatible assay for glmS riboswitch metabolite dependence", ChemBioChem, Bol., 7:602-604 (2006).
McCall, et al., "Minimal sequence requirements for ribozymes activity", PNAS, 89: 5710-5714 (1992).
McCarthy, et al., "Ligand requirements for glmS ribozyme self-cleavage", Chem. Biol., 12:1221-1226 (2005).
McCaskill, "The equilibrium partition function and base pair binding probabilities for RNA secondary structure", Biopolymers, 29:1109-1119 (1990).
McCauley, et al. "Aptamer -based biosensor arrays for detection and quantification of biological macromolecules", Anal. Biochem. 319:244-250 (2003).
McColl, et al., "Characterization and expression of the *Neurospora crassa* nmt-1 gene", Curr. Genet., 44:216-223 (2003).
McConnell, et al., "Guanosine binding to the Tetrahymena ribozyme: thermodynamic coupling with oligonucleotide binding", PNAS, 90:8362-8366 (1993).
McCurdy, et al., "Deoxyoligonucleotides with inverted polarity: synthesis and use in triple-helix formation", Nucleosde & Nucleotides, 10:287-290 (1991).
McCutcheon and Eddy, "Computational identification of non-coding RNAs in *Saccharomyces cerevisiae* by comparative genomics", Nucleic Acids Res., 31:4119-28 (2003).
McDaniel, et al., "Transcription termination control of the S box system: direct measurement of S-adenosylmethionine by the leader RNA", PNAS, 100:3083-3088 (2003).
McGarry and Linquist, "Inhibition of heat shock protein synthesis by heat-inducible antisense RNA", PNAS, 83:399-403 (1986).
Mehta, et al., "Outer membrane c-type cytochromes required for Fe(III) and Mn(VI) oxide reduction in geobacter sulfurreducens", Appl. Eviron Microbiol., 71:8634-41 (2005).
Meibom, et al., "Chitin induces natural competence in vibro cholerae", Science, 310:1824-27 (2005).
Meibom, et al., "The vibrio cholerae chitin utilization program", PNAS, 101:2524-29 2004).
Meier, et al., "Queuosine modification of the wobble base in tRNA HIS influences in viro decoding properties", EMBRO J., 4:823-27 (1985).
Meng, et al., "Ribozyme probe based on molecular beacon for real time monitoring of enzymatic cleavage process", Chinese Science Bull., 48 (23):2581-84 (2003).
Mesmaeker et al., "Novel backbone replacements for oligonucleotides", Am. Chem. Soc., 24-39 (1994).
Methe, et al., "Genome of geobacter sulfurreducens: metal reduction in subsurface environments", Science, 302:1967-69 (2003).
Michel and Westhof, "Modeling of the three-dimensional architecture of group I catalytic introns based on comparative sequence analysis", J. Mol. Biol., 216:585-610 (1990).
Michels and Pyle, "Converstaion of group II intron into a new multiple turnover ribozyme that selectively cleaves oligonucleotides: elucidation of reaction mechanism and structure/function relationships", Biochemistry, 54:3965-3977 (1995).
Migawa, et al., "A two step synthesis of the nucleoside Q precursor 2-amino-5-cyanopyrrolo[2,3-d]pyrimidine-4-one (preQ0)", Synth. Commun., 26:3317-22 (1996).

Milewski, et al., "Glucosamine-6-phosphate synthase—the multi-facets enzyme", Biochim. Biophys. Acta 1597:173-192 (2002).
Miller, et al., Nucleoside hydrolases from trypanosome cruzi, J. Biol. Chem., 259:5073-77 (1984).
Miller, "In: A Short Course in Baceterial Genetics" (Cold Spring Harbor Laboratory Press, Cold Spring Harbor, NY) p. 72 (1992).
Milligan and Uhlenbeck, "Synthesis of small RNAs using T7 RNA polymerase", Methods Enzymol, 180:51-62 (1989).
Miranda-Rios, et al., "A conserved RN structiure (thi box) is involved in regulation of thiamin biosynthetic gene expression in bacteria", PNAS, 98:9736-9741 (2001).
Miranda-Rios, et al., "the THI-box riboswitch or How RNA binds thiamin pyrophosphate", Structure Current Biology, 15(3):259-65 (2007).
Mironov, et al., "Functional organization of the riboflavin biosynthesis operon from *Bacillus subtilis* SHgw", Molecular & General Genetics, 242:201 (1994).
Mironov, et al., "Sensing small molecules by nascent RNA: a mechanism to control transcription in bacteria", Cell, 111:747-56 (2002).
Molinaro and Tinoco, "Use of ultra stable UNCG tetraloop hirpins to fold RNA structures: thermodynamic & spectroscopic applications", Nucleic Acids Res., 23:3056-63 (1995).
Montange and Batey, "Structure of the S-adenosylmethionine riboswitch regulatory mRNA element", Nature, 441:1172-75 (2006).
Moore and Sharp, "Site specific modification of Pre-mRNA: the 2'-hydroxyly groups at the splice sites", Science, 256:992-996 (1992).
Morris, et al., "Automated docking using a Larnarckian genetic algorithem and an empirical binding free energy function", J. Compute. Chem., 19:1639-1662 (1998).
Morris, et al., "Distributed automated docking of flexible ligands to proteins: Parallel applications of Autodock 2.4", J. of Computer Aided Molecular Design, 10:293-304 (1996).
Morsy, et al., "Efficient adenoviral0mediated ornithine transcarbamylase expression in deficient mouse and human hepatocytes", J. Clin. Invest., 92:1580-1586 (1993).
Moszer, et al., "SubtiList: a relational database for the *Bacillus subtilis* genome", Nucleic Acids. Res., 30:62 (2002).
Moullier, et al., "Correction of lysosomal storeage in the liver and spleen of MPS VII mice by implantation of genetically modified skin fibroblasts", Nat. Gene. 4:154-159(1993).
Muesing, et al., "Regulation of mRNA accumulation by a human immunodeficiency virus trans-activator protein," Cell, 48:691, 1987.
Muhlrad and Parker, "Aberrant mRNAs with extended 3\ UTRs are substages for rapid degradation by mRNA surveillance", RNA, 5:1299-1307 (1999).
Mulligan, "The basic science of gene therapy", Science, 260:926-932 (1993).
Mulligan and Berg, "Expression of a bacterial gene in mammalian cells", Science, 209: 1422 (1980).
Mumberg, et al., "Alternative splicing of fosB transcripts results in differentially expressed mRNAs encoding functionally antagonistic proteins", Genes Dev., 5:1212-23 (1991).
Murashige and Skoog, "A revised medium for rapid growth and bioassays with tobacco tissue cultures", Physiol. Plant, 15:473-497 (1962).
Murphy, et al., "Prediction of gene function in methylthioadenosine recycling from regulatory signals", Journal of Bacteriology, 184:2314 (2002).
Murphy-McDaniel, et al., "Transcription termination control of the S box system: direct measurement of S-adenosylmethionine by the leader RNA", PNAS, 100(6):3083-88 (2003).
Murzin, et al "SCOP: a structural classification of proteins database for the investigation of sequences and structures", J. Mol. Biol., 247:536-40 (1995).
Nahvi, et al., "Coenzyme B12 riboswitches are widespread genetic control elements in prokaryotes", Nucleic Acids Res, 32:143-150 (2004).
Nahvi, et al., "Genetic control by a metabolite binding mRNA", Chem Biol., 9:1043-49 (2002).
Nakamura, et al., High-affinity taurine uptake and its regulation by protein kinase C in human glioma cells., Adv. Exp. Med. Bio, 403:377-84 (1996).
Nathans and Smith, "Restriction endonucleases in the analysis and restructuring of DNA molecules", Ann. Rev. Biochem., 44:273-293 (1975).
Needleman and Wunsch, "A general method applicable to the search for similarities in the amino acid sequence of two proteins", J. Mol. Biol., 48:443 (1970).
Neph and Tompa, "MicroFootAPrinter: a tool for phylogenetic footprinting in prokaryotic genomes", Nucleic Acids Res., 34 (2006).
Newman, et al., "DST sequences highly conserved among plant SAURR genes, target reporter transcripts for rapid decay in tobacco", Plant Cell, 5:701-14 (1993).
Nichols and Rajagopalan, "*Escherichia coli* MoeA and MogA, function in metal incorporation step of molybdenum cofactor biosynthesis", J. Biol. Chem., 277:24995-2500 (2002).
Nielsen, et al, "Sequence-selective recognition of DNA by strand displacement with a thymine-substituted polyamide", Science, 254:1497-1500 (1991).
Nissen, et al "RNA tertiary interactions in the large ribosomal subunit: the A minor motif", PNAS, 98:4899-4903 (2001).
Noeske, et al., "An intermolecular base triple as the basis of ligand specificity and affinity in the guanine and adenine- sensing riboswitch RNAs", PNAS, 102:1372-77 (2005).
Noguchi, et al., "Isolation and characterization of an *Eschrichia coli* mutant lacking tRNA-guanine transglycosylase, function and biosynthesis of queuosine in tRNA", J. Biol. Chem.., 257:6544-50 (1982).
Noonberg, et al., "In vivo generation of high abundant sequence-specific oligonucleotides for antisnes and triplex gene regulation", Nucleic Acids Res., 22 (14) 2830-2836 (1994).
Nou and Kadner, "Adenosylcobalamin inhibits ribosome binding to btuB RNA", PNAS, 97:7190-7195 (2000).
Nudler, et al., "The riboswitch control of bacterail metabolism", Trends in Biochem Sci., 29(1):11-17 (2004).
Nudler and Gottesman, "Transcription termination and anti-termination in *E.coli*", Genes to Cells, 7, 755 (2002).
Nygard, et al., "Total homocysteine and cardiovascular disease", J. Intern. Med., 245:425-54 (1999).
Ohkawa, et al., "Activities of HIV-RNA targeted ribozymes transcribed form a shot gun type ribozyme trimming plasmid", Nucleic Acids Symp. Ser., 27:15-16 (1992).
Ojwang,et al., "Inhibition of human immunodeficiency virus type-1 expression by hairpin ribozyme", PNAS, 89:10802-10806 (1992).
Okada, et al., "Novel mechanism of post-transcriptional modification of tRNA", J. Biol. Chem., 254:3067-73 (1979).
Okada, et al, "Structure determination of a nucleoside Q precursor isolated from *E coli* tRNA: 7-(aminomethyl)7-deasaguanine", Nucleic Acids Res., 5:2289-96 (1978).
Oku, et al., "Real time analysis of liposomal trafficking in tumor-bearing mice by use of positron emission tomography", Biochimica et Biophysica Acta., 1236: 86-90 (1995).
Old, et al., "Cloning and characterization of the genes for the two homocysteine transmethylases of *Escherichia coli*", Mol. Gen. Genet., 211:78-87 (1988).
Ono, et al., "DNA triplex formation of oligonucleotide analogues consisting of linker groups and octamer segments that have opposite sugar-phosphate backbone polarities", Biochemistry, 30:9914-9921 (1992).
Orbach, et al., "Cloning and characterization of the gene for brta-tubulin from a benomyl-resistant mutant of *Neurospora crassa* and is use as a dominant selectable marker", Mol. Cell Biol., 6:2452-61 (1986).
Orengo and Thornton, "Protein families and their evolution-a structural prespective", Annu. Rev. Biochem., 74;867-900 (2005).
Orgel, et al., "Selection in vitro", Proc. R. Soc. London B., 205:435-442 (1979).
Osborne, et al., "Characterization of a native hammerhead ribozyme derived from schistosomes", RNA, 11:187-196 (2005).
Osborne, et al., "Transcription control region within the protein-coding portion of adenovirus E1A genes", Mol. Cell Bio., 4:1293 (1984).
Osborne and Ellington, "Nucleic acid selection and the challenge of combinatorial chemistry", Chem. Rev., 97:349-370 (1997).

Osman, et al., "A cis-acting element in the 3\-untransioated region of human TNF-alpha mRNA renders splicing dependent on the activation of protein kinase PRK", Genes and Devel., 13(24):3280-93 (1999).
Pan, et al"Properites of an in vitro selected Pb2+ cleavage motif.", Biochemistry, 33:9561-9564 (1994).
Patte, et al., "The leader sequence of the *Escherichia coli* lysC gene is involved in the regulation of LysC synthesis", FEMS Microbiol. Lett., 169:165-170 (1998).
Patte, "Biosynthesis of lysine and threonine. In: *Escherichia coli* and *Salmonella*", Cellular and Molecular Biology, eds, 1:528-541 (1996).
Pearson and Lipman, "Improved tools for biological sequence comparison", PNAS, 85:2444 (1988).Pearson and Lipman, "Improved tools for biological sequence comparison", PNAS, 85:2444 (1988).
Pease, et al., "Light-generated oligonucleotide arrays for rapid DNA sequence anlysis", PNAS, 91(11):5022-5026 (1994).
Pedersen, et al., "Identification and classification of conserved RNA secondary structures in the human genome", PloS computational Biology, 2(4):e33 (2006).
Penchovsky, et al., "DNA library design for molecular computation", J. Comput. Biol., 10:215-229 (2003).
Perreault, et al., "Mixed deoxyribo- and ribo-oligonucleotides with catalytic activity", Nature, 344:565-567 (1990).
Perrotta and Been, "Cleavage of oligoribonucleotides by a ribozyme derived from the hepatitis delta virus RNA sequence", Biochem., 31(1):16 (1992).
Pflugrath, "The finer things in X-ray diffraction data collection", Acta Crystallogr., D55:1718-1725 (1999).
Phadtare and Inouye, "Sequence-selective interactions eith RNA by CspB, CspC and CspE members of the CspA family of *Escherichia coli*", Mol. Microbiol., 33:1004-14 (1999).
Pieken, et al., "Kinetic characterization of ribonuclease resistant 2' modified hammerhead ribozymes", Science, 253:314-317 (1991).
Pierce, et al., "Isothermal titration calorimetry of protein-protein interactions", Methods, 19:213-221 (1999).
Pitterle, et al., In vitro synthesis of molybdopterin from precursor Z using purified converting factor, role of protein-bound sulfur in formation of the dithiolene, J, Biol. Chem., 268:13506-09 (1993).
Porta, et al.," An allosteric hammerhead ribozyme", Biotechnol., 13:161-164 (1995).
Proudfoot, et al., "Integrating mRNA processing with transcription", Cell, 108:501-12 (2002).
Proudfoot, "How RNAS polymerase II terminates transcription in higher eukaryotes", Trends Biochem. Sci, 14:105-10 (1989).
Proudfoot, "New perspectives on connecting messenger RNA 3\ end formation to transcription", Curr Opin Cell Biol., 15:272-78 (2004).
Pruitt, et al., "NCBI reference sequence (RefSeq) a curated non-redundant sequence of genomes, transcripts and protens", Nucleic Acids Res., 33:501-04 (2005).
Ragot, et al., "Replication-defective recombinant adenovirus expressing the Epstein-Barr virus (EBV) envelope glycoprolein gp340/220 induces protective immunity against EBV-induced lymphomas in the cottontop tamarin", J. Gen. Virology, 74:501-507 (1993).
Ram, et al., "In situr retroviral-mediated gene transfer for the treatment of brain tumors in rats", Cancer Res., 53:83-88 (1993).
Ravanum and Andersson, "An adenosyl-cobalamin (coenzyme-B12) repressed translational enhancer in the cob mRNA of *Salmonella typhimurium*", Mol. Microbiol., 39: 1585-1594 (2001).
Reader, et al., "Identification of four genes necessary for biosynthesis of the modified nucleoside queuosine", J. Biol. Chem.., 279:6280-85 (2004).
Recht and Williamson, "Central domain assempby: thermodynamics and kinetics of S6 and S18 binding to an S15-RNA complex", J. Mol. Biol, 313:35-48 2001).
Reguera, et al., "Extracellular electron transfer via microbial nanowires", Natue, 435:1098-1101 (2005).
Regulski, et al., "A widespread riboswitch candidate that controls bacterial genes involved in molybdenum cofactor and tungsten cofactor metabolism", Mol. Microbiol., 68:918-32 (2008).
Reinhold-Hurek and Shub, "Self-splicing introns in tRNA genes of widely divergent bacteria", Nature, 357:173-176 (1992).
Rentmeister, et al., "Conformational changes in the expression domain of the *Escherichia coli* thiM riboswitch", Nucleic Acids Res., 35(11):13-22 (2007).
Reuter, et al., "Structure and organization of *Escherichia coli* genes involved in biosynthesis of the deazaguamine derivative queunine a nutrient factor for eukaryotes", J. Bacteriol., 173:2256-64 (1991).
Rey, et al "The MchR repressor modulated by the effector substance S-adenosylhomocysteine controls directly the transcription of a regulon involved in sulphur metabolism of corynebacterium glutamicum ATCC 13032", Mol. Microbiol., 56:871-887 (2005).
Rice, et al., "Single wavelength anomalous diffraction phasing revisited", Acta Crystallogr D Biol. Crystallogr, 56 (Pt 11):1413-20 (2000).
Rich, et al., "Development and anlysis of recombinant adenovirus for gene therapy of cystic fibrosis", Human Gene Therapy, 4:461-476 (1993).
Richardson, "Phi-dependent termination and ATPases in transcript termination", Biochemica et Biophysica Acta, 1577:251 (2002).
Richardson and Schepartz, "Tethered olinucleotide probes. A strategy for the recognition of structured RNA", J. Am. Chem. Soc., 113: 5109-5111 (1991).
Robertson, et al., "Design and optimization of effector-activated ribozyme ligases", Nucleic Acids Res., 28(8):1751-9 (2000).
Robertson, et al. "In vitro selection of nucleoprotein enzymes", Nat. Biotechnol., 19(7):650-5 (2001).
Robertson, et al. "In vitro selection of ribozymes dependent on peptides for activity", RNA, 10:114-127 (2004).
Rodionov, et al., Comparative genomics of the methionine metabolism in Gram-positive bacteria: a variety of regulatory systems, Nucleic Acids Res., 32:3340-53 (2004).
Rodionov, et al., "Comparative genomics of the vitamin B12 metabolism and regulation in prokaryotes", J. Biol. Chem.., 278:41148-59 (2003a).
Rodionov, et al., "Comparative genomics of thiamin biosynthesis in procaryotes. New genes and regulatory mechanisms" , J. Biological chemistry, 277:48949-59 (2002).
Rodionov, et al., "Regulation of lysine biosynthesis and transport genes in bacteria: yet another RNA riboswitch?", Nucleic Acids Res., 31:6748-6757 (2003).
Roessler, et al, "Adenoviral-mediated gene transfer to rabbit synovium in vivo", J. Clin. Invest., 92:1085-1092 (1993).
Romling, et al., C-di-GMP: the dawning of a novel bacterial signalling system Mol. Microbiol., 57:629-39 (2005).
Rosentel, et al., "Molybdate and regulation of mod (molybdate transport), fdhF and hyc (formate hydrogenlyase) operons in *Escherichia coli*", J. Bacteriol., 177:4857-64 (1995).
Ross, et al., "An unusual guanyl oligonucleotide regulates cellulose synthesis in *Acetobacter xylinum*", FEBS Lett., 186:191-96 (1985).
Ross, et al., "Regulation of cellulose synthesis in *Acetobacter xylinum* by cyclic diguanylic acid", Nature, 325:279-81 (1987).
Rossi, et al., "Molecular Biology: ribozymes in the nucleolus", Science, 285:1685 (1999).
Rossi, et al., "Ribozymes as anti-HIV therapeutic agents: principles, applications and problems", AIDS Res. Hum. Retrovir., 8(2):183 (1992).
Roth, et al., "Finding DNA regulatory motifs within unaligned noncoding sequences clustered by whole-genome mRNA quantitation," Nat. Biotechnol., 16:939-945, 1998.
Roth, et al., "A riboswitch selective for thr queuosine precursor preQ(1) contains an unusually small aptamer domain", Nature Structural and Mol. Bio.,14 (4):308-17 (2007).
Roth, et al., "Characteristics of the glmS ribozyme suggest only structural roles for divalent metal ions", RNA, 12:607-619 (2006).
Roth and Breaker, "An amino acid as a cofactor for a catalytic polynucleotide", PNAS, 95:6027-6031 (1998).
Roth and Breaker, "Selection In vitro of allosteric ribozymes", in: Mehthods in Molecular Biology Series—Catalytic Nucleic Acid Protocols (Sioud, M, ed.) Humana, Totowa, NJ (2003).
Roychowdhury-Saha, et al., "Flavin recognition by an RNA aptamer targeted toward FAD", Biochemistry, 41:2492 (2002).
Ruffner, et al., "Sequence requirements of the hammerhead RNA self-cleavage reaction", Biochemistry, 29:10695-10 702 (1990).

Rusch, et al., "The Sorcerer II Global Ocean Sampling expedition: northwest Atlantic through eastern tropical Pacific", PloS Biol., 5:e77 (2007).
Russell, et al., "Exploring the folding landscape of a structured RNA", Proc. Natl. Acad. Sci. USA, 99:155-160 (2002).
Ryan, et al., "Cyclic di-GMP signaling in bacteria: recent advances and new puzzles", J. Bacteriol, 188:8327-34 (2006).
Ryjenkov, et al., "The PilZ domain is a receptor for the second messenger c-di-GMP: the PilZ domain protein YcgR controls motility in enterobacteria", J. Biol. Chem., 281:30310-14 (2006).
Salazar, et al., "A truncated aminoacyl-tRNA synthetase modifies RNA", PNAS, 101:7536-41 (2004).
Sambrook, et al., Molcular Cloning: A Laboratory Manual, 2nd Ed., Cold Spring Harbor Laboratory, Cold Spring Harbor, NY (1989).
Sanghvi, Antisense Research and Applications Ch15:289-302, ed, CRC Press (1993).
Sanishvili, et al., "The crystal structure of *Escherichia coli* MoaB suggests a probable role in molybdenum cofactor synthesis", J. Biol. Chem., 279:42139-46 (2004).
Sano,et al., "Detection of heavy methylation in human repetitive DNA subsets by a monoclonal antibody against 5-methylcytosine", Biochim. Biophys. Acta, 951:157-165 (1988).
Santamaria-Araujo, et al., The tetrahydropyranopterin structure of the sulfur-free and metal-free molybdenum cofactor precursor, J. Biol. Chem., 279:15994-15999 (2004).
Sarver, et al., "Ribozymes as potential anti-HIV-1 therpeutic agents", Science, 247: 1222-1225 (1990).
Saville and Collins, "A site-specific self-cleavage reaction performed by a novel RNA in *Neurospora mitochondria*", Cell, 61(4):685-696 (1990).
Saville and Collins, "RNA-mediated ligation of self-cleavage products of a *Neurospora mitochondrial* plasmid transcript", Proc. Natl. Acad. Sci. USA, 88 (19):8826-8830 (1991).
Scanlon, et al., "Riobzyme-mediated cleavage of c-fos mRNA reduces gene expression of DNA synthesis enzymes and metallothonien", PNAS, 88:10591-10595 (1991).
Scaringe, et al., "Chemical synthesis of biologically active oligoribonucleotides using beta-cyantethyl protected ribonucleoside phosphramidites", Nuceic Acids Res. 18:5433-5441 (1990).
Schaffer, et al., "Improving the accuracy of PSI-BLAST protein database searches with composition-based statistics and other refinements". Nucleic Acids Res., 29:2994-3005 (2001).
Schauder, et al., "The LuxS family of bacterial autoinducers: biosynthesis of a novel quorum-sensing signal molecule", Mol. Microbiol., 41:463-476 (2001).
Schray, et al., "Anomerization rates and enzyme specificity for biologically important sugars and sugar phosphates", Chem. Res., 11:136-141 (1978).
Schubert, et al., "Ribozyme- and deoxyribozymes-strategies for medical applications", Curr. Drug Targets, 5:667-681 (2004).
Schwarz, "Molybdenum cofactor biosynthesis and deficiency", Cell Mol. Life Sci., 62:2792-2810 (2005).
Schweitzer and Kingsmore, "Combining nucleic acid amplification and detection", Curr. Opin. Biotech., 12:21-27 (2001).
Schyns, et al., "Isolation and characterization of new thiamine-deregulated mutants of *Bacillus subtilis*", J. Bacterial., 187:8127-36 (2005).
Scott and Amy, "Molybdenum accumulation in chID mutants of *Escherichia coli*", J. Bacteriol., 171:1284-1237 (1989).
Seela and Kaiser, "Oligodeoxyribonueleotides containing 1, 3 propanedial as necleoside substitute", Nucleic Acids Res., 15:3113-3129 (1987).
Seetharaman, et al., "Immobilized riboswitches for the analysis of complex chemical and biological mixtures", Nature Biotechnol., 19:336-341 (2001).
Seliverstov, et al., "Comparative analysis of RNA regulatory elements of aminoi acid metabolism genes in actinobacteria" , BMC Microbial., 5:54 (2005).
Sengle, et al., "Novel RNA catalysts for the Michael reaction", Chem Biol., 8 (5):459-73 (2001).
Serganov, et al., "Structural basis for discriminative regulation of gene expression by adenine- and guanine-sensing mRNAs", Chem. Biol., 11:1729-1741 (2004).
Serganov, et al., "Structural basis for gene regulation by a thiamine pyrophosphate-sensing riboswitch", Nature, 441:1167-1171 (2006).
Seth, et al., "Evidence that the penton base of adenovirus is involved in potentiation of toxicity of *Pseudomonas exotoxin* conjugated to epidermal growth factor", Mol. Cell. Biol., 4: 1528-1533 (1984).
Seth, et al., "Role of a low-pH environmnet in adenovirus enhancement of the toxicity of a *Pseudomonas exotoxin*-epidermal growth factor conjugate", J. Virol., 51:650-655 (1984).
Shabarova, et al., "Chemical ligation of DNA: the first non-enzymatic assembly of a biologically active gene", Nucleic Acids Res., 19:4247-4251 (1991).
Shanmugam., et al., "Proposed nomenclature for the genes involved in molybdenum metabolism in *Escherichia coil* and *Salmonella typhimurium*", Mol. Microbiol., 6:3452-54 (1992).
Sheppard, et al., "Purification and properties of NADH-depndent 5, 10-methylenetetrahydrofolate reductase (MetF) from *Escherichia coli*", J. Bacteriol, 181:718-25 (1999).
Shimizu, et al., "Occurrence of S-adenosylihomocysteine hydrolase in prokaryote cells-characterization of the enzyme from alcaligenes faecalis and role of the enzyme in the activated methyl cycle", Eur. J. Biochem., 141:385-92 (1984).
Shiota, et al., "Inhibition of lysine utilization in bacteria by S-(beta-aminoethly) cysteine and its reversal by lysine peptides", Arch. Biochem. Biophys., 77:372-7 (1958).
Shu and Guo, "A viral Rna that binds ATP and contains a motif similar to an ATP binding aptamer from SELEX", J. Biol. Chem., 278:7119-7125 (2003).
Silverman, "Molecular switches and sensors made from RNA", RNA, 9:377-383 (2003).
Simm, et al., "GGDEF and EAL domains inversely regulate cyclic di-GMP levels and transition from sessility to motility", Mol. Microbiol., 53:1123-34 (2004).
Simmons, et al., "A Complete protocol for in situ hybridization of messager RNA in brain andother tissues with radiolabeled single-stranded RNA probes", J. Histotech., 12:169-181 (1989).
Simons, et al., "Improved single and multicopy lac-based cloning vectors for porteina nd operon fusions", Gene, 53:85-96 (1987).
Slany, et al., "A new function of S-adenosylmethionine, the ribosyl moiety of AdoMet is the precursor of cyclopentenediol moiety of the tRNSA wobble base queuine", Biochemistry, 32:7811-17 (1993).
Slany, et al., "Transfer and isomerization of thr ribose moiety of AdoMet during the biosynthesis of queuosine tRNAs, a new unique reaction catalyzed by the QueA protein from *Escherichia coil*", Biochimie, 76:389-93 (1994).
Smith and Waterman, "Comparison of Biosequences", Adv. Appl. Math., 2:482 (1981).
Sosnick and Pan, "RNA folding: Models and perspectives", Curr. Opin. Struct. Biol., 13:309-316 (2003).
Soukup, et al., "Core requirements for glmS ribozyme self-cleavage reveal a putative pseudoknot structure", Nucleic Acids Res, 34: 968-975 (2006).
Soukup et al., "Generating new ligand-binding RNAs by affinity maturation and disintegration fo allosteric ribozymes", RNA, 7:524-536 (2001).
Soukup and Breaker, "Allosteric Nucleic Acid Catalysts", Curr. Opin. Struct. Biol., 10: 318-325 (2000).
Soukup and Breaker, "Engineering precision RNA molcular switches", PNAS, 96: 3584-3589 (1999).
Soukup and Breaker, Nucleic Acid Molecular Switches. Trends Biotechnol., 17: 469-476 (1999).
Soukup and Breaker, "Relationship between internucleotie linkage geometry and the stability of P,-NA", RNA, 5:1308-1325 (1999b).
Soukup and Soukup, "Riboswitches exert genetic control through metabolite-induced conformational change", Curr. Opin, Struct. Biol., 14:344-49 (2004).
Southern and Berg, "Transformation of mammalian cells to antibiotic resistance with a bacterial gene under control of the SV40 early region promoter", J. Molec. Appl. Genet., 1: 327 (1982).
Spino and Guest, "FNR and its role in oxygen-related gene expression in *Echerichia coli*", FEMS Microbiol Rev., 6:399-428 (1990).
Srinivasan, et al., "ADP-specific sensors enable universal assay of protein kinase activity", Chem. Biol., 11:499-508 (2004).

Steffes, et al., "The lysP gene encodes the lysine-specific permease", J. Bacterial., 174: 3242-3249 (1992).
Stimpson, et al., "Real-time detection of DNA hybridization and melting on oligonucleotide arrays by using optical wave guides", PNAS, 92:6379-6383 (1995).
Stoddard and Batey, "Mix and match riboswitches", ACS Chem. Biol., 1:751-54 (2006).
Stojanovic, et al., "A deoxyribozyme-based molecular automaton", Nat. Biotechnol. 21:1069-1074 (2003).
Stojanovic, et al., "Computational methods for the analysis of differential conservation in groups of similar DNA sequences", Genome Inform., 15:21-30 (2004).
Stojanovic, et al., "Deoxyribozyme-based half-adder", J. Am. Chem. Soc., 125: 6673-6676 (2003).
Stojanovic, et al., Deoxyribozyme-based logic gates J. Am. Chem. Soc. 124:3555-3561 (2002).
Stormo and Ji, "mRNAs act as direct sensors of small moleculres to control their expression", PNAS, 98: 9465-9467 (2001).
Storz, et al., "An abundance of RNA regulators", Annu. Rev. Biochem., 74:199-217 (2005).
Street and Msyo, "Pairwise calculation of protein solvent-accessible surface areas", Folding & Design, 3:253-258 (1998).
Stulke, "Control of transcription termination in bacteria by RNA-binding proteins that modulate RNA structures", Archives of Microbiology, 177:433 (2002).
Sudarsan, et al., "An mRNA structure in bacteria that controls gene expression by binding lysine", Genes Dev., 17:2688-97 (2003a).
Sudarsan, et al., "Metabolite binding RNA domains are present in the genes of eukaryotes", RNA, 9:644-647 (2003b).
Sudarsan, et al., "Tandem riboswitch architectures exhibit complex gene control functions", Science, 314:300-4 (2006).
Sudarsan, et al., "Thiamine pyrophosphate riboswitches are targets for the antimicrobial compound pyrithiamine", Chem. Biol., 12:1325-1335 (2005).
Suess, et al., "A theophylline responsive riboswitch based on helix slipping controls gene expression in vivo", Nucleic Acids Res., 32:1610-1614 (2004).
Sugden, et al., A vector that replicates as a plasmid and can be efficiently selected in B-lymphoblasts transformed by Epstein Barr virus. Mol. Cell Biol., 5: 410-413 (1985).
Sugiyama. et al., Catalytic activities of hammerhead ribozymes with a triterpenoid linker instead of stem/loop II. FEBS Letters 392: 215-219 (1996).
Sullenger and Cech, Tethering ribozymes to a retroviral packaging signal for destruction of viral RNA. Science 262: 1566-1569 (1993).
Svensson and Persson, Role of vesicles during adenovirus 2 internalization into HeLa cells. J. Virology, 55: 442-449 (1985).
Switzer, et al., "Regulation of the *Bacillus subtilis* pyrimidine biosynthetic operon by transcriptional attenuation: control of gene expression by an mRNA-binding protein", Prog Nucleic Acids Res. Mol. Biol., 62:329-367 (1999).
Szostak, "In vitro genetics", TIBS, 17:89-93 (1992).
Szostak and Ellington, In vitro selection of functional RNA sequences, RNA World ED, Cold Spring Harbor Laboratory Press, 511-533 (1993).
Tabor and Tabor, "Methionine adenosyltransferase (S-adenosylmethionine synthetase) and S-adenosylmethionine decarboxylase, advances enzymol related areas", Mol. Biol., 56:251-82 (1984).
Taira, et al., Construction of a novel RNA transcript trimming plasmid which can be used both in vitro in place of run-off and (G) free transcriptions and in vivo as multi sequences transcription vectors, Nucleic Acid Res., 19:5125-5130 (1991).
Tamayo, et al., "Interpreting patterns of gene expression with self-organizing maps: methods and application to hematopoietic differentiation," Proc. Nat'l Acad. Sci, USA, 96:2907-2912 (1999).
Tamayo, et al., "Roles of cyclic diguanylate in pathogenesis", Ann. Review of Microbiology, 61:131-48 (2007).
Tamm, et al., "Anti sense therapy in ocology: new hope for an old idea", The Lancet, 358:489-497 (2001).
Tang, et al., "Rational design of allosteric ribozymes", Chem. Biol., 4:453-459 (1997).
Tang and Breaker, "Examniation of the catalytic fitness of the hammerhead ribozyme by in vitro selection", RNA, 3:914-925 (1997).
Tang and Guest, Direct evidence for mRNA binding and post-transcriptional regulation by *Escherichia coli* aconitases, Microbiology, 145:3069-79 (1999).
Tarasow, et al. "RNA-catalysed carbon-barbon bond formation", Nature, 389 (6646) 54-7 (1997).
Tatusov, et al. "The COG database, an updated version includes eukaryotes", BMC Biolnformatics, 4:41 (2003).
Tatusov, et al., "The COG database: new developments in phylogenetic classification of porteins from complete genomes", Nucleic Acids Res., 29:22-28 (2001).
Teixeira, et al., "Autocatalytic RNA cleavage in the human beta-globin pre-mRNA promotes transcription termination", Nature, 432:526-530 (2004).
Teplyakov, et al., "Involvement of the C terminus in intramolecular nitrogen channeling in glucosamine 6-phosphate synthase: evidence from a 1.6 A crystal structure of the isomerase domain", Structure, 6:1047-1066 (1998).
Tereshko, et al., "X-ray crystallographic observation of "in-lin" and "adjacent" conformations in a bulged self-cleaving RNA/DNA hybrid", RNA, 7:405 (2001).
Thompson, et al., "Improved accumulation and activity of ribozymes expressed froma tRNA based RNA polymerase III promoter", Nucleic Acids Res., 23:2259-2269 (1995).
Thompson, et al., "Synthesis of two stable nitrogen analogues of S-adenosyl-L-methionine", J. Org. Chem., 64:7467-73 (1999).
Thompson, et al. "Group I aptazymes as genetic regulatory switches", BCM Biotechnol., 2:21 (2002).
Thomson, et al., "In vitro selection of hammerhead ribozymes containing a bulged nucleotide in stem II", Nucleic Acids Res., 24:4401-4406 (1996).
Thore, et al., "Structure of the eukaryotic thiamine pyrophosphate riboswitch with its regulatory ligand", Science, 312:1208-11 (2006).
Tischler and Camilli, "Cyclic diguanylate regulates Vibrio cholerae virulence gene expression", Infect. Immun., 73:5873-82 (2005).
Toennies, et al., "Methionine studies.VI. Di-methionine sulfone", J. Biol. Chem., 140:131-134 (1941).
Torarinsson, et al., "Thousands of corresponding human and mouse genomic regions unalignable in primary sequence contain common RNA structure", Genome Res., 16:885-89 (2006).
Toraya, In: Chemistry and Bichemistry of B12. Banerjee, R. Ed. (Wiley, NY)pp. 783-809 (1999).
Torres-Larios, et al., "Structural basis of translational control by *Escherichia coli* threonyl tRNA synthetase", Nat. Struct. Biol., 9:343-47 (2002).
Torres-Larios, et al., "Structure of ribonuclease P-a universal ribozyme", Curr. Opin. Struct. Biol., 16:327-35 (2006).
Tringe, et al., "Comparative metagenomics of microbial communities", Science, 308:554-57 (2005).
Tucker, et al., "Riboswitches as versatile gene control elements", Curr.Opin. Struc. Bio., 15:342-348 (2005).
Turnbaugh, et al, "An obesity-associated gut microbiome with increased capacity for energy harvest", Nature, 444:1027-31 (2006).
Turner, et al., Improved parameters for prediction of RNA structure, Cold Spring Harbor Symposia on Quantitative Biology, III:123-133 (1987).
Turner.et al., "Free energy increments for dydrogen bods in nucleic acid base pairs", J. Am. Chem. Soc., 109:3783-3785 (1987).
Tyagi and Karmer, "Molecular beacons: probes that fluoresce upon hybridization", Nature Biotechnology, 14:303 (1996).
Tyson, et al., "Community structure and metabolism through reconstruction of microbial genomes from the environment", Nature, 428:37-43 (2004).
Ueland, "Pharmacological and biochemical aspects of S-adenosylhomocysteine and S-adenosylhimocysteine hydrolase", Pharm. Rev., 34:223-285 (1982).
Ulrich, et al., "One-component systems dominate signal transduction in prokaryotes", Trends Microbiol., 13:52-56 (2005).
Urbonavicius, et al., "Improvement of reading frame maintenance is a common function for several rRNA modification", EMBO J., 20:4863-73 (2001).

Usher, "On the mechanism of ribonuclease action", PNAS, 62:661-667 (1969).
Usher and McHale, "Hydorlytic stability of helical RNA: a selective advantage for the natureal 3', 5'-bond", PNAS, 73:1149-1153 (1976).
Usman, et al., "Automated chemical synthesis of long oligoribonucleofides using 2'O-silylated ribonucleoside 3'-O-phophoraladites ona controlled pore glass support: synthesis of a 43-necleotide sequence similar to the 3'half molecule of an *Escherichia coli* formylmethionine tRNA", J. Am. Chem. Soc., 109:7845-7854 (1987).
Usman, et al., "Chemical modification of hammerhead ribozymes: activity and nuclease resistance", Nucleic Acids Symposium Seires, 31:163-164 (1994).
Usman and Cedergren, "Exploiting the chemical synthesis of RNA", TIBS, 17: 334-339 (1992).
Usman and McSwiggen, "Catalytic RNA (ribozymes) as drugs", Annual rports in medicinal Chem., 30:285-294 (1995).
Vader, et al., "In vivo expression of the nucleolar group I intron-encoded al-dirl homing endonuclease involves the removal of a spliceosomal intron", EMBRO J., 18:1003-13 (1999).
Vaish, et al., "In vitro selection of a purine nucleotide specific hammerhead-like ribozyme", PNAS, 95:2158-2162 (1998).
van Aalten, et al., "PRODRG, a program for generating molecular topolgies and unique molecular descriptors from coordinates of small molecules", J. Comput. Aided Mol. Design, 10:255-262 (1996).
Van Lanen, et al., "From cyclohydrolase to oxidoreductase, discovery of nitrile reductase activity in a common fold", PNAS, 102:4264-69 (2005).
Vander Horn, et al., "Structural genes for thiamine biosynthetic enzymes (thiCEFGH) in *Echerichia coli* K-12", J. Bacteriolgoy, 175:982-992 (1993).
Vann, "Electroporation-based transformation of freshly harvested conidia of *Neurospora crassa*", Fungal Genet. Newl., 42A:53 (1995).
Varga, et al., "Infectious entry pathway of adenovirus type 2", J Virology, 65:6061-6070 (1991).
Vecerek, et al., "Translational autocontrol of the *Escherichia coli* hfq RNA chaperone gene", RNA, 11:976-84 (2005).
Venter, et al., "Enviromental gerome shotgun sequencing of the Sargasso Sea", Science, 304:66-74 (2004).
Ventura, et al., "Activation of HIV-specific ribozyme activity by self-cleavage", Nucleic Acids Res., 21:3249-3255 (1993).
Verma, "Retroviral vectors for gene transfer",Am. Soc. Microbio. :229-232, (1985).
Vicens and Cech, "Atomic level architecture of group I introns revealed", Trends Biochem. Sci., 31:41-51 (2006).
Vilela and McCarthy, "Regulation of fungal gene expression via short open reading frames in the mRNA 5\ untranslated region", Mol. Microbiol., 49:859-867 (2003).
Vitreschak, et al., "Regulation of riboflavin biosynthesis and transport genes in bacteria by transcriptional and translational attenuation", Nucleic Acids Res., 30:3141-51 (2002).
Vitreschak, et al., "Regulation of the vitamin B12 metabolism and transport in bacteria by a conserved RNA structural element", RNA 9:1084-97 (2003).
Vitreschak,et al., "Riboswitches: the oldest mechanism for the regulation of gene expression?", Trends in Genetics, 20(1):44-50 (2004).
Vold, et al., "Regulation of dihydrodipicolinate synthase and aspartate kinase in *Bacillus subtilis*", J. Bacteriol., 121:970-974 (1975).
Wachter, et al., "Riboswitch control of gene expression in plants by splicing and alternative 3\ end processing of mRNAs", Plant Cell, 19:3437-50 (2007).
Wan and Xu, "Intrinsic terminator prediction and its application in *Synechococcus* sp. WH8102", J. Comp. Sci. & Tech., 20:465-82 (2004).
Wang, et al., "A general approach for the use of oligonucleotides effectors to regulate the catalysis of RNA-cleaving ribozymes and DNAzymes", Nucleic Acids Res. 30:1735-1742 (2002).
Wang, et al., "Dual function of rice OsDR8 gene in disease resistance and thiamine accumulation", Plant Mol. Biol., 60:437-449 (2006).
Wang, et al., "Riboswitches that sense S-adenosylhomocysteine and activate genes involved in coenzyme recycling", Mol. Cell., (2008).
Wansink, et al., "Fluorescent labeling of nascent RNA reveals transcription by RNA polymerase II in domains scattered throughout the nucleus", J. Cell Biology, 122:283-293 (1993).
Washietl, et al., "Mapping of conserved RNA secondary structures predicts thousands of functional noncoding RNAs in the human genome", Nature Biotech., 23:1383-90 (2005).
Wassmann, et al., "Structure of BeF3- -modified response regulator PleD: implications for diguanylate cyclase activation, catalysis, and feedback inhibition", Structure, 15:915-27 (2007).
Waters, et al., "Quorum sensing controls biofilm formation in *Vibrio cholerae* through modulation of cyclic di-GMP levels and repression of vpsT", J. Bacteriol., 190:2527-36 (2008).
Webb, et al., "Thiamine pyrophosphate (TPP) negatively regulates transcription of some thi genes of *Salmonella typhimurium*", J. Bacteriol., 178:2533-2538 (1996).
Webb and Downs, "Characterization of thiL, encoding thiaminmonophophate kinase, in *Salmonella typhimurium*", J. Biol. Chem., 272:15702-15707 (1997).
Weerasinghe, et al., "Resistance to human immunodeficiency virus using type 1 (HIV-1) Infection human CD4+ lymphocyte dreived cell lines conferred by using retroviral vectors expressing an HIV-1 RNA specific ribozyme", J. Virol., 65:5531-5534 (1994).
Wei, et al., "Conserved sturctureal and regulatory regions in the *Salmonella typhimurium* btuB gene for the outer membrane vitamin B12 transport protein", Res. Microbiol. 143:459 (1992).
Weigand, et al., "Tetracycline aptamer-controlled regulation of pre-mRNA splicing in yeast", Nucleic Acids Res., 35(12):4179-85 (2007).
Weinberg, et al., "Identification of 22 candidate structured RNAs in bacteria using the CMfinder comparative geomics pipeline", Nucleic Acids Res., 35:4809-19 (2007).
Weinberg and Ruzzo, "Exploiting conserved structure for faster annotation of non-coding RNAs without loss of accuracy", Bioinformatics, 20 (Suppl 1):i334-41 (2004).
Weinberg and Ruzzo, "Faster genome annotation of non-coding RNA families without loss of accuracy", Proceedings of the eighth annual international conference on Computational Molecular Biology, 243-251 (2004).
Weinberg and Ruzzo, "Sequence-based heuristics for faster annotation of non-coding RNA families", Bioinformatics, 22:35-39 (2006).
Weissbluth, In Molecular Biology Biochemistry and Biophysics, A. Kleinzeller, Ed., v 15:27-41 (1974).
Welz and Breaker, "Ligand binding and gene control characteristics of tandem riboswitches in *Bacillus anthracis*", RNA, 13(4):573-82 (2007).
Weng, et al., "Identification of the *Bacillus subtilis* pur operon repressor", PNAS, 92: 7455-7459 (1995).
Werner and Uhlenbeck, "The effect of base mismatches in the substrate recognition helices of hammerhead ribozymes on binding and catalysts", Nucleic Acids Res. 23:2092-2096 (1995).
Werstuck and Green, "Controlling gene expression in living cells through small molecule-RNA interactions", Science, 282:296-298 (1998).
West, "4-Hydroxypyrrolo[2,3-d]pyrimidine, mannich reaction", J. Org. Chem., 26:4959-61 (1961).
Westergaardand Mitchell "ANeurospora V A synthetic medium favoring sexual reproduction", Amer. J. Bot., 34:573-77 (1947).
Westheimer, "Pseudo-rotation in the hydorlysis of phosphate esters", Acc. Chem. Res., 1:70-78 (1968).
White III, "Coenzymes as fossils of an earlier metabolic state", J. Mol. Evol., 7:101-104 (1976).
White IIIi, "In: The Pyridine Nucleotide Coenzymes", Acad. Press, NY pp. 1-17 (1982).
Wickham, et al., "Integrins alpha v beta 3 and alpha v beta 5 promote adenovirus internalization but not virus attachment", Cell, 73:309-319 (1993).
Wickiser, et al., "The Kinetics of Ligand Binding by an Adenine-Sensing Riboswitch", Biochemistry, 44:13404-13414 (2005).
Wickiser, et al, "The Speed of RNA Transcription and Metabolite Binding Kinetics Operate an FMN Riboswitch", Molecular cell, 18:49-60 (2005a).
Wiegand, et al, "Selection of RNA amide synthases", Chem Biol., 4(9): 675-83 (1997).

Wilkinson, et al., "A pseudoknot in the 3' non-core region of the glmS ribozyme enhances self-cleavage activity", RNA, 11:1788-1794 (2005).
Williamson, "Induced fit in RNA-protein recognition", Nat. Sturct. Biol., 7:834-837 (2000).
Wilson and von Hippel, "Transcription termination at intrinsic terminators: the role of the RNA hairpin", PNAS, 92:8793-8797 (1995).
Wimberly, et al., "The conformation of loop E of eukaryotic 5S ribosomal RNA", Biochemistry, 32:1078-1087 (1993).
Wincott, et al., "A practical method for the production of RNA and ribozymes", Methods in Mol. Biology, 74:59-69 (1997).
Wincott, et al., "Synthesis, dprotection, analysis and purification of RNA and ribozymes", Nucleic Acids Res., 23(14):2677-2684 (1995).
Winkler, "Riboswitches and the role of noncoding RNAs in bacterial metabolic control", Curr. Opin Chem. Biol., 9:594-602 (2005).
Winkler and Breaker, "Genetic control by metabolite-binding riboswitches", Chem BioChem, 4(10)1024-32 (2003).
Winkler and Breaker, "Regulation of Bacterial gene expression by riboswitches", Ann Rev. Microbiol., 59:487-517 (2005).
Winkler et al., "A mRNA sturcture that controls gene expression by binding FMN", PNAS, 99(25):15908-15913 (2002).
Winkler et al., "An mRNA structure that controls gene expression by binding S-adenosylmethionine", Nat Struct Biol, 10:701 (2003).
Winkler et al., "Control of gene expression by a natural metabolite-responsive ribozyme", Nature, 428(6980):281-6 (2004).
Winkler et al., "Thiamine derivatives bind messenger RNAs directly to regulate bacterial gene expression", Nature, 419:952-956 (2002).
Wolfe and Visick, "Get the message out: cyclic-Di-GMP regulates multiple levels of flagellum-based motility", J. Bacteriol., 190:463-75 (2008).
Wolff, et al., "Direct gene transfer into mouse muscle in vivo", Science, 247:1465-1468 (1990).
Wolff, et al., "Human dystrophin expression in mdx mice after intramuscular injection of DNA constructs", Nature, 352:815-818 (1991).
Wolfson, et al., "Holding back the tide of antiobiotic resistance". Chem. Biol., 13:1-3 (2006).
Woodson, "Folding mechanisms of group I ribozymes: Role of stability and contract order", Biochem. Soc. Trans., 30:1166-1169 (2002).
Woolf, et al., "Specificity of antisense oligonucleotides in vivo". PNAS, 89:7305-9 (1992).
Woolley, et al., "Selective reversible inhibition of microbial growth with pyrithiamine", J. Exp. Med., 78:489-497 (1943).
Woyke, et al., "Symbiosis insights through metagenomic analysis of a microbial consortium", Nature, 443:950-55 (2006).
Wuebbens and Rajagopalan, "Investigation of the early steps of molybdopterin biosynthesis in *Escherichia coli* through the use of in vivo labeling studies", J. Biol. Chem., 270:1082-87 (1995).
Yamamoto and Ishihama, "Transcriptional response of *Escherichia coli* to external copper", Mol. Microbiol., 56:215-227 (2005).
Yao, et al., "A computational pipeline for high throughput discovery of cis-regulatory noncoding RNA in prokaryotes", PLoS Comput. Biol., 3:e126 (2007).
Yao et al., "CMfinder-a covariance model based RNA motif finding algorithm", Bioinformatics, 22:445-52 (2006).
Yarnell and Roberts, "Mechanism of intrinsic transcription termination and antitermination", Science, 284:611-15 (1999).
Yen, et al., "An alternative spliced form of FosB is a negative regulator of transcriptional activation and transformation by Fos proteins", PNAS, 88:5077-81 (1991).
Yen, et al., "Exogenous control of mammalian gene expression through modulation of a self-cleavage", Nature, 431:471-476 (2004).
Yu et al., "A hairpin ribozyme inhibits expression of diverse strains of human immunodeficiency virus type 1", PNAS, 90:6340-6344 (1993).
Yu et al., "Cyanine dye dUTP analogs for enzymatic labeling of DNA probes", Nucleic Acids Res., 22:3226-3232 (1994).
Zabner, et al., "Adenovirus-mediated gene transfer transiently corrects the chloride transport defect in nasal epithelia of patients with cystic fibrosis", Cell, 75:207-216 (1993).
Zabner, et al., "Safety and efficacy of repetitive adenovirus-mediated transfer of CFTR cDNA to airway epithelia of primates and cotton rats", Nature Genetics, 6:75-83 (1994).
Zaug, et al., "The tetrahymena ribozyme acts like an RNA restirction endonuclease", Nature, 324:429-433 (1986).
Zengel and Lindahl, "Diverse mechanisms for regulating ribosomal protein synthesis in *Escherichia coli*", Prog. Nucleic Acid Res. Mol Biol., 47:331-370 (1994).
Zhang, et al., "Comparison of the three aspartokinase isozymes in *Bacillus subtilis* Marburg and 168", J. Bacteriol., 172:701-708 (1990).
Zhang, et al., Peptidyl-transferase ribozyme: trans reactions, structural characterization and ribosomal RNA-like features Chem Biol., 5(10):539-53 (1998).
Zhang, et al., "Polymorphism of the signaling molecule c-di-GMP", J Am. Chem. Soc., 128:7015-24 (2006).
Zhang, Generation and identification of recombinant adenovirus by liposome-mediated mediated transfection and PCR analysis, BioTechniques, 15:868-872 (1993).
Zhou, et al., "Synthesis of functional mRNA in mammalian cells by bacteriophage T3 RNA polymerase", Mol Cell Biol., 10:4529-4537 (1990).
Zimmermann, et al., "Interlocking sturctural motifs mediate molecualr discrimination by a theophylline-binding RNA", Nature Struct. Biol., 4:644-649 (1997).
Zolotukhin, et al., "A 'humanized' green fluorescent protein cDNA adapted for high-level expression in mammalian cells," J. Virol., 70:4646-4654 (1996).
Zuker, et al, "Algorithms and thermodynamics for RNA secondary structure prediction: a practicial guide", RNA Biochemistry and Biotechnology (eds. 11-43 NATO ASI Series, Kluwer Academic Pulbishers, (1999).
Zuker, "Mfold web server for nucleic acid folding and hybridization prediction", aNucleic Acids Res., 31:3406-15 (2003).
Zuker, "On finding all suboptimal foldings of an RNA molecule", Science, 244:48-52 (1989).

* cited by examiner

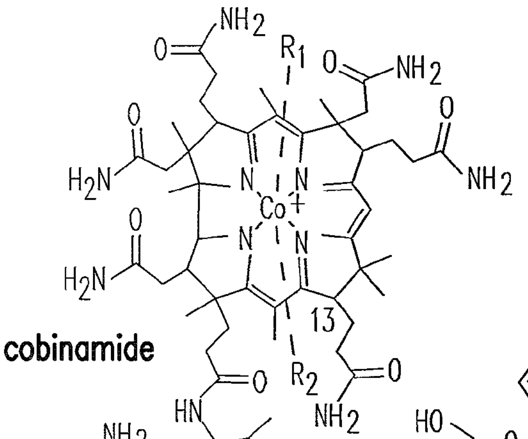

cobinamide

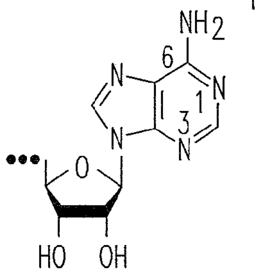

5'-deoxyadenosyl

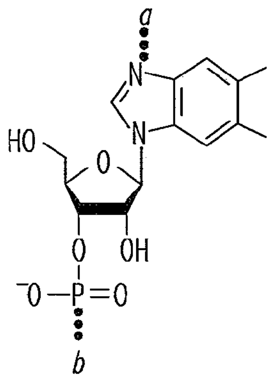

dimethylbenzimidazole-3'-phosphoryl (1) AdoCbl
$R_1$ = 5'-deoxyadenosyl
$R_2$ = dimethylbenzimidazole-3'-phosphoryl (site a)
$R_3$ = as in $R_2$(site b)

(2) methylcobalamin
$R_1$ = $CH_3$
$R_2$; $R_3$ = as in 1

(3) cobinamide dicyanide
$R_1$ = CN
$R_2$ = CN
$R_3$ = H (4) cyanocobalamin
$R_1$ = CN
$R_2$; $R_3$ = as in 1

(5) $N^6$,$N^6$-dimethyl-AdoCbl
$R_1$ = $N^6$-dimethyl-5'-deoxyadenosyl
$R_2$; $R_3$ = as in 1

(6) $N^6$-methyl-AdoCbl
$R_1$ = $N^6$-methyl-5-'deoxyadenosyl
$R_2$; $R_3$ = as in 1

(7) $N^1$-methyl-AdoCbl
$R_1$ = $N^1$-methyl-5-'deoxyadenosyl
$R_2$; $R_3$ = as in 1

(8) 3-deaza-AdoCbl
$R_1$ = 3-deaza-5'-deoxyadenosyl
$R_2$; $R_3$ = as in 1

(9) PurCbl
$R_1$ = 5'-deoxypurinyl
$R_2$; $R_3$ = as in 1

(10) 2'-deoxy-AdoCbl
$R_1$ = 2',5'-dideoxyadenosyl
$R_2$; $R_3$ = as in 1

(11) 13-epi-AdoCbl
$R_1$; $R_2$: $R_3$ = as in 1
epimer of alkylamide

FIG. 4A

○ CONSTANT SCISSION
⬡ INCREASED SCISSION
□ REDUCED SCISSION benfotiamine

TD

THZ oxythiamine amprolium

| mutant | TPP binding | SD status (+ TPP) | genetic modulation (−/+ TPP ratio) |
|---|---|---|---|
| WT | yes | closes | 18 |
| M1 | no | unchanged | 1.1 |
| M2 | yes | closes | 16 |
| M3 | no | unchanged | 1.1 |
| M4 | yes | closes | 4.8 |
| M5 | no | unchanged | 2.1 |
| M6 | yes | n.d. | 10 |
| M7 | yes | n.d. | 4.1 |
| M8 | yes | n.d. | 1.6 |
| M9 | yes | n.d. | 2.4 |

FIG.9C adenosylcobalamin
[coenzyme $B_{12}$]

~2 $\mu$M
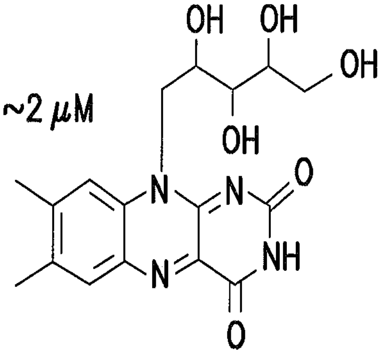
riboflavin
~5 nM
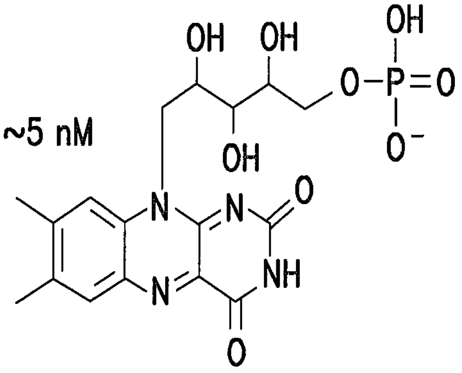
FMN
FIG.12C

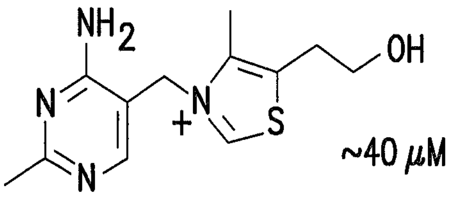
thiamine
~40 μM
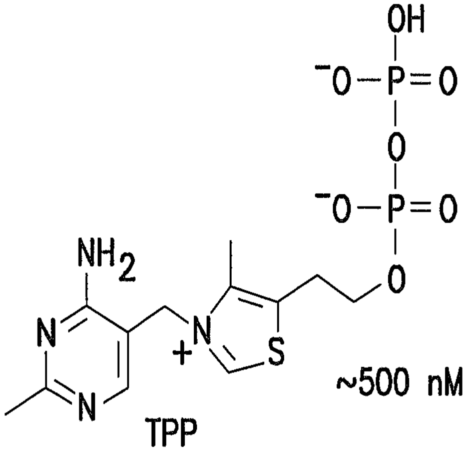
TPP
~500 nM
FIG.13C

| ID | | Position | Accession | Sequence Name | Gene | Location |
|---|---|---|---|---|---|---|
| Eco1 | − | 2183373 | NC_000913.1 | Escherichia coli K12 complete genome | thiM operon | 5'UTR |
| Eco2 | − | 4193775 | NC_000913.1 | Escherichia coli K12 complete genome | thiC operon | 5'UTR |
| Cac | − | 3156135 | NC_003030.1 | Clostridium acetobutylicum ATCC824 complete genome | thiC | 5'UTR |
| Ncr | + | 664 | AY007661.1 | Neurospora crassa thiamine biosynthesis protein nmt-1 gene | nmt-1 | 5'UTR |
| Aor | + | 622 | AF217503.1 | Aspergillus oryzae putative thiazole synthase (thiA) gene | thiA [thi4] | 5'UTR Intron |
| Fox | + | 2156 | AB033416.1 | Fusarium oxysporum sti35 gene for stress-responsive gene product | sti35 [thi4] | 5'UTR Intron |
| Fso | + | 461 | M33642.1 | Fusarium solani STI35 protein gene | sti35 [thi4] | 5'UTR Intron |
| Ath | − | 78516 | AC005496.3 | Arabidopsis thaliana chromosome 2 clone T27A16 map mi54 | thiamine gene [thiC] | 3'UTR |
| Pse | + | 2296 | AF264021.1 | Poa secunda putative thiamine biosythesis protein ThiC mRNA | putative thiC | 3'UTR |
| Osa | − | 91318 | AC084406.7 | Oryza sativa chromosome 3 BAC OSJN Ba0067E01 genomic sequence | putative thiC | 3'UTR |

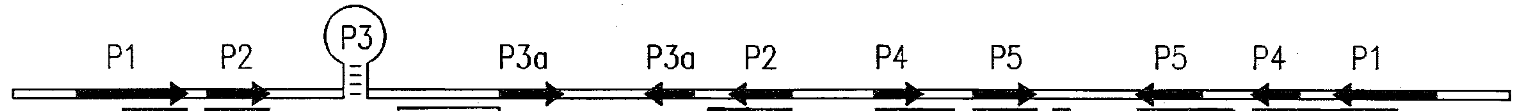

```
Eco1  ACCAAACGACU-CGGGGUG--16-CUGAGA----------AAUACCCGUAUCACCUGAUCUGGAUAAUGCCAGCGUAGGGAAGUCACGGACC
Eco2  UAAUUUCUUGU-CGGAGUG--10-CUGAGACCGUUUAUUCGGGAUCCGCGGAACCUGAUCAGGCUAAUACCUGCGAAGGGAACAAGAGUUAA
Cac1  AUAUUUUAGCU-AGGGGUG--60-CUGAGAGGA-GAAA-UCCAACCCUUUGAACUUGAUGUAGUUAAUACUACCGUAGGGAAGCAGUGCAUU
Ncr1  CAAGACAGCUA-CCGGGUG-115-CUGAGA----------AAUACCGG-CGAACUUGAUCUGGAUAAUACCAGCGAAAGGAUUGGCUUCUUG
Aor1  CUUUGGCGUGG-GCCGGUG-103-CUGAGA---------UUAUACGGCUAAAACUUGAUCUGGAUAAUACCAGCGAAAGGGUCAUGCCUUCU
Fox1  AUCAUGCAUGA-GCCGGUG--63-CUGAGA---------UUAUACGGC-AAAACUUGAUCUGGAUAAUACCAGCGAAAGGAUCAUGUCAUCU
Fso1  AUCAUGCAUGA-GCCGGUG--69-CUGAGA---------UUAUACGGC-GAAACUUGAUCUGGAUAAUACCAGCGAAAGGAUCAUGCUCUCC
Ath1  GCAAAAGCACC-AGGGGUG--46-CUGAGA----------AAGUCCCUUUGAACCUGAACAGGGUAAUGCCUGCGCAGGGAGUGUGCAGUUU
Pse1  AAAGUUGCACC-AGGGGUG--53-CUGAGA----------AAGUCCCUUUGAACCUGAACAGGAUAAUGCCUGCGUAGGGAGUGUGCAUUUC
Osa1  AAAGUUGCACC-AGGGGUG--53-CUGAGA----------AAGUCCCUUUGAACCUGAACAGGAUAAUGCCUGCGAAGGGAGUGUGCAUUUC
```

FIG. 15

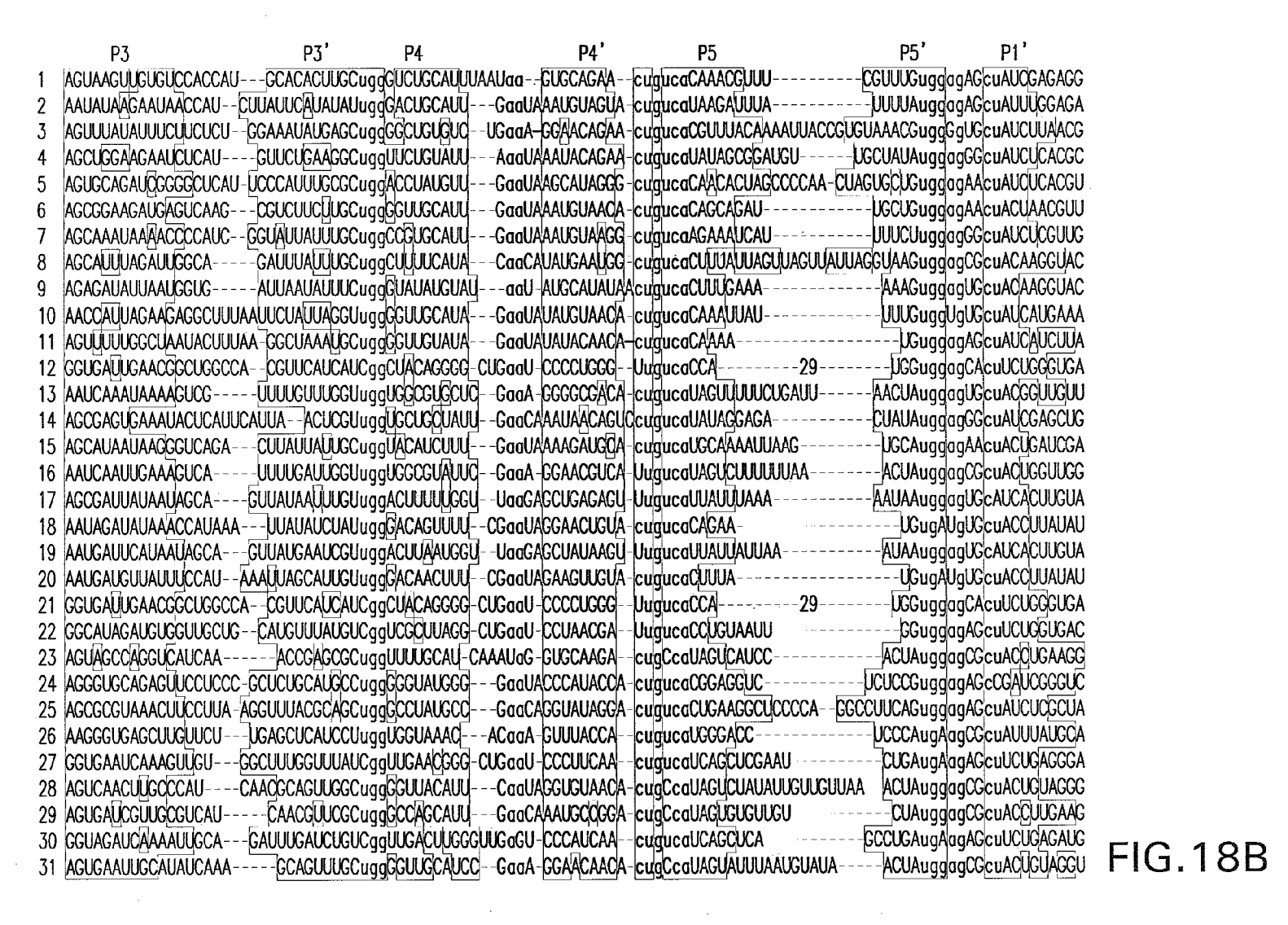

```
   P3                P3'          P4          P4'        P5                          P5'       P1'
1  AGUAAGUUGUGUCCACCAU---GCACACUUGCuggGUCUGCAUUUAAUaa--GUGCAGAA--cugucaCAAACGUUU----------CGUUUGuggagAGcuAUCGAGAGG
2  AAUAUAAGAAUAACCAU--CUUAUUCAUAUAUuggGACUGCAUU---GaaUAAAUGUAGUA-cugucaUAAGAUUUA-----------UUUUAuggagAGcuAUUUGGAGA
3  AGUUUAUAUUUCUUCUCU-GGAAAUAUGAGCuggGGCUGUGUC--UGaaA-GGAACAGAA-cugucaCGUUUACAAAAUUACCGUGUAAACGuggGgUGcuAUCUUAACG
4  AGCUGGAAGAAUCUCAU----GUUCUGAAGGCuggUUCUGUAUU---AaaUAAAUACAGAA-cugucaUAUAGCGGAUGU------UGCUAUAuggagGGcuAUCUCACGC
5  AGUGCAGAUCGGGGCUCAU-UCCCAUUUGCGCuggACCUAUGUU---GaaUAAGCAUAGGG-cugucaCAACACUAGCCCCAA-CUAGUGCUGuggagAAcuAUCUCACGU
6  AGCGGAAGAUGAGUCAAG---CGUCUUCUUGCuggGGUUGCAUU---GaaUAAAUGUAACA-cugucaCAGCAGAU-----------UGCUGuggagAAcuACUAACGUU
7  AGCAAAUAAAACCCCAUC--GGUAUUAUUUGCuggCCGUGCAUU---GaaUAAAUGUAAGG-cugucaAGAAAUCAU----------UUUCUuggagGGcuAUCUCGUUG
8  AGCAUUUAGAUUGGCA-----GAUUUAUUUGCuggCUUUUCAUA---CaaCAUAUGAAUGG-cugucaCUUUAUUAGUUAGUUAUUAGGUAAGuggagCGcuACAAGGUAC
9  AGAGAUAUUAAUGGUG-----AUUAAUAUUUCuggGUAUAUGUAU---aaU-AUGCAUAUAAcugucaCUUUGAAA---------------AAAGuggagUGcuACAAGGUAC
10 AACCAUUAGAAGAGGCUUUAAUUCUAUUAGGUuggGGUUGCAUA---GaaUAUAUGUAACA-cugucaCAAAUUAU-------------UUUGuggUgUGcuAUCAUGAAA
11 AGUUUUUGGCUAAUACUUUAA-GGCUAAAUGCuggGGUUGUAUA---GaaUAUAUACAACA-cugucaCAAAA-----------------UGuggagAGcuAUCAUCUUA
12 GGUGAUUGAACGGCUGGCCA--CGUUCAUCAUCggCUACAGGGG-CUGaaU-CCCCUGGG--UugucaCCA--------29--------UGGuggagCAcuUCUGGGUGA
13 AAUCAAAUAAAAGUCG-----UUUUGUUUGGUuggUGGCGUGCUC--GaaA-GGGGCGACA-cugucaUAGUUUUUCUGAUU------AACUAuggagUGcuACGGUUGUU
14 AGCGAGUGAAAUACUCAUUCAUUA--ACUCGUuggUGCUCGCUAUU-GaaCAAAUAACAGUCcugucaUAUAGGAGA-----------CUAUAuggagGGcuAUCGAGCUG
15 AGCAUAAUAAGGGUCAGA---CUUAUUAUUGCuggUACAUCUUU---GaaUAAAGAUGCA-cugucaUGCAAAAUUAAG----------UGCAuggagAAcuACUGAUCGA
16 AAUCAAUUGAAAGUCA-----UUUUGAUUGGUuggUGGCGUAUUC--GaaA-GGAACGUCA-UugucaUAGUCUUUUUUAA-------ACUAuggagCGcuACUGGUUGG
17 AGCGAUUAUAAUAGCA----GUUAUAAUUUGUuggACUUUUUGGU--UaaGAGCUGAGAGU-UugucaUUAUUUAAA-----------AAUAAuggagUGcAUCACUUGUA
18 AAUAGAUAUAAACCAUAAA---UUAUAUCUAUuggGACAGUUUU--CGaaUAGGAACUGUA-cugucaCAGAA--------------------UGugAUgUGcuACCUUAUAU
19 AAUGAUUCAUAAUAGCA---GUUAUGAAUCGUuggACUUAAUGGU--UaaGAGCUAUAAGU-UugucaUUAUUAUUAA----------AUAAuggagUGcAUCACUUGUA
20 AAUGAUGUUAUUUCCAU--AAAUUAGCAUUGUuggGACAACUUU--CGaaUAGAAGUUGUA-cugucaCUUUA-----------------UGugAUgUGcuACCUUAUAU
21 GGUGAUUGAACGGCUGGCCA--CGUUCAUCAUCggCUACAGGGG-CUGaaU-CCCCUGGG--UugucaCCA--------29--------UGGuggagCAcuUCUGGGUGA
22 GGCAUAGAUGUGGUUGCUG--CAUGUUUAUGUCggUCGCUUAGG-CUGaaU-CCUAACGA--UugucaCCUGUAAUU------------GGuggagAGcuUCUCGGUGAC
23 AGUAGCCAGGUCAUCAA------ACCGAGCGCuggUUUUGCAU-CAAAUaG-GUGCAAGA--cugCcaUAGUCAUCC-----------ACUAuggagCGcuACCUGAAGG
24 AGGGUGCAGAGUUCCUCCC-GCUCUGCAUGCCuggGGGUAUGGG---GaaUACCCAUACCA-cugucaCGGAGGUC-----------UCUCCGuggagAGcCGAUCGGGUC
25 AGCGCGUAAACUUCCUUA-AGGUUUACGCAGCuggGCCUAUGCC---GaaCAGGUAUAGGA-cugucaCUGAAGGCUCCCCA-GGCCUUCAGuggagAGcuAUCUCGCUA
26 AAGGGUGAGCUUGUUCU---UGAGCUCAUCCUuggUGGUAAAC---ACaaA-GUUUACCA--cugucaUGGGACC------------UCCCAugAagCGcuAUUUAUGCA
27 GGUGAAUCAAAGUUGU---GGCUUUGGUUUAUCggUUGAACGGG-CUGaaU-CCCUUCAA--cugucaUCAGCUCGAAU---------CUGAugAagAGcuUCUCAGGGA
28 AGUCAACUUGCCCAU----CAACGCAGUUGGCuggGGUUACAUU---CaaUAGGUGUAACA-cugCcaUAGUCUAUAUUGUUGUUAA ACUAuggagCGcuACUGUAGGG
29 AGUGAUCGUUGCGUCAU-----CAACGUUCGCuggGCCAGCAUU--GaaCAAAUGCCGGA-cugCcaUAGUGUGUUGU----------CUAuggagCGcuACCUUGAAG
30 GGUAGAUCAAAAUUGCA---GAUUUGAUCUGUCggUUGACUUGGUUGaGU-CCCAUCAA--cugucaUCAGCUCA----------GCCUGAugAagAGcuUCUGAGAUG
31 AGUGAAUUGCAUAUCAAA-----GCAGUUUGCuggGGUUGCAUCC--GaaA-GGAACAACA-cugCcaUAGUAUUUAAUGUAUA----ACUAuggagCGcuACUGUAGGU
```

FIG. 18B

L–lysine

D–lysine

6–amino–caproic acid

D,L–5–hydroxy–lysine cadaverine

L–nor–leucine

L–ornithine

L–$\alpha$–homolysine

L–$\beta$–homo–lysine

DL–$\alpha,\varepsilon$–diamino–pimelic acid

L–lysine hydroxamate

| media | WT | G39C | G40C |
|---|---|---|---|
| | Miller Units | | |
| I | 11 | 216 | 224 |
| II | 82 | 232 | 191 |
| III | 8 | 204 | 179 |
| IV | 87 | 235 | 152 |
| V | 17 | 197 | 99 |

guanine (G) — $K_D \leq 5$ nM hypoxanthine (H) — ~50 nM xanthine (X) — ~50 nM adenine (A) — >300,000 nM methionine [Met]

adenosine [Ade]

[5' AMP]

adenosyl moiety [A]

S–adenosyl–methionine [SAM]

S–adenosyl–homocysteine [SAH]

S–adenosyl–cysteine [SAC]

B. *subtilis*
82 *purE*

B. *subtilis*
93 *xpt*

B. *subtilis*
80 *ydhL*

C. *perfringens*
80 *add*

V. *vulnificus*
96 *add*

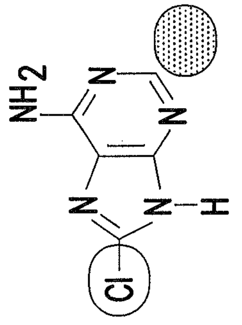
8-chloro-adenine
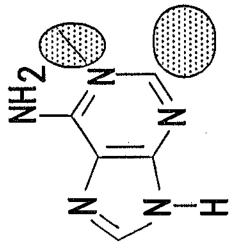
1-methyl-adenine
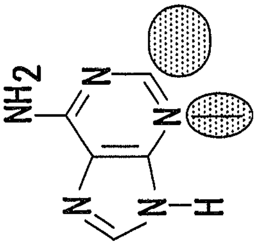
3-methyl-adenine
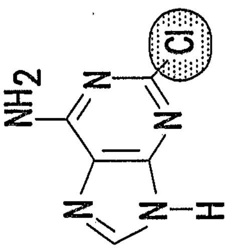
2-chloro-adenine
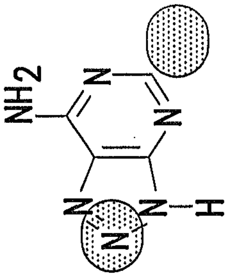
8-aza-adenine
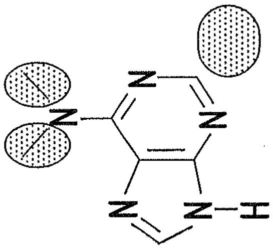
$N^6$,$N^6$-methyl-adenine
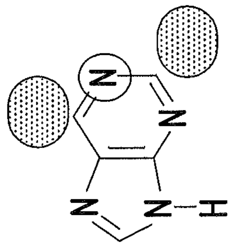
1-deazapurine
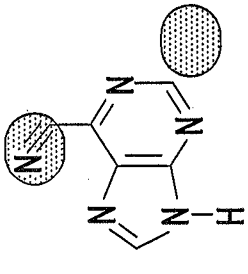
6-cyanopurine
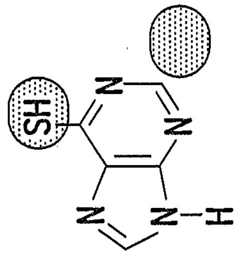
6-mercaptopurine
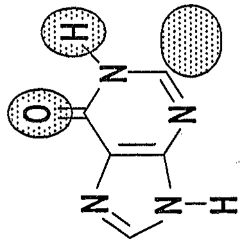
hypoxanthine
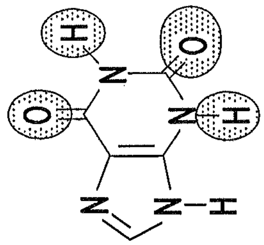
xanthine
FIG.38B A. Alignment of SAM Riboswitches.

Table S1. S Box Sequence Alignment

| ID | Position | | Genbank Acc. | Organism | Remark | Start | Operon | |
|---|---|---|---|---|---|---|---|---|
| Bs01 | - | 1180274 | NC_000964.1 | Bacillus subtilis | | 92 | metF | (yitJ) |
| Bs02 | + | 1257777 | NC_000964.1 | Bacillus subtilis | | 70 | metB-metC | (yjcI) |
| Bs03 | - | 1385353 | NC_000964.1 | Bacillus subtilis | | 130 | metE | (metC) |
| Bs04 | - | 1424147 | NC_000964.1 | Bacillus subtilis | (*) | 89 | ykrT-GCN3 | (ykrT) |
| Bs05 | + | 1426344 | NC_000964.1 | Bacillus subtilis | | 60 | rbcL-ykrX-araD-ykrZ | (ykrW) |
| Bs06 | + | 1629516 | NC_000964.1 | Bacillus subtilis | | 164 | cysH-pitA-MET3-cysC | (cysH) |
| Bs07 | - | 2024504 | NC_000964.1 | Bacillus subtilis | | 86 | ldhA-xylB | (yoaD) |
| Bs08 | - | 3128412 | NC_000964.1 | Bacillus subtilis | | 170 | metK | (metE) |
| Bs09 | - | 3363560 | NC_000964.1 | Bacillus subtilis | | 108 | abc -2011-nlpA | (yusC) |
| Bs10 | + | 3996569 | NC_000964.1 | Bacillus subtilis | | 85 | metE | (yxjH) |
| Bs11 | + | 3997959 | NC_000964.1 | Bacillus subtilis | | 80 | metE | (yxjG) |
| Bh01 | - | 910190 | NC_002570.1 | Bacillus halodurans | | 141 | ???? | |
| Bh02 | + | 1348818 | NC_002570.1 | Bacillus halodurans | | 99 | thrA | |
| Bh03 | + | 1699959 | NC_002570.1 | Bacillus halodurans | | 175 | metB-metC-metF-metH | |

FIG.41A

| | | | | | | | |
|---|---|---|---|---|---|---|---|
| Bh04 | - | 3427466 | NC_002570.1 | Bacillus halodurans | | 157 | metK |
| Bh05 | - | 3591166 | NC_002570.1 | Bacillus halodurans | | 220 | abc -2011-nlpA |
| Oi01 | + | 727028 | NC_004193.1 | Oceanobacillus iheyensis | | 78 | metH |
| Oi02 | - | 1098097 | NC_004193.1 | Oceanobacillus iheyensis | | 162 | metE |
| Oi03 | + | 1319043 | NC_004193.1 | Oceanobacillus iheyensis | (1) | 76 | ???? |
| Oi04 | - | 2134364 | NC_004193.1 | Oceanobacillus iheyensis | | 56 | abc -????-nlpA |
| Oi05 | - | 2365511 | NC_004193.1 | Oceanobacillus iheyensis | | 176 | metK |
| Oi06 | - | 2437305 | NC_004193.1 | Oceanobacillus iheyensis | | 129 | abc -????-nlpA |
| Oi07 | - | 2708643 | NC_004193.1 | Oceanobacillus iheyensis | | 177 | tran-MET17 |
| Oi10 | - | 3200636 | NC_004193.1 | Oceanobacillus iheyensis | | 81 | ????-???? |
| Oi08 | - | 2856863 | NC_004193.1 | Oceanobacillus iheyensis | | 201 | ????-???? |
| Oi09 | + | 3162075 | NC_004193.1 | Oceanobacillus iheyensis | | 105 | MET17 |
| Oi10 | - | 3200636 | NC_004193.1 | Oceanobacillus iheyensis | | 81 | ????-???? |
| Oi11 | + | 3200766 | NC_004193.1 | Oceanobacillus iheyensis | | 94 | ???? |
| Oi12 | + | 3294474 | NC_004193.1 | Oceanobacillus iheyensis | | 97 | abc-2011-nlpA-abgB |
| Oi13 | - | 3466518 | NC_004193.1 | Oceanobacillus iheyensis | | 112 | gldA-nlpA-abc-2011 |
| Ca01 | + | 453565 | NC_003030.1 | Clostridium acetobutylicum | | 78 | metB-metC |
| Ca02 | - | 671354 | NC_003030.1 | Clostridium acetobutylicum | | 77 | metH |
| Ca03 | - | 1073886 | NC_003030.1 | Clostridium acetobutylicum | (2) | | (smtA-metB-cysK) |
| Ca04 | + | 1131539 | NC_003030.1 | Clostridium acetobutylicum | | 81 | abc-2011-nlpA |

FIG.41B

| | | | | | | | |
|---|---|---|---|---|---|---|---|
| Ca05 | + | 1976373 | NC_003030.1 | Clostridium acetobutylicum | | 102 | metA |
| Ca06 | - | 2914839 | NC_003030.1 | Clostridium acetobutylicum | | 117 | CAC5 |
| Ca07 | - | 2991405 | NC_003030.1 | Clostridium acetobutylicum | | 70 | metK |
| Cp01 | - | 2500081 | NC_003366.1 | Clostridium perfringens | | 391 | metK |
| Cp02 | - | 2665229 | NC_003366.1 | Clostridium perfringens | | 102 | nhaC |
| Lm01 | + | 137135 | NC_003210.1 | Listeria monocytogenes | | 90 | oppA-dppB-dppC |
| Lm02 | - | 309383 | NC_003210.1 | Listeria monocytogenes | | 113 | nlpA-abc-2011 |
| Lm03 | - | 637924 | NC_003210.1 | Listeria monocytogenes | | 111 | MET17-MET2 |
| Lm04 | + | 882772 | NC_003210.1 | Listeria monocytogenes | | 97 | metE |
| Lm05 | - | 1716649 | NC_003210.1 | Listeria monocytogenes | | 110 | metK |
| Lm06 | - | 1739595 | NC_003210.1 | Listeria monocytogenes | | 109 | metE-metB-metC-metH |
| Lm07 | - | 2491174 | NC_003210.1 | Listeria monocytogenes | | 93 | abc-2011-nlpA |
| Li01 | + | 172401 | NC_003212.1 | Listeria innocua | (*) | 88 | oppA-dppB-dppC |
| Li02 | - | 327333 | NC_003212.1 | Listeria innocua | (*) | 113 | nlpA-abc-2011 |
| Li03 | - | 636911 | NC_003212.1 | Listeria innocua | (*) | 111 | met17-met2 |
| Li04 | + | 871751 | NC_003212.1 | Listeria innocua | (*) | 97 | metE |
| Li05 | - | 1772459 | NC_003212.1 | Listeria innocua | (*) | 110 | metK |
| Li06 | - | 1790189 | NC_003212.1 | Listeria innocua | (*) | 109 | metE-metB-metC-metH |
| Li07 | - | 2538251 | NC_003212.1 | Listeria innocua | (*) | 92 | abc-2011-nlpA |
| Sa01 | + | 15958 | NC_002745.1 | Staphylococcus aureus | | 41 | met2 |

FIG.41C

| | | | | | | |
|---|---|---|---|---|---|---|
| Sa02 | + | 875385 | NC_002745.1 | Staphylococcus aureus | 91 | abc-2011-nlpA |
| Sa03 | - | 1844603 | NC_002745.1 | Staphylococcus aureus | 108 | metK |
| Sa04 | - | 2381620 | NC_002745.1 | Staphylococcus aureus | 13 | nhaC |
| Sc01 | + | 4708438 | NC_003888.1 | Streptomyces coelicolor | 26 | rC-moaDth |

FIG.41D

| ID | | Position | Genbank Acc. | Organism | Remark | Start | Operon |
|---|---|---|---|---|---|---|---|
| Ct01 | + | 606192 | AE_006470 | Chlorobium tepidum | | 107 | CAC5-MET2 |
| Tt01 | + | 500245 | NC_003869.1 | Thermoanaerobacter tengcongensis | | 55 | metK |
| Tt02 | - | 1750367 | NC_003869.1 | Thermoanaerobacter tengcongensis | | 66 | metF-metH-ebsC |
| Tt03 | - | 2076680 | NC_003869.1 | Thermoanaerobacter tengcongensis | | 78 | thrA-CAC5 |
| Fn01 | - | 987483 | NC_003454.1 | Fusobacterium nucleatum | | 84 | metK |
| Fn02 | - | 1317650 | NC_003454.1 | Fusobacterium nucleatum | (*) | 91 | abc-2011-nlpA |
| Dr01 | + | 1363063 | NC_001263.1 | Deinococcus radiodurans, chr 1 | | 156 | abc-2011-nlpA-nlpA |
| Dr02 | + | 980704 | NC_001263.1 | Deinococcus radiodurans, chr 1 | | 41 | metH-????-metF |
| Xa01 | - | 3558018 | NC_003919.1 | Xanthomonas axonopodis | | 74 | MET2-metC-thrA |
| Xc01 | - | 3379769 | NC_003902.1 | Xanthomonas campestris | (*) | 73 | MET2-metC-thrA |
| Se01 | + | 574 | AF_269983.1 | Staphylococcus epidermidis genomic clone | | | |
| Se02 | - | 142 | AF_270301.1 | Staphylococcus epidermidis genomic clone | (*) | | |
| Gs01 | + | 342843 | contig:2947 | Geobacter sulferreducens | | | |
| Gs02 | + | 2470946 | contig:2947 | Geobacter sulferreducens | | | |
| Ba01 | - | 177272 | contig:6615 | Bacillus anthracis | | | |
| Ba02 | + | 185586 | contig:6615 | Bacillus anthracis | | | |
| Ba03 | - | 197185 | contig:6615 | Bacillus anthracis | | | |
| Ba04 | + | 320607 | contig:6615 | Bacillus anthracis | | | |

FIG.41E

| | | | | | |
|---|---|---|---|---|---|
| Ba05 | - | 371127 | contig:6615 | Bacillus anthracis | |
| Ba06 | + | 1362659 | contig:6615 | Bacillus anthracis | |
| Ba07 | + | 1375353 | contig:6615 | Bacillus anthracis | |
| Ba08 | + | 2459362 | contig:6615 | Bacillus anthracis | |
| Ba09 | - | 2953226 | contig:6615 | Bacillus anthracis | |
| Ba10 | - | 3091676 | contig:6615 | Bacillus anthracis | |
| Ba11 | - | 3890736 | contig:6615 | Bacillus anthracis | |
| Ba12 | + | 3892933 | contig:6615 | Bacillus anthracis | |
| Ba13 | + | 4074285 | contig:6615 | Bacillus anthracis | |
| Ba14 | - | 4074078 | contig:6615 | Bacillus anthracis | |
| Ba15 | - | 4553682 | contig:6615 | Bacillus anthracis | |
| Ba16 | - | 4739975 | contig:6615 | Bacillus anthracis | (*) |
| Ba17 | - | 5140322 | contig:6615 | Bacillus anthracis | |
| Bc01 | + | 26115 | contig:1617 | Bacillus anthracis | (*) |
| Bc02 | + | 748841 | contig:1617 | Bacillus cereus | |
| Bc03 | + | 1183078 | contig:1617 | Bacillus cereus | (*) |
| Bc04 | + | 1195849 | contig:1617 | Bacillus cereus | (*) |
| Bc05 | + | 2200884 | contig:1617 | Bacillus cereus | (*) |
| Bc06 | - | 2684484 | contig:1617 | Bacillus cereus | (*) |
| Bc07 | - | 2963724 | contig:1617 | Bacillus cereus | |

FIG.41F

Figure 41G:
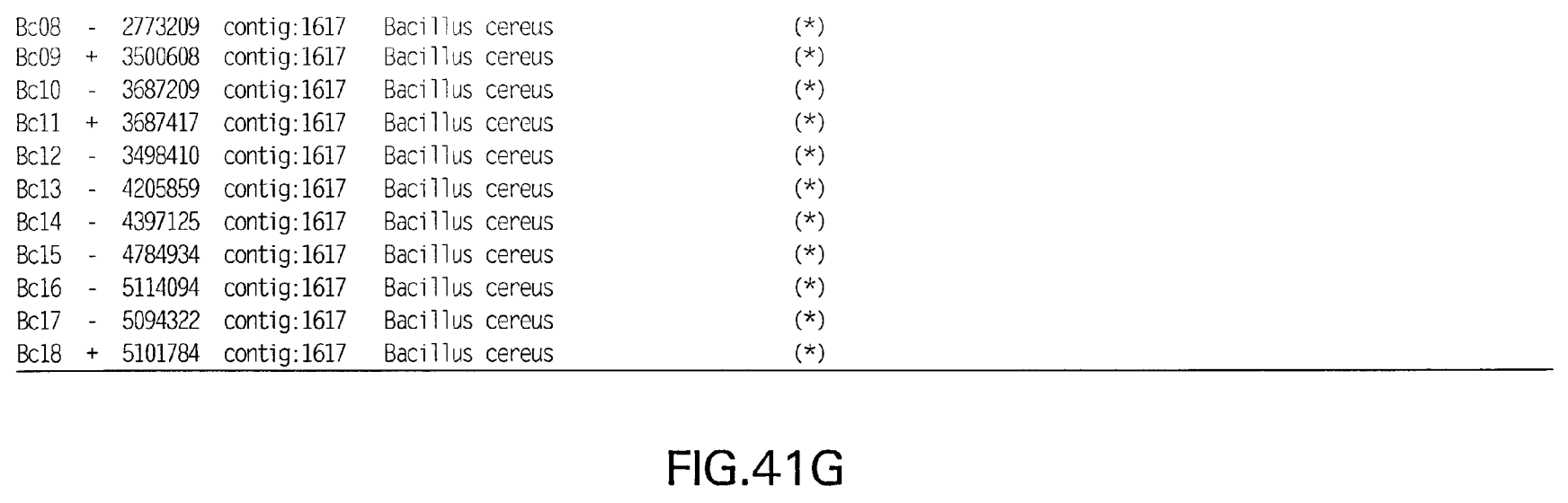

| | | | | | |
|---|---|---|---|---|---|
| Bc08 | - | 2773209 | contig:1617 | Bacillus cereus | (*) |
| Bc09 | + | 3500608 | contig:1617 | Bacillus cereus | (*) |
| Bc10 | - | 3687209 | contig:1617 | Bacillus cereus | (*) |
| Bc11 | + | 3687417 | contig:1617 | Bacillus cereus | (*) |
| Bc12 | - | 3498410 | contig:1617 | Bacillus cereus | (*) |
| Bc13 | - | 4205859 | contig:1617 | Bacillus cereus | (*) |
| Bc14 | - | 4397125 | contig:1617 | Bacillus cereus | (*) |
| Bc15 | - | 4784934 | contig:1617 | Bacillus cereus | (*) |
| Bc16 | - | 5114094 | contig:1617 | Bacillus cereus | (*) |
| Bc17 | - | 5094322 | contig:1617 | Bacillus cereus | (*) |
| Bc18 | + | 5101784 | contig:1617 | Bacillus cereus | (*) |

```
        ---P1-●--->     -  --P2-  -->   --PS--> <--   -P2--  -----  --------P3------->

Cons........ycttATc.aGAg.--.ggYrGAGGGA.-y.gg----CCc..yGA.Rcc.--cRGCAaC...y....---------------------------......-------------

Bs01  ATATCCGTTCTTATCAAGAG---AAGCAGAGGGA--CTGG----CCCGACGAAGCTT--CAGCAACCGGTGTAATGGC------------------------GATCA-------------
Bs02  TCGATATTTCTTATCGTGAG---AGGTGGAGGGA--CTGG----CCCTTAGAAACCT--CAGCAACCGGCTTGTTTTGC-----------------------ATTT--------------
Bs03  ACATTTTCTCTTATCGAGAG--TTGGGCGAGGGA--TTGG----CCTTTTGACCCCAA-CAGCAACCGACC------GTAATACCATTGTGAAATGGGGCGCACTGCTTTTCGCGCCGAGAC
Bs04  ATATATTCTCTTATCGAGAG--TTGGGCGAGGGAT-TTGG----CCTTTTGACCCCAA-AAGCAACCGACC------GTAATTCCATTGTGAAATGGGGCGCA-TTTTTTTCGCGCCGAGAC
Bs05  CTATATTTTCTTATCAAGAGCA--GGCAGAGGGA--CGAG----CCCGATGAAGCC---CGGCAACCGACTT-------------------------------ATA--------------
Bs06  ATCTAAAAACTTATCAAGAGC---GGCTGAGGGA--CTGGA--CCT-ATGAAGCC---CGGCAACCTGCA---------------------------------TAGTT-------------
Bs07  TCAATATTTTCTATCCAGAG---AGGTGGAGGGA--CTGG----CCCTATGAAACCT--CGGCAACA------------------------------------TTAT--------------
Bs08  GCGGATACTCTTATCCCGAGCT--GGCGGAGGGA--CAGG----CCCTATGAAGCC---CAGCAACCGGTTTCTC-----------------TGTTATTTATTATGTTCAACTGAGT----
Bs09  TATATTTCTCTTATCAAGAGA---GGTGGAGGGA--AGTG----CCCTATGAAGCC---CGGCAACCATCAAC------------------------------ACT---------------
Bs10  AAGTTGTACCTTATCAAGAGA---GGTGGAGGGA--CTGG---CCCT-ATGATACC---CGGCAACCGCTGTT------------------------------TCA---------------
Bs11  AAGGTTTTCCTTATCAAGAGA---GGTGGAGGGA--CTGG----CCCTGCGATACC---CGGCAACCGCTGT-------------------------------TTA---------------
Bh01  TCATATTTTCTTATCCAGAGT---GGTGGAGGGA--CTGG----CCCTGTGAAGCC---CGGCAACCTCTTT-------------------------------TTTT--------------
Bh02  ATAAAAAGACTTATCGAGAGA---GGCAGAGGGA--CTGA----CCCGATGATGCC---CGGCAACCCGTTTGTT----------------------------AGCCA-------------
Bh03  TCTCGTATTCTTATCCAGAG---AGGTGGAGGG--ACGG----CCCGAAGAAACCT--CAGCAACCAGCCACG---------------------------ATCC----------------
Bh04  ACGGATACTCTTATCCAGAGTT--GGTGGAGGGA--CAGG----CCCGAAGAAACC--CCAGCAACCAACACCT----------------------------GTTAAACAA-----------
Bh05  AAGAAAACTCTTATCATGAGA---GGTGGAGGGA--CTGG----CCCGATGAAGCC---CAGCAACCGCCAAGC--------------------------AGCAAATC---------------
Oi01  ATAGTTAGACTTATCAAGAG---AGATGGAGGGA--TTGG----CCCGATGAAGTCT--CAGCAACCAGCCT-------------------------------AGATA-------------
Oi02  ATGACAATTCTTATCCAGAG---AGGTGGAGGGA--CTGG----CCCAAGGAAGCCT--CGGCAACAGACTTA----------------------------TTTGAT-------------
Oi03  ATGAAAATACTTATCAAGAG---AGGTGGAGGGA--CTGG----CCCGCTGAAACCT--CAGCAACAGA--------------------------------ACGCATCTG-----------
Oi04  ATTGAATAACTTATCCAGAG---TGACGGAGGGAA-CAGGA---CCTA-CGATGTCA--CAGCAACCTACC-------------------------------TTTAC-------------
Oi05  ACGGATACTCTTATTCAGAGTT--GGTGGAGGGA--CAGA----CCCGATGAAGCC---CAGCAACCATCACT------------------------------ACT---------------
Oi06  ATGATATCTCTTATCTAGAG---CGGTGGAGGGA--CTGG----CCCTTTGAAACCG--CGCAACCTTCAT-----------------------------AATTAA-------------
Oi07  TACGTTTTTCTTATCATGAG---AGGCGGAGGGAA-ATGG----CCCAACGAAACCT--CGGCAACAGGTTCT-----------------------------TATT---------------
Oi10  ATGAAATATCTTATCCTGAG---AGGTGGAGGGAA-ATGG----CCCAAAGAAGCCT--CGGCAACAGGTTC-----------------------------TAGCTT-------------
Oi08  TTATTTTTCCTTATCAAGAGT--CGGGGGAGGAAT-CTGG----TCCATTGATCCCG--CAGCAACCAGTTAC----------------------------AATGAA-------------
Oi09  AGCAAATCTCTTATCAAGAGT---GGTGGAGGGAA-TAGG----CCCTGCGAAGCC--CGGCAACCTGTAGC-----------------------------AATT--------------
Oi10  ATGAAATATCTTATCCTGAG---AGGTGGAGGGAA-ATGG----CCCAAAGAAGCCT--CGGCAACAGGTTC-----------------------------TAGCTT-------------
Oi11  TTAATACTTCTTATCGAGAG---AAGCTAAGGGAC-CTGG----CCTGTTGACGCTT--CAGCAACCTCTA-----------------------------TCTCCAT-------------
```

FIG.41H

```
Oi12 ACGTTTTTTCTTATCTAGAG---AGATTGAGGGAT-CAGG----CCCTATGACATCT--CGGCAGCGGATTCTTTA---------------------------TAT--------------
Oi13 CTAATATCTCTTATTGAGAGT---GGCTGAGGGA--CTGG----CCCTGTGACGCC---CGGCAACCGTTCATCGT-------------------------AATTCCA------------
Ca01 TAATTGTTTCTTATCAAGAGT---GACGGAGGGA--TAGG----CCCTATGAAGTC---CGGCAACATCCAA------------------------------TTATT-------------
Ca02 TGTAAAAATCTTATCAAGAGT---GGTGGAGGGA--CTGG----CCCTTTGAAACC---CGGCAACCAGTATATT---------------------------TTTT--------------
Ca03 TAATATTTCCTTATCAAGAG---AAACGGAGGGA--CTGG----CCCAATGATGTTT--CAGCAACCAAGGT------------------------------TTTAT-------------
Ca04 ATTAGTGCACTTATCAAGAGA---GGTGGAGGGA--CCGG----CCCTGTGAAGCC---CAGCAACCTGTATA----------------------------TGTTAAT------------
Ca05 ATATTATTTCTTATCAAGAA----GGTGGAGGGA--CTGG----CCCTATGAAGCC---TGACAACCGGC--------------------------------AAAT--------------
Ca06 TGATAAGGTCTTATCAAGAGA---GGTGGAGGGA--CTGG----CCCTATGAAACC---CAACAACCAGCATTT---------------------------TTTAATT------------
Ca07 ATGGAAACTCTTATCAAGAGA---GGTGGAGGGAA-AGGG----CCCGTTGAAACC---CGGCAACCGATGTATT--------------------------AATTTA-------------
Cp01 TTATATACTCTTATCCAGAGA---GGTGGAGGGAAAAAGG----CCCTATGAAACC---CGGCAACCAGTGA------------------------------GAAA--------------
Cp02 TTAATAAATCTTATCAAGAGA---GGTGGAGGGA--CTGG----CCCTGTGAAACC---CAGCAACCGGTAATTCTTTGCGGTTAAAACAATGCTGATTTTAAAATAAAAAAATCAGTAGTA
Lm01 TTACGTTTTCTTATCAAGAGT---GGTGGAGGGA--ATCGG---CCCAGTGAAACC---CAGCAGCGGAGC-------------------------------GCAA--------------
Lm02 ATATTTTCTCTTATCGAGAGC---GGCAGAGGGA--CTGG----CCCGATGAAGCC---CGGCAACCTAACTTTAT-------------------------TTAAGC-------------
Lm03 TAGTATTTTCTTATCACGAA---AGGTGGAGGGA--CTGG----CCCTTTGAAGCCT--TAGCAACCGGAA-------------------------------TTTAT-------------
Lm04 ACATAGTAACTTATCAAGAA---AGGTGGAGGGTT-CTGG----CCCCGTGAAGCCT--TGGCAACCGGA--------------------------------TTTT--------------
Lm05 AATTTATCTCTTATCCAGAGC---GGTAGAGGGA--CTGA----CCCTTTGAAGCC---CAGCAACCTACAC-----------------------------ATATAA-------------
Lm06 TAAATTGCTCTTATAATGAGT---GGTAGAGGGA--CTGG----CCCGTTGAAACC---CGGCAACCTTTCAA-----------------------------TACG--------------
Lm07 TGTAGAAATCTTATCCAGAGT---GGTGGAGGGA--AATG----CCCTATGAAGCC---CAGCAACCTAAACAATAA-------------------------TTCA--------------
Li01 TTACAATTTCTTATCCAGAGT---GGTGGAGGGAA-TCGG----CCCAGTGAAACC---CGGCAGCGGAGC-------------------------------GCAA--------------
Li02 ATATTTTCTCTTATCGAGAGC---GGCAGAGGGA--CTGG----CCCGATGAAGCC---CGGCAACCTAACTTTAT-------------------------TTAAGC-------------
Li03 TAGTATTTTCTTATCACGAA---AGGTGGAGGGA--CTGG----CCCTTTGAAGCCT--TAGCAACCGGAA------------------------------TTTATT-------------
Li04 ACATAGTAACTTATCAAGAA---AGGTGGAGGGTT-CTGG----CCCAGTGAAGCCT--TGGCAACCGGA--------------------------------CTTT--------------
Li05 AATTTATCTCTTATCCAGAGC---GGTAGAGGGA--CTGA----CCCTTTGAAGCC---CAGCAACCTACAC-----------------------------ATATAA-------------
Li06 TAAATTACTCTTATTATGAGT---GGTAGAGGGA--CTGG----CCCGTTGAAACC---CAGCAACCTTTCAA-----------------------------TTCG--------------
Li07 TGTAGAAATCTTATCCAGAGT---GGTGGAGGGA--AATG----CCCTGTGAAACC---CAGCAACCTAAACAATAA-------------------------TTCA--------------
Sa01 TTCATATTTCTTATTGTGAG---AAGTTGAGGGAC-TTGG----CCCTGTGATACTT--CAGCAACCGACT-------------------------------TTAT--------------
Sa02 GCGTAAACTCTTATCGAGAGT---GGTGGAGGGA--TGTG----CCCTACGAAGCC---CGGCAACCGTCTT-----------------------------ATATA-------------
Sa03 ACGGATTCTCTTATCCTGAGT---GGTGGAGGGAC-ATGG---ACCCAATGAAACC---CAGCAACCTCTTTT-----------------------------TTTAT-------------
Sa04 TAAGCATCACTTATCTAGAG---AGGTGGAGGGA--CTGG----CCCTATGAAGCCT--CGGCAACAT----------------------------------CTCGA-------------
Sc01 TTCATACCGCTCATCCAGAG---GGGCAGAGGGAT-ACGG----CCCGATGAAGCCC--CGGCAACCCTCCAGTCGG--------------TTCTTGTCACACGGACGTGGCGAGGCTC--
```

```
         ---P1-●--->      -   --P2-  -->  --PS--> <--      -P2--  -----  --------P3------->

Cons     ........ycttATc.aGAg.--.ggYrGAGGGA.-y.gg----CCc..yGA.Rcc.--cRGCAaC...y....---------------------------......-------------

Ct01     TTTCGAGCTATCATCCAGAA---AGGCGGAGGGA--CTGG----CCCTGCGAAGCCT--TGGCAACCTTCAT------------------------------TCCAC-------------
Tt01     TAACACGCTCTTATCAAGAGA--GGTGGAGGGAA-AGAG----CCCGATGAAACC---CGGCAACCTGTCCT-----------------------------TTTAA-------------
Tt02     TTAAAATCTCTTATCAAGAGA--GGTGGAGGGA--CTGG----CCCGATGAAACC---CGGCAACCAGCC-------------------------------TTAG--------------
Tt03     CTCAATCCTCTTATCAAGAGT---GGTGGAGGGA--CTGG----CCCGATGAAACC---C GGCAACCGGCAC-----------------------------GTAA--------------
Fn01     TGGAAATAAACCATCAAGAG---AGATTGAGGGA--CAGG----CCCGTTGAGATCT--CAGCAACCTACG-------------------------------TAAAA-------------
Fn02     AAATAAATAACCATCCAGAG---AAACGGAGGGA--CTGG----CCCAATGATGTTT--CAGCAACCTAC-------------------------------TTAAAT------------
Dr01     AGGGTCACCTTTATCCAGAGT--CGGCGCAGGGAC-CTGG---CCCCATGACCGCCG--CAGCAACCGGCC-----------------------------CTCATCAC------------
Dr02     CCGTGCGCGGTCATCCAGAGT--CGCCCCAGGGTG-TTTCCTG-CCCGCCTACGGCG--CAGCAACCGGCC-----------------------------TTCATCAC------------
Xa01     CCTAGCCTCACCATCGAGAC---CGGCGGAGGGA--CAGG----CCCTTTGATGCCG--GGGCAGCCAGCGGAGCGC------------------------GCAA--------------
Xc01     CGTAGCCTCACCATCGAGAC---CGGCGGAGGGA--CAGG----CCCTTTGATGCCG--GGGCAGCCAGCGGAGCGC------------------------GCAA--------------
Se01     TTACCTAACCTTATTTTGAG---AAGCTGAGGGAT-TTGG----CCCATAGAAGCTT--CAGCAACCGACT-----------------------------TTAAAT------------
Se02     ACGGATTCTCTTATCCTGAGT---GGTGGAGGGAC-ATGG---ACCCAATGAAACC---CAGCAACCTCTTT-----------------------------ATTT--------------
Gs01     GTAGACCTTCTTATCAAGAG---TGGTGGAGGGA--AAGG----CCCTGTGAAACCA--CAGCAACCGGTCCG----------------------------GTAG--------------
Gs02     ACGGCTTAACTTATCAAGAG---CGACCGAGGGA--CAGG----CCCGGTGACGTCG--CGGCAACCTCCCC-----------------------------ATGG--------------
Ba01     ACACATACTCTTATCAAGAGT---GGCGGAGGGA--CTGG----CCCGATGATGCC---CGGCAACCGAGCTTATG--------------------------ACG---------------
Ba02     AGCAATTTACTTATCCAGAG---AGGTAGAGGGA--CTGG----CCCTATGACACCT--CAGCAGCGGGTTCT----------------------------GTAATA------------
Ba03     TTTACTCATTGTATCAAGAG---AGGTGGAGGGA--CTGG----CCCTTTGAAACCT--CGGCAGCAGGTTCA----------------------------TTTT--------------
Ba04     CGATACATTCTTATCCAGAG---AGGTGGAGGGA--CTGG----CCCTACGATACCT--CAGCAACGGGTT------------------------------TTTTT-------------
Ba05     GAATAATTCTTTATCAAGAGA---GGCAGAGGGA--CCGG----CCCTTTGAAGCC---CAGCAACCTCAGTTT---------------------------ATAC--------------
Ba06     AATACAAAGCTTATCAAGAGA---AGCGGAGGGAA-CTGG----CCCGGCGAAGCT---CGGCAACCTGCTT-----------------------------ATAGA-------------
Ba07     TGAAACCTTCTTATAAAGAG---AGGCGGAGGGA--CTGG----CCCTACGATGCCT--CGGCAGCGGACTC-----------------------------GATTTTA-----------
Ba08     AAATTAATACTTATCCAGAG---AGGTGGAGGGAA-CGG-----CCCTATGAAACCT--CAGCAACCCCTATGT---------------------------AAAT--------------
Ba09     ATGAAAATTCTTATCACGAG---AGGTGGAGGGA--CTGG----CCCTATGAAACCT--CGGCAGCGGATTCG----------------------------TTA---------------
Ba10     GAATATTTTCTTATCCAGAGA---GGTGGAGGGA--CTGG----CCCGATGAAACC---CAGCAACCGC--------------------------------GAT---------------
Ba11     TATACAACTCTTATCAAGAGCA--GGTGGAGGGAT-TTGG----CCCGATGAAGCC---CAGCAACCGACC--------------GTAATACCATTGTGAAATGCGGCGTTTATGACGCCA
Ba12     TAAATACTTCTTATCAAGAGCA--GGTGGAGGGA--CGAG----CCCGACGAAACC---CGGCAACCGATCTACA--------------------------TAAT--------------
Ba13     ACGAACATTCTTATCTAGAG---AGGTAGAGGGA--CTGG----CCCTATGACGCCT--CAGCAACCATTAAC----------------------------ATTT--------------
Ba14     AAGACAACTCTTATTGAGAGC---GGTGGAGGGA--AAGG----CCCTGTGAAACC---CGGCAACCTTCAAAC---------------------------GAAAT-------------
```

FIG.41J

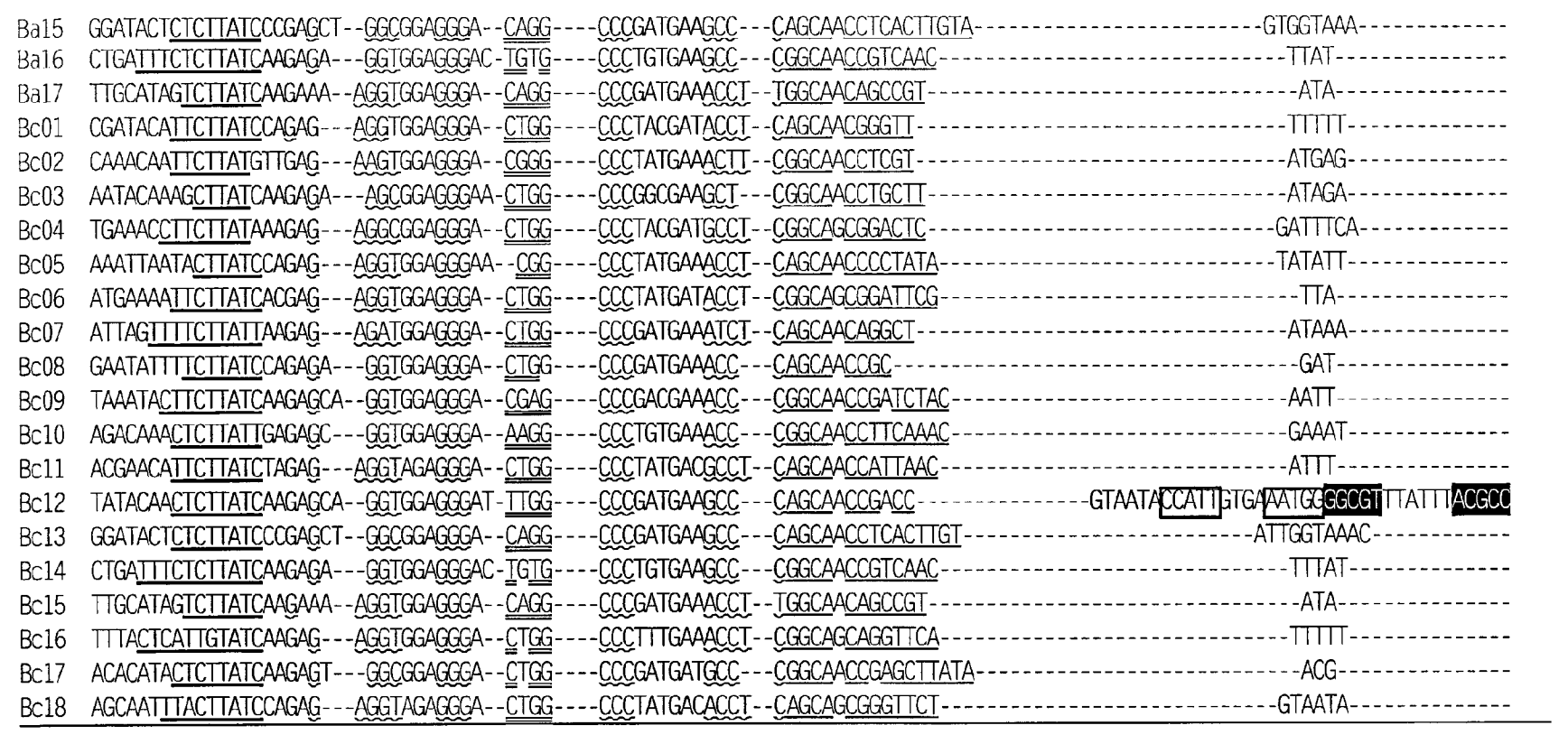

```
Ba15 GGATACTCTCTTATCCCGAGCT--GGCGGAGGGA--CAGG----CCCGATGAAGCC---CAGCAACCTCACTTGTA------------------------GTGGTAAA-------------
Ba16 CTGATTTCTCTTATCAAGAGA---GGTGGAGGGAC-TGTG----CCCTGTGAAGCC---CGGCAACCGTCAAC------------------------------TTAT---------------
Ba17 TTGCATAGTCTTATCAAGAAA--AGGTGGAGGGA--CAGG----CCCGATGAAACCT--TGGCAACAGCCGT--------------------------------ATA---------------
Bc01 CGATACATTCTTATCCAGAG---AGGTGGAGGGA--CTGG----CCCTACGATACCT--CAGCAACGGGTT--------------------------------TTTTT-------------
Bc02 CAAACAATTCTTATGTTGAG---AAGTGGAGGGA--CGGG----CCCTATGAAACTT--CGGCAACCTCGT--------------------------------ATGAG-------------
Bc03 AATACAAAGCTTATCAAGAGA---AGCGGAGGGAA-CTGG----CCCGGCGAAGCT---CGGCAACCTGCTT-------------------------------ATAGA-------------
Bc04 TGAAACCTTCTTATAAAGAG---AGGCGGAGGGA--CTGG----CCCTACGATGCCT--CGGCAGCGGACTC------------------------------GATTTCA------------
Bc05 AAATTAATACTTATCCAGAG---AGGTGGAGGGAA--CGG----CCCTATGAAACCT--CAGCAACCCCTATA-----------------------------TATATT-------------
Bc06 ATGAAAATTCTTATCACGAG---AGGTGGAGGGA--CTGG----CCCTATGATACCT--CGGCAGCGGATTCG-------------------------------TTA---------------
Bc07 ATTAGTTTTCTTATTAAGAG---AGATGGAGGGA--CTGG----CCCGATGAAATCT--CAGCAACAGGCT--------------------------------ATAAA-------------
Bc08 GAATATTTTCTTATCCAGAGA---GGTGGAGGGA--CTGG----CCCGATGAAACC---CAGCAACCGC-----------------------------------GAT---------------
Bc09 TAAATACTTCTTATCAAGAGCA--GGTGGAGGGA--CGAG----CCCGACGAAACC---CGGCAACCGATCTAC------------------------------AATT--------------
Bc10 AGACAAACTCTTATTGAGAGC---GGTGGAGGGA--AAGG----CCCTGTGAAACC---CGGCAACCTTCAAAC-----------------------------GAAAT-------------
Bc11 ACGAACATTCTTATCTAGAG---AGGTAGAGGGA--CTGG----CCCTATGACGCCT--CAGCAACCATTAAC-------------------------------ATTT--------------
Bc12 TATACAACTCTTATCAAGAGCA--GGTGGAGGGAT-TTGG----CCCGATGAAGCC---CAGCAACCGACC--------------GTAATACCATTGTGAAATGGGGCGTTTATTTACGCC
Bc13 GGATACTCTCTTATCCCGAGCT--GGCGGAGGGA--CAGG----CCCGATGAAGCC---CAGCAACCTCACTTGT------------------------ATTGGTAAAC------------
Bc14 CTGATTTCTCTTATCAAGAGA---GGTGGAGGGAC-TGTG----CCCTGTGAAGCC---CGGCAACCGTCAAC------------------------------TTTAT-------------
Bc15 TTGCATAGTCTTATCAAGAAA--AGGTGGAGGGA--CAGG----CCCGATGAAACCT--TGGCAACAGCCGT--------------------------------ATA---------------
Bc16 TTTACTCATTGTATCAAGAG---AGGTGGAGGGA--CTGG----CCCTTTGAAACCT--CGGCAGCAGGTTCA-------------------------------TTTTT-------------
Bc17 ACACATACTCTTATCAAGAGT---GGCGGAGGGA--CTGG----CCCGATGATGCC---CGGCAACCGAGCTTATA-----------------------------ACG---------------
Bc18 AGCAATTTACTTATCCAGAG---AGGTAGAGGGA--CTGG----CCCTATGACACCT--CAGCAGCGGGTTCT------------------------------GTAATA-------------
```

FIG.41K

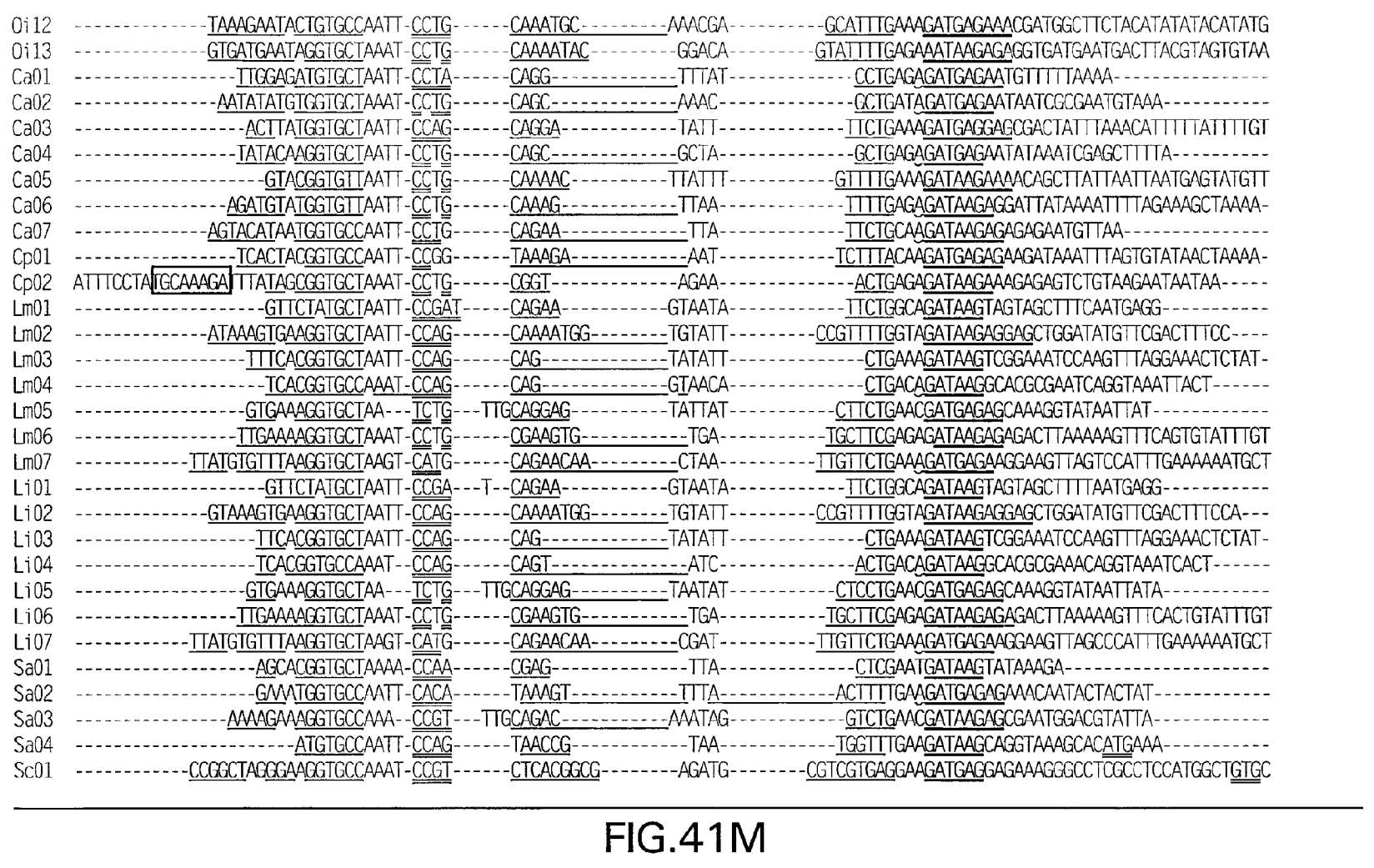

```
Oi12 -------------TAAAGAATACTGTGCCAATT-CCTG-----CAAATGC---------AAACGA---------GCATTTGAAAGATGAGAAACGATGGCTTCTACATATATACATATG
Oi13 -------------GTGATGAATAGGTGCTAAAT-CCTG-----CAAAATAC--------GGACA--------GTATTTTGAGAAATAAGAGAGGTGATGAATGACTTACGTAGTGTAA
Ca01 ----------------TTGGAGATGTGCTAATT-CCTA-----CAGG------------TTTAT-----------CCTGAGAGATGAGAATGTTTTTAAAA--------------
Ca02 --------------AATATATGTGGTGCTAAAT-CCTG-----CAGC------------AAAC-------------GCTGATAGATGAGAATAATCGCGAATGTAAA-----------
Ca03 -----------------ACTTATGGTGCTAATT-CCAG-----CAGGA-----------TATT------------TTCTGAAAGATGAGGAGCGACTATTTAAACATTTTTATTTTGT
Ca04 ----------------TATACAAGGTGCTAATT-CCTG-----CAGC------------GCTA-------------GCTGAGAGATGAGAATATAAATCGAGCTTTTA----------
Ca05 -------------------GTACGGTGTTAATT-CCTG-----CAAAAC---------TTATTT----------GTTTTGAAAGATAAGAAAACAGCTTATTAATTAATGAGTATGTT
Ca06 ---------------AGATGTATGGTGTTAATT-CCTG-----CAAAG-----------TTAA------------TTTTGAGAGATAAGAGGATTATAAAATTTTAGAAAGCTAAAA-
Ca07 -------------AGTACATAATGGTGCCAATT-CCTG-----CAGAA------------TTA------------TTCTGCAAGATAAGAGAGAGAATGTTAA--------------
Cp01 ----------------TCACTACGGTGCCAATT-CCGG-----TAAAGA-----------AAT-----------TCTTTACAAGATGAGAGAAGATAAATTTAGTGTATAACTAAAA-
Cp02 ATTTCCTATGCAAAGATTTATAGCGGTGCTAAAT-CCTG-----CGGT-------------AGAA-------------ACTGAGAGATAAGAAAGAGAGTCTGTAAGAATAATAA-----
Lm01 ------------------GTTCTATGCTAATT-CCGAT----CAGAA----------GTAATA-----------TTCTGGCAGATAAGTAGTAGCTTTCAATGAGG-----------
Lm02 -------------ATAAAGTGAAGGTGCTAATT-CCAG-----CAAAATGG--------TGTATT---------CCGTTTTGGTAGATAAGAGGAGCTGGATATGTTCGACTTTCC----
Lm03 -----------------TTTCACGGTGCTAATT-CCAG-----CAG-------------TATATT--------------CTGAAAGATAAGTCGGAAATCCAAGTTTAGGAAACTCTAT-
Lm04 -------------------TCACGGTGCCAAAT-CCAG-----CAG-------------GTAACA--------------CTGACAGATAAGGCACGCGAATCAGGTAAATTACT------
Lm05 -----------------GTGAAAGGTGCTAA---TCTG---TTGCAGGAG---------TATTAT-----------CTTCTGAACGATGAGAGCAAAGGTATAATTAT-----------
Lm06 ----------------TTGAAAAGGTGCTAAAT-CCTG-----CGAAGTG-----------TGA-----------TGCTTCGAGAGATAAGAGAGACTTAAAAAGTTTCAGTGTATTTGT
Lm07 -----------TTATGTGTTTAAGGTGCTAAGT-CATG-----CAGAACAA---------CTAA----------TTGTTCTGAAAGATGAGAAGGAAGTTAGTCCATTTGAAAAAATGCT
Li01 ------------------GTTCTATGCTAATT-CCGA---T--CAGAA----------GTAATA-----------TTCTGGCAGATAAGTAGTAGCTTTTAATGAGG-----------
Li02 -------------GTAAAGTGAAGGTGCTAATT-CCAG-----CAAAATGG--------TGTATT---------CCGTTTTGGTAGATAAGAGGAGCTGGATATGTTCGACTTTCCA---
Li03 ------------------TTCACGGTGCTAATT-CCAG-----CAG-------------TATATT--------------CTGAAAGATAAGTCGGAAATCCAAGTTTAGGAAACTCTAT-
Li04 ------------------TCACGGTGCCAAAT--CCAG-----CAGT--------------ATC-------------ACTGACAGATAAGGCACGCGAAACAGGTAAATCACT------
Li05 -----------------GTGAAAGGTGCTAA---TCTG---TTGCAGGAG---------TAATAT-----------CTCCTGAACGATGAGAGCAAAGGTATAATTATA-----------
Li06 ----------------TTGAAAAGGTGCTAAAT-CCTG-----CGAAGTG-----------TGA-----------TGCTTCGAGAGATAAGAGAGACTTAAAAAGTTTCACTGTATTTGT
Li07 -----------TTATGTGTTTAAGGTGCTAAGT-CATG-----CAGAACAA---------CGAT----------TTGTTCTGAAAGATGAGAAGGAAGTTAGCCCATTTGAAAAAATGCT
Sa01 ------------------AGCACGGTGCTAAAA-CCAA-----CGAG--------------TTA--------------CTCGAATGATAAGTATAAAGA--------------------
Sa02 ------------------GAAATGGTGCCAATT-CACA-----TAAAGT-----------TTTA-----------ACTTTTGAAGATGAGAGAAACAATACTACTAT------------
Sa03 ---------------AAAAGAAAGGTGCCAAA--CCGT---TTGCAGAC----------AAATAG-----------GTCTGAACGATAAGAGCGAATGGACGTATTA------------
Sa04 ----------------------ATGTGCCAATT-CCAG-----TAACCG------------TAA-----------TGGTTTGAAGATAAGCAGGTAAAGCACATGAAA-----------
Sc01 -----------CCGGCTAGGGAAGGTGCCAAAT-CCGT-----CTCACGGCG--------AGATG--------CGTCGTGAGGAAGATGAGGAGAAAGGGCCTCGCCTCCATGGCTGTGC
```

FIG.41M

```
                          <-------P3--------      <-PS-      ---P4-->                          <--P4---    <----*-P1--
Cons  -------------.......r..GTGCYaa.t-Cc.r------carr...-----------......------------yytgrraGATRagrr.rr.......................

Ct01  -----------------ATGAGCGGTGCCAAAT-CCAT------CCCGGA-----------GGAAA----------TCCGGGAAAGATGATGTATGCATTCCTGCTGATTTCATACCTCA
Tt01  -----------------GGATAAGGTGCCAATT-CTCT------CAGAAGA----------TTTTT----------TCTTCTGAAAGATGAGGGTATG----------------------
Tt02  ------------------GGCATGGTGCCAATT-CCTG------CAGCG------------GTTT------------CGCTGAAAGATGAGAGATTCTTGTA-----------------
Tt03  -----------------GTGCTTGGTGCCAATT-CCTG------CAGGTTGGG--------GTTA---------CCCAGCCTGAGAGATGAGAGGAGAGGCCGAGTAATTGTGA-------
Fn01  ------------------TGTGTGGTGCTAATT-CCTG-----------------------------------------ATAGATGGAAAAGATTATAATACATCT-----------
Fn02  -------------------GTGTGGTGCTAATT-CCAG-----------------------------------------AGAGATGGAGAGGAAAATTGAAACAAGAACTAA-----
Dr01  -----------------GGCAGCGGTGCT--TT-CCAG---A--CCCGCGCGAGCAGCGCCGACGATGGGCGGCGCCGCGGGAACGATAAAGGAAGGCGGGTCCTCTTCGCGGGTTCCAA
Dr02  -----------------GGTCACGGTGCT--TT-CAGGAAA---GGGCCGTTTAGGTGCGCCGACGATGGCGCGAG-CGGCCC---GATGCCCGCCAGGAGGTGCATTTCCAACCATGAGC
Xa01  ------------GCGTCCGCGTTTGGTGCCAAAT-CCTG------CGGGGAC---------CTCCGC---------GTCCGCCGAAAGATGGTTCGAATCGTGCCTTGCGCACGTCGAACGC
Xc01  ------------GCGCCCGCGTTTGGTGCCAAAT-CCTG------CGGGGAC---------CTCCGC---------GTCCGCCGAAAGATGGTTCGAATCGTGCCCTCTGCACGTCGAACGC
Se01  ------------------AGCACGGTGCTAATA-CCAA------CGAG--------------CAA-------------CTCGAATGATAAGTACGATAA--------------------
Se02  -----------------AAAGAAAGGTGCCAAA-CCGT---TTGCAGAC-----------AAATATG-----------GTCTGAACGATAAGAGCGAATGGACGTTTAAGAGCCTTCTCTC
Gs01  ---------------CGGACGCCAGGTGCTAAAT-CCTG------CCC--------------GAAA--------------GGGAGCGATGAGAGGGAGCTTGTGACCACCGACGCGTACA-
Gs02  -----------------GGGGAAGGTGCCAATT-CCTG------CGAGACC----------GACA-----------GGTTTCGGGAGATAAGGAAGAGCGTGACACCTCACGGTGAATCGA
Ba01  --------------TATAAGCTAAGGTGCTAATT-CCTG------CAAAATGA---------GTTT----------TCGTTTTGGAAGATAAGAGAGGATCCTATTTTGTCTATTCG-----
Ba02  ----------------GGAACACCGTGCTAATT-CCAG------CAAG-------------CAAGT-------------CTTGAAAGATAAGTGATGGGCCTTTGTTTATTAA--------
Ba03  ----------------TGAATACTGTGCCACTT-CCTG------CAAGCT-----------TTAT------------AGCTTGAAAGATAGAATGAGGGACTTCGTTTATATACGGGTGCA
Ba04  ------------------AATACCGTGCTAACT-CCAG------CAAGCC----------ATATAAA----------GGCTTGGAAGATGAGAAGATGTGACCGAGTACATATAA------
Ba05  --------------AAACTGAATAGGTGCTAATT-CCTG------CAAAATGC----------ATT----------GCATTTTGAAAGATAAAACGTAACTATTGTGTACAAAA--------
Ba06  -----------------AAGCAAGGTGCTAAAT-CCAG------CAAAATGG----------AAT----------CCATTTTGAAAGATAAGGTAAAATATATTACCGAACAG--------
Ba07  -----------------GAGTGCTGTGCCAAAT-CCAG------CAAGC------------ATGT-------------GCTTGAAAGATGAGAAGAGCGTTTCTTATAGATGTATAA----
Ba08  ---------------GCATAGGAAGGTGCTAATT-CCG-------CAGAGAACAC--------GTT--------GTGTTTTTTGGAAGATGAGAGGATTCTTGAACGTGAAAGAAAA-----
Ba09  ----------------TGAATACTGTGCCAATT-CCAG------CAAG-------------GTAA--------------CTTGAAAGATAAGAAAGAAGCTCATTTTGACTATATATACAG
Ba10  --------------------GCAGGTGCTAATT-CCAG------CAGAACA----------AATT-----------TGTTCTGGGAGATAAGACGAAGATATATACGTAA-----------
Ba11  AAA---------------GGCACGGTGCTAATT-CCAG------CAGAAAGT----------AAA----------ACTTTCTGGCAGATAAGAGGGGAGAAGATAAACTTCAAA-------
Ba12  ---------------TGTAGACACGGTGCTAATT-CTCG------CAGC-------------ATTAC-------------GCTGACAGATAAGGAGCTGGTTGTAAAAAAA-----------
Ba13  ----------------GTTAATAAGGTGCTAATT-CCAG------CAAATT----------GCGAAA----------AATTTGACAGATGAGAAGAAGACTCTATTCAAACCGAAA-----
Ba14  ---------------GTTTGAAACGGTGCTAATA-CCTG------CAAAAC-----------GAAT-----------GTTTTGCATAATAAGAGGAGGAACAATTATGTT-----------
```

FIG.41N

```
Ba15 ------------TACAGGTGAATAGGTGCTAAAA-CCTG---TG-CGAGGCT-----------ACA-----------GGTCTCGAACGATAAGAGCGAAGGGCAAAAAGCAGTATGCAAGTA
Ba16 ----------------GTTGAAATGGTGCCAATT-CCTG------CAAAGC-----------AAATG------------CTTTGAGAGATGAGAGAGAGGGATAATGTTGTTATATACGCAT
Ba17 -----------------ACGGAATTGTGCCAAAT-CCTG------CAGG-----------TAATAAAT------------CCTGAGAGATAAGAAAGAGCCTTTAGAGCGTGTTTTCAAA--
Bc01 -------------------AATACCGTGCTAACT-CCAG------CAAGCCT----------ATGAA----------AGGCTTGGAAGATGAGAAGATGTGAACGAGTACATATAA------
Bc02 ------------------ACGAAAGGTGCCAAAT-CCTG------CAGGTG----------AAGAAA-----------CACCTGAAAGATAAGAGCGGTTCAATTAGTCAAGAAG-------
Bc03 ------------------AAGCAAGGTGCTAAAT-CCAG------CAAAATGG----------AAT----------CCATTTTGAAAGATAAGGTAAAATATATTACCGAACAG--------
Bc04 ------------------GAGTGCTGTGCCAAAT-CCAG------CAAGC-------------ATAT-------------GCTTGAAAGATGAGAAGAGCGTTTCTTATAGATGTATAA----
Bc05 ----------------TATAGGAAGGTGCTAATT-CCG-------CAGAGAACAC---------GAT---------GTGTTTTTTGGAAGATAAGAGGATTCTTGAACGTGAAAGAAAA-----
Bc06 -----------------TGAATACTGTGCCAATT-CCAG------CAAG-------------GTAA---------------CTTGAAAGATAAGAAAGAAGCTCATTTTGACTGTATATGCAG
Bc07 -------------------AGTACTGTGCTAAGT-CCAG------CAAACGT----------ATGAA----------GCGTTTGGAAGATGAGGGGAAATGGATTAACATTCAA--------
Bc08 ---------------------GCAGGTGCTAATT-CCAG------CAGAACA----------TATT------------TGTTCTGGGAGATAAGACGAAGATATATACGTAA-----------
Bc09 ----------------GTAGACACGGTGCTAATT-CTCG------CAGC-------------ATTAC--------------GCTGACAGATAAGGAGCTGGTTGTAAAAAAA-----------
Bc10 ---------------GTTTTGAAACGGTGCTAATA-CCTG------CAAAAC-----------GAAT--------------GTTTTGCATAATAAGAGGAGGATCGATTATGT------------
Bc11 ----------------GTTAATAAGGTGCTAATT-CCAG------CAAATT----------GTGAAA-----------GATTTGACAGATGAGAAGAAGACTCTATTCAAACCGAAA-----
Bc12 AAAA---------------GGCACGGTGCTAATT-CCAG------CAGAAAGT----------AAA----------ACTTTCTGGCAGATAAGAGGGGAGAAGATAAACTTCAAA-------
Bc13 -------------ACAAGTGAATAGGTGCTAAAA-CCTG---TG-CGAGGCT-----------ACA-----------GGTCTCGAACGATAAGAGCGAAGGGCAAAAAGCAGTATGCAAGTA
Bc14 ----------------GTTGAAATGGTGCCAATT-CCTG------CAAAGC-----------AAAT------------GCTTTGAGAGATGAGAGAGAGGGATAATGTTGTTATATACGCAC
Bc15 -----------------ACGGAATTGTGCCAAAT-CCTG------CAGG-----------TAATAAAC------------CCTGAGAGATAAGAAAGAGCCTTTAGAGCGTGTTTTCAAA--
Bc16 -----------------TGAATACTGTGCCACTT-CCTG------CAAGCT-----------TTAT-------------AGCTTGAAAGATAGAATGAGGGACTTCGTTTATATACGGGTGCA
Bc17 --------------TATAAGCTAAGGTGCTAATT-CCTG------CAAAACGA---------GTTC----------TCGTTTTGGAAGATAAGAGAGGAATCTATTTTGTCTATTCG-----
Bc18 -----------------GGAACACCGTGCTAATT-CCAG------CAAG-------------CAAGT-------------CTTGAAAGATAAGTGATGGGCCTTTGTTTATTAA--------
```

FIG.41O

```
Oi12 GTACGAA-----------------TCCCTCTTTTCTTG-------TCTTT-------CAAGAAAAGAGGGATTTTTTATTTCGCTTGGGGGTTGAGACATGATTGAATTTCAGAATGTAACA
Oi13 TGTTA-------------------TGCCTCTCGAT----------TTCAC----------ATCGGGAGGCATTTTTTAGTTTCCCGGAAAAATTCACAACATGAGAAAAGAGGAAGGATTTA
Ca01 ------------------------CTGCTTCTTATTT-------TTTAAT--------GGATAAGAAGCAGTTTTATTTTTTTATTATTAGGAGGAGAAGATTATGGGAGAAATAGATTGTA
Ca02 ------------------------GCCCGAGG------------TTATTT------------CCAAGGGCTTTTTATTTTATCCTATTTTTTAAGGGGGCTAACTTATGAATTCTTCACTA
Ca03 TAATAGA-----------------TCCTCTTCTT----------TTAA-----------AAGAAGAGGATTTTATTTTGTTAATAATAGAACCAACTTATTATTATTTGGTTTTATTCTA
Ca04 ------------------------GAGCCAGAG-----------TTTATT------------CTCTGGCTCTTATTATTTTTTAATCTAATGGGAAAAGGTGAATGACATGATAGAAATAAA
Ca05 AATAA-------------------TCCGTTTTTC----------TTATT-----------GGAAAATGGATTTTTTTTATATATTAAAATTTAAACTAGGACGGTGAAAAAAATGCCTATA
Ca06 ------------------------TCCTCTTC------------AACTAA------------GAAGAGGATTTAATTTTATATATTTTTAGGTTTAGATATTGAAGTTAAAATATAATAAA
Ca07 ------------------------GTCTCTTC-------------TTATT------------GAGGAGACTTTTATTTTTATATTGTAGGAGGAAGTGGATATAATGAGAAAGTTATTTAC
Cp01 ------------------------TCTCTTCTTAAATCT------TTAA-------AGGTTTGAGAAGAGATTTTTTTATTAACAAAAATATTTTAAAGGCGCGCATTAAAATAAAGTTTGT
Cp02 ------------------------CTTCTATC-------------CTAG-------------GATAGGAGTTTTTTTATTTTGTAGGATAAAGGATAGATTTATTAAATGGATTAGGAGGA
Lm01 ------------------------TGCTTCGATTCTG------ACCAAAAAA--------CAGAGGAAGCGTTATTTTTTTAGCGCTTAAAGAGGGGAGTTTTTGTTAGATGAAGAAATTTT
Lm02 ------------------------ACTTCTCTATT----------CTAA-----------AATAGAGAAGTTTTTTTATTGCTTTCATGAATAAATCTGGATAATCACACAACATACTAGG
Lm03 ------------------------CCTCTCTGGCGG-------CTTATATA--------CTGCTAGGGAGGTTTTTTGATGGAAATTACTGATAAATACATATCAAAGAGGAGTGGATTTTA
Lm04 ------------------------CTTTCCCTTAAAAG-------CTGT--------CTTTTAAGGGAAAGTTTTTTTATACATAAAAATAATAAGAATTGAGGCGAAGAAAATGAACCAAG
Lm05 ------------------------AGCCTTTCTCTATTCGTGCGCGTTTT--GTGCAAAATAGAGAGAGGCTTTTTATATGAGACGTATTTGGAGAGAATTGAAGGAGGAAAATAAAATTGG
Lm06 GTATCGAAACTTCCAAA-------CCTCTCTAG------------TTCT------------CTAGGGAGGTTTTTTATTGGCAAAAAATCGAGAGGATAAGGTGATAGGTATGGTAAAGGC
Lm07 ------------------------GCCTTTCTGCT----------CATC-----------AGCAGAAAGGCTTTTTTTGTATATCAGAATGTAGAAAAGGTGATAGAGATGATTACGTTACA
Li01 ------------------------CGCTTCGATTCTG------ACCAAAAAA--------CAGAGGAAGCGTTATTTTTAGCGCTTAAAGAGGGGAGTTTTTGTTAGATGAAGAAATTTTTA
Li02 ------------------------CTTCTCTATT------------CTA-----------AATAGAGAAGTTTTTTTATTGCTTTCATGAATAAATCTGGATAAATAATCAACATACTAGG
Li03 ------------------------CCTCTCTGGCGG-------CTTATATA--------CTGCTAGGGAGGTTTTTTGATGGAAATTACTGATAAATACATATTAAAGAGGAGTGGATTTTA
Li04 ------------------------CTTTCCCTTAAAAG-------CTGT--------CTTTTGGGGGAAAGTTTTTTTGTACATAAAAATAACTAGAATTGAGGCGAAGAAAATGAATCAAG
Li05 ------------------------GCCTTTCTCTATTCGTGCGCG-TTT--CGTGCAAAATAGAGAGAGGCTTTTTATATGAGACGTATTTGGAGAGAACTAAAGGAGGAAAATAAAATTGG
Li06 GTATCGAAACTTCCAAA-------CCTCTCTAG------------TTCT------------CTAGGGAGGTTTTTTATTGGCAAAAAATTGAGAGGATAAGGTGATAGGTATGGTAAAGGC
Li07 ------------------------GCCTTTCTGCT----------CATT-----------AGCAGGAAGGCTTTTTTGTATATCAGAATGTAGAAAAGGTGATAGAGATGATTACGTTACAG
Sa01 ------------------------CTTCTTACTTT----------TCAAT----------AGGGTGAGAAGTTTTTTTGTTTAAGGAGGAAAGAACAATGACAAATTACACAGTAGATACTT
Sa02 ------------------------TGCTTTCTCAATTTT-----TCTATC------GATATTGAGAAAGCATTTTTTATTTTATTAAGCAACACAGGGAGGAATCAACGTGATTGAATTAAA
Sa03 ------------------------GGCCTTCTCTCTAT-------ATTA--------ATAGTTAGAAGGTCTTTTTTATTTAGCTCACAGAGAGAGAATTTTCGTAATATAAATTTAAAGGA
Sa04 ------------------------ACCTCTTTCTTCA--------TCGTT--------TGTGAGAAAGAGGTATTTTTAATTGGAAAGCAGGTAAAAAGGATGGAAGTACATAAAAAGAGCA
Sc01 AGACTGCCGAAACCTCCACGAACC----------------------------------------------------CCACCGACGCCGCCGTCGACCTCGGCCCCGCCACCGCGCTGAGCTGCCGGG
```

FIG.41Q

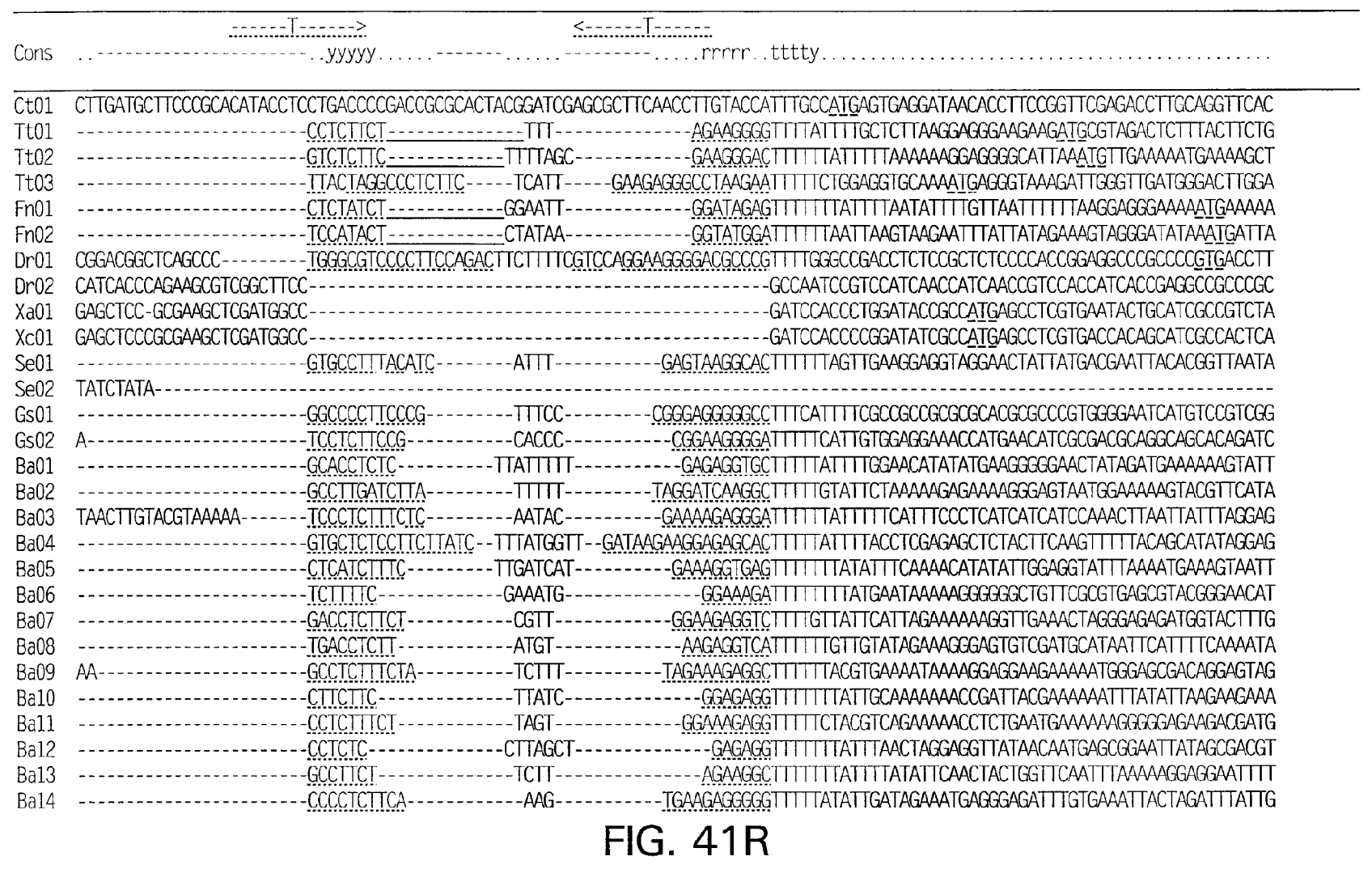

```
                      ------T------>                   <------T------
Cons  ..----------------------..yyyyy......-------.....----------.....rrrrr..tttty............................................

Ct01  CTTGATGCTTCCCGCACATACCTCCTGACCCCGACCGCGCACTACGGATCGAGCGCTTCAACCTTGTACCATTTGCCATGAGTGAGGATAACACCTTCCGGTTCGAGACCTTGCAGGTTCAC
Tt01  -----------------------CCTCTTCT-------------TTT-------------AGAAGGGGTTTTATTTTGCTCTTAAGGAGGGAAGAAGATGCGTAGACTCTTTACTTCTG
Tt02  -----------------------GTCTCTTC-----------TTTTAGC-----------GAAGGGACTTTTTTATTTTTAAAAAAGGAGGGGCATTAAATGTTGAAAAATGAAAAGCT
Tt03  -----------------------TTACTAGGCCCTCTTC-----TCATT-----GAAGAGGGCCTAAGAATTTTTCTGGAGGTGCAAAATGAGGGTAAAGATTGGGTTGATGGGACTTGGA
Fn01  -----------------------CTCTATCT-----------GGAATT------------GGATAGAGTTTTTTTATTTTAATATTTTGTTAATTTTTTAAGGAGGGAAAAATGAAAAA
Fn02  -----------------------TCCATACT-----------CTATAA------------GGTATGGATTTTTTAATTAAGTAAGAATTTATTATAGAAAGTAGGGATATAAATGATTA
Dr01  CGGACGGCTCAGCCC---------TGGGCGTCCCCTTCCAGACTTCTTTTCGTCCAGGAAGGGGACGCCCGTTTTGGGCCGACCTCTCCGCTCTCCCCACCGGAGGCCCGCCCCGTGACCTT
Dr02  CATCACCCAGAAGCGTCGGCTTCC----------------------------------------------GCCAATCCGTCCATCAACCATCAACCGTCCACCATCACCGAGGCCGCCCGC
Xa01  GAGCTCC-GCGAAGCTCGATGGCC----------------------------------------------GATCCACCCTGGATACCGCCATGAGCCTCGTGAATACTGCATCGCCGTCTA
Xc01  GAGCTCCCGCGAAGCTCGATGGCC----------------------------------------------GATCCACCCCGGATATCGCCATGAGCCTCGTGACCACAGCATCGCCACTCA
Se01  -----------------------GTGCCTTTACATC--------ATTT----------GAGTAAGGCACTTTTTTAGTTGAAGGAGGTAGGAACTATTATGACGAATTACACGGTTAATA
Se02  TATCTATA-----------------------------------------------------------------------------------------------------------------
Gs01  -----------------------GGCCCCTTCCCG---------TTTCC---------CGGGAGGGGGCCTTTCATTTTCGCCGCCGCGCGCACGCGCCCGTGGGGAATCATGTCCGTCGG
Gs02  A----------------------TCCTCTTCCG-----------CACCC-----------CGGAAGGGGATTTTTCATTGTGGAGGAAACCATGAACATCGCGACGCAGGCAGCACAGATC
Ba01  -----------------------GCACCTCTC----------TTATTTTT-----------GAGAGGTGCTTTTTATTTTGGAACATATATGAAGGGGGAACTATAGATGAAAAAAGTATT
Ba02  -----------------------GCCTTGATCTTA---------TTTTT---------TAGGATCAAGGCTTTTTGTATTCTAAAAAGAGAAAAGGGAGTAATGGAAAAAGTACGTTCATA
Ba03  TAACTTGTACGTAAAAA-------TCCCTCTTTCTC---------AATAC----------GAAAAGAGGGATTTTTTATTTTTCATTTCCCTCATCATCATCCAAACTTAATTATTTAGGAG
Ba04  -----------------------GTGCTCTCCTTCTTATC--TTTATGGTT--GATAAGAAGGAGAGCACTTTTTATTTTACCTCGAGAGCTCTACTTCAAGTTTTTACAGCATATAGGAG
Ba05  -----------------------CTCATCTTTC---------TTGATCAT----------GAAAGGTGAGTTTTTTTATATTTCAAAACATATATTGGAGGTATTTAAAATGAAAGTAATT
Ba06  -----------------------TCTTTTC-------------GAAATG--------------GGAAAGATTTTTTTTATGAATAAAAAGGGGGGCTGTTCGCGTGAGCGTACGGGAACAT
Ba07  -----------------------GACCTCTTCT-----------CGTT------------GGAAGAGGTCTTTTGTTATTCATTAGAAAAAAGGTTGAAACTAGGGAGAGATGGTACTTTG
Ba08  -----------------------TGACCTCTT------------ATGT-------------AAGAGGTCATTTTTTGTTGTATAGAAAGGGAGTGTCGATGCATAATTCATTTTCAAAATA
Ba09  AA---------------------GCCTCTTTCTA----------TCTTT-----------TAGAAAGAGGCTTTTTTACGTGAAAATAAAAGGAGGAAGAAAAATGGGAGCGACAGGAGTAG
Ba10  -----------------------CTTCTTC--------------TTATC--------------GGAGAGGTTTTTTTATTGCAAAAAAACCGATTACGAAAAAATTTATATTAAGAAGAAA
Ba11  -----------------------CCTCTTTCT------------TAGT-------------GGAAAGAGGTTTTTCTACGTCAGAAAAACCTCTGAATGAAAAAAGGGGGAGAAGACGATG
Ba12  -----------------------CCTCTC--------------CTTAGCT---------------GAGAGGTTTTTTTATTTAACTAGGAGGTTATAACAATGAGCGGAATTATAGCGACGT
Ba13  -----------------------GCCTTCT--------------TCTT---------------AGAAGGCTTTTTTTATTTTATATTCAACTACTGGTTCAATTTAAAAAGGAGGAATTTT
Ba14  -----------------------CCCCTCTTCA------------AAG-----------TGAAGAGGGGGTTTTTATATTGATAGAAATGAGGGAGATTTGTGAAATTACTAGATTTATTG
```

FIG. 41R

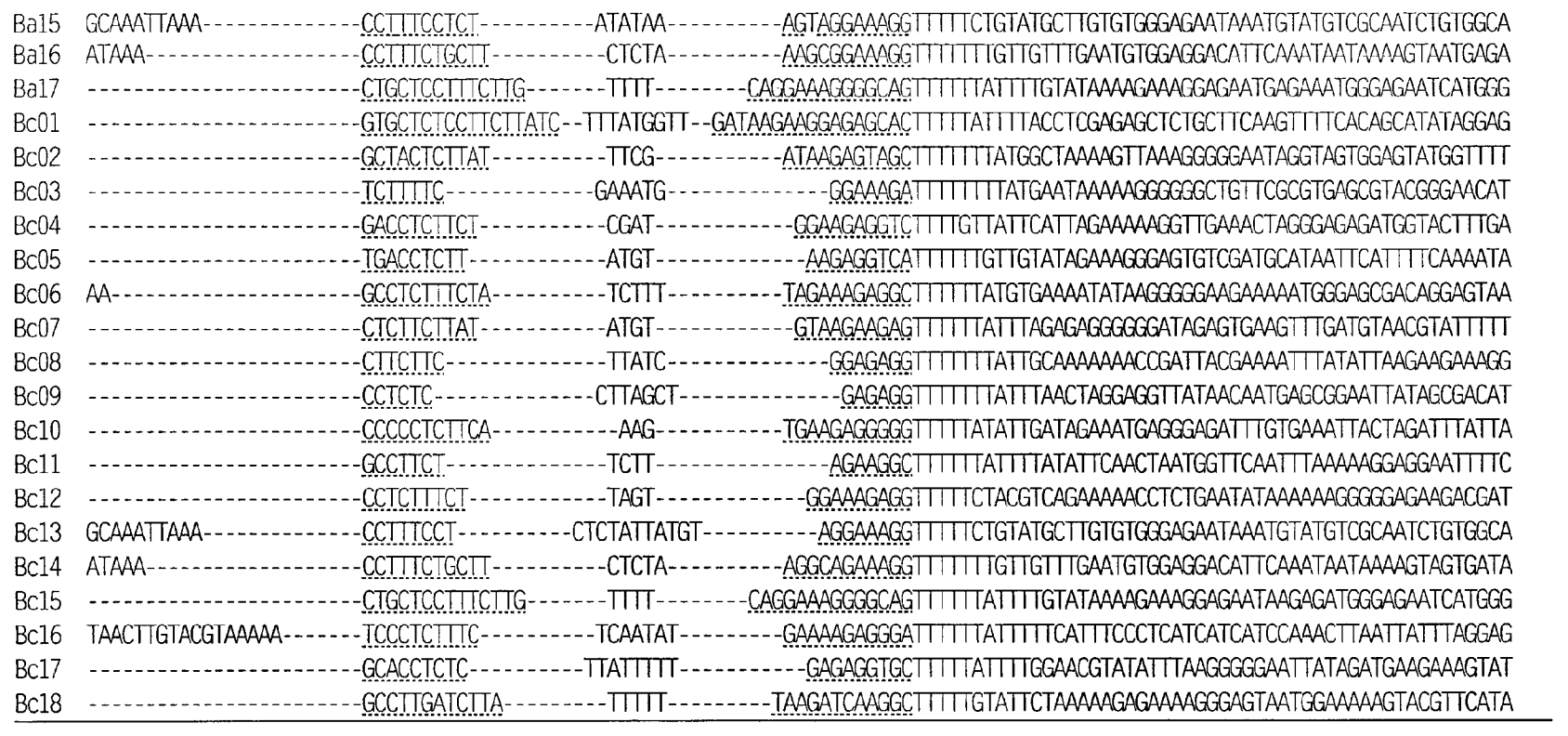

```
Ba15 GCAAATTAAA--------------CCTTTCCTCT----------ATATAA----------AGTAGGAAAGGTTTTTCTGTATGCTTGTGTGGGAGAATAAATGTATGTCGCAATCTGTGGCA
Ba16 ATAAA-------------------CCTTTCTGCTT----------CTCTA----------AAGCGGAAAGGTTTTTTTGTTGTTTGAATGTGGAGGACATTCAAATAATAAAAGTAATGAGA
Ba17 ------------------------CTGCTCCTTTCTTG-------TTTT--------CAGGAAAGGGGCAGTTTTTTATTTTGTATAAAAGAAAGGAGAATGAGAAATGGGAGAATCATGGG
Bc01 ------------------------GTGCTCTCCTTCTTATC--TTTATGGTT--GATAAGAAGGAGAGCACTTTTTATTTTACCTCGAGAGCTCTGCTTCAAGTTTTCACAGCATATAGGAG
Bc02 ------------------------GCTACTCTTAT----------TTCG-----------ATAAGAGTAGCTTTTTTTATGGCTAAAAGTTAAAGGGGGAATAGGTAGTGGAGTATGGTTTT
Bc03 ------------------------TCTTTTC-------------GAAATG--------------GGAAAGATTTTTTTTATGAATAAAAAGGGGGGCTGTTCGCGTGAGCGTACGGGAACAT
Bc04 ------------------------GACCTCTTCT-----------CGAT------------GGAAGAGGTCTTTTGTTATTCATTAGAAAAAGGTTGAAACTAGGGAGAGATGGTACTTTGA
Bc05 ------------------------TGACCTCTT------------ATGT-------------AAGAGGTCATTTTTTGTTGTATAGAAAGGGAGTGTCGATGCATAATTCATTTTCAAAATA
Bc06 AA----------------------GCCTCTTTCTA----------TCTTT----------TAGAAAGAGGCTTTTTTATGTGAAAATATAAGGGGGAAGAAAAATGGGAGCGACAGGAGTAA
Bc07 ------------------------CTCTTCTTAT-----------ATGT------------GTAAGAAGAGTTTTTTATTTAGAGAGGGGGGATAGAGTGAAGTTTGATGTAACGTATTTTT
Bc08 ------------------------CTTCTTC--------------TTATC--------------GGAGAGGTTTTTTTATTGCAAAAAAACCGATTACGAAAATTTATATTAAGAAGAAAGG
Bc09 ------------------------CCTCTC--------------CTTAGCT--------------GAGAGGTTTTTTTATTTAACTAGGAGGTTATAACAATGAGCGGAATTATAGCGACAT
Bc10 ------------------------CCCCCTCTTCA-----------AAG-----------TGAAGAGGGGGTTTTTATATTGATAGAAATGAGGGAGATTTGTGAAATTACTAGATTTATTA
Bc11 ------------------------GCCTTCT--------------TCTT---------------AGAAGGCTTTTTTATTTTATATTCAACTAATGGTTCAATTTAAAAAGGAGGAATTTTC
Bc12 ------------------------CCTCTTTCT------------TAGT-------------GGAAAGAGGTTTTTCTACGTCAGAAAAACCTCTGAATATAAAAAAGGGGAGAAGACGAT
Bc13 GCAAATTAAA--------------CCTTTCCT----------CTCTATTATGT----------AGGAAAGGTTTTTCTGTATGCTTGTGTGGGAGAATAAATGTATGTCGCAATCTGTGGCA
Bc14 ATAAA-------------------CCTTTCTGCTT----------CTCTA----------AGGCAGAAAGGTTTTTTTGTTGTTTGAATGTGGAGGACATTCAAATAATAAAAGTAGTGATA
Bc15 ------------------------CTGCTCCTTTCTTG-------TTTT--------CAGGAAAGGGGCAGTTTTTTATTTTGTATAAAAGAAAGGAGAATAAGAGATGGGAGAATCATGGG
Bc16 TAACTTGTACGTAAAAA-------TCCCTCTTTC----------TCAATAT---------GAAAAGAGGGATTTTTTATTTTTCATTTCCCTCATCATCATCCAAACTTAATTATTTAGGAG
Bc17 ------------------------GCACCTCTC----------TTATTTTT-----------GAGAGGTGCTTTTTATTTTGGAACGTATATTTAAGGGGGAATTATAGATGAAGAAAGTAT
Bc18 ------------------------GCCTTGATCTTA---------TTTTT---------TAAGATCAAGGCTTTTTGTATTCTAAAAAGAGAAAAGGGAGTAATGGAAAAAGTACGTTCATA
```

FIG.41S

| | |
|---|---|
| Cons | ........................................................................................................ |
| Bs01 | GGGACTTTTAGAAGATTTGCAAAGACAGGTGTTAATCGGTGACGGCGCCATGGGGACGCTCCTCTACTCCTATGGCATTGACAGGTGTTTTGAGGAGCTCAATATTTCAAAGCCGGAGGA |
| Bs02 | CGAAATTAGCTCAAATTGGGAACCGTAGCGATGAAGTCACGGGAACAGTGAGTGCTCCTATCTATTTATCAACAGCATACCGCCACAGAGGGATCGGAGAATCTACCGGATTTGATTATG |
| Bs03 | GTGTTTTACATATAAAGGAGGAGAAACAATGACAACCATCAAAACATCGAATTTAGGATTTCCGAGAATCGACCTGAACCGGGAATGGAAAAAAGCACTTGAAGCGTATTGGAAAGGCAG |
| Bs04 | GGAGTCACAAAAACACCTTTATACGAAACGTTAAATGAAAGCTCCGCTGTGGCGTTGGCGGTGAAGCTTGGCCTATTTCCAAGCAAAAGCACGCTGACATGCCAGGAGATCGGAGACGGC |
| Bs05 | GCGACATATCTCCTGACCGAACCGGGAGCCGATACAGAGAAGAAAGCAGAACAAATCGCAACAGGATTGACAGTAGGCTCCTGGACTGATCTGCCCCTTGTAAAACAGGAGCAAATGCAA |
| Bs06 | CACATTACATGGGAAAAGACAACCGGCAGAAAGCTACTGTTTGTTTGTCTCCGAAAGGAGGAAAGAAGAAATGTTAACGTATGATAATTGGGAAGAACCAACGATTACATTTCCGGAAGA |
| Bs07 | TGGTTACAGCACCGTACAACGAAGAAGGACGAAAAGAGCTTGAAAACTTGTTTGGCTCAGTTGCTTATCAATCTTGGAAGGAACAAGGTAGGGCATATCGGGAGGATGAACTCATTCAGC |
| Bs08 | TTGTATAAGAGGGAGCGAGTTCCGTATCATATATACAAGGTCTTTCGGGAGGCCTTGTGCAGGAGGAAGCAAATCATGAGTAAAAATCGTCGTTTATTTACATCAGAATCTGTTACGGAG |
| Bs09 | GTGATTGCTTTGATCAATCTTCAGGATGTTTCAAAAGTTTACAAGTCGAAACATGGAGATGTCAATGCTGTCCAAAACGTCTCGCTTTCCATTAAAAAAGGTGAGATTTTTGGAATTATA |
| Bs10 | ACGAATGTTGCAGGACAAAAAACAGAAAAACAACGCAAAGCACCTTTCCGCGCCGATCATGTCGGCAGCTTGCTTCGTTCCGTTCCGGTAAAGGAAGCCCGGCAAAAAAAAGCGGCTGGT |
| Bs11 | ACACCCGCAGAACAAAAATCACTTCAAAGAAAAAAACCGCCGTTTCGCGCGGATCAAGTCGGAAGCCTGCTAAGATCTGAGCCCGTCAAAAAAGCGCGGCTGCAAAAAGCGGCCGGCGAA |
| Bh01 | CCGAAAACAGCAAGACAAAAAAAGAACAACTTGGAATGAGGAGGCGTTGTACATGAAAAAAATTTACGTAATCCACGAAAACGATGAATGGACGGTTCACCTATTTAAACGACTTGAGGA |
| Bh02 | AAGGGGAAATAATCAGATGATTAAAGTTGGTGTGATCGGATTTGGCACCGTTGGGCAAGGTGTTGTCGAGAGTCTAGTTCAATTGGAGCGAGGATTAAGGAAAGAAGTTACTCTCGAAAT |
| Bh03 | TGAAGGCTTTCGCAACTTGGCGACGAGCTGATTTTTCCAATAGATGGATAGGAGGAGCAACCATGAATCGTAAAGAATTAGAAACAGCTTTAGTACAAATCGGAAATCGAATGGATGATC |
| Bh04 | ATCATGTTTTGCGCAGCCTGCCGTTGGTAAGGGTGTGCTTAAGGGAGGATATTCGTAAATGGCAGATACAAGAAGTCGTCGCTTATTTACATCAGAGTCTGTTACAGAAGGACATCCTGA |
| Bh05 | TAATGATTTGCGTGCTCCTTGAGACGAAATTTGCGAGAGTGAGAGTTTTTGCTCTCGTACTGACTTTCGTTAAATTGGTAACGCGTAGACGAACTGATATATTTTTAGAAAAGAGGGCTT |
| Oi01 | GACGTTTGCAAGAAGGCACGGTAATAGCAGGAGAAGGGTATTTATTTGAATTAGAGAGGAGGGGGTACTTACAGGCAGGTTCGTTTGTACCAGAAGTAGCCCTTGAAAATCCGGATGCGT |
| Oi02 | GAGCAAGACCCTACTCTATAAGACTAGCCCAAATCTAAAGGAGAAAGAAGGAAATTAACATGACAAAAACAGTTATTAAAGCACCATTTCGCGCAGACCATGTAGGTAGCTTACTACGAC |
| Oi03 | ACAAAGAAGAAATGATCTAATTGAGAAATTAATTGCATCTAATCATTTTAAAAAAGGGAACAAACATCTATATGAACTGACAACAGCAGAGTTGGAATACGAATACTTTAAATTACAATA |
| Oi04 | CACTATGAATCTAAAAAGAGAAGAGTGATAGGGGTAGATCAAGTTTCCCTTGATATCAAAAAGGGAGAAATATATGGCATCGTTGGATATAGCGGTGCAGGTAAAAGTACGCTTTTACGT |
| Oi05 | TCTTTTATTGGCACTTTGAATAGGATAGAAGTTATAAAGAGATCCGTACCAACATATATCAAAGGAGAGTTTAGCCTTATGGCTGCAAATCGACGTTTATTTACTTCAGAGTCAGTAACT |
| Oi06 | TAAGAGGAGGAATAAAGATTGATATCCATCGAAGGGTTAAGTAAAGTATTTTCATTAAATAAAAAAGACATCAAAGCTGTAGACTCATTGACCCTCAATATTGAAAATGGCGATATTTAT |
| Oi07 | TAAAAAACACGCAATCTCCTATTTTTGTTATCATTGTTTAAACCACTAAACCAAACAAAAAGGAGATGCGTGCAATTGAATTCTAACATAACATTACCTGGGTTGGAAGAAGGAAATATA |
| Oi10 | CTGGTTGCCGATTTTTGGAGGGTGGTTGCGTAATGTAGAAGATGAACAGATGCCTCCTACTTTTGAATATGCAAAACAGGTAATTCAGCACGCGGAAGAATGGGGATATGATACGACTTT |
| Oi08 | CTTCAAATATGAGTAAACCAATCAGGTAACTAAAGTAGGGGGATCGAAACTGTCAAGTGATCGTAGTTTATAAAAATCTAAAATGAAGAGGAGAGCGTGTATTATGCCAACTATAAAAAC |
| Oi09 | ACACGATGTCTAAATTTCAATCTTTGCAAGCAGAAACAATCTTACTTCATGGAGGACAGGAACCAGACCCATCAACTGGTTCACGTGCAGTTCCAATTTATCAAACTACGTCCTATGTGT |
| Oi10 | CTGGTTGCCGATTTTTGGAGGGTGGTTGCGTAATGTAGAAGATGAACAGATGCCTCCTACTTTTGAATATGCAAAACAGGTAATTCAGCACGCGGAAGAATGGGGATATGATACGACTTT |
| Oi11 | TGTGACATTGTCCGGCAGCCCCTCCGAACTATCTAGATCTGAAAAAGTACTACATTATTTAGGGAATCAATTAAGTGAACAGAAATTCTATGTGACCCATATTTCTGTTAAAGATGTACC |

FIG.41T

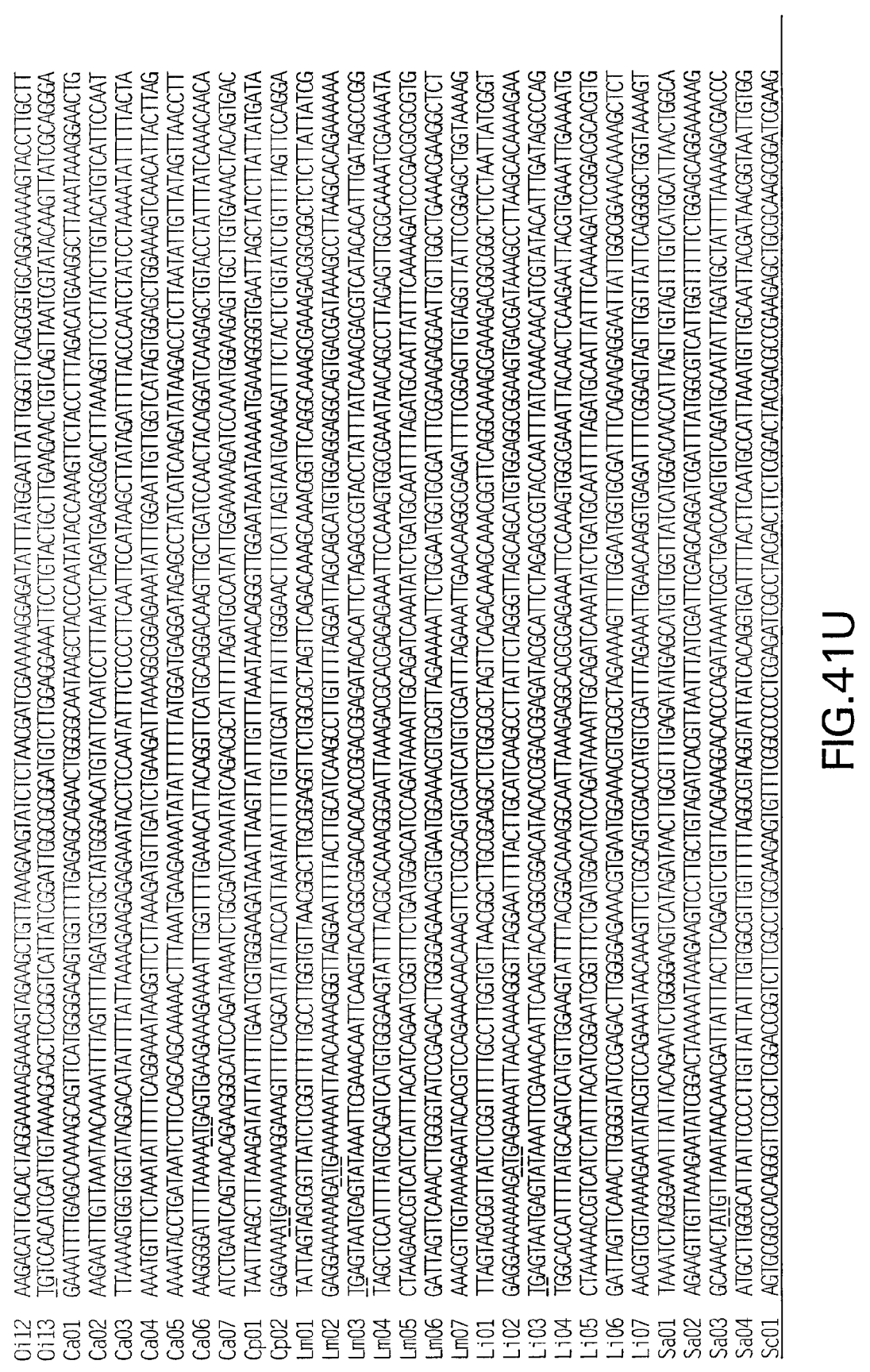

```
Oi12  AAGACATTCACACTAGGAAAAAGAAAAGTAGAAGCTGTTAAAGAAGTATCTCTAACGATCGAAAAAGGAGATATTTATGGAATTATTGGGTTCAGCGGTGCAGGAAAAAGTACCTTGCTT
Oi13  TGTCCACATCGATTGTAAAAGGAGCTCCGGGTCATTATCGGATTGGCGCGGATGTCTTGGAGGAAATTCCTGTACTGCTTGAAGAACTGTCAGTTAATCGTATACAAGTTATCGCAGGGA
Ca01  GAAATTTTGAGACAAAAGCAGTTCATGGGGAGAGTGGTTTTGAGAGCAGAACTGGGGCAATAAGCTACCCAATATACCAAAGTTCTACCTTTAGACATGAAGGCTTAAATAAAGGAACTG
Ca02  AAGAATTTGTTAAATAACAAAATTTTAGTTTTAGATGGTGCTATGGGAACATGTATTCAATCCTTTAATCTAGATGAAGGCGACTTTAAAGGTTCCTTATCTTGTACATGTCATTCCAAT
Ca03  TTAAAAGTGGTGGTATAGGACATATTTTATTAAAAGAAGAGAGAAATACCTCCAATATTTCTCCCTTCAATTCCATAAGCTTATAGATTTTACCCAATCTATCCTAAAATATTTTTACTA
Ca04  AAATGTTTCTAAATATTTTTCAGGAAATAAGGTTCTTAAAGATGTTGATCTGAAGATTAAAGGCGGAGAAATATTTGGAATTGTTGGTCATAGTGGAGCTGGAAAGTCAACATTACTTAG
Ca05  AAAATACCTGATAATCTTCCAGCAGCAAAAACTTTAAATGAAGAAAATATATTTTTTATGGATGAGGATAGAGCCTATCATCAAGATATAAGACCTCTTAATATTGTTATAGTTAACCTT
Ca06  AAGGGGATTTTAAAAATGAGTGAAGAAAGAAAATTTGGTTTTGAAACATTACAGGTTCATGCAGGACAAGTTGCTGATCCAACTACAGGATCAAGAGCTGTACCTATTTATCAAACAACA
Ca07  ATCTGAATCAGTAACAGAAGGGCATCCAGATAAAATCTGCGATCAAATATCAGACGCTATTTTAGATGCCATATTGGAAAAAGATCCAAATGGAAGAGTTGCTTGTGAAACTACAGTGAC
Cp01  TAATTAAGCTTTAAAGATATTATTTTGAATCGTGGGAAGATAAATTAAGTTATTTGTTTAAATAAACAGGGTTGGAATAAATAAAAATGAAAGGGGTGAATTAGCTATCTTATTATGATA
Cp02  GAGAAAATGAAAAAAGGAAAGTTTTCAGCATTATTACCATTAATAATTTTTGTATCGATTTATTTGGGAACTTCATTAGTAATGAAAGATTTCTACTCTGTATCTGTTTTAGTTCCAGGA
Lm01  TATTAGTAGCGGTTATCTCGGTTTTTGCCTTGGTGTTAACGGCTTGCGGAGGTTCTGGCGCTAGTTCAGACAAAGCAAACGGTTCAGGCAAAGCGAAAGACGGCGGCTCTCTTATTATCG
Lm02  GAGGAAAAAAGATGAAAAAATTAACAAAAGGGTTAGGAATTTTACTTGCATCAAGCCTTGTTTTAGGATTAGCAGCATGTGGAGGAGGCAGTGACGATAAAGCCTTAAGCACAGAAAAAA
Lm03  TGAGTAATGAGTATAAATTCGAAACAATTCAAGTACACGGCGGACACACACCGGACGGAGATACACATTCTAGAGCCGTACCTATTTATCAAACGACGTCATACACATTTGATAGCCCGG
Lm04  TAGCTCCATTTTATGCAGATCATGTGGGAAGTATTTTACGCACAAAGGGAATTAAAGACGCACGAGAGAAATTCCAAAGTGGCGAAATAACAGCCTTAGAGTTGCGCAAAATCGAAAATA
Lm05  CTAAGAACCGTCATCTATTTACATCAGAATCGGTTTCTGATGGACATCCAGATAAAATTGCAGATCAAATATCTGATGCAATTTTAGATGCAATTATTTCAAAAGATCCCGACGCGCGTG
Lm06  GATTAGTTCAAACTTGGGGTATCCGAGACTTGGGGAGAAACGTGAATGGAAACGTGCGTTAGAAAAATTCTGGAATGGTGCGATTTCGGAAGAGGAATTGTTGGCTGAAACGAAGGCTCT
Lm07  AAACGTTGTAAAAGAATACACGTCCAGAAACAACAAAGTTCTCGCAGTCGATCATGTCGATTTAGAAATTGAACAAGGCGAGATTTTCGGAGTTGTAGGTTATTCCGGAGCTGGTAAAAG
Li01  TTAGTAGCGGTTATCTCGGTTTTTGCCTTGGTGTTAACGGCTTGCGGAGGCTCTGGCGCTAGTTCAGACAAAGCAAACGGTTCAGGCAAAGCGAAAGACGGCGGCTCTCTAATTATCGGT
Li02  GAGGAAAAAAAGATGAGAAAATTAACAAAAGGGTTAGGAATTTTACTTGCATCAAGCCTTATTCTAGGGTTAGCAGCATGTGGAGGCGGAAGTGACGATAAAGCCTTAAGCACAAAAGAA
Li03  TGAGTAATGAGTATAAATTCGAAACAATTCAAGTACACGGCGGACATACACCGGACGGAGATACGCATTCTAGAGCCGTACCAATTTATCAAACAACATCGTATACATTTGATAGCCCAG
Li04  TGGCACCATTTTATGCAGATCATGTTGGAAGTATTTTACGGACAAAGGCAATTAAAGAGGCACGCGAGAAATTCCAAAGTGGCGAAATTACAACTCAAGAATTACGTGAAATTGAAAATG
Li05  CTAAAAACCGTCATCTATTTACATCGGAATCGGTTTCTGATGGACATCCAGATAAAATTGCAGATCAAATATCTGATGCAATTTTAGATGCAATTATTTCAAAAGATCCGGACGCACGTG
Li06  GATTAGTTCAAACTTGGGGTATCCGAGACTTGGGGAGAAACGTGAATGGAAACGTGCGCTAGAAAAGTTTTGGAATGGTGCGATTTCAGAAGAGGAATTATTGGCGGAAACAAAAGCTCT
Li07  AACGTCGTAAAAGAATATACGTCCAGAAATAACAAAGTTCTCGCAGTCGACCATGTCGATTTAGAAATTGAACAAGGTGAGATTTTCGGAGTAGTTGGTTATTCAGGGGCTGGTAAAAGT
Sa01  TAAATCTAGGGAAATTTATTACAGAATCTGGGGAAGTCATAGATAACTTGCGTTTGAGATATGAGCATGTTGGTTATCATGGACAACCATTAGTTGTAGTTTGTCATGCATTAACTGGCA
Sa02  AGAAGTTGTTAAAGAATATCGGACTAAAAATAAAGAAGTCCTTGCTGTAGATCACGTTAATTTATCGATTCGAGCAGGATCGATTTATGGCGTCATTGGTTTTTCTGGAGCAGGAAAAAG
Sa03  GCAAACTATGTTAAATAACAAACGATTATTTACTTCAGAGTCTGTTACAGAAGGACACCCAGATAAAATCGCTGACCAAGTGTCAGATGCAATATTAGATGCTATTTTAAAAGACGACCC
Sa04  ATGCTTGGGCATTATTCCCCTTGTTATTATTTGTGGCGTTGTTTTTAGGCGTAGGTATTATCACAGGTGATTTTACTTCAATGCCATTAAATGTTGCAATTACGATAACGGTAATTGTGG
Sc01  AGTGCGGCCACAGGGTTCCGCTCGGACCGGTCTTCGCCTGCGAAGAGTGTTTCGGCCCCCTCGAGATCGCCTACGACTTCTCGGACTACGACGCCGAAGAGCTGCGCAAGCGGATCGAAG
```

FIG.41U

```
Cons  ..........................................................................................................

Ct01  GCCGGGCAGGAGCCTGATCCGGTGACCGGATCGCGCGCCGTGCCCATTTACCAGACCACCTCCTACGTGTTCGAGAACGCCGAGCACGGCGCTGACCTGTTCGCGCTTCGCAAGGCGGGC
Tt01  AGTCAGTCACTGAAGGGCATCCTGACAAGATCTGTGACCAGATTTCAGATGCCATTTTGGATGAAATTTTAAAAAAAGACCCTTACGCCCGCGTGGCATGTGAGACAGCTGTAACTACCG
Tt02  GTGTAATAAACTTAAAGAAAAGAAATTTGTAATAACTGTGGAAATTTCTCCCCCCAAACGGATAGATGTAACTAAAACTATCGAGGAAGCTCGAAAACTTAAAGGTGTGGCAGATGCTCT
Tt03  ACTGTTGGGACAGGAGTATTTAAAATAGTTAATTCTAGAGGGAGATATATCAAGGAGAGTACGGGATTTTATCCGGAGATAAAGAAAGTGCTTGTGAAGGATTTGCACAAAAGAGAAAA
Fn01  GTTTACATACTTTACATCAGAATTTGTTTCACCAGGACATCCAGATAAAATTTCAGATCAAATATCAGATGCAATTTTAGATGCTTGTTTAAAAGATGACCCTAATTCAAGAGTTGCCTG
Fn02  CACTTGAAAATGTAAATAAAATTTATTCCAATAACTTGCATGCTGTAAAAGATGTTAATTTAAAAGTTAATGAAGGAGATATCTTTGGAATTATAGGTTTAAGTGGTGCTGGAAAATCTT
Dr01  ACCGTCCTCCCCCCCAGCCTTGCACTTCGAAGGCGTCAGCAAAACCTACCCCGGCCAGCCGGCGCCGGCGCTGAGCGATTTGACCCTCACCGTTGCGCGCGGCAGCCGCACCGGCATCAT
Dr02  CAGCGCATCCTGATTCTCGACGGCGCCTGGGGTACGCAGCTTCAGCGAGCCAACCTCACCGAAGCGGACTTCCGCTGGGACGAAGCCGACCCCACGCGGATGTACCGGGGCAACTTCGAC
Xa01  CCAACGATTTCGTTGACACCCCCGCCAGCAGCGACGACGGCATCACTGCCGTGCGCGGCGAACTTGTCATCGCCCTGCCGATGCGCCATGCCGGCATGCGCGAGCTGCGGCTGCGCTATG
Xc01  CCACCGCTGACACCTACACGCCCGCCGCTGATAGCGACGCCCCGCCTGCCGTGCGCGGCGAGCTCGTCATCAATCTACCGATGCGCCACGCCGGCCAACGCGAGCTGCGCCTGCGCTACG
Se01  CATTAGAACTAGGTGAGTTTAAAACTGAATCTGGTGAAACGATTGATCATTTACGTCTACGTTATGAACATGTAGGACTTCCTGGTCAACCCCTTGTCGTTGTTTGCCATGCACTTACTG
Se02  ------------------------------------------------------------------------------------------------------------------------
Gs01  CATCGTCGAAGAACAATCCGTCACCTTCGAAACGGATCTCAGGCTGGAAAGCGGCCGGATACTGGGGCCCATCACCCTGGCCTACGAGACCTACGGCCGGCTGAACGCCGACCGGTCCAA
Gs02  GGTCTCGACTGGGATACCCGCACCGGGGCGGTGACGGTACCCATCTACCAGACGGCAACCTTCCGGCATCCGGGATTGGGCCAGAGCACGGGCTACGATTATTCCCGCTCCGGCAACCCC
Ba01  ATTAAGCATTGTAAGCGGAGCGGTACTATTATTAGGCGCATGTAGCGCTGGTTCGGATAAAGAAGTAAAAGCGTTAGATGAGAAAAAGATTACTGTCGGTGTAACAGGCGGGCCGCATGA
Ba02  AAACAAAGTAAATTCATGTGTTTAGGGGGTTATGGAAGTGTATGTAATTAAAAAATTATCGGTTATGGTGTTCACACTATGGGTTATTACGACAGTGACATTTCTAATTATGCATATTAT
Ba03  GAAAATCAAATGAAAAAGAAGTTTGTACCCGGTATTGCATCAGTTGTAGGAGTAAGTATTTTATTAACTGGTTGCGGTAGTTATAAAAACGAAGCAAGCGGAGCAAATGCAAAAGACGAG
Ba04  GGGGAAAAATGATTTCTTTTAATAATGTAAGTAAAGTATATGAATCAGGTGGCAATCTGTTCATGCGGTGGAGGATGTAACGTTATCAGTTGAGAAAGGCGAAATTTTTGGCATTATCG
Ba05  GACCTATCACAAACATTCGAAAATAATATGTCTCAATTTCCTGGAACACCAAAAATCAATTTAGAAGCCATTACAAGCGTTGAAGAAACAGGTTATCAAGTTACAGATTTCCATTCTGTC
Ba06  TTTGAGGAAGTGTCTGAGAGAATTCAAGCGATGCTTGCTGATATGAAATATGGTTCAATTACAATTGTTGTACAAGATGGAAAAGTCATTCAACTAGAGAAAAGTGAAAAAGTACGTTTA
Ba07  AAAGAAACGAGAGGAAATGGTTTGGCTTTATTACCACTTGGGATATTTTTGGCGCTATTTATAGGTTCTGGAATTATTACAGGTGATTTCTATAAATTGCCGATACTTGTAGCAATTTCA
Ba08  AATATAGAGTAATAAAAGTTGACTATTAAGAGAGGGGAATTATAATGAACAGATTATCAACAAAATTAGTAGTAGCAATCGGAATTGGATCAGCATTATACGGGATATTAGGACTTTGGG
Ba09  CGTCACAAAGAAAAACAATTGAAGAGAGTATCGAAAGAAATAAGGAAAAGTACATAGAAACAAGTCATGATATTCATGCGAATCCGGAGATTGGTAATCAAGAATTTTACGCATCTAGAA
Ba10  GGGGTTGCGAAGTACTGTGACACTCGAAAAATACGTAAAACTGCGTAGTACAGTTTATGAATATATGATAGAGCAAGATAAGCCAATATCATTGTTAGATATTCAAGAACATATCGTTTC
Ba11  GGATATTATTCATTAACAGAAGTAACCGCTGTACAATATGCGAAAGAACATGGTTATTTTGAAAAGAAAGCAAATGTAGTTTGTCATGAAATTGGAGATGGAAATTTAAATTATGTGTTC
Ba12  ATTTAATCCATGATGATTCACATAACTTAGAAAAAAAAGCTGAGCAAATTGCACTCGGTTTAACAATTGGCTCTTGGACTCATTTGCCACACTTATTGCAAGAACAGTTAAAGCAGCATA
Ba13  TACATGTCAACTATCGAAACAAAACTAGCGCAAATCGGAAACCGGAGTGAAACTACAACAGGAACTGTTAATCCGCCTGTTTACTTTTCAACTGCTTATCGTCACGAAGGAATTGGTAAA
```

FIG.41V

| | |
|---|---|
| Ba14 | TCAAAAGGAATTGTAATAGGTGATGGTGCGGTTGGAACATTATTACATTCACACGGTTTGCAAAGTAGTTTTGAAGAATTGAATATATCTGATCCAGATTTAATTATATCGATTCATAAG |
| Ba15 | AATTAAGGATGAGTTCCGTACAATATATACAATTACTGTAGGGAGGTTTACCACATGACAAAAAAACGTCATCTGTTCACATCTGAGTCTGTAACTGAAGGACATCCAGATAAAATTTGT |
| Ba16 | ACGGTGGGCTACCGTATCAAAAATAAAAAATTGCGGAGTCAATCAAAAATCTAGCTCCAGCGGCTAGAACAGTCGGTCGTTTCATCCCTTCCTATGAGGCAAAAAGCGCCTCTAAGTCTG |
| Ba17 | GGAAAGGAACGATTTGTGTGCAAGGTGGCTATACGCCAAAGAATGGAGAACCGCGTGTTTTACCGCTTTATCAAAGCACGACGTATAAATATGATACTTCGGATGATTTAGCAGCATTAT |
| Bc01 | GGGAAAAAATGATTTCTTTTAACAATGTAAGTAAAGTATATGAAACAGGTGGGCAATCTGTTCATGCGGTGGAGGATGTAACATTATCAGTTGAGAAAGGCGAAATTTTTGGCATTATCG |
| Bc02 | TGGTTGCCGATTTTTGGGGGATGGCTTCGGAATGTAAATGATGAATCTATGCCGCCTACGTTTGAGTATGCAAAACAAACGGCGCAAGCGGCAGAACAATTAGGTTTTTCAACAACACTT |
| Bc03 | TTTGAGGAAGTATCTGAGAAAATTGAAGCGATGCTTGCTGATATGAAATATGGTTCAATTACAATTGTTGTGCAAGATGGCAAAGTCATTCAATTAGAGAAAAGTGAAAAAGTACGTTTA |
| Bc04 | AAGAAACGAGAGGAAATGGTTTGGCATTATTACCACTTGGGATATTTTTGGCGCTATTTATTGGTTCTGGAATTATTACAGGTGATTTCTATAAATTGCCGATACTTGTAGCAATTTCAA |
| Bc05 | AATATAGAGTAATAAAAGTTGACTATTAAGAGGGGAGAATTGTAATGAATAAATTATCAACAAAATTAGTAGTGGCAATCGGAATTGGAGCAGCATTATACGGGATATTAGGACTTTGGG |
| Bc06 | CGTCACAAAGAAAAACAATTGAAGAGAGTATTGAAAGAAATAAGGAAAAGTACATAGAAACAAGTCACGATATTCATGCGAATCCGGAGATTGGTAACCAAGAGTTTTACGCATCAAGAA |
| Bc07 | TAGAAAGTTTTCCGCAATTATTTAAGTATGTATACATAACTTTAGGAATTACTGTAGTTTCAATGATTATTTCTTTTGTTATAGGGATAGGTTTGGCGATCATAACGAAAAACAAAACGA |
| Bc08 | GGTTGCGCATTACTGTGACACTCGAAAAATACGTCAAACTGCGTAGTACAGTTTATGAATATATGATAGAGCAAGATAAGCCAATATCATTGTTAGATATTCAAGAACATATCGTTTCGC |
| Bc09 | ATTTAATCCATGATGATTCACATAACTTAGAAAAAAAAGCTGAGCAAATTGCACTCGGTTTAACAATTGGCTCTTGGACTCATTTGCCACATTTATTGCAAGAACAATTAAAGCAGCATA |
| Bc10 | TCAAAAGGAATTGTAATAGGTGATGGTGCGGTTGGGACGTTATTACATTCACATGGTTTACAAAGTAGTTTTGAAGAATTGAATATATCTGATCCAGATTTAATTATATCGATTCATAAG |
| Bc11 | ACATGTCAACTATCGAAACAAAATTAGCGCAAATCGGAAACCGGAGTGAAACTACAACAGGAACTGTTAATCCACCTGTTTATTTTTCAACTGCTTATCGTCACGAAGGAATTGGTAAAT |
| Bc12 | GGGATATTATGCATTAACTGAAACAACAGCTATACAATATGCGAAAGAACACGGTTATTTTGAAAAGAAAGCAAATGTATTTTGTCATGAAATTGGAGATGGAAATTTAAATTACGTGTT |
| Bc13 | AATTAAGGATGAGTTCCGTACAATATATACAATTACTGTAGGGAGGTTTACCACATGACAAAAAAACGTCATCTGTTCACATCTGAGTCTGTAACTGAAGGACATCCAGATAAAATTTGT |
| Bc14 | ACGGTGGACTACACGCATTAAACATAAAAAATTGCGGAGTCGATCCAAACAAAAAAGGGGTGATACACCATGATTCTATTAGAGAATGTAAAGAAAATATATAAAGCAAAAAGCGGTGAT |
| Bc15 | GGAAAGGAACAATTTGCGTGCAAGGTGGCTATACGCCAAAGAATGGTGAACCGCGTGTTTTACCGCTTTATCAAAGTACAACGTATAAATACGATACTTCGGATGATTTAGCAGCCTTAT |
| Bc16 | GAAAATCAAATGAAAAAAAAGTTTGTACCCGGTATTGCATCAGTTGTAGGAGTAAGTATTTTATTAACTGGTTGCGGTAGTTATAAAAACGAAGCAAGCGGAGCAAATGCAAAAGACGAG |
| Bc17 | TATTAAGCATTGTAAGTGGGGCTGTATTATTATTAAGCGCATGTAGCGGGAGTTCAGATAAAGAAGTAAAAGCGTTAGATGAGAAAAAGATTACTGTCGGTGTAACAGGAGGGCCTCATG |
| Bc18 | AAACTAAGTAAATATATGTGTTTAGGGGGTTATTGGAGTGTATGTAATTAAAAAATTATCAGTTATGGTGTTCACGCTATGGGTTATTACGACGGTGACATTTCTAATTATGCATATTAT |

FIG.41W

B. Cobalamin Riboswitch Alignment.

| ID | | Start | End | Accession | Organism |
|---|---|---|---|---|---|
| Atu01 | + | 70441 | 70625 | NC_003304.1 | Agrobacterium tumefaciens |
| Atu02 | - | 441331 | 441136 | NC_003305.1 | Agrobacterium tumefaciens |
| Atu03 | + | 877645 | 877833 | NC_003304.1 | Agrobacterium tumefaciens |
| Atu04 | + | 921717 | 921886 | NC_003305.1 | Agrobacterium tumefaciens |
| Atu05 | - | 1640563 | 1640420 | NC_003304.1 | Agrobacterium tumefaciens |
| Atu06 | - | 2810076 | 2809899 | NC_003304.1 | Agrobacterium tumefaciens |
| Bha01 | - | 466904 | 466746 | NC_002570.1 | Bacillus halodurans |
| Bha02 | + | 528894 | 529051 | NC_002570.1 | Bacillus halodurans |
| Bha03 | + | 870599 | 870748 | NC_002570.1 | Bacillus halodurans |
| Bha04 | + | 1661078 | 1661219 | NC_002570.1 | Bacillus halodurans |
| Bsu01 | - | 3403719 | 3403620 | NC_000964.1 | Bacillus subtilis |
| Bja01 | + | 2232813 | 2232975 | NC_004463.1 | Bradyrhizobium japonicum |
| Bja02 | + | 3617311 | 3617490 | NC_004463.1 | Bradyrhizobium japonicum |
| Bja03 | + | 3630677 | 3630857 | NC_004463.1 | Bradyrhizobium japonicum |
| Bja04 | + | 3634122 | 3634284 | NC_004463.1 | Bradyrhizobium japonicum |
| Bja05 | - | 5279669 | 5279495 | NC_004463.1 | Bradyrhizobium japonicum |
| Bme01 | + | 679030 | 679218 | NC_003317.1 | Brucella melitensis chromosome I |
| Bme02 | + | 717388 | 717585 | NC_003317.1 | Brucella melitensis chromosome I |

FIG.41X

| | | | | | |
|---|---|---|---|---|---|
| Bme03 | + | 559758 | 559950 | NC_003318.1 | Brucella melitensis chromosome II |
| Bme04 | - | 973106 | 972933 | NC_003318.1 | Brucella melitensis chromosome II |
| Ccr01 | + | 502968 | 503156 | NC_002696.2 | Caulobacter crescentus |
| Ccr02 | + | 1925017 | 1925166 | NC_002696.2 | Caulobacter crescentus |
| Cte01 | - | 409802 | 409630 | NC_002932.3 | Chlorobium tepidum |
| Cte02 | + | 422045 | 422244 | NC_002932.3 | Chlorobium tepidum |
| Cte03 | + | 443769 | 443951 | NC_002932.3 | Chlorobium tepidum |
| Cte04 | + | 584183 | 584411 | NC_002932.3 | Chlorobium tepidum |
| Cte05 | + | 882576 | 882770 | NC_002932.3 | Chlorobium tepidum |
| Cac01 | + | 1509969 | 1510116 | NC_003030.1 | Clostridium acetobutylicum |
| Cac02 | + | 2557903 | 2558041 | NC_003030.1 | Clostridium acetobutylicum |
| Cpe01 | + | 248269 | 248429 | NC_003366.1 | Clostridium perfringens |
| Cpe02 | + | 1241749 | 1241887 | NC_003366.1 | Clostridium perfringens |
| Cpe03 | - | 1431291 | 1431152 | NC_003366.1 | Clostridium perfringens |
| Cpe04 | - | 1549481 | 1549348 | NC_003366.1 | Clostridium perfringens |
| Eco01 | + | 4160983 | 4161133 | NC_000913.1 | Escherichia coli |
| Fnu01 | + | 934517 | 934658 | NC_003454.1 | Fusobacterium nucleatum |
| Lig01 | + | 1347854 | 1347994 | NC_004342.1 | Leptospira interrogans chromosome I |
| Lmo01 | + | 1179829 | 1179979 | NC_003210.1 | Listeria monocytogenes |
| Mlo01 | - | 1101076 | 1100918 | NC_002678.1 | Mesorhizobium loti |

FIG.41Y

| | | | | | |
|---|---|---|---|---|---|
| Mlo02 | + | 1149143 | 1149308 | NC_002678.1 | Mesorhizobium loti |
| Mlo03 | - | 4044577 | 4044416 | NC_002678.1 | Mesorhizobium loti |
| Mlo04 | - | 4957334 | 4957164 | NC_002678.1 | Mesorhizobium loti |
| Mlo05 | - | 6170855 | 6170715 | NC_002678.1 | Mesorhizobium loti |
| Mlo06 | + | 6749148 | 6749315 | NC_002678.1 | Mesorhizobium loti |
| Mle01 | - | 1130394 | 1130222 | NC_002677.1 | Mycobacterium leprae |
| Mtu01 | - | 309822 | 309703 | NC_000962.1 | Mycobacterium tuberculosis |
| Mtu02 | - | 1261701 | 1261497 | NC_000962.1 | Mycobacterium tuberculosis |
| Pae01 | + | 1381520 | 1381688 | NC_002516.1 | Pseudomonas aeruginosa |
| Pae02 | - | 3261415 | 3261204 | NC_002516.1 | Pseudomonas aeruginosa |
| Pae03 | + | 3265563 | 3265728 | NC_002516.1 | Pseudomonas aeruginosa |

FIG.41Z

| ID | | Start | End | Accession | Organism |
|---|---|---|---|---|---|
| Pae04 | - | 3305780 | 3305629 | NC_002516.1 | Pseudomonas aeruginosa |
| Ppu01 | - | 2765203 | 2765045 | NC_002947.3 | Pseudomonas putida |
| Ppu02 | - | 2768953 | 2768785 | NC_002947.3 | Pseudomonas putida |
| Ppu03 | + | 3857563 | 3857746 | NC_002947.3 | Pseudomonas putida |
| Ppu04 | - | 3981958 | 3981816 | NC_002947.3 | Pseudomonas putida |
| Rso01 | - | 2609233 | 2609017 | NC_003295.1 | Ralstonia solanacearum |
| Sme01 | + | 954780 | 954943 | NC_003047.1 | Sinorhizobium meliloti |
| Sme02 | - | 1999747 | 1999574 | NC_003047.1 | Sinorhizobium meliloti |
| Sme03 | - | 2122891 | 2122516 | NC_003047.1 | Sinorhizobium meliloti |
| Sme04 | + | 66265 | 66456 | NC_003078.1 | Sinorhizobium meliloti plasmid pSymB |
| Sme05 | + | 580403 | 580578 | NC_003078.1 | Sinorhizobium meliloti plasmid pSymB |
| Sco01 | + | 1037869 | 1038053 | NC_003888.1 | Streptomyces coelicolor |
| Sco02 | + | 1045899 | 1046106 | NC_003888.1 | Streptomyces coelicolor |
| Sco03 | + | 1051420 | 1051563 | NC_003888.1 | Streptomyces coelicolor |
| Sco04 | - | 5688395 | 5688291 | NC_003888.1 | Streptomyces coelicolor |
| Sco05 | - | 6532337 | 6532191 | NC_003888.1 | Streptomyces coelicolor |
| Sfl01 | + | 4183416 | 4183566 | NC_004337.1 | Shigella flexneri (*) |
| Son01 | + | 826836 | 827026 | NC_004347.1 | Shewanella oneidensis |

FIG.41AA

| | | | | | |
|---|---|---|---|---|---|
| Son02 | + | 1071692 | 1071874 | NC_004347.1 | Shewanella oneidensis |
| Sti01 | - | 2114053 | 2113918 | NC_003197.1 | Salmonella typhimurium |
| Sti02 | + | 4347871 | 4348024 | NC_003197.1 | Salmonella typhimurium |
| Tma01 | - | 84288 | 84144 | NC_000853.1 | Thermotoga maritima |
| Tte01 | + | 395153 | 395353 | NC_003869.1 | Thermoanaerobacter tengcongensis |
| Tte02 | + | 396075 | 396275 | NC_003869.1 | Thermoanaerobacter tengcongensis (*) |
| Vch01 | + | 145142 | 145306 | NC_002505.1 | Vibrio cholerae chromosome I |
| Vvu01 | + | 1165724 | 1165882 | NC_004459.1 | Vibrio vulnificus chromosome I |
| Xac01 | - | 3631166 | 3630987 | NC_003902.1 | Xanthomonas campestris |
| Xax01 | - | 3758428 | 3758245 | NC_003919.1 | Xanthomonas citri |
| Ype01 | - | 4393235 | 4393008 | NC_003143.1 | Yersinia pestis |
| Aca01 | - | 340 | 170 | M34485.1 | Acinetobacter calcoaceticus |
| Avi01 | - | 388 | 214 | U45329.1 | Agrobacterium vitis |
| Bfr01 | + | 580 | 762 | AY043208.1 | Bacteroides fragilis |
| Bmg01 | + | 1211 | 1350 | AJ000758.1 | Bacillus megaterium |
| Lma01 | - | 76392 | 76234 | AL499620.1 | Leishmania major |
| Pfr01 | - | 543 | 373 | AY033236.1 | Propionibacterium freudenreichii |
| Rca01 | + | 105327 | 105521 | AF010496.1 | Rhodobacter capsulatus |
| Rca02 | + | 116991 | 117174 | AF010496.1 | Rhodobacter capsulatus |
| Rca03 | - | 39849 | 39672 | AF010496.1 | Rhodobacter capsulatus |

FIG.41AB

| | | | | | |
|---|---|---|---|---|---|
| Rsp01 | + | 201 | 341 | B07728.1 | Rhodobacter sphaeroides |
| Sbi01 | - | 330 | 147 | BH245584.1 | Sorghum bicolor |
| Sgi01 | - | 9209 | 9035 | AF263012.1 | Streptomyces griseus |
| Svi01 | - | 1235 | 1052 | U27616.3 | Stealth virus 1 |
| Zmo01 | - | 24942 | 24808 | AF193754.1 | Zymomonas mobilis |
| Zmo02 | - | 4323 | 4162 | AF193754.1 | Zymomonas mobilis |

Accession numbers are for Genbank sequence entries. Start and end positions are the 5' and 3' nucleotides of the first interior UG base pair of stem P1 (orange). Secondary structure (SS) and sequence consensus (Cons) lines are shown above the alignment. In the consensus sequence, uppercase and lowercase letters represent ≥=90% and ≥=80% conservation at a position, respectively. The degenerate bases R (A,G) and Y (C,U) appear only when a single base is not 80% conserved. Sequences marked with an asterisk (*) were excluded when determining the sequence consensus because they have >90% identity to another sequence in the alignment.

FIG.41AC

```
Avi01 CCGUGGCUGCCCCCGCAACUGUGA-ACGG-----------------------------------------------CGAGCGAUGUCCAUCAU-------------------------------
Bfr01 CCCGGACAGU-CCCGCUGCUGUGAAGCUCC-------------------------------------------GUCUGAAUUUCCGAUAACAACUGUU-------------------------
Bmg01 CCAGUACUGCCCCCGCAACUGUAA-GUGUG---------------------------------------------GACGAACGAGUAU---------------------------------
Lma01 CCGGUGCUGCCCCCGCAACGGUAA-GCGAG---------------------------------------------UGAAGCGUCAAAU---------------------------------
Pfr01 CCGGAACUGU-CCCGCAGCGGUCA-AUGGG-------------------------------------------AACGACACAACGUAAG--------------------------------
Rca01 CCGCAGCCGCCCCCGCGACCGUGACCGGA--------------------------------------------GAGGGCGCCCCGAG----------------------------------
Rca02 CCGUGGCUGCCCCCGCAACUGUGA-GCGG-----------------------------------------CGAGACGACGGUCGAAG---------------------------------
Rca03 CCGUAACUGCCCCCGCAACUGUAA-GCGG-------------------------------------------CGAGCACCCCCCGGCA--------------------------------
Rsp01 CCGGCGCGGG-CCCGCCGCUGUGA-CGG------------------------------------------GGAUGCUCCGGGCAAGAG--------------------------------
Sbi01 CCGGCGCUGCCCCCGCAACGGUAA-GCACGUC------------------------------------------AGUCCCAGGCAACAAC--------------------------------
Sgi01 CCGGGACUGC-CCCGCAGCGGUGA-GUGGG-----------------------------------------AACGACCGCCGUCAUA----------------------------------
Svi01 CCGAGACUGCCCCCGCAACUGUAA-CCGG-----------------------------------------AGAGUCAUCCUCCUAUGAUCGUAUCUUACGAUUAUA--------------
Zmo01 CCUUGGCUGCCCCUGCAACUGUAA-ACAGU-----------------------------------------------UGAAACGCCAAAAA------------------------------
Zmo02 CCAGUGCUGCCCCCGCAACUGUAA-ACGG-----------------------------------------CGAGCAAAGAUCAAAAU---------------------------------
```

FIG.41AK

| | | | |
|---|---|---|---|
| SS | <<<< <<<<<<< | | >>>>>>> >>>> |
| Cons | ryCACUG | YGGGAAGGy | |
| Atu01 | AGCCACUGGAGC | CAAAA | GCUCCGGGAAGGCUG |
| Atu02 | GCCACUGUUUUU | UUCG | GAAUGCGGGAAGGC-A |
| Atu03 | GCCAUCUC | GCCUCCAUCAA | GGGGGAAGGCAA |
| Atu04 | GUCACUGAGG | CCGG | CCUCGGGAAGAC-- |
| Atu05 | GCCACUGAA | GCAA | UUCGGGAAGGC-- |
| Atu06 | GCCACUGAACC | UUUAUGAUC | GGUUCGGGAAGGC-- |
| Bha01 | GUCACUGACCG | UUCAU | UGGUUGGGAAGAC-- |
| Bha02 | GCCACUGUACAUCCUC | UACUUCUU | GAGAAAUGUAUGGGAAGGC-- |
| Bha03 | ACCACUGUCC | AAA | GGAUGGGAAGGU-A |
| Bha04 | UCCACUGUC | UAGC | GACGGGAAGGG-G |
| Bsu01 | | CAAGC | |
| Bja01 | GUCGCUGAAGCC | UGCAC | GGCUUCGGGAAGGC-- |
| Bja02 | GCCACUGAUCCC | UGAC | GGGAUCGGGAAGGC-- |
| Bja03 | GCCACUGGGCC | GCAA | GGUCCGGGAAGGC-- |
| Bja04 | GCCACUGGG | UCCUCGGU | CCCGGGAAGGC-- |
| Bja05 | GCCACUGGGA | AUCUCGG | UCCUGGGAAGGC-- |
| Bme01 | GCCACUGAAAGCAGC | AAUAU | GCUGCAAUCGGGAAGGC-- |
| Bme02 | GCCACUGGAAAUC | AGAUG | GAUUUCUGGGAAGGC-- |
| Bme03 | GCCACUGUGCC | CAC | GGCACGGGAAGGC-A |
| Bme04 | GCCACUGGC | GAAA | GCCGGGAAGGC-- |
| Ccr01 | GUCACUGACGCGCCGAA | GCUGG | UUCGGGGAUGCGUCGGGAAGGCCA |
| Ccr02 | GCCACUGGGCC | CAAAA | GGCCUGGGAAGGC-- |
| Cte01 | GCCACUGUCCC | GUUCA | GGGAUGGGAAGGC-- |
| Cte02 | GUCACUGCCGGUUUUCC | UCCAC | GGAAAACUGCGGGAAGGU-- |
| Cte03 | GGCCACUGGUUCGC | GCCC | GCGAACCGGGAAGGCC- |
| Cte04 | --CCACUCCGCCAACCUCUG | AUAAC | CACGGGGAAUGCGGGGGAAGG--C |
| Cte05 | GUCACUGCCAGGCUCC | UCCAC | GGAGCGGGCGGGAAGGC-- |

FIG.41AL

```
Avi01 GGACAAAGCCCAGAC-----------------------------------------------------------CCGU--GAGCCAGGAGACCUGCCGAUAAGCAUGCGCGAAAGC
Bfr01 GUCGGAAACAA-------------------------------------------------------------GGAGU--CAGUCAGAAGACCUGCCGCUUAUCAAAGGCUGUUUC
Bmg01 CUCAAGUAGAAUGA----------------------------------------------------------UACAC--AAGUCAGGAGACCUGUCUUUAUUGUGAAGUUUCUAU
Lma01 UGAUGCUUUCAAGGCCCAGGCCC-------------------------------------------------CUCGC--AAGCCCGGAGACCGGCCCGAAAAAAUCAGAUAACAA
Pfr01 GUAGUGGAGGAAGUCGGGAGUGAUCUCGCAAUG---------------------------------------CCCAU--GAGUCCGAAGACCUGCCAGCAGCGACAACAUCUGUU
Rca01 GGGGCGACCGUGAGGGGACCCCCCCUCGCA-------------------------------------------UCCG-CAAGCCGGGAGACCUGCCAGCGCAUGGAUUUCGGGCG
Rca02 GACCCGAGUUGAUCGAA--------------------------------------------------------CCGC--AAGUCAGGAGACCUGCCAUCGCUCUGGCGUCGCAAG
Rca03 GGGGAAGCCACGAC-----------------------------------------------------------CCGC--AAGUCAGGAGACCUGCCAUCAGCGUCAUCAACCGCC
Rsp01 GCCCGGCGGCAGAUGAA---------------------------------------------------------CCG--GAGCCAGAAGACCGGCCUGACGCAGAGGUUCCCGCC
Sbi01 GCCUGGACGGUGGCCUCGCGCCACCC---------------------------------------------GGCGGC--AAGCCCGGAGACCGGCCCGGAAGCCUCAGGUCGCGA
Sgi01 ACGGCCACUAGGUGUCUGCCCGGCAGACGUG-----------------------------------------CCCGC--GAGUCCGAAGACCUGCCCGCUGCCCGCACGCGACCG
Svi01 GGAGGACCGAUGAAGAC--------------------------------------------------------CCGG--AAGUCAGGAGACCUGCCGUAUCCAGUCACCCAUGGC
Zmo01 GGUUGUUUCGAU------------------------------------------------------------GCUGU--GAGCCAGGAGACCGACCCUAUGUAAUCGUUCCACGA
Zmo02 UGAUCGGACGCGGUGAC--------------------------------------------------------CCGU-CAAGUCAGGAGACCUGCCUUAAACCAAGUCAUCCACU
```

FIG.41AS

C. G-Box

NC_002570.1/648448-648540 ACATGTAGATATCATCCCTTTCGtataTACTTGGAGataagg.TCCAGGAgtttctacCAGATCAccGtaaaTGATCTG.actaTGAAGGTGGAATGGCTCGATA
Bacillus halodurans NC_002570.1/650317-650406 AATAAATCGAAAACATCATTTCGtataATGGCAGGAataggg.CCTGCGAgtttctacCAAGCTAccGtaaaTAGCTTG.actaCGAAAATAATGGGTTTTTTAC
Bacillus halodurans NC_002570.1/676483-676572 CGTTCTTTATATAAAGTACCTCAtataATCTTGGGAatatgg.CCCAAAAgtttctacCTGCTGAccGtaaaTCGGCGG.actaTGGGGAAAGATTTTGGATCTT
Bacillus halodurans NC_002570.1/806882-806965 TTAATCGAGCTCAACACTCTTCGtata.TCCTCTCAatatgg.GATGAGGgtCtctacAGGTA..ccGtaaaTACCT..AGctaCGAAAAGAATGCAGTTAATGT
Bacillus halodurans NC_002570.1/1593067-1592976 ATTTACATTAAAAAAAGCACTCGtataATCGCGGGAataggg.CCCGCAAgtttctacCAGGCTGccGtaaaCAGCCTG.actaCGAGTGATACTTTGACATAGA
Bacillus halodurans NC_000964.1/693955-694038 AGAAATCAAATAAGATGAATTCGtataATCGCGGGAatatgg.CTCGCAAgtCctcacCAAGCTAccGtaaaTGGCTTG.actaCGTAAACATTTCTTTCGTTTG
Bacillus subtilis NC_000964.1/697886-697976 CATGAAATCAAAACACGACCTCAtataATCTTGGGAatatgg.CCCATAAgtttctacCCGGCAAccGtaaaTTGCCGG.actaTGCAGGAAAGTGATCGATAAA
Bacillus subtilis NC_000964.1/2319120-2319031 TTACAATATAATAGGAACACTCAtataATCGCGTGGatatgg.CACGCAAgtttctacCGGGCA.ccGtaaa.TGTCCG.actaTGGGTGAGCAATGGAACCGCA
Bacillus subtilis NC_000964.1/4004319-4004410 CATCTTAGAAAAAGACATTCTTGtataTGATCAGTAatatgg.TCTGATTgtttctacCTAGTAAccGtaaaAAACTAG.actaCAAGAAAGTTTGAATAAATTT
Bacillus subtilis NC_003030.1/1002184-1002270 TATATAAAAAACTAAATTTCTCGtataC.ACCGGTAatatgg.TCCGGAAgtttctacCTGCTG.ccAtaaa.TAGCAG.actaCGGGGTGTTATTGATAATATA
Clostridium acetobutylicum NC_003030.1/2904259-2904168 GAAAAGTAATAACATATTACCCGtataTGCTTAGAAatatgg.TCTAAGCgtCtctacCGGACTGccGtaaaTTGTCTG.actaTGGGTGTTTATAAGTATTTTA
Clostridium acetobutylicum

FIG.41AT

NC_003030.1/2824539-2824454 AATCGTTAATATAGTTTAACTCAtataT.TTCCTGAatatgg..CAGGATgtttctacAAGGAA.ccTtaaa.TTTCTT.actaTGAGTGATTTGTTTGTATGCA
Clostridium acetobutylicum NC_003366.1/422828-422924 TATGTACTTATATAAGTATATCGtataTGCTCGACGatatgg.GTTGAGTgtttctacTAGGAGGccGtaaaCATCCTA.actaCGAATATATAGGTGATTTCTA
Clostridium perfringens NC_003366.1/512410-512323 TAAGTGTATTAAATTTTAACTCGtataTAATCGGTAatatgg.TCCGAAAgtttctacCTGCTAAccGtaaaATAGCAG.actaCGAGGAGTTGTACTATAAATT
Clostridium perfringens NC_003366.1/2617892-2617807 AAAACGGAATATAAACAAACTCGtataA.GCTTTGAataagg..CAAGGCgtttctacCGGAAA.ccTtaaa.TTTCCG.TctaTGAGTGAATTTGATATACTAT
Clostridium perfringens NC_003454.1/1645257-1645173 TAAATAATTTTAATAAAAATTCGtataA.GCCTAATatatgg..AAGGGTgtCCctacGGTTAA.ccAtaaa.TTAACCAGctaCGAAAAATGTTTTACTGTGTT
Fusobacterium nucleatum NC_002662.1/1159519-1159604 GTCTATAATAGAACAATCTTATTtata...CCTAGGatatgg..CTGGGCgtttctacCTCGTA.ccGtaaa.TGCGAG.acaaTAAGGAAATTCGATTTTTTAG
Lactococcus lactis subsp. lactis NC_003210.1/610773-610679 AATCCGCTACAATAATATAGTCGtataAGTTCGGTAatatgg.ACCGTTCgtttctacCAGGCAAccGtaaaATGCCAG.GctaCGAGCTATTGTAAAATTTAAT
Listeria monocytogenes strain EGD NC_003210.1/1958601-1958511 ATAACTTAAAACCGAAATACTTGtataATAGTTGCGat.tgg.GCGACGAgtttctacCTGGTTAccGtaaaTAACCGG.actaTGAGTAGTTTGTATAAAGAAG
Listeria monocytogenes strain EGD NC_004193.1/760480-760571 CAATTTTTATCCAATGCCTTTCGtataTCCTCGATAatatgg.TTCGAAAgtAtctacCGGGTCAccGtaaaTGATCTG.actaTGAAGGCAGAAGCAGGTTCGG
Oceanobacillus iheyensis NC_004193.1/769695-769781 TGATGTAATTGAATAGAAATGCGtataATTAAGGGGatatgg..CCCACAgtttctacCAGACCAccGtaaaTGGTTTG.actaCGCAGTAATTATATTTGTATC
Oceanobacillus iheyensis NC_004193.1/786775-786863 CCGACAATTGAAAATGAACCTCAtataAATTTGAGAatatgg.CTCAGAAgtttctacCCAGCA.ccGtaaaTGGCTGG.actaTGAGGGAAGATGGATCATTTC
Oceanobacillus iheyensis NC_004193.1/1103947-1104044 AAACCTTATATATAGTTTTTTCAtataATCGCGGGGatatgg.CCTGCAAgtttctacCGGTTTAccGtaaaTGAACCG.actaTGGAAAAGCGGAAAATTCGAT
Oceanobacillus iheyensis

FIG.41AU

```
NC_002745.1/430771-430861    GTTAAATAATTTACATAAACTCAtataATCTAAAGAatatggCTTTAGAAgtttctacCATGTTGccTtGaaCGACATG.actaTGAGTAACAACACAATACTAG
Staphylococcus aureus subsp. aureus
NC_004461.1/2432384-2432294 CATAAAATAATTTATATGACTCAtataATCTAGAGAatatggCTTTAGAAgtttctacCGTGTCGccAtaaaCGACACG.actaTGAGTAACAATCCAATACATT
Staphylococcus epidermidis
NC_004116.1/1093950-1093860 CAATTAAATATATGATTTACTTATTtaT.GCTGAGgat•tgg..CTTAGCgtCtctacAAGACA.ccGt.aa.TGTCTA.acAATAAGTAAGCTAATAAATAGCT
Streptococcus agalactiae
NC_002737.1/930757-930842    TGAATTCAATAATGACATACTTATTtaT.GCTGTGAat.tgg..CGCAGCgtCtctacAAGACA.cc.ttaa.TGTCTA.acAATAAGTAAGCTTTTAGGCTTGC
Streptococcus pyogenes
NC_003028.1/1754791-1754878 AAAATTGAATATCGTTTTACTTGTTtaT.GTCGTGaat.tgg..CACGACgtTtctacAAGGTG.cc.Ggaa.CACCT.AacAATAAGTAAGTCAGCAGTGAGAT
Streptococcus pneumoniae
NC_003869.1/586372-586463    AAAAATTTAATAAGAAGCACTCAtataATCCCGAGAatatgg.CTCGGGAgtCtctacCGAACAAccGtaaaTTGTTCG.actaTGAGTGAAAGTGTACCTAGGG
Thermoanaerobacter tengcongensis

Cosensus                          ..........<<<<<<<<...<<<<<<<........>>>>>>>........<<<<<<<.......>>>>>>>...>>>>>>>>..........

                                      *********Y*TWTA*********AT**GG********GT*YCTAC*******CC***AA*********YWAYR*R****
```

FIG.41AV

D. A-Box

NC_000964.1/626134-626051 AATTAAATAGCTATTATCACTTGtataACCTCAATAatatgg.TTTGAGGgtGtctacCAGGAA.ccGtaaaATCCTG..aTtaCAAAATTTGTTTATGACATTT
Bacillus subtilis NC_003366.1/2870819-2870732 ATAAAAAAATAAATTTTGCTTCGtataACTCTAATGatatgg.ATTAGAGgtCtctacCAAGAA.ccGAGaa.TTCTTG.aTtaCGAAGAAAGCTTATTTGCTTT
Clostridium perfringens NC_004460.1/504378-504467 GACTTTCGGCGATCAACGCTTCAtataATCCTAATGatatggTTTGGGA.gtttctacCAAGAG.ccTtaaa.CTCTTG.aTTATGAAGTCTGTCGCTTTATCCG
Vibrio vulnificus

FIG.41AW

E. Lysine riboswitch comparison

Command-1 Plain Text

Command-2 Base paired stem 1

Command-3 Base paired stem 2 i. Command-4 Base paired stem 3

Command-5 Base paired stem 4

Command-6 Base paired stem 5 ii. Command-7 Base paired stem 6

Command-8 Terminator poly-U

Command-9 Downstream AT stem paired to stem 1

Command-0 Optional base paired stem 2 cuag is 90% sequence similarity

2. CUAG is the Anti-Terminator

CUAG is the Terminator stem

1. Bha_LysC AGUGAUGGUagaggU-gcGAAAACC--aAG-aguaC-ACAGUCUGAGAGAAAUG----AGAAU----CGUUGAC----GACUGUUGGAAagg--GGGAUUCgccgaagUGCAGAUCGGGG-CUCAUUCCC-AUUUGCGCUggACCUAUGUU---gaaUA-AGCAUAGGGcugucaCAACACUAG-----CCCCAA------CUAGUGCUGuggagAAcuAUCUCACGU 2. Bha_dapA AGUGAGGAUagaggU-gcAAAAACC--aAG-agua--CACAAUUGGA---GGA---GAAUGAGA----UCCGUUGAGAAUUGUG--GAAagg--GGAAUUUgccgaagCUGGAAGAAU---CUCAU--GUUCUGAAGGCUggUUCUGUAUU---AaaUA-AAUACAGAAcugucaUAUAGCG-------GAUGU---------UGCUAUAuggagGGcuAUCUCACGC 3. Bha_nhaC AGAUGGGGUagaggA-gcGGGUUUU--aAG-aguaA-GCGCUUG---------GAGGAUGACAACGAGGA-------UAAGCGC-CGAAagg--AAAACUCgccgaagCG-GAAGAUG--AGUCAAG-CGUCUUCUUGCUggGGUUGCAUU---gaaUA-AAUGUAACAcugucaCAGC---------AGAUU-----------GCUGuggagAAcuACUAACGUU 4. Bsu_LysC GGUGAAGAUagaggU-gcGAA-CUUC-aAG-aguaU-GCCUUUGGAGAA-AGA-----UGGAU------UCUGUGAA-AAAGGC-UGAAagg-GGAGCGUCgccgaagCAAAUAAAACC--CCAUC-GGUAUUAUUUGCUggCCGUGCAUU---gaaUA-AAUGUAAGGcugucaAGAAA---------UCAU-----------UUUCUuggagGGcuAUCUCGUUG 5. Cac_lysA ACCUUUUGUagaggU-gcUUUAAGUC-aAG-aguaA-CCGUUUG---GAGUU-------GGCA------AACUUAGAUGAACGG-UAAAagg•GGCUUUUAgccgaagCAUUUAGAUU---GGCA---GAUUUAUUUGCUggCUUUUCAUA---CaaCA-UAUGAAUGGcugucaCUUUAUUAGU----UAGUU-----AUUAG-GUAAGuggagCGcuACAA--GGU

FIG. 41AX

6. Cpe_nhaC AAAGA-GGUagaggC-gcGAGAAUC-aAG-auua--CUAAAAUGGA---GUU------AAGU-----AGCGUAGAAGUUUUAG--GAAagg--
GAUUAUCgccgaagUUUUUGGCU-AAUACUUUAA-GGCUAAAUGCUggGGUUGUAUA---gaaUA-UAUACAACAcugucaCA------------AAA-------------
UGuggagAGcuAUCAUCUUA 7. Cpe_lysA GACCAAAGUagaggU-gcCGUAAUU--aAG-agua--GUCAUAAGUAGCUGAC-----AAGU-----GUU--UUAUGUAUGAU--GAAagg--
GAUUAUGgccgaagAGAUAUUAAU---GGUG---AUUAAUAUUUCUggGUAUAUGUAU---aaU-AUGCAUAUAAcugucaCUUU---------GAAA------------
AAAGuggagUGcuACAAGGUAC 8. Cpe_lysP AACUGAGAUagaggC-gcGAUG-AUU-aAU-agua--UCUUUGCAGAGGU--------AAGCA-------AUUGAAGCAAAG-UGAAagg--
AUGAAUCgccgaaACCAU-UAGAAGAGGCUUUAAUUCUAUUAGGUUggGGUUGCAUA---gaaUA-UAUGUAACAcugucaCAAA---------UUAU------------
UUUGuggUgUGcuAUCAUGAAA 9. Eco_lysC CAGGCCAGAagaggC-gcG-U-UGCCCa---aguaACGGUGUUGG---AGGA------GCCAG----UCCUGUGAUAACACC-----
UggGGGUGCAUCgccgaGgUGAUUGAACG-GCUGGCCA-CGUUCA-UCAUCggCUACAGGGG-CUgaaU--CCCCUG-
GGUugucaCCAGAAGCGCUCGCAGUCGGGCGUUUCGCAAGUGGuggagCAcuUCUGGGUGA 10. Hin_nhaC UACAAAAGUagaggC-gcAAUUAUU--aUA-agua--UUUUUUCAGAG-UG-------GAUAA------CGAAGAAGAAAAAA--GAAagg--
AAUAGUUgccgaaAUCAAAUAAAA---GUCG---UUUUGUUUGGUUggUGGCGUGCUC--gaaA-GGG-GCGACAcugucaUAGUU-------UUUCUGAUU-------
AACUAuggagUGcuACGGUUGUU 11. Oih_dapA GUUUUGGAUagaggU-gcGGAGACC--aUC-agua--UAUACGCGGA---AGGG---AAAUGAG---CCCUAGUGAAGCGUAUG--GAAagg--
GGAAUCUgccgaagCGAGU--GAAAUACUCAUUCAUUA-ACUCGUUggUGCUGCUAUU--gaaCAAAUAACAGUCcugucaUAUAG--------GAGA-----------
CUAUAuggagGGcuAUCGAGCUG 12. Oih_nhaC UCGGUGGGUagaggA-gcAUACAAC--aUU-agua--AUCGAC-------AAGAGGAUGACAACGAUGAUA-----GUUGGU--GGAagg--
GUUGUUUgccgaagCA-UAAUAAG--GGUCAGA-CUUAUUAUUGCUggUACAUCUUU---gaaUA-AAAGAUGCAcugucaUGCA---------AAAUUAAG---------
UGCAuggagAAcuACUGAUCGA 13. Pmu_nhaC UACUUGUGUagaggA-gcGAUCACU--aUA-agua--UUUUUUCUGAG-UG-------GAUAA------CGAAGAGGAAAAAG--GAAagg--
AGUGACCgccgaaAUCAAUUGAAA---GUCA---UUUUGAUUGGUUggUGGCGUAUUC--gaaA-GGA-ACGUCAUugucaUAGU---------CUUUUUUAA--------
ACUAuggagCGcuACUGGUUGG

FIG. 41AY

14. Sau_lysC AUAUUUUGAugaggC-gcAUCA-AUC-aUG-agua--AAGUUUAGA--UUA------CUGUCUGC-----UAACAGCUGAAUUU--
GAAagg••GUGCGAUgccgaagCGA-UUAUAAU--AGCA--GUUAUAAUUUGUUggACUUUUUGGU--UaaGAGCU-GAGAGUUugucaUUAUU---------
UAAA----------AAUAAuggagUGcAUCACUUGUA 15. Sau_lysP AAUUGAGUUagaggUUgcAUGUUUA--aUU-agua--ACUUGU-----CAGAAGUAUUUAUGGUACAUAAGUUGA---ACAAGU--
GAAagg••UAAAGAUgccgaaAUAGAUAUAA--ACCAUAAA--UUAUAUCUAUUggGACAGUUUU--CgaaUA-GGAACUGUAcugucaCA------------GAA-
-------------UGUGAugUGcuA-C-CUUAU 16. Sep_lysC AGAUUUUGAUgaggC-gcAUCA-AUC-aUG-agua--AACUUUAGAUAAUUUG---UCUGCUAA----CAA-UUA--UAGAGUU--AAAagg•G-
UGAGAUgccgaaAUGAUUCAUAAU--AGCA--GUUAUGAAUCGUUggACUUAAUGGU--UaaGAGCUAU-AAGUUugucaUUAUU---------AUUAA---------
---AUAAuggagUGcAUCACUUGUA 17. Sep_lysP AAUAGAGUUagagcUUgcAUUAUUA--aUG-aCUa--ACUUAU-----CAGAAGUCGUAUGGGACAUGUGUUGA----AUAAGU--
GAAagg••UAAUAAUgccgaaAUGAUGUUA-UUU-CCAU-AAAUUAGCAUUguuggGACAACUUU--CgaaUA-GAAGUUGUAcugucaC-------------
UUUA-------------UGUGAugUGcuA-C-CUUAU 18. Sfl_lysC CAGGCCAGAagagcC-gcG-U-UGCCCa---aguaACGGUGUUGG---AGGA-------GCCAG-----UCCUGUGAUAACACC---
UGaggGGGUGCAUCgccgaGgUGAUUGAACG-GCUGGCCA-CGUUCA-UCAUCggCUACAGGGG-CUgaaU--CCCCUG-
GGUugucaCCAGAAGCGUUCGCAGUCGGGCGUUUCGCAAGUGGuggagCAcuUCUGGGUGA 19. Son_lysC AGGAACAGAagagcA-gcGUUAA-CU-a---Ggua--GUCAAUCAGA---GGAG----CACAAA---CUCCAGCGAUGAUUGAU---
GAGgg•AGAUUAGCgccgaGgCAUAGAUGUG--GUUGCUG-CAUGUUUAUGUCggUCGCUUAGG-CUgaaU---CCUAACGAUugucaCC-----------
UGUAAUU-----------GGuggagAGcuUCUGGUGAC 20. Son_nhaC CCUUUAAGUagagcC-gcGCUGCCU--aUG-aCua--CUUGUGCG--------GAGGGUGAUGCCGCAGA------UGUACAAG--
GAAagg••AGUCAGCgccgaagUAGC-CAGGU--CAUCAA---ACCGAGC-GCUggUUUUGCAU-CAAAUaG---GUGCAAGAcugCcaUAGU---------
CAUCC-----------ACUAuggagCGcuACcUGAAGG 21. Tma_asd GACCCGA-CGgagcC-gcGCCCGAG--aUG-agua--GGCUGUCCC--------AUCAGGGGAGGAAUCG-----GGGACGGCU--
GAAagg••CGAGGGCgccgaagG-GUGCAGAGUUCCUCCC-GCUCUGCAUGCCUggGGGUAUGGG---gaaUA-CCCAUACCAcugucaCGGAGG---------UC--
---------UCUCCGUGGagAGcCGAUCGGGUC 22. Tte_lysA AGGUGAGGUagagcC-gcGGGUCAUC-aAG-agua--ACAUGCCAGA---GGU---GUUAAGG-----GCCGAUGAAGGUGUGU--GAAagg-
GGUG-CCCgccgaagC-GCGUAAACUU-CCUUAAGGUUUACGCAGCUggGCCUAUGCC---gaaCA-GGUAUAGGAcugucaCUGAAGGCU-----CCCCA-------
GGCCUUCAGuggagAGcuAUCUCGCUA

FIG. 41AZ

23. Tte_pspF CGCAUAAAUagaggA-gcUGCCAAGC-aU---guaUUUGGCGAGGUGUUAAGGAGAAGAACCUCC-------AAUA-CUCGCUG-
AAGAagg••UUUGGCUgccgaaAGGGUGAGCUUG--UUCU--UGAGCUCAUCcuuggUGGUAAAC---ACaaA---GUUUACCAcugucaUGGGA---------CC-
-----------UCCCAUGAagCGcuAUUUAUGCA 24. Vch_lysC UCUAGCAGAagaggA-gcACUG--CCCaGGCag-aUGUUUUGUGGA--------GCCUCAACUCCAAU---------
ACAGAACAUUCaggGGGAGUAGUgccgaGgUGAAUCAAAGUU-GU---GGCUUUGGUUUAUC ggUUGAACGGG-CUgaaU--CCC-UUCAAcugucaUCAG------
---CUCGAAU----------CUGAugAagAGcuUCUGAGGGA 25. Vch_nhaC UUUCGCCGUagaggA-gcGGUUACG--aAA-agua--UCCACAGUU-------GGGGUGAUGCCAAUG-----AAUUGUGGA--
AAAagg••CGUUGCCgccgaagUCAACUUGC--CCAUCAAC--GC-AGUUGGCUggGGUUACAUU---CaaUA-GGUGUAACACuGCcaUAGU------
CUAUAUUGUUGUUAA------ACUAUGGagCGcuAC--UGUAG 26. Vch_nhaC2 CUUUAA-GUagaggC-gcGCUGUUC--aUG-aguCG-CCAGUCGU--------AGGUUGACCCCGAUG-------AUGACUGG-
UUAAagg••GUACAGCgccgaagUGAUCGUUG---CGUCAU---CAACGUUCGCUggGCCAGCAUU---gaaCA-AAUGCCGGAcugCcaUAG---------
UGUGUUGU-----------CUAUGGagCGcuACCUUGAAG 27. Vvu_lysC UUUUGCAGAagaggA-gcACUG--CCCaGGCag-aUGUUUUGUGGA--------GCCGCAACUCCAAC---------
ACAGAACAUUCaggGGGAGUAGUgccgaGgUAGAUCAAAAUU-GCA--GAUUU-GAUCUGUCggUUGACUUGGGUUgagU-CCCA--UCAAcugucaUCAGC------
----UCA----------GCCUGAugAagAGcuUCUGAGAUG 28. Vvu_nhaC UAUCGACGUagaggC-gcAAUGG-UA-aAG-agua--ACUAUUAUU-------GGGGUGAUGCCAAUG-----AAUAAUAGU--
GAAagg•UAUCCAUUgccgaagUGAAUUGC---AUAUCAAA---GCAGUUUGCUggGGUUGCAUCC--gaaA-GGAA-CAACAcugCcaUAGU-------
AUUUAAUGUAUA--------ACUAUGGagCGcuACUGUAGGU 29. #=GC SS_cons
.....<<<<<<.....<<<<<<<<<<<.........<<<<<<<<............................>>>>>>>>.......>>>>>>>>>>>...<<
<<<<<<<<<<.........>>>>>>>>>>>><<<<<<<<<<<<......>>>>>>>>>>>>.<<<<<<<<<<<<................>>>>>>>>>>>>...
.>>>>>>.....

FIG. 41BA

SEQUENCE LISTING

<160> NUMBER OF SEQ ID NOS: 410

<210> SEQ ID NO 1
<211> LENGTH: 202
<212> TYPE: RNA
<213> ORGANISM: Escherichia coli

<400> SEQUENCE: 1
gccgguccug ugaguuaaua gggaauccag ugcgaaucug gagcugacgc gcagcgguaa 60
ggaaaggugc gaugauugcg uuaugcggac acugccauuc ggugggaagu caucaucucu 120
uaguaucuua gauaccccuc caagcccgaa gaccugccgg ccaacgucgc aucugguucu 180
caucaucgcg uaauauugau ga 202

<210> SEQ ID NO 2
<211> LENGTH: 165
<212> TYPE: RNA
<213> ORGANISM: Escherichia coli
<220> FEATURE:
<221> NAME/KEY: misc_feature
<222> LOCATION: 155
<223> OTHER INFORMATION: r = a or g
<220> FEATURE:
<221> NAME/KEY: misc_feature
<222> LOCATION: 157
<223> OTHER INFORMATION: y = c or u

<400> SEQUENCE: 2
ggaaccaaac gacucggggu gcccuucugc gugaaggcug agaaauaccc guaucaccug 60
aucuggauaa ugccagcgua gggaagucac ggaccaccag gucauugcuu cuucacguua 120
uggcaggagc aaacuaugca agucgaccug cuggruycag cgcaa 165

<210> SEQ ID NO 3
<211> LENGTH: 240
<212> TYPE: RNA
<213> ORGANISM: Escherichia coli
<220> FEATURE:
<221> NAME/KEY: misc_feature
<222> LOCATION: 155-240
<223> OTHER INFORMATION: n = g, a, c or u

<400> SEQUENCE: 3
ggaaugcccc auuugcgggg cuaauuucuu gucggagugc cuuaacuggc ugagaccguu 60
uauucgggau ccgcggaacc ugaucaggcu aauaccugcg aagggaacaa gaguuaaucu 120
gcuaucgcau cgccccugcg gcgaucgucu cuugnnnnnn nnnnnnnnnn nnnnnnnnnn 180
nnnnnnnnnn nnnnnnnnnn nnnnnnnnnn nnnnnnnnnn nnnnnnnnnn nnnnnnnnnn 240

<210> SEQ ID NO 4
<211> LENGTH: 165
<212> TYPE: RNA
<213> ORGANISM: Escherichia coli
<220> FEATURE:
<221> NAME/KEY: misc_feature
<222> LOCATION: 65, 74, 107, 130
<223> OTHER INFORMATION: s = g or c
<220> FEATURE:
<221> NAME/KEY: misc_feature
<222> LOCATION: 25, 26, 34, 35, 64, 75, 106, 131
<223> OTHER INFORMATION: w = a or u

<400> SEQUENCE: 4
ggaaccaaac gacucggggu gcccwwcugc gugwwggcug agaaauaccc guaucaccug 60

-continued

```
aucwsgauaa ugcswgcgua gggaagucac ggaccaccag gucauwscuu cuucacguua    120

uggcaggags waacuaugca agucgaccug cuggauccag cgcaa                   165


<210> SEQ ID NO 5
<211> LENGTH: 176
<212> TYPE: RNA
<213> ORGANISM: Artificial Sequence
<220> FEATURE:
<223> OTHER INFORMATION: Description of Artificial Sequence:/Note =
      synthetic construct
<220> FEATURE:
<221> NAME/KEY: misc_feature
<222> LOCATION: 39-156
<223> OTHER INFORMATION: n = g, a, c or u

<400> SEQUENCE: 5

ggauaauagc cguagguugc gaaagcgacc cugaguagnn nnnnncaaga gaagcagagg     60

gacuggcccg acgaagcuuc agcaaccggu guaauggcga ucagccauga ccaaggugcu    120

aaauccagca agcucgaaca gcuuggaagn nnnnnncgaa acgguagcga gagcuc        176


<210> SEQ ID NO 6
<211> LENGTH: 4
<212> TYPE: RNA
<213> ORGANISM: Artificial Sequence
<220> FEATURE:
<223> OTHER INFORMATION: Description of Artificial Sequence:/Note =
      synthetic construct
<220> FEATURE:
<221> NAME/KEY: misc_feature
<222> LOCATION: 4
<223> OTHER INFORMATION: n = g, a, c or u

<400> SEQUENCE: 6

ggun                                                                   4


<210> SEQ ID NO 7
<211> LENGTH: 6
<212> TYPE: RNA
<213> ORGANISM: Artificial Sequence
<220> FEATURE:
<223> OTHER INFORMATION: Description of Artificial Sequence:/Note =
      synthetic construct
<220> FEATURE:
<221> NAME/KEY: misc_feature
<222> LOCATION: 6
<223> OTHER INFORMATION: d = g, a or u
<220> FEATURE:
<221> NAME/KEY: misc_feature
<222> LOCATION: 1-4
<223> OTHER INFORMATION: n = g, a, c or u

<400> SEQUENCE: 7

nnnngd                                                                 6


<210> SEQ ID NO 8
<211> LENGTH: 36
<212> TYPE: RNA
<213> ORGANISM: Artificial Sequence
<220> FEATURE:
<223> OTHER INFORMATION: Description of Artificial Sequence:/Note =
      synthetic construct
<220> FEATURE:
<221> NAME/KEY: misc_feature
<222> LOCATION: 11, 17, 20, 25, 36
<223> OTHER INFORMATION: n = g, a, c or u
<220> FEATURE:
<221> NAME/KEY: misc_feature
<222> LOCATION: 6, 35
<223> OTHER INFORMATION: r = a or g
<220> FEATURE:
```

<221> NAME/KEY: misc_feature
<222> LOCATION: 1-3, 15, 31
<223> OTHER INFORMATION: y = c or u

<400> SEQUENCE: 8
yyyucrgggc ngggygnaan ucccnaccgg yggurn 36

<210> SEQ ID NO 9
<211> LENGTH: 51
<212> TYPE: RNA
<213> ORGANISM: Artificial Sequence
<220> FEATURE:
<223> OTHER INFORMATION: Description of Artificial Sequence:/Note = synthetic construct
<220> FEATURE:
<221> NAME/KEY: misc_feature
<222> LOCATION: 1, 7-9, 13, 14, 16, 18, 25, 26, 32, 33, 37, 39, 42, 43, 50, 51
<223> OTHER INFORMATION: n = g, a, c or u
<220> FEATURE:
<221> NAME/KEY: misc_feature
<222> LOCATION: 38, 44
<223> OTHER INFORMATION: r = a or g
<220> FEATURE:
<221> NAME/KEY: misc_feature
<222> LOCATION: 17, 34
<223> OTHER INFORMATION: y = c or u

<400> SEQUENCE: 9
ncuuaunnng agnngnynga gggannggcc cnnyganrnc cnnrgcaacn n 51

<210> SEQ ID NO 10
<211> LENGTH: 69
<212> TYPE: RNA
<213> ORGANISM: Artificial Sequence
<220> FEATURE:
<223> OTHER INFORMATION: Description of Artificial Sequence:/Note = synthetic construct
<220> FEATURE:
<221> NAME/KEY: misc_feature
<222> LOCATION: 1, 2, 10-17, 22, 25-31, 34, 40-46, 54-60, 68, 69
<223> OTHER INFORMATION: n = g, a, c or u
<220> FEATURE:
<221> NAME/KEY: misc_feature
<222> LOCATION: 5, 18, 67
<223> OTHER INFORMATION: r = a or g
<220> FEATURE:
<221> NAME/KEY: misc_feature
<222> LOCATION: 65
<223> OTHER INFORMATION: y = c or u

<400> SEQUENCE: 10
nnucruauan nnnnnnnrau anggnnnnnn ngunucuacn nnnnnnccgu aaannnnnnn 60 acuaygrnn 69

<210> SEQ ID NO 11
<211> LENGTH: 69
<212> TYPE: RNA
<213> ORGANISM: Artificial Sequence
<220> FEATURE:
<223> OTHER INFORMATION: Description of Artificial Sequence:/Note = synthetic construct
<220> FEATURE:
<221> NAME/KEY: misc_feature
<222> LOCATION: 1, 2, 10-17, 22, 25-31, 34, 40-46, 54-60, 68, 69
<223> OTHER INFORMATION: n = g, a, c or u
<220> FEATURE:
<221> NAME/KEY: misc_feature
<222> LOCATION: 5, 18, 67
<223> OTHER INFORMATION: r = a or g
<220> FEATURE:
<221> NAME/KEY: misc_feature
<222> LOCATION: 65

<223> OTHER INFORMATION: y = c or u

<400> SEQUENCE: 11
nnucruauan nnnnnnnrau anggnnnnnn ngunucuacn nnnnnnccgu aaannnnnnn 60 auuaygrnn 69

<210> SEQ ID NO 12
<211> LENGTH: 33
<212> TYPE: RNA
<213> ORGANISM: Artificial Sequence
<220> FEATURE:
<223> OTHER INFORMATION: Description of Artificial Sequence:/Note =
synthetic construct
<220> FEATURE:
<221> NAME/KEY: misc_feature
<222> LOCATION: 13-18, 20, 21, 26-33
<223> OTHER INFORMATION: n = g, a, c or u
<220> FEATURE:
<221> NAME/KEY: misc_feature
<222> LOCATION: 2, 12
<223> OTHER INFORMATION: r = a or g
<220> FEATURE:
<221> NAME/KEY: misc_feature
<222> LOCATION: 3
<223> OTHER INFORMATION: w = a or u
<220> FEATURE:
<221> NAME/KEY: misc_feature
<222> LOCATION: 8
<223> OTHER INFORMATION: h = a or c or u

<400> SEQUENCE: 12
rwagagghgc rnnnnnnann aguannnnnn nnn 33

<210> SEQ ID NO 13
<211> LENGTH: 165
<212> TYPE: RNA
<213> ORGANISM: Bacillus subtilis

<400> SEQUENCE: 13
ggaaggacaa augaauaaag auuguauccu ucggggcagg guggaaaucc cgaccggcgg 60
uaguaaagca cauuugcuuu agagcccgug acccgugugc auaagcacgc gguggauuca 120
guuuaagcug aagccgacag ugaaagucug gaugggagaa ggaug 165

<210> SEQ ID NO 14
<211> LENGTH: 128
<212> TYPE: RNA
<213> ORGANISM: Arabidopsis thaliana

<400> SEQUENCE: 14
ggugaauuga caugcaaaag caccaggggu gcuugaacca ggauagccug cgaaaaggcg 60
ggcuauccgg gaccaggcug agaaaguccc uuugaaccug aacaggguaa ugccugcgca 120
gggagugu 128

<210> SEQ ID NO 15
<211> LENGTH: 135
<212> TYPE: RNA
<213> ORGANISM: Oryza sativa
<220> FEATURE:
<221> NAME/KEY: misc_feature
<222> LOCATION: 33-83
<223> OTHER INFORMATION: n = g, a, c or u

<400> SEQUENCE: 15
ggugaauuga caugcaaaag caccaggggu gcnnnnnnnn nnnnnnnnnn nnnnnnnnnn 60
nnnnnnnnnn nnnnnnnnnn nnngcugaga aagucccuuu gaaccugaac aggauaaugc 120

```
cugcgaaggg agugu                                                    135

<210> SEQ ID NO 16
<211> LENGTH: 135
<212> TYPE: RNA
<213> ORGANISM: Poa secunda
<220> FEATURE:
<221> NAME/KEY: misc_feature
<222> LOCATION: 33-83
<223> OTHER INFORMATION: n = g, a, c or u

<400> SEQUENCE: 16

ggugaauuga caugcaaaag caccaggggu gcnnnnnnnn nnnnnnnnnn nnnnnnnnnn    60

nnnnnnnnnn nnnnnnnnnn nnngcugaga aagucccuuu gaaccugaac aggauaaugc   120

cugcguaggg agugu                                                    135

<210> SEQ ID NO 17
<211> LENGTH: 176
<212> TYPE: RNA
<213> ORGANISM: Neurospora crassa
<220> FEATURE:
<221> NAME/KEY: misc_feature
<222> LOCATION: 15-123
<223> OTHER INFORMATION: n = g, a, c or u

<400> SEQUENCE: 17

gcuaccgggu guccnnnnnn nnnnnnnnnn nnnnnnnnnn nnnnnnnnnn nnnnnnnnnn    60

nnnnnnnnnn nnnnnnnnnn nnnnnnnnnn nnnnnnnnnn nnnnnnnnnn nnnnnnnnnn   120

nnnggucuga gaaauaccgg cgaacuugau cuggauaaua ccagcgaaag gauggc        176

<210> SEQ ID NO 18
<211> LENGTH: 22
<212> TYPE: RNA
<213> ORGANISM: Arabidopsis thaliana
<220> FEATURE:
<221> NAME/KEY: misc_feature
<222> LOCATION: 9
<223> OTHER INFORMATION: d = g, a or u
<220> FEATURE:
<221> NAME/KEY: misc_feature
<222> LOCATION: 1-7, 10-16
<223> OTHER INFORMATION: n = g, a, c or u

<400> SEQUENCE: 18

nnnnnnngdn nnnnnncuga ga                                             22

<210> SEQ ID NO 19
<211> LENGTH: 103
<212> TYPE: RNA
<213> ORGANISM: Escherichia coli
<220> FEATURE:
<221> NAME/KEY: misc_feature
<222> LOCATION: 12-51
<223> OTHER INFORMATION: n = g, a, c or u

<400> SEQUENCE: 19

accaaacgac uncggggugn nnnnnnnnnn nnnnncugag annnnnnnnn naauacccgu    60

aucaccugau cuggauaaug ccagcguagg gaagucacgg acc                     103

<210> SEQ ID NO 20
<211> LENGTH: 97
<212> TYPE: RNA
<213> ORGANISM: Escherichia coli
<220> FEATURE:
<221> NAME/KEY: misc_feature
```

<222> LOCATION: 12-29
<223> OTHER INFORMATION: n = g, a, c or u

<400> SEQUENCE: 20
uaauuucuug uncggagugn nnnnnnnnnc ugagaccguu uauucgggau ccgcggaacc 60
ugaucaggcu aauaccugcg aagggaacaa gaguuaa 97

<210> SEQ ID NO 21
<211> LENGTH: 147
<212> TYPE: RNA
<213> ORGANISM: Clostridium acetobutylicum
<220> FEATURE:
<221> NAME/KEY: misc_feature
<222> LOCATION: 12-94
<223> OTHER INFORMATION: n = g, a, c or u

<400> SEQUENCE: 21
auauuuuagc unaggggugn nnnnnnnnnn nnnnnnnnnn nnnnnnnnnn nnnnnnnnnn 60
nnnnnnnnnn nnnnnnnnnc ugagaggang aaanuccaac ccuuugaacu ugauguaguu 120
aauacuaccg uagggaagca gugcauu 147

<210> SEQ ID NO 22
<211> LENGTH: 202
<212> TYPE: RNA
<213> ORGANISM: Neurospora crassa
<220> FEATURE:
<221> NAME/KEY: misc_feature
<222> LOCATION: 19-159
<223> OTHER INFORMATION: n = g, a, c or u

<400> SEQUENCE: 22
caagacagcu accgggugnn nnnnnnnnnn nnnnnnnnnn nnnnnnnnnn nnnnnnnnnn 60
nnnnnnnnnn nnnnnnnnnn nnnnnnnnnn nnnnnnnnnn nnnnnnnnnn nnnnnnnnnn 120
nnnnnnnnnn nnnncugaga nnnnnnnnnn aauaccggnc gaacuugauc uggauaauac 180
cagcgaaagg auuggcuucu ug 202

<210> SEQ ID NO 23
<211> LENGTH: 190
<212> TYPE: RNA
<213> ORGANISM: Aspergillus oryzaa
<220> FEATURE:
<221> NAME/KEY: misc_feature
<222> LOCATION: 12-137
<223> OTHER INFORMATION: n = g, a, c or u

<400> SEQUENCE: 23
cuuuggcgug gngccggugn nnnnnnnnnn nnnnnnnnnn nnnnnnnnnn nnnnnnnnnn 60
nnnnnnnnnn nnnnnnnnnn nnnnnnnnnn nnnnnnnnnn nnnnnnnnnn nnnnnnnnnn 120
nncugagann nnnnnnnuua uacggcuaaa acuugaucug gauaauacca gcgaaagggu 180
caugccuucu 190

<210> SEQ ID NO 24
<211> LENGTH: 150
<212> TYPE: RNA
<213> ORGANISM: Fusarium oxyaporum
<220> FEATURE:
<221> NAME/KEY: misc_feature
<222> LOCATION: 12-117
<223> OTHER INFORMATION: n = g, a, c or u

<400> SEQUENCE: 24
aucaugcaug angccggugn nnnnnnnnnn nnnnnnnnnn nnnnnnnnnn nnnnnnnnnn 60
nnnnnnnnnn nnnnnnnnnn nncugagann nnnnnnnuua uacggcnaaa acuugaucug 120
gauaauacca gcgaaaggau caugucaucu 150

<210> SEQ ID NO 25
<211> LENGTH: 156
<212> TYPE: RNA
<213> ORGANISM: Fusarium solani
<220> FEATURE:
<221> NAME/KEY: misc_feature
<222> LOCATION: 12-113
<223> OTHER INFORMATION: n = g, a, c or u

<400> SEQUENCE: 25
aucaugcaug angccggugn nnnnnnnnnn nnnnnnnnnn nnnnnnnnnn nnnnnnnnnn 60
nnnnnnnnnn nnnnnnnnnn nnnnnnnncu gagannnnnn nnnuuauacg gcngaaacuu 120
gaucuggaua auaccagcga aaggaucaug cucucc 156

<210> SEQ ID NO 26
<211> LENGTH: 133
<212> TYPE: RNA
<213> ORGANISM: Arabidopsis thaliana
<220> FEATURE:
<221> NAME/KEY: misc_feature
<222> LOCATION: 12-81
<223> OTHER INFORMATION: n = g, a, c or u

<400> SEQUENCE: 26
gcaaaagcac cnaggggugn nnnnnnnnnn nnnnnnnnnn nnnnnnnnnn nnnnnnnnnn 60
nnnnncugag annnnnnnnn naagucccuu ugaaccugaa cagguaaug ccugcgcagg 120 gagugugcag uuu 133

<210> SEQ ID NO 27
<211> LENGTH: 140
<212> TYPE: RNA
<213> ORGANISM: Poa secunda
<220> FEATURE:
<221> NAME/KEY: misc_feature
<222> LOCATION: 12-88
<223> OTHER INFORMATION: n = g, a, c or u

<400> SEQUENCE: 27
aaaguugcac cnaggggugn nnnnnnnnnn nnnnnnnnnn nnnnnnnnnn nnnnnnnnnn 60
nnnnnnnnnn nncugagann nnnnnnnnaa gucccuuuga accugaacag gauaaugccu 120
gcguagggag ugugcauuuc 140

<210> SEQ ID NO 28
<211> LENGTH: 140
<212> TYPE: RNA
<213> ORGANISM: Oryza sativa
<220> FEATURE:
<221> NAME/KEY: misc_feature
<222> LOCATION: 12-88
<223> OTHER INFORMATION: n = g, a, c or u

<400> SEQUENCE: 28
aaaguugcac cnaggggugn nnnnnnnnnn nnnnnnnnnn nnnnnnnnnn nnnnnnnnnn 60
nnnnnnnnnn nncugagann nnnnnnnnaa gucccuuuga accugaacag gauaaugccu 120
gcgaagggag ugugcauuuc 140

<210> SEQ ID NO 29
<211> LENGTH: 214

<212> TYPE: RNA
<213> ORGANISM: Bacillus anthracis
<220> FEATURE:
<221> NAME/KEY: misc_feature
<222> LOCATION: 26-190
<223> OTHER INFORMATION: n = g, a, c or u

<400> SEQUENCE: 29
cggugaggua gagguugcag ucauunaagn aguannucau uucugnnngn agnnauagug 60
nnnnnaugau ganaggaaug anngaaagga augaunnugc cgaaguaagu uguguccacc 120
aunnngcaca cuugcugggu cugcauuuaa uaanngugca gaanncuguc acaaacguuu 180
nnnnnnnnnn cguuugugga gagcuaucga gagg 214

<210> SEQ ID NO 30
<211> LENGTH: 214
<212> TYPE: RNA
<213> ORGANISM: Bacillus anthracis
<220> FEATURE:
<221> NAME/KEY: misc_feature
<222> LOCATION: 25-191
<223> OTHER INFORMATION: n = g, a, c or u

<400> SEQUENCE: 30
cucaaaggua gaggccgcga uaggnnaaag aguannagcu auggnnnngn agnnuuaaug 60
nnnnnaannn nnnnnnnggu unngaaaggg acuaunnugc cgaaauauaa gaauaaccau 120
nncuuauuca uauauuggga cugcauunnn gaauaaaugu aguancuguc auaagauuua 180
nnnnnnnnnn nuuuuaugga gagcuauuug gaga 214

<210> SEQ ID NO 31
<211> LENGTH: 214
<212> TYPE: RNA
<213> ORGANISM: Bacillus anthracis
<220> FEATURE:
<221> NAME/KEY: misc_feature
<222> LOCATION: 26-165
<223> OTHER INFORMATION: n = g, a, c or u

<400> SEQUENCE: 31
cgaugaggua gagguugcga cuuuunaagn aguannaaac ggacnnnngn agauacgaga 60
annnngucua aganuccguu unngaaagga aaagunnugc cgaaguuuau auuucuucuc 120
unnggaaaua ugagcugggg cugugucnnu gaaanggaac agaancuguc acguuuacaa 180
aauuaccgug uaaacguggg gugcuaucuu aacg 214

<210> SEQ ID NO 32
<211> LENGTH: 214
<212> TYPE: RNA
<213> ORGANISM: Bacillus halodurans
<220> FEATURE:
<221> NAME/KEY: misc_feature
<222> LOCATION: 16-189
<223> OTHER INFORMATION: n = g, a, c or u

<400> SEQUENCE: 32
agugaggaua gaggungcaa aaaccnaagn aguanncaca auunnnnggn agnngagaau 60
gaganuccgu ugagaauugu gnngaaaggg gaannuuugc cgaagcugga agaaucucau 120
nnnnguucug aaggcugguu cuguauunnn aaauaaaauac agaancuguc auauagcgga 180
ugunnnnnnu gcuauaugga gggcuaucuc acgc 214

<210> SEQ ID NO 33
<211> LENGTH: 214

<212> TYPE: RNA
<213> ORGANISM: Bacillus halodurans
<220> FEATURE:
<221> NAME/KEY: misc_feature
<222> LOCATION: 16-187
<223> OTHER INFORMATION: n = g, a, c or u

<400> SEQUENCE: 33
agugauggua gaggungcga aaaccnaagn aguacnacag ucnnnugagn agnaaaugag 60
aaucguugac nnnnngacug uuggaaaggg ggannuucgc cgaagugcag aucggggcuc 120
aunucccauu ugcgcuggac cuauguunnn gaauaagcau agggncuguc acaacacuag 180
ccccaancua gugcugugga gaacuaucuc acgu 214

<210> SEQ ID NO 34
<211> LENGTH: 214
<212> TYPE: RNA
<213> ORGANISM: Bacillus halodurans
<220> FEATURE:
<221> NAME/KEY: misc_feature
<222> LOCATION: 16-191
<223> OTHER INFORMATION: n = g, a, c or u

<400> SEQUENCE: 34 agaugggua gaggangcgg guuuunaagn aguaangcgc uugnnnnngn aggaugacaa 60
nnnnncgagg annnuaagcg cncgaaagga aaanncucgc cgaagcggaa gaugagucaa 120
gnnncgucuu cuugcugggg uugcauunnn gaauaaaugu aacancuguc acagcagaun 180
nnnnnnnnnn nugcugugga gaacuacuaa cguu 214

<210> SEQ ID NO 35
<211> LENGTH: 214
<212> TYPE: RNA
<213> ORGANISM: Bacillus subtilis
<220> FEATURE:
<221> NAME/KEY: misc_feature
<222> LOCATION: 16-191
<223> OTHER INFORMATION: n = g, a, c or u

<400> SEQUENCE: 35
ggugaagaua gaggungcga acuucnaagn aguaungccu uunnnnnggn agnaaagaug 60
gannnuucug ugaanaaagg cnugaaaggg gagcgnucgc cgaagcaaau aaaaccccau 120
cnngguauua uuugcuggcc gugcauunnn gaauaaaugu aaggncuguc aagaaaucau 180
nnnnnnnnnn nuuucuugga gggcuaucuc guug 214

<210> SEQ ID NO 36
<211> LENGTH: 214
<212> TYPE: RNA
<213> ORGANISM: Clostridium acetobutylicum
<220> FEATURE:
<221> NAME/KEY: misc_feature
<222> LOCATION: 16-165
<223> OTHER INFORMATION: n = g, a, c or u

<400> SEQUENCE: 36
accuuuugua gaggungcuu uaagucaagn aguaanccgu uugnnnnngn agnnuuggca 60
nnnnnaacuu aganugaacg gnuaaaaggg gcuuuunagc cgaagcauuu agauuggcan 120
nnnngauuua uuugcuggcu uuucauannn caacauauga auggncuguc acuuuauuag 180
uuaguuauua gguaagugga gcgcuacaag guac 214

<210> SEQ ID NO 37
<211> LENGTH: 215

<212> TYPE: RNA
<213> ORGANISM: Clostridium perfringens
<220> FEATURE:
<221> NAME/KEY: misc_feature
<222> LOCATION: 16-193
<223> OTHER INFORMATION: n = g, a, c or u

<400> SEQUENCE: 37
gaccaaagua gaggungccg uaauunaagn aguannguca uannnnnagu agnncugaca 60
nnnnnagnnn nnnnnnuaug aunngaaagg gauunnaugg ccgaagagau auuaauggug 120
nnnnnauuaa uauuucuggg uauauguaun nnaaunaugc auauaacugu cacuuugaaa 180
nnnnnnnnnn nnnaaagugg agugcuacaa gguac 215

<210> SEQ ID NO 38
<211> LENGTH: 214
<212> TYPE: RNA
<213> ORGANISM: Clostridium perfringens
<220> FEATURE:
<221> NAME/KEY: misc_feature
<222> LOCATION: 16-192
<223> OTHER INFORMATION: n = g, a, c or u

<400> SEQUENCE: 38
aacugagaua gaggcngcga ugauunaaun aguannucuu ugcnnnnagn agnnguaagc 60
annnnauuga annnngcaaa gnugaaagga ugannaucgc cgaaaccauu agaagaggcu 120
uuaauucuau uagguugggg uugcauannn gaauauaugu aacancuguc acaaauuaun 180
nnnnnnnnnn nnuuuguggu gugcuaucau gaaa 214

<210> SEQ ID NO 39
<211> LENGTH: 214
<212> TYPE: RNA
<213> ORGANISM: Clostridium perfringens
<220> FEATURE:
<221> NAME/KEY: misc_feature
<222> LOCATION: 16-194
<223> OTHER INFORMATION: n = g, a, c or u

<400> SEQUENCE: 39
aaaagaggua gaggcngcga gaaucnaagn auuanncuaa aaunnnnggn agnnuuaagu 60
nnnnnagcgu agaaguuuua gnngaaaggg auuaunncgc cgaaguuuuu ggcuaauacu 120
uuaanggcua aaugcugggg uuguauannn gaauauauac aacancuguc acaaaannnn 180
nnnnnnnnnn nnnnugugga gagcuaucau cuua 214

<210> SEQ ID NO 40
<211> LENGTH: 225
<212> TYPE: RNA
<213> ORGANISM: Escherichia coli
<220> FEATURE:
<221> NAME/KEY: misc_feature
<222> LOCATION: 16-204
<223> OTHER INFORMATION: n = g, a, c or u

<400> SEQUENCE: 40
caggccagaa gaggcngcgu ugcccnannn aguaacggug uugnnnnngn agnngagcca 60
gnnnnuccug uganuaacac cnnnnnuggg ggugcaucgc cgaggugauu gaacggcugg 120
ccanncguuc aucaucggcu acaggggncu gaauncccccu gggnnuuguc accannnnnn 180
nnnnnnnnnn nnnnnnnnnn nnnnuggugg agcacuucug gguga 225

<210> SEQ ID NO 41
<211> LENGTH: 214

<212> TYPE: RNA
<213> ORGANISM: Haemophilus influenzae
<220> FEATURE:
<221> NAME/KEY: misc_feature
<222> LOCATION: 16-191
<223> OTHER INFORMATION: n = g, a, c or u

<400> SEQUENCE: 41
uacaaaagua gaggcngcaa uuauunauan aguannuuuu uucnnnnagn agnnuggaua 60
annnncgaag aanngaaaaa anngaaagga auagunnugc cgaaaucaaa uaaaagucgn 120
nnnnuuuugu uugguuggug gcgugcucnn gaaangggc gacancuguc auaguuuuuc 180
ugauunnnnn naacuaugga gugcuacggu uguu 214

<210> SEQ ID NO 42
<211> LENGTH: 215
<212> TYPE: RNA
<213> ORGANISM: Oceanobacillus iheyensis
<220> FEATURE:
<221> NAME/KEY: misc_feature
<222> LOCATION: 16-192
<223> OTHER INFORMATION: n = g, a, c or u

<400> SEQUENCE: 42
guuuuggaua gaggungcgg agaccnaucn aguannuaua cgcnnnngga agnnggaaau 60
gagnnccnnn nnnnngcgua ugnngaaagg ggaannucug ccgaagcgag ugaaauacuc 120
auucauuann acucguuggu gcugcuauun ngaacaaaua acaguccugu cauauaggag 180
annnnnnnnn nncuauaugg agggcuaucg agcug 215

<210> SEQ ID NO 43
<211> LENGTH: 214
<212> TYPE: RNA
<213> ORGANISM: Oceanobacillus iheyensis
<220> FEATURE:
<221> NAME/KEY: misc_feature
<222> LOCATION: 16-192
<223> OTHER INFORMATION: n = g, a, c or u

<400> SEQUENCE: 43
ucggugggua gaggangcau acaacnauun aguannaucg acnnnnaagn aggaugacaa 60
nnnnncgaug auannguugg unnggaaggg uuguunnugc cgaagcauaa uaagggucag 120
annncuuauu auugcuggua caucuuunnn gaauaaaaga ugcancuguc augcaaaauu 180
aagnnnnnnn nnugcaugga gaacuacuga ucga 214

<210> SEQ ID NO 44
<211> LENGTH: 214
<212> TYPE: RNA
<213> ORGANISM: Pasteurella multocida
<220> FEATURE:
<221> NAME/KEY: misc_feature
<222> LOCATION: 16-192
<223> OTHER INFORMATION: n = g, a, c or u

<400> SEQUENCE: 44
uacuugugua gaggangcga ucacunauan aguannuuuu uucunnnngn agnnuggaua 60
annnncgaag annggaaaaa gnngaaagga gugacnncgc cgaaaucaau ugaaagucan 120
nnnnuuuuga uugguuggug gcguauucnn gaaanggaac gucanuuguc auagucuuuu 180
uuaannnnnn nnacuaugga gcgcuacugg uugg 214

<210> SEQ ID NO 45
<211> LENGTH: 214

```
<212> TYPE: RNA
<213> ORGANISM: Staphylococcus aureus
<220> FEATURE:
<221> NAME/KEY: misc_feature
<222> LOCATION: 16-191
<223> OTHER INFORMATION: n = g, a, c or u

<400> SEQUENCE: 45

auauuuugau gaggcngcau caaucnaugn aguannaagu uuannnnngn aunnuacugu      60

cugcnuaaca gcnnugaauu unngaaaggg ugcnngaugc cgaagcgauu auaauagcan     120

nnnguuauaa uuuguuggac uuuuuggunn uaagagcuga gagunuuguc auuauuuaaa     180

nnnnnnnnnn naauaaugga gugcaucacu ugua                                 214

<210> SEQ ID NO 46
<211> LENGTH: 216
<212> TYPE: RNA
<213> ORGANISM: Staphylococcus aureus
<220> FEATURE:
<221> NAME/KEY: misc_feature
<222> LOCATION: 26-196
<223> OTHER INFORMATION: n = g, a, c or u

<400> SEQUENCE: 46

aauugaguua gagguugcau guuuanauun aguannacuu gunnnncaga agnnuauuua      60

uggnnuannn nnnnnnnaca agunngaaag guaaagnnau gccgaaauag auauaaacca    120

uaaannnuua uaucuauugg gacaguuuun ncgaauagga acuguancug ucacagaann    180

nnnnnnnnnn nnnnnnugug augugcuacc uuauau                               216

<210> SEQ ID NO 47
<211> LENGTH: 214
<212> TYPE: RNA
<213> ORGANISM: Staphylococcus epidermidis
<220> FEATURE:
<221> NAME/KEY: misc_feature
<222> LOCATION: 16-192
<223> OTHER INFORMATION: n = g, a, c or u

<400> SEQUENCE: 47

agauuuugau gaggcngcau caaucnaugn aguannaacu uuannnnngn aunnuauuug      60

ucugcuaaca auuauagagu unnaaaaggg uganngaugc cgaaaugauu cauaauagca    120

nnnguuauga aucguuggac uuaauggunn uaagagcuau aagunuuguc auuauuauua    180

annnnnnnnn nnauaaugga gugcaucacu ugua                                 214

<210> SEQ ID NO 48
<211> LENGTH: 216
<212> TYPE: RNA
<213> ORGANISM: Staphylococcus epidermidis
<220> FEATURE:
<221> NAME/KEY: misc_feature
<222> LOCATION: 26-196
<223> OTHER INFORMATION: n = g, a, c or u

<400> SEQUENCE: 48

aauagaguua gagguugcau uauuanaugn acuannacuu aunnnncaga agnnucguau      60

ggnnngannn nnnnnnnaua agunngaaag guaauaaunn gccgaaauga uguuauuucc    120

aunnaaauua gcauuguugg gacaacuuun ncgaauagaa guuguancug ucacuuuann    180

nnnnnnnnnn nnnnnnugug augugcuacc uuauau                               216

<210> SEQ ID NO 49
<211> LENGTH: 225
```

<212> TYPE: RNA
<213> ORGANISM: Shigella flexneri
<220> FEATURE:
<221> NAME/KEY: misc_feature
<222> LOCATION: 16-204
<223> OTHER INFORMATION: n = g, a, c or u

<400> SEQUENCE: 49
caggccagaa gaggcngcgu ugcccnannn aguaacggug uugnnnnngn agnngagcca 60
gnnnnuccug uganuaacac cnnnugaggg ggugcaucgc cgaggugauu gaacggcugg 120
ccanncguuc aucaucggcu acaggggncu gaaunccccu gggnnuuguc accannnnnn 180
nnnnnnnnnn nnnnnnnnnn nnnnuggugg agcacuucug gguga 225

<210> SEQ ID NO 50
<211> LENGTH: 214
<212> TYPE: RNA
<213> ORGANISM: Shewanella oneidensis
<220> FEATURE:
<221> NAME/KEY: misc_feature
<222> LOCATION: 16-194
<223> OTHER INFORMATION: n = g, a, c or u

<400> SEQUENCE: 50
aggaacagaa gaggangcgu uaacunannn gguannguca aucangaggn agcacaaacu 60
ccagcgannn nnnugauuga unnngaggga ganuuagcgc cgaggcauag augugguugc 120
ugnncauguu uaugucgguc gcuuaggncu gaaunccuaa cgannuuguc accuguaauu 180
nnnnnnnnnn nnnnggugga gagcuucugg ugac 214

<210> SEQ ID NO 51
<211> LENGTH: 214
<212> TYPE: RNA
<213> ORGANISM: Shewanella oneidensis
<220> FEATURE:
<221> NAME/KEY: misc_feature
<222> LOCATION: 16-192
<223> OTHER INFORMATION: n = g, a, c or u

<400> SEQUENCE: 51
ccuuuaagua gaggcngcgc ugccunaugn acuanncuug ugcgnnnngn agnnggugau 60
gnnnnccgca ganuguacaa gnngaaagga gunncagcgc cgaaguagcc aggucaucaa 120
nnnnnnaccg agcgcugguu uugcauncaa auagngugca aganncugcc auagucaucc 180
nnnnnnnnnn nnacuaugga gcgcuaccug aagg 214

<210> SEQ ID NO 52
<211> LENGTH: 218
<212> TYPE: RNA
<213> ORGANISM: Thermatoga maritima
<220> FEATURE:
<221> NAME/KEY: misc_feature
<222> LOCATION: 16-194
<223> OTHER INFORMATION: n = g, a, c or u

<400> SEQUENCE: 52
ugacccgacg gaggcngcgc ccgagnaugn aguannggcu gucccnnnnn nngnaggaau 60
cgnnnnnnnn nnnnnnggga cggcunngaa aggcgagggn ncgccgaagg gugcagaguu 120
ccucccngcu cugcaugccu gggguaugg gnnngaauac ccauaccanc ugucacggag 180
gucnnnnnnn nnnnucuccg uggagagccg aucggguc 218

<210> SEQ ID NO 53
<211> LENGTH: 215

<212> TYPE: RNA
<213> ORGANISM: Thermoanaerobacter tengcongensis
<220> FEATURE:
<221> NAME/KEY: misc_feature
<222> LOCATION: 16-188
<223> OTHER INFORMATION: n = g, a, c or u

<400> SEQUENCE: 53
aggugaggua gaggcngcgg gucaucaagn aguannacau gccnnnnagn agnnguguua 60
nnnnnagnnn nnnnnnnggu gugunngaaa ggggugnncc cgccgaagcg cguaaacuuc 120
cuuanagguu uacgcagcug ggcuaugccn nngaacaguu auaggancug ucacucaagg 180
cuccccangg ccuucagugg agagcuaucu cgcua 215

<210> SEQ ID NO 54
<211> LENGTH: 218
<212> TYPE: RNA
<213> ORGANISM: Thermoanaerobacter tengcongensis
<220> FEATURE:
<221> NAME/KEY: misc_feature
<222> LOCATION: 16-195
<223> OTHER INFORMATION: n = g, a, c or u

<400> SEQUENCE: 54
cgcauaaaua gaggangcug ccaagcaunn nguauuuggc gagnnnnnnn nnngaagaac 60
cuccaauann nnnnnnnnnc ucgcugnaag aagguuuggc nnugccgaaa gggugagcuu 120
guucunnnug agcucauccu uggugguaaa cnnnacaaan guuuaccanc ugucauggga 180
ccnnnnnnnn nnnnnuccca ugaagcgcua uuuaugca 218

<210> SEQ ID NO 55
<211> LENGTH: 214
<212> TYPE: RNA
<213> ORGANISM: Vibrio cholerae
<220> FEATURE:
<221> NAME/KEY: misc_feature
<222> LOCATION: 16-192
<223> OTHER INFORMATION: n = g, a, c or u

<400> SEQUENCE: 55
ucuagcagaa gaggangcac ugcccnaggc agnauguuuu gugnnnnngn agccucaacu 60
ccaannnnnn nnnnuacaga acauucaggg ggaguagugc cgaggugaau caaaguugun 120
nnggcuuugg uuuaucgguu gaacgggncu gaaunccuu caanncuguc aucagcucga 180
aunnnnnnnn nncugaugaa gagcuucuga ggga 214

<210> SEQ ID NO 56
<211> LENGTH: 214
<212> TYPE: RNA
<213> ORGANISM: Vibrio cholerae
<220> FEATURE:
<221> NAME/KEY: misc_feature
<222> LOCATION: 16-192
<223> OTHER INFORMATION: n = g, a, c or u

<400> SEQUENCE: 56
uuucgccgua gaggangcgg uuacgnaaan aguannucca caguunnngn ggngugaugc 60
nnnnncaaug nnaauugugg annaaaaggc guunngccgc cgaagucaac uugcccaunn 120
nncaacgcag uuggcugggg uuacauunnn caauaggugu aacancugcc auagucuaua 180
uuguuguuaa nnacuaugga gcgcuacugu aggg 214

<210> SEQ ID NO 57
<211> LENGTH: 214

<212> TYPE: RNA
<213> ORGANISM: Vibrio cholerae
<220> FEATURE:
<221> NAME/KEY: misc_feature
<222> LOCATION: 16-193
<223> OTHER INFORMATION: n = g, a, c or u

<400> SEQUENCE: 57
ccuuuaagua gaggcngcgc uguucnaugn agucgnccag ucnnnnnngu agnguugacc 60
ccnnngaugn nnnaugacug gnuuaaaggg unnacagcgc cgaagugauc guugcgucau 120
nnnnncaacg uucgcugggc cagcauunnn gaacaaaugc cggancugcc auagugugu 180 gunnnnnnnn nnncuaugga gcgcuaccuu gaag 214

<210> SEQ ID NO 58
<211> LENGTH: 214
<212> TYPE: RNA
<213> ORGANISM: Vibrio vulnificus
<220> FEATURE:
<221> NAME/KEY: misc_feature
<222> LOCATION: 16-190
<223> OTHER INFORMATION: n = g, a, c or u

<400> SEQUENCE: 58
uuuugcagaa gaggangcac ugcccnaggc agnauguuuu gugnnnnngn agccgcaacu 60
ccaannnnnn nnnncacaga acauucaggg ggaguagugc cgagguagau caaaauugca 120
nnngauuuga ucugucgguu gacuuggguu gaguncccau caanncuguc aucagcucan 180
nnnnnnnnnn gccugaugaa gagcuucuga gaug 214

<210> SEQ ID NO 59
<211> LENGTH: 214
<212> TYPE: RNA
<213> ORGANISM: Vibrio vulnificus
<220> FEATURE:
<221> NAME/KEY: misc_feature
<222> LOCATION: 16-192
<223> OTHER INFORMATION: n = g, a, c or u

<400> SEQUENCE: 59
uaucgacgua gaggcngcaa ugguanaagn aguannacua uuauunnngn ggnngugaun 60
nnnnngccaa ugaauaauag unngaaaggu aunccauugc cgaagugaau ugcauaucaa 120
annnnngcag uuugcugggg uugcauccnn gaaanggaac aacancugcc auaguauuua 180
auguauannn nnacuaugga gcgcuacugu aggu 214

<210> SEQ ID NO 60
<211> LENGTH: 23
<212> TYPE: RNA
<213> ORGANISM: Bacillus subtilis
<220> FEATURE:
<221> NAME/KEY: misc_feature
<222> LOCATION: 12-131
<223> OTHER INFORMATION: n = g, a, c or u
<220> FEATURE:
<221> NAME/KEY: misc_feature
<222> LOCATION: 2, 11, 52, 53, 70, 92, 132
<223> OTHER INFORMATION: r = a or g
<220> FEATURE:
<221> NAME/KEY: misc_feature
<222> LOCATION: 3, 135
<223> OTHER INFORMATION: w = a or u
<220> FEATURE:
<221> NAME/KEY: misc_feature
<222> LOCATION: 64, 72, 93, 119, 136
<223> OTHER INFORMATION: y = c or u

<400> SEQUENCE: 60
rwagagggcr nnnnnnanna gua 23

<210> SEQ ID NO 61
<211> LENGTH: 237
<212> TYPE: RNA
<213> ORGANISM: Bacillus subtilis

<400> SEQUENCE: 61
aauuucauag uuagaucgug uuauauggug aagauagagg ugcgaacuuc aagaguaugc 60
cuuuggagaa agauggauuc ugugaaaaag gcugaaaggg gagcgucgcc gaagcaaaua 120
aaaccccauc gguauuauuu gcuggccgug cauugaauaa auguaaggcu gucaagaaau 180
cauuuucuug gagggcuauc ucguuguuca uaaucauuua ugaugauuaa uugauaa 237

<210> SEQ ID NO 62
<211> LENGTH: 239
<212> TYPE: RNA
<213> ORGANISM: Bacillus subtilis
<220> FEATURE:
<221> NAME/KEY: misc_feature
<222> LOCATION: 11
<223> OTHER INFORMATION: r = a or g
<220> FEATURE:
<221> NAME/KEY: misc_feature
<222> LOCATION: 78, 117, 177, 210, 232
<223> OTHER INFORMATION: s = g or c
<220> FEATURE:
<221> NAME/KEY: misc_feature
<222> LOCATION: 10
<223> OTHER INFORMATION: v = g, c or a
<220> FEATURE:
<221> NAME/KEY: misc_feature
<222> LOCATION: 123, 176, 211, 231
<223> OTHER INFORMATION: w = a or u
<220> FEATURE:
<221> NAME/KEY: misc_feature
<222> LOCATION: 167
<223> OTHER INFORMATION: y = c or u

<400> SEQUENCE: 62
gaagauagav rugcgaacuu caagaguaug ccuuuggaga aagauggauu cugugaaaaa 60
ggcugaaagg ggagcgusgc cgaagcaaau aaaaccccau cgguauuauu ugcuggscgu 120
gcwuugaaua aauguaaggc ugucaagaaa ucauuuucuu ggagggyuau cucguwsuuc 180
auaaucauuu augaugauua auugauaags waugagagua uuccucucau wscuuuuuu 239

<210> SEQ ID NO 63
<211> LENGTH: 82
<212> TYPE: RNA
<213> ORGANISM: Bacillus subtilis
<220> FEATURE:
<221> NAME/KEY: misc_feature
<222> LOCATION: 31-68
<223> OTHER INFORMATION: n = g, a, c or u

<400> SEQUENCE: 63
caucccuuuc guauauacuu ggagauaagg nuccaggagu uucuaccaga ucaccguaaa 60
ugaucugnac uaugaaggug ga 82

<210> SEQ ID NO 64
<211> LENGTH: 82
<212> TYPE: RNA
<213> ORGANISM: Bacillus subtilis
<220> FEATURE:
<221> NAME/KEY: misc_feature
<222> LOCATION: 31-68
<223> OTHER INFORMATION: n = g, a, c or u

<400> SEQUENCE: 64
acaucauuuc guauaauggc aggaauaggg nccugcgagu uucuaccaag cuaccguaaa 60
uagcuugnac uacgaaaaua au 82

<210> SEQ ID NO 65
<211> LENGTH: 82
<212> TYPE: RNA
<213> ORGANISM: Bacillus halodurans
<220> FEATURE:
<221> NAME/KEY: misc_feature
<222> LOCATION: 31-68
<223> OTHER INFORMATION: n = g, a, c or u

<400> SEQUENCE: 65
aaaguaccuc auauaaucuu gggaauaugg ncccaaaagu uucuaccugc ugaccguaaa 60
ucggcggnac uauggggaaa ga 82

<210> SEQ ID NO 66
<211> LENGTH: 82
<212> TYPE: RNA
<213> ORGANISM: Bacillus halodurans
<220> FEATURE:
<221> NAME/KEY: misc_feature
<222> LOCATION: 16-67
<223> OTHER INFORMATION: n = g, a, c or u

<400> SEQUENCE: 66
aacacucuuc guauanuccu cucaauaugg ngaugagggu cucuacaggu annccguaaa 60
uaccunnagc uacgaaaaga au 82

<210> SEQ ID NO 67
<211> LENGTH: 82
<212> TYPE: RNA
<213> ORGANISM: Bacillus halodurans
<220> FEATURE:
<221> NAME/KEY: misc_feature
<222> LOCATION: 31-68
<223> OTHER INFORMATION: n = g, a, c or u

<400> SEQUENCE: 67
aaaagcacuc guauaaucgc gggaauaggg ncccgcaagu uucuaccagg cugccguaaa 60
cagccugnac uacgagugau ac 82

<210> SEQ ID NO 68
<211> LENGTH: 82
<212> TYPE: RNA
<213> ORGANISM: Bacillus subtilis
<220> FEATURE:
<221> NAME/KEY: misc_feature
<222> LOCATION: 31-68
<223> OTHER INFORMATION: n = g, a, c or u

<400> SEQUENCE: 68
agaugaauuc guauaaucgc gggaauaugg ncucgcaagu cucuaccaag cuaccguaaa 60
uggcuugnac uacguaaaca uu 82

<210> SEQ ID NO 69
<211> LENGTH: 82
<212> TYPE: RNA
<213> ORGANISM: Bacillus subtilis
<220> FEATURE:
<221> NAME/KEY: misc_feature
<222> LOCATION: 31-68
<223> OTHER INFORMATION: n = g, a, c or u

<400> SEQUENCE: 69
acacgaccuc auauaaucuu gggaauaugg ncccauaagu uucuacccgg caaccguaaa 60
uugccggnac uaugcaggaa ag 82

<210> SEQ ID NO 70
<211> LENGTH: 82
<212> TYPE: RNA
<213> ORGANISM: Bacillus subtilis
<220> FEATURE:
<221> NAME/KEY: misc_feature
<222> LOCATION: 31-68
<223> OTHER INFORMATION: n = g, a, c or u

<400> SEQUENCE: 70
aggaacacuc auauaaucgc guggauaugg ncacgcaagu uucuaccggg canccguaaa 60
nuguccgnac uaugggugag ca 82

<210> SEQ ID NO 71
<211> LENGTH: 82
<212> TYPE: RNA
<213> ORGANISM: Bacillus subtilis
<220> FEATURE:
<221> NAME/KEY: misc_feature
<222> LOCATION: 31-68
<223> OTHER INFORMATION: n = g, a, c or u

<400> SEQUENCE: 71
agacauucuu guauaugauc aguaauaugg nucugauugu uucuaccuag uaaccguaaa 60
aaacuagnac uacaagaaag uu 82

<210> SEQ ID NO 72
<211> LENGTH: 82
<212> TYPE: RNA
<213> ORGANISM: Bacillus subtilis
<220> FEATURE:
<221> NAME/KEY: misc_feature
<222> LOCATION: 31-68
<223> OTHER INFORMATION: n = g, a, c or u

<400> SEQUENCE: 72
auuaucacuu guauaacccuc aauaauaugg nuuugagggu gucuaccagg aanccguaaa 60
auccugnnau uacaaaauuu gu 82

<210> SEQ ID NO 73
<211> LENGTH: 82
<212> TYPE: RNA
<213> ORGANISM: Clostridium acetobutylicum
<220> FEATURE:
<221> NAME/KEY: misc_feature
<222> LOCATION: 16-68
<223> OTHER INFORMATION: n = g, a, c or u

<400> SEQUENCE: 73
uaaauuucuc guauancacc gguaauaugg nuccggaagu uucuaccugc ugnccauaaa 60
nuagcagnac uacggggugu ua 82

<210> SEQ ID NO 74
<211> LENGTH: 82
<212> TYPE: RNA
<213> ORGANISM: Clostridium acetobutylicum
<220> FEATURE:
<221> NAME/KEY: misc_feature
<222> LOCATION: 31-68
<223> OTHER INFORMATION: n = g, a, c or u -continued

<400> SEQUENCE: 74
cauauuaccc guauaugcuu agaaauaugg nucuaagcgu cucuaccgga cugccguaaa 60
uugucugnac uaugggugu ua 82

<210> SEQ ID NO 75
<211> LENGTH: 82
<212> TYPE: RNA
<213> ORGANISM: Clostridium acetobutylicum
<220> FEATURE:
<221> NAME/KEY: misc_feature
<222> LOCATION: 16-68
<223> OTHER INFORMATION: n = g, a, c or u

<400> SEQUENCE: 75
aguuuaacuc auauanuuuc cugaauaugg nncaggaugu uucuacaagg aanccuuaaa 60
nuuucuunac uaugagugau uu 82

<210> SEQ ID NO 76
<211> LENGTH: 82
<212> TYPE: RNA
<213> ORGANISM: Clostridium perfringens
<220> FEATURE:
<221> NAME/KEY: misc_feature
<222> LOCATION: 31-68
<223> OTHER INFORMATION: n = g, a, c or u

<400> SEQUENCE: 76
uaaguauauc guauaugcuc gacgauaugg nguugagugu uucuacuagg aggccguaaa 60
cauccuanac uacgaauaua ua 82

<210> SEQ ID NO 77
<211> LENGTH: 82
<212> TYPE: RNA
<213> ORGANISM: Clostridium perfringens
<220> FEATURE:
<221> NAME/KEY: misc_feature
<222> LOCATION: 31-68
<223> OTHER INFORMATION: n = g, a c or u

<400> SEQUENCE: 77
auuuuaacuc guauauaauc gguaauaugg nuccgaaagu uucuaccugc uaaccguaaa 60
auagcagnac uacgaggagu ug 82

<210> SEQ ID NO 78
<211> LENGTH: 82
<212> TYPE: RNA
<213> ORGANISM: Clostridium perfringens
<220> FEATURE:
<221> NAME/KEY: misc_feature
<222> LOCATION: 16-68
<223> OTHER INFORMATION: n = g, a, c or u

<400> SEQUENCE: 78
aaacaaacuc guauanagcu uugaauaagg nncaaggcgu uucuaccgga aanccuuaaa 60
nuuuccgnuc uaugagugaa uu 82

<210> SEQ ID NO 79
<211> LENGTH: 82
<212> TYPE: RNA
<213> ORGANISM: Clostridium perfringens
<220> FEATURE:
<221> NAME/KEY: misc_feature
<222> LOCATION: 31-68
<223> OTHER INFORMATION: n = g, a, c or u

<400> SEQUENCE: 79
auuuugcuuc guauaacucu aaugauaugg nauuagaggu cucuaccaag aanccgagaa 60
nuucuugnau uacgaagaaa gc 82

<210> SEQ ID NO 80
<211> LENGTH: 82
<212> TYPE: RNA
<213> ORGANISM: Fusobacterium nucleatum
<220> FEATURE:
<221> NAME/KEY: misc_feature
<222> LOCATION: 16-61
<223> OTHER INFORMATION: n = g, a, c or u

<400> SEQUENCE: 80
auaaaaauuc guauanagcc uaauauaugg nnaagggugu cccuacgguu aanccauaaa 60
nuuaaccagc uacgaaaaau gu 82

<210> SEQ ID NO 81
<211> LENGTH: 82
<212> TYPE: RNA
<213> ORGANISM: Lactococcus lactis
<220> FEATURE:
<221> NAME/KEY: misc_feature
<222> LOCATION: 16-68
<223> OTHER INFORMATION: n = g, a, c or u

<400> SEQUENCE: 81
acaaucuuau uuauannncc uaggauaugg nncugggcgu uucuaccucg uanccguaaa 60
nugcgagnac aauaaggaaa uu 82

<210> SEQ ID NO 82
<211> LENGTH: 82
<212> TYPE: RNA
<213> ORGANISM: Listeria monocytogenes
<220> FEATURE:
<221> NAME/KEY: misc_feature
<222> LOCATION: 31-68
<223> OTHER INFORMATION: n = g, a, c or u

<400> SEQUENCE: 82
uaauauaguc guauaaguuc gguaauaugg naccguucgu uucuaccagg caaccguaaa 60
augccagngc uacgagcuau ug 82

<210> SEQ ID NO 83
<211> LENGTH: 82
<212> TYPE: RNA
<213> ORGANISM: Listeria monocytogenes
<220> FEATURE:
<221> NAME/KEY: misc_feature
<222> LOCATION: 27-68
<223> OTHER INFORMATION: n = g, a, c or u

<400> SEQUENCE: 83
cgaaauacuu guauaauagu ugcgaunugg ngcgacgagu uucuaccugg uuaccguaaa 60
uaaccggnac uaugaguagu uu 82

<210> SEQ ID NO 84
<211> LENGTH: 82
<212> TYPE: RNA
<213> ORGANISM: Oceanobacillus iheyensis
<220> FEATURE:
<221> NAME/KEY: misc_feature
<222> LOCATION: 31-68
<223> OTHER INFORMATION: n = g, a c or u

<400> SEQUENCE: 84
aaugccuuuc guauauccuc gauaauaugg nuucgaaagu aucuaccggg ucaccguaaa    60
ugaucugnac uaugaaggca ga                                             82

<210> SEQ ID NO 85
<211> LENGTH: 82
<212> TYPE: RNA
<213> ORGANISM: Oceanobacillus iheyensis
<220> FEATURE:
<221> NAME/KEY: misc_feature
<222> LOCATION: 31-68
<223> OTHER INFORMATION: n = g, a, c or u

<400> SEQUENCE: 85
auagaaaugc guauaauuaa ggggauaugg nncccacagu uucuaccaga ccaccguaaa    60
ugguuugnac uacgcaguaa uu                                             82

<210> SEQ ID NO 86
<211> LENGTH: 82
<212> TYPE: RNA
<213> ORGANISM: Oceanobacillus iheyensis
<220> FEATURE:
<221> NAME/KEY: misc_feature
<222> LOCATION: 31-68
<223> OTHER INFORMATION: n = g, a, c or u

<400> SEQUENCE: 86
aaugaaccuc auauaaauuu gagaauaugg ncucagaagu uucuacccag canccguaaa    60
uggcuggnac uaugagggaa ga                                             82

<210> SEQ ID NO 87
<211> LENGTH: 82
<212> TYPE: RNA
<213> ORGANISM: Oceanobacillus iheyensis
<220> FEATURE:
<221> NAME/KEY: misc_feature
<222> LOCATION: 31-68
<223> OTHER INFORMATION: n = g, a, c or u

<400> SEQUENCE: 87
uaguuuuuuc auauaaucgc ggggauaugg nccugcaagu uucuaccggu uuaccguaaa    60
ugaaccgnac uauggaaaag cg                                             82

<210> SEQ ID NO 88
<211> LENGTH: 82
<212> TYPE: RNA
<213> ORGANISM: Staphylococcus aureus
<220> FEATURE:
<221> NAME/KEY: misc_feature
<222> LOCATION: 68
<223> OTHER INFORMATION: n = g, a, c or u

<400> SEQUENCE: 88
acauaaacuc auauaaucua aagaauaugg cuuuagaagu uucuaccaug uugccuugaa    60
cgacaugnac uaugaguaac aa                                             82

<210> SEQ ID NO 89
<211> LENGTH: 82
<212> TYPE: RNA
<213> ORGANISM: Staphylococcus epidermidis
<220> FEATURE:
<221> NAME/KEY: misc_feature
<222> LOCATION: 68
<223> OTHER INFORMATION: n = g, a, c or u

<400> SEQUENCE: 89
uauaugacuc auauaaucua gagaauaugg cuuuagaagu uucuaccgug ucgccauaaa 60
cgacacgnac uaugaguaac aa 82

<210> SEQ ID NO 90
<211> LENGTH: 82
<212> TYPE: RNA
<213> ORGANISM: Streptococcus agalactiae
<220> FEATURE:
<221> NAME/KEY: misc_feature
<222> LOCATION: 16-67
<223> OTHER INFORMATION: n = g, a, c or u

<400> SEQUENCE: 90
ugauuuacuu auuuanugcu gaggaunugg nncuuagcgu cucuacaaga canccgunaa 60
nugucunaac aauaaguaag cu 82

<210> SEQ ID NO 91
<211> LENGTH: 82
<212> TYPE: RNA
<213> ORGANISM: Streptococcus pyogenes
<220> FEATURE:
<221> NAME/KEY: misc_feature
<222> LOCATION: 16-67
<223> OTHER INFORMATION: n = g, a, c or u

<400> SEQUENCE: 91
ugacauacuu auuuanugcu gugaaunugg nncgcagcgu cucuacaaga canccnuuaa 60
nugucunaac aauaaguaag cu 82

<210> SEQ ID NO 92
<211> LENGTH: 82
<212> TYPE: RNA
<213> ORGANISM: Streptococcus pneumoniae
<220> FEATURE:
<221> NAME/KEY: misc_feature
<222> LOCATION: 16-67
<223> OTHER INFORMATION: n = g, a, c or u

<400> SEQUENCE: 92
cguuuuacuu guuuanuguc gugaaunugg nncacgacgu uucuacaagg ugnccnggaa 60
ncaccunaac aauaaguaag uc 82

<210> SEQ ID NO 93
<211> LENGTH: 82
<212> TYPE: RNA
<213> ORGANISM: Thermoanaerobacter tengcogensis
<220> FEATURE:
<221> NAME/KEY: misc_feature
<222> LOCATION: 31-68
<223> OTHER INFORMATION: n = g, a, c or u

<400> SEQUENCE: 93
agaagcacuc auauaauccc gagaauaugg ncucgggagu cucuaccgaa caaccguaaa 60
uuguucgnac uaugagugaa ag 82

<210> SEQ ID NO 94
<211> LENGTH: 82
<212> TYPE: RNA
<213> ORGANISM: Vibrio vulnificus
<220> FEATURE:
<221> NAME/KEY: misc_feature
<222> LOCATION: 31-68
<223> OTHER INFORMATION: n = g, a, c or u

<400> SEQUENCE: 94
ucaacgcuuc auauaauccu aaugauaugg nuuugggagu uucuaccaag agnccuuaaa 60
ncucuugnau uaugaagucu gu 82

<210> SEQ ID NO 95
<211> LENGTH: 69
<212> TYPE: RNA
<213> ORGANISM: Bacillus subtilis
<220> FEATURE:
<221> NAME/KEY: misc_feature
<222> LOCATION: 1-69
<223> OTHER INFORMATION: n = g, a, c or u
<220> FEATURE:
<221> NAME/KEY: misc_feature
<222> LOCATION: 5, 18, 67
<223> OTHER INFORMATION: r = a or g
<220> FEATURE:
<221> NAME/KEY: misc_feature
<222> LOCATION: 65
<223> OTHER INFORMATION: y = c or u

<400> SEQUENCE: 95
nnucruauan nnnnnnnrau auggnnnnnn ngunucuacc nnnnnnccgu aaannnnnng 60 acuaygrnn 69

<210> SEQ ID NO 96
<211> LENGTH: 201
<212> TYPE: RNA
<213> ORGANISM: Bacillus subtilis

<400> SEQUENCE: 96
gggaauauaa uaggaacacu cauauaaucg cguggauaug gcacgcaagu uucuaccggg 60
caccguaaau guccgacuau gggugagcaa uggaaccgca cguguacggu uuuuugugau 120
aucagcauug cuugcucuuu auuugagcgg gcaaugcuuu uuuuauucuc auaacggagg 180
uagacaggau ggauccacug a 201

<210> SEQ ID NO 97
<211> LENGTH: 93
<212> TYPE: RNA
<213> ORGANISM: Bacillus subtilis
<220> FEATURE:
<221> NAME/KEY: misc_feature
<222> LOCATION: 20
<223> OTHER INFORMATION: k = g or u
<220> FEATURE:
<221> NAME/KEY: misc_feature
<222> LOCATION: 19, 32, 44, 58, 59, 73, 74, 82, 83
<223> OTHER INFORMATION: s = g or c
<220> FEATURE:
<221> NAME/KEY: misc_feature
<222> LOCATION: 18, 25, 26, 33, 43, 84
<223> OTHER INFORMATION: w = a or u

<400> SEQUENCE: 97
gggaauauaa uaggaacwsk cauawwaucg cswggauaug gcwsgcaagu uucuaccssg 60
caccguaaau gussgacuau gsswgagcaa ugg 93

<210> SEQ ID NO 98
<211> LENGTH: 51
<212> TYPE: RNA
<213> ORGANISM: Bacillus subtilis
<220> FEATURE:
<221> NAME/KEY: misc_feature
<222> LOCATION: 8, 13, 14, 26, 32, 33, 37, 41, 42, 50, 51, 54, 55, 63,
67

<223> OTHER INFORMATION: n = g, a, c or u
<220> FEATURE:
<221> NAME/KEY: misc_feature
<222> LOCATION: 18, 38, 44, 53, 68, 71, 72, 78, 79, 84, 87
<223> OTHER INFORMATION: r = a or g
<220> FEATURE:
<221> NAME/KEY: misc_feature
<222> LOCATION: 1, 17, 25, 34, 60, 74, 75
<223> OTHER INFORMATION: y = c or u

<400> SEQUENCE: 98
ycuuaucnag agnnggyrga gggaynggcc cnnyganrcc nncrgcaacn n 51

<210> SEQ ID NO 99
<211> LENGTH: 251
<212> TYPE: RNA
<213> ORGANISM: Bacillus subtilis
<220> FEATURE:
<221> NAME/KEY: misc_feature
<222> LOCATION: 152-251
<223> OTHER INFORMATION: n = g, a, c or u

<400> SEQUENCE: 99
ggacuuccug acacgaaaau uucauauccg uucuuaucaa gagaagcaga gggacuggcc 60
cgacgaagcu ucagcaaccg guguaauggc gaucagccau gaccaaggug cuaaauccag 120
caagcucgaa cagcuuggaa gauaagaaga gnnnnnnnnn nnnnnnnnnn nnnnnnnnnn 180
nnnnnnnnnn nnnnnnnnnn nnnnnnnnnn nnnnnnnnnn nnnnnnnnnn nnnnnnnnnn 240
nnnnnnnnnn n 251

<210> SEQ ID NO 100
<211> LENGTH: 124
<212> TYPE: RNA
<213> ORGANISM: Bacillus subtilis
<220> FEATURE:
<221> NAME/KEY: misc_feature
<222> LOCATION: 106
<223> OTHER INFORMATION: k = g or u
<220> FEATURE:
<221> NAME/KEY: misc_feature
<222> LOCATION: 13, 14, 46, 47
<223> OTHER INFORMATION: r = a or g
<220> FEATURE:
<221> NAME/KEY: misc_feature
<222> LOCATION: 19, 42, 97
<223> OTHER INFORMATION: s = g or c
<220> FEATURE:
<221> NAME/KEY: misc_feature
<222> LOCATION: 98
<223> OTHER INFORMATION: v = g, c or a
<220> FEATURE:
<221> NAME/KEY: misc_feature
<222> LOCATION: 8, 9, 17, 18, 43, 44, 116, 117
<223> OTHER INFORMATION: w = a or u
<220> FEATURE:
<221> NAME/KEY: misc_feature
<222> LOCATION: 84, 85
<223> OTHER INFORMATION: y = c or u

<400> SEQUENCE: 100
ggguucuwwu carragwwsc agagggacug gcccgacgaa gswwcrrcaa ccgguguaau 60
ggcgaucagc caugaccaag gugyyaaauc cagcaasvuc gaacakcuug gaagawwaga 120
agag 124

<210> SEQ ID NO 101
<211> LENGTH: 245
<212> TYPE: RNA
<213> ORGANISM: Bacillus subtilis
<220> FEATURE:

<221> NAME/KEY: misc_feature
<222> LOCATION: 186-245
<223> OTHER INFORMATION: n = g, a, c or u
<220> FEATURE:
<221> NAME/KEY: misc_feature
<222> LOCATION: 149, 160, 177
<223> OTHER INFORMATION: s = g or c
<220> FEATURE:
<221> NAME/KEY: misc_feature
<222> LOCATION: 148, 161, 176
<223> OTHER INFORMATION: w = a or u

<400> SEQUENCE: 101
ggucagaaaa auugaaaucg auauuucuua ucgugagagg uggagggacu ggcccuuaga 60
aaccucagca accggcuugu uuugcauuug caaagcgcca aggugcuaaa uccagcaagc 120
guuuuuuaug cuuggaagau aagaagawsc guuaaacccs wucuucuuau gaagawsggg 180
uuuuunnnnn nnnnnnnnnn nnnnnnnnnn nnnnnnnnnn nnnnnnnnnn nnnnnnnnnn 240 nnnnn 245

<210> SEQ ID NO 102
<211> LENGTH: 167
<212> TYPE: RNA
<213> ORGANISM: Bacillus subtilis

<400> SEQUENCE: 102
gguacaaucu aaaaacuuau caagagcggc ugagggacug gaccuaugaa gcccggcaac 60
cugcauaguu uguaaggugc uacuuccagc aaaaugaauu ccauuuugaa agauaagggc 120
ugcaugcugu uccugucuuu cuuuccgccg gauugaaagu uuuuuuu 167

<210> SEQ ID NO 103
<211> LENGTH: 160
<212> TYPE: RNA
<213> ORGANISM: Bacillus anthracis

<400> SEQUENCE: 103
ggagcuuauc aagagaagcg gagggaacug gcccggcgaa gcucggcaac cugcuuauag 60
aaagcaaggu gcuaaaucca gcaaaaugga auccauuuug aaagauaagg uaaaauauau 120
uaccgaacag ucuuuucgaa augggaaaga uuuuuuuuau 160

<210> SEQ ID NO 104
<211> LENGTH: 80
<212> TYPE: RNA
<213> ORGANISM: Bacillus subtilis

<400> SEQUENCE: 104
acacgaccuc auauaaucuu gggaauaugg cccauaaguu ucuacccggc aaccguaaau 60
ugccggacua ugcaggaaag 80

<210> SEQ ID NO 105
<211> LENGTH: 80
<212> TYPE: RNA
<213> ORGANISM: Bacillus subtilis
<220> FEATURE:
<221> NAME/KEY: misc_feature
<222> LOCATION: 52-60
<223> OTHER INFORMATION: n = g, a, c or u

<400> SEQUENCE: 105
aggaacacuc auauaaucgc guggauaugg cacgcaaguu ucuaccgggc anccguaaan 60
uguccgacua ugggugagca 80

```
<210> SEQ ID NO 106
<211> LENGTH: 80
<212> TYPE: RNA
<213> ORGANISM: Bacillus subtilis
<220> FEATURE:
<221> NAME/KEY: misc_feature
<222> LOCATION: 52, 60
<223> OTHER INFORMATION: n = g, a, c or u

<400> SEQUENCE: 106

auuaucacuu guauaaccuc aauaauaugg uuugagggug ucuaccagga anccguaaan     60

auccugauua caaaauuugu                                                 80


<210> SEQ ID NO 107
<211> LENGTH: 80
<212> TYPE: RNA
<213> ORGANISM: Clostridium perfringens
<220> FEATURE:
<221> NAME/KEY: misc_feature
<222> LOCATION: 52, 60
<223> OTHER INFORMATION: n = g, a, c or u

<400> SEQUENCE: 107

auuuugcuuc guauaacucu aaugauaugg auuagagguc ucuaccaaga anccgagaan     60

uucuugauua cgaagaaagc                                                 80


<210> SEQ ID NO 108
<211> LENGTH: 80
<212> TYPE: RNA
<213> ORGANISM: Vibrio vulnificus
<220> FEATURE:
<221> NAME/KEY: misc_feature
<222> LOCATION: 52, 60
<223> OTHER INFORMATION: n = g, a, c or u

<400> SEQUENCE: 108

ucaacgcuuc auauaauccu aaugauaugg uuugggaguu ucuaccaaga gnccuuaaan     60

cucuugauua ugaagucugu                                                 80


<210> SEQ ID NO 109
<211> LENGTH: 69
<212> TYPE: RNA
<213> ORGANISM: Bacillus subtilis

<400> SEQUENCE: 109

cacucauaua aucgcgugga uauggcacgc aaguuucuac cgggcaccgu aaauguccga     60

cuaugggug                                                             69


<210> SEQ ID NO 110
<211> LENGTH: 63
<212> TYPE: RNA
<213> ORGANISM: Bacillus subtilis

<400> SEQUENCE: 110

uuguauaacc ucaauaauau gguuugaggg ugucuaccag gaaccguaaa auccugauua     60

caa                                                                   63


<210> SEQ ID NO 111
<211> LENGTH: 102
<212> TYPE: RNA
<213> ORGANISM: Bacillus subtilis

<400> SEQUENCE: 111
```

uuguauaacc ucaauaauau gguuugaggg ugucuaccag gaaccguaaa auccugauua 60
caaaauuugu uuaugacauu uuuuguaauc aggauuuuuu uu 102

<210> SEQ ID NO 112
<211> LENGTH: 486
<212> TYPE: DNA
<213> ORGANISM: Bacillus subtilis
<220> FEATURE:
<221> NAME/KEY: misc_feature
<222> LOCATION: 21-307
<223> OTHER INFORMATION: n = g, a, c or t/u

<400> SEQUENCE: 112
atatccgttc ttatcaagag nnnaagcaga gggannctgg nnnncccgac gaagcttnnc 60
agcaaccggt gtaatggcnn nnnnnnnnnn nnnnnnnnnn nnngatcann nnnnnnnnnn 120
nnnnnnnnnn nnnnngccat gaccaaggtg ctaaatncca gnnnnnncaa gctnnnnnnn 180
nnnncgaaca nnnnnnnnnn ngcttggaag ataagaagag acaaaatcac tgacaaannn 240
nnnnnnnnnn nnnnnnnnnn nnnnnnnngt cttcttnnnn nnnnnnnnnn cttnnnnnnn 300
nnnnnnnaag aggacttttt tatttctctt ttttccttgc tgatgtgaat aaaggaggca 360
gacaatggga cttttagaag atttgcaaag acaggtgtta atcggtgacg gcgccatggg 420
gacgctcctc tactcctatg gcattgacag gtgttttgag gagctcaata tttcaaagcc 480
ggagga 486

<210> SEQ ID NO 113
<211> LENGTH: 486
<212> TYPE: DNA
<213> ORGANISM: Bacillus subtilis
<220> FEATURE:
<221> NAME/KEY: misc_feature
<222> LOCATION: 21-305
<223> OTHER INFORMATION: n = g, a, c or t/u

<400> SEQUENCE: 113
tcgatatttc ttatcgtgag nnnaggtgga gggannctgg nnnnccctta gaaacctnnc 60
agcaaccggc ttgttttgcn nnnnnnnnnn nnnnnnnnnn nnnatttnnn nnnnnnnnnn 120
nnnnnnnnnn nnnngcaaag cgccaaggtg ctaaatncca gnnnnnncaa gcgtnnnnnn 180 nnnnttttn nnnnnnnnna tgcttggaag ataagaagaa gcgttaaann nnnnnnnnnn 240
nnnnnnnnnn nnnnnnnnnn nnnnnnnncc ccttcttcnn nnnnnnnnnt tatnnnnnnn 300
nnnnngaaga aggggttttt attttgaaaa gggaaggtgt cagctatatg tcacagcacg 360
ttgaaacgaa attagctcaa attgggaacc gtagcgatga agtcacggga acagtgagtg 420
ctcctatcta tttatcaaca gcataccgcc acagagggat cggagaatct accggatttg 480
attatg 486

<210> SEQ ID NO 114
<211> LENGTH: 486
<212> TYPE: DNA
<213> ORGANISM: Bacillus subtilis
<220> FEATURE:
<221> NAME/KEY: misc_feature
<222> LOCATION: 21-304
<223> OTHER INFORMATION: n = g, a, c or t/u

<400> SEQUENCE: 114
acattttctc ttatcgagag nnttgggcga gggannttgg nnnncctttt gaccccaanc 60
agcaaccgac cnnnnnngta ataccattgt gaaatggggc gcactgcttt tcgcgccgag 120
actgatgtct cataannnnn nggcacggtg ctaattncca tnnnnnncag atnnnnnnnn 180
nnnnntgtnn nnnnnnnnnn ngtctgagag atgagagagg cagtgtttta cgtagaaaan 240
nnnnnnnnnn nnnnnnnnnn nnnnnnnngc ctctttctcn nnnnnnnnnt catnnnnnnn 300
nnnngggaaa gaggcttttt gttgtgagaa aacctcttag cagcctgtat ccgcgggtga 360
aagagagtgt tttacatata aaggaggaga aacaatgaca accatcaaaa catcgaattt 420
aggatttccg agaatcgacc tgaaccggga atggaaaaaa gcacttgaag cgtattggaa 480
aggcag 486

<210> SEQ ID NO 115
<211> LENGTH: 486
<212> TYPE: DNA
<213> ORGANISM: Bacillus subtilis
<220> FEATURE:
<221> NAME/KEY: misc_feature
<222> LOCATION: 21-304
<223> OTHER INFORMATION: n = g, a, c or t/u

<400> SEQUENCE: 115
atatattctc ttatcgagag nnttgggcga gggatnttgg nnnnnccttt gaccccaana 60
agcaaccgac cnnnnnngta attccattgt gaaatggggc gcanttttt tcgcgccgag 120 acgctggtct cttaannnnn nggcacggtg ctaattncca tnnntnncag atnnnnnnnn 180
nnnnnctgnn nnnnnnnnnn natctgagag ataagagagg cggacataga tgttaannnn 240
nnnnnnnnnn nnnnnnnnnn nnnnnnnngc ctccttctcn nnnnnnnnnn tctnnnnnnn 300
nnnngagaag gaggcttttt tacggccaca tattaattaa ttacataatt ggaggttatg 360
atgatgggag tcacaaaaac acctttatac gaaacgttaa atgaaagctc cgctgtggcg 420
ttggcggtga agcttggcct atttccaagc aaaagcacgc tgacatgcca ggagatcgga 480
gacggc 486

<210> SEQ ID NO 116
<211> LENGTH: 486
<212> TYPE: DNA
<213> ORGANISM: Bacillus subtilis
<220> FEATURE:
<221> NAME/KEY: misc_feature
<222> LOCATION: 23-301
<223> OTHER INFORMATION: n = g, a, c or t/u

<400> SEQUENCE: 116 ctatatttc ttatcaagag cannggcaga ggganncgag nnnnncccgat gaagccnnnc 60 ggcaaccgac ttnnnnnnnn nnnnnnnnnn nnnnnnnnnn nnnnatannn nnnnnnnnnn 120
nnnnnnnnnn nnnnnnnnnn aagcacggtg ctaattnctt gnnnnnncag ctnnnnnnnn 180
nnnnnagcnn nnnnnnnnnn nggctgagag ataagattcg gacgagaaac gaaannnnnn 240
nnnnnnnnnn nnnnnnnnnn nnnnnnnncc tctttagacg cnnnnnnnng attnnnnnnn 300
ngcagtttga agaggttttt tgatatggat gaaaatgaaa ggagctctgg catgagtgag 360
ttattagcga catatctcct gaccgaaccg ggagccgata cagagaagaa agcagaacaa 420
atcgcaacag gattgacagt aggctcctgg actgatctgc cccttgtaaa acaggagcaa 480
atgcaa 486

<210> SEQ ID NO 117
<211> LENGTH: 486
<212> TYPE: DNA
<213> ORGANISM: Bacillus subtilis
<220> FEATURE:

<221> NAME/KEY: misc_feature
<222> LOCATION: 22-305
<223> OTHER INFORMATION: n = g, a, c or t/u

<400> SEQUENCE: 117
atctaaaaac ttatcaagag cnnnggctga gggannctgg annncctnat gaagccnnnc 60
ggcaacctgc annnnnnnnn nnnnnnnnnn nnnnnnnnnn nnntagttnn nnnnnnnnnn 120
nnnnnnnnnn nnnnnnnnnn ntgtaaggtg ctnacttcca gnnnnnncaa aatgnnnnnn 180
nnnnaattcn nnnnnnnnnc attttgaaag ataagggctg catgctgttc ctgtnnnnnn 240
nnnnnnnnnn nnnnnnnnnn nnnnnnnnct ttctttccnn nnnnnnnnnn gccnnnnnnn 300
nnnnnggatt gaaagttttt tattttaaga ggtaaaaagg ctatctgtat atcagcagcc 360
gcgaatcaca ttacatggga aaagacaacc ggcagaaagc tactgtttgt ttgtctccga 420
aaggaggaaa gaagaaatgt taacgtatga taattgggaa gaaccaacga ttacatttcc 480
ggaaga 486

<210> SEQ ID NO 118
<211> LENGTH: 486
<212> TYPE: DNA
<213> ORGANISM: Bacillus subtilis
<220> FEATURE:
<221> NAME/KEY: misc_feature
<222> LOCATION: 21-306
<223> OTHER INFORMATION: n = g, a, c or t/u

<400> SEQUENCE: 118
tcaatatttt ctatccagag nnnaggtgga gggannctgg nnnnccctat gaaacctnnc 60
ggcaacannn nnnnnnnnnn nnnnnnnnnn nnnnnnnnnn nnnttatnnn nnnnnnnnnn 120
nnnnnnnnnn nnnnnnnnnn nnnnnntgtg ccaattncca gnnnnnncaa gcnnnnnnnn 180
nnnngctann nnnnnnnnnn ngcttgaaag ataggaaagc aaggtttata ccggcgtctg 240
cctgtaacag agcgcgccta tatatgaatc tctttccnnn nnnnnnnnat cttcnnnnnn 300
nnnnnnggaa agagattttt tttatgaaaa atacgatgaa aaggatgttt tgcagcatga 360
cggttttggt tacagcaccg tacaacgaag aaggacgaaa agagcttgaa aacttgtttg 420
gctcagttgc ttatcaatct tggaaggaac aaggtagggc atatcgggag gatgaactca 480
ttcagc 486

<210> SEQ ID NO 119
<211> LENGTH: 486
<212> TYPE: DNA
<213> ORGANISM: Bacillus subtilis
<220> FEATURE:
<221> NAME/KEY: misc_feature
<222> LOCATION: 23-307
<223> OTHER INFORMATION: n = g, a, c or t/u

<400> SEQUENCE: 119
gcggatactc ttatcccgag ctnnggcgga ggganncagg nnnnccctat gaagccnnnc 60
agcaaccggt ttctcnnnnn nnnnnnnnnn nnntgttatt tattatgttc aactgagtnn 120
nnnnnnnnnn nnnnngagac aaccaaggtg ctaannncct gnnnttgcaa ggnnnnnnnn 180
nttgtatgat tnnnnnnnnn nccttgagcg ataagagtga aaggcacaaa gaccaaannn 240
nnnnnnnnnn nnnnnnnnnn nnnnnnnncc ctttccnnnn nnnnnnnnnt cgatnnnnnn 300
nnnnnnngga aaaggttttt ttatttcata aatatgccaa ttaacattct ctaatataac 360
tgtacattgt ataagaggga gcgagttccg tatcatatat acaaggtctt tcgggaggcc 420
ttgtgcagga ggaagcaaat catgagtaaa aatcgtcgtt tatttacatc agaatctgtt 480
acggag 486

<210> SEQ ID NO 120
<211> LENGTH: 486
<212> TYPE: DNA
<213> ORGANISM: Bacillus subtilis
<220> FEATURE:
<221> NAME/KEY: misc_feature
<222> LOCATION: 22-305
<223> OTHER INFORMATION: n = g, a, c or t/u

<400> SEQUENCE: 120
tatatttctc ttatcaagag annnggtgga gggannagtg nnnnccctat gaagccnnnc 60
ggcaaccatc aacnnnnnnn nnnnnnnnnn nnnnnnnnnn nnnnactnnn nnnnnnnnnn 120
nnnnnnnnnn nnnnnnnngt tgaaatggtg ccaattncac annnnnncga agcnnnnnnn 180
nnnngttcan nnnnnnnnnn gctttgaaag atgagagaaa ggcattttat ataannnnnn 240
nnnnnnnnnn nnnnnnnnnn nnnnnnnngc ctttctgcnn nnnnnnntca agtgtnnnnn 300
nnnnngcaga aaggcttttc ttttgcagaa aaaaccggaa gatttcttag aatagtgtta 360
aggcaggtga ttgctttgat caatcttcag gatgtttcaa aagtttacaa gtcgaaacat 420
ggagatgtca atgctgtcca aaacgtctcg ctttccatta aaaaaggtga gatttttgga 480
attata 486

<210> SEQ ID NO 121
<211> LENGTH: 486
<212> TYPE: DNA
<213> ORGANISM: Bacillus subtilis
<220> FEATURE:
<221> NAME/KEY: misc_feature
<222> LOCATION: 22-305
<223> OTHER INFORMATION: n = g, a, c or t/u

<400> SEQUENCE: 121
aagttgtacc ttatcaagag annnggtgga gggannctgg nnncccctnat gataccnnnc 60 ggcaaccgct gttnnnnnnn nnnnnnnnnn nnnnnnnnnn nnnntcannn nnnnnnnnnn 120
nnnnnnnnnn nnnnnnnnaa cagaatggtg ctaaatncct tnnnnnnaag aacnnnnnnn 180
nnnnattgcn nnnnnnnnnn gttcttgcag atgaggcgga gatttgatcg ttcaannnnn 240
nnnnnnnnnn nnnnnnnnnn nnnnnnnngc tcttccttnn nnnnnnnnna cacannnnnn 300
nnnnnaagga agagcttttt acatgcttaa tatttcagaa aagaggcgaa taacatggct 360
caacaaacga atgttgcagg acaaaaaaca gaaaaacaac gcaaagcacc tttccgcgcc 420
gatcatgtcg gcagcttgct tcgttccgtt ccggtaaagg aagcccggca aaaaaaagcg 480
gctggt 486

<210> SEQ ID NO 122
<211> LENGTH: 486
<212> TYPE: DNA
<213> ORGANISM: Bacillus subtilis
<220> FEATURE:
<221> NAME/KEY: misc_feature
<222> LOCATION: 22-305
<223> OTHER INFORMATION: n = g, a, c or t/u

<400> SEQUENCE: 122
aaggttttcc ttatcaagag annnggtgga gggannctgg nnnnccctgc gataccnnnc 60
ggcaaccgct gtnnnnnnnn nnnnnnnnnn nnnnnnnnnn nnnnttannn nnnnnnnnnn 120
nnnnnnnnnn nnnnnnnnna cagaatggtg ctaaatncct tnnnnnntag agcaannnnn 180
nnnnntgann nnnnnnnntt gctcttgaag ataaggttga gattgtcacg caannnnnnn 240
nnnnnnnnnn nnnnnnnnnn nnnnnnnngc tcttccttnn nnnnnnnnna tccannnnnn 300
nnnnnaagga agagcttttt tatatttgaa tggaaagaag gaatggacaa catgtcacaa 360
caaacaacac ccgcagaaca aaaatcactt caaagaaaaa aaccgccgtt tcgcgcggat 420
caagtcggaa gcctgctaag atctgagccc gtcaaaaaag cgcggctgca aaaagcggcc 480
ggcgaa 486

<210> SEQ ID NO 123
<211> LENGTH: 486
<212> TYPE: DNA
<213> ORGANISM: Bacillus halodurans
<220> FEATURE:
<221> NAME/KEY: misc_feature
<222> LOCATION: 22-306
<223> OTHER INFORMATION: n = g, a, c or t/u

<400> SEQUENCE: 123
tcatattttc ttatccagag tnnnggtgga gggannctgg nnnnccctgt gaagccnnnc 60
ggcaacctct ttnnnnnnnn nnnnnnnnnn nnnnnnnnnn nnnttttnnn nnnnnnnnnn 120
nnnnnnnnnn nnnnnnnnnn aaagaaggtg ccaattncca gnnnnnncag aacannnnnn 180
nnnnntgann nnnnnnnnnt gttctgaaag ataagaagcg aacggatcgn nnnnnnnnnn 240
nnnnnnnnnn nnnnnnnnnn nnnnnnnnca cgtcttcnnn nnnnnnnnnt tatcnnnnnn 300
nnnnnngaag aggtgttttt tcttgtttta acaccttatc tgtcggaaag attacttgtt 360
attgtaccga aaacagcaag acaaaaaaag aacaacttgg aatgaggagg cgttgtacat 420
gaaaaaaatt tacgtaatcc acgaaaacga tgaatggacg gttcacctat ttaaacgact 480
tgagga 486

<210> SEQ ID NO 124
<211> LENGTH: 486
<212> TYPE: DNA
<213> ORGANISM: Bacillus halodurans
<220> FEATURE:
<221> NAME/KEY: misc_feature
<222> LOCATION: 22-308
<223> OTHER INFORMATION: n = g, a, c or t/u

<400> SEQUENCE: 124
ataaaaagac ttatcgagag annnggcaga gggannctga nnnncccgat gatgccnnnc 60
ggcaacccgt ttgttnnnnn nnnnnnnnnn nnnnnnnnnn nnnagccann nnnnnnnnnn 120
nnnnnnnnnn nagcaaacga aggtgctaat tntcagnnnn nncagaatgn nnnnnnnnna 180
tttnnnnnnn nnnncattct ggaagataag cgaaggcgaa aannnnnnnn nnnnnnnnnn 240
nnnnnnnnnn nnnnnnnnnn nnnnnnnncc tttccnnnnn nnnnnnnnnt tatcnnnnnn 300
nnnnnnnngg aaaggttttt ttgttagaga gccaagtttt tataaaaatg aggagagggc 360
atacgaaagg ggaaataatc agatgattaa agttggtgtg atcggatttg gcaccgttgg 420
gcaaggtgtt gtcgagagtc tagttcaatt ggagcgagga ttaaggaaag aagttactct 480
cgaaat 486

<210> SEQ ID NO 125
<211> LENGTH: 486
<212> TYPE: DNA
<213> ORGANISM: Bacillus halodurans
<220> FEATURE:

<221> NAME/KEY: misc_feature
<222> LOCATION: 21-302
<223> OTHER INFORMATION: n = g, a, c or t/u

<400> SEQUENCE: 125
tctcgtattc ttatccagag nnnaggtgga gggannacgg nnnncccgaa gaaacctnnc 60
agcaaccagc cacgnnnnnn nnnnnnnnnn nnnnnnnnnn nnnatccnnn nnnnnnnnnn 120
nnnnnnnnnn nnnnnnnntg tggtcaggtg ctaattncct gnnnnnncaa gcannnnnnn 180
nnnnttattn nnnnnnnnnn tgcttgagag ataagaggaa gcgagtgaga tccaannnnn 240
nnnnnnnnnn nnnnnnnnnn nnnnnnnnca cctacttctt cttnnaatct tacatgacnn 300
nngagaaggt aggtgttttt ttacacaatc agaaaagatc gaacttttca gatagtttaa 360
gaaaaatgaa ggctttcgca acttggcgac gagctgattt ttccaataga tggataggag 420
gagcaaccat gaatcgtaaa gaattagaaa cagctttagt acaaatcgga aatcgaatgg 480
atgatc 486

<210> SEQ ID NO 126
<211> LENGTH: 486
<212> TYPE: DNA
<213> ORGANISM: Bacillus halodurans
<220> FEATURE:
<221> NAME/KEY: misc_feature
<222> LOCATION: 23-306
<223> OTHER INFORMATION: n = g, a, c or t/u

<400> SEQUENCE: 126
acggatactc ttatccagag ttnnggtgga ggganncagg nnnncccgaa gaaaccnncc 60
agcaaccaac acctnnnnnn nnnnnnnnnn nnnnnnnnnn ngttaaacaa nnnnnnnnnn 120
nnnnnnnnnn nnnnnnnagg tgaaaaggtg ctaannncct gnnnnnncaa ggcnnnnnnn 180
nnnnngttnn nnnnnnnnnn gccttgaaag ataagaggcg aaaggtatgt taattaannn 240
nnnnnnnnnn nnnnnnnnnn nnnnnnnncc cttttccnnn nnnnnnnntc ataatnnnnn 300
nnnnnnggaa aagggtttc ctcattttta tacttttgca agtgtgctgt ggagaatgag 360
tgccgtatca tgttttgcgc agcctgccgt tggtaagggt gtgcttaagg gaggatattc 420
gtaaatggca gatacaagaa gtcgtcgctt atttacatca gagtctgtta cagaaggaca 480
tcctga 486

<210> SEQ ID NO 127
<211> LENGTH: 486
<212> TYPE: DNA
<213> ORGANISM: Bacillus halodurans
<220> FEATURE:
<221> NAME/KEY: misc_feature
<222> LOCATION: 22-306
<223> OTHER INFORMATION: n = g, a, c or t/u

<400> SEQUENCE: 127
aagaaaactc ttatcatgag annnggtgga gggannctgg nnnncccgat gaagccnnnc 60
agcaaccgcc aagcnnnnnn nnnnnnnnnn nnnnnnnnnn nagcaaatcn nnnnnnnnnn 120
nnnnnnnnnn nnnnnngctt ggaaaaggtg ctaattncct gnnnnnncaa agcnnnnnnn 180
nnnnngatnn nnnnnnnnnn gctttgagag atgagagaag ggaagacgta aaacattnnn 240
nnnnnnnnnn nnnnnnnnnn nnnnnnnncc tttctgcnnn nnnnnnnnnt catgnnnnnn 300
nnnnnngcgg aaaggttttt ttgttctatt atgcagtttg attcacggaa ttgtactttc 360
ttacgataat gatttgcgtg ctccttgaga cgaaatttgc gagagtgaga gtttttgctc 420

-continued

```
tcgtactgac tttcgttaaa ttggtaacgc gtagacgaac tgatatattt ttagaaaaga    480

gggctt                                                               486


<210> SEQ ID NO 128
<211> LENGTH: 486
<212> TYPE: DNA
<213> ORGANISM: Oceanobacillus iheyensis
<220> FEATURE:
<221> NAME/KEY: misc_feature
<222> LOCATION: 21-305
<223> OTHER INFORMATION: n = g, a, c or t/u

<400> SEQUENCE: 128

atagttagac ttatcaagag nnnagatgga gggannttgg nnnncccgat gaagtctnnc     60

agcaaccagc ctnnnnnnnn nnnnnnnnnn nnnnnnnnnn nnnagatann nnnnnnnnnn    120

nnnnnnnnnn nnnnnnnnnn aggtatggtg ctaattncca annnnnntag gctnnnnnnn    180

nnnntacann nnnnnnnnnn agccttaaag ataagaagag ctatgtattt taannnnnnn    240

nnnnnnnnnn nnnnnnnnnn nnnnnnnncc cttcttctnn nnnnnnnnta cttttnnnnn    300

nnnnnagaag aggggttttt tgatttttag aataggagga gattattatg aagcggagtt    360

tacaaagacg tttgcaagaa ggcacggtaa tagcaggaga agggtattta tttgaattag    420

agaggagggg gtacttacag gcaggttcgt ttgtaccaga agtagccctt gaaaatccgg    480

atgcgt                                                               486


<210> SEQ ID NO 129
<211> LENGTH: 486
<212> TYPE: DNA
<213> ORGANISM: Ocenobacillus iheyensis
<220> FEATURE:
<221> NAME/KEY: misc_feature
<222> LOCATION: 21-306
<223> OTHER INFORMATION: n = g, a, c or t/u

<400> SEQUENCE: 129

atgacaattc ttatccagag nnnaggtgga gggannctgg nnnncccaag gaagcctnnc     60

ggcaacagac ttannnnnnn nnnnnnnnnn nnnnnnnnnn nntttgatnn nnnnnnnnnn    120

nnnnnnnnnn nnnntaagta ctgtgccaat tnccagnnnn nntagcgnnn nnnnnnnnnt    180

aatnnnnnnn nnnnnntgct agaagatgag aagagtatat agtacggttt cctgtannnn    240

nnnnnnnnnn nnnnnnnnnn nnnnnnnncc ctcttctnnn nnnnnnnnta cttgtnnnnn    300

nnnnnnagaa gggggttttt acttttccct attctctgta cagaactgtc atatgctagt    360

ttcatagagc aagaccctac tctataagac tagcccaaat ctaaaggaga aagaaggaaa    420

ttaacatgac aaaaacagtt attaaagcac catttcgcgc agaccatgta ggtagcttac    480

tacgac                                                               486


<210> SEQ ID NO 130
<211> LENGTH: 486
<212> TYPE: DNA
<213> ORGANISM: Oceanobacillus iheyensis
<220> FEATURE:
<221> NAME/KEY: misc_feature
<222> LOCATION: 21-315
<223> OTHER INFORMATION: n = g, a, c or t/u

<400> SEQUENCE: 130

atgaaaatac ttatcaagag nnnaggtgga gggannctgg nnnncccgct gaaacctnnc     60

agcaacagan nnnnnnnnnn nnnnnnnnnn nnnnnnnnnn nacgcatctg nnnnnnnnnn    120
```

nnnnnnnnnn nnnnnnnnnn nnnntctgtg ctaaatncct gnnnnnncaa gcnnnnnnnn 180
nnnnaatann nnnnnnnnnn ngcttgaaag ataagttgag gttatcgtaa tatccaagtt 240
ctctcttctt atctttatca tgttttttnn nnnnnnnnnn nnnnnnnnnn nnnnnnnnnn 300
nnnnnnnnnn nnnnnaatag aagggatgga tttatatatg agcatacgga atgaagatga 360
aacggaacaa agaagaaatg atctaattga gaaattaatt gcatctaatc attttaaaaa 420
agggaacaaa catctatatg aactgacaac agcagagttg gaatacgaat actttaaatt 480
acaata 486

<210> SEQ ID NO 131
<211> LENGTH: 486
<212> TYPE: DNA
<213> ORGANISM: Oceanobacillus iheyensis
<220> FEATURE:
<221> NAME/KEY: misc_feature
<222> LOCATION: 21-306
<223> OTHER INFORMATION: n = g, a, c or t/u

<400> SEQUENCE: 131
attgaataac ttatccagag nnntgacgga gggaancagg annncctanc gatgtcannc 60
agcaacctac cnnnnnnnnn nnnnnnnnnn nnnnnnnnnn nnntttacnn nnnnnnnnnn 120
nnnnnnnnnn nnnnnnnnnn nggagtggtg ctntcttcct gnnnnnncag aannnnnnnn 180
nnnnttttnn nnnnnnnnnn nttctgaaag ataaggtaat gatatgtaaa aannnnnnnn 240
nnnnnnnnnn nnnnnnnnnn nnnnnnnncc ttctttctnn nnnnnnnnng aatnnnnnnn 300
nnnnnngaaa gaaggttttt ttgatgggat gtgttatgta tgattcagtt ggaaaatatc 360
gagaaacact atgaatctaa aaagagaaga gtgatagggg tagatcaagt ttcccttgat 420
atcaaaaagg gagaaatata tggcatcgtt ggatatagcg gtgcaggtaa aagtacgctt 480
ttacgt 486

<210> SEQ ID NO 132
<211> LENGTH: 486
<212> TYPE: DNA
<213> ORGANISM: Oceanobacillus iheyensis
<220> FEATURE:
<221> NAME/KEY: misc_feature
<222> LOCATION: 23-303
<223> OTHER INFORMATION: n = g, a, c or t/u

<400> SEQUENCE: 132
acggatactc ttattcagag ttnnggtgga ggganncaga nnnncccgat gaagccnnnc 60
agcaaccatc actnnnnnnn nnnnnnnnnn nnnnnnnnnn nnnnactnnn nnnnnnnnnn 120
nnnnnnnnnn nnnnnnnngg tgaaaaggtg ctaannntct gnnnatgcaa gganannnnn 180
nnntaatagt nnnnnnnnnn tccttgaaca ataagagcga aaggccataa ttcttnnnnn 240
nnnnnnnnnn nnnnnnnnnn nnnnnnnncc tttcctcatn nnnnnnnnnn gttnnnnnnn 300
nnnatgaagg aaaggttttt ttgtttttat ctataatttt aggtaccgcg ttttttagta 360
cgaggttctt ttattggcac tttgaatagg atagaagtta taaagagatc cgtaccaaca 420
tatatcaaag gagagtttag ccttatggct gcaaatcgac gtttatttac ttcagagtca 480
gtaact 486

<210> SEQ ID NO 133
<211> LENGTH: 486
<212> TYPE: DNA
<213> ORGANISM: Oceanobacillus iheyensis
<220> FEATURE:

<221> NAME/KEY: misc_feature
<222> LOCATION: 21-304
<223> OTHER INFORMATION: n = g, a, c or t/u

<400> SEQUENCE: 133
atgatatctc ttatctagag nnncggtgga gggannctgg nnnncccttt gaaaccgnnc 60
ggcaaccttc atnnnnnnnn nnnnnnnnnn nnnnnnnnnn nnaattaann nnnnnnnnnn 120
nnnnnnnnnn nnnnnnnnnn atgaaaggtg ccaattncct gnnnnnncan nnnnnnnnnn 180
nnnngaaaan nnnnnnnnnn nnnntgaaag atgagagaac gtcagacgat atacgataaa 240
tacgtannnn nnnnnnnnnn nnnnnnnncg tctttctgtn nnnnnnnntc tcttnnnnnn 300
nnnnacagaa aggcgttttt attttgacga attatgggga aactatacga aatggttgct 360
ggagagtaag aggaggaata aagattgata tccatcgaag ggttaagtaa agtattttca 420
ttaaataaaa aagacatcaa agctgtagac tcattgaccc tcaatattga aaatggcgat 480
atttat 486

<210> SEQ ID NO 134
<211> LENGTH: 486
<212> TYPE: DNA
<213> ORGANISM: Oceanobacillus iheyensis
<220> FEATURE:
<221> NAME/KEY: misc_feature
<222> LOCATION: 21-306
<223> OTHER INFORMATION: n = g, a, c or t/u

<400> SEQUENCE: 134 tacgttttc ttatcatgag nnnaggcgga gggaanatgg nnnncccaac gaaacctnnc 60
ggcaacaggt tctnnnnnnn nnnnnnnnnn nnnnnnnnnn nnntattnnn nnnnnnnnnn 120
nnnnnnnnnn nnnnnnnnna gaatactgtg ccaattncca tnnnnnncaa gcannnnnnn 180
nnnnnaatnn nnnnnnnnnn tgcttgaaag ataagagtag aataatttat tagctttaaa 240
annnnnnnnn nnnnnnnnnn nnnnnnnnct ctattctnnn nnnnnnnnta ttacnnnnnn 300
nnnnnnggaa tagagttttt tgttacatag aatggctcta taatatttgt tggggtaaaa 360
gaaaaataaa aaacacgcaa tctcctattt ttgttatcat tgtttaaacc actaaaccaa 420
acaaaaagga gatgcgtgca attgaattct aacataacat tacctgggtt ggaagaagga 480
aatata 486

<210> SEQ ID NO 135
<211> LENGTH: 486
<212> TYPE: DNA
<213> ORGANISM: Oceanobacillus iheyensis
<220> FEATURE:
<221> NAME/KEY: misc_feature
<222> LOCATION: 21-304
<223> OTHER INFORMATION: n = g, a, c or t/u

<400> SEQUENCE: 135
atgaaatatc ttatcctgag nnnaggtgga gggaanatgg nnnncccaaa gaagcctnnc 60
ggcaacaggt tcnnnnnnnn nnnnnnnnnn nnnnnnnnnn nntagcttnn nnnnnnnnnn 120
nnnnnnnnnn nnnnnnnnnn gaatactgtg ccaaatncca tnnnnnncaa gtatnnnnnn 180
nnnnntctnn nnnnnnnnna tgcttggtag ataagagaag tcggcgacag agnnnnnnnn 240
nnnnnnnnnn nnnnnnnnnn nnnnnnnnct cttttcttan nnnnnnnnnt cttnnnnnnn 300
nnnntatgaa aagggttttt taattactaa cgatagataa tgggggatga aaatgaagta 360
tggtttctgg ttgccgattt ttggagggtg gttgcgtaat gtagaagatg aacagatgcc 420
tcctactttt gaatatgcaa aacaggtaat tcagcacgcg gaagaatggg gatatgatac 480
gacttt 486

<210> SEQ ID NO 136
<211> LENGTH: 486
<212> TYPE: DNA
<213> ORGANISM: Oceanobacillus iheyensis
<220> FEATURE:
<221> NAME/KEY: misc_feature
<222> LOCATION: 22-308
<223> OTHER INFORMATION: n = g, a, c or t/u

<400> SEQUENCE: 136
ttatttttcc ttatcaagag tnncggggga ggaatnctgg nnnntccatt gatcccgnnc 60
agcaaccagt tacnnnnnnn nnnnnnnnnn nnnnnnnnnn nnaatgaann nnnnnnnnnn 120
nnnnnnnnnn nnnnnnnnng taacatggtg ctcattncca gnnnnnncaa gcnnnnnnnn 180
nnnngtagnn nnnnnnnnnn ngcttgatag atgagaaaag tgtttatacc ttttaaataa 240
aannnnnnnn nnnnnnnnnn nnnnnnnnct ctttcnnnnn nnnnnnnnnt catcnnnnnn 300
nnnnnnnngg aagagttttt tctttgttgt cagtgagggt ttggaaaaat aagtggaaca 360
gtttgacttc aaatatgagt aaaccaatca ggtaactaaa gtagggggat cgaaactgtc 420
aagtgatcgt agtttataaa aatctaaaat gaagaggaga gcgtgtatta tgccaactat 480
aaaaac 486

<210> SEQ ID NO 137
<211> LENGTH: 486
<212> TYPE: DNA
<213> ORGANISM: Oceanobacillus iheyensis
<220> FEATURE:
<221> NAME/KEY: misc_feature
<222> LOCATION: 22-306
<223> OTHER INFORMATION: n = g, a, c or t/u

<400> SEQUENCE: 137
agcaaatctc ttatcaagag tnnnggtgga gggaantagg nnnnccctgc gaagccnnnc 60
ggcaacctgt agcnnnnnnn nnnnnnnnnn nnnnnnnnnn nnnaattnnn nnnnnnnnnn 120
nnnnnnnnnn nnnnnngcta ttgaaaggtg ctaaatncct annnnnncag acnnnnnnnn 180
nnnttcatcn nnnnnnnnnn ngtctggaag ataagaggag gttcggtttt aaacagacaa 240
annnnnnnnn nnnnnnnnnn nnnnnnnngt cctcttcnnn nnnnnnnnnt tatnnnnnnn 300
nnnnnngaag gggcttttt ttaatccttc tcttattact ttaaaaataa taaattcaag 360
gaggaaacac gatgtctaaa tttcaatctt tgcaagcaga aacaatctta cttcatggag 420
gacaggaacc agacccatca actggttcac gtgcagttcc aatttatcaa actacgtcct 480
atgtgt 486

<210> SEQ ID NO 138
<211> LENGTH: 486
<212> TYPE: DNA
<213> ORGANISM: Oceanobacillus iheyensis
<220> FEATURE:
<221> NAME/KEY: misc_feature
<222> LOCATION: 21-304
<223> OTHER INFORMATION: n = g, a, c or t/u

<400> SEQUENCE: 138
atgaaatatc ttatcctgag nnnaggtgga gggaanatgg nnnncccaaa gaagcctnnc 60
ggcaacaggt tcnnnnnnnn nnnnnnnnnn nnnnnnnnnn nntagcttnn nnnnnnnnnn 120

```
nnnnnnnnnn nnnnnnnnnn gaatactgtg ccaaatncca tnnnnnncaa gtatnnnnnn    180

nnnnntctnn nnnnnnnnna tgcttggtag ataagagaag tcggcgacag agnnnnnnnn    240

nnnnnnnnnn nnnnnnnnnn nnnnnnnnct cttttcttan nnnnnnnnnt cttnnnnnnn    300

nnnntatgaa aagggttttt taattactaa cgatagataa tgggggatga aaatgaagta    360

tggtttctgg ttgccgattt ttggagggtg gttgcgtaat gtagaagatg aacagatgcc    420

tcctactttt gaatatgcaa aacaggtaat tcagcacgcg gaagaatggg gatatgatac    480

gacttt                                                               486
```

<210> SEQ ID NO 139
<211> LENGTH: 486
<212> TYPE: DNA
<213> ORGANISM: Oceanobacillus iheyensis
<220> FEATURE:
<221> NAME/KEY: misc_feature
<222> LOCATION: 21-300
<223> OTHER INFORMATION: n = g, a, c or t/u

<400> SEQUENCE: 139

```
ttaatacttc ttatcgagag nnnaagctaa gggacnctgg nnnncctgtt gacgcttnnc     60

agcaacctct annnnnnnnn nnnnnnnnnn nnnnnnnnnn nntctccatn nnnnnnnnnn    120

nnnnnnnnnn nnnnnnnnnn tagaaaggtg ctacctncca gnnnnnncaa gatnnnnnnn    180

nnnngtatnn nnnnnnnnnn gtcttgaaag ataagagtcc agattaaaaa aaannnnnnn    240

nnnnnnnnnn nnnnnnnnnn nnnnnnnntc cgcgacgctc ttannnnnnt ttatnnnnnn    300

taagggcatc gcggattttc ttatattaat tttattttta aaggagattg gtaaaatgaa    360

caacattgtg acattgtccg gcagcccctc cgaactatct agatctgaaa aagtactaca    420

ttatttaggg aatcaattaa gtgaacagaa attctatgtg acccatattt ctgttaaaga    480

tgtacc                                                               486
```

<210> SEQ ID NO 140
<211> LENGTH: 486
<212> TYPE: DNA
<213> ORGANISM: Oceanobacillus iheyensis
<220> FEATURE:
<221> NAME/KEY: misc_feature
<222> LOCATION: 21-301
<223> OTHER INFORMATION: n = g, a, c or t/u

<400> SEQUENCE: 140

```
acgtttttc ttatctagag nnnagattga gggatncagg nnnnccctat gacatctnnc     60

ggcagcggat tctttannnn nnnnnnnnnn nnnnnnnnnn nnnntatnnn nnnnnnnnnn    120

nnnnnnnnnn nnnnnnntaaa gaatactgtg ccaattncct gnnnnnncaa atgcnnnnnn    180

nnnaaacgan nnnnnnnnng catttgaaag atgagaaacg atggcttcta catatataca    240

tatggtacga annnnnnnnn nnnnnnnntc cctcttttct tgnnnnnnnt ctttnnnnnn    300

ncaagaaaag agggattttt tatttcgctt gggggttgag acatgattga atttcagaat    360

gtaacaaaga cattcacact aggaaaaaga aaagtagaag ctgttaaaga agtatctcta    420

acgatcgaaa aaggagatat ttatggaatt attgggttca gcggtgcagg aaaaagtacc    480

ttgctt                                                               486
```

<210> SEQ ID NO 141
<211> LENGTH: 486
<212> TYPE: DNA
<213> ORGANISM: Oceanobacillus iheyensis
<220> FEATURE:

<221> NAME/KEY: misc_feature
<222> LOCATION: 22-304
<223> OTHER INFORMATION: n = g, a, c or t/u

<400> SEQUENCE: 141

```
ctaatatctc ttattgagag tnnnggctga gggannctgg nnnnccctgt gacgccnnnc     60

ggcaaccgtt catcgtnnnn nnnnnnnnnn nnnnnnnnnn nnaattccan nnnnnnnnnn    120

nnnnnnnnnn nnnnnngtga tgaataggtg ctaaatncct gnnnnnncaa aatacnnnnn    180

nnnnggacan nnnnnnnngt attttgagaa ataagagagg tgatgaatga cttacgtagt    240

gtaatgttan nnnnnnnnnn nnnnnnnntg cctctcgatn nnnnnnnnnt tcacnnnnnn    300

nnnnatcggg aggcattttt tagtttcccg gaaaaattca caacatgaga aaagaggaag    360

gatttatgtc cacatcgatt gtaaaaggag ctccgggtca ttatcggatt ggcgcggatg    420

tcttggagga aattcctgta ctgcttgaag aactgtcagt taatcgtata caagttatcg    480

caggga                                                               486
```

<210> SEQ ID NO 142
<211> LENGTH: 486
<212> TYPE: DNA
<213> ORGANISM: Clostridium acetobutylicum
<220> FEATURE:
<221> NAME/KEY: misc_feature
<222> LOCATION: 22-302
<223> OTHER INFORMATION: n = g, a, c or t/u

<400> SEQUENCE: 142

```
taattgtttc ttatcaagag tnnngacgga gggannntagg nnnnccctat gaagtcnnnc     60

ggcaacatcc aannnnnnnn nnnnnnnnnn nnnnnnnnnn nnnttattnn nnnnnnnnnn    120

nnnnnnnnnn nnnnnnnnnt tggagatgtg ctaattncct annnnnncag gnnnnnnnnn    180

nnnntttatn nnnnnnnnnn nncctgagag atgagaatgt ttttaaaann nnnnnnnnnn    240

nnnnnnnnnn nnnnnnnnnn nnnnnnnnct gcttcttatt tnnnnnnntt taatnnnnnn    300

nnggataaga agcagtttta ttttttttatt attaggagga gaagattatg ggagaaatag    360

attgtagaaa ttttgagaca aaagcagttc atggggagag tggttttgag agcagaactg    420

gggcaataag ctacccaata taccaaagtt ctacctttag acatgaaggc ttaaataaag    480

gaactg                                                               486
```

<210> SEQ ID NO 143
<211> LENGTH: 486
<212> TYPE: DNA
<213> ORGANISM: Clostridium acetobutylicum
<220> FEATURE:
<221> NAME/KEY: misc_feature
<222> LOCATION: 22-307
<223> OTHER INFORMATION: n = g, a, c or t/u

<400> SEQUENCE: 143

```
tgtaaaaatc ttatcaagag tnnnggtgga gggannctgg nnnnccccttt gaaaccnnnc     60

ggcaaccagt atattnnnnn nnnnnnnnnn nnnnnnnnnn nnnttttnnn nnnnnnnnnn    120

nnnnnnnnnn nnnnnnnaat atatgtggtg ctaaatncct gnnnnnncag cnnnnnnnnn    180

nnnnaaacnn nnnnnnnnnn nngctgatag atgagaataa tcgcgaatgt aaannnnnnn    240

nnnnnnnnnn nnnnnnnnnn nnnnnnnngc ccgaggnnnn nnnnnnnntt atttnnnnnn    300

nnnnnnncca agggcttttt attttatcct attttttaag ggggctaact tatgaattct    360

tcactaaaga atttgttaaa taacaaaatt ttagttttag atggtgctat gggaacatgt    420
```

attcaatcct ttaatctaga tgaaggcgac tttaaaggtt ccttatcttg tacatgtcat 480
tccaat 486

<210> SEQ ID NO 144
<211> LENGTH: 486
<212> TYPE: DNA
<213> ORGANISM: Clostridium acetobutylicum
<220> FEATURE:
<221> NAME/KEY: misc_feature
<222> LOCATION: 21-305
<223> OTHER INFORMATION: n = g, a, c or t/u

<400> SEQUENCE: 144
taatatttcc ttatcaagag nnnaaacgga gggannctgg nnnncccaat gatgtttnnc 60
agcaaccaag gtnnnnnnnn nnnnnnnnnn nnnnnnnnnn nnntttatnn nnnnnnnnnn 120
nnnnnnnnnn nnnnnnnnnn acttatggtg ctaattncca gnnnnnncag gannnnnnnn 180
nnnntattnn nnnnnnnnnn nttctgaaag atgaggagcg actatttaaa catttttatt 240
ttgttaatag annnnnnnnn nnnnnnnntc ctcttcttnn nnnnnnnnnt taannnnnnn 300
nnnnnaagaa gaggatttta ttttgttaat aatagaacca acttattatt atttggtttt 360
attctattaa aagtggtggt ataggacata ttttattaaa agaagagaga aatacctcca 420
atatttctcc cttcaattcc ataagcttat agattttacc caatctatcc taaaatattt 480
ttacta 486

<210> SEQ ID NO 145
<211> LENGTH: 486
<212> TYPE: DNA
<213> ORGANISM: Clostridium acetobutylicum
<220> FEATURE:
<221> NAME/KEY: misc_feature
<222> LOCATION: 22-306
<223> OTHER INFORMATION: n = g, a, c or t/u

<400> SEQUENCE: 145
attagtgcac ttatcaagag annnggtgga gggannccgg nnnnccctgt gaagccnnnc 60
agcaacctgt atannnnnnn nnnnnnnnnn nnnnnnnnnn nntgttaatn nnnnnnnnnn 120
nnnnnnnnnn nnnnnnnnnt atacaaggtg ctaattncct gnnnnnncag cnnnnnnnnn 180
nnnngctann nnnnnnnnnn nngctgagag atgagaatat aaatcgagct tttannnnnn 240
nnnnnnnnnn nnnnnnnnnn nnnnnnnnga gccagagnnn nnnnnnnntt tattnnnnnn 300
nnnnnnctct ggctcttatt attttttaat ctaatgggaa aaggtgaatg acatgataga 360
aataaaaaat gtttctaaat atttttcagg aaataaggtt cttaaagatg ttgatctgaa 420
gattaaaggc ggagaaatat ttggaattgt tggtcatagt ggagctggaa agtcaacatt 480
acttag 486

<210> SEQ ID NO 146
<211> LENGTH: 486
<212> TYPE: DNA
<213> ORGANISM: Clostridium acetobutylicum
<220> FEATURE:
<221> NAME/KEY: misc_feature
<222> LOCATION: 21-305
<223> OTHER INFORMATION: n = g, a, c or t/u

<400> SEQUENCE: 146
atattatttc ttatcaagaa nnnnggtgga gggannctgg nnnnccctat gaagccnnnt 60
gacaaccggc nnnnnnnnnn nnnnnnnnnn nnnnnnnnnn nnnaaatnnn nnnnnnnnnn 120
nnnnnnnnnn nnnnnnnnnn nngtacggtg ttaattncct gnnnnnncaa aacnnnnnnn 180
nnnttatttn nnnnnnnnnn gttttgaaag ataagaaaac agcttattaa ttaatgagta 240
tgttaataan nnnnnnnnnn nnnnnnnntc cgtttttcnn nnnnnnnnnt tattnnnnnn 300
nnnnnggaaa atggattttt tttatatatt aaaatttaaa ctaggacggt gaaaaaaatg 360
cctataaaaa tacctgataa tcttccagca gcaaaaactt taaatgaaga aaatatattt 420
tttatggatg aggatagagc ctatcatcaa gatataagac ctcttaatat tgttatagtt 480
aacctt 486

<210> SEQ ID NO 147
<211> LENGTH: 486
<212> TYPE: DNA
<213> ORGANISM: Clostridium acetobutylicum
<220> FEATURE:
<221> NAME/KEY: misc_feature
<222> LOCATION: 22-307
<223> OTHER INFORMATION: n = g, a, c or t/u

<400> SEQUENCE: 147
tgataaggtc ttatcaagag annnggtgga gggannctgg nnnnccctat gaaaccnnnc 60
aacaaccagc atttnnnnnn nnnnnnnnnn nnnnnnnnnn nntttaattn nnnnnnnnnn 120
nnnnnnnnnn nnnnnnnnag atgtatggtg ttaattncct gnnnnnncaa agnnnnnnnn 180
nnnnttaann nnnnnnnnnn nttttgagag ataagaggat tataaaattt tagaaagcta 240
aaannnnnnn nnnnnnnnnn nnnnnnnntc ctcttcnnnn nnnnnnnnaa ctaannnnnn 300
nnnnnnngaa gaggatttaa ttttatatat ttttaggttt agatattgaa gttaaaatat 360
aataaaaagg ggattttaaa aatgagtgaa gaaagaaaat ttggttttga aacattacag 420
gttcatgcag gacaagttgc tgatccaact acaggatcaa gagctgtacc tatttatcaa 480
acaaca 486

<210> SEQ ID NO 148
<211> LENGTH: 486
<212> TYPE: DNA
<213> ORGANISM: Clostridium acetobutylicum
<220> FEATURE:
<221> NAME/KEY: misc_feature
<222> LOCATION: 22-307
<223> OTHER INFORMATION: n = g, a, c or t/u

<400> SEQUENCE: 148
atggaaactc ttatcaagag annnggtgga gggaanaggg nnnncccgtt gaaaccnnnc 60
ggcaaccgat gtattnnnnn nnnnnnnnnn nnnnnnnnnn nnaatttann nnnnnnnnnn 120
nnnnnnnnnn nnnnnnagta cataatggtg ccaattncct gnnnnnncag aannnnnnnn 180
nnnnnttann nnnnnnnnnn nttctgcaag ataagagaga gaatgttaan nnnnnnnnnn 240
nnnnnnnnnn nnnnnnnnnn nnnnnnnngt ctcttcnnnn nnnnnnnnnt tattnnnnnn 300
nnnnnnngag gagactttta tttttatatt gtaggaggaa gtggatataa tgagaaagtt 360
atttacatct gaatcagtaa cagaagggca tccagataaa atctgcgatc aaatatcaga 420
cgctatttta gatgccatat tggaaaaaga tccaaatgga agagttgctt gtgaaactac 480
agtgac 486

<210> SEQ ID NO 149
<211> LENGTH: 486
<212> TYPE: DNA
<213> ORGANISM: Clostridium perfringens
<220> FEATURE:

<221> NAME/KEY: misc_feature
<222> LOCATION: 22-300
<223> OTHER INFORMATION: n = g, a, c or t/u

<400> SEQUENCE: 149

```
ttatatactc ttatccagag annnggtgga gggaaaaagg nnnnccctat gaaaccnnnc     60

ggcaaccagt gannnnnnnn nnnnnnnnnn nnnnnnnnnn nnngaaannn nnnnnnnnnn    120

nnnnnnnnnn nnnnnnnnnt cactacggtg ccaattnccg gnnnnnntaa agannnnnnn    180

nnnnnaatnn nnnnnnnnnn tctttacaag atgagagaag ataaatttag tgtataacta    240

aaannnnnnn nnnnnnnnnn nnnnnnnntc tcttcttaaa tctnnnnnnt taannnnnnn    300

aggtttgaga agagattttt ttattaacaa aaatatttta aaggcgcgca ttaaaataaa    360

gtttgttaat taagctttaa agatattatt ttgaatcgtg ggaagataaa ttaagttatt    420

tgtttaaata aacagggttg gaataaataa aaatgaaagg ggtgaattag ctatcttatt    480

atgata                                                                486
```

<210> SEQ ID NO 150
<211> LENGTH: 486
<212> TYPE: DNA
<213> ORGANISM: Clostridium perfringens
<220> FEATURE:
<221> NAME/KEY: misc_feature
<222> LOCATION: 22-307
<223> OTHER INFORMATION: n = g, a, c or t/u

<400> SEQUENCE: 150

```
ttaataaatc ttatcaagag annnggtgga gggannctgg nnnnccctgt gaaaccnnnc     60

agcaaccggt aattctttgc ggttaaaaca atgctgattt taaaataaaa aaatcagtag    120

taatttccta tgcaaagatt tatagcggtg ctaaatncct gnnnnnncgg tnnnnnnnnn    180

nnnnagaann nnnnnnnnnn nnactgagag ataagaaaga gagtctgtaa gaataataan    240

nnnnnnnnnn nnnnnnnnnn nnnnnnnnct tctatcnnnn nnnnnnnnnc tagnnnnnnn    300

nnnnnnngat aggagttttt ttattttgta ggataaagga tagatttatt aaatggatta    360

ggaggagaga aaatgaaaaa aggaaagttt tcagcattat taccattaat aatttttgta    420

tcgatttatt tgggaacttc attagtaatg aaagatttct actctgtatc tgttttagtt    480

ccagga                                                                486
```

<210> SEQ ID NO 151
<211> LENGTH: 486
<212> TYPE: DNA
<213> ORGANISM: Listeria monocytogenes
<220> FEATURE:
<221> NAME/KEY: misc_feature
<222> LOCATION: 22-304
<223> OTHER INFORMATION: n = g, a, c or t/u

<400> SEQUENCE: 151

```
ttacgttttc ttatcaagag tnnnggtgga ggganatcg gnnncccagt gaaaccnnnc     60

agcagcggag cnnnnnnnnn nnnnnnnnnn nnnnnnnnnn nnngcaannn nnnnnnnnnn    120

nnnnnnnnnn nnnnnnnnnn nngttctatg ctaattnccg atnnnnncag aannnnnnnn    180

nnngtaatan nnnnnnnnnn nttctggcag ataagtagta gctttcaatg aggnnnnnnn    240

nnnnnnnnnn nnnnnnnnnn nnnnnnnntg cttcgattct gnnnnnnacc aaaaaannnn    300

nnnncagagg aagcgttatt tttttagcgc ttaaagaggg gagtttttgt tagatgaaga    360

aatttttatt agtagcggtt atctcggttt ttgccttggt gttaacggct tgcggaggtt    420
```

ctggcgctag ttcagacaaa gcaaacggtt caggcaaagc gaaagacggc ggctctctta 480
ttatcg 486

<210> SEQ ID NO 152
<211> LENGTH: 486
<212> TYPE: DNA
<213> ORGANISM: Listeria monocytogenes
<220> FEATURE:
<221> NAME/KEY: misc_feature
<222> LOCATION: 22-305
<223> OTHER INFORMATION: n = g, a, c or t/u

<400> SEQUENCE: 152
atattttctc ttatcgagag cnnnggcaga gggannctgg nnnncccgat gaagccnnnc 60
ggcaacctaa ctttatnnnn nnnnnnnnnn nnnnnnnnnn nnttaagcnn nnnnnnnnnn 120
nnnnnnnnnn nnnnnnataa agtgaaggtg ctaattncca gnnnnnncaa aatggnnnnn 180
nnntgtattn nnnnnnnncc gttttggtag ataagaggag ctggatatgt tcgactttcc 240
nnnnnnnnnn nnnnnnnnnn nnnnnnnnac ttctctattn nnnnnnnnnc taannnnnnn 300
nnnnnaatag agaagttttt ttattgcttt catgaataaa tctggataat cacacaacat 360
actagggagg aaaaaagatg aaaaaattaa caaaagggtt aggaatttta cttgcatcaa 420
gccttgtttt aggattagca gcatgtggag gaggcagtga cgataaagcc ttaagcacag 480
aaaaaa 486

<210> SEQ ID NO 153
<211> LENGTH: 486
<212> TYPE: DNA
<213> ORGANISM: Listeria monocytogenes
<220> FEATURE:
<221> NAME/KEY: misc_feature
<222> LOCATION: 21-303
<223> OTHER INFORMATION: n = g, a, c or t/u

<400> SEQUENCE: 153
tagtattttc ttatcacgaa nnnaggtgga gggannctgg nnnncccttt gaagcctnnt 60
agcaaccgga annnnnnnnn nnnnnnnnnn nnnnnnnnnn nnntttatnn nnnnnnnnnn 120
nnnnnnnnnn nnnnnnnnnn tttcacggtg ctaattncca gnnnnnncag nnnnnnnnnn 180
nnntatattn nnnnnnnnnn nnnctgaaag ataagtcgga aatccaagtt taggaaactc 240
tatnnnnnnn nnnnnnnnnn nnnnnnnncc tctctggcgg nnnnnnnctt atatannnnn 300
nnnctgctag ggaggttttt tgatggaaat tactgataaa tacatatcaa agaggagtgg 360
attttatgag taatgagtat aaattcgaaa caattcaagt acacggcgga cacacaccgg 420
acggagatac acattctaga gccgtaccta tttatcaaac gacgtcatac acatttgata 480
gcccgg 486

<210> SEQ ID NO 154
<211> LENGTH: 486
<212> TYPE: DNA
<213> ORGANISM: Listeria monocytogenes
<220> FEATURE:
<221> NAME/KEY: misc_feature
<222> LOCATION: 21-301
<223> OTHER INFORMATION: n = g, a, c or t/u

<400> SEQUENCE: 154
acatagtaac ttatcaagaa nnnaggtgga gggttnctgg nnnnccccgt gaagcctnnt 60
ggcaaccgga nnnnnnnnnn nnnnnnnnnn nnnnnnnnnn nnnttttnnn nnnnnnnnnn 120

-continued nnnnnnnnnn nnnnnnnnnn nntcacggtg ccaaatncca gnnnnnncag nnnnnnnnnn 180
nnngtaacan nnnnnnnnnn nnnctgacag ataaggcacg cgaatcaggt aaattactnn 240
nnnnnnnnnn nnnnnnnnnn nnnnnnnnct ttcccttaaa agnnnnnnnc tgtnnnnnnn 300
ncttttaagg gaaagttttt ttatacataa aaataataag aattgaggcg aagaaaatga 360
accaagtagc tccattttat gcagatcatg tgggaagtat tttacgcaca aagggaatta 420
aagacgcacg agagaaattc caaagtggcg aaataacagc cttagagttg cgcaaaatcg 480
aaaata 486

<210> SEQ ID NO 155
<211> LENGTH: 486
<212> TYPE: DNA
<213> ORGANISM: Listeria monocytogenes
<220> FEATURE:
<221> NAME/KEY: misc_feature
<222> LOCATION: 22-296
<223> OTHER INFORMATION: n = g, a, c or t/u

<400> SEQUENCE: 155
aatttatctc ttatccagag cnnnggtaga gggannctga nnnncccttt gaagccnnnc 60
agcaacctac acnnnnnnnn nnnnnnnnnn nnnnnnnnnn nnatataann nnnnnnnnnn 120
nnnnnnnnnn nnnnnnnnnn gtgaaaggtg ctaannntct gnnnttgcag gagnnnnnnn 180
nnntattatn nnnnnnnnnn cttctgaacg atgagagcaa aggtataatt atnnnnnnnn 240
nnnnnnnnnn nnnnnnnnnn nnnnnnnnag cctttctcta ttcgtgcgcg ttttnngtgc 300
aaaatagaga gaggcttttt atatgagacg tatttggaga gaattgaagg aggaaaataa 360
aattggctaa gaaccgtcat ctatttacat cagaatcggt ttctgatgga catccagata 420
aaattgcaga tcaaatatct gatgcaattt tagatgcaat tatttcaaaa gatcccgacg 480
cgcgtg 486

<210> SEQ ID NO 156
<211> LENGTH: 486
<212> TYPE: DNA
<213> ORGANISM: Listeria monocytogenes
<220> FEATURE:
<221> NAME/KEY: misc_feature
<222> LOCATION: 22-306
<223> OTHER INFORMATION: n = g, a, c or t/u

<400> SEQUENCE: 156
taaattgctc ttataatgag tnnnggtaga gggannctgg nnnncccgtt gaaaccnnnc 60
ggcaaccttt caannnnnnn nnnnnnnnnn nnnnnnnnnn nnntacgnnn nnnnnnnnnn 120
nnnnnnnnnn nnnnnnnnnt tgaaaaggtg ctaaatncct gnnnnnncga agtgnnnnnn 180
nnnnntgann nnnnnnnnnt gcttcgagag ataagagaga cttaaaaagt ttcagtgtat 240
ttgtgtatcg aaacttccaa annnnnnncc tctctagnnn nnnnnnnnnt tctnnnnnnn 300
nnnnnnctag ggaggttttt tattggcaaa aaatcgagag gataaggtga taggtatggt 360
aaaggcgatt agttcaaact tggggtatcc gagacttggg gagaaacgtg aatggaaacg 420
tgcgttagaa aaattctgga atggtgcgat ttcggaagag gaattgttgg ctgaaacgaa 480
ggctct 486

<210> SEQ ID NO 157
<211> LENGTH: 486
<212> TYPE: DNA
<213> ORGANISM: Listeria monocytogenes
<220> FEATURE:

<221> NAME/KEY: misc_feature
<222> LOCATION: 22-304
<223> OTHER INFORMATION: n = g, a, c or t/u

<400> SEQUENCE: 157

```
tgtagaaatc ttatccagag tnnnggtgga gggannaatg nnnnccctat gaagccnnnc      60

agcaacctaa acaataannn nnnnnnnnnn nnnnnnnnnn nnnttcannn nnnnnnnnnn     120

nnnnnnnnnn nnnnttatgt gtttaaggtg ctaagtncat gnnnnnncag aacaannnnn     180

nnnnctaann nnnnnnnntt gttctgaaag atgagaagga agttagtcca tttgaaaaaa     240

tgctnnnnnn nnnnnnnnnn nnnnnnnngc ctttctgctn nnnnnnnnnc atcnnnnnnn     300

nnnnagcaga aaggcttttt ttgtatatca gaatgtagaa aaggtgatag agatgattac     360

gttacaaaac gttgtaaaag aatacacgtc cagaaacaac aaagttctcg cagtcgatca     420

tgtcgattta gaaattgaac aaggcgagat tttcggagtt gtaggttatt ccggagctgg     480

taaaag                                                                486
```

<210> SEQ ID NO 158
<211> LENGTH: 486
<212> TYPE: DNA
<213> ORGANISM: Listeria innocua
<220> FEATURE:
<221> NAME/KEY: misc_feature
<222> LOCATION: 22-304
<223> OTHER INFORMATION: n = g, a, c or t/u

<400> SEQUENCE: 158

```
ttacaatttc ttatccagag tnnnggtgga gggaantcgg nnnncccagt gaaaccnnnc      60

ggcagcggag cnnnnnnnnn nnnnnnnnnn nnnnnnnnnn nnngcaannn nnnnnnnnnn     120

nnnnnnnnnn nnnnnnnnnn nngttctatg ctaattnccg annntnncag aannnnnnnn     180

nnngtaatan nnnnnnnnnn nttctggcag ataagtagta gcttttaatg aggnnnnnnn     240

nnnnnnnnnn nnnnnnnnnn nnnnnnnncg cttcgattct gnnnnnnacc aaaaaannnn     300

nnnncagagg aagcgttatt tttagcgctt aaagagggga gtttttgtta gatgaagaaa     360

tttttattag tagcggttat ctcggttttt gccttggtgt taacggcttg cggaggctct     420

ggcgctagtt cagacaaagc aaacggttca ggcaaagcga aagacggcgg ctctctaatt     480

atcggt                                                                486
```

<210> SEQ ID NO 159
<211> LENGTH: 486
<212> TYPE: DNA
<213> ORGANISM: Listeria innocua
<220> FEATURE:
<221> NAME/KEY: misc_feature
<222> LOCATION: 22-305
<223> OTHER INFORMATION: n = g, a, c or t/u

<400> SEQUENCE: 159

```
atattttctc ttatcgagag cnnnggcaga gggannctgg nnnncccgat gaagccnnnc      60

ggcaacctaa ctttatnnnn nnnnnnnnnn nnnnnnnnnn nnttaagcnn nnnnnnnnnn     120

nnnnnnnnnn nnnnnngtaa agtgaaggtg ctaattncca gnnnnnncaa aatggnnnnn     180

nnntgtattn nnnnnnnncc gttttggtag ataagaggag ctggatatgt tcgactttcc     240

annnnnnnnn nnnnnnnnnn nnnnnnnnct tctctattnn nnnnnnnnnn ctannnnnnn     300

nnnnnaatag agaagttttt ttattgcttt catgaataaa tctggataaa taatcaacat     360

actagggagg aaaaaaagat gagaaaatta acaaaagggt taggaatttt acttgcatca     420
```

agccttattc tagggttagc agcatgtgga ggcggaagtg acgataaagc cttaagcaca 480
aaagaa 486

<210> SEQ ID NO 160
<211> LENGTH: 486
<212> TYPE: DNA
<213> ORGANISM: Listeria innocua
<220> FEATURE:
<221> NAME/KEY: misc_feature
<222> LOCATION: 21-303
<223> OTHER INFORMATION: n = g, a, c or t/u

<400> SEQUENCE: 160
tagtattttc ttatcacgaa nnnaggtgga gggannctgg nnnnccettt gaagcctnnt 60 agcaaccgga annnnnnnnn nnnnnnnnnn nnnnnnnnnn nntttattnn nnnnnnnnnn 120
nnnnnnnnnn nnnnnnnnnn nttcacggtg ctaattncca gnnnnnncag nnnnnnnnnn 180
nnntatattn nnnnnnnnnn nnnctgaaag ataagtcgga aatccaagtt taggaaactc 240
tatnnnnnnn nnnnnnnnnn nnnnnnnncc tctctggcgg nnnnnnnctt atatannnnn 300
nnnctgctag ggaggttttt tgatggaaat tactgataaa tacatattaa agaggagtgg 360
attttatgag taatgagtat aaattcgaaa caattcaagt acacggcgga catacaccgg 420
acggagatac gcattctaga gccgtaccaa tttatcaaac aacatcgtat acatttgata 480
gcccag 486

<210> SEQ ID NO 161
<211> LENGTH: 486
<212> TYPE: DNA
<213> ORGANISM: Listeria innocua
<220> FEATURE:
<221> NAME/KEY: misc_feature
<222> LOCATION: 21-301
<223> OTHER INFORMATION: n = g, a, c or t/u

<400> SEQUENCE: 161
acatagtaac ttatcaagaa nnnaggtgga gggttnctgg nnnncccagt gaagcctnnt 60
ggcaaccgga nnnnnnnnnn nnnnnnnnnn nnnnnnnnnn nnnctttnnn nnnnnnnnnn 120
nnnnnnnnnn nnnnnnnnnn ntcacggtgc caaatnncca gnnnnnncag tnnnnnnnnn 180
nnnnnatcnn nnnnnnnnnn nnactgacag ataaggcacg cgaaacaggt aaatcactnn 240
nnnnnnnnnn nnnnnnnnnn nnnnnnnnct ttcccttaaa agnnnnnnnc tgtnnnnnnn 300
ncttttgggg gaaagttttt ttgtacataa aaataactag aattgaggcg aagaaaatga 360
atcaagtggc accattttat gcagatcatg ttggaagtat tttacggaca aaggcaatta 420
aagaggcacg cgagaaattc caaagtggcg aaattacaac tcaagaatta cgtgaaattg 480
aaaatg 486

<210> SEQ ID NO 162
<211> LENGTH: 486
<212> TYPE: DNA
<213> ORGANISM: Listeria innocua
<220> FEATURE:
<221> NAME/KEY: misc_feature
<222> LOCATION: 22-295
<223> OTHER INFORMATION: n = g, a, c or t/u

<400> SEQUENCE: 162
aatttatctc ttatccagag cnnnggtaga gggannctga nnnnccettt gaagccnnnc 60 agcaacctac acnnnnnnnn nnnnnnnnnn nnnnnnnnnn nnatataann nnnnnnnnnn 120

-continued

```
nnnnnnnnnn nnnnnnnnnn gtgaaaggtg ctaannntct gnnnttgcag gagnnnnnnn    180

nnntaatatn nnnnnnnnnn ctcctgaacg atgagagcaa aggtataatt atannnnnnn    240

nnnnnnnnnn nnnnnnnnnn nnnnnnnngc ctttctctat tcgtgcgcgn tttnncgtgc    300

aaaatagaga gaggcttttt atatgagacg tatttggaga gaactaaagg aggaaaataa    360

aattggctaa aaaccgtcat ctatttacat cggaatcggt ttctgatgga catccagata    420

aaattgcaga tcaaatatct gatgcaattt tagatgcaat tatttcaaaa gatccggacg    480

cacgtg                                                               486
```

```
<210> SEQ ID NO 163
<211> LENGTH: 486
<212> TYPE: DNA
<213> ORGANISM: Listeria innocua
<220> FEATURE:
<221> NAME/KEY: misc_feature
<222> LOCATION: 22-306
<223> OTHER INFORMATION: n = g, a, c or t/u

<400> SEQUENCE: 163

taaattactc ttattatgag tnnnggtaga gggannctgg nnnncccgtt gaaaccnnnc     60

agcaaccttt caannnnnnn nnnnnnnnnn nnnnnnnnnn nnnttcgnnn nnnnnnnnnn    120

nnnnnnnnnn nnnnnnnnnt tgaaaaggtg ctaaatncct gnnnnnncga agtgnnnnnn    180

nnnnntgann nnnnnnnnnt gcttcgagag ataagagaga cttaaaaagt ttcactgtat    240

ttgtgtatcg aaacttccaa annnnnnncc tctctagnnn nnnnnnnnnt tctnnnnnnn    300

nnnnnnctag ggaggttttt tattggcaaa aaattgagag gataaggtga taggtatggt    360

aaaggcgatt agttcaaact tggggtatcc gagacttggg gagaaacgtg aatggaaacg    420

tgcgctagaa aagttttgga atggtgcgat ttcagaagag gaattattgg cggaaacaaa    480

agctct                                                               486
```

```
<210> SEQ ID NO 164
<211> LENGTH: 486
<212> TYPE: DNA
<213> ORGANISM: Listeria innocua
<220> FEATURE:
<221> NAME/KEY: misc_feature
<222> LOCATION: 22-304
<223> OTHER INFORMATION: n = g, a, c or t/u

<400> SEQUENCE: 164

tgtagaaatc ttatccagag tnnnggtgga gggannaatg nnnnccctgt gaaaccnnnc     60

agcaacctaa acaataannn nnnnnnnnnn nnnnnnnnnn nnnttcannn nnnnnnnnnn    120

nnnnnnnnnn nnnnttatgt gtttaaggtg ctaagtncat gnnnnnncag aacaannnnn    180

nnnncgatnn nnnnnnnntt gttctgaaag atgagaagga agttagccca tttgaaaaaa    240

tgctnnnnnn nnnnnnnnnn nnnnnnnngc ctttctgctn nnnnnnnnnc attnnnnnnn    300

nnnnagcagg aaggcttttt tgtatatcag aatgtagaaa aggtgataga gatgattacg    360

ttacagaacg tcgtaaaaga atatacgtcc agaaataaca aagttctcgc agtcgaccat    420

gtcgatttag aaattgaaca aggtgagatt ttcggagtag ttggttattc aggggctggt    480

aaaagt                                                               486
```

```
<210> SEQ ID NO 165
<211> LENGTH: 486
<212> TYPE: DNA
<213> ORGANISM: Staphylococcus aureus
<220> FEATURE:
```

<221> NAME/KEY: misc_feature
<222> LOCATION: 21-304
<223> OTHER INFORMATION: n = g, a, c or t/u

<400> SEQUENCE: 165
ttcatatttc ttattgtgag nnnaagttga gggacnttgg nnnnccctgt gatacttnnc 60
agcaaccgac tnnnnnnnnn nnnnnnnnnn nnnnnnnnnn nnnttatnnn nnnnnnnnnn 120
nnnnnnnnnn nnnnnnnnnn nagcacggtg ctaaaancca annnnnncga gnnnnnnnnn 180
nnnnnttann nnnnnnnnnn nnctcgaatg ataagtataa agannnnnnn nnnnnnnnnn 240
nnnnnnnnnn nnnnnnnnnn nnnnnnnnct tcttactttn nnnnnnnnnt caatnnnnnn 300
nnnnagggtg agaagttttt ttgtttaagg aggaaagaac aatgacaaat tacacagtag 360
atactttaaa tctagggaaa tttattacag aatctgggga agtcatagat aacttgcgtt 420
tgagatatga gcatgttggt tatcatggac aaccattagt tgtagtttgt catgcattaa 480
ctggca 486

<210> SEQ ID NO 166
<211> LENGTH: 486
<212> TYPE: DNA
<213> ORGANISM: Staphylococcus aureus
<220> FEATURE:
<221> NAME/KEY: misc_feature
<222> LOCATION: 22-300
<223> OTHER INFORMATION: n = g, a, c or t/u

<400> SEQUENCE: 166
gcgtaaactc ttatcgagag tnnnggtgga ggganntgtg nnnnccctac gaagccnnnc 60
ggcaaccgtc ttnnnnnnnn nnnnnnnnnn nnnnnnnnnn nnnatatann nnnnnnnnnn 120
nnnnnnnnnn nnnnnnnnnn ngaaatggtg ccaattncac annnnnntaa agtnnnnnnn 180
nnnntttann nnnnnnnnnn acttttgaag atgagagaaa caatactact atnnnnnnnn 240
nnnnnnnnnn nnnnnnnnnn nnnnnnnntg ctttctcaat tttnnnnntc tatcnnnnnn 300
gatattgaga aagcattttt tattttatta agcaacacag ggaggaatca acgtgattga 360
attaaaagaa gttgttaaag aatatcggac taaaaataaa gaagtccttg ctgtagatca 420
cgttaattta tcgattcgag caggatcgat ttatggcgtc attggttttt ctggagcagg 480
aaaaag 486

<210> SEQ ID NO 167
<211> LENGTH: 486
<212> TYPE: DNA
<213> ORGANISM: Staphylococcus aureus
<220> FEATURE:
<221> NAME/KEY: misc_feature
<222> LOCATION: 22-301
<223> OTHER INFORMATION: n = g, a, c or t/u

<400> SEQUENCE: 167
acggattctc ttatcctgag tnnnggtgga gggacnatgg nnnacccaat gaaaccnnnc 60
agcaacctct tttnnnnnnn nnnnnnnnnn nnnnnnnnnn nnntttatnn nnnnnnnnnn 120
nnnnnnnnnn nnnnnnnnaa aagaaaggtg ccaaannccg tnnnttgcag acnnnnnnnn 180
nnnaaatagn nnnnnnnnnn ngtctgaacg ataagagcga atggacgtat tannnnnnnn 240
nnnnnnnnnn nnnnnnnnnn nnnnnnnngg ccttctctct atnnnnnnna ttannnnnnn 300
natagttaga aggtcttttt tatttagctc acagagagag aattttcgta atataaattt 360
aaaggagcaa actatgttaa ataacaaacg attatttact tcagagtctg ttacagaagg 420
acacccagat aaaatcgctg accaagtgtc agatgcaata ttagatgcta ttttaaaaga 480
cgaccc 486

<210> SEQ ID NO 168
<211> LENGTH: 486
<212> TYPE: DNA
<213> ORGANISM: Staphylococcus aureus
<220> FEATURE:
<221> NAME/KEY: misc_feature
<222> LOCATION: 21-302
<223> OTHER INFORMATION: n = g, a, c or t/u

<400> SEQUENCE: 168
taagcatcac ttatctagag nnnaggtgga ggganctgg nnnnccctat gaagcctnnc 60
ggcaacatnn nnnnnnnnnn nnnnnnnnnn nnnnnnnnnn nnnctcgann nnnnnnnnnn 120
nnnnnnnnnn nnnnnnnnnn nnnnnatgtg ccaattncca gnnnnnntaa ccgnnnnnnn 180
nnnnntaann nnnnnnnnnn tggtttgaag ataagcaggt aaagcacatg aaannnnnnn 240
nnnnnnnnnn nnnnnnnnnn nnnnnnnnac ctctttcttc annnnnnnnt cgttnnnnnn 300
nntgtgagaa agaggtattt ttaattggaa agcaggtaaa aaggatggaa gtacataaaa 360
agagcaatgc ttgggcatta ttccccttgt tattatttgt ggcgttgttt ttaggcgtag 420
gtattatcac aggtgatttt acttcaatgc cattaaatgt tgcaattacg ataacggtaa 480
ttgtgg 486

<210> SEQ ID NO 169
<211> LENGTH: 486
<212> TYPE: DNA
<213> ORGANISM: Streptomyces coelicolor
<220> FEATURE:
<221> NAME/KEY: misc_feature
<222> LOCATION: 21-315
<223> OTHER INFORMATION: n = g, a, c or t/u

<400> SEQUENCE: 169
ttcataccgc tcatccagag nnngggcaga gggatnacgg nnnncccgat gaagcccnnc 60
ggcaaccctc cagtcggnnn nnnnnnnnnn nnttcttgtc acacggacgt ggcgaggctc 120
nnnnnnnnnn nnnnccggct agggaaggtg ccaaatnccg tnnnnnnctc acggcgnnnn 180
nnnnagatgn nnnnnnncgt cgtgaggaag atgaggagaa agggcctcgc ctccatggct 240
gtgcagactg ccgaaacctc cacgaaccnn nnnnnnnnnn nnnnnnnnnn nnnnnnnnnn 300
nnnnnnnnnn nnnnnccacc gacgccgccg tcgacctcgg ccccgccacc gcgctgagct 360
gccgggagtg cggccacagg gttccgctcg gaccggtctt cgcctgcgaa gagtgtttcg 420 gcccccctcga gatcgcctac gacttctcgg actacgacgc cgaagagctg cgcaagcgga 480
tcgaag 486

<210> SEQ ID NO 170
<211> LENGTH: 486
<212> TYPE: DNA
<213> ORGANISM: Chlorobium tepidum
<220> FEATURE:
<221> NAME/KEY: misc_feature
<222> LOCATION: 21-200
<223> OTHER INFORMATION: n = g, a, c or t/u

<400> SEQUENCE: 170
tttcgagcta tcatccagaa nnnaggcgga ggganctgg nnnnccctgc gaagcctnnt 60
ggcaaccttc atnnnnnnnn nnnnnnnnnn nnnnnnnnnn nnntccacnn nnnnnnnnnn 120

-continued

```
nnnnnnnnnn nnnnnnnnnn atgagcggtg ccaaatncca tnnnnnnccc ggannnnnnn    180

nnnnggaaan nnnnnnnnnn tccgggaaag atgatgtatg cattcctgct gatttcatac    240

ctcacttgat gcttcccgca catacctcct gaccccgacc gcgcactacg gatcgagcgc    300

ttcaaccttg taccatttgc catgagtgag gataacacct tccggttcga gaccttgcag    360

gttcacgccg ggcaggagcc tgatccggtg accggatcgc gcgccgtgcc catttaccag    420

accacctcct acgtgttcga gaacgccgag cacggcgctg acctgttcgc gcttcgcaag    480

gcgggc                                                                486
```

```
<210> SEQ ID NO 171
<211> LENGTH: 486
<212> TYPE: DNA
<213> ORGANISM: Thermoanaerobacter tengcongensis
<220> FEATURE:
<221> NAME/KEY: misc_feature
<222> LOCATION: 22-307
<223> OTHER INFORMATION: n = g, a, c  or t/u

<400> SEQUENCE: 171

taacacgctc ttatcaagag annnggtgga gggaanagag nnnncccgat gaaaccnnnc     60

ggcaacctgt cctnnnnnnn nnnnnnnnnn nnnnnnnnnn nnntttaann nnnnnnnnnn    120

nnnnnnnnnn nnnnnnnnnn ggataaggtg ccaattnctc tnnnnnncag aagannnnnn    180

nnnntttttn nnnnnnnnnt cttctgaaag atgagggtat gnnnnnnnnn nnnnnnnnnn    240

nnnnnnnnnn nnnnnnnnnn nnnnnnnncc tcttctnnnn nnnnnnnnnn tttnnnnnnn    300

nnnnnnnaga aggggtttta ttttgctctt aaggagggaa gaagatgcgt agactcttta    360

cttctgagtc agtcactgaa gggcatcctg acaagatctg tgaccagatt tcagatgcca    420

ttttggatga aattttaaaa aaagaccctt acgcccgcgt ggcatgtgag acagctgtaa    480

ctaccg                                                                486
```

```
<210> SEQ ID NO 172
<211> LENGTH: 486
<212> TYPE: DNA
<213> ORGANISM: Thermoanaerobacter tengcongensis
<220> FEATURE:
<221> NAME/KEY: misc_feature
<222> LOCATION: 22-307
<223> OTHER INFORMATION: n = g, a, c or t/u

<400> SEQUENCE: 172

ttaaaatctc ttatcaagag annnggtgga gggannctgg nnnncccgat gaaaccnnnc     60

ggcaaccagc cnnnnnnnnn nnnnnnnnnn nnnnnnnnnn nnnttagnnn nnnnnnnnnn    120

nnnnnnnnnn nnnnnnnnnn nggcatggtg ccaattncct gnnnnnncag cgnnnnnnnn    180

nnnngtttnn nnnnnnnnnn ncgctgaaag atgagagatt cttgtannnn nnnnnnnnnn    240

nnnnnnnnnn nnnnnnnnnn nnnnnnnngt ctcttcnnnn nnnnnnnntt ttagcnnnnn    300

nnnnnnngaa gggacttttt tatttttaaa aaaggagggg cattaaatgt tgaaaaatga    360

aaagctgtgt aataaactta aagaaaagaa atttgtaata actgtggaaa tttctccccc    420

caaagggata gatgtaacta aaactatcga ggaagctcga aaacttaaag gtgtggcaga    480

tgctct                                                                486
```

```
<210> SEQ ID NO 173
<211> LENGTH: 486
<212> TYPE: DNA
<213> ORGANISM: Thermoanaerobacter tengcongensis
<220> FEATURE:
```

<221> NAME/KEY: misc_feature
<222> LOCATION: 22-299
<223> OTHER INFORMATION: n = g, a, c or t/u

<400> SEQUENCE: 173

```
ctcaatcctc ttatcaagag tnnnggtgga gggannctgg nnnncccgat gaaaccnnnc     60

ggcaaccggc acnnnnnnnn nnnnnnnnnn nnnnnnnnnn nnngtaannn nnnnnnnnnn    120

nnnnnnnnnn nnnnnnnnnn gtgcttggtg ccaattncct gnnnnnncag gttgggnnnn    180

nnnngttann nnnnnnnccc agcctgagag atgagaggag aggccgagta attgtgannn    240

nnnnnnnnnn nnnnnnnnnn nnnnnnnntt actaggccct cttcnnnnnt cattnnnnng    300

aagagggcct aagaattttt ctggaggtgc aaaatgaggg taaagattgg gttgatggga    360

cttggaactg ttgggacagg agtatttaaa atagttaatt ctagagggag atatatcaag    420

gagagtacgg gattttatcc ggagataaag aaagtgcttg tgaaggattt gcacaaaaag    480

agaaaa                                                               486
```

<210> SEQ ID NO 174
<211> LENGTH: 486
<212> TYPE: DNA
<213> ORGANISM: Fusobacterium nucleatum
<220> FEATURE:
<221> NAME/KEY: misc_feature
<222> LOCATION: 21-307
<223> OTHER INFORMATION: n = g, a, c or t/u

<400> SEQUENCE: 174

```
tggaaataaa ccatcaagag nnnagattga ggganncagg nnnncccgtt gagatctnnc     60

agcaacctac gnnnnnnnnn nnnnnnnnnn nnnnnnnnnn nnntaaaann nnnnnnnnnn    120

nnnnnnnnnn nnnnnnnnnn ntgtgtggtg ctaattncct gnnnnnnnnn nnnnnnnnnn    180

nnnnnnnnnn nnnnnnnnnn nnnnnnatag atggaaaaga ttataataca tctnnnnnnn    240

nnnnnnnnnn nnnnnnnnnn nnnnnnnnct ctatctnnnn nnnnnnnngg aattnnnnnn    300

nnnnnnngga tagagttttt ttattttaat attttgttaa ttttttaagg agggaaaaat    360

gaaaaagttt acatacttta catcagaatt tgtttcacca ggacatccag ataaaatttc    420

agatcaaata tcagatgcaa ttttagatgc ttgtttaaaa gatgacccta attcaagagt    480

tgcctg                                                               486
```

<210> SEQ ID NO 175
<211> LENGTH: 486
<212> TYPE: DNA
<213> ORGANISM: Fusobacterium nucleatum
<220> FEATURE:
<221> NAME/KEY: misc_feature
<222> LOCATION: 21-307
<223> OTHER INFORMATION: n = g, a, c or t/u

<400> SEQUENCE: 175

```
aaataaataa ccatccagag nnnaaacgga gggannctgg nnnncccaat gatgtttnnc     60

agcaacctac nnnnnnnnnn nnnnnnnnnn nnnnnnnnnn nnttaaatnn nnnnnnnnnn    120

nnnnnnnnnn nnnnnnnnnn nngtgtggtg ctaattncca gnnnnnnnnn nnnnnnnnnn    180

nnnnnnnnnn nnnnnnnnnn nnnnnnagag atggagagga aaattgaaac aagaactaan    240

nnnnnnnnnn nnnnnnnnnn nnnnnnnntc catactnnnn nnnnnnnnct ataannnnnn    300

nnnnnnnggt atggattttt taattaagta agaatttatt atagaaagta gggatataaa    360

tgattacact tgaaaatgta aataaaattt attccaataa cttgcatgct gtaaaagatg    420
```

ttaatttaaa agttaatgaa ggagatatct ttggaattat aggtttaagt ggtgctggaa 480
aatctt 486

<210> SEQ ID NO 176
<211> LENGTH: 486
<212> TYPE: DNA
<213> ORGANISM: Deinococcus radiodurans
<220> FEATURE:
<221> NAME/KEY: misc_feature
<222> LOCATION: 22-268
<223> OTHER INFORMATION: n = g, a, c or t/u

<400> SEQUENCE: 176
agggtcacct ttatccagag tnncggcgca gggacnctgg nnnccccatg accgccgnnc 60
agcaaccggc cnnnnnnnnn nnnnnnnnnn nnnnnnnnnn nctcatcacn nnnnnnnnnn 120
nnnnnnnnnn nnnnnnnnnn ggcagcggtg ctnnttncca gnnnannccc gcgcgagcag 180
cgcccgacga tgggcggcgc cgcgggaacg ataaaggaag gcgggtcctc ttcgcgggtt 240
ccaacggacg gctcagcccn nnnnnnnntg ggcgtcccct tccagacttc ttttcgtcca 300
ggaaggggac gcccgttttg ggccgacctc tccgctctcc ccaccggagg cccgccccgt 360
gaccttaccg tcctcccccc cagccttgca cttcgaaggc gtcagcaaaa cctaccccgg 420
ccagccggcg ccggcgctga gcgatttgac cctcaccgtt gcgcgcggca gccgcaccgg 480
catcat 486

<210> SEQ ID NO 177
<211> LENGTH: 486
<212> TYPE: DNA
<213> ORGANISM: Deinococcus radiodurans
<220> FEATURE:
<221> NAME/KEY: misc_feature
<222> LOCATION: 22-315
<223> OTHER INFORMATION: n = g, a, c or t/u

<400> SEQUENCE: 177
ccgtgcgcgg tcatccagag tnncgcccca gggtgntttc ctgncccgcc tacggcgnnc 60
agcaaccggc cnnnnnnnnn nnnnnnnnnn nnnnnnnnnn nttcatcacn nnnnnnnnnn 120
nnnnnnnnnn nnnnnnnnnn ggtcacggtg ctnnttncag gaaannnggg ccgtttaggt 180
gcgccgacga tggcgcgagn cggcccnnng atgcccgcca ggaggtgcat ttccaaccat 240
gagccatcac ccagaagcgt cggcttccnn nnnnnnnnnn nnnnnnnnnn nnnnnnnnnn 300
nnnnnnnnnn nnnnngccaa tccgtccatc aaccatcaac cgtccaccat caccgaggcc 360
gcccgccagc gcatcctgat tctcgacggc gcctggggta cgcagcttca gcgagccaac 420
ctcaccgaag cggacttccg ctgggacgaa gccgacccca cgcggatgta ccggggcaac 480
ttcgac 486

<210> SEQ ID NO 178
<211> LENGTH: 486
<212> TYPE: DNA
<213> ORGANISM: Xanthomonas axanopodis
<220> FEATURE:
<221> NAME/KEY: misc_feature
<222> LOCATION: 21-315
<223> OTHER INFORMATION: n = g, a, c or t/u

<400> SEQUENCE: 178
cctagcctca ccatcgagac nnncggcgga ggganncagg nnnncccttt gatgccgnng 60
ggcagccagc ggagcgcnnn nnnnnnnnnn nnnnnnnnnn nnngcaannn nnnnnnnnnn 120
nnnnnnnnnn nnnngcgtcc gcgtttggtg ccaaatncct gnnnnnncgg ggacnnnnnn 180
nnnctccgcn nnnnnnnngt ccgccgaaag atggttcgaa tcgtgccttg cgcacgtcga 240
acgcgagctc cngcgaagct cgatggccnn nnnnnnnnnn nnnnnnnnnn nnnnnnnnnn 300
nnnnnnnnnn nnnnngatcc accctggata ccgccatgag cctcgtgaat actgcatcgc 360
cgtctaccaa cgatttcgtt gacacccccg ccagcagcga cgacggcatc actgccgtgc 420
gcggcgaact tgtcatcgcc ctgccgatgc gccatgccgg catgcgcgag ctgcggctgc 480
gctatg 486

<210> SEQ ID NO 179
<211> LENGTH: 486
<212> TYPE: DNA
<213> ORGANISM: Xanthomonas campestris
<220> FEATURE:
<221> NAME/KEY: misc_feature
<222> LOCATION: 21-315
<223> OTHER INFORMATION: n = g, a, c or t/u

<400> SEQUENCE: 179
cgtagcctca ccatcgagac nnncggcgga ggganncagg nnnncccttt gatgccgnng 60
ggcagccagc ggagcgcnnn nnnnnnnnnn nnnnnnnnnn nnngcaannn nnnnnnnnnn 120
nnnnnnnnnn nnnngcgccc gcgtttggtg ccaaatncct gnnnnnncgg ggacnnnnnn 180
nnnctccgcn nnnnnnnngt ccgccgaaag atggttcgaa tcgtgccctc tgcacgtcga 240
acgcgagctc ccgcgaagct cgatggccnn nnnnnnnnnn nnnnnnnnnn nnnnnnnnnn 300
nnnnnnnnnn nnnnngatcc accccggata tcgccatgag cctcgtgacc acagcatcgc 360
cactcaccac cgctgacacc tacacgcccg ccgctgatag cgacgccccg cctgccgtgc 420
gcggcgagct cgtcatcaat ctaccgatgc gccacgccgg ccaacgcgag ctgcgcctgc 480
gctacg 486

<210> SEQ ID NO 180
<211> LENGTH: 486
<212> TYPE: DNA
<213> ORGANISM: Staphylococcus epidermidis
<220> FEATURE:
<221> NAME/KEY: misc_feature
<222> LOCATION: 21-304
<223> OTHER INFORMATION: n = g, a, c or t/u

<400> SEQUENCE: 180
ttacctaacc ttattttgag nnnaagctga gggatnttgg nnnncccata gaagcttnnc 60
agcaaccgac tnnnnnnnnn nnnnnnnnnn nnnnnnnnnn nnttaaatnn nnnnnnnnnn 120
nnnnnnnnnn nnnnnnnnnn nagcacggtg ctaatancca annnnnncga gnnnnnnnnn 180
nnnnncaann nnnnnnnnnn nnctcgaatg ataagtacga taannnnnnn nnnnnnnnnn 240
nnnnnnnnnn nnnnnnnnnn nnnnnnnngt gcctttacat cnnnnnnnna tttnnnnnnn 300
nnnngagtaa ggcacttttt tagttgaagg aggtaggaac tattatgacg aattacacgg 360
ttaatacatt agaactaggt gagtttaaaa ctgaatctgg tgaaacgatt gatcatttac 420
gtctacgtta tgaacatgta ggacttcctg gtcaacccct tgtcgttgtt tgccatgcac 480
ttactg 486

<210> SEQ ID NO 181
<211> LENGTH: 486
<212> TYPE: DNA
<213> ORGANISM: Staphylococcus epidermidis
<220> FEATURE:

<221> NAME/KEY: misc_feature
<222> LOCATION: 22-486
<223> OTHER INFORMATION: n = g, a, c or t/u

<400> SEQUENCE: 181
acggattctc ttatcctgag tnnnggtgga gggacnatgg nnnacccaat gaaaccnnnc 60
agcaacctct ttnnnnnnnn nnnnnnnnnn nnnnnnnnnn nnnatttnnn nnnnnnnnnn 120
nnnnnnnnnn nnnnnnnnnn aaagaaaggt gccaaanccg tnnnttgcag acnnnnnnnn 180
nnnaaatatg nnnnnnnnnn ngtctgaacg ataagagcga atggacgttt aagagccttc 240
tctctatcta tannnnnnnn nnnnnnnnnn nnnnnnnnnn nnnnnnnnnn nnnnnnnnnn 300
nnnnnnnnnn nnnnnnnnnn nnnnnnnnnn nnnnnnnnnn nnnnnnnnnn nnnnnnnnnn 360
nnnnnnnnnn nnnnnnnnnn nnnnnnnnnn nnnnnnnnnn nnnnnnnnnn nnnnnnnnnn 420
nnnnnnnnnn nnnnnnnnnn nnnnnnnnnn nnnnnnnnnn nnnnnnnnnn nnnnnnnnnn 480 nnnnnn 486

<210> SEQ ID NO 182
<211> LENGTH: 486
<212> TYPE: DNA
<213> ORGANISM: Geobacter sulferreducens
<220> FEATURE:
<221> NAME/KEY: misc_feature
<222> LOCATION: 21-303
<223> OTHER INFORMATION: n = g, a, c or t/u

<400> SEQUENCE: 182
gtagaccttc ttatcaagag nnntggtgga gggannaagg nnnnccctgt gaaaccannc 60
agcaaccggt ccgnnnnnnn nnnnnnnnnn nnnnnnnnnn nnngtagnnn nnnnnnnnnn 120
nnnnnnnnnn nnnnnnncgg acgccaggtg ctaaatncct gnnnnnnccc nnnnnnnnnn 180
nnnngaaann nnnnnnnnnn nnngggagcg atgagaggga gcttgtgacc accgacgcgt 240
acannnnnnn nnnnnnnnnn nnnnnnnngg ccccttcccg nnnnnnnnnt ttccnnnnnn 300
nnncgggagg gggcctttca ttttcgccgc cgcgcgcacg cgcccgtggg gaatcatgtc 360
cgtcggcatc gtcgaagaac aatccgtcac cttcgaaacg gatctcaggc tggaaagcgg 420
ccggatactg gggcccatca ccctggccta cgagacctac ggccggctga acgccgaccg 480
gtccaa 486

<210> SEQ ID NO 183
<211> LENGTH: 486
<212> TYPE: DNA
<213> ORGANISM: Geobacter sulferreducens
<220> FEATURE:
<221> NAME/KEY: misc_feature
<222> LOCATION: 21-305
<223> OTHER INFORMATION: n = g, a, c or t/u

<400> SEQUENCE: 183
acggcttaac ttatcaagag nnncgaccga gggannccagg nnnncccggt gacgtcgnnc 60
ggcaacctcc ccnnnnnnnn nnnnnnnnnn nnnnnnnnnn nnnatggnnn nnnnnnnnnn 120
nnnnnnnnnn nnnnnnnnnn ggggaaggtg ccaattncct gnnnnnncga gaccnnnnnn 180
nnnngacann nnnnnnnnng gtttcgggag ataaggaaga gcgtgacacc tcacggtgaa 240
tcgaannnnn nnnnnnnnnn nnnnnnnntc ctcttccgnn nnnnnnnnnc acccnnnnnn 300
nnnnncggaa ggggattttt cattgtggag gaaaccatga acatcgcgac gcaggcagca 360
cagatcggtc tcgactggga tacccgcacc ggggcggtga cggtacccat ctaccagacg 420

```
gcaaccttcc ggcatccggg attgggccag agcacgggct acgattattc ccgctccggc    480

aacccc                                                               486


<210> SEQ ID NO 184
<211> LENGTH: 486
<212> TYPE: DNA
<213> ORGANISM: Bacillus anthracis
<220> FEATURE:
<221> NAME/KEY: misc_feature
<222> LOCATION: 22-306
<223> OTHER INFORMATION: n = g, a, c or t/u

<400> SEQUENCE: 184

acacatactc ttatcaagag tnnnggcgga gggannctgg nnnncccgat gatgccnnnc     60

ggcaaccgag cttatgnnnn nnnnnnnnnn nnnnnnnnnn nnnnacgnnn nnnnnnnnnn    120

nnnnnnnnnn nnnnnntata agctaaggtg ctaattncct gnnnnnncaa aatgannnnn    180

nnnngtttnn nnnnnnnntc gttttggaag ataagagagg atcctatttt gtctattcgn    240

nnnnnnnnnn nnnnnnnnnn nnnnnnnngc acctctcnnn nnnnnnntta tttttnnnnn    300

nnnnnngaga ggtgcttttt attttggaac atatatgaag ggggaactat agatgaaaaa    360

agtattatta agcattgtaa gcggagcggt actattatta ggcgcatgta gcgctggttc    420

ggataaagaa gtaaaagcgt tagatgagaa aaagattact gtcggtgtaa caggcgggcc    480

gcatga                                                               486


<210> SEQ ID NO 185
<211> LENGTH: 486
<212> TYPE: DNA
<213> ORGANISM: Bacillus anthracis
<220> FEATURE:
<221> NAME/KEY: misc_feature
<222> LOCATION: 21-303
<223> OTHER INFORMATION: n = g, a, c or t/u

<400> SEQUENCE: 185

agcaatttac ttatccagag nnnaggtaga gggannctgg nnnnccctat gacacctnnc     60

agcagcgggt tctnnnnnnn nnnnnnnnnn nnnnnnnnnn nngtaatann nnnnnnnnnn    120

nnnnnnnnnn nnnnnnnnng gaacaccgtg ctaattncca gnnnnnncaa gnnnnnnnnn    180

nnnncaagtn nnnnnnnnnn nncttgaaag ataagtgatg ggcctttgtt tattaannnn    240

nnnnnnnnnn nnnnnnnnnn nnnnnnnngc cttgatctta nnnnnnnnnt ttttnnnnnn    300

nnntaggatc aaggcttttt gtattctaaa aagagaaaag ggagtaatgg aaaaagtacg    360

ttcataaaac aaagtaaatt catgtgttta gggggttatg gaagtgtatg taattaaaaa    420

attatcggtt atggtgttca cactatgggt tattacgaca gtgacatttc taattatgca    480

tattat                                                               486


<210> SEQ ID NO 186
<211> LENGTH: 486
<212> TYPE: DNA
<213> ORGANISM: Bacillus anthracis
<220> FEATURE:
<221> NAME/KEY: misc_feature
<222> LOCATION: 21-304
<223> OTHER INFORMATION: n = g, a, c or t/u

<400> SEQUENCE: 186

tttactcatt gtatcaagag nnnaggtgga gggannctgg nnnncccttt gaaacctnnc     60

ggcagcaggt tcannnnnnn nnnnnnnnnn nnnnnnnnnn nnnttttnnn nnnnnnnnnn    120
```

-continued

```
nnnnnnnnnn nnnnnnnnnt gaatactgtg ccacttncct gnnnnnncaa gctnnnnnnn    180

nnnnttatnn nnnnnnnnnn agcttgaaag atagaatgag ggacttcgtt tatatacggg    240

tgcataactt gtacgtaaaa annnnnnntc cctctttctc nnnnnnnnna atacnnnnnn    300

nnnngaaaag agggattttt tatttttcat ttccctcatc atcatccaaa cttaattatt    360

taggaggaaa atcaaatgaa aaagaagttt gtacccggta ttgcatcagt tgtaggagta    420

agtattttat taactggttg cggtagttat aaaaacgaag caagcggagc aaatgcaaaa    480

gacgag                                                                486
```

<210> SEQ ID NO 187
<211> LENGTH: 486
<212> TYPE: DNA
<213> ORGANISM: Bacillus anthracis
<220> FEATURE:
<221> NAME/KEY: misc_feature
<222> LOCATION: 21-298
<223> OTHER INFORMATION: n = g, a, c or t/u

<400> SEQUENCE: 187

```
cgatacattc ttatccagag nnnaggtgga gggannctgg nnnnccctac gatacctnnc     60

agcaacgggt tnnnnnnnnn nnnnnnnnnn nnnnnnnnnn nnnttttttnn nnnnnnnnnn    120

nnnnnnnnnn nnnnnnnnnn naataccgtg ctaactncca gnnnnnncaa gccnnnnnnn    180

nnnatataaa nnnnnnnnnn ggcttggaag atgagaagat gtgaccgagt acatataann    240

nnnnnnnnnn nnnnnnnnnn nnnnnnnngt gctctccttc ttatcnnttt atggttnnga    300

taagaaggag agcacttttt attttacctc gagagctcta cttcaagttt ttacagcata    360

taggaggggg aaaaatgatt tcttttaata atgtaagtaa agtatatgaa tcaggtgggc    420

aatctgttca tgcggtggag gatgtaacgt tatcagttga gaaaggcgaa atttttggca    480

ttatcg                                                                486
```

<210> SEQ ID NO 188
<211> LENGTH: 486
<212> TYPE: DNA
<213> ORGANISM: Bacillus anthracis
<220> FEATURE:
<221> NAME/KEY: misc_feature
<222> LOCATION: 22-305
<223> OTHER INFORMATION: n = g, a, c or t/u

<400> SEQUENCE: 188

```
gaataattct ttatcaagag annnggcaga ggganncggg nnnncccttt gaagccnnnc     60

agcaacctca gtttnnnnnn nnnnnnnnnn nnnnnnnnnn nnnatacnnn nnnnnnnnnn    120

nnnnnnnnnn nnnnnnaaac tgaataggtg ctaattncct gnnnnnncaa aatgcnnnnn    180

nnnnnattnn nnnnnnnngc atttgaaag ataaaacgta actattgtgt acaaaannnn    240

nnnnnnnnnn nnnnnnnnnn nnnnnnnnct catctttcnn nnnnnnnttg atcatnnnnn    300

nnnnngaaag gtgagttttt ttatatttca aaacatatat tggaggtatt taaaatgaaa    360

gtaattgacc tatcacaaac attcgaaaat aatatgtctc aatttcctgg aacaccaaaa    420

atcaatttag aagccattac aagcgttgaa gaaacaggtt atcaagttac agatttccat    480

tctgtc                                                                486
```

<210> SEQ ID NO 189
<211> LENGTH: 486
<212> TYPE: DNA
<213> ORGANISM: Bacillus anthracis
<220> FEATURE:

<221> NAME/KEY: misc_feature
<222> LOCATION: 22-308
<223> OTHER INFORMATION: n = g, a, c or t/u

<400> SEQUENCE: 189
aatacaaagc ttatcaagag annnagcgga gggaanctgg nnnncccggc gaagctnnnc 60
ggcaacctgc ttnnnnnnnn nnnnnnnnnn nnnnnnnnnn nnnatagann nnnnnnnnnn 120
nnnnnnnnnn nnnnnnnnnn aagcaaggtg ctaaatncca gnnnnnncaa aatggnnnnn 180
nnnnnaatnn nnnnnnnncc attttgaaag ataaggtaaa atatattacc gaacagnnnn 240
nnnnnnnnnn nnnnnnnnnn nnnnnnnntc ttttcnnnnn nnnnnnnnga aatgnnnnnn 300
nnnnnnnngg aaagattttt tttatgaata aaaagggggg ctgttcgcgt gagcgtacgg 360
gaacattttg aggaagtgtc tgagagaatt caagcgatgc ttgctgatat gaaatatggt 420
tcaattacaa ttgttgtaca agatggaaaa gtcattcaac tagagaaaag tgaaaaagta 480
cgttta 486

<210> SEQ ID NO 190
<211> LENGTH: 486
<212> TYPE: DNA
<213> ORGANISM: Bacillus anthracis
<220> FEATURE:
<221> NAME/KEY: misc_feature
<222> LOCATION: 21-305
<223> OTHER INFORMATION: n = g, a, c or t/u

<400> SEQUENCE: 190
tgaaaccttc ttataaagag nnnaggcgga gggannctgg nnnnccctac gatgcctnnc 60
ggcagcggac tcnnnnnnnn nnnnnnnnnn nnnnnnnnnn nngattttan nnnnnnnnnn 120
nnnnnnnnnn nnnnnnnnnn gagtgctgtg ccaaatncca gnnnnnncaa gcnnnnnnnn 180
nnnnatgtnn nnnnnnnnnn ngcttgaaag atgagaagag cgtttcttat agatgtataa 240
nnnnnnnnnn nnnnnnnnnn nnnnnnnnga cctcttctnn nnnnnnnnnc gttnnnnnnn 300
nnnnnggaag aggtcttttg ttattcatta gaaaaaaggt tgaaactagg gagagatggt 360
actttgaaag aaacgagagg aaatggtttg gctttattac cacttgggat atttttggcg 420
ctatttatag gttctggaat tattacaggt gatttctata aattgccgat acttgtagca 480
atttca 486

<210> SEQ ID NO 191
<211> LENGTH: 486
<212> TYPE: DNA
<213> ORGANISM: Bacillus anthracis
<220> FEATURE:
<221> NAME/KEY: misc_feature
<222> LOCATION: 21-306
<223> OTHER INFORMATION: n = g, a, c or t/u

<400> SEQUENCE: 191
aaattaatac ttatccagag nnnaggtgga gggaancggn nnnnccctat gaaacctnnc 60
agcaacccct atgtnnnnnn nnnnnnnnnn nnnnnnnnnn nnnaaatnnn nnnnnnnnnn 120
nnnnnnnnnn nnnnnnngca taggaaggtg ctaattnccg nnnnnnncag agaacacnnn 180
nnnnngttnn nnnnnngtgt tttttggaag atgagaggat tcttgaacgt gaaagaaaan 240
nnnnnnnnnn nnnnnnnnnn nnnnnnnntg acctcttnnn nnnnnnnnna tgtnnnnnnn 300
nnnnnnaaga ggtcattttt tgttgtatag aaagggagtg tcgatgcata attcattttc 360
aaaataaata tagagtaata aaagttgact attaagagag gggaattata atgaacagat 420
tatcaacaaa attagtagta gcaatcggaa ttggatcagc attatacggg atattaggac 480
tttggg 486

<210> SEQ ID NO 192
<211> LENGTH: 486
<212> TYPE: DNA
<213> ORGANISM: Bacillus anthracis
<220> FEATURE:
<221> NAME/KEY: misc_feature
<222> LOCATION: 21-304
<223> OTHER INFORMATION: n = g, a, c or t/u

<400> SEQUENCE: 192
atgaaaattc ttatcacgag nnnaggtgga gggannctgg nnnnccctat gaaacctnnc 60
ggcagcggat tcgnnnnnnn nnnnnnnnnn nnnnnnnnnn nnnnttannn nnnnnnnnnn 120
nnnnnnnnnn nnnnnnnnnt gaatactgtg ccaattncca gnnnnnncaa gnnnnnnnnn 180
nnnngtaann nnnnnnnnnn nncttgaaag ataagaaaga agctcatttt gactatatat 240
acagaannnn nnnnnnnnnn nnnnnnnngc ctctttctan nnnnnnnnnt ctttnnnnnn 300
nnnntagaaa gaggcttttt tacgtgaaaa taaaaggagg aagaaaaatg ggagcgacag 360
gagtagcgtc acaaagaaaa acaattgaag agagtatcga aagaaataag gaaaagtaca 420
tagaaacaag tcatgatatt catgcgaatc cggagattgg taatcaagaa ttttacgcat 480
ctagaa 486

<210> SEQ ID NO 193
<211> LENGTH: 486
<212> TYPE: DNA
<213> ORGANISM: Bacillus anthracis
<220> FEATURE:
<221> NAME/KEY: misc_feature
<222> LOCATION: 22-308
<223> OTHER INFORMATION: n = g, a, c or t/u

<400> SEQUENCE: 193
gaatattttc ttatccagag annnggtgga gggannctgg nnnncccgat gaaaccnnnc 60
agcaaccgcn nnnnnnnnnn nnnnnnnnnn nnnnnnnnnn nnnngatnnn nnnnnnnnnn 120
nnnnnnnnnn nnnnnnnnnn nnngcaggtg ctaattncca gnnnnnncag aacannnnnn 180
nnnnaattnn nnnnnnnnnt gttctgggag ataagacgaa gatatatacg taannnnnnn 240
nnnnnnnnnn nnnnnnnnnn nnnnnnnnct tcttcnnnnn nnnnnnnnnt tatcnnnnnn 300
nnnnnnnngg agaggttttt ttattgcaaa aaaaccgatt acgaaaaaat ttatattaag 360
aagaaagggg ttgcgaagta ctgtgacact cgaaaaatac gtaaaactgc gtagtacagt 420
ttatgaatat atgatagagc aagataagcc aatatcattg ttagatattc aagaacatat 480
cgtttc 486

<210> SEQ ID NO 194
<211> LENGTH: 486
<212> TYPE: DNA
<213> ORGANISM: Bacillus anthracis
<220> FEATURE:
<221> NAME/KEY: misc_feature
<222> LOCATION: 23-306
<223> OTHER INFORMATION: n = g, a, c or t/u

<400> SEQUENCE: 194
tatacaactc ttatcaagag canngggtgga gggatnttgg nnnncccgat gaagccnnnc 60
agcaaccgac cnnnnnnnnn nnnnnngtaa taccattgtg aaatggggcg tttatgacgc 120
caaaannnnn nnnnnnnnnn nggcacggtg ctaattncca gnnnnnncag aaagtnnnnn 180
nnnnnaaann nnnnnnnnac tttctggcag ataagagggg agaagataaa cttcaaannn 240
nnnnnnnnnn nnnnnnnnnn nnnnnnnncc tctttctnnn nnnnnnnnnt agtnnnnnnn 300
nnnnnnggaa agaggttttt ctacgtcaga aaaacctctg aatgaaaaaa gggggagaag 360
acgatgggat attattcatt aacagaagta accgctgtac aatatgcgaa agaacatggt 420
tattttgaaa agaaagcaaa tgtagtttgt catgaaattg gagatggaaa tttaaattat 480
gtgttc 486

<210> SEQ ID NO 195
<211> LENGTH: 486
<212> TYPE: DNA
<213> ORGANISM: Bacillus anthracis
<220> FEATURE:
<221> NAME/KEY: misc_feature
<222> LOCATION: 23-309
<223> OTHER INFORMATION: n = g, a, c or t/u

<400> SEQUENCE: 195
taaatacttc ttatcaagag canngggtgga ggganncgag nnnncccgac gaaaccnnnc 60
ggcaaccgat ctacannnnn nnnnnnnnnn nnnnnnnnnn nnntaatnnn nnnnnnnnnn 120
nnnnnnnnnn nnnnnnntgt agacacggtg ctaattnctc gnnnnnncag cnnnnnnnnn 180
nnnnattacn nnnnnnnnnn nngctgacag ataaggagct ggttgtaaaa aaannnnnnn 240
nnnnnnnnnn nnnnnnnnnn nnnnnnnncc tctcnnnnnn nnnnnnnnct tagctnnnnn 300
nnnnnnnnng agaggttttt ttatttaact aggaggttat aacaatgagc ggaattatag 360
cgacgtattt aatccatgat gattcacata acttagaaaa aaaagctgag caaattgcac 420
tcggtttaac aattggctct tggactcatt tgccacactt attgcaagaa cagttaaagc 480
agcata 486

<210> SEQ ID NO 196
<211> LENGTH: 486
<212> TYPE: DNA
<213> ORGANISM: Bacillus anthracis
<220> FEATURE:
<221> NAME/KEY: misc_feature
<222> LOCATION: 21-308
<223> OTHER INFORMATION: n = g, a, c or t/u

<400> SEQUENCE: 196
acgaacattc ttatctagag nnnaggtaga ggganntctgg nnnnccctat gacgcctnnc 60
agcaaccatt aacnnnnnnn nnnnnnnnnn nnnnnnnnnn nnnatttnnn nnnnnnnnnn 120
nnnnnnnnnn nnnnnnnngt taataaggtg ctaattncca gnnnnnncaa attnnnnnnn 180
nnngcgaaan nnnnnnnnnn aatttgacag atgagaagaa gactctattc aaaccgaaan 240
nnnnnnnnnn nnnnnnnnnn nnnnnnnngc cttctnnnnn nnnnnnnnnt cttnnnnnnn 300
nnnnnnnnag aaggcttttt ttattttata ttcaactact ggttcaattt aaaaaggagg 360
aatttttaca tgtcaactat cgaaacaaaa ctagcgcaaa tcggaaaccg gagtgaaact 420
acaacaggaa ctgttaatcc gcctgtttac ttttcaactg cttatcgtca cgaaggaatt 480
ggtaaa 486

<210> SEQ ID NO 197
<211> LENGTH: 486
<212> TYPE: DNA
<213> ORGANISM: Bacillus anthracis
<220> FEATURE:

<221> NAME/KEY: misc_feature
<222> LOCATION: 22-304
<223> OTHER INFORMATION: n = g, a, c or t/u
<400> SEQUENCE: 197
aagacaactc ttattgagag cnnnggtgga gggannaagg nnnnccctgt gaaaccnnnc 60
ggcaaccttc aaacnnnnnn nnnnnnnnnn nnnnnnnnnn nnngaaatnn nnnnnnnnnn 120
nnnnnnnnnn nnnnnnngtt tgaaacggtg ctaatancct gnnnnnncaa aacnnnnnnn 180
nnnngaatnn nnnnnnnnnn gttttgcata ataagaggag gaacaattat gttnnnnnnn 240
nnnnnnnnnn nnnnnnnnnn nnnnnnnncc cctcttcann nnnnnnnnnn aagnnnnnnn 300
nnnntgaaga gggggttttt atattgatag aaatgaggga gatttgtgaa attactagat 360
ttattgtcaa aaggaattgt aataggtgat ggtgcggttg gaacattatt acattcacac 420
ggtttgcaaa gtagttttga agaattgaat atatctgatc cagatttaat tatatcgatt 480
cataag 486

<210> SEQ ID NO 198
<211> LENGTH: 486
<212> TYPE: DNA
<213> ORGANISM: Bacillus anthracis
<220> FEATURE:
<221> NAME/KEY: misc_feature
<222> LOCATION: 23-304
<223> OTHER INFORMATION: n = g, a, c or t/u
<400> SEQUENCE: 198
ggatactctc ttatcccgag ctnnggcgga ggganncagg nnnncccgat gaagccnnnc 60
agcaacctca cttgtannnn nnnnnnnnnn nnnnnnnnnn ngtggtaaan nnnnnnnnnn 120
nnnnnnnnnn nnnntacagg tgaataggtg ctaaaancct gnnntgncga ggctnnnnnn 180
nnnnnacann nnnnnnnnng gtctcgaacg ataagagcga agggcaaaaa gcagtatgca 240
agtagcaaat taaannnnnn nnnnnnnncc tttcctctnn nnnnnnnnat ataannnnnn 300
nnnnagtagg aaaggttttt ctgtatgctt gtgtgggaga ataaatgtat gtcgcaatct 360
gtggcaaatt aaggatgagt tccgtacaat atatacaatt actgtaggga ggtttaccac 420
atgacaaaaa aacgtcatct gttcacatct gagtctgtaa ctgaaggaca tccagataaa 480
atttgt 486

<210> SEQ ID NO 199
<211> LENGTH: 486
<212> TYPE: DNA
<213> ORGANISM: Bacillus anthracis
<220> FEATURE:
<221> NAME/KEY: misc_feature
<222> LOCATION: 22-304
<223> OTHER INFORMATION: n = g, a, c or t/u
<400> SEQUENCE: 199
ctgatttctc ttatcaagag annnggtgga gggacntgtg nnnnccctgt gaagccnnnc 60
ggcaaccgtc aacnnnnnnn nnnnnnnnnn nnnnnnnnnn nnnttatnnn nnnnnnnnnn 120
nnnnnnnnnn nnnnnnnngt tgaaatggtg ccaattncct gnnnnnncaa agcnnnnnnn 180
nnnnaaatgn nnnnnnnnnn nctttgagag atgagagaga gggataatgt tgttatatac 240
gcatataaan nnnnnnnnnn nnnnnnnncc tttctgcttn nnnnnnnnnc tctannnnnn 300
nnnnaagcgg aaaggttttt ttgttgtttg aatgtggagg acattcaaat aataaaagta 360
atgagaacgg tgggctaccg tatcaaaaat aaaaaattgc ggagtcaatc aaaaatctag 420
ctccagcggc tagaacagtc ggtcgtttca tcccttccta tgaggcaaaa agcgcctcta 480
agtctg 486

<210> SEQ ID NO 200
<211> LENGTH: 486
<212> TYPE: DNA
<213> ORGANISM: Bacillus anthracis
<220> FEATURE:
<221> NAME/KEY: misc_feature
<222> LOCATION: 22-301
<223> OTHER INFORMATION: n = g, a, c or t/u

<400> SEQUENCE: 200
ttgcatagtc ttatcaagaa annaggtgga ggganncagg nnnncccgat gaaacctnnt 60
ggcaacagcc gtnnnnnnnn nnnnnnnnnn nnnnnnnnnn nnnnatannn nnnnnnnnnn 120
nnnnnnnnnn nnnnnnnnna cggaattgtg ccaaatncct gnnnnnncag gnnnnnnnnn 180
nntaataaat nnnnnnnnnn nncctgagag ataagaaaga gcctttagag cgtgttttca 240
aannnnnnnn nnnnnnnnnn nnnnnnnnct gctcctttct tgnnnnnnnt tttnnnnnnn 300
ncaggaaagg ggcagttttt tattttgtat aaaagaaagg agaatgagaa atgggagaat 360
catgggggaa aggaacgatt tgtgtgcaag gtggctatac gccaaagaat ggagaaccgc 420
gtgttttacc gctttatcaa agcacgacgt ataaatatga tacttcggat gatttagcag 480
cattat 486

<210> SEQ ID NO 201
<211> LENGTH: 486
<212> TYPE: DNA
<213> ORGANISM: Bacillus cereus
<220> FEATURE:
<221> NAME/KEY: misc_feature
<222> LOCATION: 21-298
<223> OTHER INFORMATION: n = g, a, c or t/u

<400> SEQUENCE: 201
cgatacattc ttatccagag nnnaggtgga gggannctgg nnnnccctac gatacctnnc 60
agcaacgggt tnnnnnnnnn nnnnnnnnnn nnnnnnnnnn nnntttttnn nnnnnnnnnn 120
nnnnnnnnnn nnnnnnnnnn naataccgtg ctaactncca gnnnnnncaa gcctnnnnnn 180
nnnnatgaan nnnnnnnnna ggcttggaag atgagaagat gtgaacgagt acatataann 240
nnnnnnnnnn nnnnnnnnnn nnnnnnnngt gctctccttc ttatcnnttt atggttnnga 300
taagaaggag agcacttttt attttacctc gagagctctg cttcaagttt tcacagcata 360
taggagggga aaaaatgatt tcttttaaca atgtaagtaa agtatatgaa acaggtgggc 420
aatctgttca tgcggtggag gatgtaacat tatcagttga gaaaggcgaa atttttggca 480
ttatcg 486

<210> SEQ ID NO 202
<211> LENGTH: 486
<212> TYPE: DNA
<213> ORGANISM: Bacillus cereus
<220> FEATURE:
<221> NAME/KEY: misc_feature
<222> LOCATION: 21-304
<223> OTHER INFORMATION: n = g, a, c or t/u

<400> SEQUENCE: 202
caaacaattc ttatgttgag nnnaagtgga ggganncggg nnnnccctat gaaacttnnc 60
ggcaacctcg tnnnnnnnnn nnnnnnnnnn nnnnnnnnnn nnnatgagnn nnnnnnnnnn 120

-continued nnnnnnnnnn nnnnnnnnnn acgaaaggtg ccaaatncct gnnnnnncag gtgnnnnnnn 180
nnnaagaaan nnnnnnnnnn cacctgaaag ataagagcgg ttcaattagt caagaagnnn 240
nnnnnnnnnn nnnnnnnnnn nnnnnnnngc tactcttatn nnnnnnnnnt tcgnnnnnnn 300
nnnnataaga gtagcttttt ttatggctaa aagttaaagg gggaataggt agtggagtat 360
ggtttttggt tgccgatttt tgggggatgg cttcggaatg taaatgatga atctatgccg 420
cctacgtttg agtatgcaaa acaaacggcg caagcggcag aacaattagg tttttcaaca 480
acactt 486

<210> SEQ ID NO 203
<211> LENGTH: 486
<212> TYPE: DNA
<213> ORGANISM: Bacillus cereus
<220> FEATURE:
<221> NAME/KEY: misc_feature
<222> LOCATION: 22-308
<223> OTHER INFORMATION: n = g, a, c or t/u

<400> SEQUENCE: 203
aatacaaagc ttatcaagag annnagcgga gggaanctgg nnnncccggc gaagctnnnc 60
ggcaacctgc ttnnnnnnnn nnnnnnnnnn nnnnnnnnnn nnnatagann nnnnnnnnnn 120
nnnnnnnnnn nnnnnnnnnn aagcaaggtg ctaaatncca gnnnnnncaa aatggnnnnn 180
nnnnnaatnn nnnnnnnncc attttgaaag ataaggtaaa atatattacc gaacagnnnn 240
nnnnnnnnnn nnnnnnnnnn nnnnnnnntc ttttcnnnnn nnnnnnnnga aatgnnnnnn 300
nnnnnnnngg aaagattttt tttatgaata aaaagggggg ctgttcgcgt gagcgtacgg 360
gaacattttg aggaagtatc tgagaaaatt gaagcgatgc ttgctgatat gaaatatggt 420
tcaattacaa ttgttgtgca agatggcaaa gtcattcaat tagagaaaag tgaaaaagta 480
cgttta 486

<210> SEQ ID NO 204
<211> LENGTH: 486
<212> TYPE: DNA
<213> ORGANISM: Bacillus cereus
<220> FEATURE:
<221> NAME/KEY: misc_feature
<222> LOCATION: 21-305
<223> OTHER INFORMATION: n = g, a, c or t/u

<400> SEQUENCE: 204
tgaaaccttc ttataaagag nnnaggcgga gggannctgg nnnnccctac gatgcctnnc 60
ggcagcggac tcnnnnnnnn nnnnnnnnnn nnnnnnnnnn nngatttcan nnnnnnnnnn 120
nnnnnnnnnn nnnnnnnnnn gagtgctgtg ccaaatncca gnnnnnncaa gcnnnnnnnn 180
nnnnatatnn nnnnnnnnnn ngcttgaaag atgagaagag cgtttcttat agatgtataa 240
nnnnnnnnnn nnnnnnnnnn nnnnnnnnga cctcttctnn nnnnnnnnnc gatnnnnnnn 300
nnnnnggaag aggtcttttg ttattcatta gaaaaaggtt gaaactaggg agagatggta 360
ctttgaaaga aacgagagga aatggtttgg cattattacc acttgggata tttttggcgc 420
tatttattgg ttctggaatt attacaggtg atttctataa attgccgata cttgtagcaa 480
tttcaa 486

<210> SEQ ID NO 205
<211> LENGTH: 486
<212> TYPE: DNA
<213> ORGANISM: Bacillus cereus
<220> FEATURE:

<221> NAME/KEY: misc_feature
<222> LOCATION: 21-306
<223> OTHER INFORMATION: n = g, a, c or t/u

<400> SEQUENCE: 205
aaattaatac ttatccagag nnnaggtgga gggaanncgg nnnnccctat gaaacctnnc 60
agcaacccct atannnnnnn nnnnnnnnnn nnnnnnnnnn nntatattnn nnnnnnnnnn 120
nnnnnnnnnn nnnnnnnnta taggaaggtg ctaattnccg nnnnnnncag agaacacnnn 180
nnnnngatnn nnnnnngtgt tttttggaag ataagaggat tcttgaacgt gaaagaaaan 240
nnnnnnnnnn nnnnnnnnnn nnnnnnnntg acctcttnnn nnnnnnnnna tgtnnnnnnn 300
nnnnnnaaga ggtcattttt tgttgtatag aaagggagtg tcgatgcata attcattttc 360
aaaataaata tagagtaata aaagttgact attaagaggg gagaattgta atgaataaat 420
tatcaacaaa attagtagtg gcaatcggaa ttggagcagc attatacggg atattaggac 480
tttggg 486

<210> SEQ ID NO 206
<211> LENGTH: 486
<212> TYPE: DNA
<213> ORGANISM: Bacillus cereus
<220> FEATURE:
<221> NAME/KEY: misc_feature
<222> LOCATION: 21-304
<223> OTHER INFORMATION: n = g, a, c or t/u

<400> SEQUENCE: 206
atgaaaattc ttatcacgag nnnaggtgga gggannctgg nnnnccctat gatacctnnc 60
ggcagcggat tcgnnnnnnn nnnnnnnnnn nnnnnnnnnn nnnnttannn nnnnnnnnnn 120
nnnnnnnnnn nnnnnnnnnt gaatactgtg ccaattncca gnnnnnncaa gnnnnnnnnn 180
nnnngtaann nnnnnnnnnn nncttgaaag ataagaaaga agctcatttt gactgtatat 240
gcagaannnn nnnnnnnnnn nnnnnnnngc ctctttctan nnnnnnnnnt ctttnnnnnn 300
nnnntagaaa gaggcttttt tatgtgaaaa tataaggggg aagaaaaatg ggagcgacag 360
gagtaacgtc acaaagaaaa acaattgaag agagtattga aagaaataag gaaaagtaca 420
tagaaacaag tcacgatatt catgcgaatc cggagattgg taaccaagag ttttacgcat 480
caagaa 486

<210> SEQ ID NO 207
<211> LENGTH: 486
<212> TYPE: DNA
<213> ORGANISM: Bacillus cereus
<220> FEATURE:
<221> NAME/KEY: misc_feature
<222> LOCATION: 21-305
<223> OTHER INFORMATION: n = g, a, c or t/u

<400> SEQUENCE: 207
attagttttc ttattaagag nnnagatgga gggannctgg nnnncccgat gaaatctnnc 60
agcaacaggc tnnnnnnnnn nnnnnnnnnn nnnnnnnnnn nnnataaann nnnnnnnnnn 120
nnnnnnnnnn nnnnnnnnnn nagtactgtg ctaagtncca gnnnnnncaa acgtnnnnnn 180
nnnnatgaan nnnnnnnnng cgtttggaag atgaggggaa atggattaac attcaannnn 240
nnnnnnnnnn nnnnnnnnnn nnnnnnnnct cttcttatnn nnnnnnnnna tgtnnnnnnn 300
nnnnngtaag aagagttttt tatttagaga ggggggatag agtgaagttt gatgtaacgt 360 atttttttaga aagttttccg caattattta agtatgtata cataacttta ggaattactg 420
tagtttcaat gattatttct tttgttatag ggataggttt ggcgatcata acgaaaaaca 480
aaacga 486

<210> SEQ ID NO 208
<211> LENGTH: 486
<212> TYPE: DNA
<213> ORGANISM: Bacillus cereus
<220> FEATURE:
<221> NAME/KEY: misc_feature
<222> LOCATION: 22-308
<223> OTHER INFORMATION: n = g, a, c or t/u

<400> SEQUENCE: 208
gaatattttc ttatccagag annnggtgga gggannctgg nnnncccgat gaaaccnnnc 60
agcaaccgcn nnnnnnnnnn nnnnnnnnnn nnnnnnnnnn nnnngatnnn nnnnnnnnnn 120
nnnnnnnnnn nnnnnnnnnn nnngcaggtg ctaattncca gnnnnnncag aacannnnnn 180
nnnntattnn nnnnnnnnnt gttctgggag ataagacgaa gatatatacg taannnnnnn 240
nnnnnnnnnn nnnnnnnnnn nnnnnnnnct tcttcnnnnn nnnnnnnnnt tatcnnnnnn 300
nnnnnnnngg agaggttttt ttattgcaaa aaaaccgatt acgaaaattt atattaagaa 360
gaaaggggtt gcgcattact gtgacactcg aaaaatacgt caaactgcgt agtacagttt 420
atgaatatat gatagagcaa gataagccaa tatcattgtt agatattcaa gaacatatcg 480
tttcgc 486

<210> SEQ ID NO 209
<211> LENGTH: 486
<212> TYPE: DNA
<213> ORGANISM: Bacillus cereus
<220> FEATURE:
<221> NAME/KEY: misc_feature
<222> LOCATION: 23-309
<223> OTHER INFORMATION: n = g, a, c or t/u

<400> SEQUENCE: 209
taaatacttc ttatcaagag cannggtgga ggganncgag nnnncccgac gaaaccnnnc 60
ggcaaccgat ctacnnnnnn nnnnnnnnnn nnnnnnnnnn nnnaattnnn nnnnnnnnnn 120
nnnnnnnnnn nnnnnnnngt agacacggtg ctaattnctc gnnnnnncag cnnnnnnnnn 180
nnnnattacn nnnnnnnnnn nngctgacag ataaggagct ggttgtaaaa aaannnnnnn 240
nnnnnnnnnn nnnnnnnnnn nnnnnnnncc tctcnnnnnn nnnnnnnnct tagctnnnnn 300
nnnnnnnnng agaggttttt ttatttaact aggaggttat aacaatgagc ggaattatag 360
cgacatattt aatccatgat gattcacata acttagaaaa aaaagctgag caaattgcac 420
tcggtttaac aattggctct tggactcatt tgccacattt attgcaagaa caattaaagc 480
agcata 486

<210> SEQ ID NO 210
<211> LENGTH: 486
<212> TYPE: DNA
<213> ORGANISM: Bacillus cereus
<220> FEATURE:
<221> NAME/KEY: misc_feature
<222> LOCATION: 22-304
<223> OTHER INFORMATION: n = g, a, c or t/u

<400> SEQUENCE: 210
agacaaactc ttattgagag cnnnggtgga ggganaaagg nnnnccctgt gaaaccnnnc 60
ggcaaccttc aaacnnnnnn nnnnnnnnnn nnnnnnnnnn nnngaaatnn nnnnnnnnnn 120
nnnnnnnnnn nnnnnnngtt tgaaacggtg ctaatancct gnnnnnncaa aacnnnnnnn 180
nnnngaatnn nnnnnnnnnn gttttgcata ataagaggag gatcgattat gtnnnnnnnn 240
nnnnnnnnnn nnnnnnnnnn nnnnnnnncc ccctcttcan nnnnnnnnnn aagnnnnnnn 300
nnnntgaaga gggggttttt atattgatag aaatgaggga gatttgtgaa attactagat 360
ttattatcaa aaggaattgt aataggtgat ggtgcggttg ggacgttatt acattcacat 420
ggtttacaaa gtagttttga agaattgaat atatctgatc cagatttaat tatatcgatt 480
cataag 486

<210> SEQ ID NO 211
<211> LENGTH: 486
<212> TYPE: DNA
<213> ORGANISM: Bacillus cereus
<220> FEATURE:
<221> NAME/KEY: misc_feature
<222> LOCATION: 21-308
<223> OTHER INFORMATION: n = g, a, c or t/u

<400> SEQUENCE: 211
acgaacattc ttatctagag nnnaggtaga gggannctgg nnnnccctat gacgcctnnc 60
agcaaccatt aacnnnnnnn nnnnnnnnnn nnnnnnnnnn nnnatttnnn nnnnnnnnnn 120
nnnnnnnnnn nnnnnnnngt taataaggtg ctaattncca gnnnnnncaa attnnnnnnn 180
nnngtgaaan nnnnnnnnnn gatttgacag atgagaagaa gactctattc aaaccgaaan 240
nnnnnnnnnn nnnnnnnnnn nnnnnnnngc cttctnnnnn nnnnnnnnnt cttnnnnnnn 300
nnnnnnnnag aaggcttttt tattttatat tcaactaatg gttcaattta aaaaggagga 360
attttcacat gtcaactatc gaaacaaaat tagcgcaaat cggaaaccgg agtgaaacta 420
caacaggaac tgttaatcca cctgtttatt tttcaactgc ttatcgtcac gaaggaattg 480
gtaaat 486

<210> SEQ ID NO 212
<211> LENGTH: 486
<212> TYPE: DNA
<213> ORGANISM: Bacillus cereus
<220> FEATURE:
<221> NAME/KEY: misc_feature
<222> LOCATION: 23-306
<223> OTHER INFORMATION: n = g, a, c or t/u

<400> SEQUENCE: 212
tatacaactc ttatcaagag canngggtgga gggatnttgg nnnncccgat gaagccnnnc 60
agcaaccgac cnnnnnnnnn nnnnnngtaa taccattgtg aaatggggcg tttatttacg 120
ccaaaannnn nnnnnnnnnn nggcacggtg ctaattncca gnnnnnncag aaagtnnnnn 180
nnnnnaaann nnnnnnnnac tttctggcag ataagagggg agaagataaa cttcaaannn 240
nnnnnnnnnn nnnnnnnnnn nnnnnnnncc tctttctnnn nnnnnnnnnt agtnnnnnnn 300
nnnnnnggaa agaggttttt ctacgtcaga aaaacctctg aatataaaaa agggggagaa 360
gacgatggga tattatgcat taactgaaac aacagctata caatatgcga aagaacacgg 420
ttattttgaa aagaaagcaa atgtattttg tcatgaaatt ggagatggaa atttaaatta 480
cgtgtt 486

<210> SEQ ID NO 213
<211> LENGTH: 486
<212> TYPE: DNA
<213> ORGANISM: Bacillus cereus
<220> FEATURE:

<221> NAME/KEY: misc_feature
<222> LOCATION: 23-307
<223> OTHER INFORMATION: n = g, a, c or t/u

<400> SEQUENCE: 213
ggatactctc ttatcccgag ctnnggcgga ggganncagg nnnncccgat gaagccnnnc 60
agcaacctca cttgtnnnnn nnnnnnnnnn nnnnnnnnnn attggtaaac nnnnnnnnnn 120
nnnnnnnnnn nnnnnacaag tgaataggtg ctaaaancct gnnntgncga ggctnnnnnn 180
nnnnnacann nnnnnnnnng gtctcgaacg ataagagcga agggcaaaaa gcagtatgca 240
agtagcaaat taaannnnnn nnnnnnnncc tttcctnnnn nnnnnnctct attatgtnnn 300
nnnnnnnagg aaaggttttt ctgtatgctt gtgtgggaga ataaatgtat gtcgcaatct 360
gtggcaaatt aaggatgagt tccgtacaat atatacaatt actgtaggga ggtttaccac 420
atgacaaaaa aacgtcatct gttcacatct gagtctgtaa ctgaaggaca tccagataaa 480
atttgt 486

<210> SEQ ID NO 214
<211> LENGTH: 486
<212> TYPE: DNA
<213> ORGANISM: Bacillus cereus
<220> FEATURE:
<221> NAME/KEY: misc_feature
<222> LOCATION: 22-304
<223> OTHER INFORMATION: n = g, a, c or t/u

<400> SEQUENCE: 214
ctgatttctc ttatcaagag annnggtgga gggacntgtg nnnnccctgt gaagccnnnc 60
ggcaaccgtc aacnnnnnnn nnnnnnnnnn nnnnnnnnnn nnntttatnn nnnnnnnnnn 120
nnnnnnnnnn nnnnnnnngt tgaaatggtg ccaattncct gnnnnnncaa agcnnnnnnn 180
nnnnaaatnn nnnnnnnnnn gctttgagag atgagagaga gggataatgt tgttatatac 240
gcacataaan nnnnnnnnnn nnnnnnnncc tttctgcttn nnnnnnnnnc tctannnnnn 300
nnnnaggcag aaaggttttt ttgttgtttg aatgtggagg acattcaaat aataaaagta 360
gtgataacgg tggactacac gcattaaaca taaaaaattg cggagtcgat ccaaacaaaa 420
aaggggtgat acaccatgat tctattagag aatgtaaaga aaatatataa agcaaaaagc 480
ggtgat 486

<210> SEQ ID NO 215
<211> LENGTH: 486
<212> TYPE: DNA
<213> ORGANISM: Bacillus cereus
<220> FEATURE:
<221> NAME/KEY: misc_feature
<222> LOCATION: 22-301
<223> OTHER INFORMATION: n = g, a, c or t/u

<400> SEQUENCE: 215
ttgcatagtc ttatcaagaa annaggtgga ggganncagg nnnncccgat gaaacctnnt 60
ggcaacagcc gtnnnnnnnn nnnnnnnnnn nnnnnnnnnn nnnnatannn nnnnnnnnnn 120
nnnnnnnnnn nnnnnnnnna cggaattgtg ccaaatncct gnnnnnncag gnnnnnnnnn 180
nntaataaac nnnnnnnnnn nncctgagag ataagaaaga gcctttagag cgtgttttca 240
aannnnnnnn nnnnnnnnnn nnnnnnnnct gctcctttct tgnnnnnnnt tttnnnnnnn 300
ncaggaaagg ggcagttttt tattttgtat aaaagaaagg agaataagag atgggagaat 360
catgggggaa aggaacaatt tgcgtgcaag gtggctatac gccaaagaat ggtgaaccgc 420
gtgttttacc gctttatcaa agtacaacgt ataaatacga tacttcggat gatttagcag 480
ccttat 486

<210> SEQ ID NO 216
<211> LENGTH: 486
<212> TYPE: DNA
<213> ORGANISM: Bacillus cereus
<220> FEATURE:
<221> NAME/KEY: misc_feature
<222> LOCATION: 21-304
<223> OTHER INFORMATION: n = g, a, c or t/u

<400> SEQUENCE: 216
tttactcatt gtatcaagag nnnaggtgga gggannctgg nnnncccttt gaaacctnnc 60
ggcagcaggt tcannnnnnn nnnnnnnnnn nnnnnnnnnn nnnttttttnn nnnnnnnnnn 120 nnnnnnnnnn nnnnnnnnnt gaatactgtg ccacttncct gnnnnnncaa gctnnnnnnn 180
nnnnttatnn nnnnnnnnnn agcttgaaag atagaatgag ggacttcgtt tatatacggg 240
tgcataactt gtacgtaaaa annnnnnntc cctctttcnn nnnnnnnntc aatatnnnnn 300
nnnngaaaag agggattttt tatttttcat ttccctcatc atcatccaaa cttaattatt 360
taggaggaaa atcaaatgaa aaaaaagttt gtacccggta ttgcatcagt tgtaggagta 420
agtattttat taactggttg cggtagttat aaaaacgaag caagcggagc aaatgcaaaa 480
gacgag 486

<210> SEQ ID NO 217
<211> LENGTH: 486
<212> TYPE: DNA
<213> ORGANISM: Bacillus cereus
<220> FEATURE:
<221> NAME/KEY: misc_feature
<222> LOCATION: 22-306
<223> OTHER INFORMATION: n = g, a, c or t/u

<400> SEQUENCE: 217
acacatactc ttatcaagag tnnnggcgga gggannctgg nnnncccgat gatgccnnnc 60
ggcaaccgag cttatannnn nnnnnnnnnn nnnnnnnnnn nnnnacgnnn nnnnnnnnnn 120
nnnnnnnnnn nnnnnnntata agctaaggtg ctaattncct gnnnnnncaa aacgannnnn 180
nnnngttcnn nnnnnnnntc gttttggaag ataagagagg aatctatttt gtctattcgn 240
nnnnnnnnnn nnnnnnnnnn nnnnnnnngc acctctcnnn nnnnnnntta tttttnnnnn 300
nnnnnngaga ggtgcttttt attttggaac gtatatttaa gggggaatta tagatgaaga 360
aagtattatt aagcattgta agtggggctg tattattatt aagcgcatgt agcgggagtt 420
cagataaaga agtaaaagcg ttagatgaga aaaagattac tgtcggtgta acaggagggc 480
ctcatg 486

<210> SEQ ID NO 218
<211> LENGTH: 486
<212> TYPE: DNA
<213> ORGANISM: Bacillus cereus
<220> FEATURE:
<221> NAME/KEY: misc_feature
<222> LOCATION: 21-303
<223> OTHER INFORMATION: n = g, a, c or t/u

<400> SEQUENCE: 218
agcaatttac ttatccagag nnnaggtaga gggannctgg nnnnccctat gacacctnnc 60
agcagcgggt tctnnnnnnn nnnnnnnnnn nnnnnnnnnn nngtaatann nnnnnnnnnn 120

```
nnnnnnnnnn nnnnnnnnng gaacaccgtg ctaattncca gnnnnnncaa gnnnnnnnnn    180

nnnncaagtn nnnnnnnnnn nncttgaaag ataagtgatg ggcctttgtt tattaannnn    240

nnnnnnnnnn nnnnnnnnnn nnnnnnnngc cttgatctta nnnnnnnnnt ttttnnnnnn    300

nnntaagatc aaggcttttt gtattctaaa aagagaaaag ggagtaatgg aaaaagtacg    360

ttcataaaac taagtaaata tatgtgttta gggggttatt ggagtgtatg taattaaaaa    420

attatcagtt atggtgttca cgctatgggt tattacgacg gtgacatttc taattatgca    480

tattat                                                               486
```

```
<210> SEQ ID NO 219
<211> LENGTH: 505
<212> TYPE: RNA
<213> ORGANISM: Agrobacterium tumefaciens
<220> FEATURE:
<221> NAME/KEY: misc_feature
<222> LOCATION: 24-469
<223> OTHER INFORMATION: n = g, a, c or u

<400> SEQUENCE: 219

uacuauaugu gguguucaag guuncuuccg auucnnnnnn nnnnnngcua nnnnnnnnnn     60

nnngggguugg gagcunnaag acgggaaunu cggugcguaa cgccnnnauc acnnnnggcg   120

gagcaaggcc gaaacugccc ccgcaacugu gangcggnnn nnnnnnnnnn nnnnnnnnnn    180

nnnnnnnnnn nnnnnnnnnn cgagcaucgu uccgauuugn nnnnnnnnnn nnnnnnnnnn    240

nnnnnnnnnn nnnnnnnnnn nnnnnnnnnn nnnnnnnnnn nnnnnnnnag ccacuggagc    300

nnnnnnnnnn nnnnnnnnnn nnnnnnnnnncaa aannnnnnnn nnnnnnnnnn nnnnnnnnnn    360

nnnnnnngcu ccgggaaggc uggaauagau guugugacnn nnnnnnnnnn nnnnnnnnnn    420

nnnnnnnnnn nnnnnnnnnn nnnnnnnnnn nnnnnnnnnn nnnccgcnna agucaggaga    480

ccugccuuga gcgcaaaugu ccacg                                          505
```

```
<210> SEQ ID NO 220
<211> LENGTH: 505
<212> TYPE: RNA
<213> ORGANISM: Agrobacterium tumefaciens
<220> FEATURE:
<221> NAME/KEY: misc_feature
<222> LOCATION: 23-469
<223> OTHER INFORMATION: n = g, a, c or u

<400> SEQUENCE: 220

ccuuauguga gaaagcgacg gunnuccuac agccnnnnnn nnnnnngaaa nnnnnnnnnn     60

nnnggcgaag ggauunnaau angggaacna uggugcgggc gannnnnucu uuunnnnnuc    120

guccaaugcc uuggcugccc ccgcaacugu aangcggauu nnnnnnnnnn nnnnnnnnnn    180

nnnnnnnnnn nnnnnnnnnn nnnnnnnngu uguucauccc agugacgcuu gaaggcguca    240

unnnnnnnnn nnnnnnnnnn nnnnnnnnnn nnnnnnnnnn nnnnnnnnng ccacuguuuu    300

unnnnnnnnn nnnnnnnnnn nnnnnnnnuu cgnnnnnnnn nnnnnnnnnn nnnnnnnnnn    360

nnnnnngaau gcgggaaggc nagaugaggg acgcannnnn nnnnnnnnnn nnnnnnnnnn    420

nnnnnnnnnn nnnnnnnnnn nnnnnnnnnn nnnnnnnnnn aauccgunng agccaggaga    480

ccugccguca aaauggaaac caucg                                          505
```

```
<210> SEQ ID NO 221
<211> LENGTH: 505
<212> TYPE: RNA
<213> ORGANISM: Agrobacterium tumefaciens
<220> FEATURE:
```

<221> NAME/KEY: misc_feature
<222> LOCATION: 24-469
<223> OTHER INFORMATION: n = g, a, c or u

<400> SEQUENCE: 221
cggauaacau guccgugaug guunccuucc gggnnnnnnn nnnnnncgun nnnnnnnnnn 60
nnnnuccgga aggugnnaaa angggaacna cgauagggan nnnnnnnnca aannnnnnnn 120
nuccucauuc guggcugccc ccgcaacugu gangcggnnn nnnnnnnnnn nnnnnnnnnn 180
nnnnnnnnnn nagagccuga aacgaaaugc cacuggcaan nnnnnnnnnn nnnnnnnnnn 240
nnnnnnnnnn nnnnnnnnnn nnnnnnnnnn nnnnnnnnnn nnnnnnnnng ccaucucnnn 300
nnnnnnnnnn nnnnnnnnnn nnnngccucc aucaannnnn nnnnnnnnnn nnnnnnnnnn 360
nnnnnnnnnn gggggaaggc aaugccggga agguguuuca gguuuugacn nnnnnnnnnn 420
nnnnnnnnnn nnnnnnnnnn nnnnnnnnnn nnnnnnnnnn nnnccgunna agccaggaga 480
ccugccauca cggaaauauc caugc 505

<210> SEQ ID NO 222
<211> LENGTH: 505
<212> TYPE: RNA
<213> ORGANISM: Agrobacterium tumefaciens
<220> FEATURE:
<221> NAME/KEY: misc_feature
<222> LOCATION: 24-469
<223> OTHER INFORMATION: n = g, a, c or u

<400> SEQUENCE: 222
gacauugguu agccaucgug guuncugcgg acnnnnnnnn nnnnnngaag nnnnnnnnnn 60
nnnnnguccg gagcunnaag angggaaunu cggugagggc unnnnnuuaa ucacnnnnna 120
gccugaaucc gaagcugccc ccgcaacugu aangcgnnnn nnnnnnnnnn nnnnnnnnnn 180
nnnnnnnnnn nnnnnnnnnn nnnnacgagc gaaaguccau caunnnnnnn nnnnnnnnnn 240
nnnnnnnnnn nnnnnnnnnn nnnnnnnnnn nnnnnnnnnn nnnnnnnnng ucacugaggn 300
nnnnnnnnnn nnnnnnnnnn nnnnnnnncc ggnnnnnnnn nnnnnnnnnn nnnnnnnnnn 360
nnnnnnnncc ucgggaagac nnggaccaaa gcuaugaccn nnnnnnnnnn nnnnnnnnnn 420
nnnnnnnnnn nnnnnnnnnn nnnnnnnnnn nnnnnnnnnn nnnncgcnna agccaggaga 480
ccugccgcga uagauaacgu ccacg 505

<210> SEQ ID NO 223
<211> LENGTH: 505
<212> TYPE: RNA
<213> ORGANISM: Agrobacterium tumefaciens
<220> FEATURE:
<221> NAME/KEY: misc_feature
<222> LOCATION: 24-469
<223> OTHER INFORMATION: n = g, a, c or u

<400> SEQUENCE: 223
cccauagcuu cuccggucag gugncccgcc nnnnnnnnnn nnnnnncuug cnnnnnnnnn 60
nnnnnnnggc gggagnnaau cngggaaunc cggugannnn nnnnnnnnnn nnnnnnnnnn 120
nnnnaagacc ggaacgugnc ccaacgcugu aanggcnnnn nnnnnnnnnn nnnnnnnnnn 180
nnnnnnnnnn nnnnnnnnnn nnnnnggaug cucuuuuucu caunnnnnnn nnnnnnnnnn 240
nnnnnnnnnn nnnnnnnnnn nnnnnnnnnn nnnnnnnnnn nnnnnnnnng ccacugaann 300
nnnnnnnnnn nnnnnnnnnn nnnnnnnnng caannnnnnn nnnnnnnnnn nnnnnnnnnn 360
nnnnnnnnnu ucgggaaggc nngaaagggg cggaugaann nnnnnnnnnn nnnnnnnnnn 420
nnnnnnnnnn nnnnnnnnnn nnnnnnnnnn nnnnnnnnnn nnnngcunnu agucagaaga 480
ccggccuggc aggauagacc gaacc 505

<210> SEQ ID NO 224
<211> LENGTH: 505
<212> TYPE: RNA
<213> ORGANISM: Agrobacterium tumefaciens
<220> FEATURE:
<221> NAME/KEY: misc_feature
<222> LOCATION: 23-469
<223> OTHER INFORMATION: n = g, a, c or u

<400> SEQUENCE: 224
cuaaggguaa gggacugacg gunncuuuuc ccgnnnnnnn nnnnnngcaa nnnnnnnnnn 60
nnnncgggaa aagcunnaag angggaacna cgguuccgcc cnnnnnncga gaaannnnnn 120
gggucauucc guggcugccc ccgcaacugu aangcggunn nnnnnnnnnn nnnnnnnnnn 180
nnnnnnnnnn nnnnnnnnnn nnnnnnnaag cccgcaccgu aaannnnnnn nnnnnnnnnn 240
nnnnnnnnnn nnnnnnnnnn nnnnnnnnnn nnnnnnnnnn nnnnnnnnng ccacugaacc 300
nnnnnnnnnn nnnnnnnnnn nnnnuuuaug aucnnnnnnn nnnnnnnnnn nnnnnnnnnn 360
nnnnnnnggu ucgggaaggc nnggugacag gguguugaua nnnnnnnnnn nnnnnnnnnn 420
nnnnnnnnnn nnnnnnnnnn nnnnnnnnnn nnnnnnnnnn nngccgcnna agccaggaga 480
ccugccguuu caggaaaaag cgucu 505

<210> SEQ ID NO 225
<211> LENGTH: 505
<212> TYPE: RNA
<213> ORGANISM: Bacillus halodurans
<220> FEATURE:
<221> NAME/KEY: misc_feature
<222> LOCATION: 23-469
<223> OTHER INFORMATION: n = g, a, c or u

<400> SEQUENCE: 225
auuucaucgu uugggaacag gunnacguua agucnnnnnn nnnnacauga uannnnnnnn 60
nnngacuuaa uguuunnaaa angggaaunc cggugcnnnn nnnnnnnnnn nnnnnnnnnn 120
nnnnaaaucc ggagcggucc cngccacugu canuagcnnn nnnnnnnnnn nnnnnnnnnn 180
nnnnnnnnnn nnnnnnnnnn nnnnnnugag uuguaacgau auunnnnnnn nnnnnnnnnn 240
nnnnnnnnnn nnnnnnnnnn nnnnnnnnnn nnnnnnnnnn nnnnnnnnng ucacugaccg 300
nnnnnnnnnn nnnnnnnnnn nnnnnnuuca unnnnnnnnn nnnnnnnnnn nnnnnnnnnn 360
nnnnnnnugg uugggaagac nnuguugcaa uguugacnnn nnnnnnnnnn nnnnnnnnnn 420
nnnnnnnnnn nnnnnnnnnn nnnnnnnnnn nnnnnnnnnn nnngcuanng agccaggaga 480
ccugccuguu cuaacagcac ugcuu 505

<210> SEQ ID NO 226
<211> LENGTH: 505
<212> TYPE: RNA
<213> ORGANISM: Bacillus halodurans
<220> FEATURE:
<221> NAME/KEY: misc_feature
<222> LOCATION: 23-469
<223> OTHER INFORMATION: n = g, a, c or u

<400> SEQUENCE: 226
uaguguuugu ggacgguaag gunngccnnn nnnnnnnnnn nnnnncgaag cnnnnnnnnn 60
nnnnnnnnnn ggcuunnaaa angggaaunc uggugcnnnn nnnnnnnnnn nnnnnnnnnn 120
nnnnaaaucc ggagcugucc ccgcaacugu gangugcunn nnnnnnnnnn nnnnnnnnnn 180
nnnnnnnnnn nnnnnnnnnn nnnnnnnnac gaacggaacg auuunnnnnn nnnnnnnnnn 240
nnnnnnnnnn nnnnnnnnnn nnnnnnnnnn nnnnnnnnnn nnnnnnnnng ccacuguaca 300
uccucnnnnn nnnnnnnnnn nnnnuacuuc uunnnnnnnn nnnnnnnnnn nnnnnnnnnn 360
ngagaaaugu augggaaggc nnuucuaagu agguaannnn nnnnnnnnnn nnnnnnnnnn 420
nnnnnnnnnn nnnnnnnnnn nnnnnnnnnn nnnnnnnnnn nnagcacnng agucaggaga 480
ccugccuuac uuccacaagu uucgc 505

<210> SEQ ID NO 227
<211> LENGTH: 505
<212> TYPE: RNA
<213> ORGANISM: Bacillus halodurans
<220> FEATURE:
<221> NAME/KEY: misc_feature
<222> LOCATION: 23-469
<223> OTHER INFORMATION: n = g, a, c or u

<400> SEQUENCE: 227
uaagcacgcu caagcauuag gunngguuca annnnnnnnn nnnnacaauc ggnnnnnnnn 60
nnnnnnuuga aucugnnaaa angggaagnc uggugannnn nnnnnnnnnn nnnnnnnnnn 120
nnnnaagucc agcacggunc gcgccacugu aauaaaggnnn nnnnnnnnnn nnnnnnnnnn 180
nnnnnnnnnn nnnnnnnnnn nnnnnnnnagc uacaugugag gaannnnnnn nnnnnnnnnn 240
nnnnnnnnnn nnnnnnnnnn nnnnnnnnnn nnnnnnnnnn nnnnnnnnna ccacuguccn 300
nnnnnnnnnn nnnnnnnnnn nnnnnnnnaa annnnnnnnn nnnnnnnnnn nnnnnnnnnn 360
nnnnnnnngg augggaaggu nacacaugga guguugannn nnnnnnnnnn nnnnnnnnnn 420
nnnnnnnnnn nnnnnnnnnn nnnnnnnnnn nnnnnnnnnn nnnucuunna agucaggaga 480
ccugccuaau guaugcacuu gcacc 505

<210> SEQ ID NO 228
<211> LENGTH: 505
<212> TYPE: RNA
<213> ORGANISM: Bacillus halodurans
<220> FEATURE:
<221> NAME/KEY: misc_feature
<222> LOCATION: 23-469
<223> OTHER INFORMATION: n = g, a, c or u

<400> SEQUENCE: 228
aucguauauc gcgcugaagg gunncguuca annnnnnnnn nnnnnnnugu nnnnnnnnnn 60
nnnnnnuuga gcgugnnaaa angggaagnu cggugannnn nnnnnnnnnn nnnnnnnnnn 120
nnnnaaaucc gacacggunc ccgccacugu aanaugnnnn nnnnnnnnnn nnnnnnnnnn 180
nnnnnnnnnn nnnnnnnnnn nnnnnnggag aggcuugcaa gannnnnnnn nnnnnnnnnn 240
nnnnnnnnnn nnnnnnnnnn nnnnnnnnnn nnnnnnnnnn nnnnnnnnnu ccacugucnn 300
nnnnnnnnnn nnnnnnnnnn nnnnnnnnua gcnnnnnnnn nnnnnnnnnn nnnnnnnnnn 360
nnnnnnnnng acgggaaggg nggcaaguac ucgaugaann nnnnnnnnnn nnnnnnnnnn 420
nnnnnnnnnn nnnnnnnnnn nnnnnnnnnn nnnnnnnnnn nnnncaunna agucaggaga 480
ccugccuuuc aguuugagug uguag 505

<210> SEQ ID NO 229
<211> LENGTH: 505
<212> TYPE: RNA
<213> ORGANISM: Bacillus subtilis
<220> FEATURE:

<221> NAME/KEY: misc_feature
<222> LOCATION: 23-469
<223> OTHER INFORMATION: n = g, a, c or u

<400> SEQUENCE: 229
cggauacgaa ugucaaauag gunngccggu ccgunnnnnn nnnnnngaac annnnnnnnn 60
nnnnacagcc ggcuunnaaa angggaaanc cgguannnnn nnnnnnnnnn nnnnnnnnnn 120
nnnnaaagcc ggugcggunc ccgccacugu aanuuggcnn nnnnnnnnnn nnnnnnnnnn 180
nnnnnnnnnn nnnnnnnnnn nnnnnnnnnn nnnnnnnnnn nnnnnnnnnn nnnnnnnnnn 240
nnnnnnnnnn nnnnnnnnnn nnnnnnnnnn nnnnnnnnnn nnnnnnnnnn nnnnnnnnnn 300
nnnnnnnnnn nnnnnnnnnn nnnnnnncaa gcnnnnnnnn nnnnnnnnnn nnnnnnnnnn 360
nnnnnnnnnn nnnnnnnnnn nnnnnnnnnn nnnnnnnnnn nnnnnnnnnn nnnnnnnnnn 420
nnnnnnnnnn nnnnnnnnnn nnnnnnnnnn nnnnnnnnnn nngccaanng agccaggaua 480
ccugccuguu ugaucagcac gaauu 505

<210> SEQ ID NO 230
<211> LENGTH: 505
<212> TYPE: RNA
<213> ORGANISM: Bradyrhizobium japonicum
<220> FEATURE:
<221> NAME/KEY: misc_feature
<222> LOCATION: 24-469
<223> OTHER INFORMATION: n = g, a, c or u

<400> SEQUENCE: 230
cgauaaucca agucgucgag guuncuccgg uucnnnnnnn nnnnnnccau unnnnnnnnn 60
nnnngauccg gagcunnaag angggaagnc cggugcnnnn nnnnnnnnnn nnnnnnnnnn 120
nnnaaaugcc ggcucugccc ccgcaacugu gangcggnnn nnnnnnnnnn nnnnnnnnnn 180
nnnnnnnnnn nnnnnnnnnn nnnnncgagcc gcuguccgac gaunnnnnnn nnnnnnnnnn 240
nnnnnnnnnn nnnnnnnnnn nnnnnnnnnn nnnnnnnnnn nnnnnnnnng ucgcugaagc 300
cnnnnnnnnn nnnnnnnnnn nnnnnnnnug cacnnnnnnn nnnnnnnnnn nnnnnnnnnn 360
nnnnnnggcu ucgggaaggc nncggacagc agcgaugann nnnnnnnnnn nnnnnnnnnn 420
nnnnnnnnnn nnnnnnnnnn nnnnnnnnnn nnnnnnnnnn nnccagcnna agccaggaga 480
ccggccccga caauauauug gucca 505

<210> SEQ ID NO 231
<211> LENGTH: 505
<212> TYPE: RNA
<213> ORGANISM: Bradyrhizobium japonicum
<220> FEATURE:
<221> NAME/KEY: misc_feature
<222> LOCATION: 24-468
<223> OTHER INFORMATION: n = g, a, c or u

<400> SEQUENCE: 231
caaauggugg cccggcguug guunccuguc nnnnnnnnnn nnnnnncuau nnnnnnnnnn 60
nnnnnnngac aggcgnnaag angggaaung cgauangggu ccgaaucggc aangauuugg 120
guccaaaaun gcagccgccc ccgcgaccgu gaccggagnn nnnnnnnnnn nnnnnnnnnn 180
nnnnnnnnnn nnnnnnnnnn nnnnnnnnnn agaugcccga gnnnnnnnnn nnnnnnnnnn 240
nnnnnnnnnn nnnnnnnnnn nnnnnnnnnn nnnnnnnnnn nnnnnnnnng ccacugaucc 300
cnnnnnnnnn nnnnnnnnnn nnnnnnnnug acnnnnnnnn nnnnnnnnnn nnnnnnnnnn 360
nnnnnnggga ucgggaaggc nnggggaucg aagggcaaaa cccugnnnnn nnnnnnnnnn 420
nnnnnnnnnn nnnnnnnnnn nnnnnnnnnn nnnnnnnnnn nncuccgnca agccgggaga 480
ccugccagcg cggacgauuu uggac 505

<210> SEQ ID NO 232
<211> LENGTH: 505
<212> TYPE: RNA
<213> ORGANISM: Bradyrhizobium japonicum
<220> FEATURE:
<221> NAME/KEY: misc_feature
<222> LOCATION: 23-469
<223> OTHER INFORMATION: n = g, a, c or u

<400> SEQUENCE: 232
gggcacacag gacgggcaug gunngcucga gguggcgcnn nnnnnnnaaa nnnnnnnnnn 60
nnngcgccgg agcaunnaau cngggaaung gggaungggc ggacccnagu ugcnnnnggc 120
gcccaaaacc ccagccgccc ccgcgacugu aangcggunn nnnnnnnnnn nnnnnnnnnn 180
nnnnnnnnnn nnnnnnnnnn nnnnnnngag gggcuccgaa ccnnnnnnnn nnnnnnnnnn 240
nnnnnnnnnn nnnnnnnnnn nnnnnnnnnn nnnnnnnnnn nnnnnnnnng ccacugggcc 300
nnnnnnnnnn nnnnnnnnnn nnnnnnnnng caannnnnnn nnnnnnnnnn nnnnnnnnnn 360
nnnnnnnggu ccgggaaggc nncggagaac cccagugann nnnnnnnnnn nnnnnnnnnn 420
nnnnnnnnnn nnnnnnnnnn nnnnnnnnnn nnnnnnnnnn nnaccgcnng agccaggaga 480
ccggccgugc auguuuugag gccaa 505

<210> SEQ ID NO 233
<211> LENGTH: 505
<212> TYPE: RNA
<213> ORGANISM: Bradyrhizobium japonicum
<220> FEATURE:
<221> NAME/KEY: misc_feature
<222> LOCATION: 24-469
<223> OTHER INFORMATION: n = g, a, c or u

<400> SEQUENCE: 233
aauccuagau gcucgcgacg guunuccccc nnnnnnnnnn nnnnnngaga nnnnnnnnnn 60
nnnnnnnngg ggaugnnaaa angggaaung cggugcgggg annnnnnnug uunnnnnnnu 120
ccccaaugcc gcggcugccc ccgcaacugu aangcggnnn nnnnnnnnnn nnnnnnnnnn 180
nnnnnnnnnn nnnnnnnnnn nnnnnauaau ccuucgucag aannnnnnnn nnnnnnnnnn 240
nnnnnnnnnn nnnnnnnnnn nnnnnnnnnn nnnnnnnnnn nnnnnnnnng ccacugggnn 300
nnnnnnnnnn nnnnnnnnnn nnnnnnuccu cggunnnnnn nnnnnnnnnn nnnnnnnnnn 360
nnnnnnnnnc ccgggaaggc nngacgaagu ggugacgacn nnnnnnnnnn nnnnnnnnnn 420
nnnnnnnnnn nnnnnnnnnn nnnnnnnnnn nnnnnnnnnn nnnccgcnng agccaggaga 480
ccugccguca gccgugguca cacgc 505

<210> SEQ ID NO 234
<211> LENGTH: 505
<212> TYPE: RNA
<213> ORGANISM: Bradyrhizobium japonicum
<220> FEATURE:
<221> NAME/KEY: misc_feature
<222> LOCATION: 23-469
<223> OTHER INFORMATION: n = g, a, c or u

<400> SEQUENCE: 234
ucguagauug aucggugacg gunnucuccn nnnnnnnnnn nnnnnngcac nnnnnnnnnn 60
nnnnnnnngg agaucnnaaa angggaacng uggugcgaga uugucccaau gccgggauug 120

-continued

```
ucccaacgcc acggcugccc ccgcaacugu aangcggnnn nnnnnnnnnn nnnnnnnnnn    180

nnnnnnnnnn nnnnnnnnnn nnnnnugaau cuuucgucau aunnnnnnnn nnnnnnnnnn    240

nnnnnnnnnn nnnnnnnnnn nnnnnnnnnn nnnnnnnnnn nnnnnnnnng ccacugggan    300

nnnnnnnnnn nnnnnnnnnn nnnnnnaucu cggnnnnnnn nnnnnnnnnn nnnnnnnnnn    360

nnnnnnnnuc cugggaaggc nngacguaag guaacgacnn nnnnnnnnnn nnnnnnnnnn    420

nnnnnnnnnn nnnnnnnnnn nnnnnnnnnn nnnnnnnnnn nnnccgcnng agccaggaga    480

ccugccguca gccgugguca cacgc                                          505
```

<210> SEQ ID NO 235
<211> LENGTH: 505
<212> TYPE: RNA
<213> ORGANISM: Brucella melitensis
<220> FEATURE:
<221> NAME/KEY: misc_feature
<222> LOCATION: 23-469
<223> OTHER INFORMATION: n = g, a, c or u

<400> SEQUENCE: 235

```
aucgcaauuu ucaggagacg gunnuccgcc nnnnnnnnnn nnnnnnauug cnnnnnnnnn     60

nnnnnnnggc ggaugnnaaa angggaacna cggugaagcc nnnnnnnnau agnnnnnnnn    120

ggcugaaacc gagacugccc ccgcaacugu aanccggnnn nnnnnnnnnn nnnnnnnnnn    180

nnnnnnnnnn nnnnnnnnnn nnnnnagagc uauccuccac aggccgcgca agcggccaaa    240

nnnnnnnnnn nnnnnnnnnn nnnnnnnnnn nnnnnnnnnn nnnnnnnnng ccacugaaag    300

cagcnnnnnn nnnnnnnnnn nnnnnnnaau aunnnnnnnn nnnnnnnnnn nnnnnnnnnn    360

nnngcugcaa ucgggaaggc nnggaggcaa agcgaagacn nnnnnnnnnn nnnnnnnnnn    420

nnnnnnnnnn nnnnnnnnnn nnnnnnnnnn nnnnnnnnnn nnnccggnna agucaggaga    480

ccugccguau ccggucaccc augcu                                          505
```

<210> SEQ ID NO 236
<211> LENGTH: 505
<212> TYPE: RNA
<213> ORGANISM: Brucella melitensis
<220> FEATURE:
<221> NAME/KEY: misc_feature
<222> LOCATION: 23-469
<223> OTHER INFORMATION: n = g, a, c or u

<400> SEQUENCE: 236

```
agugucaaac caugugacag gunnuuugcc ggnnnnnnnn nnnnaacgaa uccnnnnnnn     60

nnnnccggca auaccnnaaa angggaaung cgacgngacg gacccnnacg ccnnnnnggg    120

cgucuuuauc gcagccgacc ccgcgacugu agagcggnnn nnnnnnnnnn nnnnnnnnnn    180

nnnnnnnnnn nnnnnnnnnn nnnnnagagg gaagaggcaa gccgggcaac cggcannnnn    240

nnnnnnnnnn nnnnnnnnnn nnnnnnnnnn nnnnnnnnnn nnnnnnnnng ccacuggaaa    300

ucnnnnnnnn nnnnnnnnnn nnnnnnnaga ugnnnnnnnn nnnnnnnnnn nnnnnnnnnn    360

nnnnngauuu cugggaaggc nngcuuuauu ccccaagacn nnnnnnnnnn nnnnnnnnnn    420

nnnnnnnnnn nnnnnnnnnn nnnnnnnnnn nnnnnnnnnn nnnccgcnng agccaggaga    480

ccugccuguu gcaugagggc auugc                                          505
```

<210> SEQ ID NO 237
<211> LENGTH: 505
<212> TYPE: RNA
<213> ORGANISM: Brucella melitensis
<220> FEATURE:

<221> NAME/KEY: misc_feature
<222> LOCATION: 23-469
<223> OTHER INFORMATION: n = g, a, c or u

<400> SEQUENCE: 237
gccguaauac cgucaugacg gunnuccccg accgnnnnnn nnnnnnagag nnnnnnnnnn 60
nnnncgaagg ggauunnaau angggaacna cggugaggac gacccnnauc aannnnnngg 120
ggccgagacc guggcugccc ccgcaacugu aangcggann nnnnnnnnnn nnnnnnnnnn 180
nnnnnnnnnn nnnnnnnnnn nnnnnnuugc cguucauccu cgugacgccg aaagcgucau 240
nnnnnnnnnn nnnnnnnnnn nnnnnnnnnn nnnnnnnnnn nnnnnnnnng ccacugugcc 300
nnnnnnnnnn nnnnnnnnnn nnnnnnnnca cnnnnnnnnn nnnnnnnnnn nnnnnnnnnn 360
nnnnnnnggc acgggaaggc nagauggacg gcgauuannn nnnnnnnnnn nnnnnnnnnn 420
nnnnnnnnnn nnnnnnnnnn nnnnnnnnnn nnnnnnnnnn nnuccgcnna agccaggaga 480
ccugccgucu uacguagucc auugu 505

<210> SEQ ID NO 238
<211> LENGTH: 505
<212> TYPE: RNA
<213> ORGANISM: Brucella melitensis
<220> FEATURE:
<221> NAME/KEY: misc_feature
<222> LOCATION: 24-469
<223> OTHER INFORMATION: n = g, a, c or u

<400> SEQUENCE: 238
uaccauaucu uguguucgag guuncuuucg auucnnnnnn nnnnnngacn nnnnnnnnnn 60
nnngagucgg gagcunnaag acgggaaunc cggugcgcuu gcccnnnaug gunnnngggc 120
gggcaaugcc ggagcugccc ccgcaacugu aangcggcnn nnnnnnnnnn nnnnnnnnnn 180
nnnnnnnnnn nnnnnnnnnn nnnnngagcu uugcgcccca unnnnnnnnn nnnnnnnnnn 240
nnnnnnnnnn nnnnnnnnnn nnnnnnnnnn nnnnnnnnnn nnnnnnnnng ccacuggcnn 300
nnnnnnnnnn nnnnnnnnnn nnnnnnngaa annnnnnnnn nnnnnnnnnn nnnnnnnnnn 360
nnnnnnnnng ccgggaaggc nngggguggaa gcguugannn nnnnnnnnnn nnnnnnnnnn 420
nnnnnnnnnn nnnnnnnnnn nnnnnnnnnn nnnnnnnnnn nngccgunng agccaggaga 480
ccugccuuga gcgugaacgu ccacg 505

<210> SEQ ID NO 239
<211> LENGTH: 505
<212> TYPE: RNA
<213> ORGANISM: Caulobacter crescentus
<220> FEATURE:
<221> NAME/KEY: misc_feature
<222> LOCATION: 23-469
<223> OTHER INFORMATION: n = g, a, c or u

<400> SEQUENCE: 239
ggucuguugc cguugucgug gunncugcgg acgnnnnnnn nnnnnnuucg nnnnnnnnnn 60
nnnncguccg gagcunnaag angggaagnu cggugnaggg nnnnnncgug aaannnnnnn 120
cccugaaucc ggcgcugccc ccgcaacugu gangcggnnn nnnnnnnnnn nnnnnnnnnn 180
nnnnnnnnnn nnnnnnnnnn nnnnncgagc cgcuguccgu uucgunnnnn nnnnnnnnnn 240
nnnnnnnnnn nnnnnnnnnn nnnnnnnnnn nnnnnnnnnn nnnnnnnnng ucacugacgc 300
gccgaannnn nnnnnnnnnn nnnnnnngcu ggnnnnnnnn nnnnnnnnnn nnnnnnnnuu 360
cggggaugcg ucgggaaggc cagggcaggg gugacgacnn nnnnnnnnnn nnnnnnnnnn 420
nnnnnnnnnn nnnnnnnnnn nnnnnnnnnn nnnnnnnnnn nnnccgunng agccaggaga 480
ccugccucga cagauaacgu ccucc 505

<210> SEQ ID NO 240
<211> LENGTH: 505
<212> TYPE: RNA
<213> ORGANISM: Caulobacter crescentus
<220> FEATURE:
<221> NAME/KEY: misc_feature
<222> LOCATION: 23-469
<223> OTHER INFORMATION: n = g, a, c or u

<400> SEQUENCE: 240
uagcucuagc uucgcgucag gunnuccucn nnnnnnnnnn nnnnnngaaa nnnnnnnnnn 60
nnnnnnnnga ggaugnnaaa angggaacng agguugnnnn nnnnnnnnnn nnnnnnnnnn 120
nnnnaagacc ucggcugccc ccgcaacugu aangcggnnn nnnnnnnnnn nnnnnnnnnn 180
nnnnnnnnnn nnnnnnnnnn nnnnncgagc uucgcgucac aunnnnnnnn nnnnnnnnnn 240
nnnnnnnnnn nnnnnnnnnn nnnnnnnnnn nnnnnnnnnn nnnnnnnnng ccacugggcc 300
nnnnnnnnnn nnnnnnnnnn nnnnnnncaa aannnnnnnn nnnnnnnnnn nnnnnnnnnn 360
nnnnnnnggc cugggaaggc nngacgccca gaagcauuga cnnnnnnnnn nnnnnnnnnn 420
nnnnnnnnnn nnnnnnnnnn nnnnnnnnnn nnnnnnnnnn nnnccgunng agccaggaga 480
ccugcccggc gcagucguuc aucgc 505

<210> SEQ ID NO 241
<211> LENGTH: 505
<212> TYPE: RNA
<213> ORGANISM: Chlorobium tepidum
<220> FEATURE:
<221> NAME/KEY: misc_feature
<222> LOCATION: 23-469
<223> OTHER INFORMATION: n = g, a, c or u

<400> SEQUENCE: 241
auacuucauc cgauuaugug gunngcccgc caugnnnnnn nnnnnngaaa nnnnnnnnnn 60
nnnncauacg ggcuunnaaa angggaaunc cggugannnn nnnnnnnnnn nnnnnnnnnn 120
nnnngagucc ggaacaguac ccgcugcugu aanuuccnnn nnnnnnnnnn nnnnnnnnnn 180
nnnnnggcug gccgcaaggc uggcgacaag guuugccgca caaunnnnnn nnnnnnnnnn 240
nnnnnnnnnn nnnnnnnnnn nnnnnnnnnn nnnnnnnnnn nnnnnnnnng ccacuguccc 300
nnnnnnnnnn nnnnnnnnnn nnnnnnnguu cannnnnnnn nnnnnnnnnn nnnnnnnnnn 360
nnnnnnnggg augggaaggc nncggcagaa uccnnnnnnn nnnnnnnnnn nnnnnnnnnn 420
nnnnnnnnnn nnnnnnnnnn nnnnnnnnnn nnnnnnnnnn nnngggganna agucagaaga 480 ccugccucau auuuuuuggc uucgg 505

<210> SEQ ID NO 242
<211> LENGTH: 505
<212> TYPE: RNA
<213> ORGANISM: Chlorobium tepidum
<220> FEATURE:
<221> NAME/KEY: misc_feature
<222> LOCATION: 24-462
<223> OTHER INFORMATION: n = g, a, c or u

<400> SEQUENCE: 242
guucuuucuc gccaugacag gugnccgguu nnnnnnnnnn nnnnnnuaaa nnnnnnnnnn 60
nnnnnnnagc cggagnnaau angggaagnu acgugannnn nnnnnnnnnn nnnnnnnnnn 120
nnnngauucg uacacuguac ccgcaacugu acaacggunn nnnnnnuaac cgccgggcaa 180
auuccguggc cacacggaug cgcaaggcgg gcuuucagnn nnnnnnnnnn nnnnnnnnnn 240
nnnnnnnnnn nnnnnnnnnn nnnnnnnnnn nnnnnnnnnn nnnnnnnnng ucacugccgg 300
uuuuccnnnn nnnnnnnnnn nnnnnnnucc acnnnnnnnn nnnnnnnnnn nnnnnnnnnn 360
nnggaaaacu gcgggaaggu nnuuggaggc gcucgaunnn nnnnnnnnnn nnnnnnnnnn 420
nnnnnnnnnn nnnnnnnnnn nnnnnnnnnn nnnnnnnnnn nngccgugaa agucaggaga 480
ccugccaguc augcauuugc accaa 505

<210> SEQ ID NO 243
<211> LENGTH: 505
<212> TYPE: RNA
<213> ORGANISM: Chlorobium tepidum
<220> FEATURE:
<221> NAME/KEY: misc_feature
<222> LOCATION: 23-469
<223> OTHER INFORMATION: n = g, a, c or u

<400> SEQUENCE: 243
caauaaauaa uucaguuacg gunnuuccgg ugcccnnnnn nnnnnnggug nnnnnnnnnn 60
nngggcgccg gaaugnnaaa angggaacnc cggugannnn nnnnnnnnnn nnnnnnnnnn 120
nnnnaaaucc gggacagugc ccgcugcugu ganucccucnn nnnnnnnnnn nnnnnnnnnn 180
nccgucggcc acaaucgggu cggcggacga ucgcuuccga ugannnnnnn nnnnnnnnnn 240
nnnnnnnnnn nnnnnnnnnn nnnnnnnnnn nnnnnnnnnn nnnnnnnngg ccacugguuc 300
gcnnnnnnnn nnnnnnnnnn nnnnnngccc nnnnnnnnnn nnnnnnnnnn nnnnnnnnnn 360
nnnnngcgaa ccgggaaggc cnggaagcga nnnnnnnnnn nnnnnnnnnn nnnnnnnnnn 420
nnnnnnnnnn nnnnnnnnnn nnnnnnnnnn nnnnnnnnnn nnggggganng agucagaaga 480 ccugccguaa ugcaguaaau gcucc 505

<210> SEQ ID NO 244
<211> LENGTH: 505
<212> TYPE: RNA
<213> ORGANISM: Chlorobium tepidum
<220> FEATURE:
<221> NAME/KEY: misc_feature
<222> LOCATION: 24-468
<223> OTHER INFORMATION: n = g, a, c or u

<400> SEQUENCE: 244
ugaguucuuu cagcauuacg gugnccggau nnnnnnnnnn nnnnnngaaa gnnnnnnnnn 60
nnnnnnaugc cggaunnaau angggaagnu gcgugunnnn nnnnnnnnnn nnnnnnnnnn 120
nnnngaaucg cacacugugc ccgcaacugu aangauggun nnnnaugucg cgcgacgaca 180
ggagcagcuc ugcuuuugug gccguugcgg aucgggugua unnnnnnnnn nnnnnnnnnn 240
nnnnnnnnnn nnnnnnnnnn nnnnnnnnnn nnnnnnnnnn nnnnnnnnnn ccacuccgcc 300
aaccucugnn nnnnnnnnnn nnnnnnauaa cnnnnnnnnn nnnnnnnnnn nnnnnnnnca 360
cggggaaugc gggggaaggn ncugcccgga ggaaaacguc gaaguaauuu cgcannnnnn 420
nnnnnnnnnn nnnnnnnnnn nnnnnnnnnn nnnnnnnnnn ngccaucnga agucaggaga 480
ccugccguag ugguuggcgc cgaau 505

<210> SEQ ID NO 245
<211> LENGTH: 505
<212> TYPE: RNA
<213> ORGANISM: Chlorobium tepidum
<220> FEATURE:

<221> NAME/KEY: misc_feature
<222> LOCATION: 24-468
<223> OTHER INFORMATION: n = g, a, c or u

<400> SEQUENCE: 245

```
guucuuucuc gccaugacag gugnccgguu nnnnnnnnnn nnnnnnuaaa nnnnnnnnnn     60

nnnnnnnagc cggagnnaau angggaagnu acgugannnn nnnnnnnnnn nnnnnnnnnn    120

nnnngauucg uacacuguac ccgcaacugu acaacggnnn nnnnnnaaaa cugccgcugg    180

cagguauggc cacaugccuc aaagccgcag ccggugcacn nnnnnnnnnn nnnnnnnnnn    240

nnnnnnnnnn nnnnnnnnnn nnnnnnnnnn nnnnnnnnnn nnnnnnnnng ucacugccag    300

gcuccnnnnn nnnnnnnnnn nnnnnnnucc acnnnnnnnn nnnnnnnnnn nnnnnnnnnn    360

nnnggagcgg gcgggaaggc nnugcaucgn nnnnauucaa gnnnnnnnnn nnnnnnnnnn    420

nnnnnnnnnn nnnnnnnnnn nnnnnnnnnn nnnnnnnnnn nnnccgunaa agucaggaga    480

ccugccaguu acucuuugcu cggaa                                          505
```

<210> SEQ ID NO 246
<211> LENGTH: 505
<212> TYPE: RNA
<213> ORGANISM: Clostridium acetobutylicum
<220> FEATURE:
<221> NAME/KEY: misc_feature
<222> LOCATION: 23-469
<223> OTHER INFORMATION: n = g, a, c or u

<400> SEQUENCE: 246

```
auugcuacua aaauuuguag gunnucaacu gagnnnnnnn nnnnnngagu nnnnnnnnnn     60

nnnncuuagu ugauunnaaa anaggaaunc aggugannnn nnnnnnnnnn nnnnnnnnnn    120

nnnnaaagcc ugagcggunc ccgccacugu aauaaaggnn nnnnnnnnnn nnnnnnnnnn    180

nnnnnnnnnn nnnnnnnnnn nnnnnnnagu uuaaguacaa uaunnnnnnn nnnnnnnnnn    240

nnnnnnnnnn nnnnnnnnnn nnnnnnnnnn nnnnnnnnnn nnnnnnnnng ucacuggnnn    300

nnnnnnnnnn nnnnnnnnnn nnnnnnngaa annnnnnnnn nnnnnnnnnn nnnnnnnnnn    360

nnnnnnnnnn cugggaaggc nnguacuuaa gcaaugannn nnnnnnnnnn nnnnnnnnnn    420

nnnnnnnnnn nnnnnnnnnn nnnnnnnnnn nnnnnnnnnn nnuuuuunng agccaggaua    480

cuugccauau ucuaguaugu uuuuu                                          505
```

<210> SEQ ID NO 247
<211> LENGTH: 505
<212> TYPE: RNA
<213> ORGANISM: Clostridium acetobutylicum
<220> FEATURE:
<221> NAME/KEY: misc_binding
<222> LOCATION: 23-469
<223> OTHER INFORMATION: n = g, a, c or u

<400> SEQUENCE: 247

```
gaaauaauac cauauuuuag gcnnaccuan nnnnnnnnnn nnnnnnaucu nnnnnnnnnn     60

nnnnnnnnua gguuunnaau angggaaanu uggugannnn nnnnnnnnnn nnnnnnnnnn    120

nnnnaaaucc aaugcaaccc ccguuacugu aunacaguun nnnnnnnnnn nnnnnnnnnn    180

nnnnnnnnnn nnnnnnnnnn nnnnnnnnna caaaaccaau gnnnnnnnnn nnnnnnnnnn    240

nnnnnnnnnn nnnnnnnnnn nnnnnnnnnn nnnnnnnnnn nnnnnnnnnu ccacuggagn    300

nnnnnnnnnn nnnnnnnnnn nnnnnnnuuu unnnnnnnnn nnnnnnnnnn nnnnnnnnnn    360

nnnnnnnncu cugggaagga nnugguugag gcuannnnnn nnnnnnnnnn nnnnnnnnnn    420
```

```
nnnnnnnnnn nnnnnnnnnn nnnnnnnnnn nnnnnnnnnn naacugunng agccaggaga    480

ccuaccuaaa auauuaugga acuuc                                          505
```

<210> SEQ ID NO 248
<211> LENGTH: 505
<212> TYPE: RNA
<213> ORGANISM: Clostridium perfringens
<220> FEATURE:
<221> NAME/KEY: misc_feature
<222> LOCATION: 23-469
<223> OTHER INFORMATION: n = g, a, c or u

<400> SEQUENCE: 248

```
aauuaaauau uuagaaauag gunnuaaaua guuacnnnnn nnnnnnauuu nnnnnnnnnn     60

nnguaacuau auauunnaaa angggaaguu ggguuunnnn nnnnnnnnnn nnnnnnnnnn    120

nnnnaaaucc cacgcggunc ccgccgcugu aanuagnnnn nnnnnnnnnn nnnnnnnnnn    180

nnnnnnnnnn nnnnnnnnnn nnnnnaggag cuuuuuguac uuuaannnnn nnnnnnnnnn    240

nnnnnnnnnn nnnnnnnnnn nnnnnnnnnn nnnnnnnnnn nnnnnnnnng ccacuggaau    300

annnnnnnnn nnnnnnnnnn nnnnnnnnua annnnnnnnn nnnnnnnnnn nnnnnnnnnn    360

nnnnnnuauu uugggaaggc ncacaaaaag ugaugauann nnnnnnnnnn nnnnnnnnnn    420

nnnnnnnnnn nnnnnnnnnn nnnnnnnnnn nnnnnnnnnn nnnncuunng agccagaaga    480

ccugccuauu uuuaaaacau caaga                                          505
```

<210> SEQ ID NO 249
<211> LENGTH: 505
<212> TYPE: RNA
<213> ORGANISM: Clostridium perfringens
<220> FEATURE:
<221> NAME/KEY: misc_feature
<222> LOCATION: 23-468
<223> OTHER INFORMATION: n = g, a, c or u

<400> SEQUENCE: 249

```
aguugauuaa cuaauaauug gunngugnnn nnnnnnnnnn nnnnnnauuu unnnnnnnnn     60

nnnnnnnnnn cgcuunnaau angggaaung aaguuannnn nnnnnnnnnn nnnnnnnnnn    120

nnnnaagucu ucaacuaccu caguaaccgu gaagcnnnnn nnnnnnnnnn nnnnnnnnnn    180

nnnnnnnnnn nnnnnnnnnn nnnnnnagac aaaaucucaa uaunnnnnnn nnnnnnnnnn    240

nnnnnnnnnn nnnnnnnnnn nnnnnnnnnn nnnnnnnnnn nnnnnnnnng ucacugcaun    300

nnnnnnnnnn nnnnnnnnnn nnnnnnnuuu uunnnnnnnn nnnnnnnnnn nnnnnnnnnn    360

nnnnnnnngu gugggaagac nngagaugga ggaagaannn nnnnnnnnnn nnnnnnnnnn    420

nnnnnnnnnn nnnnnnnnnn nnnnnnnnnn nnnnnnnnnn nnnnngcnaa agucgggaua    480

ccugccuuuu auuuaaguac uauua                                          505
```

<210> SEQ ID NO 250
<211> LENGTH: 505
<212> TYPE: RNA
<213> ORGANISM: Clostridium perfringens
<220> FEATURE:
<221> NAME/KEY: misc_feature
<222> LOCATION: 23-468
<223> OTHER INFORMATION: n = g, a, c or u

<400> SEQUENCE: 250

```
auaauauuuu auauuuuuag gunnuugnnn nnnnnnnnnn nnnnnnauuu nnnnnnnnnn     60

nnnnnnnnnn uaauunnaaa angggaaang ugguuannnn nnnnnnnnnn nnnnnnnnnn    120
```

-continued

```
nnnnaagucc acuacagccc ccgcuacugu gauaggnnnn nnnnnnnnnn nnnnnnnnnn    180

nnnnnnnnnn nnnnnnnnnn nnnnnnauac aaguuucuau uugannnnnn nnnnnnnnnn    240

nnnnnnnnnn nnnnnnnnnn nnnnnnnnnn nnnnnnnnnn nnnnnnnnnn ccacugauun    300

nnnnnnnnnn nnnnnnnnnn nnnnnnnaua uannnnnnnn nnnnnnnnnn nnnnnnnnnn    360

nnnnnnnnaa uugggaaggn ngagaaauga ggauaagnnn nnnnnnnnnn nnnnnnnnnn    420

nnnnnnnnnn nnnnnnnnnn nnnnnnnnnn nnnnnnnnnn nnnnccunua agucaggaua    480

ccugccuaaa gaucaugaac uaagc                                          505
```

```
<210> SEQ ID NO 251
<211> LENGTH: 505
<212> TYPE: RNA
<213> ORGANISM: Clostridium perfringens
<220> FEATURE:
<221> NAME/KEY: misc_feature
<222> LOCATION: 23-469
<223> OTHER INFORMATION: n = g, a, c or u

<400> SEQUENCE: 251

aaauaaaaua agagcauuag gunnguunnn nnnnnnnnnn nnnnnnuagu nnnnnnnnnn     60

nnnnnnnnnn aacuunnaau angggaaang uunnnnnnnn nnnnnnnnnn nnnnnnnnnn    120

nnnnaaanna acugcagccc ccgcuacugu ugnauaagnn nnnnnnnnnn nnnnnnnnnn    180

nnnnnnnnnn nnnnnnnnnn nnnnnnngac gagaauaaaa agnnnnnnnn nnnnnnnnnn    240

nnnnnnnnnn nnnnnnnnnn nnnnnnnnnn nnnnnnnnnn nnnnnnnnnn ccacugugau    300

nnnnnnnnnn nnnnnnnnnn nnnnnnnaaa uannnnnnnn nnnnnnnnnn nnnnnnnnnn    360

nnnnnnnguc auggaaaggn nauuguuuua ggaugannnn nnnnnnnnnn nnnnnnnnnn    420

nnnnnnnnnn nnnnnnnnnn nnnnnnnnnn nnnnnnnnnn nnuuuaunnu agccaggaga    480

ccugccuagu augcuauucu uauug                                          505
```

```
<210> SEQ ID NO 252
<211> LENGTH: 505
<212> TYPE: RNA
<213> ORGANISM: Escherichia coli
<220> FEATURE:
<221> NAME/KEY: misc_feature
<222> LOCATION: 24-469
<223> OTHER INFORMATION: n = g, a, c or u

<400> SEQUENCE: 252

ccuguagcau ccacuugccg gucncunnnn nnnnnnnnnn nnnnnnngug nnnnnnnnnn     60

nnnnnnnnnn naguunnaau angggaaunc cagugcnnnn nnnnnnnnnn nnnnnnnnnn    120

nnnngaaucu ggagcuganc gcgcagcggu aanggannnn nnnnnnnnnn nnnnnnnnnn    180

nnnnnnnnnn nnnnnnnnnn nnnnnaaggu gcgaugauug cguuaugcgn nnnnnnnnnn    240

nnnnnnnnnn nnnnnnnnnn nnnnnnnnnn nnnnnnnnnn nnnnnnnnng acacugccnn    300

nnnnnnnnnn nnnnnnnnnn nnnnnnnauu cnnnnnnnnn nnnnnnnnnn nnnnnnnnnn    360

nnnnnnnnng gugggaaguc nnaucaucuc uuaguaucuu agauaccccn nnnnnnnnnn    420

nnnnnnnnnn nnnnnnnnnn nnnnnnnnnn nnnnnnnnnn nnnnuccnna agcccgaaga    480

ccugccggcc aacgucgcau cuggu                                          505
```

```
<210> SEQ ID NO 253
<211> LENGTH: 505
<212> TYPE: RNA
<213> ORGANISM: Fusobacterium nucleatum
<220> FEATURE:
```

<221> NAME/KEY: misc_feature
<222> LOCATION: 24-468
<223> OTHER INFORMATION: n = g, a, c or u

<400> SEQUENCE: 253
uuuaauauca ugucaauuau guunccuuan nnnnnnnnnn nnnnnnuuuu unnnnnnnnn 60
nnnnnnnnua aggcunnaag angggaaunu uggugannnn nnnnnnnnnn nnnnnnnnnn 120
nnnngauacc aaaacgagnc ccgucgcugu aauugannnn nnnnnnnnnn nnnnnnnnnn 180
nnnnnnnnnn nnnnnnnnnn nnnnnnnngu uuuuucuugu uuuannnnnn nnnnnnnnnn 240
nnnnnnnnnn nnnnnnnnnn nnnnnnnnnn nnnnnnnnnn nnnnnnnnua ccacuggaun 300
nnnnnnnnnn nnnnnnnnnn nnnnnnnuuu unnnnnnnnn nnnnnnnnnn nnnnnnnnnn 360
nnnnnnnnau uugggaaggu anaagaaaua uaaannnnnn nnnnnnnnnn nnnnnnnnnn 420
nnnnnnnnnn nnnnnnnnnn nnnnnnnnnn nnnnnnnnnn nnnnucanua agucagaaga 480
ccugcauaau ugaauuacuc uaucu 505

<210> SEQ ID NO 254
<211> LENGTH: 505
<212> TYPE: RNA
<213> ORGANISM: Leptospira interrogans
<220> FEATURE:
<221> NAME/KEY: misc_feature
<222> LOCATION: 24-469
<223> OTHER INFORMATION: n = g, a, c or u

<400> SEQUENCE: 254
aucuuggaac ggaaaacuug uuunauunnn nnnnnnnnnn nnnnncucgu nnnnnnnnnn 60
nnnnnnnnnn gauganngga angggaaunc cgguucnnnn nnnnnnnnnn nnnnnnnnnn 120
nnnnaaaucc ggagcugaac ccgcagcugu aanucgccga nnnnnnnnnn nnnnnnnnnn 180
nnnnnnnnnn nnnnnnnnnn nnnnnaugag auuucgcaau caunnnnnnn nnnnnnnnnn 240
nnnnnnnnnn nnnnnnnnnn nnnnnnnnnn nnnnnnnnnn nnnnnnnnng ccacugcgun 300
nnnnnnnnnn nnnnnnnnnn nnnnnnuaaa unnnnnnnnn nnnnnnnnnn nnnnnnnnnn 360
nnnnnnnnac gcgggaaggc nnugcgaaan nnnnnnnnnn nnnnnnnnnn nnnnnnnnnn 420
nnnnnnnnnn nnnnnnnnnn nnnnnnnnnn nnnnnnnnnn ucggcganna agccagaaga 480
ccuaacaagu aaaaaaacaa acuaa 505

<210> SEQ ID NO 255
<211> LENGTH: 505
<212> TYPE: RNA
<213> ORGANISM: Listeria monocytogenes
<220> FEATURE:
<221> NAME/KEY: misc_feature
<222> LOCATION: 23-469
<223> OTHER INFORMATION: n = g, a, c or u

<400> SEQUENCE: 255
guuaaauagg ucuuauguug gunnggaaug unnnnnnnnn nnnnnnaugu nnnnnnnnnn 60
nnnnnnnaca uuucugnaaa gnaggaaunu cggugcnnnn nnnnnnnnnn nnnnnnnnnn 120
nnnngaugcc gaaacugccc ccgcaacugu aanggunnnn nnnnnnnnnn nnnnnnnnnn 180
nnnnnnnnnn nnnnnnnnnn nnnnggacaa gaaucgagau nnnnnnnnnn nnnnnnnnnn 240
nnnnnnnnnn nnnnnnnnnn nnnnnnnnnn nnnnnnnnnn nnnnnnnnaa ccacuguacg 300
unnnnnnnnn nnnnnnnnnn nnnnnnuuuu annnnnnnnn nnnnnnnnnn nnnnnnnnnn 360
nnnnnngcgu augggaaggu uncgauuguu ggaugaannn nnnnnnnnnn nnnnnnnnnn 420
nnnnnnnnnn nnnnnnnnnn nnnnnnnnnn nnnnnnnnnn nnnngccnna agucaggaua 480
cucgccaaau aagacggaag caacu 505

<210> SEQ ID NO 256
<211> LENGTH: 505
<212> TYPE: RNA
<213> ORGANISM: Mesorhizobium loti
<220> FEATURE:
<221> NAME/KEY: misc_feature
<222> LOCATION: 23-469
<223> OTHER INFORMATION: n = g, a, c or u

<400> SEQUENCE: 256
cuauagucau gcagucgucg gunnuccnnn nnnnnnnnnn nnnnnnguuu unnnnnnnnn 60
nnnnnnnnnn ggagccnaag angggaaung cggugcgggc gannnnnaau ucnnnnnnuu 120
gcccaaugcc guggcugccc ccgcaacugu gungcggnnn nnnnnnnnnn nnnnnnnnnn 180
nnnnnnnnnn nnnnnnnnnn nnnnnnnuag uccucuccau aunnnnnnnn nnnnnnnnnn 240
nnnnnnnnnn nnnnnnnnnn nnnnnnnnnn nnnnnnnnnn nnnnnnnnng ccacugaaga 300
nnnnnnnnnn nnnnnnnnnn nnnnnnnuuc gnnnnnnnnn nnnnnnnnnn nnnnnnnnnn 360
nnnnnnnucu ucgggaaggu nnggggaagg gcgcugaunn nnnnnnnnnn nnnnnnnnnn 420
nnnnnnnnnn nnnnnnnnnn nnnnnnnnnn nnnnnnnnnn nnnccgunng agccaggaga 480
ccugccgacg acggcaaaac ugaca 505

<210> SEQ ID NO 257
<211> LENGTH: 505
<212> TYPE: RNA
<213> ORGANISM: Mesorhizobium loti
<220> FEATURE:
<221> NAME/KEY: misc_feature
<222> LOCATION: 23-469
<223> OTHER INFORMATION: n = g, a, c or u

<400> SEQUENCE: 257
gccuaaaucc gcuccagacg gunncccuug ccnnnnnnnn nnnnncgcaa cnnnnnnnnn 60
nnnnnnggca ggggcunaag angggaaung cggugcggga unnnnnnnuu cgnnnnnnna 120
ucucaaaucc gcggcugucc ccgcaacugu aangcgnnnn nnnnnnnnnn nnnnnnnnnn 180
nnnnnnnnnn nnnnnnnnnn nnnnaagagc caaggccgaa agnnnnnnnn nnnnnnnnnn 240
nnnnnnnnnn nnnnnnnnnn nnnnnnnnnn nnnnnnnnnn nnnnnnnnnn ccacugggnn 300
nnnnnnnnnn nnnnnnnnnn nnnnnnnacg uunnnnnnnn nnnnnnnnnn nnnnnnnnnn 360
nnnnnnnnnc ccgggaaggn nncggcaccc aaggcgauga ccnnnnnnnn nnnnnnnnnn 420
nnnnnnnnnn nnnnnnnnnn nnnnnnnnnn nnnnnnnnnn nnnncgcnng agccaggaga 480
ccugccgucu gcgacaaaag aaucc 505

<210> SEQ ID NO 258
<211> LENGTH: 505
<212> TYPE: RNA
<213> ORGANISM: Mesorhizobium loti
<220> FEATURE:
<221> NAME/KEY: misc_feature
<222> LOCATION: 24-469
<223> OTHER INFORMATION: n = g, a, c or u

<400> SEQUENCE: 258
auuagaucau gucaucucag gugnccgcuu cgunnnnnnn nnnnnngacg nnnnnnnnnn 60
nnnnacgggg cggagnnaau ungggaagnc cggucannnn nnnnnnnnnn nnnnnnnnnn 120
nnnnaagucc ggcgcugccc ccgcaacggu ggnuggagnn nnnnnnnnnn nnnnnnnnnn 180
nnnnnnnnnn nnnnnnnnnn nnnnnuucaa gucgcaacgg gagnnnnnnn nnnnnnnnnn 240
nnnnnnnnnn nnnnnnnnnn nnnnnnnnnn nnnnnnnnnn nnnnnnnnna ccacugggcn 300
nnnnnnnnnn nnnnnnnnnn nnnnnnnaaa annnnnnnnn nnnnnnnnnn nnnnnnnnnn 360
nnnnnnnngc cugggaaggu nngucgcgac cguccgcaag gacannnnnn nnnnnnnnnn 420
nnnnnnnnnn nnnnnnnnnn nnnnnnnnnn nnnnnnnnnn nncuccanng agcccggaaa 480
ccagcccgag auuuuugaac ucgac 505

<210> SEQ ID NO 259
<211> LENGTH: 505
<212> TYPE: RNA
<213> ORGANISM: Mesorhizobium loti
<220> FEATURE:
<221> NAME/KEY: misc_feature
<222> LOCATION: 24-469
<223> OTHER INFORMATION: n = g, a, c or u

<400> SEQUENCE: 259
gugauugugc gcaugucgug guuncuccgc gcggcnnnnn nnnnnnnacu nnnnnnnnnn 60
ngccguagcg gagcunnaag angggaagnc cggugcnnnn nnnnnnnnnn nnnnnnnnnn 120
nnnngaugcc ggcgcugccc ccgcaacugu uangcggnnn nnnnnnnnnn nnnnnnnnnn 180
nnnnnnnnnn nnnnnnnnnn nnnnnncgag ccaagcccau uggunnnnnn nnnnnnnnnn 240
nnnnnnnnnn nnnnnnnnnn nnnnnnnnnn nnnnnnnnnn nnnnnnnnng ucacugaggc 300
nnnnnnnnnn nnnnnnnnnn nnnnnnngaa cgnnnnnnnn nnnnnnnnnn nnnnnnnnnn 360
nnnnnnngcc ucgggaagac nngggcagag gcuuugacnn nnnnnnnnnn nnnnnnnnnn 420
nnnnnnnnnn nnnnnnnnnn nnnnnnnnnn nnnnnnnnnn nnnccgcnng agccaggaga 480
ccugccacga cgaacaacgu ccacg 505

<210> SEQ ID NO 260
<211> LENGTH: 505
<212> TYPE: RNA
<213> ORGANISM: Mesorhizobium loti
<220> FEATURE:
<221> NAME/KEY: misc_feature
<222> LOCATION: 24-469
<223> OTHER INFORMATION: n = g, a, c or u

<400> SEQUENCE: 260
aaggucgccg ccacugccug gugncccgcn nnnnnnnnnn nnnnnncgca annnnnnnnn 60
nnnnnnnngc gggagnnaau cngggaacna cgguugnnnn nnnnnnnnnn nnnnnnnnnn 120
nnnnaacucc guggcgugnc ccaacgcugu aangggggnnn nnnnnnnnnn nnnnnnnnnn 180
nnnnnnnnnn nnnnnnnnnn nnnnnngacc gcgccgguaa aunnnnnnnn nnnnnnnnnn 240
nnnnnnnnnn nnnnnnnnnn nnnnnnnnnn nnnnnnnnnn nnnnnnnnng ccacugucnn 300
nnnnnnnnnn nnnnnnnnnn nnnnnnnnga unnnnnnnnn nnnnnnnnnn nnnnnnnnnn 360
nnnnnnnnng acgggaaggc nnaccggacg cggguugann nnnnnnnnnn nnnnnnnnnn 420
nnnnnnnnnn nnnnnnnnnn nnnnnnnnnn nnnnnnnnnn nnnucccnng agccagaaga 480
ccggccuggc aggcaucguc auccg 505

<210> SEQ ID NO 261
<211> LENGTH: 505
<212> TYPE: RNA
<213> ORGANISM: Mesorhizobium loti
<220> FEATURE:

<221> NAME/KEY: misc_feature
<222> LOCATION: 23-469
<223> OTHER INFORMATION: n = g, a, c or u

<400> SEQUENCE: 261
ucuacggugg gugcgugaug gunnccccgc gccnnnnnnn nnnnnngaaa nnnnnnnnnn 60
nnnnggcaag gggugnnaaa angggaacna cggugagacc unnnnnnnca aannnnnnna 120
ggucgagacc guggcugccc ccgcaacugu aangcggnnn nnnnnnnnnn nnnnnnnnnn 180
nnnnnnnnnn nnnnnnnnnn nnnnnnagag caagauccga cannnnnnnn nnnnnnnnnn 240
nnnnnnnnnn nnnnnnnnnn nnnnnnnnnn nnnnnnnnnn nnnnnnnnug ccacuggccn 300
nnnnnnnnnn nnnnnnnnnn nnnnnnnngg caannnnnnn nnnnnnnnnn nnnnnnnnnn 360
nnnnnnnngg cugggaaggc anggauugcg cugagacnnn nnnnnnnnnn nnnnnnnnnn 420
nnnnnnnnnn nnnnnnnnnn nnnnnnnnnn nnnnnnnnnn nnnccgcnng agccaggaga 480
ccugccauca cugaguugac cggac 505

<210> SEQ ID NO 262
<211> LENGTH: 505
<212> TYPE: RNA
<213> ORGANISM: Mycobacterium leprae
<220> FEATURE:
<221> NAME/KEY: misc_feature
<222> LOCATION: 23-469
<223> OTHER INFORMATION: n = g, a, c or u

<400> SEQUENCE: 262
ccacacggcg ccaguaucga gunngaugcu nnnnnnnnnn nnnnnnagcu cnnnnnnnnn 60
nnnnnnnagc aucgcnngag angggaacnc cggugannnn nnnnnnnnnn nnnnnnnnnn 120
nnnngaaucc gggacugunc ccgcagcggu aungcaggnn nnnnnnnnnn nnnnnnnnnn 180
nnnnnnnnnn nnnnnnnnnn nnnnnnaacg accgccgucu ggaannnnnn nnnnnnnnnn 240
nnnnnnnnnn nnnnnnnnnn nnnnnnnnnn nnnnnnnnnn nnnnnnnnnn gcacuggucu 300
uagannnnnn nnnnnnnnnn nnnnnnnnaa aannnnnnnn nnnnnnnnnn nnnnnnnnnn 360
nnnuccgaga cugggaagcn ngauggccau uagaagcacc uauccagugc gcgnnnnnnn 420
nnnnnnnnnn nnnnnnnnnn nnnnnnnnnn nnnnnnnnnn nnccugcnng aguccgaaga 480
ccugccggcu gugucgggcg cgccg 505

<210> SEQ ID NO 263
<211> LENGTH: 505
<212> TYPE: RNA
<213> ORGANISM: Mycobacterium tuberculosis
<220> FEATURE:
<221> NAME/KEY: misc_feature
<222> LOCATION: 23-469
<223> OTHER INFORMATION: n = g, a, c or u

<400> SEQUENCE: 263
cuucccguca ggcgaugacg aunnnnnnnn nnnnnnnnnn nnnnnnnnnn nnnnnnnnnn 60
nnnnnnnnnn nnnnnnnnnn gcaggaagnc cggugannnn nnnnnnnnnn nnnnnnnnnn 120
nnnngaaucc ggcgcggunc ccgccacugu canccgggnn nnnnnnnnnn nnnnnnnnnn 180
nnnnnnnnnn nnnnnnnnnn nnnnnnngag cgacccucgu aannnnnnnn nnnnnnnnnn 240
nnnnnnnnnn nnnnnnnnnn nnnnnnnnnn nnnnnnnnnn nnnnnnnnng ccacggccnn 300
nnnnnnnnnn nnnnnnnnnn nnnnnnnnac annnnnnnnn nnnnnnnnnn nnnnnnnnnn 360
nnnnnnnnng gcuggaaggc nngaggcaag caacgannnn nnnnnnnnnn nnnnnnnnnn 420
nnnnnnnnnn nnnnnnnnnn nnnnnnnnnn nnnnnnnnnn nnuccggnng agccaggaga 480
cucgcgucau cgcguccugc caccc 505

<210> SEQ ID NO 264
<211> LENGTH: 505
<212> TYPE: RNA
<213> ORGANISM: Mycobacterium tuberculosis
<220> FEATURE:
<221> NAME/KEY: misc_feature
<222> LOCATION: 1-469
<223> OTHER INFORMATION: n = g, a, c or u

<400> SEQUENCE: 264
nnnnnuugac cacgcagcug gucnugcugg cguccgaaag ggcgucggca ucgagcgggg 60
caacgaugcu ucgcnnngag angggaacnc uggugannn nnnnnnnnnn nnnnnnnnnn 120
nnnngaaucc gggacugunc ccgcagcggu aungcaggnn nnnnnnnnnn nnnnnnnnnn 180
nnnnnnnnnn nnnnnnnnnn nnnnnaacga ccgccgucuu ggaaguagac aannnnnnnn 240
nnnnnnnnnn nnnnnnnnnn nnnnnnnnnn nnnnnnnnnn nnnnnnnnnn gcacuggucn 300
nnnnnnnnnn nnnnnnnnnn nnnnnnnuca acnnnnnnnn nnnnnnnnnn nnnnnnnnnn 360
nnnnnnnnga cugggaagcn nngacggcca guaggagcac ccaccgggug cgagnnnnnn 420
nnnnnnnnnn nnnnnnnnnn nnnnnnnnnn nnnnnnnnnn nnccugcnng aguccgaaga 480
ccugccagcc gugccggacg cgccg 505

<210> SEQ ID NO 265
<211> LENGTH: 505
<212> TYPE: RNA
<213> ORGANISM: Pseudomonas aeruginosa
<220> FEATURE:
<221> NAME/KEY: misc_feature
<222> LOCATION: 24-469
<223> OTHER INFORMATION: n = g, a, c or u

<400> SEQUENCE: 265
agcugcgcgc cuugcgacag gugnccccnn nnnnnnnnnn nnnnnngcaa nnnnnnnnnn 60
nnnnnnnnng gggugnnaaa cagggaagnc uggugcguuc cnnnnnnngu cnnnnnnnng 120
gaaccaggcc agcgcugccc ccgcaacggu agngcgannn nnnnnnnnnn nnnnnnnnnn 180
nnnnnnnnnn nnnnnnnnnn nnnnnaucag acagccgcuc gaugannnnn nnnnnnnnnn 240
nnnnnnnnnn nnnnnnnnnn nnnnnnnnnn nnnnnnnnnn nnnnnnnnnn ccacugugcn 300
nnnnnnnnnn nnnnnnnnnn nnnnnnnnuc cgnnnnnnnn nnnnnnnnnn nnnnnnnnnn 360
nnnnnnnngc augggaaggn ncgcggcugg aagcguccag cgcuucgcnn nnnnnnnnnn 420
nnnnnnnnnn nnnnnnnnnn nnnnnnnnnn nnnnnnnnnn nnnucgcnng agcccggaga 480
ccggccugac gcacccacgg caucg 505

<210> SEQ ID NO 266
<211> LENGTH: 505
<212> TYPE: RNA
<213> ORGANISM: Pseudomonas aeruginosa
<220> FEATURE:
<221> NAME/KEY: misc_feature
<222> LOCATION: 23-469
<223> OTHER INFORMATION: n = g, a, c or u

<400> SEQUENCE: 266
gcauaauagc gcguucgucg gunngcccgg cccuuucgcg nnnnnnuuag nnnnncgcgg 60
ggccaacgag ggccgnnaag angggaacna cggagccgcg gucuunnnuu cgnnaagccc 120

-continued

```
gggccuagcc guggcugccc ccgcaacugu aungcagccu gnnnnnnnnn nnnnnnnnnn    180

nnnnnnnnnn nnnnnnnnnn nnnnnnnnua uucgcgccau ucnnnnnnnn nnnnnnnnnn    240

nnnnnnnnnn nnnnnnnnnn nnnnnnnnnn nnnnnnnnnn nnnnnnnnng ccacuggnnn    300

nnnnnnnnnn nnnnnnnnnn nnnnnnnauu annnnnnnnn nnnnnnnnnn nnnnnnnnnn    360

nnnnnnnnnn ccgggaaggc nnggcgcgaa gcggagguuc cucccccggg uggaacgcnn    420

nnnnnnnnnn nnnnnnnnnn nnnnnnnnnn nnnnnnnnnc gggcugcnng agccaggaga    480

ccugccgccg aaaccagucg cgagu                                          505
```

<210> SEQ ID NO 267
<211> LENGTH: 505
<212> TYPE: RNA
<213> ORGANISM: Pseudomonas aeruginosa
<220> FEATURE:
<221> NAME/KEY: misc_feature
<222> LOCATION: 24-469
<223> OTHER INFORMATION: n = g, a, c or u

<400> SEQUENCE: 267

```
ucccauccgg cccguuccag gugnccuccu gcnnnnnnnn nnnnncgccg cnnnnnnnnn     60

nnnnngcagg aggugnnaaa cngggaagnc cggugcguca cnnnnnnnuu cgnnnnnnng    120

ugaucagucc ggcgcugccc ccgcaacggu aangcgagnn nnnnnnnnnn nnnnnnnnnn    180

nnnnnnnnnn nnnnnnnnnn nnnnnnnncg aaauccucuu cagnnnnnnn nnnnnnnnnn    240

nnnnnnnnnn nnnnnnnnnn nnnnnnnnnn nnnnnnnnnn nnnnnnnnng ccacugugcn    300

nnnnnnnnnn nnnnnnnnnn nnnnnnnnuc cgnnnnnnnn nnnnnnnnnn nnnnnnnnnn    360

nnnnnnnngc augggaaggc nngaggauuu cacgaccnnn nnnnnnnnnn nnnnnnnnnn    420

nnnnnnnnnn nnnnnnnnnn nnnnnnnnnn nnnnnnnnnn nncucgcnna agcccggaga    480

ccggccugca acgcccuguu ggcac                                          505
```

<210> SEQ ID NO 268
<211> LENGTH: 505
<212> TYPE: RNA
<213> ORGANISM: Pseudomonas aeruginosa
<220> FEATURE:
<221> NAME/KEY: misc_feature
<222> LOCATION: 24-469
<223> OTHER INFORMATION: n = g, a, c or u

<400> SEQUENCE: 268

```
cguagccuug ccgguucgag guuncucgc cgnnnnnnnn nnnnnngcga nnnnnnnnnn     60

nnnnncggcg gggcunnaag angggaacng cggucgnnnn nnnnnnnnnn nnnnnnnnnn    120

nnnnnaugcc gcggcugccc ccgcaacugu ganacggnnn nnnnnnnnnn nnnnnnnnnn    180

nnnnnnnnnn nnnnnnnnnn nnnnnncgau cguuccccaa unnnnnnnnn nnnnnnnnnn    240

nnnnnnnnnn nnnnnnnnnn nnnnnnnnnn nnnnnnnnnn nnnnnnnnng ccacugcgnn    300

nnnnnnnnnn nnnnnnnnnn nnnnnnnnug annnnnnnnn nnnnnnnnnn nnnnnnnnnn    360

nnnnnnnnnc gcgggaaggc nnggggaacc ggcggagacg ccagannnnn nnnnnnnnnn    420

nnnnnnnnnn nnnnnnnnnn nnnnnnnnnn nnnnnnnnnn nnnccgunng agccaggaga    480

ccugccucgu cgaucccgug gcgcg                                          505
```

<210> SEQ ID NO 269
<211> LENGTH: 505
<212> TYPE: RNA
<213> ORGANISM: Pseudomonas putida
<220> FEATURE:

<221> NAME/KEY: misc_feature
<222> LOCATION: 23-469
<223> OTHER INFORMATION: n = g, a, c or u

<400> SEQUENCE: 269

```
gucuaccaug cgggccgccg gunnuuccnn nnnnnnnnnn nnnnnnacca cnnnnnnnnn     60

nnnnnnnnng gaacunnaac angggaaunc ccannnggcc ugnnnnncca auannnnnca    120

ggccnnaauc ggaacugccc ccgcaacugu agngugcnnn nnnnnnnnnn nnnnnnnnnn    180

nnnnnnnnnn nnnnnnnnnn nnnnnncgag ccugcuccau cgaunnnnnn nnnnnnnnnn    240

nnnnnnnnnn nnnnnnnnnn nnnnnnnnnn nnnnnnnnnn nnnnnnnnng ccacugggcn    300

nnnnnnnnnn nnnnnnnnnn nnnnnncugc cnnnnnnnnn nnnnnnnnnn nnnnnnnnnn    360

nnnnnnnngc ccgggaaggc ncggagccgg gccgugacnn nnnnnnnnnn nnnnnnnnnn    420

nnnnnnnnnn nnnnnnnnnn nnnnnnnnnn nnnnnnnnnn nnngcacnnc agucaggaga    480

ccugccggcc uacauucacc aaccg                                          505
```

<210> SEQ ID NO 270
<211> LENGTH: 505
<212> TYPE: RNA
<213> ORGANISM: Pseudomonas putida
<220> FEATURE:
<221> NAME/KEY: misc_feature
<222> LOCATION: 24-469
<223> OTHER INFORMATION: n = g, a, c or u

<400> SEQUENCE: 270

```
cagaugcgcg ccaguuucag gugncccugc gcnnnnnnnn nnnnncgccg cnnnnnnnnn     60

nnnnngcgca gggugnnaaa cngggaaanc cggugcgucg ugnnnnnuug ccnnnnnnca    120

cgacaagucc ggugcugccc ccgcaacggu aangcgagnn nnnnnnnnnn nnnnnnnnnn    180

nnnnnnnnnn nnnnnnnnnn nnnnnnnncg aacccuucga gaunnnnnnn nnnnnnnnnn    240

nnnnnnnnnn nnnnnnnnnn nnnnnnnnnn nnnnnnnnnn nnnnnnnnna ccacugugcn    300

nnnnnnnnnn nnnnnnnnnn nnnnnnnuca annnnnnnnn nnnnnnnnnn nnnnnnnnnn    360

nnnnnnnngc augggaaggu nngaagguuu caugcccnnn nnnnnnnnnn nnnnnnnnnn    420

nnnnnnnnnn nnnnnnnnnn nnnnnnnnnn nnnnnnnnnn nncucgcnna agcccggaga    480

ccggccugga gcuucacuug gcaac                                          505
```

<210> SEQ ID NO 271
<211> LENGTH: 505
<212> TYPE: RNA
<213> ORGANISM: Pseudomonas putida
<220> FEATURE:
<221> NAME/KEY: misc_feature
<222> LOCATION: 24-469
<223> OTHER INFORMATION: n = g, a, c or u

<400> SEQUENCE: 271

```
uccuuaugcc ucgcguucag gugnccccnn nnnnnnnnnn nnnnnnucag nnnnnnnnnn     60

nnnnnnnnng gggugnnaaa cngggaaanc cggugcgucc caggcccuuc agcnagggcc    120

ggacaaugcc ggugcugccc ccgcaacggu aangcgagnn nnnnnnnnnn nnnnnnnnnn    180

nnnnnnnnnn nnnnnnnnnn nnnnnnnnnu gaagcgucug unnnnnnnnn nnnnnnnnnn    240

nnnnnnnnnn nnnnnnnnnn nnnnnnnnnn nnnnnnnnnn nnnnnnnnna ccacugugcc    300

nnnnnnnnnn nnnnnnnnnn nnnnucguag uacnnnnnnn nnnnnnnnnn nnnnnnnnnn    360

nnnnnnnggc augggaaggu nngacgcguu ccaggagccc agcucuucnn nnnnnnnnnn    420
```

nnnnnnnnnn nnnnnnnnnn nnnnnnnnnn nnnnnnnnnn nncucgcnna agcccggaga 480
ccggccuggc guucaugaac acccc 505

<210> SEQ ID NO 272
<211> LENGTH: 505
<212> TYPE: RNA
<213> ORGANISM: Pseudomonas putida
<220> FEATURE:
<221> NAME/KEY: misc_feature
<222> LOCATION: 24-469
<223> OTHER INFORMATION: n = g, a, c or u

<400> SEQUENCE: 272
cguagccuug ccacuucgag guuncuucgg cnnnnnnnnn nnnnnncugn nnnnnnnnnn 60
nnnnnngccg aagcunnaag acgggaacng cgguacnnnn nnnnnnnnnn nnnnnnnnnn 120
nnnnnaagcc gcggcugccc ccgcaacugu aangcaccgn nnnnnnnnnn nnnnnnnnnn 180
nnnnnnnnnn nnnnnnnnnn nnnnnacaac ggaucgacac annnnnnnnn nnnnnnnnnn 240
nnnnnnnnnn nnnnnnnnnn nnnnnnnnnn nnnnnnnnnn nnnnnnnnng ccacugcgcn 300
nnnnnnnnnn nnnnnnnnnn nnnnnnncaa cnnnnnnnnn nnnnnnnnnn nnnnnnnnnn 360
nnnnnnnngc gcgggaaggc nngucauccc gccagcccga acggggacau ggaannnnnn 420
nnnnnnnnnn nnnnnnnnnn nnnnnnnnnn nnnnnnnnnn ncggugcnna agccaggaga 480
ccugccucgu cacguuuucg acuuu 505

<210> SEQ ID NO 273
<211> LENGTH: 505
<212> TYPE: RNA
<213> ORGANISM: Ralstonia solanacearum
<220> FEATURE:
<221> NAME/KEY: misc_feature
<222> LOCATION: 32-469
<223> OTHER INFORMATION: n = g, a, c or u

<400> SEQUENCE: 273
guuacacucg ccgcguccug gugcccgcag annnnnnnnn nnnnnngccg annnnnnnnn 60
nnnnnnucug caguunnaaa cngggaagnc agggagcggc cgccnnncca aacnnnnngg 120
ugcgccaacc ugcgcugccc ccgcaacggu aagcgaacgc cgucgaaggc cgcgcuaccu 180
cuggccagaa gagggcgcgg cgucgcgcag guccguccac aunnnnnnnn nnnnnnnnnn 240
nnnnnnnnnn nnnnnnnnnn nnnnnnnnnn nnnnnnnnnn nnnnnnnnng ccacuguucn 300
nnnnnnnnnn nnnnnnnnnn nnnnnnncgc gnnnnnnnnn nnnnnnnnnn nnnnnnnnnn 360
nnnnnnnnga acgggaaggc nnggccggac ccgnnnnnnn nnnnnnnnnn nnnnnnnnnn 420
nnnnnnnnnn nnnnnnnnnn nnnnnnnnnn nnnnnnnnnn nguucgcnnc agcccggaua 480
ccggccagga caguggguuu cagag 505

<210> SEQ ID NO 274
<211> LENGTH: 505
<212> TYPE: RNA
<213> ORGANISM: Sinorhizobium meliloti
<220> FEATURE:
<221> NAME/KEY: misc_feature
<222> LOCATION: 24-469
<223> OTHER INFORMATION: n = g, a, c or u

<400> SEQUENCE: 274
cuuagaugag gacacucaag gugnccgccu cnnnnnnnnn nnnnnngaag nnnnnnnnnn 60
nnnnggaggg cggagnnaau ungggaagnc cggucannnn nnnnnnnnnn nnnnnnnnnn 120
nnnnaauccc ggcgcugccc ccgcaacggu ggnuggagcn nnnnnnnnnn nnnnnnnnnn 180
nnnnnnnnnn nnnnnnnnnn nnnnngaaca gccacggcag aagnnnnnnn nnnnnnnnnn 240
nnnnnnnnnn nnnnnnnnnn nnnnnnnnnn nnnnnnnnnn nnnnnnnnng ccacuggacn 300
nnnnnnnnnn nnnnnnnnnn nnnnnnnacc gcnnnnnnnn nnnnnnnnnn nnnnnnnnnn 360
nnnnnnnngu ccgggaaggc nngccgggcn nnnnaggucc cuugcggacg nnnnnnnnnn 420
nnnnnnnnnn nnnnnnnnnn nnnnnnnnnn nnnnnnnnnn ngcuccanng agcccggaaa 480
ccagccuuga agcagaaaua gaccg 505

<210> SEQ ID NO 275
<211> LENGTH: 505
<212> TYPE: RNA
<213> ORGANISM: Sinorhizobium meliloti
<220> FEATURE:
<221> NAME/KEY: misc_feature
<222> LOCATION: 24-468
<223> OTHER INFORMATION: n = g, a, c or u

<400> SEQUENCE: 275
uggccauaug ccgccgucag gugncccgcn nnnnnnnnnn nnnnnngaaa unnnnnnnnn 60
nnnnnnnngc gggggnnaau cngggaagnc cggugcnnnn nnnnnnnnnn nnnnnnnnnn 120
nnnnaguucc ggcacgugnc ccaacgcugu gaagggnnnn nnnnnnnnnn nnnnnnnnnn 180
nnnnnnnnnn nnnnnnnnnn nnnnnngacg uucucgccaa aaagggcucu gaaucuuuuc 240
agagcuuunn nnnnnnnnnn nnnnnnnnnn nnnnnnnnnn nnnnnnnnng ccacugaaua 300
nnnnnnnnnn nnnnnnnnnn nnnnnnuuga agcnnnnnnn nnnnnnnnnn nnnnnnnnnn 360
nnnnnnnuau ucgggaaggc nnggcgcgaa cggauganna nnnnnnnnnn nnnnnnnnnn 420
nnnnnnnnnn nnnnnnnnnn nnnnnnnnnn nnnnnnnnnn nnnnuccnga agucagaaga 480
ccggccuggc gagauagacc ggccc 505

<210> SEQ ID NO 276
<211> LENGTH: 505
<212> TYPE: RNA
<213> ORGANISM: Sinorhizobium meliloti
<220> FEATURE:
<221> NAME/KEY: misc_feature
<222> LOCATION: 23-469
<223> OTHER INFORMATION: n = g, a, c or u

<400> SEQUENCE: 276
uaauuaacgc aguauggaug gunnucucuc gugccnnnnn nnnnnngagg unnnnnnnnn 60
nnggggcgag ggagunnaaa ungggaaung cgaaggggcg gacccnnacg ccnnnnnggg 120
cgcccuuauc gcagccgacc ccgcgacugu agaacggunn nnnnnnnnnn nnnnnnnnnn 180
nnnnnnnnnn nnnnnnnnnn nnnnnnncag gguucgccau cgggcauuuc gccggauuuc 240
aacgcgcugc augggcaguc ucgugaaguu uggcggcaug ucggaaaang ccacuggcgu 300
ggcauugcga ucagccgggc aggacgccuc uucuucuacg aaucguccgc cuuucgcgau 360
gccgcaaacg ccgggaaggc gaggcgagcc cguucggucu uuugccgcau cguuuuucgg 420
gccgagccgg uccggcgaac gugcggccau gaggaucgug acgccgunng agccaggaga 480
ccugccaucc gucagggcau uccgc 505

<210> SEQ ID NO 277
<211> LENGTH: 505
<212> TYPE: RNA
<213> ORGANISM: Sinorhizobium meliloti
<220> FEATURE:

<221> NAME/KEY: misc_feature
<222> LOCATION: 23-468
<223> OTHER INFORMATION: n = g, a, c or u

<400> SEQUENCE: 277
cacauuaacu gggaccgacg gunnuccccu acccnnnnnn nnnnnnguga nnnnnnnnnn 60
nngguggagg ggauunnaau angggaacna cggugcggac gacccnnnaa gannnnnngg 120
gaccaaaacc guggcugccc ccgcaacugu aagcggaunn nnnnnnnnnn nnnnnnnnnn 180
nnnnnnnnnn nnnnnnnnnn nnnnnnncgu cguucauccu uguggcgcca aggcgccann 240
nnnnnnnnnn nnnnnnnnnn nnnnnnnnnn nnnnnnnnnn nnnnnnnnng ccacugcgcn 300
nnnnnnnnnn nnnnnnnnnn nnnnnnngcg uunnnnnnnn nnnnnnnnnn nnnnnnnnnn 360
nnnnnnnngc gcgggaaggc nagaugagcg acucunnnnn nnnnnnnnnn nnnnnnnnnn 420
nnnnnnnnnn nnnnnnnnnn nnnnnnnnnn nnnnnnnnnn nnguccgnug agccaggaga 480
ccugccguca aaucgaucca acguc 505

<210> SEQ ID NO 278
<211> LENGTH: 505
<212> TYPE: RNA
<213> ORGANISM: Sinorhizobium meliloti
<220> FEATURE:
<221> NAME/KEY: misc_feature
<222> LOCATION: 23-469
<223> OTHER INFORMATION: n = g, a, c or u

<400> SEQUENCE: 278
gcauaccaga ucaugugaug gunnuccgcc nnnnnnnnnn nncgacugaa gaacnnnnnn 60
nnnnnnnggc ggaugnnaaa angggaacna cggugaggac gacccnnnau cannnnnngg 120
ggcuaaaacc guggcugccc ccgcaacugu gangcggnnn nnnnnnnnnn nnnnnnnnnn 180
nnnnnnnnnn nnnnnnnnnn nnnnnncgag caaaguccaa ggaunnnnnn nnnnnnnnnn 240
nnnnnnnnnn nnnnnnnnnn nnnnnnnnnn nnnnnnnnnn nnnnnnnnng ccauuggccn 300
nnnnnnnnnn nnnnnnnnnn nnnnnnauga aucnnnnnnn nnnnnnnnnn nnnnnnnnnn 360
nnnnnnnngg cugauaaggc nnggacaaag cuacgacnnn nnnnnnnnnn nnnnnnnnnn 420
nnnnnnnnnn nnnnnnnnnn nnnnnnnnnn nnnnnnnnnn nnnccgcnna agccaggaga 480
ccugccauca ccuugggcga cacgc 505

<210> SEQ ID NO 279
<211> LENGTH: 505
<212> TYPE: RNA
<213> ORGANISM: Streptomyces coelicolor
<220> FEATURE:
<221> NAME/KEY: misc_feature
<222> LOCATION: 24-469
<223> OTHER INFORMATION: n = g, a, c or u

<400> SEQUENCE: 279
uaggcuggcc cgugcagcug guuncgcccc guccnnnnnn nnnnnngcca nnnnnnnnnn 60
nnggcgggau gcgucgcaag angggaacnc cgguggnnnn nnnnnnnnnn nnnnnnnnnn 120
nnnngaaucc gggacugcnc ccgcagcggu gangcgggnn nnnnnnnnnn nnnnnnnnnn 180
nnnnnnnnnn nnnnnnnnnn nnnnnaacga ccgccgucau annnnnnnnn nnnnnnnnnn 240
nnnnnnnnnn nnnnnnnnnn nnnnnnnnnn nnnnnnnnnn nnnnnnnnnc gcacugggcc 300
cgnnnnnnnn nnnnnnnnnn nnnnnnnacg uacnnnnnnn nnnnnnnnnn nnnnnnnnnn 360
nnnnncgggc ccgggaagcg nnacggccag uaggugucccu ccggacagga gggugggnnn 420
nnnnnnnnnn nnnnnnnnnn nnnnnnnnnn nnnnnnnnnn nncccgcnng aguccgaaga 480
ccugccaccu gcccgcgcgc ggacc 505

<210> SEQ ID NO 280
<211> LENGTH: 505
<212> TYPE: RNA
<213> ORGANISM: Streptomyces coelicolor
<220> FEATURE:
<221> NAME/KEY: misc_feature
<222> LOCATION: 23-469
<223> OTHER INFORMATION: n = g, a, c or u

<400> SEQUENCE: 280
uacgcugaug cccgcaguug gunnucgcgc cuccuguccn nnnnngauca nnnnnnnggu 60
cucggcggcg cgacgcnaag angggaacnc cgguggnnnn nnnnnnnnnn nnnnnnnnnn 120
nnnngaaucc gggacugunc ccgcagcggu gangugggnn nnnnnnnnnn nnnnnnnnnn 180
nnnnnnnnnn nnnnnnnnnn nnnnnaacga aagccgucaa cannnnnnnn nnnnnnnnnn 240
nnnnnnnnnn nnnnnnnnnn nnnnnnnnnn nnnnnnnnnn nnnnnnnnnn gcacugggcc 300
ccagnnnnnn nnnnnnnnnn nnnnnnnaug agnnnnnnnn nnnnnnnnnn nnnnnnnnnn 360
nnnuuggagc ccgggaagcn nngacggccg guaggugccc gccggugauc cguguccccg 420
gugagcgcgn nnnnnnnnnn nnnnnnnnnn nnnnnnnnnn nncccacnng aguccgaaga 480
ccugccacug cgcccguacg cgaug 505

<210> SEQ ID NO 281
<211> LENGTH: 505
<212> TYPE: RNA
<213> ORGANISM: Streptomyces coelicolor
<220> FEATURE:
<221> NAME/KEY: misc_feature
<222> LOCATION: 23-469
<223> OTHER INFORMATION: n = g, a, c or u

<400> SEQUENCE: 281
gcagaccgua guaucagcgg gunncaucgn nnnnnnnnnn nnnnnnccgn nnnnnnnnnn 60
nnnnnnnncg acgggnnaga cnaggaagnc cggugunnnn nnnnnnnnnn nnnnnnnnnn 120
nnnngaaucc ggcacggucc cngccacugu ganccgggnn nnnnnnnnnn nnnnnnnnnn 180
nnnnnnnnnn nnnnnnnnnn nnnnngagug cacccuucga cacnnnnnnn nnnnnnnnnn 240
nnnnnnnnnn nnnnnnnnnn nnnnnnnnnn nnnnnnnnnn nnnnnnnnng ccacugcgcn 300
nnnnnnnnnn nnnnnnnnnn nnnnnnnngc cnnnnnnnnn nnnnnnnnnn nnnnnnnnnn 360
nnnnnnnngc gcgggaaggc cagggaggag cgucgannnn nnnnnnnnnn nnnnnnnnnn 420
nnnnnnnnnn nnnnnnnnnn nnnnnnnnnn nnnnnnnnnn nnuccggnng agucaggaca 480
cuggccuguc gcgggcccgu uccga 505

<210> SEQ ID NO 282
<211> LENGTH: 505
<212> TYPE: RNA
<213> ORGANISM: Streptomyces coelicolor
<220> FEATURE:
<221> NAME/KEY: misc_feature
<222> LOCATION: 23-468
<223> OTHER INFORMATION: n = g, a, c or u

<400> SEQUENCE: 282
uaugcucaug cucgcugucg ccnnnnnnnn nnnnnnnnnn nnnnnnnnnn nnnnnnnnnn 60
nnnnnnnnnn nnnnnnngca gngggaaunc cggugcnnnn nnnnnnnnnn nnnnnnnnnn 120
nnnngaaucc ggaacugunc ccgcaacggu gunacnnnnn nnnnnnnnnn nnnnnnnnnn 180
nnnnnnnnnn nnnnnnnnnn nnnnnnnnnn uugcgugcau cnnnnnnnnn nnnnnnnnnn 240
nnnnnnnnnn nnnnnnnnnn nnnnnnnnnn nnnnnnnnnn nnnnnnnnnn cguacgunnn 300
nnnnnnnnnn nnnnnnnnnn nnnnnncuuc gcnnnnnnnn nnnnnnnnnn nnnnnnnnnn 360
nnnnnnnnnn nnacgugcgn ncgcacgccu nnnnnnnnnn nnnnnnnnnn nnnnnnnnnn 420
nnnnnnnnnn nnnnnnnnnn nnnnnnnnnn nnnnnnnnnn nnnnnguncc aguccgagga 480
ccugccgaca gugcgcccgg ccgcc 505

<210> SEQ ID NO 283
<211> LENGTH: 505
<212> TYPE: RNA
<213> ORGANISM: Streptomyces coelicolor
<220> FEATURE:
<221> NAME/KEY: misc_feature
<222> LOCATION: 23-469
<223> OTHER INFORMATION: n = g, a, c or u

<400> SEQUENCE: 283
acuacugucg ccacgccuug gunnnnnnnn nnnnnnnnnn nnnnnnnnnn nnnnnnnnnn 60
nnnnnnnnnn nnnnnnngaa cngggaaauc cggugunnnn nnnnnnnnnn nnnnnnnnnn 120
nnnngaugcc ggugcggccc ucgccacugu ganaucgggn nnnnnnnnnn nnnnnnnnnn 180
nnnnnnnnnn nnnnnnnnnn nnnnnnnaag uccggcuccg gcccugacgg gcannnnnnn 240
nnnnnnnnnn nnnnnnnnnn nnnnnnnnnn nnnnnnnnnn nnnnnnnnng ccacuggauc 300
gnnnnnnnnn nnnnnnnnnn nnnnnnncuu gnnnnnnnnn nnnnnnnnnn nnnnnnnnnn 360
nnnnnncggu ccgggaaggc nnggagcacg ggcgguggua nnnnnnnnnn nnnnnnnnnn 420
nnnnnnnnnn nnnnnnnnnn nnnnnnnnnn nnnnnnnnnn nncccgunna agccaggaga 480
ccggccaagg cgcgucgucc aucca 505

<210> SEQ ID NO 284
<211> LENGTH: 505
<212> TYPE: RNA
<213> ORGANISM: Shigella flexneri
<220> FEATURE:
<221> NAME/KEY: misc_feature
<222> LOCATION: 24-469
<223> OTHER INFORMATION: n = g, a, c or u

<400> SEQUENCE: 284
ccuguagcau ccacuugccg gucncunnnn nnnnnnnnnn nnnnnngugn nnnnnnnnnn 60
nnnnnnnnnn naguunnaau angggaaunc cagugcnnnn nnnnnnnnnn nnnnnnnnnn 120
nnnngaaucu agagcuganc gcgcagcggu aanggannnn nnnnnnnnnn nnnnnnnnnn 180
nnnnnnnnnn nnnnnnnnnn nnnnnaaggu gcgaugauug cguuaugcgn nnnnnnnnnn 240
nnnnnnnnnn nnnnnnnnnn nnnnnnnnnn nnnnnnnnnn nnnnnnnnng acacugccnn 300
nnnnnnnnnn nnnnnnnnnn nnnnnnnauc cnnnnnnnnn nnnnnnnnnn nnnnnnnnnn 360
nnnnnnnnng gugggaaguc nnaucaucuc uuaguaucuu agauaccccn nnnnnnnnnn 420
nnnnnnnnnn nnnnnnnnnn nnnnnnnnnn nnnnnnnnnn nnnnuccnna agcccgaaga 480
ccugccggcc aacgucgcau cuggu 505

<210> SEQ ID NO 285
<211> LENGTH: 505
<212> TYPE: RNA
<213> ORGANISM: Shewanella oneidensis
<220> FEATURE:

<221> NAME/KEY: misc_feature
<222> LOCATION: 24-469
<223> OTHER INFORMATION: n = g, a, c or u

<400> SEQUENCE: 285
uuuugaguca accuucugug gugncuugcg augnnnnnnn nnnnnnauag nnnnnnnnnn 60
nnnncgucgc gagaunnaau cngggaagnc cagugannnn nnnnnnnnnn nnnnnnnnnn 120
nnnnaauucu ggcacugccc ccgcaacggu aaaaggunnn nnnnnnnnnn nnnnnnnnnn 180
nnnnnnnnnn nnnnnnnnnn nngagagacg gccgcauunn nnnnnnnnnn nnnnnnnnnn 240
nnnnnnnnnn nnnnnnnnnn nnnnnnnnnn nnnnnnnnnn nnnnnnnncg auaggugquc 300 nnnnnnnnnn nnnnnnnnnn nnnnnnnacg aunnnnnnnn nnnnnnnnnn nnnnnnnnnn 360
nnnnnnngaa cccguaaauc gcagugugca aaggucaguu ucgcguuuau cucuagugag 420
auggauuaua nnnnnnnnnn nnnnnnnnnn nnnnnnnnnn nnngccunna aguccggaga 480
ccggcccuaa agguguuuuu gagau 505

<210> SEQ ID NO 286
<211> LENGTH: 505
<212> TYPE: RNA
<213> ORGANISM: Shewanella oneidensis
<220> FEATURE:
<221> NAME/KEY: misc_feature
<222> LOCATION: 24-469
<223> OTHER INFORMATION: n = g, a, c or u

<400> SEQUENCE: 286
accuaugcua uugcauuaag gucnauaaac gccggannnn nnnnnnnnnn nnnnnnnnnn 60
ucaacccaaa uaunnnnaau angggaaunc ggggcgcugn nnnnnnnccc gunnnnnnnn 120
ncagccagcc cgaacuguac ccgcaacugu ganguagnnn nnnnnnnnnn nnnnnnnnnn 180
nnnnnnnnnn nnnnnnnnnn nuuaaaagaa gcgccuagau unnnnnnnnn nnnnnnnnnn 240
nnnnnnnnnn nnnnnnnnnn nnnnnnnnnn nnnnnnnnnn nnnnnnnnnn cuagauucua 300
gauucuagnn nnnnnnnnnn nnnnnnnauu nnnnnnnnnn nnnnnnnnnn nnnnnnnnnc 360
uagauucuag auucuaaagn nccuagcacc uucuuuunnn nnnnnnnnnn nnnnnnnnnn 420
nnnnnnnnnn nnnnnnnnnn nnnnnnnnnn nnnnnnnnnn nnncuacnna agucaggaga 480
ccugccuauu gcuguuuucg cugcg 505

<210> SEQ ID NO 287
<211> LENGTH: 505
<212> TYPE: RNA
<213> ORGANISM: Salmonella typhimurium
<220> FEATURE:
<221> NAME/KEY: misc_feature
<222> LOCATION: 30-468
<223> OTHER INFORMATION: n = g, a, c or u

<400> SEQUENCE: 287
gccauaacgu aaaccaacag guuugccacn nnnnnnnnnn nnnnnnauuu nnnnnnnnnn 60
nnnnnnnngu ggunnnnnnn angggaagng gggugannnn nnnnnnnnnn nnnnnnnnnn 120
nnnnaaaucc cccgcagccc ccgcugcugu gaugcnnnnn nnnnnnnnnn nnnnnnnnnn 180
nnnnnnnnnn nnnnnnnnnn nnnnnnugac gaccccguaa agannnnnnn nnnnnnnnnn 240
nnnnnnnnnn nnnnnnnnnn nnnnnnnnnn nnnnnnnnnn nnnnnnnnnn ccacugaucn 300
nnnnnnnnnn nnnnnnnnnn nnnnnnngca annnnnnnnn nnnnnnnnnn nnnnnnnnnn 360
nnnnnnnnga uugggaaggn nnacgggcga ggaggacnnn nnnnnnnnnn nnnnnnnnnn 420
nnnnnnnnnn nnnnnnnnnn nnnnnnnnnn nnnnnnnnnn nnnnngcnua agccagaaga 480
ccugccuguc ggugauaacc aacaa 505

<210> SEQ ID NO 288
<211> LENGTH: 505
<212> TYPE: RNA
<213> ORGANISM: Salmonella typhimurium
<220> FEATURE:
<221> NAME/KEY: misc_feature
<222> LOCATION: 24-469
<223> OTHER INFORMATION: n = g, a, c or u

<400> SEQUENCE: 288
acgguagcau ccgugggccg gucncunnnn nnnnnnnnnn nnnnnnngug nnnnnnnnnn 60
nnnnnnnnnn naguunnaau angggaaunc caguganmnn nnnnnnnnnn nnnnnnnnnn 120
nnnnaaaucu ggagcuganc gcgcagcggu aanggannnn nnnnnnnnnn nnnnnnnnnn 180
nnnnnnnnnn nnnnnnnnnn nnnnnnaagg ugagaugaga gcguaagcan nnnnnnnnnn 240
nnnnnnnnnn nnnnnnnnnn nnnnnnnnnn nnnnnnnnnn nnnnnnnnng acacugccnn 300
nnnnnnnnnn nnnnnnnnnn nnnnnnnnuc cnnnnnnnnn nnnnnnnnnn nnnnnnnnnn 360
nnnnnnnnng gcgggaaguc naucauuucu gcuauccagc caacggauaa cccnnnnnnn 420
nnnnnnnnnn nnnnnnnnnn nnnnnnnnnn nnnnnnnnnn nnnnuccnna agcccgaaga 480
ccugccggcu aacgucgcau cuggu 505

<210> SEQ ID NO 289
<211> LENGTH: 505
<212> TYPE: RNA
<213> ORGANISM: Thermotoga maritima
<220> FEATURE:
<221> NAME/KEY: misc_feature
<222> LOCATION: 23-469
<223> OTHER INFORMATION: n = g, a, c or u

<400> SEQUENCE: 289
gaagccuccc ucaccgugcg gunnacccnn nnnnnnnnnn nnnnnnuucg nnnnnnnnnn 60
nnnnnnnnng gguucnnaaa gngggaagnc cgguganmnn nnnnnnnnnn nnnnnnnnnn 120
nnnnaaaucc ggcgcggggn ccgccaccgu ganccgggnn nnnnnnnnnn nnnnnnnnnn 180
nnnnnnnnnn nnnnnnnnnn nnnnnngacg aaacccgcag aacnnnnnnn nnnnnnnnnn 240
nnnnnnnnnn nnnnnnnnnn nnnnnnnnnn nnnnnnnnnn nnnnnnnnng ccacuggggn 300
nnnnnnnnnn nnnnnnnnnn nnnnnncgau cannnnnnnn nnnnnnnnnn nnnnnnnnnn 360
nnnnnnnncc cugggaaggc nngcggggag uaggaugann nnnnnnnnnn nnnnnnnnnn 420
nnnnnnnnnn nnnnnnnnnn nnnnnnnnnn nnnnnnnnnn nnuccggnna agccgggaaa 480
cccgcccgcg gugaagggga accac 505

<210> SEQ ID NO 290
<211> LENGTH: 505
<212> TYPE: RNA
<213> ORGANISM: Thermoanaerobacter tengcongensis
<220> FEATURE:
<221> NAME/KEY: misc_feature
<222> LOCATION: 23-469
<223> OTHER INFORMATION: n = g, a, c or u

<400> SEQUENCE: 290
uugaauauua aagccuuaug gunncccnnn nnnnnnnnnn nnnnnaugau nnnnnnnnnn 60
nnnnnnnnnn ggguunnaaa angggaagac ggguganmnn nnnnnnnnnn nnnnnnnnnn 120

-continued

```
nnnngaaucc cgcgcagccc ccgcuacugu gangggannn nnnnnnnnnn nnnnnnnnnn    180

nnnnnnnnnn nnnnnnnnnn nnnnnnggac gaagcccuag uaannnnnnn nnnnnnnnnn    240

nnnnnnnnnn nnnnnnnnnn nnnnnnnnnn nnnnnnnnnn nnnnnnnnng ccacuguccg    300

gcacucaacu gagcgcgnnn uuaguaagga gaaaagaggg agagaaaunn ugcguucagu    360

ugagugccgg gugggaaggc nnagggugga ggaugagnnn nnnnnnnnnn nnnnnnnnnn    420

nnnnnnnnnn nnnnnnnnnn nnnnnnnnnn nnnnnnnnnn nnnucccnng agccaggaga    480

ccugccauaa gguuuuagaa guucg                                          505


<210> SEQ ID NO 291
<211> LENGTH: 505
<212> TYPE: RNA
<213> ORGANISM: Thermoanaerobacter tengcongensis
<220> FEATURE:
<221> NAME/KEY: misc_feature
<222> LOCATION: 23-469
<223> OTHER INFORMATION: n = g, a, c or u

<400> SEQUENCE: 291

ugaauauaaa aagccuuaug gunncccnnn nnnnnnnnnn nnnnngugau nnnnnnnnnn     60

nnnnnnnnnn ggguunnaaa angggaagac ggguganmnn nnnnnnnnnn nnnnnnnnnn    120

nnnngaaucc cgcgcagccc ccgcuacugu gangggannn nnnnnnnnnn nnnnnnnnnn    180

nnnnnnnnnn nnnnnnnnnn nnnnnnggac gaagcccuag uaannnnnnn nnnnnnnnnn    240

nnnnnnnnnn nnnnnnnnnn nnnnnnnnnn nnnnnnnnnn nnnnnnnnng ccacuguccg    300

gcacucaacu gagcgcgnnn uuaguaagga gaaaagaggg agagaaaunn ugcguucagu    360

ugagugccgg augggaaggc nnagggugga ggaugagnnn nnnnnnnnnn nnnnnnnnnn    420

nnnnnnnnnn nnnnnnnnnn nnnnnnnnnn nnnnnnnnnn nnnucccnng agccaggaga    480

ccugccauaa gguuuuuaaa aguuc                                          505


<210> SEQ ID NO 292
<211> LENGTH: 505
<212> TYPE: RNA
<213> ORGANISM: Vibrio cholerae
<220> FEATURE:
<221> NAME/KEY: misc_feature
<222> LOCATION: 23-469
<223> OTHER INFORMATION: n = g, a, c or u

<400> SEQUENCE: 292

auacuaucag cgccaagcug gunngcuauu uagaugccnn nnnnnnugga unnnnnnnnn     60

ggcuaaaaau ggcugnnaaa angggaaunc cggugunnnn nnnnnnnnnn nnnnnnnnnn    120

nnnnaacucc ggaacuganc gcgcagcggu aangagagnn nnnnnnnnnn nnnnnnnnnn    180

nnnnnnnnnn nnnnnnnnnn nnnnnnnaac gaacgcucaa acnnnnnnnn nnnnnnnnnn    240

nnnnnnnnnn nnnnnnnnnn nnnnnnnnnn nnnnnnnnnn nnnnnnnnng acacugcunn    300

nnnnnnnnnn nnnnnnnnnn nnnnnnnuuu cgnnnnnnnn nnnnnnnnnn nnnnnnnnnn    360

nnnnnnnnna gugggaaguc nngagccagu aggccaacag ugnnnnnnnn nnnnnnnnnn    420

nnnnnnnnnn nnnnnnnnnn nnnnnnnnnn nnnnnnnnnn nncucucnna aguccgaaga    480

ccugccagca acugaguuau gcagu                                          505


<210> SEQ ID NO 293
<211> LENGTH: 505
<212> TYPE: RNA
<213> ORGANISM: Vibrio vulnificus
<220> FEATURE:
```

```
<221> NAME/KEY: misc_feature
<222> LOCATION: 23-468
<223> OTHER INFORMATION: n = g, a, c or u

<400> SEQUENCE: 293

auaguaugcg cuucaagcug gunngcuauc ugnnnnnnnn nnnnngaagu annnnnnnnn      60

nnnnnuagau ggcugnnaaa angggaaunc cggugunnnn nnnnnnnnnn nnnnnnnnnn     120

nnnngaaucc ggaacuganc gcgcagcggu aauagagnnn nnnnnnnnnn nnnnnnnnnn     180

nnnnnnnnnn nnnnnnnnnn nnnnnnnaac gaaagcuuaa ucannnnnnn nnnnnnnnnn     240

nnnnnnnnnn nnnnnnnnnn nnnnnnnnnn nnnnnnnnnn nnnnnnnnng acacugcacg     300

aunnnnnnnn nnnnnnnnnn nnnnnnngga nnnnnnnnnn nnnnnnnnnn nnnnnnnnnn     360

nnnnnaucgu gugggaaguc nnaggcaagu agguuaacag nnnnnnnnnn nnnnnnnnnn     420

nnnnnnnnnn nnnnnnnnnn nnnnnnnnnn nnnnnnnnnn nnncucunug aguccgaaua     480

ccugccagca acugagcaaa cacug                                           505


<210> SEQ ID NO 294
<211> LENGTH: 505
<212> TYPE: RNA
<213> ORGANISM: Xanthomonas campestris
<220> FEATURE:
<221> NAME/KEY: misc_feature
<222> LOCATION: 24-469
<223> OTHER INFORMATION: n = g, a, c or u

<400> SEQUENCE: 294

cuaccaugcg cgccccugag gugnacugcc ggnnnnnnnn nnnnnnaauu nnnnnnnnnn      60

nnnnnccggu gguuunnaaa cngggaaunc cggugcgcgc aucgcnnncu ugnnngcgag     120

acgcaagucc ggagcugccc ccgcaacggu ggngcgagnn nnnnnnnnnn nnnnnnnnnn     180

nnnnnnnnnn nnnnnnnnnn nnnnnnguca ggugccgcaa cagnnnnnnn nnnnnnnnnn     240

nnnnnnnnnn nnnnnnnnnn nnnnnnnnnn nnnnnnnnnn nnnnnnnnng ccacugugcn     300

nnnnnnnnnn nnnnnnnnnn nnnnnnnaca cnnnnnnnnn nnnnnnnnnn nnnnnnnnnn     360

nnnnnnnngc augggaaggc nngcgguacc ggaagcgcag gcuuccannn nnnnnnnnnn     420

nnnnnnnnnn nnnnnnnnnn nnnnnnnnnn nnnnnnnnnn nncucgcnng agcccggaga     480

ccggccugag ggauugaccc ggcac                                           505


<210> SEQ ID NO 295
<211> LENGTH: 505
<212> TYPE: RNA
<213> ORGANISM: Xanthomonas citri
<220> FEATURE:
<221> NAME/KEY: misc_feature
<222> LOCATION: 24-469
<223> OTHER INFORMATION: n = g, a, c or u

<400> SEQUENCE: 295

cuaccaugcg cgccccugag gugnacugcc ggnnnnnnnn nnnnnnuugg nnnnnnnnnn      60

nnnnnccggu gguuunnaaa cngggaaunc cggugcgcgg aucgcnnncu ugnnngcgag     120

cugcaauucc ggagcugccc ccgcaacggu ggngcgagnn nnnnnnnnnn nnnnnnnnnn     180

nnnnnnnnnn nnnnnnnnnn nnnnnnguca gaugccgcac uacnnnnnnn nnnnnnnnnn     240

nnnnnnnnnn nnnnnnnnnn nnnnnnnnnn nnnnnnnnnn nnnnnnnnng ccacugugcn     300

nnnnnnnnnn nnnnnnnnnn nnnnnnnagu cnnnnnnnnn nnnnnnnnnn nnnnnnnnnn     360

nnnnnnnngc augggaaggc nngcggcauc ggaagcgcca gcuuccannn nnnnnnnnnn     420
```

nnnnnnnnnn nnnnnnnnnn nnnnnnnnnn nnnnnnnnnn nncucgcnna agcccggaga 480
ccggccugag ggauugaccc ggcac 505

<210> SEQ ID NO 296
<211> LENGTH: 505
<212> TYPE: RNA
<213> ORGANISM: Yersinia pestis
<220> FEATURE:
<221> NAME/KEY: misc_feature
<222> LOCATION: 39-469
<223> OTHER INFORMATION: n = g, a, c or u

<400> SEQUENCE: 296
uacuugaucg uagcauugug guccggccuc augcuguunn nnnnnnauuu annnnnnnnn 60
naacaccuaa gaguunnaaa angggaaunc cggugunnnn nnnnnnnnnn nnnnnnnnnn 120
nnnnaaaucc ggagcuganc gcgcagcggu aaggggannn nnnnnnnnnn nnnnnnnnnn 180
nnnnnnnnnn nnnnnnnnnn nnnnnnaguc acggcgauag guuucuaaca nnnnnnnnnn 240
nnnnnnnnnn nnnnnnnnnn nnnnnnnnnn nnnnnnnnnn nnnnnnnnng acacuguccn 300
nnnnnnnnnn nnnnnnnnnn nnnnnnngca annnnnnnnn nnnnnnnnnn nnnnnnnnnn 360
nnnnnnnngg augggaaguc nnaucgccug cucuauuucg cgccauuuau uuaucacagu 420
auuuuuacug ucauaaccau ggccugauac cagagannnn nnnuccunna agcccgaaga 480
ccugccggua uuacgucgca auauu 505

<210> SEQ ID NO 297
<211> LENGTH: 506
<212> TYPE: RNA
<213> ORGANISM: Acinetobacter calcoaceticus
<220> FEATURE:
<221> NAME/KEY: misc_feature
<222> LOCATION: 30-470
<223> OTHER INFORMATION: n = g, a, c or u

<400> SEQUENCE: 297
cuuuacacaa uucguaacaa guuaaaagcn nnnnnnnnnn nnnnnnauuc nnnnnnnnnn 60
nnnnnnnngc uuunnnnnnn angggaaanc uggugcnnnn nnnnnnnnnn nnnnnnnnnn 120
nnnnaaauac cagugcugcc cccgcaacgg uaanaaaugn nnnnnnnnnn nnnnnnnnnn 180
nnnnnnnnnn nnnnnnnnnn nnnnnnnnua aaccauauua aaaaagucau uuagacuuan 240
nnnnnnnnnn nnnnnnnnnn nnnnnnnnnn nnnnnnnnnn nnnnnnnnnc gccacugcau 300
nnnnnnnnnn nnnnnnnnnn nnnnnnngca uagnnnnnnn nnnnnnnnnn nnnnnnnnnn 360
nnnnnnnnna ugugggaagg ugnaauaugc uugucucuuu uugagaugcn nnnnnnnnnn 420
nnnnnnnnnn nnnnnnnnnn nnnnnnnnnn nnnnnnnnnn nnncauuunn gaguccggag 480
accugcuugu uacaucuauc cacuca 506

<210> SEQ ID NO 298
<211> LENGTH: 505
<212> TYPE: RNA
<213> ORGANISM: Agrobacterium vitis
<220> FEATURE:
<221> NAME/KEY: misc_feature
<222> LOCATION: 23-469
<223> OTHER INFORMATION: n = g, a, c or u

<400> SEQUENCE: 298
ccuaaagugg cagcguaucg gunnucugca agugunnnnn nnnnnncaaa nnnnnnnnnn 60
nnacgcncgc ggaugnnaaa angggaauna cggugaggac gacccnnaag uaannnnnng 120

```
ggccgaaacc guggcugccc ccgcaacugu ganacggnnn nnnnnnnnnn nnnnnnnnnn    180

nnnnnnnnnn nnnnnnnnnn nnnnnncgag cgauguccau caunnnnnnn nnnnnnnnnn    240

nnnnnnnnnn nnnnnnnnnn nnnnnnnnnn nnnnnnnnnn nnnnnnnnng ccauuggccn    300

nnnnnnnnnn nnnnnnnnnn nnnnnnncca cnnnnnnnnn nnnnnnnnnn nnnnnnnnnn    360

nnnnnnnngg ccgauaaggc nnggacaaag cccagacnnn nnnnnnnnnn nnnnnnnnnn    420

nnnnnnnnnn nnnnnnnnnn nnnnnnnnnn nnnnnnnnnn nnnccgunng agccaggaga    480

ccugccgaua agcaugcgcg aaagc                                          505


<210> SEQ ID NO 299
<211> LENGTH: 505
<212> TYPE: RNA
<213> ORGANISM: Bacteroides fragilis
<220> FEATURE:
<221> NAME/KEY: misc_feature
<222> LOCATION: 23-469
<223> OTHER INFORMATION: n = g, a, c or u

<400> SEQUENCE: 299

uuaucuuugc ucccugaucg gunnuccgaa uagnnnnnnn nnnnnucauu ccunnnnnnn     60

nnnncuaucc ggauunnaaa angggaaunc gggugunnnn nnnnnnnnnn nnnnnnnnnn    120

nnnnaaaucc cggacagunc ccgcugcugu gaagcuccnn nnnnnnnnnn nnnnnnnnnn    180

nnnnnnnnnn nnnnnnnnnn nnngucugaa uuuccgauaa caacuguunn nnnnnnnnnn    240

nnnnnnnnnn nnnnnnnnnn nnnnnnnnnn nnnnnnnnnn nnnnnnnnng ccacugggau    300

accuuuuugn nnnnnnnnnn nnnnnnnuaa annnnnnnnn nnnnnnnnnn nnnnnnuaga    360

uaaggaguca ccgggaaggc nngucggaaa caannnnnnn nnnnnnnnnn nnnnnnnnnn    420

nnnnnnnnnn nnnnnnnnnn nnnnnnnnnn nnnnnnnnnn nnggagunnc agucagaaga    480

ccugccgcuu aucaaaggcu guuuc                                          505


<210> SEQ ID NO 300
<211> LENGTH: 505
<212> TYPE: RNA
<213> ORGANISM: Bacillus megaterium
<220> FEATURE:
<221> NAME/KEY: misc_feature
<222> LOCATION: 23-469
<223> OTHER INFORMATION: n = g, a, c or u

<400> SEQUENCE: 300

aucaaacagc aacaguaaag gunngccnnn nnnnnnnnnn nnnnnnaaga annnnnnnnn     60

nnnnnnnnnn ggcuunnaau angggaaanc uggugannnn nnnnnnnnnn nnnnnnnnnn    120

nnnnaagacc aguacugccc ccgcaacugu aangugugnn nnnnnnnnnn nnnnnnnnnn    180

nnnnnnnnnn nnnnnnnnnn nnnnnnnnga cgaacgagua unnnnnnnnn nnnnnnnnnn    240

nnnnnnnnnn nnnnnnnnnn nnnnnnnnnn nnnnnnnnnn nnnnnnnnaa ccacugugan    300

nnnnnnnnnn nnnnnnnnnn nnnnnnaaaa annnnnnnnn nnnnnnnnnn nnnnnnnnnn    360

nnnnnnnnuc acgggaaggu uncucaagua gaaugannnn nnnnnnnnnn nnnnnnnnnn    420

nnnnnnnnnn nnnnnnnnnn nnnnnnnnnn nnnnnnnnnn nnuacacnna agucaggaga    480

ccugucuuua uugugaaguu ucuau                                          505


<210> SEQ ID NO 301
<211> LENGTH: 505
<212> TYPE: RNA
<213> ORGANISM: Leishmania major
<220> FEATURE:
```

<221> NAME/KEY: misc_feature
<222> LOCATION: 1-469
<223> OTHER INFORMATION: n = g, a, c or u

<400> SEQUENCE: 301

```
nnnnnnnnnn nnnnnnucgg gugncccunn nnnnnnnnnn nnnnnnucac nnnnnnnnnn     60

nnnnnnnnna gggugnnaaa cngggaaanc cggugaguca uguuccuuua cucaagggcg    120

ugacgagucc ggugcugccc ccgcaacggu aangcgagnn nnnnnnnnnn nnnnnnnnnn    180

nnnnnnnnnn nnnnnnnnnn nnnnnnnnug aagcgucaaa unnnnnnnnn nnnnnnnnnn    240

nnnnnnnnnn nnnnnnnnnn nnnnnnnnnn nnnnnnnnnn nnnnnnnnnn ccacugugcc    300

nnnnnnnnnn nnnnnnnnnn nnnnnnucca gnnnnnnnnn nnnnnnnnnn nnnnnnnnnn    360

nnnnnnnggc augggaaggn nnugaugcuu ucaaggccca ggcccnnnnn nnnnnnnnnn    420

nnnnnnnnnn nnnnnnnnnn nnnnnnnnnn nnnnnnnnnn nncucgcnna agcccggaga    480

ccggcccgaa aaaaucagau aacaa                                          505
```

<210> SEQ ID NO 302
<211> LENGTH: 505
<212> TYPE: RNA
<213> ORGANISM: Propionibacterium freudenreichii
<220> FEATURE:
<221> NAME/KEY: misc_feature
<222> LOCATION: 24-469
<223> OTHER INFORMATION: n = g, a, c or u

<400> SEQUENCE: 302

```
uguguaggcu aguagugcug guuncggcug ccnnnnnnnn nnnnnnccac nnnnnnnnnn     60

nnnnnggcag ucgucgcaag angggaaunc cggugunnnn nnnnnnnnnn nnnnnnnnnn    120

nnnnaauucc ggaacugunc ccgcagcggu canaugggnn nnnnnnnnnn nnnnnnnnnn    180

nnnnnnnnnn nnnnnnnnnn nnnnnnnaac gacacaacgu aagnnnnnnn nnnnnnnnnn    240

nnnnnnnnnn nnnnnnnnnn nnnnnnnnnn nnnnnnnnnn nnnnnnnnnn gcacugggcg    300

nnnnnnnnnn nnnnnnnnnn nnnnnnngca annnnnnnnn nnnnnnnnnn nnnnnnnnnn    360

nnnnnnncgc cugggaagun naguagugga ggaagucggg agugaucucg caaugnnnnn    420

nnnnnnnnnn nnnnnnnnnn nnnnnnnnnn nnnnnnnnnn nncccaunng aguccgaaga    480

ccugccagca gcgacaacau cuguu                                          505
```

<210> SEQ ID NO 303
<211> LENGTH: 505
<212> TYPE: RNA
<213> ORGANISM: Rhodobacter capsulatus
<220> FEATURE:
<221> NAME/KEY: misc_feature
<222> LOCATION: 24-468
<223> OTHER INFORMATION: n = g, a, c or u

<400> SEQUENCE: 303

```
gccacucagg gcgggcgcug guunucuguc nnnnnnnnnn nnnnnncuau nnnnnnnnnn     60

nnnnnnngac aggcgnnaag angggaaung ugaagggaau ugcgacggcu uunngccgcg    120

aaacccgacc gcagccgccc ccgcgaccgu gaccggannn nnnnnnnnnn nnnnnnnnnn    180

nnnnnnnnnn nnnnnnnnnn nnnnnnngag ggcgccccga gnnnnnnnnn nnnnnnnnnn    240

nnnnnnnnnn nnnnnnnnnn nnnnnnnnnn nnnnnnnnnn nnnnnnnnng ccacuggcnn    300

nnnnnnnnnn nnnnnnnnnn nnnnnnacca nnnnnnnnnn nnnnnnnnnn nnnnnnnnnn    360

nnnnnnnnng ccgggaaggc nngggggcgac cgugagggga ccccccccucg cannnnnnnn    420
```

nnnnnnnnnn nnnnnnnnnn nnnnnnnnnn nnnnnnnnnn nnnuccgnca agccgggaga 480
ccugccagcg cauggauuuc gggcg 505

<210> SEQ ID NO 304
<211> LENGTH: 505
<212> TYPE: RNA
<213> ORGANISM: Rhodobacter capsulatus
<220> FEATURE:
<221> NAME/KEY: misc_feature
<222> LOCATION: 23-469
<223> OTHER INFORMATION: n = g, a, c or u

<400> SEQUENCE: 304
ggcuacucca acaggcgaug gunnucccnn nnnnnnnnnn nnnnaacugg acnnnnnnnn 60
nnnnnnnnng ggauunnaau angggaacna cggugaggau uacccnnnau cannnnnngg 120
ggccuaaucc guggcugccc ccgcaacugu gangcggnnn nnnnnnnnnn nnnnnnnnnn 180
nnnnnnnnnn nnnnnnnnnn nnnnncgaga cgacggucga agnnnnnnnn nnnnnnnnnn 240
nnnnnnnnnn nnnnnnnnnn nnnnnnnnnn nnnnnnnnnn nnnnnnnnna ccacuggccc 300
ccccgnnnnn nnnnnnnnnn nnnnnaucca cnnnnnnnnn nnnnnnnnnn nnnnnnnncg 360
gggagaacgg ccgggaaggu nngacccgag uugaucgaan nnnnnnnnnn nnnnnnnnnn 420
nnnnnnnnnn nnnnnnnnnn nnnnnnnnnn nnnnnnnnnn nnnccgcnna agucaggaga 480
ccugccaucg cucuggcguc gcaag 505

<210> SEQ ID NO 305
<211> LENGTH: 505
<212> TYPE: RNA
<213> ORGANISM: Rhodobacter capsulatus
<220> FEATURE:
<221> NAME/KEY: misc_feature
<222> LOCATION: 24-469
<223> OTHER INFORMATION: n = g, a, c or u

<400> SEQUENCE: 305
gggcaccuuc gcggcagaug guuncccggc caagcnnnnn nnnnnncacn nnnnnnnnnn 60
nngcgcggcc gggugnnaaa angggaauna cggugugggug uaggcnnnau cannnnnngc 120
cgccaaaucc guaacugccc ccgcaacugu aangcggnnn nnnnnnnnnn nnnnnnnnnn 180
nnnnnnnnnn nnnnnnnnnn nnnnnnnncg agcacccccc ggcannnnnn nnnnnnnnnn 240
nnnnnnnnnn nnnnnnnnnn nnnnnnnnnn nnnnnnnnnn nnnnnnnnna ccacuggccc 300
cgnnnnnnnn nnnnnnnnnn nnnnnnaccg nnnnnnnnnn nnnnnnnnnn nnnnnnnnnn 360
nnnnncgggg ccgggaaggu nnggggaagc cacgacnnnn nnnnnnnnnn nnnnnnnnnn 420
nnnnnnnnnn nnnnnnnnnn nnnnnnnnnn nnnnnnnnnn nnnccgcnna agucaggaga 480
ccugccauca gcgucaucaa ccgcc 505

<210> SEQ ID NO 306
<211> LENGTH: 505
<212> TYPE: RNA
<213> ORGANISM: Rhodobacter sphaeroides
<220> FEATURE:
<221> NAME/KEY: misc_feature
<222> LOCATION: 22-469
<223> OTHER INFORMATION: n = g, a, c or u

<400> SEQUENCE: 306
uguuuugugg caggggucag gngnccgccn nnnnnnnnnn nnnnnnuucg nnnnnnnnnn 60
nnnnnnnngg cggagnnaau cngggaagnc cgguggnnnn nnnnnnnnnn nnnnnnnnnn 120

-continued

```
nnnnaaaucc ggcgcgggnc ccgccgcugu gancggnnnn nnnnnnnnnn nnnnnnnnnn    180

nnnnnnnnnn nnnnnnnnnn nnnnnggaug cuccgggcaa gagnnnnnnn nnnnnnnnnn    240

nnnnnnnnnn nnnnnnnnnn nnnnnnnnnn nnnnnnnnnn nnnnnnnnng ccaccggunn    300

nnnnnnnnnn nnnnnnnnnn nnnnnnuucn nnnnnnnnnn nnnnnnnnnn nnnnnnnnnn    360

nnnnnnnnng ccgggaaggc nngcccggcg gcagaugaan nnnnnnnnnn nnnnnnnnnn    420

nnnnnnnnnn nnnnnnnnnn nnnnnnnnnn nnnnnnnnnn nnnnccgnng agccagaaga    480

ccggccugac gcagagguuc ccgcc                                          505
```

```
<210> SEQ ID NO 307
<211> LENGTH: 505
<212> TYPE: RNA
<213> ORGANISM: Sorghum bicdor
<220> FEATURE:
<221> NAME/KEY: misc_feature
<222> LOCATION: 24-469
<223> OTHER INFORMATION: n = g, a, c or u

<400> SEQUENCE: 307

uagacugcgc ccacuuccag gugnaccugc ggcnnnnnnn nnnnnncaug nnnnnnnnnn     60

nnngccggca gguugnnaaa cnggnaagnc cggugacgcg ugnnnnnnau ucnnnnnnnc    120

acgccaggcc ggcgcugccc ccgcaacggu aangcacguc nnnnnnnnnn nnnnnnnnnn    180

nnnnnnnnnn nnnnnnnnnn nnnnnnnnag ucccaggcaa caacnnnnnn nnnnnnnnnn    240

nnnnnnnnnn nnnnnnnnnn nnnnnnnnnn nnnnnnnnnn nnnnnnnnng ccacugugcc    300

nnnnnnnnnn nnnnnnnnnn nnnnnnacgn nnnnnnnnnn nnnnnnnnnn nnnnnnnnnn    360

nnnnnnnggc augggaaggc nngccuggac gguggccucg cgccacccnn nnnnnnnnnn    420

nnnnnnnnnn nnnnnnnnnn nnnnnnnnnn nnnnnnnnnn nggcggcnna agcccggaga    480

ccggcccgga agccucaggu cgcga                                          505
```

```
<210> SEQ ID NO 308
<211> LENGTH: 505
<212> TYPE: RNA
<213> ORGANISM: Streptomyces griseus
<220> FEATURE:
<221> NAME/KEY: misc_feature
<222> LOCATION: 24-469
<223> OTHER INFORMATION: n = g, a, c or u

<400> SEQUENCE: 308

uaggcugacc ggugcagcug guuncgcccu guccnnnnnn nnnnnngcca nnnnnnnnnn     60

nnnnggcagg gugucgcaag angggaacnc cgguggnnnn nnnnnnnnnn nnnnnnnnnn    120

nnnnaaaucc gggacugcnc ccgcagcggu gangugggnn nnnnnnnnnn nnnnnnnnnn    180

nnnnnnnnnn nnnnnnnnnn nnnnnnaacg accgccguca uannnnnnnn nnnnnnnnnn    240

nnnnnnnnnn nnnnnnnnnn nnnnnnnnnn nnnnnnnnnn nnnnnnnnnc gcacugggcc    300

cnnnnnnnnn nnnnnnnnnn nnnnnnngga cnnnnnnnnn nnnnnnnnnn nnnnnnnnnn    360

nnnnnngggu cugggaagcg nnacggccac uaggugucug cccggcagac gugnnnnnnn    420

nnnnnnnnnn nnnnnnnnnn nnnnnnnnnn nnnnnnnnnn nncccgcnng aguccgaaga    480

ccugcccgcu gcccgcacgc gaccg                                          505
```

```
<210> SEQ ID NO 309
<211> LENGTH: 505
<212> TYPE: RNA
<213> ORGANISM: Stealth virus
<220> FEATURE:
```

<221> NAME/KEY: misc_feature
<222> LOCATION: 23-469
<223> OTHER INFORMATION: n = g, a, c or u

<400> SEQUENCE: 309
aucgcucgcu ucaggaaacg gunnucugcc cnnnnnnnnn nnnnnngaga nnnnnnnnnn 60
nnnnnngggu ggaugnnaaa angggaacna cggugaagca nnnnnnnuua aaunnnnnnn 120
ugcugaugcc gagacugccc ccgcaacugu aanccggnnn nnnnnnnnnn nnnnnnnnnn 180
nnnnnnnnnn nnnnnnnnnn nnnnnagagu cauccuccua ugaucguauc uuacgauuau 240
annnnnnnnn nnnnnnnnnn nnnnnnnnnn nnnnnnnnnn nnnnnnnnng ccacugagca 300
nnnnnnnnnn nnnnnnnnnn nnnnnnuucg nnnnnnnnnn nnnnnnnnnn nnnnnnnnnn 360
nnnnnnnugu ucgggaaggc nnggaggacc gaugaagacn nnnnnnnnnn nnnnnnnnnn 420
nnnnnnnnnn nnnnnnnnnn nnnnnnnnnn nnnnnnnnnn nnnccggnna agucaggaga 480
ccugccguau ccagucaccc auggc 505

<210> SEQ ID NO 310
<211> LENGTH: 505
<212> TYPE: RNA
<213> ORGANISM: Zymomonas mobilis
<220> FEATURE:
<221> NAME/KEY: misc_feature
<222> LOCATION: 23-469
<223> OTHER INFORMATION: n = g, a, c or u

<400> SEQUENCE: 310
cggaaauuuu uuugcauagg gunnuuccuu cnnnnnnnnn nnnnnngagu nnnnnnnnnn 60
nnnnnngaag gaannnnaau ungggaacna aggugcnnnn nnnnnnnnnn nnnnnnnnnn 120
nnnnaaaacc uuggcugccc cugcaacugu aanacagunn nnnnnnnnnn nnnnnnnnnn 180
nnnnnnnnnn nnnnnnnnnn nnnnnnnnnu gaaacgccaa aaannnnnnn nnnnnnnnnn 240
nnnnnnnnnn nnnnnnnnnn nnnnnnnnnn nnnnnnnnnn nnnnnnnnng ccacugaann 300
nnnnnnnnnn nnnnnnnnnn nnnnnnnucu annnnnnnnn nnnnnnnnnn nnnnnnnnnn 360
nnnnnnnnnu ucgggaaggc nngguuguuu cgaunnnnnn nnnnnnnnnn nnnnnnnnnn 420
nnnnnnnnnn nnnnnnnnnn nnnnnnnnnn nnnnnnnnnn nngcugunng agccaggaga 480
ccgacccuau guaaucguuc cacga 505

<210> SEQ ID NO 311
<211> LENGTH: 505
<212> TYPE: RNA
<213> ORGANISM: Zymomonas mobilis
<220> FEATURE:
<221> NAME/KEY: misc_feature
<222> LOCATION: 24-468
<223> OTHER INFORMATION: n = g, a, c or u

<400> SEQUENCE: 311
agcaaugagg aaggauuaag guuncuuugu nnnnnnnnnn nnnnncauug nnnnnnnnnn 60
nnnnnnngca aagcunnaag angggaaanc uggugcgaaa nnnnnnnnga aunnnnnnnn 120
uuucaaagcc agugcugccc ccgcaacugu aanacggnnn nnnnnnnnnn nnnnnnnnnn 180
nnnnnnnnnn nnnnnnnnnn nnnnncgagc aaagaucaaa aunnnnnnnn nnnnnnnnnn 240
nnnnnnnnnn nnnnnnnnnn nnnnnnnnnn nnnnnnnnnn nnnnnnnnng ccacugauan 300
nnnnnnnnnn nnnnnnnnnn nnnnnnuuau nnnnnnnnnn nnnnnnnnnn nnnnnnnnnn 360
nnnnnnnnua ucgggaaggc nnugaucgga cgcggugacn nnnnnnnnnn nnnnnnnnnn 420
nnnnnnnnnn nnnnnnnnnn nnnnnnnnnn nnnnnnnnnn nnnccgunca agucaggaga 480
ccugccuuaa accaagucau ccacu 505

<210> SEQ ID NO 312
<211> LENGTH: 105
<212> TYPE: DNA
<213> ORGANISM: Bacillus halodurans
<220> FEATURE:
<221> NAME/KEY: misc_feature
<222> LOCATION: 43-80
<223> OTHER INFORMATION: n = g, a, c or t/u

<400> SEQUENCE: 312
acatgtagat atcatccctt tcgtatatac ttggagataa ggntccagga gtttctacca 60
gatcaccgta aatgatctgn actatgaagg tggaatggct cgata 105

<210> SEQ ID NO 313
<211> LENGTH: 105
<212> TYPE: DNA
<213> ORGANISM: Bacillus halodurans
<220> FEATURE:
<221> NAME/KEY: misc_feature
<222> LOCATION: 43-80
<223> OTHER INFORMATION: n = g, a, c or t/u

<400> SEQUENCE: 313
aataaatcga aaacatcatt tcgtataatg gcaggaatag ggncctgcga gtttctacca 60
agctaccgta aatagcttgn actacgaaaa taatgggttt tttac 105

<210> SEQ ID NO 314
<211> LENGTH: 105
<212> TYPE: DNA
<213> ORGANISM: Bacillus halodurans
<220> FEATURE:
<221> NAME/KEY: misc_feature
<222> LOCATION: 43-80
<223> OTHER INFORMATION: n = g, a, c or t/u

<400> SEQUENCE: 314
cgttctttat ataaagtacc tcatataatc ttgggaatat ggncccaaaa gtttctacct 60
gctgaccgta aatcggcggn actatgggga aagattttgg atctt 105

<210> SEQ ID NO 315
<211> LENGTH: 105
<212> TYPE: DNA
<213> ORGANISM: Bacillus halodurans
<220> FEATURE:
<221> NAME/KEY: misc_feature
<222> LOCATION: 28-79
<223> OTHER INFORMATION: n = g, a, c or t/u

<400> SEQUENCE: 315
ttaatcgagc tcaacactct tcgtatantc ctctcaatat ggngatgagg gtctctacag 60
gtannccgta aatacctnna gctacgaaaa gaatgcagtt aatgt 105

<210> SEQ ID NO 316
<211> LENGTH: 105
<212> TYPE: DNA
<213> ORGANISM: Bacillus halodurans
<220> FEATURE:
<221> NAME/KEY: misc_feature
<222> LOCATION: 43-80
<223> OTHER INFORMATION: n = g, a, c or t/u

<400> SEQUENCE: 316

```
atttacatta aaaaaagcac tcgtataatc gcgggaatag ggncccgcaa gtttctacca     60

ggctgccgta aacagcctgn actacgagtg atactttgac ataga                     105


<210> SEQ ID NO 317
<211> LENGTH: 105
<212> TYPE: DNA
<213> ORGANISM: Bacillus subtilis
<220> FEATURE:
<221> NAME/KEY: misc_feature
<222> LOCATION: 43-80
<223> OTHER INFORMATION: n = g, a, c or t/u

<400> SEQUENCE: 317

agaaatcaaa taagatgaat tcgtataatc gcgggaatat ggnctcgcaa gtctctacca     60

agctaccgta aatggcttgn actacgtaaa catttctttc gtttg                     105


<210> SEQ ID NO 318
<211> LENGTH: 105
<212> TYPE: DNA
<213> ORGANISM: Bacillus subtilis
<220> FEATURE:
<221> NAME/KEY: misc_feature
<222> LOCATION: 43-80
<223> OTHER INFORMATION: n = g, a, c or t/u

<400> SEQUENCE: 318

catgaaatca aaacacgacc tcatataatc ttgggaatat ggncccataa gtttctaccc     60

ggcaaccgta aattgccggn actatgcagg aaagtgatcg ataaa                     105


<210> SEQ ID NO 319
<211> LENGTH: 105
<212> TYPE: DNA
<213> ORGANISM: Bacillus subtilis
<220> FEATURE:
<221> NAME/KEY: misc_feature
<222> LOCATION: 43-80
<223> OTHER INFORMATION: n = g, a, c or t/u

<400> SEQUENCE: 319

ttacaatata ataggaacac tcatataatc gcgtggatat ggncacgcaa gtttctaccg     60

ggcanccgta aantgtccgn actatgggtg agcaatggaa ccgca                     105


<210> SEQ ID NO 320
<211> LENGTH: 105
<212> TYPE: DNA
<213> ORGANISM: Bacillus subtilis
<220> FEATURE:
<221> NAME/KEY: misc_feature
<222> LOCATION: 43-80
<223> OTHER INFORMATION: n = g, a, c or t/u

<400> SEQUENCE: 320

catcttagaa aaagacattc ttgtatatga tcagtaatat ggntctgatt gtttctacct     60

agtaaccgta aaaaactagn actacaagaa agtttgaata aattt                     105


<210> SEQ ID NO 321
<211> LENGTH: 105
<212> TYPE: DNA
<213> ORGANISM: Clostridium acetobutylicum
<220> FEATURE:
<221> NAME/KEY: misc_feature
<222> LOCATION: 29-80
<223> OTHER INFORMATION: n = g, a, c or t/u

<400> SEQUENCE: 321
```

-continued tatataaaaa actaaatttc tcgtatacna ccggtaatat ggntccggaa gtttctacct 60
gctgnccata aantagcagn actacggggt gttattgata atata 105

<210> SEQ ID NO 322
<211> LENGTH: 105
<212> TYPE: DNA
<213> ORGANISM: Clostridium acetobutylicum
<220> FEATURE:
<221> NAME/KEY: misc_feature
<222> LOCATION: 43-80
<223> OTHER INFORMATION: n = g, a, c or t/u

<400> SEQUENCE: 322
gaaaagtaat aacatattac ccgtatatgc ttagaaatat ggntctaagc gtctctaccg 60
gactgccgta aattgtctgn actatgggtg tttataagta tttta 105

<210> SEQ ID NO 323
<211> LENGTH: 105
<212> TYPE: DNA
<213> ORGANISM: Clostridium acetobutylicum
<220> FEATURE:
<221> NAME/KEY: misc_feature
<222> LOCATION: 29-80
<223> OTHER INFORMATION: n = g, a, c or t/u

<400> SEQUENCE: 323
aatcgttaat atagtttaac tcatatatnt tcctgaatat ggnncaggat gtttctacaa 60
ggaancctta aantttcttn actatgagtg atttgtttgt atgca 105

<210> SEQ ID NO 324
<211> LENGTH: 105
<212> TYPE: DNA
<213> ORGANISM: Clostridium perfringens
<220> FEATURE:
<221> NAME/KEY: misc_feature
<222> LOCATION: 43-80
<223> OTHER INFORMATION: n = g, a, c or t/u

<400> SEQUENCE: 324
tatgtactta tataagtata tcgtatatgc tcgacgatat ggngttgagt gtttctacta 60
ggaggccgta aacatcctan actacgaata tataggtgat ttcta 105

<210> SEQ ID NO 325
<211> LENGTH: 105
<212> TYPE: DNA
<213> ORGANISM: Clostridium perfringens
<220> FEATURE:
<221> NAME/KEY: misc_feature
<222> LOCATION: 43-80
<223> OTHER INFORMATION: n = g, a, c or t/u

<400> SEQUENCE: 325
taagtgtatt aaattttaac tcgtatataa tcggtaatat ggntccgaaa gtttctacct 60
gctaaccgta aaatagcagn actacgagga gttgtactat aaatt 105

<210> SEQ ID NO 326
<211> LENGTH: 105
<212> TYPE: DNA
<213> ORGANISM: Clostridium perfringens
<220> FEATURE:
<221> NAME/KEY: misc_feature
<222> LOCATION: 29-80
<223> OTHER INFORMATION: n = g, a, c or t/u

<400> SEQUENCE: 326
aaaacggaat ataaacaaac tcgtataang ctttgaataa ggnncaaggc gtttctaccg 60
gaaancctta aantttccgn tctatgagtg aatttgatat actat 105

<210> SEQ ID NO 327
<211> LENGTH: 105
<212> TYPE: DNA
<213> ORGANISM: Fusobacterium nucleatum
<220> FEATURE:
<221> NAME/KEY: misc_feature
<222> LOCATION: 29-73
<223> OTHER INFORMATION: n = g, a, c or t/u

<400> SEQUENCE: 327
taaataattt taataaaaat tcgtataang cctaatatat ggnnaagggt gtccctacgg 60
ttaanccata aanttaacca gctacgaaaa atgttttact gtgtt 105

<210> SEQ ID NO 328
<211> LENGTH: 105
<212> TYPE: DNA
<213> ORGANISM: Lactococcus lactis
<220> FEATURE:
<221> NAME/KEY: misc_feature
<222> LOCATION: 28-80
<223> OTHER INFORMATION: n = g, a, c or t/u

<400> SEQUENCE: 328
gtctataata gaacaatctt atttatannn cctaggatat ggnnctgggc gtttctacct 60
cgtanccgta aantgcgagn acaataagga aattcgattt tttag 105

<210> SEQ ID NO 329
<211> LENGTH: 105
<212> TYPE: DNA
<213> ORGANISM: Listeria monocytogenes
<220> FEATURE:
<221> NAME/KEY: misc_feature
<222> LOCATION: 43-80
<223> OTHER INFORMATION: n = g, a, c or t/u

<400> SEQUENCE: 329
aatccgctac aataatatag tcgtataagt tcggtaatat ggnaccgttc gtttctacca 60
ggcaaccgta aaatgccagn gctacgagct attgtaaaat ttaat 105

<210> SEQ ID NO 330
<211> LENGTH: 105
<212> TYPE: DNA
<213> ORGANISM: Listeria monocytogenes
<220> FEATURE:
<221> NAME/KEY: misc_feature
<222> LOCATION: 39-80
<223> OTHER INFORMATION: n = g, a, c or t/u

<400> SEQUENCE: 330
ataacttaaa accgaaatac ttgtataata gttgcgatnt ggngcgacga gtttctacct 60
ggttaccgta aataaccggn actatgagta gtttgtataa agaag 105

<210> SEQ ID NO 331
<211> LENGTH: 105
<212> TYPE: DNA
<213> ORGANISM: Oceanobacillus iheyensis
<220> FEATURE:
<221> NAME/KEY: misc_feature
<222> LOCATION: 43-80
<223> OTHER INFORMATION: n = g, a, c or t/u

<400> SEQUENCE: 331
caatttttat ccaatgcctt tcgtatatcc tcgataatat ggnttcgaaa gtatctaccg 60
ggtcaccgta aatgatctgn actatgaagg cagaagcagg ttcgg 105

<210> SEQ ID NO 332
<211> LENGTH: 105
<212> TYPE: DNA
<213> ORGANISM: Oceanobacillus iheyensis
<220> FEATURE:
<221> NAME/KEY: misc_feature
<222> LOCATION: 43-80
<223> OTHER INFORMATION: n = g, a, c or t/u

<400> SEQUENCE: 332
tgatgtaatt gaatagaaat gcgtataatt aaggggatat ggnncccaca gtttctacca 60
gaccaccgta aatggtttgn actacgcagt aattatattt gtatc 105

<210> SEQ ID NO 333
<211> LENGTH: 105
<212> TYPE: DNA
<213> ORGANISM: Oceanobacillus iheyensis
<220> FEATURE:
<221> NAME/KEY: misc_feature
<222> LOCATION: 43-80
<223> OTHER INFORMATION: n = g, a, c or t/u

<400> SEQUENCE: 333
ccgacaattg aaaatgaacc tcatataaat ttgagaatat ggnctcagaa gtttctaccc 60
agcanccgta aatggctggn actatgaggg aagatggatc atttc 105

<210> SEQ ID NO 334
<211> LENGTH: 105
<212> TYPE: DNA
<213> ORGANISM: Oceanobacillus iheyensis
<220> FEATURE:
<221> NAME/KEY: misc_feature
<222> LOCATION: 43-80
<223> OTHER INFORMATION: n = g, a, c or t/u

<400> SEQUENCE: 334
aaaccttata tatagttttt tcatataatc gcggggatat ggncctgcaa gtttctaccg 60
gtttaccgta aatgaaccgn actatggaaa agcggaaaat tcgat 105

<210> SEQ ID NO 335
<211> LENGTH: 105
<212> TYPE: DNA
<213> ORGANISM: Staphylococcus aureus
<220> FEATURE:
<221> NAME/KEY: misc_feature
<222> LOCATION: 80
<223> OTHER INFORMATION: n = g, a, c or t/u

<400> SEQUENCE: 335
gttaaataat ttacataaac tcatataatc taaagaatat ggctttagaa gtttctacca 60
tgttgccttg aacgacatgn actatgagta acaacacaat actag 105

<210> SEQ ID NO 336
<211> LENGTH: 105
<212> TYPE: DNA
<213> ORGANISM: Staphylococcus epidermidis
<220> FEATURE:
<221> NAME/KEY: misc_feature
<222> LOCATION: 80
<223> OTHER INFORMATION: n = g, a, c or t/u

<400> SEQUENCE: 336

```
cataaaataa tttatatgac tcatataatc tagagaatat ggctttagaa gtttctaccg     60

tgtcgccata aacgacacgn actatgagta acaatccaat acatt                    105


<210> SEQ ID NO 337
<211> LENGTH: 105
<212> TYPE: DNA
<213> ORGANISM: Streptococcus agalactiae
<220> FEATURE:
<221> NAME/KEY: misc_feature
<222> LOCATION: 29-80
<223> OTHER INFORMATION: n = g, a, c or t/u

<400> SEQUENCE: 337

caattaaata tatgatttac ttatttatng ctgaggatnt ggnncttagc gtctctacaa     60

gacanccgtn aantgtctan acaataagta agctaataaa tagct                    105


<210> SEQ ID NO 338
<211> LENGTH: 105
<212> TYPE: DNA
<213> ORGANISM: Streptococcus pyogenes
<220> FEATURE:
<221> NAME/KEY: misc_feature
<222> LOCATION: 29-80
<223> OTHER INFORMATION: n = g, a, c or t/u

<400> SEQUENCE: 338

tgaattcaat aatgacatac ttatttatng ctgtgaatnt ggnncgcagc gtctctacaa     60

gacanccntt aantgtctan acaataagta agcttttagg cttgc                    105


<210> SEQ ID NO 339
<211> LENGTH: 105
<212> TYPE: DNA
<213> ORGANISM: Streptococcus pneumoniae
<220> FEATURE:
<221> NAME/KEY: misc_feature
<222> LOCATION: 29-79
<223> OTHER INFORMATION: n = g, a, c or t/u

<400> SEQUENCE: 339

aaaattgaat atcgttttac ttgtttatng tcgtgaatnt ggnncacgac gtttctacaa     60

ggtgnccngg aancacctna acaataagta agtcagcagt gagat                    105


<210> SEQ ID NO 340
<211> LENGTH: 105
<212> TYPE: DNA
<213> ORGANISM: Thermoanaerobacter tengcongensis
<220> FEATURE:
<221> NAME/KEY: misc_feature
<222> LOCATION: 43-80
<223> OTHER INFORMATION: n = g, a, c or t/u

<400> SEQUENCE: 340

aaaaatttaa taagaagcac tcatataatc ccgagaatat ggnctcggga gtctctaccg     60

aacaaccgta aattgttcgn actatgagtg aaagtgtacc taggg                    105


<210> SEQ ID NO 341
<211> LENGTH: 105
<212> TYPE: DNA
<213> ORGANISM: Bacillus subtilis
<220> FEATURE:
<221> NAME/KEY: misc_feature
<222> LOCATION: 43-80
<223> OTHER INFORMATION: n = g, a, c or t/u

<400> SEQUENCE: 341
```

aattaaatag ctattatcac ttgtataacc tcaataatat ggntttgagg gtgtctacca 60
ggaanccgta aaatcctgnn attacaaaat ttgtttatga cattt 105

<210> SEQ ID NO 342
<211> LENGTH: 105
<212> TYPE: DNA
<213> ORGANISM: Clostridium perfringens
<220> FEATURE:
<221> NAME/KEY: misc_feature
<222> LOCATION: 43-80
<223> OTHER INFORMATION: n = g, a, c or t/u

<400> SEQUENCE: 342
ataaaaaaat aaattttgct tcgtataact ctaatgatat ggnattagag gtctctacca 60
agaanccgag aanttcttgn attacgaaga aagcttattt gcttt 105

<210> SEQ ID NO 343
<211> LENGTH: 105
<212> TYPE: DNA
<213> ORGANISM: Vibrio vulnificus
<220> FEATURE:
<221> NAME/KEY: misc_feature
<222> LOCATION: 50-80
<223> OTHER INFORMATION: n = g, a, c or t/u

<400> SEQUENCE: 343
gactttcggc gatcaacgct tcatataatc ctaatgatat ggtttgggan gtttctacca 60
agagncctta aanctcttgn attatgaagt ctgtcgcttt atccg 105

<210> SEQ ID NO 344
<211> LENGTH: 228
<212> TYPE: RNA
<213> ORGANISM: Clostridium perfringens
<220> FEATURE:
<221> NAME/KEY: misc_feature
<222> LOCATION: 16-201
<223> OTHER INFORMATION: n = g, a, c or u

<400> SEQUENCE: 344
agugauggua gaggungcga aaaccnnaag naguacnaca gucugagaga aaugnnnnag 60
aaunnnncgu ugacnnnnga cuguuggaaa ggnngggauu cgccgaagug cagaucgggg 120
ncucauuccc nauuugcgcu ggaccuaugu unnngaauan agcauagggc ugucacaaca 180
cuagnnnnnc cccaannnnn ncuagugcug uggagaacua ucucacgu 228

<210> SEQ ID NO 345
<211> LENGTH: 228
<212> TYPE: RNA
<213> ORGANISM: Vibrio vulnificus
<220> FEATURE:
<221> NAME/KEY: misc_feature
<222> LOCATION: 16-203
<223> OTHER INFORMATION: n = g, a, c or u

<400> SEQUENCE: 345
agugaggaua gaggungcaa aaaccnnaag naguanncac aauuggannn ggannngaau 60
gagannnnuc cguugagaau ugugnngaaa ggnnggaauu ugccgaagcu ggaagaaunn 120
ncucaunngu ucugaaggcu gguucuguau unnnaaauan aauacagaac ugucauauag 180
cgnnnnnnng augunnnnnn nnnugcuaua uggagggcua ucucacgc 228

<210> SEQ ID NO 346
<211> LENGTH: 228
<212> TYPE: RNA

<213> ORGANISM: Bacillus halodurans
<220> FEATURE:
<221> NAME/KEY: misc_feature
<222> LOCATION: 16-206
<223> OTHER INFORMATION: n = g, a, c or u

<400> SEQUENCE: 346
agauggggua gaggangcgg guuuunnaag naguaangcg cuugnnnnnn nnngaggaug 60
acaacgagga nnnnnnnuaa gcgcncgaaa ggnnaaaacu cgccgaagcg ngaagaugnn 120
agucaagncg ucuucuugcu ggggguugcau unnngaauan aauguaacac ugucacagcn 180
nnnnnnnnna gauunnnnnn nnnnnngcug uggagaacua cuaacguu 228

<210> SEQ ID NO 347
<211> LENGTH: 228
<212> TYPE: RNA
<213> ORGANISM: Bacillus subtilis
<220> FEATURE:
<221> NAME/KEY: misc_feature
<222> LOCATION: 16-205
<223> OTHER INFORMATION: n = g, a, c or u

<400> SEQUENCE: 347
ggugaagaua gaggungcga ancuucnaag naguaungcc uuuggagaan agannnnnug 60
gaunnnnnnu cugugaanaa aggcnugaaa ggnggagcgu cgccgaagca aauaaaaccn 120
nccaucnggu auuauuugcu ggccgugcau unnngaauan aauguaaggc ugucaagaaa 180
nnnnnnnnnu caunnnnnnn nnnnnuuucu uggagggcua ucucguug 228

<210> SEQ ID NO 348
<211> LENGTH: 228
<212> TYPE: RNA
<213> ORGANISM: Clostridium acetobutylicum
<220> FEATURE:
<221> NAME/KEY: misc_feature
<222> LOCATION: 16-225
<223> OTHER INFORMATION: n = g, a, c or u

<400> SEQUENCE: 348
accuuuugua gaggungcuu uaagucnaag naguaanccg uuugnnngag uunnnnnnng 60
gcannnnnna acuuagauga acggnuaaaa ggnggcuuuu agccgaagca uuuagauunn 120
nggcannnga uuuauuugcu ggcuuuucau annncaacan uaugaauggc ugucacuuua 180
uuagunnnnu aguunnnnna uuagnguaag uggagcgcua caannggu 228

<210> SEQ ID NO 349
<211> LENGTH: 228
<212> TYPE: RNA
<213> ORGANISM: Clostridium perfringens
<220> FEATURE:
<221> NAME/KEY: misc_feature
<222> LOCATION: 6-208
<223> OTHER INFORMATION: n = g, a, c or u

<400> SEQUENCE: 349
aaaganggua gaggcngcga gaaucnnaag nauuanncua aaauggannn guunnnnnna 60
agunnnnnag cguagaaguu uuagnngaaa ggnngauuau cgccgaaguu uuuggcunaa 120
uacuuuaang gcuaaaugcu gggguuguau annngaauan uauacaacac ugucacannn 180
nnnnnnnnnn aaannnnnnn nnnnnnnnug uggagagcua ucaucuua 228

<210> SEQ ID NO 350
<211> LENGTH: 229
<212> TYPE: RNA

<213> ORGANISM: Clostridium perfringens
<220> FEATURE:
<221> NAME/KEY: misc_feature
<222> LOCATION: 16-207
<223> OTHER INFORMATION: n = g, a, c or u
<400> SEQUENCE: 350
gaccaaagua gaggungccg uaauunnaag naguannguc auaaguagcu gacnnnnnna 60
agunnnnngu unnuuaugua ugaunngaaa ggnngauuau ggccgaagag auauuaaunn 120
nggugnnnau uaauauuucu ggguauaugu aunnnnaaun augcauauaa cugucacuuu 180
nnnnnnnnnn gaaannnnnn nnnnnnnaaa guggagugcu acaagguac 229

<210> SEQ ID NO 351
<211> LENGTH: 228
<212> TYPE: RNA
<213> ORGANISM: Clostridium perfringens
<220> FEATURE:
<221> NAME/KEY: misc_feature
<222> LOCATION: 16-206
<223> OTHER INFORMATION: n = g, a, c or u
<400> SEQUENCE: 351
aacugagaua gaggcngcga ugnauunaau naguannucu uugcagaggu nnnnnnnnna 60
agcannnnnn nnauugaagc aaagnugaaa ggnnaugaau cgccgaaacc aunuagaaga 120
ggcuuuaauu cuauuagguu gggguugcau annngaauan uauguaacac ugucacaaan 180
nnnnnnnnnu uaunnnnnnn nnnnnnuuug uggugugcua ucaugaaa 228

<210> SEQ ID NO 352
<211> LENGTH: 228
<212> TYPE: RNA
<213> ORGANISM: Escherichia coli
<220> FEATURE:
<221> NAME/KEY: misc_feature
<222> LOCATION: 16-167
<223> OTHER INFORMATION: n = g, a, c or u
<400> SEQUENCE: 352
caggccagaa gaggcngcgn unugcccann naguaacggu guuggnnnag gannnnnnng 60
ccagnnnnnu ccugugauaa caccnnnnnu gggggugcau cgccgaggug auugaacgng 120
cuggccancg uucanucauc ggcuacaggg gncugaaunn ccccugnggu ugucaccaga 180
agcgcucgca gucgggcguu ucgcaagugg uggagcacuu cuggguga 228

<210> SEQ ID NO 353
<211> LENGTH: 228
<212> TYPE: RNA
<213> ORGANISM: Haemophilus influenzae
<220> FEATURE:
<221> NAME/KEY: misc_feature
<222> LOCATION: 16-205
<223> OTHER INFORMATION: n = g, a, c or u
<400> SEQUENCE: 353
uacaaaagua gaggcngcaa uuauunnaua naguannuuu uuucagagnu gnnnnnnnng 60
auaannnnnn cgaagaagaa aaaanngaaa ggnnaauagu ugccgaaauc aaauaaaann 120
ngucgnnnuu uuguuugguu gguggcgugc ucnngaaang ggngcgacac ugucauaguu 180
nnnnnnnnuu ucugauunnn nnnnnaacua uggagugcua cgguuguu 228

<210> SEQ ID NO 354
<211> LENGTH: 228
<212> TYPE: RNA

<213> ORGANISM: Oceanobacillus iheyensis
<220> FEATURE:
<221> NAME/KEY: misc_feature
<222> LOCATION: 16-205
<223> OTHER INFORMATION: n = g, a, c or u

<400> SEQUENCE: 354
guuuuggaua gaggungcgg agaccnnauc naguannuau acgcggannn agggnnnaaa 60
ugagnnnccc uagugaagcg uaugnngaaa ggnnggaauc ugccgaagcg agunngaaau 120
acucauucau uanacucguu ggugcugcua uunngaacaa auaacagucc ugucauauag 180
nnnnnnnnng agannnnnnn nnnnncuaua uggagggcua ucgagcug 228

<210> SEQ ID NO 355
<211> LENGTH: 228
<212> TYPE: RNA
<213> ORGANISM: Oceanobacillus iheyensis
<220> FEATURE:
<221> NAME/KEY: misc_feature
<222> LOCATION: 16-206
<223> OTHER INFORMATION: n = g, a, c or u

<400> SEQUENCE: 355
ucggugggua gaggangcau acaacnnauu naguannauc gacnnnnnnn naagaggaug 60
acaacgauga uannnnnngu uggunnggaa ggnnguuguu ugccgaagca nuaauaagnn 120
ggucagancu uauuauugcu gguacaucuu unnngaauan aaagaugcac ugucaugcan 180
nnnnnnnnaa auuaagnnnn nnnnnnugca uggagaacua cugaucga 228

<210> SEQ ID NO 356
<211> LENGTH: 228
<212> TYPE: RNA
<213> ORGANISM: Pasteurella multocida
<220> FEATURE:
<221> NAME/KEY: misc_feature
<222> LOCATION: 16-206
<223> OTHER INFORMATION: n = g, a, c or u

<400> SEQUENCE: 356
uacuugugua gaggangcga ucacunnaua naguannuuu uuucugagnu gnnnnnnnng 60
auaannnnnn cgaagaggaa aaagnngaaa ggnnagugac cgccgaaauc aauugaaann 120
ngucannnuu uugauugguu gguggcguau ucnngaaang ganacgucau ugucauagun 180
nnnnnnnncu uuuuuaannn nnnnnnacua uggagcgcua cugguugg 228

<210> SEQ ID NO 357
<211> LENGTH: 228
<212> TYPE: RNA
<213> ORGANISM: Staphylococcus aureus
<220> FEATURE:
<221> NAME/KEY: misc_feature
<222> LOCATION: 16-205
<223> OTHER INFORMATION: n = g, a, c or u

<400> SEQUENCE: 357
auauuuugau gaggcngcau canaucnaug naguannaag uuuagannuu annnnnncug 60
ucugcnnnnn uaacagcuga auuunngaaa ggnngugcga ugccgaagcg anuuauaaun 120
nagcannguu auaauuuguu ggacuuuuug gunnuaagag cungagaguu ugucauuauu 180
nnnnnnnnnn uaaannnnnn nnnnnaauaa uggagugcau cacuugua 228

<210> SEQ ID NO 358
<211> LENGTH: 228
<212> TYPE: RNA

<213> ORGANISM: Staphylococcus aureus
<220> FEATURE:
<221> NAME/KEY: misc_feature
<222> LOCATION: 26-223
<223> OTHER INFORMATION: n = g, a, c or u

<400> SEQUENCE: 358
aauugaguua gagguugcau guuuannauu naguannacu ugunnnnnca gaaguauuua 60
ugguacauaa guugannnac aagunngaaa ggnnuaaaga ugccgaaaua gauauaanna 120
ccauaaannu uauaucuauu gggacaguuu unncgaauan ggaacuguac ugucacannn 180
nnnnnnnnnn gaannnnnnn nnnnnnnnug ugaugugcua ncncuuau 228

<210> SEQ ID NO 359
<211> LENGTH: 228
<212> TYPE: RNA
<213> ORGANISM: Staphylococcus epidermidis
<220> FEATURE:
<221> NAME/KEY: misc_feature
<222> LOCATION: 16-206
<223> OTHER INFORMATION: n = g, a, c or u

<400> SEQUENCE: 359
agauuuugau gaggcngcau canaucnaug naguannaac uuuagauaau uugnnnucug 60
cuaannnnca anuuannuag aguunnaaaa ggngnugaga ugccgaaaug auucauaaun 120
nagcannguu augaaucguu ggacuuaaug gunnuaagag cuaunaaguu ugucauuauu 180
nnnnnnnnna uuaannnnnn nnnnnnauaa uggagugcau cacuugua 228

<210> SEQ ID NO 360
<211> LENGTH: 228
<212> TYPE: RNA
<213> ORGANISM: Staphylococcus epidermidis
<220> FEATURE:
<221> NAME/KEY: misc_feature
<222> LOCATION: 26-223
<223> OTHER INFORMATION: n = g, a, c or u

<400> SEQUENCE: 360
aauagaguua gagguugcau uauuannaug nacuannacu uaunnnnnca gaagucguau 60
gggacaugug uugannnnau aagunngaaa ggnnuaauaa ugccgaaaug auguuanuuu 120
nccaunaaau uagcauuguu gggacaacuu unncgaauan gaaguuguac ugucacnnnn 180
nnnnnnnnnn uuuannnnnn nnnnnnnnug ugaugugcua ncncuuau 228

<210> SEQ ID NO 361
<211> LENGTH: 228
<212> TYPE: RNA
<213> ORGANISM: Shigella flexneri
<220> FEATURE:
<221> NAME/KEY: misc_feature
<222> LOCATION: 16-167
<223> OTHER INFORMATION: n = g, a, c or u

<400> SEQUENCE: 361
caggccagaa gaggcngcgn unugcccann naguaacggu guuggnnnag gannnnnnng 60
ccagnnnnnu ccugugauaa caccnnnuga gggggugcau cgccgaggug auugaacgng 120
cuggccancg uucanucauc ggcuacaggg gncugaaunn ccccugnggu ugucaccaga 180
agcguucgca gucgggcguu ucgcaagugg uggagcacuu cuggguga 228

<210> SEQ ID NO 362
<211> LENGTH: 228
<212> TYPE: RNA

<213> ORGANISM: Shewanella oneidensis
<220> FEATURE:
<221> NAME/KEY: misc_feature
<222> LOCATION: 16-208
<223> OTHER INFORMATION: n = g, a, c or u

<400> SEQUENCE: 362
aggaacagaa gaggangcgu uaancunann ngguannguc aaucagannn ggagnnnnca 60
caaannncuc cagcgaugau ugaunnngag ggnagauuag cgccgaggca uagaugugnn 120
guugcugnca uguuuauguc ggucgcuuag gncugaaunn nccuaacgau ugucaccnnn 180
nnnnnnnnnu guaauunnnn nnnnnnnngg uggagagcuu cuggugac 228

<210> SEQ ID NO 363
<211> LENGTH: 228
<212> TYPE: RNA
<213> ORGANISM: Shewanella oneidensis
<220> FEATURE:
<221> NAME/KEY: misc_feature
<222> LOCATION: 16-206
<223> OTHER INFORMATION: n = g, a, c or u

<400> SEQUENCE: 363
ccuuuaagua gaggcngcgc ugccunnaug nacuanncuu gugcgnnnnn nnngagggug 60
augccgcaga nnnnnnugua caagnngaaa ggnnagucag cgccgaagua gcncaggunn 120
caucaannna ccgagcngcu gguuuugcau ncaaauagnn ngugcaagac ugccauagun 180
nnnnnnnnnc auccnnnnnn nnnnnnacua uggagcgcua ccugaagg 228

<210> SEQ ID NO 364
<211> LENGTH: 228
<212> TYPE: RNA
<213> ORGANISM: Thermatoga maritima
<220> FEATURE:
<221> NAME/KEY: misc_feature
<222> LOCATION: 8-204
<223> OTHER INFORMATION: n = g, a, c or u

<400> SEQUENCE: 364
gacccgancg gaggcngcgc ccgagnnaug naguanngge ugucccnnnn nnnnaucagg 60
ggaggaaucg nnnnngggac ggcunngaaa ggnncgaggg cgccgaaggn gugcagaguu 120
ccucccngcu cugcaugccu gggggguaugg gnnngaauan cccauaccac ugucacggag 180
gnnnnnnnnn ucnnnnnnnn nnnnucuccg uggagagccg aucggguc 228

<210> SEQ ID NO 365
<211> LENGTH: 228
<212> TYPE: RNA
<213> ORGANISM: Thermoanaerobacter tengcongensis
<220> FEATURE:
<221> NAME/KEY: misc_feature
<222> LOCATION: 16-201
<223> OTHER INFORMATION: n = g, a, c or u

<400> SEQUENCE: 365
aggugaggua gaggcngcgg gucaucnaag naguannaca ugccagannn ggunnnguua 60
aggnnnnngc cgaugaaggu gugunngaaa ggnggugncc cgccgaagcn gcguaaacuu 120
nccuuaaggu uuacgcagcu gggccuaugc cnnngaacan gguauaggac ugucacugaa 180
ggcunnnnnc cccannnnnn nggccuucag uggagagcua ucucgcua 228

<210> SEQ ID NO 366
<211> LENGTH: 228
<212> TYPE: RNA

<213> ORGANISM: Thermoanaerobacter tengcongensis
<220> FEATURE:
<221> NAME/KEY: misc_feature
<222> LOCATION: 16-205
<223> OTHER INFORMATION: n = g, a, c or u

<400> SEQUENCE: 366
cgcauaaaua gaggangcug ccaagcnaun nnguauuugg cgagguguua aggagaagaa 60
ccuccnnnnn nnaauancuc gcugnaagaa ggnnuuuggc ugccgaaagg gugagcuugn 120
nuucunnuga gcucauccuu ggugguaaac nnnacaaann nguuuaccac ugucauggga 180
nnnnnnnnnn ccnnnnnnnn nnnnnuccca ugaagcgcua uuuaugca 228

<210> SEQ ID NO 367
<211> LENGTH: 228
<212> TYPE: RNA
<213> ORGANISM: Vibrio cholerae
<220> FEATURE:
<221> NAME/KEY: misc_feature
<222> LOCATION: 16-206
<223> OTHER INFORMATION: n = g, a, c or u

<400> SEQUENCE: 367
ucuagcagaa gaggangcac ugnncccagg cagnauguuu uguggannnn nnnngccuca 60
acuccaaunn nnnnnnnnac agaacauuca gggggaguag ugccgaggug aaucaaaguu 120
ngunnnggcu uugguuuauc gguugaacgg gncugaaunn cccnuucaac ugucaucagn 180
nnnnnnnncu cgaaunnnnn nnnnnncuga ugaagagcuu cugaggga 228

<210> SEQ ID NO 368
<211> LENGTH: 228
<212> TYPE: RNA
<213> ORGANISM: Vibrio cholerae
<220> FEATURE:
<221> NAME/KEY: misc_feature
<222> LOCATION: 16-223
<223> OTHER INFORMATION: n = g, a, c or u

<400> SEQUENCE: 368
uuucgccgua gaggangcgg uuacgnnaaa naguannucc acaguunnnn nnnngggqug 60 augccaaugn nnnnnaauug uggannaaaa ggnncguugc cgccgaaguc aacuugcnnc 120
caucaacnng cnaguuggcu gggguuacau unnncaauan gguguaacac ugccauagun 180
nnnnncuaua uuguuguuaa nnnnnnacua uggagcgcua cnnuguag 228

<210> SEQ ID NO 369
<211> LENGTH: 228
<212> TYPE: RNA
<213> ORGANISM: Vibrio cholerae
<220> FEATURE:
<221> NAME/KEY: misc_feature
<222> LOCATION: 7-207
<223> OTHER INFORMATION: n = g, a, c or u

<400> SEQUENCE: 369
cuuuaangua gaggcngcgc uguucnnaug nagucgncca gucgunnnnn nnnnagguug 60
accccgaugn nnnnnnauga cuggnuuaaa ggnnguacag cgccgaagug aucguugnnn 120
cgucaunnnc aacguucgcu gggccagcau unnngaacan aaugccggac ugccauagnn 180
nnnnnnnnug uguugunnnn nnnnnnncua uggagcgcua ccuugaag 228

<210> SEQ ID NO 370
<211> LENGTH: 228
<212> TYPE: RNA

<213> ORGANISM: Vibrio vulnificus
<220> FEATURE:
<221> NAME/KEY: misc_feature
<222> LOCATION: 16-204
<223> OTHER INFORMATION: n = g, a, c or u

<400> SEQUENCE: 370
uuuugcagaa gaggangcac ugnncccagg cagnauguuu uguggannnn nnnngccgca 60
acuccaacnn nnnnnnnnac agaacauuca gggggaguag ugccgaggua gaucaaaauu 120
ngcanngauu ungaucuguc gguugacuug gguugagunc ccannucaac ugucaucagc 180
nnnnnnnnnn ucannnnnnn nnnngccuga ugaagagcuu cugagaug 228

<210> SEQ ID NO 371
<211> LENGTH: 228
<212> TYPE: RNA
<213> ORGANISM: Vibrio vulnificus
<220> FEATURE:
<221> NAME/KEY: misc_feature
<222> LOCATION: 16-206
<223> OTHER INFORMATION: n = g, a, c or u

<400> SEQUENCE: 371
uaucgacgua gaggcngcaa uggnuanaag naguannacu auuauunnnn nnnnggggug 60
augccaaugn nnnnnaauaa uagunngaaa ggnuauccau ugccgaagug aauugcnnna 120
uaucaaannn gcaguuugcu gggguugcau ccnngaaang gaancaacac ugccauagun 180
nnnnnnauuu aauguauann nnnnnnacua uggagcgcua cuguaggu 228

<210> SEQ ID NO 372
<211> LENGTH: 486
<212> TYPE: DNA
<213> ORGANISM: Artificial Sequence
<220> FEATURE:
<223> OTHER INFORMATION: Description of Artificial
Sequence:/Note=Synthetic construct
<220> FEATURE:
<221> NAME/KEY: misc_feature
<222> LOCATION: 1-486
<223> OTHER INFORMATION: n = g, a, c or t/u
<220> FEATURE:
<221> NAME/KEY: misc_feature
<222> LOCATION: 28, 54, 61, 145, 161, 170, 171, 207, 208, 213, 216, 217,
219, 220, 309-313
<223> OTHER INFORMATION: r = a or g
<220> FEATURE:
<221> NAME/KEY: misc_feature
<222> LOCATION: 9, 27, 37, 50, 70, 152, 203, 204, 271-275, 320
<223> OTHER INFORMATION: y = c or t/u

<400> SEQUENCE: 372
nnnnnnnnyc ttatcnagag nnnnggyrga gggannyngg nnnncccnny ganrccnnnc 60
rgcaacnnny nnnnnnnnnn nnnnnnnnnn nnnnnnnnnn nnnnnnnnnn nnnnnnnnnn 120
nnnnnnnnnn nnnnnnnnnn nnnnrnngtg cyaantnccn rnnnnnncar rnnnnnnnnn 180
nnnnnnnnnn nnnnnnnnnn nnyytgrrag atragrrnrr nnnnnnnnnn nnnnnnnnnn 240
nnnnnnnnnn nnnnnnnnnn nnnnnnnnnn yyyyynnnnn nnnnnnnnnn nnnnnnnnnn 300
nnnnnnnnrr rrrnnttttty nnnnnnnnnn nnnnnnnnnn nnnnnnnnnn nnnnnnnnnn 360
nnnnnnnnnn nnnnnnnnnn nnnnnnnnnn nnnnnnnnnn nnnnnnnnnn nnnnnnnnnn 420
nnnnnnnnnn nnnnnnnnnn nnnnnnnnnn nnnnnnnnnn nnnnnnnnnn nnnnnnnnnn 480 nnnnnn 486

<210> SEQ ID NO 373

```
<211> LENGTH: 504
<212> TYPE: RNA
<213> ORGANISM: Artificial Sequence
<220> FEATURE:
<223> OTHER INFORMATION: Description of Artificial
      Sequence:/Note=Synthetic construct
<220> FEATURE:
<221> NAME/KEY: misc_feature
<222> LOCATION: 1-504
<223> OTHER INFORMATION: n = g, a, c or u
<220> FEATURE:
<221> NAME/KEY: misc_feature
<222> LOCATION: 75, 98, 128, 136, 139, 151, 156, 161, 297, 479, 486
<223> OTHER INFORMATION: r = a or g
<220> FEATURE:
<221> NAME/KEY: misc_feature
<222> LOCATION: 29, 94, 143, 298, 379, 387, 474, 476, 482
<223> OTHER INFORMATION: y = c or u

<400> SEQUENCE: 373

nnnnnnnnnn nnnnnnnnnn nnggunnnyn nnnnnnnnnn nnnnnnnnnn nnnnnnnnnn     60

nnnnnnnnnn nnnnrnnnnn aannngggaa nnnyggurnn nnnnnnnnnn nnnnnnnnnn    120

nnnnnnnran nnnccrnnrc ngynccccgcn rcngurannn rnnnnnnnnn nnnnnnnnnn    180

nnnnnnnnnn nnnnnnnnnn nnnnnnnnnn nnnnnnnnnn nnnnnnnnnn nnnnnnnnnn    240

nnnnnnnnnn nnnnnnnnnn nnnnnnnnnn nnnnnnnnnn nnnnnnnnnn nnnnnnryca    300

cugnnnnnnn nnnnnnnnnn nnnnnnnnnn nnnnnnnnnn nnnnnnnnnn nnnnnnnnnn    360

nnnnnnnnnn nnnnnnnnyg ggaaggynnn nnnnnnnnnn nnnnnnnnnn nnnnnnnnnn    420

nnnnnnnnnn nnnnnnnnnn nnnnnnnnnn nnnnnnnnnn nnnnnnnnnn nnnynynnra    480

gycngragac cngccnnnnn nnnn                                            504


<210> SEQ ID NO 374
<211> LENGTH: 83
<212> TYPE: DNA
<213> ORGANISM: Artificial Sequence
<220> FEATURE:
<223> OTHER INFORMATION: Description of Artificial Sequence:/Note =
      synthetic construct
<220> FEATURE:
<221> NAME/KEY: misc_feature
<222> LOCATION: 1-83
<223> OTHER INFORMATION: n = g, a, c or t/u
<220> FEATURE:
<221> NAME/KEY: misc_feature
<222> LOCATION: 74, 76
<223> OTHER INFORMATION: r = a or g
<220> FEATURE:
<221> NAME/KEY: misc_feature
<222> LOCATION: 13, 71
<223> OTHER INFORMATION: w = a or t/u
<220> FEATURE:
<221> NAME/KEY: misc_feature
<222> LOCATION: 10, 42, 70, 73
<223> OTHER INFORMATION: y = c or t/u

<400> SEQUENCE: 374

nnnnnnnnny ntwtannnnn nnnnatnngg nnnnnnnngt nyctacnnnn nnnccnnnaa     60

nnnnnnnnny wayrnrnnnn nnn                                             83


<210> SEQ ID NO 375
<211> LENGTH: 238
<212> TYPE: DNA
<213> ORGANISM: Artificial Sequence
<220> FEATURE:
<223> OTHER INFORMATION: Description of Artificial Sequence:/Note =
      Synthetic construct
<220> FEATURE:
<221> NAME/KEY: misc_feature
```

<222> LOCATION: 7-233
<223> OTHER INFORMATION: n = g, a, c or t/u
<220> FEATURE:
<221> NAME/KEY: misc_feature
<222> LOCATION: 234, 237
<223> OTHER INFORMATION: r = a or g
<220> FEATURE:
<221> NAME/KEY: misc_feature
<222> LOCATION: 209
<223> OTHER INFORMATION: y = c or t/u

<400> SEQUENCE: 375
ctgagannnn nnnnnnnnnn nnnnnnnnnn nnnnnnnnnn nnnnnnnnnn nnnnnnnnnn 60
nnnnnnnnnn nnnnnnnnnn nnnnnnnnnn nnnnnnnnnn nnnnnnnnnn nnnnnnnnnn 120
nnnnnnnnnn nnnnnnnnnn nnnnnnnnnn nnnnnnnnnn nnnnnnnnnn nnnnnnnnnn 180
nnnnnnnnnn nnnnnnnnnn nnnnnnacyt gannnnngnt nnnncnnnnn cgnrggra 238

<210> SEQ ID NO 376
<211> LENGTH: 221
<212> TYPE: DNA
<213> ORGANISM: Bacillus subtilis
<220> FEATURE:
<221> NAME/KEY: misc_feature
<222> LOCATION: 25
<223> OTHER INFORMATION: k = g or t/u
<220> FEATURE:
<221> NAME/KEY: misc_feature
<222> LOCATION: 7-217
<223> OTHER INFORMATION: n = g, a, c or t/u
<220> FEATURE:
<221> NAME/KEY: misc_feature
<222> LOCATION: 24, 78, 79, 81, 96, 97, 213
<223> OTHER INFORMATION: r = a or g
<220> FEATURE:
<221> NAME/KEY: misc_feature
<222> LOCATION: 153
<223> OTHER INFORMATION: v = g, c or a
<220> FEATURE:
<221> NAME/KEY: misc_feature
<222> LOCATION: 1, 214, 220
<223> OTHER INFORMATION: w = a or t/u
<220> FEATURE:
<221> NAME/KEY: misc_feature
<222> LOCATION: 169, 221
<223> OTHER INFORMATION: y = c or t/u

<400> SEQUENCE: 376
wagaggngcn nnnnnnnnna nnnrktannn nnnnnnnnnn nnnnnnnnnn nnnnnnnnnn 60
nnnnnnnnnn nnnnnnnrrg rnnnnnnnnn nccgarrnnn nnnnnnnnnn nnnnnnnnnn 120
nnnnnnnnnn nnnnnnnggn nnnnnnnnnn nnvaannnnn nnnnnnnnyt gtcannnnnn 180
nnnnnnnnnn nnnnnnnnnn nnnnnnnnnn tgrwgnnctw y 221

<210> SEQ ID NO 377
<211> LENGTH: 54
<212> TYPE: DNA
<213> ORGANISM: Artificial Sequence
<220> FEATURE:
<223> OTHER INFORMATION: Description of Artificial Sequence:/Note =
Synthetic construct
<220> FEATURE:
<221> NAME/KEY: misc_feature
<222> LOCATION: 1-54
<223> OTHER INFORMATION: n = g, a, c or t/u

<400> SEQUENCE: 377
nntannnnnn nnatnnggnn nnnnngtntc tacnnnnnnc cnnnaannnn nnnn 54

<210> SEQ ID NO 378

```
<211> LENGTH: 19
<212> TYPE: RNA
<213> ORGANISM: Artificial Sequence
<220> FEATURE:
<223> OTHER INFORMATION: Description of Artificial Sequence:/Note =
      synthetic construct
<220> FEATURE:
<221> NAME/KEY: misc_feature
<222> LOCATION: 1-2, 5-6, 12-14, 18-19
<223> OTHER INFORMATION: n = g, a, c or u

<400> SEQUENCE: 378

nnaannggga annnggunn                                                  19

<210> SEQ ID NO 379
<211> LENGTH: 31
<212> TYPE: RNA
<213> ORGANISM: Artificial Sequence
<220> FEATURE:
<223> OTHER INFORMATION: Description of Artificial Sequence:/Note =
      synthetic construct
<220> FEATURE:
<221> NAME/KEY: misc_feature
<222> LOCATION: 3-4, 7-9, 12, 14-15, 21, 24, 28-30
<223> OTHER INFORMATION: n = g, a, c or u
<220> FEATURE:
<221> NAME/KEY: misc_feature
<222> LOCATION: 1, 10, 22, 27, 31
<223> OTHER INFORMATION: r = a or g

<400> SEQUENCE: 379

rannccnnnr cgnncccgc nrcngurnnn r                                     31

<210> SEQ ID NO 380
<211> LENGTH: 7
<212> TYPE: RNA
<213> ORGANISM: Artificial Sequence
<220> FEATURE:
<223> OTHER INFORMATION: Description of Artificial Sequence:/Note =
      synthetic construct
<220> FEATURE:
<221> NAME/KEY: misc_feature
<222> LOCATION: 1-2
<223> OTHER INFORMATION: n = g, a, c or u

<400> SEQUENCE: 380

nncacug                                                                7

<210> SEQ ID NO 381
<211> LENGTH: 9
<212> TYPE: RNA
<213> ORGANISM: Artificial Sequence
<220> FEATURE:
<223> OTHER INFORMATION: Description of Artificial Sequence:/Note =
      synthetic construct
<220> FEATURE:
<221> NAME/KEY: misc_feature
<222> LOCATION: 9
<223> OTHER INFORMATION: n = g, a, c or u
<220> FEATURE:
<221> NAME/KEY: misc_feature
<222> LOCATION: 1
<223> OTHER INFORMATION: y = c or u

<400> SEQUENCE: 381

ygggaaggn                                                              9

<210> SEQ ID NO 382
<211> LENGTH: 20
<212> TYPE: RNA
<213> ORGANISM: Artificial Sequence
<220> FEATURE:
```

<223> OTHER INFORMATION: Description of Artificial Sequence:/Note =
synthetic construct
<220> FEATURE:
<221> NAME/KEY: misc_feature
<222> LOCATION: 1-3, 9, 13, 17
<223> OTHER INFORMATION: n = g, a, c or u
<220> FEATURE:
<221> NAME/KEY: misc_feature
<222> LOCATION: 4, 11
<223> OTHER INFORMATION: r = a or g
<220> FEATURE:
<221> NAME/KEY: misc_feature
<222> LOCATION: 7
<223> OTHER INFORMATION: y = c or u

<400> SEQUENCE: 382
nnnragycng ranaccngcc 20

<210> SEQ ID NO 383
<211> LENGTH: 6
<212> TYPE: RNA
<213> ORGANISM: Artificial Sequence
<220> FEATURE:
<223> OTHER INFORMATION: Description of Artificial Sequence:/Note =
synthetic construct

<400> SEQUENCE: 383 cugaga 6

<210> SEQ ID NO 384
<211> LENGTH: 20
<212> TYPE: RNA
<213> ORGANISM: Artificial Sequence
<220> FEATURE:
<223> OTHER INFORMATION: Description of Artificial Sequence:/Note =
synthetic construct
<220> FEATURE:
<221> NAME/KEY: misc_feature
<222> LOCATION: 2-9, 15-19
<223> OTHER INFORMATION: n = g, a, c or u

<400> SEQUENCE: 384
annnnnnnna ccugnnnnnc 20

<210> SEQ ID NO 385
<211> LENGTH: 19
<212> TYPE: RNA
<213> ORGANISM: Artificial Sequence
<220> FEATURE:
<223> OTHER INFORMATION: Description of Artificial Sequence:/Note =
synthetic construct
<220> FEATURE:
<221> NAME/KEY: misc_feature
<222> LOCATION: 14
<223> OTHER INFORMATION: d = g, a, or u
<220> FEATURE:
<221> NAME/KEY: misc_feature
<222> LOCATION: 2-7, 9-11
<223> OTHER INFORMATION: n = g, a, c or u
<220> FEATURE:
<221> NAME/KEY: misc_feature
<222> LOCATION: 18
<223> OTHER INFORMATION: r = a or g

<400> SEQUENCE: 385
unnnnnngnn ncgdaggra 19

<210> SEQ ID NO 386
<211> LENGTH: 9
<212> TYPE: RNA
<213> ORGANISM: Artificial Sequence
<220> FEATURE:

<223> OTHER INFORMATION: Description of Artificial Sequence:/Note = synthetic construct
<220> FEATURE:
<221> NAME/KEY: misc_feature
<222> LOCATION: 9
<223> OTHER INFORMATION: n = g, a, c or u
<220> FEATURE:
<221> NAME/KEY: misc_feature
<222> LOCATION: 6
<223> OTHER INFORMATION: r = a or g
<220> FEATURE:
<221> NAME/KEY: misc_feature
<222> LOCATION: 3, 7
<223> OTHER INFORMATION: y = c or u

<400> SEQUENCE: 386 agyccrygn 9

<210> SEQ ID NO 387
<211> LENGTH: 50
<212> TYPE: RNA
<213> ORGANISM: Artificial Sequence
<220> FEATURE:
<223> OTHER INFORMATION: Description of Artificial Sequence:/Note = synthetic construct
<220> FEATURE:
<221> NAME/KEY: misc_feature
<222> LOCATION: 10, 15
<223> OTHER INFORMATION: k = g or u
<220> FEATURE:
<221> NAME/KEY: misc_feature
<222> LOCATION: 1, 11, 14, 30-32
<223> OTHER INFORMATION: n = g, a, c or u
<220> FEATURE:
<221> NAME/KEY: misc_feature
<222> LOCATION: 7, 12, 18-21, 27, 43-44, 48-50
<223> OTHER INFORMATION: r = a or g
<220> FEATURE:
<221> NAME/KEY: misc_feature
<222> LOCATION: 4-6, 17, 37
<223> OTHER INFORMATION: y = c or u

<400> SEQUENCE: 387
ngayyyrguk nrankcyrrr rccgacrgun nnagucygga ugrragarrr 50

<210> SEQ ID NO 388
<211> LENGTH: 18
<212> TYPE: RNA
<213> ORGANISM: Artificial Sequence
<220> FEATURE:
<223> OTHER INFORMATION: Description of Artificial Sequence:/Note = synthetic construct
<220> FEATURE:
<221> NAME/KEY: misc_feature
<222> LOCATION: 1-2, 9-10, 13-16, 18
<223> OTHER INFORMATION: n = g, a, c or u
<220> FEATURE:
<221> NAME/KEY: misc_feature
<222> LOCATION: 17
<223> OTHER INFORMATION: r = a or g
<220> FEATURE:
<221> NAME/KEY: misc_feature
<222> LOCATION: 7
<223> OTHER INFORMATION: y = c or u

<400> SEQUENCE: 388
nngugcyann ccnnnnrn 18

<210> SEQ ID NO 389
<211> LENGTH: 14
<212> TYPE: RNA
<213> ORGANISM: Artificial Sequence
<220> FEATURE:
<223> OTHER INFORMATION: Description of Artificial Sequence:/Note = synthetic construct
<220> FEATURE:
<221> NAME/KEY: misc_feature
<222> LOCATION: 1, 3-4, 6-7, 14
<223> OTHER INFORMATION: n = g, a, c or u
<220> FEATURE:
<221> NAME/KEY: misc_feature
<222> LOCATION: 5, 11
<223> OTHER INFORMATION: r = a or g
<220> FEATURE:
<221> NAME/KEY: misc_feature
<222> LOCATION: 2
<223> OTHER INFORMATION: y = c or u

<400> SEQUENCE: 389
nynnrnngau ragn 14

<210> SEQ ID NO 390
<211> LENGTH: 3
<212> TYPE: RNA
<213> ORGANISM: Artificial Sequence
<220> FEATURE:
<223> OTHER INFORMATION: Description of Artificial Sequence:/Note =
synthetic construct

<400> SEQUENCE: 390 gag 3

<210> SEQ ID NO 391
<211> LENGTH: 2
<212> TYPE: RNA
<213> ORGANISM: Artificial Sequence
<220> FEATURE:
<223> OTHER INFORMATION: Description of Artificial Sequence:/Note =
synthetic construct
<220> FEATURE:
<221> NAME/KEY: misc_feature
<222> LOCATION: 1-2
<223> OTHER INFORMATION: n = g, a, c or u

<400> SEQUENCE: 391 nn 2

<210> SEQ ID NO 392
<211> LENGTH: 2
<212> TYPE: RNA
<213> ORGANISM: Artificial Sequence
<220> FEATURE:
<223> OTHER INFORMATION: Description of Artificial Sequence:/Note =
synthetic construct
<220> FEATURE:
<221> NAME/KEY: misc_feature
<222> LOCATION: 1-2
<223> OTHER INFORMATION: n = g, a, c or u

<400> SEQUENCE: 392 nn 2

<210> SEQ ID NO 393
<211> LENGTH: 44
<212> TYPE: RNA
<213> ORGANISM: Artificial Sequence
<220> FEATURE:
<223> OTHER INFORMATION: Description of Artificial Sequence:/Note =
synthetic construct
<220> FEATURE:
<221> NAME/KEY: misc_feature
<222> LOCATION: 1-8, 14-20, 21-22, 32-44
<223> OTHER INFORMATION: n = g, a, c or u
<220> FEATURE:
<221> NAME/KEY: misc_feature
<222> LOCATION: 9-10, 29

<223> OTHER INFORMATION: r = a or g
<220> FEATURE:
<221> NAME/KEY: misc_feature
<222> LOCATION: 23, 31
<223> OTHER INFORMATION: y = c or u

<400> SEQUENCE: 393
nnnnnnnnrr aggnnnnnnn nnygccgarg ynnnnnnnnn nnnn 44

<210> SEQ ID NO 394
<211> LENGTH: 28
<212> TYPE: RNA
<213> ORGANISM: Artificial Sequence
<220> FEATURE:
<223> OTHER INFORMATION: Description of Artificial Sequence:/Note = synthetic construct
<220> FEATURE:
<221> NAME/KEY: misc_feature
<222> LOCATION: 1-12, 18-28
<223> OTHER INFORMATION: n = g, a, c or u
<220> FEATURE:
<221> NAME/KEY: misc_feature
<222> LOCATION: 13
<223> OTHER INFORMATION: r = a or g
<220> FEATURE:
<221> NAME/KEY: misc_feature
<222> LOCATION: 14
<223> OTHER INFORMATION: y = c or u

<400> SEQUENCE: 394
nnnnnnnnnn nnryuggnnn nnnnnnnn 28

<210> SEQ ID NO 395
<211> LENGTH: 2
<212> TYPE: RNA
<213> ORGANISM: Artificial Sequence
<220> FEATURE:
<223> OTHER INFORMATION: Description of Artificial Sequence:/Note = synthetic construct

<400> SEQUENCE: 395 aa 2

<210> SEQ ID NO 396
<211> LENGTH: 17
<212> TYPE: RNA
<213> ORGANISM: Artificial Sequence
<220> FEATURE:
<223> OTHER INFORMATION: Description of Artificial Sequence:/Note = synthetic construct
<220> FEATURE:
<221> NAME/KEY: misc_feature
<222> LOCATION: 1-11
<223> OTHER INFORMATION: n = g, a, c or u
<220> FEATURE:
<221> NAME/KEY: misc_feature
<222> LOCATION: 12
<223> OTHER INFORMATION: y = c or u

<400> SEQUENCE: 396
nnnnnnnnnn nyuguca 17

<210> SEQ ID NO 397
<211> LENGTH: 11
<212> TYPE: RNA
<213> ORGANISM: Artificial Sequence
<220> FEATURE:
<223> OTHER INFORMATION: Description of Artificial Sequence:/Note = synthetic construct
<220> FEATURE:
<221> NAME/KEY: misc_feature
<222> LOCATION: 6

<223> OTHER INFORMATION: n = g, a, c or u
<220> FEATURE:
<221> NAME/KEY: misc_feature
<222> LOCATION: 7
<223> OTHER INFORMATION: r = a or g
<220> FEATURE:
<221> NAME/KEY: misc_feature
<222> LOCATION: 10
<223> OTHER INFORMATION: w = a or u
<220> FEATURE:
<221> NAME/KEY: misc_feature
<222> LOCATION: 11
<223> OTHER INFORMATION: y = c or u

<400> SEQUENCE: 397
uggagnrcuw y 11

<210> SEQ ID NO 398
<211> LENGTH: 20
<212> TYPE: RNA
<213> ORGANISM: Arabidopsis thaliana
<220> FEATURE:
<221> NAME/KEY: misc_feature
<222> LOCATION: 2-9, 17-19
<223> OTHER INFORMATION: n = g, a, c or u

<400> SEQUENCE: 398
annnnnnnna ccugaunnng 20

<210> SEQ ID NO 399
<211> LENGTH: 22
<212> TYPE: RNA
<213> ORGANISM: Arabidopsis thaliana
<220> FEATURE:
<221> NAME/KEY: misc_feature
<222> LOCATION: 14
<223> OTHER INFORMATION: d = g, a, or u
<220> FEATURE:
<221> NAME/KEY: misc_feature
<222> LOCATION: 2-7, 9-11, 20-22
<223> OTHER INFORMATION: n = g, a, c or u
<220> FEATURE:
<221> NAME/KEY: misc_feature
<222> LOCATION: 18
<223> OTHER INFORMATION: r = a or g

<400> SEQUENCE: 399
unnnnnncnn ncgdaggran nn 22

<210> SEQ ID NO 400
<211> LENGTH: 7
<212> TYPE: RNA
<213> ORGANISM: Bacillus subtilis
<220> FEATURE:
<221> NAME/KEY: misc_feature
<222> LOCATION: 1-7
<223> OTHER INFORMATION: n = g, a, c or u

<400> SEQUENCE: 400 nnnnnnn 7

<210> SEQ ID NO 401
<211> LENGTH: 3
<212> TYPE: RNA
<213> ORGANISM: Bacillus subtilis

<400> SEQUENCE: 401 gag 3

-continued

<210> SEQ ID NO 402
<211> LENGTH: 2
<212> TYPE: RNA
<213> ORGANISM: Bacillus subtilis
<220> FEATURE:
<221> NAME/KEY: misc_feature
<222> LOCATION: 1-2
<223> OTHER INFORMATION: n = g, a, c or u

<400> SEQUENCE: 402 nn 2

<210> SEQ ID NO 403
<211> LENGTH: 2
<212> TYPE: RNA
<213> ORGANISM: Bacillus subtilis
<220> FEATURE:
<221> NAME/KEY: misc_feature
<222> LOCATION: 1-2
<223> OTHER INFORMATION: n = g, a, c or u

<400> SEQUENCE: 403 nn 2

<210> SEQ ID NO 404
<211> LENGTH: 38
<212> TYPE: RNA
<213> ORGANISM: Bacillus subtilis
<220> FEATURE:
<221> NAME/KEY: misc_feature
<222> LOCATION: 1-8, 14-20, 30-38
<223> OTHER INFORMATION: n = g, a, c or u
<220> FEATURE:
<221> NAME/KEY: misc_feature
<222> LOCATION: 9-10, 27
<223> OTHER INFORMATION: r = a or g
<220> FEATURE:
<221> NAME/KEY: misc_feature
<222> LOCATION: 21, 29
<223> OTHER INFORMATION: y = c or u

<400> SEQUENCE: 404
nnnnnnnnrr aggnnnnnnn ygccgargyn nnnnnnnn 38

<210> SEQ ID NO 405
<211> LENGTH: 23
<212> TYPE: RNA
<213> ORGANISM: Bacillus subtilis
<220> FEATURE:
<221> NAME/KEY: misc_feature
<222> LOCATION: 1-9, 15-23
<223> OTHER INFORMATION: n = g, a, c or u
<220> FEATURE:
<221> NAME/KEY: misc_feature
<222> LOCATION: 10
<223> OTHER INFORMATION: r = a or g
<220> FEATURE:
<221> NAME/KEY: misc_feature
<222> LOCATION: 11
<223> OTHER INFORMATION: y = c or u

<400> SEQUENCE: 405
nnnnnnnnnr yuggnnnnnn nnn 23

<210> SEQ ID NO 406
<211> LENGTH: 2
<212> TYPE: RNA
<213> ORGANISM: Bacillus subtilis

<400> SEQUENCE: 406 aa 2

<210> SEQ ID NO 407
<211> LENGTH: 15
<212> TYPE: RNA
<213> ORGANISM: Bacillus subtilis
<220> FEATURE:
<221> NAME/KEY: misc_feature
<222> LOCATION: 1-9
<223> OTHER INFORMATION: n = g, a, c or u
<220> FEATURE:
<221> NAME/KEY: misc_feature
<222> LOCATION: 10
<223> OTHER INFORMATION: y = c or u

<400> SEQUENCE: 407
nnnnnnnnny uguca 15

<210> SEQ ID NO 408
<211> LENGTH: 11
<212> TYPE: RNA
<213> ORGANISM: Bacillus subtilis
<220> FEATURE:
<221> NAME/KEY: misc_feature
<222> LOCATION: 6
<223> OTHER INFORMATION: n = g, a, c or u
<220> FEATURE:
<221> NAME/KEY: misc_feature
<222> LOCATION: 7
<223> OTHER INFORMATION: r = a or g
<220> FEATURE:
<221> NAME/KEY: misc_feature
<222> LOCATION: 10
<223> OTHER INFORMATION: w = c or u
<220> FEATURE:
<221> NAME/KEY: misc_feature
<222> LOCATION: 11
<223> OTHER INFORMATION: y = c or u

<400> SEQUENCE: 408
uggagnrcuw y 11

<210> SEQ ID NO 409
<211> LENGTH: 20
<212> TYPE: RNA
<213> ORGANISM: Bacillus subtilis
<220> FEATURE:
<221> NAME/KEY: misc_feature
<222> LOCATION: 2-3, 11, 15
<223> OTHER INFORMATION: n = g, a, c or u
<220> FEATURE:
<221> NAME/KEY: misc_feature
<222> LOCATION: 1, 16, 19-20
<223> OTHER INFORMATION: r = a or g
<220> FEATURE:
<221> NAME/KEY: misc_feature
<222> LOCATION: 8
<223> OTHER INFORMATION: y = c or u

<400> SEQUENCE: 409
rnngugcyaa nuccnrcarr 20

<210> SEQ ID NO 410
<211> LENGTH: 14
<212> TYPE: RNA
<213> ORGANISM: Bacillus subtilis
<220> FEATURE:
<221> NAME/KEY: misc_feature
<222> LOCATION: 5-6, 11, 14
<223> OTHER INFORMATION: r = a or g
<220> FEATURE:

-continued

```
<221> NAME/KEY: misc_feature
<222> LOCATION: 1-2
<223> OTHER INFORMATION: y = c or u

<400> SEQUENCE: 410

yyugrragau ragr                                                    14
```

RIBOSWITCHES, METHODS FOR THEIR USE, AND COMPOSITIONS FOR USE WITH RIBOSWITCHES

CROSS-REFERENCE TO RELATED APPLICATIONS

This application is a Divisional Application of U.S. application Ser. No. 12/492,866, filed Jun. 26, 2009, which is a Divisional Application of U.S. application Ser. No. 10/669,162, filed Sep. 22, 2003, which claims benefit of U.S. Provisional Application No. 60/412,468, filed Sep. 20, 2002. U.S. application Ser. No. 12/492,866, filed Jun. 26, 2009, U.S. application Ser. No. 10/669,162, filed Sep. 22, 2003, and U.S. Provisional Application No. 60/412,468, filed Sep. 20, 2002, are hereby incorporated herein by reference in their entirety.

STATEMENT REGARDING FEDERALLY SPONSORED RESEARCH

This invention was made with government support under Grants NIH GM48858 and NIH GM559343 awarded by the National Institutes of Health, and Grant NSF EIA-0129939 awared by the National Science Foundation. The government has certain rights in the invention.

REFERENCE TO SEQUENCE LISTING

The Sequence Listing submitted February 23, 2011 as a text file named "YU_6_8405_AMD_AFD_Sequence_Listing.txt," created on Feb. 17, 2011, and having a size of 234,979 bytes is hereby incorporated by reference pursuant to 37 C.F.R. §1.52(e)(5).

FIELD OF THE INVENTION

The disclosed invention is generally in the field of gene expression and specifically in the area of regulation of gene expression.

BACKGROUND OF THE INVENTION

Precision genetic control is an essential feature of living systems, as cells must respond to a multitude of biochemical signals and environmental cues by varying genetic expression patterns. Most known mechanisms of genetic control involve the use of protein factors that sense chemical or physical stimuli and then modulate gene expression by selectively interacting with the relevant DNA or messenger RNA sequence. Proteins can adopt complex shapes and carry out a variety of functions that permit living systems to sense accurately their chemical and physical environments. Protein factors that respond to metabolites typically act by binding DNA to modulate transcription initiation (e.g. the lac repressor protein; Matthews, K. S., and Nichols, J. C., 1998, Prog. Nucleic Acids Res. Mol. Biol. 58, 127-164) or by binding RNA to control either transcription termination (e.g. the PyrR protein; Switzer, R. L., et al., 1999, Prog. Nucleic Acids Res. Mol. Biol. 62, 329-367) or translation (e.g. the TRAP protein; Babitzke, P., and Gollnick, P., 2001, J. Bacteriol. 183, 5795-5802). Protein factors responds to environmental stimuli by various mechanisms such as allosteric modulation or post-translational modification, and are adept at exploiting these mechanisms to serve as highly responsive genetic switches (e.g. see Ptashne, M., and Gann, A. (2002). Genes and Signals. Cold Spring Harbor Laboratory Press, Cold Spring Harbor, N.Y.).

In addition to the widespread participation of protein factors in genetic control, it is also known that RNA can take an active role in genetic regulation. Recent studies have begun to reveal the substantial role that small non-coding RNAs play in selectively targeting mRNAs for destruction, which results in down-regulation of gene expression (e.g. see Hannon, G. J. 2002, Nature 418, 244-251 and references therein). This process of RNA interference takes advantage of the ability of short RNAs to recognize the intended mRNA target selectively via Watson-Crick base complementation, after which the bound mRNAs are destroyed by the action of proteins. RNAs are ideal agents for molecular recognition in this system because it is far easier to generate new target-specific RNA factors through evolutionary processes than it would be to generate protein factors with novel but highly specific RNA binding sites.

Although proteins fulfill most requirements that biology has for enzyme, receptor and structural functions, RNA also can serve in these capacities. For example, RNA has sufficient structural plasticity to form numerous ribozyme domains (Cech & Golden, Building a catalytic active site using only RNA. In: *The RNA World* R. F. Gesteland, T. R. Cech, J. F. Atkins, eds., pp. 321-350 (1998); Breaker, In vitro selection of catalytic polynucleotides. *Chem. Rev.* 97, 371-390 (1997)) and receptor domains (Osborne & Ellington, Nucleic acid selection and the challenge of combinatorial chemistry. *Chem. Rev.* 97, 349-370 (1997); Hermann & Patel, Adaptive recognition by nucleic acid aptamers. *Science* 287, 820-825 (2000)) that exhibit considerable enzymatic power and precise molecular recognition. Furthermore, these activities can be combined to create allosteric ribozymes (Soukup & Breaker, Engineering precision RNA molecular switches. *Proc. Natl. Acad. Sci. USA* 96, 3584-3589 (1999); Seetharaman et al., Immobilized riboswitches for the analysis of complex chemical and biological mixtures. *Nature Biotechnol.* 19, 336-341 (2001)) that are selectively modulated by effector molecules.

These properties of RNA are consistent with speculation (Gold et al., From oligonucleotide shapes to genomic SELEX: novel biological regulatory loops. *Proc. Natl. Acad. Sci. USA* 94, 59-64 (1997); Gold et al., SELEX and the evolution of genomes. *Curr. Opin. Gen. Dev.* 7, 848-851 (1997); Nou & Kadner, Adenosylcobalamin inhibits ribosome binding to btuB RNA. *Proc. Natl. Acad. Sci. USA* 97, 7190-7195 (2000); Gelfand et al., A conserved RNA structure element involved in the regulation of bacterial riboflavin synthesis genes. *Trends Gen.* 15, 439-442 (1999); Miranda-Rios et al., A conserved RNA structure (thi box) is involved in regulation of thiamin biosynthetic gene expression in bacteria. *Proc. Natl. Acad. Sci. USA* 98, 9736-9741 (2001); Stormo & Ji, Do mRNAs act as direct sensors of small molecules to control their expression? *Proc. Natl. Acad. Sci. USA* 98, 9465-9467 (2001)) that certain mRNAs might employ allosteric mechanisms to provide genetic regulatory responses to the presence of specific metabolites. Although a thiamine pyrophosphate (TPP)-dependent sensor/regulatory protein had been proposed to participate in the control of thiamine biosynthetic genes (Webb & Downs, Characterization of thiL, encoding thiamin-monophosphate kinase, in *Salmonella typhimurium*. *J. Biol. Chem.* 272, 15702-15707 (1997)), no such protein factor has been shown to exist.

Transcription of the lysC gene of *B. subtilis* is repressed by high concentrations of lysine (Kochhar, S., and Paulus, H. 1996, *Microbiol.* 142:1635-1639; Mader, U., et al., 2002, *J. Bacteriol.* 184:4288-4295; Patte, J. C. 1996. Biosynthesis of lysine and threonine. In: *Escherichia coli* and *Salmonella: Cellular and Molecular Biology*, F. C. Neidhardt, et al., eds., Vol. 1, pp. 528-541. ASM Press, Washington, DC; Patte, J.-C., et al., 1998, *FEMS Microbiol. Lett.* 169:165-170), but that no protein factor had been identified that served as the genetic regulator (Liao, H.-H., and Hseu, T.-H. 1998, *FEMS Microbiol. Lett.* 168:31-36). The lysC gene encodes aspartokinase II, which catalyzes the first step in the metabolic pathway that converts L-aspartic acid into L-lysine (Belitsky, B. R. 2002. Biosynthesis of amino acids of the glutamate and aspartate families, alanine, and polyamines. In: *Bacillus subtilis* and its *Closest Relatives: from Genes to Cells*. A. L. Sonenshein, J.A. Hoch, and R. Losick, eds., ASM Press, Washington, D.C.).

BRIEF SUMMARY OF THE INVENTION

It has been discovered that certain natural mRNAs serve as metabolite-sensitive genetic switches wherein the RNA directly binds a small organic molecule. This binding process changes the conformation of the mRNA, which causes a change in gene expression by a variety of different mechanisms. Modified versions of these natural "riboswitches" (created by using various nucleic acid engineering strategies) can be employed as designer genetic switches that are controlled by specific effector compounds. Such effector compounds that activate a riboswitch are referred to herein as trigger molecules. The natural switches are targets for antibiotics and other small molecule therapies. In addition, the architecture of riboswitches allows actual pieces of the natural switches to be used to construct new non-immunogenic genetic control elements, for example the aptamer (molecular recognition) domain can be swapped with other non-natural aptamers (or otherwise modified) such that the new recognition domain causes genetic modulation with user-defined effector compounds. The changed switches become part of a therapy regimen—turning on, or off, or regulating protein synthesis. Newly constructed genetic regulation networks can be applied in such areas as living biosensors, metabolic engineering of organisms, and in advanced forms of gene therapy treatments.

Disclosed are isolated and recombinant riboswitches, recombinant constructs containing such riboswitches, heterologous sequences operably linked to such riboswitches, and cells and transgenic organisms harboring such riboswitches, riboswitch recombinant constructs, and riboswitches operably linked to heterologous sequences. The heterologous sequences can be, for example, sequences encoding proteins or peptides of interest, including reporter proteins or peptides. Preferred riboswitches are, or are derived from, naturally occurring riboswitches.

Also disclosed are chimeric riboswitches containing heterologous aptamer domains and expression platform domains. That is, chimeric riboswitches are made up an aptamer domain from one source and an expression platform domain from another source. The heterologous sources can be from, for example, different specific riboswitches or different classes of riboswitches. The heterologous aptamers can also come from non-riboswitch aptamers. The heterologous expression platform domains can also come from non-riboswitch sources.

Also disclosed are compositions and methods for selecting and identifying compounds that can activate, deactivate or block a riboswitch. Activation of a riboswitch refers to the change in state of the riboswitch upon binding of a trigger molecule. A riboswitch can be activated by compounds other than the trigger molecule and in ways other than binding of a trigger molecule. The term trigger molecule is used herein to refer to molecules and compounds that can activate a riboswitch. This includes the natural or normal trigger molecule for the riboswitch and other compounds that can activate the riboswitch. Natural or normal trigger molecules are the trigger molecule for a given riboswitch in nature or, in the case of some non-natural riboswitches, the trigger molecule for which the riboswitch was designed or with which the riboswitch was selected (as in, for example, in vitro selection or in vitro evolution techniques). Non-natural trigger molecules can be referred to as non-natural trigger molecules.

Deactivation of a riboswitch refers to the change in state of the riboswitch when the trigger molecule is not bound. A riboswitch can be deactivated by binding of compounds other than the trigger molecule and in ways other than removal of the trigger molecule. Blocking of a riboswitch refers to a condition or state of the riboswitch where the presence of the trigger molecule does not activate the riboswitch.

Also disclosed are compounds, and compositions containing such compounds, that can activate, deactivate or block a riboswitch. Also disclosed are compositions and methods for activating, deactivating or blocking a riboswitch. Riboswitches function to control gene expression through the binding or removal of a trigger molecule. Compounds can be used to activate, deactivate or block a riboswitch. The trigger molecule for a riboswitch (as well as other activating compounds) can be used to activate a riboswitch. Compounds other than the trigger molecule generally can be used to deactivate or block a riboswitch. Riboswitches can also be deactivated by, for example, removing trigger molecules from the presence of the riboswitch. A riboswitch can be blocked by, for example, binding of an analog of the trigger molecule that does not activate the riboswitch.

Also disclosed are compositions and methods for altering expression of an RNA molecule, or of a gene encoding an RNA molecule, where the RNA molecule includes a riboswitch, by bringing a compound into contact with the RNA molecule. Riboswitches function to control gene expression through the binding or removal of a trigger molecule. Thus, subjecting an RNA molecule of interest that includes a riboswitch to conditions that activate, deactivate or block the riboswitch can be used to alter expression of the RNA. Expression can be altered as a result of, for example, termination of transcription or blocking of ribosome binding to the RNA. Binding of a trigger molecule can, depending on the nature of the riboswitch, reduce or prevent expression of the RNA molecule or promote or increase expression of the RNA molecule.

Also disclosed are compositions and methods for regulating expression of an RNA molecule, or of a gene encoding an RNA molecule, by operably linking a riboswitch to the RNA molecule. A riboswitch can be operably linked to an RNA molecule in any suitable manner, including, for example, by physically joining the riboswitch to the RNA molecule or by engineering nucleic acid encoding the RNA molecule to include and encode the riboswitch such that the RNA produced from the engineered nucleic acid has the riboswitch operably linked to the RNA molecule. Subjecting a riboswitch operably linked to an RNA molecule of interest to conditions that activate, deactivate or block the riboswitch can be used to alter expression of the RNA.

Also disclosed are compositions and methods for regulating expression of a naturally occurring gene or RNA that contains a riboswitch by activating, deactivating or blocking the riboswitch. If the gene is essential for survival of a cell or organism that harbors it, activating, deactivating or blocking the riboswitch can in death, stasis or debilitation of the cell or organism. For example, activating a naturally occurring riboswitch in a naturally occurring gene that is essential to survival of a microorganism can result in death of the microorganism (if activation of the riboswitch turns off or represses expression). This is one basis for the use of the disclosed compounds and methods for antimicrobial and antibiotic effects.

Also disclosed are compositions and methods for regulating expression of an isolated, engineered or recombinant gene or RNA that contains a riboswitch by activating, deactivating or blocking the riboswitch. The gene or RNA can be engineered or can be recombinant in any manner. For example, the riboswitch and coding region of the RNA can be heterologous, the riboswitch can be recombinant or chimeric, or both. If the gene encodes a desired expression product, activating or deactivating the riboswitch can be used to induce expression of the gene and thus result in production of the expression product. If the gene encodes an inducer or repressor of gene expression or of another cellular process, activation, deactivation or blocking of the riboswitch can result in induction, repression, or de-repression of other, regulated genes or cellular processes. Many such secondary regulatory effects are known and can be adapted for use with riboswitches. An advantage of riboswitches as the primary control for such regulation is that riboswitch trigger molecules can be small, non-antigenic molecules.

Also disclosed are compositions and methods for altering the regulation of a riboswitch by operably linking an aptamer domain to the expression platform domain of the riboswitch (which is a chimeric riboswitch). The aptamer domain can then mediate regulation of the riboswitch through the action of, for example, a trigger molecule for the aptamer domain. Aptamer domains can be operably linked to expression platform domains of riboswitches in any suitable manner, including, for example, by replacing the normal or natural aptamer domain of the riboswitch with the new aptamer domain. Generally, any compound or condition that can activate, deactivate or block the riboswitch from which the aptamer domain is derived can be used to activate, deactivate or block the chimeric riboswitch.

Also disclosed are compositions and methods for inactivating a riboswitch by covalently altering the riboswitch (by, for example, crosslinking parts of the riboswitch or coupling a compound to the riboswitch). Inactivation of a riboswitch in this manner can result from, for example, an alteration that prevents the trigger molecule for the riboswitch from binding, that prevents the change in state of the riboswitch upon binding of the trigger molecule, or that prevents the expression platform domain of the riboswitch from affecting expression upon binding of the trigger molecule.

Also disclosed are methods of identifying compounds that activate, deactivate or block a riboswitch. For examples, compounds that activate a riboswitch can be identified by bringing into contact a test compound and a riboswitch and assessing activation of the riboswitch. If the riboswitch is activated, the test compound is identified as a compound that activates the riboswitch. Activation of a riboswitch can be assessed in any suitable manner. For example, the riboswitch can be linked to a reporter RNA and expression, expression level, or change in expression level of the reporter RNA can be measured in the presence and absence of the test compound. As another example, the riboswitch can include a conformation dependent label, the signal from which changes depending on the activation state of the riboswitch. Such a riboswitch preferably uses an aptamer domain from or derived from a naturally occurring riboswitch. As can be seen, assessment of activation of a riboswitch can be performed with the use of a control assay or measurement or without the use of a control assay or measurement. Methods for identifying compounds that deactivate a riboswitch can be performed in analogous ways.

Identification of compounds that block a riboswitch can be accomplished in any suitable manner. For example, an assay can be performed for assessing activation or deactivation of a riboswitch in the presence of a compound known to activate or deactivate the riboswitch and in the presence of a test compound. If activation or deactivation is not observed as would be observed in the absence of the test compound, then the test compound is identified as a compound that blocks activation or deactivation of the riboswitch.

Also disclosed are biosensor riboswitches. Biosensor riboswitches are engineered riboswitches that produce a detectable signal in the presence of their cognate trigger molecule. Useful biosensor riboswitches can be triggered at or above threshold levels of the trigger molecules. Biosensor riboswitches can be designed for use in vivo or in vitro. For example, biosensor riboswitches operably linked to a reporter RNA that encodes a protein that serves as or is involved in producing a signal can be used in vivo by engineering a cell or organism to harbor a nucleic acid construct encoding the riboswitch/reporter RNA. An example of a biosensor riboswitch for use in vitro is a riboswitch that includes a conformation dependent label, the signal from which changes depending on the activation state of the riboswitch. Such a biosensor riboswitch preferably uses an aptamer domain from or derived from a naturally occurring riboswitch. Also disclosed are methods of detecting compounds using biosensor riboswitches. The method can include bringing into contact a test sample and a biosensor riboswitch and assessing the activation of the biosensor riboswitch. Activation of the biosensor riboswitch indicates the presence of the trigger molecule for the biosensor riboswitch in the test sample.

Also disclosed are compounds made by identifying a compound that activates, deactivates or blocks a riboswitch and manufacturing the identified compound. This can be accomplished by, for example, combining compound identification methods as disclosed elsewhere herein with methods for manufacturing the identified compounds. For example, compounds can be made by bringing into contact a test compound and a riboswitch, assessing activation of the riboswitch, and, if the riboswitch is activated by the test compound, manufacturing the test compound that activates the riboswitch as the compound.

Also disclosed are compounds made by checking activation, deactivation or blocking of a riboswitch by a compound and manufacturing the checked compound. This can be accomplished by, for example, combining compound activation, deactivation or blocking assessment methods as disclosed elsewhere herein with methods for manufacturing the checked compounds. For example, compounds can be made by bringing into contact a test compound and a riboswitch, assessing activation of the riboswitch, and, if the riboswitch is activated by the test compound, manufacturing the test compound that activates the riboswitch as the compound. Checking compounds for their ability to activate, deactivate or block a riboswitch refers to both identification of compounds previously unknown to activate, deactivate or block a riboswitch and to assessing the ability of a compound to activate, deactivate or block a riboswitch where the compound was already known to activate, deactivate or block the riboswitch.

Also disclosed are methods for selecting, designing or deriving new riboswitches and/or new aptamers that recognize new trigger molecules. Such methods can involve production of a set of aptamer variants in a riboswitch, assessing the activation of the variant riboswitches in the presence of a compound of interest, selecting variant riboswitches that were activated (or, for example, the riboswitches that were the most highly or the most selectively activated), and repeating these steps until a variant riboswitch of a desired activity, specificity, combination of activity and specificity, or other combination of properties results. Also disclosed are riboswitches and aptamer domains produced by these methods.

The disclosed riboswitches, including the derivatives and recombinant forms thereof, generally can be from any source, including naturally occurring riboswitches and riboswitches designed de novo. Any such riboswitches can be used in or with the disclosed methods. However, different types of riboswitches can be defined and some such sub-types can be useful in or with particular methods (generally as described elsewhere herein). Types of riboswitches include, for example, naturally occurring riboswitches, derivatives and modified forms of naturally occurring riboswitches, chimeric riboswitches, and recombinant riboswitches. A naturally occurring riboswitch is a riboswitch having the sequence of a riboswitch as found in nature. Such a naturally occurring riboswitch can be an isolated or recombinant form of the naturally occurring riboswitch as it occurs in nature. That is, the riboswitch has the same primary structure but has been isolated or engineered in a new genetic or nucleic acid context. Chimeric riboswitches can be made up of, for example, part of a riboswitch of any or of a particular class or type of riboswitch and part of a different riboswitch of the same or of any different class or type of riboswitch; part of a riboswitch of any or of a particular class or type of riboswitch and any non-riboswitch sequence or component. Recombinant riboswitches are riboswitches that have been isolated or engineered in a new genetic or nucleic acid context.

Different classes of riboswitches refer to riboswitches that have the same or similar trigger molecules or riboswitches that have the same or similar overall structure (predicted, determined, or a combination). Riboswitches of the same class generally, but need not, have both the same or similar trigger molecules and the same or similar overall structure.

Additional advantages of the disclosed method and compositions will be set forth in part in the description which follows, and in part will be understood from the description, or can be learned by practice of the disclosed method and compositions. The advantages of the disclosed method and compositions will be realized and attained by means of the elements and combinations particularly pointed out in the appended claims. It is to be understood that both the foregoing general description and the following detailed description are exemplary and explanatory only and are not restrictive of the invention as claimed.

BRIEF DESCRIPTION OF THE DRAWINGS

The accompanying drawings, which are incorporated in and constitute a part of this specification, illustrate several embodiments of the disclosed method and compositions and together with the description, serve to explain the principles of the disclosed method and compositions.

FIG. 1A shows separation of spontaneous RNA-cleavage products of the btuB leader using denaturing 10% polyacrylamide gel electrophoresis (PAGE). 5'-32p-labeled mRNA leader molecules (arrow) were incubated for 41 hr at 25° C. in 20 mM $MgCl_2$, 50 mM Tris-HCl (pH 8.3 at 25° C.) in the presence (+) or absence (−) of 20 μM of AdoCbl. Lanes containing RNAs that have undergone no reaction, partial digest with alkali, and partial digest with RNase T1 (G-specific cleavage) are identified by NR, $^{-}$OH, and T1, respectively. The location of product bands corresponding to cleavage after selected guanosine residues are identified by filled arrowheads. Arrowheads labeled 1 through 8 identify eight of the nine locations that exhibit effector-induced structure modulation, which experience an increase or decrease in the rate of spontaneous RNA cleavage. The image was generated using a phosphorimager (Molecular Dynamics), and cleavage yields were quantitated by using ImageQuant software. FIG. 1B shows sequence and secondary-structure model for the 202-nucleotide leader sequence of btuB mRNA (SEQ ID NO:1) in the presence of AdoCbl. Putative base-paired elements are designated P1 through P9. Complementary nucleotides in the loops of P4 and P9 that have the potential to form a pseudoknot are juxtaposed. Nine specific sites of structure modulation are identified by arrowheads. The asterisks demark the boundaries of the $B_{12}$ box (nucleotides 141-162). The coding region and the 38 nucleotides that reside immediately 5' of the start codon (nucleotides 241-243) were not included in the 202-nucleotide fragment. The 315-nucleotide fragment includes the 202-nucleotide fragment, the remaining 38 nucleotides of the leader sequence, and the first 75 nucleotides of the coding region.

FIG. 2A shows the dependence of spontaneous cleavage of btuB mRNA leader on the concentration of AdoCbl effector as represented by site 1 (G23) and site 2 (U68). 5'-$^{32}$P-labeled mRNA leader molecules were incubated, separated, and analyzed as described in the in the brief description of FIG. 1, and include identical control and marker lanes as indicated. Incubations contained concentrations of AdoCbl ranging from 10 nM to 100 μM (lanes 1 though 8) or did not include AdoCbl (−). FIG. 2B shows a composite plot of the fraction of RNA cleaved at six locations along the mRNA leader versus the logarithm of the concentration (c) of AdoCbl. Fraction cleaved values were normalized relative to the highest and lowest cleavage values measured for each location, including the values obtained upon incubation in the absence of AdoCbl. The inset defines the symbols used for each of six sites, while the remaining three sites were excluded from the analysis due to weak or obscured cleavage bands. Filled and open symbols represent increasing and decreasing cleavage yields, respectively, upon increasing the concentration of AdoCbl. The dashed line reflects a $K_D$ of ~300 nM, as predicted by the concentration needed to generate half-maximal structural modulation. Data plotted were derived from a single PAGE analysis, of which two representative sections are depicted in FIG. 1A.

FIGS. 4A and 4B show selective molecular recognition of effectors by the btuB mRNA leader. FIG. 4A shows a chemical structure of AdoCbl (1) and various effector analogs (2 through 11, ref 30). FIG. 4B shows a determination of analog binding by monitoring modulation of spontaneous cleavage of the 202-nucleotide btuB RNA leader. 5'-$^{32}$P-labeled mRNA leader molecules were incubated, separated, and analyzed as described in the legend to FIG. 1A, and include identical control and marker lanes as indicated. The sections of three PAGE analyses encompassing site 2 (U68) are depicted. Below each image is plotted the amount of RNA cleaved (normalized with relation to the lowest and highest levels of cleavage at U68 in each gel) for each effector as indicated, or for no effector (−). The compound 11 (13-epi-AdoCbl) is an epimer of AdoCbl wherein the configuration at C 13 is inverted, so that the e propionamide side chain is above the plane of the corrin ring; see Brown et al., Conformational studies of 5'-deoxyadenosyl-13-epicobalamin, a coenzymatically active structural analog of coenzyme $B_{12}$. Polyhedron 17, 2213 (1998).

FIG. 5A shows sequence of the putative P5 element of the wild-type 202-nucleotide btuB leader exhibits AdoCbl-dependent modulation of structure as indicated by the observed increase in spontaneous RNA cleavage at position U68 (10% denaturing PAGE gel). Assays were conducted in the absence (−) or presence (+) of 5 μM AdoCbl. The remaining lanes are as described in the legend to FIG. 1A. The composite bar graph reflects the ability of the RNA to shift the equilibrium of AdoCbl in an equilibrium dialysis apparatus and the ability of a reporter gene (see Experimental Procedures) to be regulated by AdoCbl addition to a bacterial culture. (Left) Plotted is the cpm ratio derived by equilibrium dialysis, wherein chamber b contains the RNA. Details of the equilibrium dialysis experiments are described in the brief description of FIG. 3. (Right) Plotted are the expression levels of β-galactosidase as determined from cells grown in the absence (−) or presence (+) of 5 μM AdoCbl. Boxed numbers on the left and right, respectively, reflect the approximate $K_D$ and the fold repression of β-galactosidase activity in the presence of AdoCbl. N.D. designates not determined. FIG. 5B-5F shows sequences and performance characteristics of various mutant leader sequences as indicated. Constructs were created as described in the Experimental Procedures section.

FIG. 6A shows TPP-dependent modulation of the spontaneous cleavage of 165 thiM RNA was visualized by polyacrylamide gel electrophoresis (PAGE). 5' $^{32}$P-labeled RNAs (arrow, 20 nM) were incubated for approximately 40 hr at 25° C. in 20 mM $MgCl_2$, 50 mM Tris-HCl (pH 8.3 at 25° C.) in the presence (+) or absence (−) of 100 μM TPP. NR, $^{-}$OH and T1 represent RNAs subjected to no reaction, partial digestion with alkali, or partial digestion with RNase T1 (G-specific cleavage), respectively. Product bands representing cleavage after selected G residues are numbered and identified by filled arrowheads. The asterisk identifies modulation of RNA structure involving the Shine-Dalgarno (SD) sequence. Gel separations were analyzed using a phosphorimager (Molecular Dynamics) and quantitated using ImageQuant software. FIG. 6B shows a secondary-structure model of 165 thiM (SEQ ID NO:2) as predicted by computer modeling (Zuker et al., Algorithms and thermodynamics for RNA secondary structure prediction: a practical guide. In *RNA Biochemistry and Biotechnology* (eds. Barciszewski J. & Clark, B.F.C.) 11-43 (NATO ASI Series, Kluwer Academic Publishers, 1999); Mathews et al., Expanded sequence dependence of thermodynamic parameters improves prediction of RNA secondary structure. *J. Mol. Biol.* 288, 911-940 (1999)) and by the structure probing data depicted in FIG. 6A. Spontaneous cleavage characteristics are as noted in the inset. Unmarked nucleotides exhibit a constant but low level of degradation. The truncated 91 thiM RNA (residues 1-91 of SEQ ID NO:2) is boxed and the thi box element (Miranda-Rios et al., A conserved RNA structure (thi box) is involved in regulation of thiamin biosynthetic gene expression in bacteria. *Proc. Natl. Acad. Sci. USA* 98, 9736-9741 (2001)) is shaded. Nucleotides enclosed in boxes identify an alternative pairing, designated P8*. The RNA carries two mutations (G156A and U157C) relative to wild type that were introduced in a non-essential portion of the construct to form a restriction site for cloning, while all RNAs carry two 5'-terminal G residues to facilitate in vitro transcription. FIG. 6C shows TPP-dependent modulation of the spontaneous cleavage of 240 thiC RNA. Reactions were conducted and analyzed as described in above for FIG. 6A. FIG. 6D shows a secondary-structure model of 240 thiC (SEQ ID NO:3). Base-paired elements that are similar to those of thiM are labeled P1 through P5. The truncated RNA 111 thiC (residues 1-111 of SEQ ID NO:3) is boxed. Nucleotides enclosed in boxes identify an alternative pairing.

FIG. 7A shows the extent of spontaneous modulation of RNA cleavage at several sites within 165 thiM (left) and 240 thiC (right) plotted for different concentrations (c) of TPP. Arrows reflect the estimated concentration of TPP needed to attain half maximal modulation of RNA (apparent $K_D$). FIG. 7B shows the logarithm of the apparent $K_D$ values plotted for both RNAs with TPP, TP and thiamine as indicated. The boxed data was generated using TPP with the truncated RNAs 91 thiM and 111 thiC. FIG. 7C shows that patterns of spontaneous cleavage of 165 thiM differ between thiamine and TPP ligands as depicted by PAGE analysis (left) and as reflected by graphs (right) representing the relative phosphorimager counts for the three lanes as indicated. Details for the RNA probing analysis are similar to those described above in connection with FIG. 6A. The graphs were generated by ImageQuant software.

FIG. 8A shows chemical structures of several analogues of thiamine. TD is thiamine disulfide and THZ is 4-methyl-5-β-hydroxyethylthiazole. FIG. 8B shows PAGE analysis of 165 thiM RNA structure probing using TPP and various chemical analogues (40 μM each) as indicated. Locations of significant structural modulation within the RNA spanning nucleotides ~113 to ~150 are indicated by open arrowheads. The asterisk identifies the site (C144) used to compare the normalized fraction of RNA that is cleaved (bottom) in the presence of specific compounds. Details for the RNA probing analysis are similar to those described above in connection with FIG. 6*a*. FIG. 8C shows a summary of the features of TPP that are critical for molecular recognition. FIG. 8D shows equilibrium dialysis using $^{3}$H-thiamine as a tracer. Plotted are the ratios for tritium distribution in a two-chamber system (a and b) that were established upon equilibration in the presence of the RNA constructs in chamber b as indicated (see below for a description of the non-TPP-binding mutant M3). 100 μM TPP or oxythiamine were added to chamber a, as denoted, upon the start of equilibration.

FIGS. 9A, 9B, 9C and 9D show mutational analysis of the structure and function of the thiM riboswitch. FIG. 9A shows mutations present in constructs M1 through M8 relative to the 165 thiM RNA (SEQ ID NO:4). P8* is a putative base-paired element between portions (encircled) of the P1 and P8 stems. FIGS. 9B and 9C show in vitro ligand-binding and genetic control functions of the wild-type (WT), M1 and M2 RNAs as reflected by PAGE analysis of in-line probing experiments (10 μM TPP) and by β-galactosidase expression assays. Labels on PAGE gels are as described above in connection with FIG. 6A. Bars represent the levels of gene expression in the presence (+) and the absence (–) of TPP in the culture medium. FIG. 9D is a summary of similar analyses of WT through M9 is presented in table form. The SD status "n.d." (not determined) indicates either that the level of spontaneous cleavage detected in the absence and presence of TPP is near the limit of detection (M6, M7 and M8) or that the region adopts an atypical structure (M9) compared to WT.

FIG. 12A shows the results of in-line probing assays. Internucleotide linkages identified with squares exhibit decreased amounts of spontaneous cleavage when ribD is incubated in the presence of FMN (indicating an increase in order for these nucleotides) relative to incubation in the absence of FMN. Circles identify linkages that exhibit consistently high levels of scission, which indicates they are not modulated by presence of FMN. FIG. 12C shows the chemical structure and apparent dissociation constants for riboflavin and FMN.

FIG. 13A shows results of in-line probing assays. Internucleotide linkages identified with squares exhibit decreased amounts of spontaneous cleavage when thiM is incubated in the presence of TPP compared to incubation in the absence of ligand. In contrast, linkages identified with hexagons exhibit increased amounts of cleavage when thiM is incubated with TPP compared to incubation in the absence of ligand. The boxed nucleotides indicate pyrophosphate-recognition region (as described in text). FIG. 13C shows the chemical structure and apparent dissociation constants for thiamine and TPP.

FIG. 14A shows the consensus TPP binding domain based on 100 bacteria and archaea RNAs (SEQ ID NO:18 and SEQ ID NOs:398-399). Nucleotides shown as lower case letters are most conserved (>90%). Open circles represent nucleotide positions and domains that vary in sequence and length are designated var. The consensus model is similar to that reported recently (Rodionov et al., 2002). FIG. 14B the TPP-binding domain of *A. thaliana* (SEQ ID NO:14). Variations in *O. sativa* (nucleotides enclosed in a circle) (SEQ ID NO:15) and P. secunda (nucleotides enclosed in a hexagon) (SEQ ID NO:16) are shown. FIG. 14C shows a putative TPP-binding domain in the intron of N. crassa (SEQ ID NO:17).

FIG. 15 shows sequence alignments of eukaryotic domains related to bacterial TPP-dependent riboswitches, Eco1, Eco2, Cac1, Ncr1, Aor1, Fox1, Fso1, Ath1, Pse1, Osa1, which are represented by SEQ ID NOs:19-28 respectively. Base paired stems are shaded in black and labeled as defined in Example 2). The P3 sequences, which in eukaryotes are significantly expanded in length and number of base pairs, are represented as a stem-loop structure. The highly conserved nucleotide positions in bacteria that were used to search for eukaryotic domains are enclosed in a box. For each identified (ID) sequence, the position of the conserved CUGAGA sequence within the given Genbank entry is given along with the accession identification, sequence name, and gene identification. Additional protein annotations based on sequence similarity are shown in brackets. Methods: Riboswitch-like domains were initially identified by sequence similarity to bacterial sequences (Eco2 and Cac) by a blastn search of Genbank using default parameters. These hits were verified and expanded by searching for degenerate matches to the pattern (CTGAGA[200]ACYTGA[5]<<<GNTNNNNC>>>[5] CGNRGGRA) (SEQ ID NO:375). Angle brackets indicate base pairing and bracketed numbers are variable gaps with constrained maximum lengths. All of the eukaryotic sequences have one or zero mismatches to this pattern except for one (Aor) that initially had three mismatches due to a single A insertion in the final search element. This mutation was removed to simplify the alignment. Comparison of mRNA (M33643.1) and genomic (AB033416.1) sequences demonstrated that the *F. oxysporum* element is in an intron in the 5' UTR of the sti35 gene. Other fungal sequences (Ncr, Aor, and Fso) are flanked by consensus splicing sequences.

FIG. 16A shows the fragmentation pattern of the 128-nucleotide RNA (arrow) of *A. thaliana* (FIG. 14B) which was generated by incubation in the absence (–) or presence (+) of 100 μM TPP. T1, OH and NR identify RNAs that were partially digested with RNase T1 (cleaves 3' to G residues), alkali, or were not reacted, respectively. Reactions were conducted as described in Example 2. FIG. 16B shows the apparent $K_D$ for TPP binding by the *A. thaliana* RNA. Fraction bound was determined by in-line probing as described in Examples 1-3.

FIGS. 18A and 18B show the L box—a highly conserved sequence and structural domain is present in the 5'-UTRs of Gram-positive and Gram-negative bacterial mRNAs that are related to lysine metabolism. Conserved portions of the L box sequence and secondary structure were identified by alignment of 28 representative mRNAs as noted. Base pairing potential representing P1 through P5 are enumerated and set off by boxes. Nucleotides shown as lower case letters are conserved in greater than 80% of the examples. The asterisk identifies the representative (*B. subtilis* lysC 5'-UTR) that was examined in this study. Gene names are as annotated in GenBank or were derived by protein sequence similarity. Organism abbreviations are as follows: *Bacillus anthracis* (BA), *Bacillus halodurans* (BH), *Bacillus subtilis* (BS), *Clostridium acetobutylicum* (CA), *Clostridium perfringens* (CP), *Escherichia coli* (EC), *Haemophilus influenzae* (HI), *Oceanobacillus iheyensis* OI), *Pasteurella multocida* (PM), *Staphylococcus aureus* (SA), *Staphylococcus epidermidis* (SE), *Shigella flexneri* (SF), *Shewanella oneidensis* (SO), *Thermatoga maritima* (TM), *Thermoanaerobacter tengcongensis* (TT), *Vibrio cholerae* (VC), *Vibrio vulnificus* (VV), *Thermoanaerobacter tengcongensis* (TE).

FIG. 20A shows the chemical structures of L-lysine, D-lysine and nine closely-related analogs. Small circles represent chiral carbon centers wherein the enantiomeric configuration is defined for each compound. Encircled atoms identify chemical differences between L-lysine and the analog depicted. FIG. 20B shows in-line probing analysis of the 179 lysC RNA in the absence (−) of ligand, or in the presence of 10 μM L-lysine or 100 μM of various analogs as indicated for each lane. For each lane, the relative extent of spontaneous cleavage at site 3 is compared to that of the zone of constant cleavage immediately below this site, where a cleavage ratio significantly below ~1.5 reflects modulation. FIG. 20C shows a schematic representation of dipeptide digestion by hydrochloric acid. All dipetide forms are expected to be incapable of binding the lysine aptamer (inactive), while lysine-containing dipeptides should induce conformational changes in the aptamer (active) upon acid digestion. FIG. 20D shows in-line probing analysis of the 179 lysC RNA in the absence of lysine (−) or in the presence of various amino acids and dipeptides. Underlined lanes carry dipeptide preparations that were pretreated with HCl as depicted in a. FIG. 20E shows the fraction of spontaneous cleavage at site 3 in d is plotted after normalization to the extent of processing in the absence of added ligand.

FIG. 21A shows in-line probing with increasing concentrations of L-lysine ranging from 3 nM to 3 mM. Details are as defined for FIG. 19C. FIG. 20B shows a plot depicting the normalized fraction of RNA undergoing spontaneous cleavage versus the concentration of amino acid for sites 1 through 3. The dashed line identifies the concentration of L-lysine required to bring about half-maximal structural modulation, which indicates the apparent $K_D$ for ligand binding. FIG. 20C shows the 179 lysC RNA (10 μM) shifts the equilibrium of tritiated L-lysine (50 nM) in an equilibrium dialysis chamber. To investigate competitive binding, unlabeled L-(L) and D-lysine (D), or L-ornithine (5) were added to a final concentration of 50 μM each to one chamber of a pre-equilibrated assay as indicated. FIG. 21D shows a scatchard analysis of L-lysine binding by the 179 lysC RNA. The variable r represents the ratio of bound ligand concentration versus the total RNA concentration and the variable $[L_F]$ represents the concentration of free ligand.

FIG. 22A shows a sequence and repressed-state model for the lysC riboswitch secondary structure (SEQ ID NO:62). The encircled nucleotides identify the putative anti-terminator interaction that could form in the absence of L-lysine. Boxed nucleotides identify sites of disruption (M1) and compensatory mutations for the terminator stem (M2) and for the terminator and anti-terminator stems (M3). Nucleotides enclosed in squares identify some of the positions where mutations exhibit lysC derepression that were reported previously (Vold et al. 1975; Lu et al. 1992). FIG. 22B shows In vitro transcription assays conducted in the absence (−) or presence (+) of 10 mM L-lysine or other analogs as indicated. FL and T identify the full-length and terminated transcripts, respectively. The percent of the terminated RNAs relative to the total terminated and full-length transcripts are provided for each lane (% term.). FIG. 22C shows In vivo expression of a β-galactosidase reporter gene fused to wild-type (WT), G39A and G40A mutant lysC 5'-UTR fragments. Media conditions are as follows: I, normal medium (0.27 mM lysine); II, minimal medium (0.012 mM); III, lysine-supplemented minimal medium (1 mM); IV, lysine hydroxamate-supplemented (medium II plus 1 mM lysine hydroxamate) minimal media; V, thiosine-supplemented (medium II plus 1 mM thiosine) minimal medium.

FIG. 24A shows the consensus sequence and secondary model for the G box RNA domain that resides in the 5' UTR of genes that are largely involved in purine metabolism (SEQ ID NO:95). Phylogenetic analysis is consistent with the formation of a three-stem (P1 through P3) junction. Nucleotides depicted shown as lower case letters and capitals are present in greater than 90% and 80% of the representatives examined, respectively (FIG. 23). Encircled nucleotides exhibit base complementation, which might indicate the formation of a pseudoknot. FIG. 24B shows sequence and ligand-induced structural alterations of the 5'-UTR of the xpt-pbuX transcriptional unit (SEQ ID NO:96). The putative anti-terminator interaction is represented by the boxes. Nucleotides that undergo structural alteration as determined by in-line probing (from C) are identified with squares. The 93 xpt fragment (boxed) of the 201 xpt RNA retains guanine-binding function. Asterisks denote alterations to the RNA sequence that facilitate in vitro transcription (5' terminus) or that generate a restriction site (3' terminus). Nucleotide numbers begin at the first nucleotide of the natural transcription start site. The translation start codon begins at position 186. FIG. 24C shows guanine and related purines selectively induce structural modulation of the 93 xpt mRNA fragment. Precursor RNAs (Pre; 5' $^{32}$P-labeled) were subjected to in-line probing by incubation for 40 hr in the absence (−) or presence of guanine, hypoxanthine, xanthine and adenine as indicated by G, H, X and A, respectively. Lanes designated NR, T1 and $^{-}$OH contain RNA that was not reacted, subjected to partial digestion with RNase T1 (G-specific cleavage), or subjected to partial alkaline digestion, respectively. Selected bands corresponding to G-specific cleavage are identified. Regions 1 through 4 identify major sites of ligand-induced modulation of spontaneous RNA cleavage.

FIG. 25A shows in-line probing reveals that spontaneous RNA cleavage of the 201 xpt RNA at four regions decreases with increasing guanine concentrations. Only those locations of the PAGE image corresponding to the four regions of modulation as indicated in FIG. 25C are depicted. Other details and notations are as described in the legend to FIG. 25C. FIG. 25B shows a plot depicting the normalized fraction of RNA that experienced spontaneous cleavage versus the concentration of guanine for modulated regions 1 through 4 in FIG. 25A. Fraction cleaved values were normalized to the maximum cleavage measured in the absence of guanine and to the minimum cleavage measured in the presence of 10 μM guanine. The apparent $K_D$ value (less than or equal to 5 nM) reflects the limits of detection for these assay conditions.

FIG. 26A shows the chemical structures and apparent $K_D$ values for guanine, hypoxanthine and xanthine (active natural regulators of xpt-pbuX genetic expression in *B. subtilis*) versus that of adenine (inactive). Differences in chemical structure relative to guanine are encircled. $K_D$ values were established as shown in FIG. 26 with the 201 xpt RNA. Numbers on guanine represent the positions of the ring nitrogen atoms. FIG. 26B shows chemical structures and $K_D$ values for various analogs of guanine reveal that all alterations of this purine cause a loss of binding affinity. Open circles identify $K_D$ values that most likely are significantly higher than indicated, as concentrations of analog above 500 μM were not examined in this analysis. The apparent $K_D$ values of G, H, X and A as indicated are plotted as triangles for comparison. FIG. 26C shows a schematic representation of the molecular recognition features of the guanine aptamer in 201 xpt. Hydrogen bond formation at position 9 of guanine is expected because guanosine ($K_D$>100 μM) and inosine ($K_D$>100 μM), which are 9-ribosyl derivatives of guanine and hypoxanthine, respectively, do not exhibit measurable binding (see FIG. 27).

FIG. 27A shows an equilibrium dialysis strategy was used to confirm that in vitro-transcribed 93 xpt RNAs bind to guanine and can discriminate against various analogs. Each data point was generated by adding $^{3}$H-guanine to chamber a, which is separated from RNA and other analogs by a dialysis membrane with a molecular weight cut-off (MWCO) of 5,000 daltons. Left: If no guanine binding sites are present in chamber b, or if an excess of unlabeled competitor is present, then no shift in the distribution of tritium is expected. Right: If an excess of guanine-binding RNAs are present in chamber b, and if no competitor is present, then a substantial shift in the distribution of tritium towards chamber b is expected. FIG. 27B shows the 93 xpt RNA can shift the distribution of $^{3}$H-guanine in an equilibrium dialysis apparatus, while analogs of guanine are poor competitors. The plot depicts the fraction of counts per minute (cpm) of tritium in chamber b relative to the total amount of cpm counted from both chambers. A value of ~0.5 is expected if no shift occurs, as is the case when RNA is absent (none), or in the presence of excess unlabeled competitor (G). A value approaching 1 is expected if the majority of $^{3}$H-guanine is bound by the RNA in chamber b in the absence (−) of unlabeled analog, or in the presence of unlabeled analogs that do not serve as effective competitors under the assay conditions (100 nM $^{3}$H-guanine, 300 nM RNA, 500 nM analog). Ino and Gua represents inosine and guanosine, respectively.

FIG. 28A shows mutations used to examine the importance of various structural features of the guanine aptamer domain (SEQ ID NO:97). FIG. 28B shows examination of the binding function of aptamer variants by equilibrium dialysis. WT designates the wild-type 93 xpt construct. Details are as described for FIG. 27. FIG. 28C shows genetic modulation of a β-galactosidase reporter gene upon the introduction of various purines as indicated. FIG. 28D shows regulation of β-galactosidase reporter gene expression by WT and mutants M1 through M7. Open and filled bars represent enzyme activity generated when growing cells in the absence and presence of guanine, respectively.

FIGS. 29A and 29B are schematic representations of the seven known riboswitches and the metabolites they sense. The secondary structure models were obtained as follows: coenzyme $B_{12}$ (see Example 1); TPP (see Example 2); FMN (see Example 3), SAM (see Example 7); guanine (see Example 6); lysine (see Example 5); adenine (see Example 8). Coenzyme $B_{12}$ is depicted in exploded form wherein a, b and c designate covalent attachment sites between fragments. FIG. 29C shows a genetic map of *B. subtilis* riboswitch regulons and their positions on the bacterial chromosome. Genes are controlled by riboswitches as identified by matching numbers. All nomenclature is derived from the SubtiList database release R16.1 (Moszer, I., et al., 1995, Microbiol. 141, 261-268) except for metI and metC, which are recent designations (Auger, S., et al., 2002, Microbiol. 148, 507-518).

FIG. 30B shows a sequence and secondary structure model for the 251 yitJ mRNA fragment (SEQ ID NO:99). Sites of structural modulation upon introduction of SAM are depicted as described. Nucleotide 1 corresponds to the putative transcriptional start site. Asterisks identify nucleotides that were added to the construct to permit efficient transcription in vitro. The first nucleotide of the AUG start codon is 212 (not shown). Other notations are as described in a. FIG. 30C shows the spontaneous cleavage patterns of 251 yitJ (~1 nM 5' $^{32}$P-labeled) RNA incubated for ~40 hr at 25° C. in 50 mM Tris-HCl (pH 8.3 at 25° C.), 20 mM $MgCl_2$, 100 mM KCl, and without (−) or with methionine or SAM as indicated for each lane. NR, T1 and $^-$OH represent no reaction, partial digest with RNase T1, and partial digest with alkali, respectively. Certain fragment bands corresponding to T1 digestion (cleaves after G residues) are depicted. Arrowheads identify positions of significant modulation of spontaneous cleavage, and the numbered sites were used for quantitation (see FIG. 31B). Experimental procedures are similar to those described in Examples 1-3.

FIG. 31A shows the chemical structures of various compounds used to probe the binding characteristics of the SAM yitJ riboswitch. Other than methionine, each compound as depicted is coupled to an adenosyl moiety ([A]; inset) coupled via the 5' carbon (as signified by R). FIG. 31B Left: The $K_D$ of 251 yitJ for SAM was determined by plotting the normalized fraction of RNA cleaved at regions 1 through 6 (see FIG. 30C) versus the logarithm of the concentration of SAM in molar units. The dashed line indicates the concentration needed to induce half maximal modulation of cleavage activity. Right: $K_D$ values for SAM and various analogs as determined by this method. FIG. 31C shows molecular discrimination determined by equilibrium dialysis. Assays employed 100 nM of S-adenosyl-L-methionine-methyl-$^3$H ($^3$H-SAM; 14.5 μCi $mmol^{-1}$; ~7,000 cpm) added to side A of an equilibrium dialysis chamber (1, 2), and were conducted in the absence (none) or the presence of 3 μM RNA on the B side of the chamber as indicated. Equilibrations were carried out for ~10 hr in the absence (−) of unlabeled analogs, and then were subsequently incubated in the presence of 25 μM unlabeled compounds (added to side B) as indicated. M1 is a variant of 124 yitJ that carries disruptive mutations in the junction between stems P1 and P2 (FIG. 32*a*). Line at a cpm ratio of 1 identifies the bar height expected if a shift in $^3$H-SAM has not occurred. Additional experimental details are similar to those described in Examples 1 and 2.

FIG. 32A shows the sequence and secondary structure model for the 124 yitJ RNA (SEQ ID NO:100). Mutations M1 through M9 were generated in plasmids containing fusions of the yitJ5'-UTR upstream from a lacZ reporter gene. Templates for preparation of mutant RNAs for in vitro studies were then created by PCR, and the mutant DNA constructs were integrated into the chromosome for in vivo studies. See Methods for experimental details. FIG. 32B shows the analysis of SAM-binding function by equilibrium dialysis in the presence of wild-type (WT) and mutant RNAs as denoted. Details are described in the legend to FIG. 31C, except that 300 nM RNA was used and all assays were conducted without the addition of unlabeled analogs. FIG. 32C shows In vivo control of β-galactosidase expression in *B. subtilis* cells transformed with various riboswitch constructs as indicated. β-galactosidase activities were measured as described in Example 2. Cells were grown in glucose minimal media in 0.75 μg $mL^{-1}$ methionine (−) 50 μg $mL^{-1}$ methionine (+). M6 through M9 were not examined in vivo.

FIG. 33A shows In vitro transcription using T7 RNA polymerase results in increased termination of four mRNA leader sequences. Reactions were conducted in the absence (−) or presence (+) of 50 μM of the effector as indicated for each lane. For example, the metI template includes the 5' UTR and coding sequences through mRNA position 242, while the termination site is expected to occur at position 189. Below each gel is indicated the percentage of transcription termination (T) at the expected location relative the total amount of expected termination plus full length RNA (FL). FIGS. 33B-33D show sequence and structural model for the metI riboswitch in two structural states (SEQ ID NO:101). Residues shown in hexagons and squares correspond to the P1 (anti-anti-terminator) and the terminator stems, respectively. The encircled residues correspond to the anti-terminator stem. Sequences boxed in black define the location and identity of mutations used to examine the proposed mechanism of genetic control. Gel: Analysis of mutant metI riboswitches wherein disruptive (Ma, Mab and Mc) or the corresponding compensatory mutations (Mabc) have been inserted. The metI mutant templates and wild-type control template (WT) are identical to the templates used in A, except that the FL product is 220 nucleotides. Other notations are as describe in A.

FIG. 34A shows structural modulation of the *B. subtilis* cysH aptamer as determined by in-line probing (SEQ ID NO:102). Inset: Apparent $K_D$ values determined by monitoring structural modulation over a range of SAM or SAM analog concentrations. Two G residues (asterisks) were included at the 5' terminus of the RNA construct to facilitate in vitro transcription. Nucleotide numbers are given relative to the putative transcription start site. In-line probing was conducted with an RNA extending to nucleotide 117, while the remainder of the RNA is shown to depict the putative transcription terminator stem. Experiments were similar to those described in FIG. 30B and FIG. 31B. See the legend for FIG. 30B for details. FIG. 34B shows structural modulation of the *B. subtilis* cysH aptamer as determined by in-line probing (SEQ ID NO:103). The transcription start point of the *B. anthracis* cysH mRNA has not been determined, and so numbering of nucleotides begins immediately after the two inserted G residues (asterisks). In-line probing was conducted with an RNA extending to nucleotide 112. See A for additional details.

FIG. 35A shows sequence and structural features of the two guanine-specific (purE and xpt) and three adenine-specific aptamer domains that are examined in this study BS2-purE, BS3-xpt, BS5-ydhL, CP4-add, VV1-add, which are represented by SEQ ID NOs:104-108, respectively. P1 through P3 identify the three base-paired stems comprising the secondary structure of the aptamer domain. Lowercase nucleotides identify positions whose base identity is conserved in greater than 90% of representatives in the phylogeny'. The arrow identifies a nucleotide within the conserved core of the aptamer that is a determinant of ligand specificity. BS, CP and VV designate *B. subtilis, Clostridium perfringens* and *Vibrio vulnificus*, respectively. FIG. 35B shows sequence and secondary structure of the xpt and ydhL aptamers (SEQ ID NO:109). Encircled nucleotides identify positions within the ydhL aptamer that differ from those in the xpt aptamer. The sequence disclosed in FIG. 35C is SEQ ID NO:110. Nucleotides in xpt are numbered as described in Example 6. Other notations are as described in A.

FIG. 37A shows the in-line probing assay for the 80 ydhL RNA at various concentrations of adenine. For each lane, sites 1 through 4 were quantitated and the fraction of RNA cleaved was used to determine the apparent $K_D$. FIG. 37B shows a plot of the normalized fraction of RNA that has undergone spontaneous cleavage at sites 1 through 4 versus the concentration of adenine. See Example 8 for additional details.

FIGS. 38A and 38B show the specificity of molecular recognition by the adenine aptamer from ydhL. FIG. 38A Top: Chemical structures of adenine, guanine and other purine analogs that exhibit measurable binding to the 80 ydhL RNA. Chemical changes relative to 2,6-DAP, which is the tightest-binding compound, are encircled. Bottom left: Plot of the apparent $K_D$ values for various purines. Bottom right: Model for the chemical features on adenine that serve as molecular recognition contacts for ydhL. Note that the importance of N7 and N9 has not been determined. Encircled arrow indicated that a contact could exist if a hydrogen bond donor is appended to C2. FIG. 38B shows chemical structures of various purines that are not bound by the 80 ydhL RNA ($K_D$ values poorer than 300 μM).

FIG. 39A Left: Plot of the normalized fraction of wild-type 93 xpt RNA cleavage product for a given site versus the logarithm of the concentration of ligand present during incubation in an in-line probing assay. Cleavage products monitored for modulation correspond to site 3 (FIG. 37A). Right: Plot of the fraction of the total counts per minute (cpm) present in chamber B relative to the total counts per minute from sides A and B of an equilibrium dialysis chamber. Value of ~0.5 indicate an equal distribution of ligand (no binding) while values of ~1 indicate that most of the ligand is bound to the RNA within side B of the chamber. (B, C, D) In-line probing plots and equilibrium dialysis plots for 93 xpt (C to U mutation), 80 ydhL, and 80 ydhL (U to C mutation), respectively. Details are describe in a, or are described in the Example 8.

FIG. 40A sequence of the adenine riboswitch from *B. subtilis* ydhL and secondary structure models for the 'ON' and 'OFF' states for gene regulation (SEQ ID NO:111). FIG. 40B In vivo function of the wild-type ydhL riboswitch and of a variant form as determined by fusion to a β-galactosidase reporter gene.

Figure 1A:
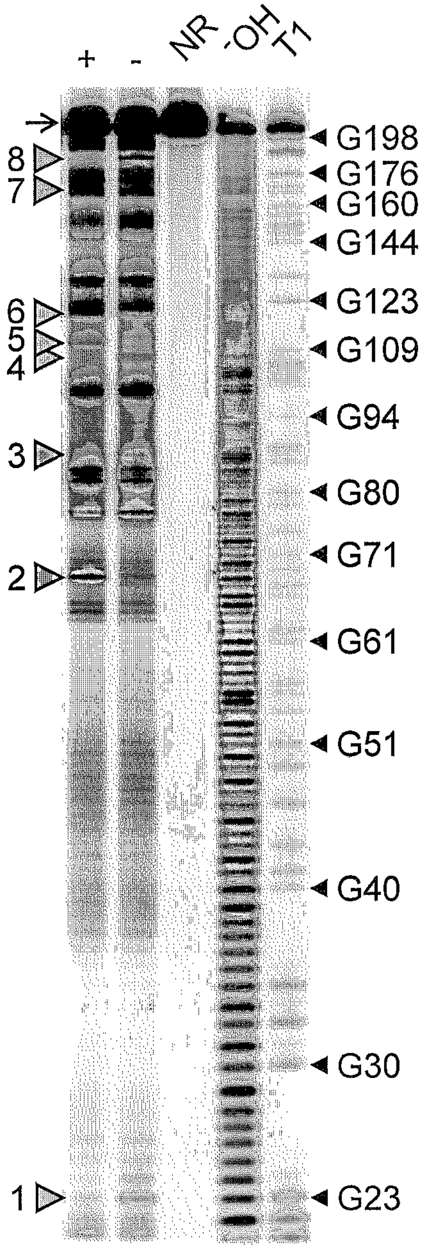
FIGS. 1A and 1B show metabolite-dependent conformational changes in the 202-nucleotide leader sequence of the btuB mRNA.

1958511, NC_004193.1/760480-760571, NC_004193.1/769695-769781, NC_004193.1/786775-786863, NC_004193.1/1103947-1104044, NC_002745.1/430771-430861, NC_004461.1/2432384-2432294, NC_004116.1/1093950-1093860, NC_002737.1/930757-930842, NC_003028.1/1754791-1754878, NC_003869.1/586372-586463, NC_000964.1/626134-626051, NC_003366.1/2870819-2870732, NC_004460.1/504378-504467, Bha_LysC, Bha_dapA, Bha_nhaC, Bsu_LysC, Cac_lysA, Cpe_nhaC, Cpe_lysA, Cpe_lysP, Eco_lysC, Hin_nhaC, Oih_dapA, Oih_nhaC, Pmu_nhaC, Sau_lysC, Sau_lysP, Sep lysC, Sep lysP, Sfl lysC, Son lysC, Son nhaC, Tma asd, Tte lysA, TtepspF, Vch_lysC, Vch_nhaC, Vch_nhaC, 2Vvu_lysC, Vvu_nhaC, Cons, Cons and Consensus, which are represented by SEQ ID NOs:112-374, respectively.

DETAILED DESCRIPTION OF THE INVENTION

The disclosed methods and compositions can be understood more readily by reference to the following detailed description of particular embodiments and the Example included therein and to the Figures and their previous and following description.

Certain natural mRNAs serve as metabolite-sensitive genetic switches wherein the RNA directly binds a small organic molecule. This binding process changes the conformation of the mRNA, which causes a change in gene expression by a variety of different mechanisms. Modified versions of these natural "riboswitches" (created by using various nucleic acid engineering strategies) can be employed as designer genetic switches that are controlled by specific effector compounds (referred to herein as trigger molecules). The natural switches are targets for antibiotics and other small molecule therapies. In addition, the architecture of riboswitches allows actual pieces of the natural switches to be used to construct new non-immunogenic genetic control elements, for example the aptamer (molecular recognition) domain can be swapped with other non-natural aptamers (or otherwise modified) such that the new recognition domain causes genetic modulation with user-defined effector compounds. The changed switches become part of a therapy regimen - turning on, or off, or regulating protein synthesis. Newly constructed genetic regulation networks can be applied in such areas as living biosensors, metabolic engineering of organisms, and in advanced forms of gene therapy treatments.

Messenger RNAs are typically thought of as passive carriers of genetic information that are acted upon by protein- or small RNA-regulatory factors and by ribosomes during the process of translation. It was discovered that certain mRNAs carry natural aptamer domains and that binding of specific metabolites directly to these RNA domains leads to modulation of gene expression. Natural riboswitches exhibit two surprising functions that are not typically associated with natural RNAs. First, the mRNA element can adopt distinct structural states wherein one structure serves as a precise binding pocket for its target metabolite. Second, the metabolite-induced allosteric interconversion between structural states causes a change in the level of gene expression by one of several distinct mechanisms. Riboswitches typically can be dissected into two separate domains: one that selectively binds the target (aptamer domain) and another that influences genetic control (expression platform). It is the dynamic interplay between these two domains that results in metabolite-dependent allosteric control of gene expression.

As disclosed herein, distinct classes of riboswitches have been identified and are shown to selectively recognize activating compounds (referred to herein as trigger molecules). For example, coenzyme $B_{12}$, thiamine pyrophosphate (TPP), and flavin mononucleotide (FMN) activate riboswitches present in genes encoding key enzymes in metabolic or transport pathways of these compounds. The aptamer domain of each riboswitch class conforms to a highly conserved consensus sequence and structure. Thus, sequence homology searches can be used to identify related riboswitch domains. Riboswitch domains have been discovered in various organisms from bacteria, archaea, and eukarya.

One class of riboswitches that recognizes guanine and discriminates against most other purine analogs has been discovered. Representative RNAs that carry the consensus sequence and structural features of guanine riboswitches are located in the 5'-untranslated region (UTR) of numerous genes of prokaryotes, where they control expression of proteins involved in purine salvage and biosynthesis. Three representatives of this phylogenetic collection bind adenine with values for apparent dissociation constant (apparent $K_D$) that are several orders of magnitude better than for guanine The preference for adenine is due to a single nucleotide substitution in the core of the riboswitch, wherein each representative most likely recognizes its corresponding ligand by forming a Watson/Crick base pair. In addition, the adenine-specific riboswitch associated with the ydhL gene of *Bacillus subtilis* functions as a genetic 'ON' switch, wherein adenine binding causes a structural rearrangement that precludes formation of an intrinsic transcription terminator stem. Guanine-sensing riboswitches are a class of RNA genetic control elements that modulate gene expression in response to changing concentrations of this compound.

It was discovered that the 5'-untranslated sequence of the *Escherichia coli* btuB mRNA assumes a more proactive role in metabolic monitoring and genetic control. The mRNA serves as a metabolite-sensing genetic switch by selectively binding coenzyme $B_{12}$ without the need for proteins. This binding event establishes a distinct RNA structure that is likely to be responsible for inhibition of ribosome binding and consequent reduction in synthesis of the cobalamin transport protein BtuB. This discovery, along with related observations described herein, supports the hypothesis that metabolic monitoring through RNA-metabolite interactions is a widespread mechanism of genetic control.

RNA structure probing data indicate that the thiamine pyrophosphate (TPP) riboswitch operates as an allosteric sensor of its target compound, wherein binding of TPP by the aptamer domain stabilizes a conformational state within the aptamer and within the neighboring expression platform that precludes translation. The diversity of expression platforms appears to be expansive. The thiM RNA uses a Shine-Dalgarno (SD)-blocking mechanism to control translation. In contrast, the thiC RNA controls gene expression both at transcription and translation, and therefore might make use of a somewhat more complex expression platform that converts the TPP binding event into a transcription termination event and into inhibition of translation of completed mRNAs.

A. General Organization of Riboswitch RNAs

Bacterial riboswitch RNAs are genetic control elements that are located primarily within the 5'-untranslated region (5'-UTR) of the main coding region of a particular mRNA. Structural probing studies (discussed further below) reveal that riboswitch elements are generally composed of two domains: a natural aptamer (T. Hermann, D. J. Patel, *Science* 2000, 287, 820; L. Gold, et al., *Annual Review of Biochemistry* 1995, 64, 763) that serves as the ligand-binding domain, and an 'expression platform' that interfaces with RNA elements that are involved in gene expression (e.g. Shine-Dalgarno (SD) elements; transcription terminator stems). These conclusions are drawn from the observation that aptamer domains synthesized in vitro bind the appropriate ligand in the absence of the expression platform (see Examples 2, 3 and 6). Moreover, structural probing investigations suggest that the aptamer domain of most riboswitches adopts a particular secondary- and tertiary-structure fold when examined independently, that is essentially identical to the aptamer structure when examined in the context of the entire 5' leader RNA. This implies that, in many cases, the aptamer domain is a modular unit that folds independently of the expression platform (see Examples 2, 3 and 6).

Ultimately, the ligand-bound or unbound status of the aptamer domain is interpreted through the expression platform, which is responsible for exerting an influence upon gene expression. The view of a riboswitch as a modular element is further supported by the fact that aptamer domains are highly conserved amongst various organisms (and even between kingdoms as is observed for the TPP riboswitch), (N. Sudarsan, et al., *RNA* 2003, 9, 644) whereas the expression platform varies in sequence, structure, and in the mechanism by which expression of the appended open reading frame is controlled. For example, ligand binding to the TPP riboswitch of the tenA mRNA of *B. subtilis* causes transcription termination (A. S. Mironov, et al., *Cell* 2002, 111, 747). This expression platform is distinct in sequence and structure compared to the expression platform of the TPP riboswitch in the thiM mRNA from *E. coli*, wherein TPP binding causes inhibition of translation by a SD blocking mechanism (see Example 2). The TPP aptamer domain is easily recognizable and of near identical functional character between these two transcriptional units, but the genetic control mechanisms and the expression platforms that carry them out are very different.

Aptamer domains for riboswitch RNAs typically range from ~70 to 170 nt in length (FIG. 11). This observation was somewhat unexpected given that in vitro evolution experiments identified a wide variety of small molecule-binding aptamers, which are considerably shorter in length and structural intricacy (T. Hermann, D. J. Patel, *Science* 2000, 287, 820; L. Gold, et al., *Annual Review of Biochemistry* 1995, 64, 763; M. Famulok, *Current Opinion in Structural Biology* 1999, 9, 324). Although the reasons for the substantial increase in complexity and information content of the natural aptamer sequences relative to artificial aptamers remains to be proven, this complexity is most likely required to form RNA receptors that function with high affinity and selectivity. Apparent $K_D$ values for the ligand-riboswitch complexes range from low nanomolar to low micromolar. It is also worth noting that some aptamer domains, when isolated from the appended expression platform, exhibit improved affinity for the target ligand over that of the intact riboswitch. (~10 to 100-fold) (see Example 2). Presumably, there is an energetic cost in sampling the multiple distinct RNA conformations required by a fully intact riboswitch RNA, which is reflected by a loss in ligand affinity. Since the aptamer domain must serve as a molecular switch, this might also add to the functional demands on natural aptamers that might help rationalize their more sophisticated structures.

B. Riboswitch Regulation of Transcription Termination in Bacteria

Bacteria primarily make use of two methods for termination of transcription.

Certain genes incorporate a termination signal that is dependent upon the Rho protein, (J. P. Richardson, *Biochimica et Biophysica Acta* 2002, 1577, 251). while others make use of Rho-independent terminators (intrinsic terminators) to destabilize the transcription elongation complex (I. Gusarov, E. Nudler, *Molecular Cell* 1999, 3, 495; E. Nudler, M. E. Gottesman, *Genes to Cells* 2002, 7, 755). The latter RNA elements are composed of a GC-rich stem-loop followed by a stretch of 6-9 uridyl residues. Intrinsic terminators are widespread throughout bacterial genomes (F. Lillo, et al., 2002, 18, 971), and are typically located at the 3'-termini of genes or operons. Interestingly, an increasing number of examples are being observed for intrinsic terminators located within 5'-UTRs.

Amongst the wide variety of genetic regulatory strategies employed by bacteria there is a growing class of examples wherein RNA polymerase responds to a termination signal within the 5'-UTR in a regulated fashion (T. M. Henkin, *Current Opinion in Microbiology* 2000, 3, 149). During certain conditions the RNA polymerase complex is directed by external signals either to perceive or to ignore the termination signal. Although transcription initiation might occur without regulation, control over mRNA synthesis (and of gene expression) is ultimately dictated by regulation of the intrinsic terminator. Presumably, one of at least two mutually exclusive mRNA conformations results in the formation or disruption of the RNA structure that signals transcription termination. A trans-acting factor, which in some instances is a RNA (F. J. Grundy, et al., *Proceedings of the National Academy of Sciences of the United States of America* 2002, 99, 11121; T. M. Henkin, C. Yanofsky, *Bioessays* 2002, 24, 700) and in others is a protein (J. Stulke, *Archives of Microbiology* 2002, 177, 433), is generally required for receiving a particular intracellular signal and subsequently stabilizing one of the RNA conformations. Riboswitches offer a direct link between RNA structure modulation and the metabolite signals that are interpreted by the genetic control machinery. A brief overview of the FMN riboswitch from a *B. subtilis* mRNA is provided below to illustrate this mechanism.

It was discovered that certain mRNAs involved in thiamine biosynthesis bind to thiamine (vitamin $B_1$) or its bioactive pyrophosphate derivative (TPP) without the participation of protein factors. The mRNA-effector complex adopts a distinct structure that sequesters the ribosome-binding site and leads to a reduction in gene expression. This metabolite-sensing mRNA system provides an example of a genetic “riboswitch” (referred to herein as a riboswitch) whose origin might predate the evolutionary emergence of proteins. It has been discovered that the mRNA leader sequence of the btuB gene of *Escherichia coli* can bind coenzyme $B_{12}$ selectively, and that this binding event brings about a structural change in the RNA that is important for genetic control (see Example 1). It was also discovered that mRNAs that encode thiamine biosynthetic proteins also employ a riboswitch mechanism (see Example 2).

It was also discovered that the 5'-UTR of the lysC gene of *Bacillus subtilis* carries a conserved RNA element that serves as a lysine-responsive riboswitch. The ligand-binding domain of the riboswitch binds to L-lysine with an apparent dissociation constant ($K_D$) of approximately 1 μM, and exhibits a high level of molecular discrimination against closely related analogs including D-lysine and ornithine. This widespread class of riboswitches serves as a target for the antimicrobial agent thiosine.

It was also discovered that the xpt-pbuX operon (Christiansen, L. C., et al., 1997, J. Bacteriol. 179, 2540-2550) is controlled by a riboswitch that exhibits high affinity and high selectivity for guanine This class of riboswitches is present in the 5'-untranslated region (5'-UTR) of five transcriptional units in *B. subtilis*, including that of the 12-gene pur operon. Direct binding of guanine by mRNAs serves as a critical determinant of metabolic homeostasis for purine metabolism in certain bacteria. Furthermore, the discovered classes of riboswitches, which respond to seven distinct target molecules, control at least 68 genes in *Bacillus subtilis* that are of fundamental importance to central metabolic pathways.

It was discovered that a highly conserved RNA domain termed the S box serves as a selective aptamer for SAM. Allosteric modulation of secondary and tertiary structures are induced upon SAM binding to the aptamer domain, and these structural changes are responsible for inducing termination of mRNA transcription.

A variant class of riboswitches that responds to adenine is also disclosed. These riboswitches carry an aptamer domain that corresponds closely in sequence and secondary structure to the guanine aptamer. However, each representative of the adenine sub-class of riboswitches carries a C to U mutation in the conserved core of the aptamer, indicating that this residue is involved in metabolite recognition. The identity of this single nucleotide determines the binding specificity between guanine and adenine, which provides an example of how complex riboswitch structures can be mutated to recognize new metabolite targets.

Although the specific natural riboswitches disclosed herein are the first examples of mRNA elements that control genetic expression by metabolite binding, it is expected that this genetic control strategy is widespread in biology. It has been suggested (White III, Coenzymes as fossils of an earlier metabolic state. *J. Mol. Evol.* 7, 101-104 (1976); White III, In: *The Pyridine Nucleotide Coenzymes*. Acad. Press, N.Y. pp. 1-17 (1982); Benner et al., Modern metabolism as a palimpsest of the RNA world. *Proc. Natl. Acad. Sci. USA* 86, 7054-7058 (1989)) that TPP, coenzyme $B_{12}$ and FMN emerged as biological cofactors during the RNA world (Joyce, The antiquity of RNA-based evolution. *Nature* 418, 214-221 (2002)). If these metabolites were being biosynthesized and used before the advent of proteins, then certain riboswitches might be modern examples of the most ancient form of genetic control. A search of genomic sequence databases has revealed that sequences corresponding to the TPP aptamer exist in organisms from bacteria, archaea and eukarya—largely without major alteration. Although new metabolite-binding mRNAs are likely to emerge as evolution progresses, it is possible that the known riboswitches are molecular fossils from the RNA world.

Disclosed are mRNA elements that have been identified in fungi and in plants that match the consensus sequence and structure of thiamine pyrophosphate-binding domains of prokaryotes. In Arabidopsis, the consensus motif resides in the 3'-UTR of a thiamine biosynthetic gene, and the isolated RNA domain binds the corresponding coenzyme in vitro. These results indicate that metabolite-binding mRNAs are involved in eukaryotic gene regulation and that some riboswitches might be representatives of an ancient form of genetic control.

It is to be understood that the disclosed method and compositions are not limited to specific synthetic methods, specific analytical techniques, or to particular reagents unless otherwise specified, and, as such, can vary. It is also to be understood that the terminology used herein is for the purpose of describing particular embodiments only and is not intended to be limiting.

Materials

Disclosed are materials, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference to each of various individual and collective combinations and permutation of these compounds can not be explicitly disclosed, each is specifically contemplated and described herein. For example, if a riboswitch or aptamer domain is disclosed and discussed and a number of modifications that can be made to a number of molecules including the riboswitch or aptamer domain are discussed, each and every combination and permutation of riboswitch or aptamer domain and the modifications that are possible are specifically contemplated unless specifically indicated to the contrary. Thus, if a class of molecules A, B, and C are disclosed as well as a class of molecules D, E, and F and an example of a combination molecule, A-D is disclosed, then even if each is not individually recited, each is individually and collectively contemplated. Thus, in this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods, and that each such combination is specifically contemplated and should be considered disclosed.

A. Riboswitches

Riboswitches are expression control elements that are part of the RNA molecule to be expressed and that change state when bound by a trigger molecule. Riboswitches typically can be dissected into two separate domains: one that selectively binds the target (aptamer domain) and another that influences genetic control (expression platform domain). It is the dynamic interplay between these two domains that results in metabolite-dependent allosteric control of gene expression. Disclosed are isolated and recombinant riboswitches, recombinant constructs containing such riboswitches, heterologous sequences operably linked to such riboswitches, and cells and transgenic organisms harboring such riboswitches, riboswitch recombinant constructs, and riboswitches operably linked to heterologous sequences. The heterologous sequences can be, for example, sequences encoding proteins or peptides of interest, including reporter proteins or peptides. Preferred riboswitches are, or are derived from, naturally occurring riboswitches.

The disclosed riboswitches, including the derivatives and recombinant forms thereof, generally can be from any source, including naturally occurring riboswitches and riboswitches designed de novo. Any such riboswitches can be used in or with the disclosed methods. However, different types of riboswitches can be defined and some such sub-types can be useful in or with particular methods (generally as described elsewhere herein). Types of riboswitches include, for example, naturally occurring riboswitches, derivatives and modified forms of naturally occurring riboswitches, chimeric riboswitches, and recombinant riboswitches. A naturally occurring riboswitch is a riboswitch having the sequence of a riboswitch as found in nature. Such a naturally occurring riboswitch can be an isolated or recombinant form of the naturally occurring riboswitch as it occurs in nature. That is, the riboswitch has the same primary structure but has been isolated or engineered in a new genetic or nucleic acid context. Chimeric riboswitches can be made up of, for example, part of a riboswitch of any or of a particular class or type of riboswitch and part of a different riboswitch of the same or of any different class or type of riboswitch; part of a riboswitch of any or of a particular class or type of riboswitch and any non-riboswitch sequence or component. Recombinant riboswitches are riboswitches that have been isolated or engineered in a new genetic or nucleic acid context.

Different classes of riboswitches refer to riboswitches that have the same or similar trigger molecules or riboswitches that have the same or similar overall structure (predicted, determined, or a combination). Riboswitches of the same class generally, but need not, have both the same or similar trigger molecules and the same or similar overall structure.

Also disclosed are chimeric riboswitches containing heterologous aptamer domains and expression platform domains. That is, chimeric riboswitches are made up an aptamer domain from one source and an expression platform domain from another source. The heterologous sources can be from, for example, different specific riboswitches, different types of riboswitches, or different classes of riboswitches. The heterologous aptamers can also come from non-riboswitch aptamers. The heterologous expression platform domains can also come from non-riboswitch sources.

Riboswitches can be modified from other known, developed or naturally-occurring riboswitches. For example, switch domain portions can be modified by changing one or more nucleotides while preserving the known or predicted secondary, tertiary, or both secondary and tertiary structure of the riboswitch. For example, both nucleotides in a base pair can be changed to nucleotides that can also base pair. Changes that allow retention of base pairing are referred to herein as base pair conservative changes.

Modified or derivative riboswitches can also be produced using in vitro selection and evolution techniques. In general, in vitro evolution techniques as applied to riboswitches involve producing a set of variant riboswitches where part(s) of the riboswitch sequence is varied while other parts of the riboswitch are held constant. Activation, deactivation or blocking (or other functional or structural criteria) of the set of variant riboswitches can then be assessed and those variant riboswitches meeting the criteria of interest are selected for use or further rounds of evolution. Useful base riboswitches for generation of variants are the specific and consensus riboswitches disclosed herein. Consensus riboswitches can be used to inform which part(s) of a riboswitch to vary for in vitro selection and evolution.

Also disclosed are modified riboswitches with altered regulation. The regulation of a riboswitch can be altered by operably linking an aptamer domain to the expression platform domain of the riboswitch (which is a chimeric riboswitch). The aptamer domain can then mediate regulation of the riboswitch through the action of, for example, a trigger molecule for the aptamer domain. Aptamer domains can be operably linked to expression platform domains of riboswitches in any suitable manner, including, for example, by replacing the normal or natural aptamer domain of the riboswitch with the new aptamer domain. Generally, any compound or condition that can activate, deactivate or block the riboswitch from which the aptamer domain is derived can be used to activate, deactivate or block the chimeric riboswitch.

Also disclosed are inactivated riboswitches. Riboswitches can be inactivated by covalently altering the riboswitch (by, for example, crosslinking parts of the riboswitch or coupling a compound to the riboswitch). Inactivation of a riboswitch in this manner can result from, for example, an alteration that prevents the trigger molecule for the riboswitch from binding, that prevents the change in state of the riboswitch upon binding of the trigger molecule, or that prevents the expression platform domain of the riboswitch from affecting expression upon binding of the trigger molecule.

Also disclosed are biosensor riboswitches. Biosensor riboswitches are engineered riboswitches that produce a detectable signal in the presence of their cognate trigger molecule. Useful biosensor riboswitches can be triggered at or above threshold levels of the trigger molecules. Biosensor riboswitches can be designed for use in vivo or in vitro. For example, biosensor riboswitches operably linked to a reporter RNA that encodes a protein that serves as or is involved in producing a signal can be used in vivo by engineering a cell or organism to harbor a nucleic acid construct encoding the riboswitch/reporter RNA. An example of a biosensor riboswitch for use in vitro is a riboswitch that includes a conformation dependent label, the signal from which changes depending on the activation state of the riboswitch. Such a biosensor riboswitch preferably uses an aptamer domain from or derived from a naturally occurring riboswitch. Biosensor riboswitches can be used in various situations and platforms. For example, biosensor riboswitches can be used with solid supports, such as plates, chips, strips and wells.

Also disclosed are modified or derivative riboswitches that recognize new trigger molecules. New riboswitches and/or new aptamers that recognize new trigger molecules can be selected for, designed or derived from known riboswitches. This can be accomplished by, for example, producing a set of aptamer variants in a riboswitch, assessing the activation of the variant riboswitches in the presence of a compound of interest, selecting variant riboswitches that were activated (or, for example, the riboswitches that were the most highly or the most selectively activated), and repeating these steps until a variant riboswitch of a desired activity, specificity, combination of activity and specificity, or other combination of properties results.

Particularly useful aptamer domains can form a stem structure referred to herein as the P1 stem structure (or simply P1). The P1 stems of a variety of riboswitches are shown in FIG. 11 (and in other figures). The hybridizing strands in the P1 stem structure are referred to as the aptamer strand (also referred to as the P1a strand) and the control strand (also referred to as the P lb strand). The control strand can form a stem structure with both the aptamer strand and a sequence in a linked expression platform that is referred to as the regulated strand (also referred to as the P 1 c strand). Thus, the control strand (P1b) can form alternative stem structures with the aptamer strand (P1a) and the regulated strand (P1c). Activation and deactivation of a riboswitch results in a shift from one of the stem structures to the other (from P1a/P1b to P1b/P1c or vice versa). The formation of the P1b/P1c stem structure affects expression of the RNA molecule containing the riboswitch. Riboswitches that operate via this control mechanism are referred to herein as alternative stem structure riboswitches (or as alternative stem riboswitches).

In general, any aptamer domain can be adapted for use with any expression platform domain by designing or adapting a regulated strand in the expression platform domain to be complementary to the control strand of the aptamer domain. Alternatively, the sequence of the aptamer and control strands of an aptamer domain can be adapted so that the control strand is complementary to a functionally significant sequence in an expression platform. For example, the control strand can be adapted to be complementary to the Shine-Dalgarno sequence of an RNA such that, upon formation of a stem structure between the control strand and the SD sequence, the SD sequence becomes inaccessible to ribosomes, thus reducing or preventing translation initiation. Note that the aptamer strand would have corresponding changes in sequence to allow formation of a P1 stem in the aptamer domain.

As another example, a transcription terminator can be added to an RNA molecule (most conveniently in an untranslated region of the RNA) where part of the sequence of the transcription terminator is complementary to the control strand of an aptamer domain (the sequence will be the regulated strand). This will allow the control sequence of the aptamer domain to form alternative stem structures with the aptamer strand and the regulated strand, thus either forming or disrupting a transcription terminator stem upon activation or deactivation of the riboswitch. Any other expression element can be brought under the control of a riboswitch by similar design of alternative stem structures.

Figure 12A:
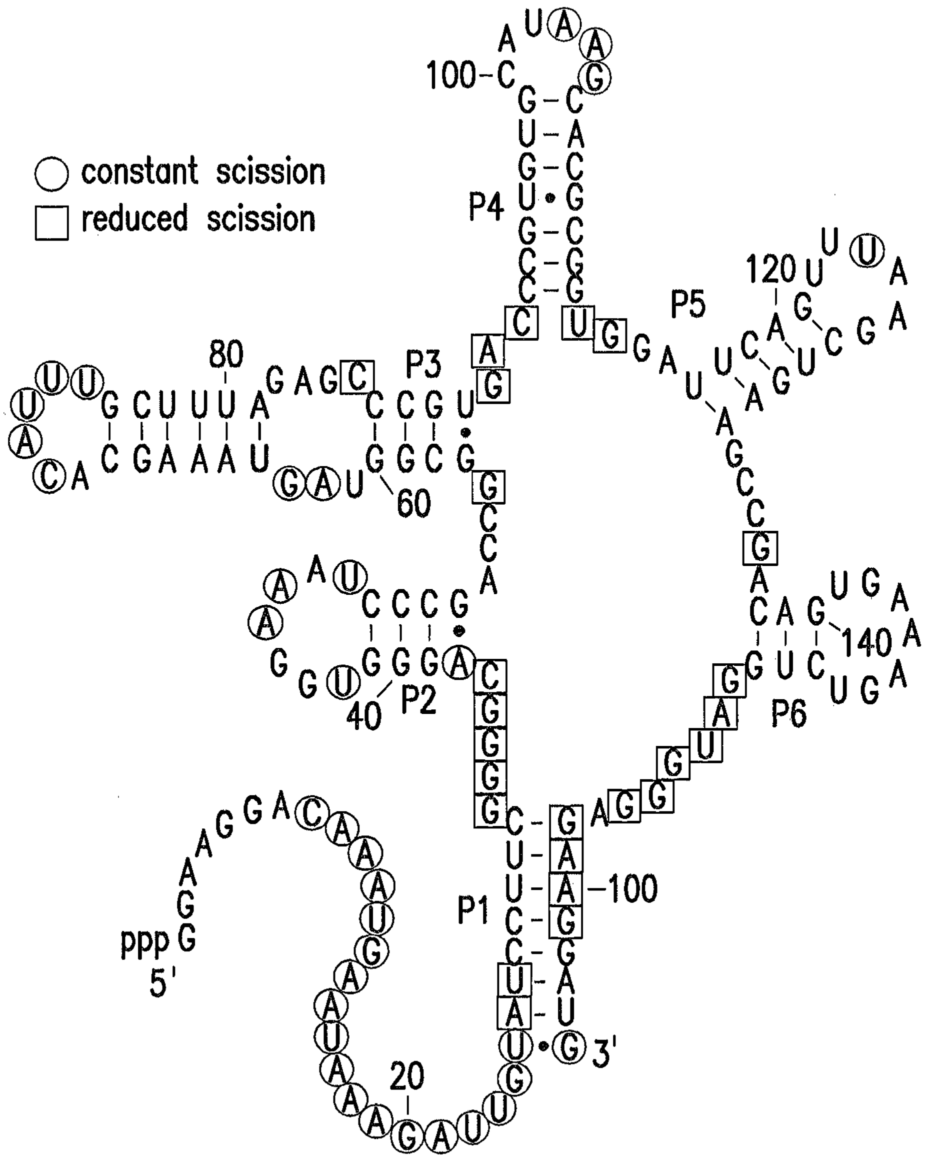
FIGS. 12A (SEQ ID NO:13), 12B and 12C show the regulation of the *B. subtilis* ribD mRNA by FMN.
Figure 12B:
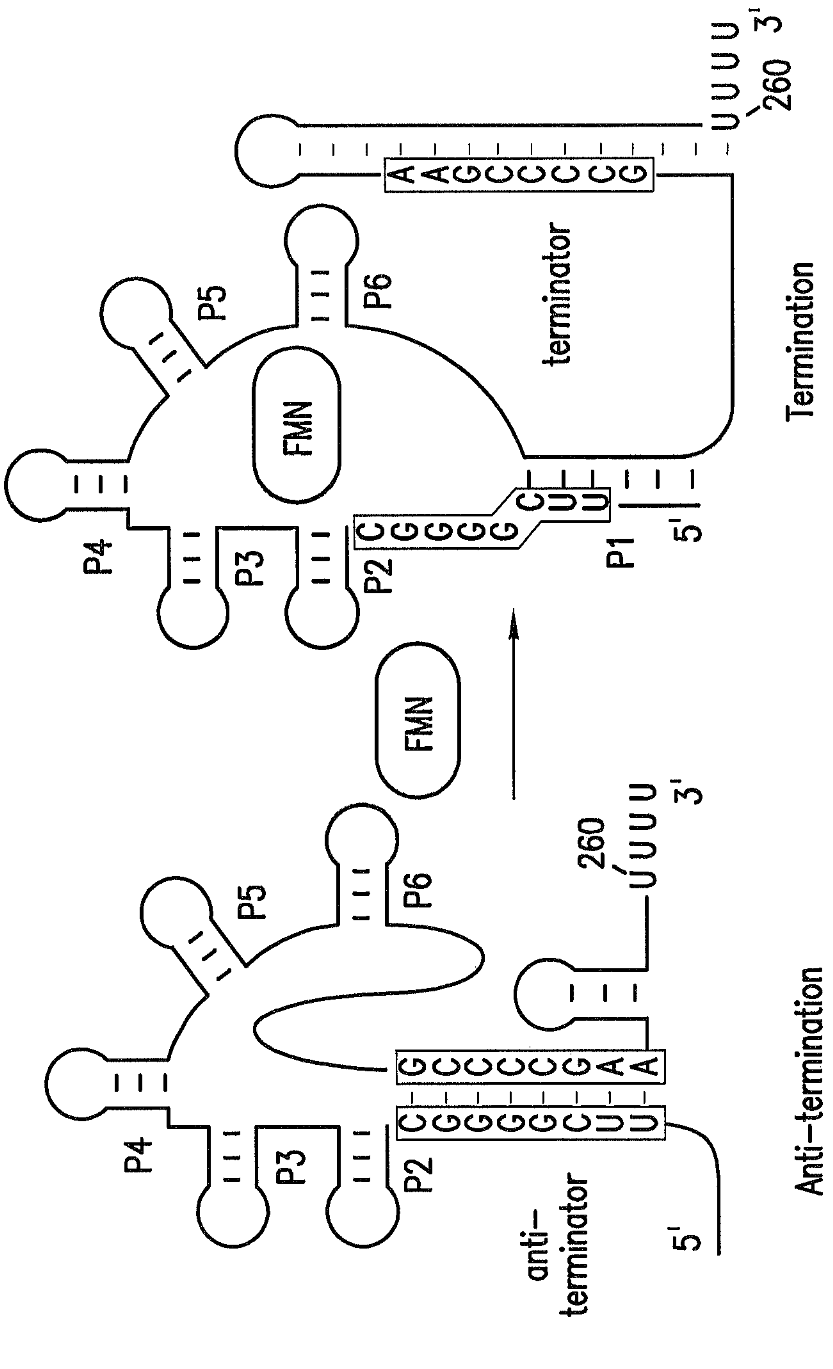
FIG. 12B shows a model for the mechanism of ribD regulation. The ribD mRNA adopts anti-termination conformation in the absence of FMN. Increased levels of FMN stabilize an RFN-FMN complex that permits formation of the terminator structure.

For transcription terminators controlled by riboswitches, the speed of transcription and spacing of the riboswitch and expression platform elements can be important for proper control. Transcription speed can be adjusted by, for example, by including polymerase pausing elements (e.g., a series of uridine residues) to pause transcription and allow the riboswitch to form and sense trigger molecules. For example, with the FMN riboswitch, if FMN is bound to its aptamer domain, then the antiterminator sequence is sequestered and is unavailable for formation of an antiterminator structure (FIG. 12). However, if FMN is absent, the antiterminator can form once its nucleotides emerge from the polymerase. RNAP then breaks free of the pause site only to reach another U-stretch and pause again. The transcriptional terminator then forms only if the terminator nucleotides are not tied up by the antiterminator.

Disclosed are regulatable gene expression constructs comprising a nucleic acid molecule encoding an RNA comprising a riboswitch operably linked to a coding region, wherein the riboswitch regulates expression of the RNA, wherein the riboswitch and coding region are heterologous. The riboswitch can comprise an aptamer domain and an expression platform domain, wherein the aptamer domain and the expression platform domain are heterologous. The riboswitch can comprise an aptamer domain and an expression platform domain, wherein the aptamer domain comprises a P1 stem, wherein the P1 stem comprises an aptamer strand and a control strand, wherein the expression platform domain comprises a regulated strand, wherein the regulated strand, the control strand, or both have been designed to form a stem structure.

Disclosed are riboswitches, wherein the riboswitch is a non-natural derivative of a naturally-occurring riboswitch. The riboswitch can comprise an aptamer domain and an expression platform domain, wherein the aptamer domain and the expression platform domain are heterologous. The riboswitch can be derived from a naturally-occuring guanine-responsive riboswitch, adenine-responsive riboswitch, lysine-responsive riboswitch, thiamine pyrophosphate-responsive riboswitch, adenosylcobalamin-responsive riboswitch, flavin mononucleotide-responsive riboswitch, or a S-adenosylmethionine-responsive riboswitch. The riboswitch can be activated by a trigger molecule, wherein the riboswitch produces a signal when activated by the trigger molecule.

Numerous riboswitches and riboswitch constructs are described and referred to herein. It is specifically contemplated that any specific riboswitch or riboswitch construct or group of riboswitches or riboswitch constructs can be excluded from some aspects of the invention disclosed herein. For example, fusion of the xpt-pbuX riboswitch with a reporter gene could be excluded from a set of riboswitches fused to reporter genes.

1. Aptamer Domains

Aptamers are nucleic acid segments and structures that can bind selectively to particular compounds and classes of compounds. Riboswitches have aptamer domains that, upon binding of a trigger molecule result in a change the state or structure of the riboswitch. In functional riboswitches, the state or structure of the expression platform domain linked to the aptamer domain changes when the trigger molecule binds to the aptamer domain. Aptamer domains of riboswitches can be derived from any source, including, for example, natural aptamer domains of riboswitches, artificial aptamers, engineered, selected, evolved or derived aptamers or aptamer domains. Aptamers in riboswitches generally have at least one portion that can interact, such as by forming a stem structure, with a portion of the linked expression platform domain. This stem structure will either form or be disrupted upon binding of the trigger molecule.

Consensus aptamer domains of a variety of natural riboswitches are shown in FIG. 11. These aptamer domains (including all of the direct variants embodied therein) can be used in riboswitches. The consensus sequences and structures indicate variations in sequence and structure. Aptamer domains that are within the indicated variations are referred to herein as direct variants. These aptamer domains can be modified to produce modified or variant aptamer domains. Conservative modifications include any change in base paired nucleotides such that the nucleotides in the pair remain complementary. Moderate modifications include changes in the length of stems or of loops (for which a length or length range is indicated) of less than or equal to 20% of the length range indicated. Loop and stem lengths are considered to be "indicated" where the consensus structure shows a stem or loop of a particular length or where a range of lengths is listed or depicted. Moderate modifications include changes in the length of stems or of loops (for which a length or length range is not indicated) of less than or equal to 40% of the length range indicated. Moderate modifications also include and functional variants of unspecified portions of the aptamer domain. Unspecified portions of the aptamer domains are indicated by solid lines in FIG. 11.

The P1 stem and its constituent strands can be modified in adapting aptamer domains for use with expression platforms and RNA molecules. Such modifications, which can be extensive, are referred to herein as P1 modifications. P1 modifications include changes to the sequence and/or length of the P1 stem of an aptamer domain.

The aptamer domains shown in FIG. 11 (including any direct variants) are particularly useful as initial sequences for producing derived aptamer domains via in vitro selection or in vitro evolution techniques.

Aptamer domains of the disclosed riboswitches can also be used for any other purpose, and in any other context, as aptamers. For example, aptamers can be used to control ribozymes, other molecular switches, and any RNA molecule where a change in structure can affect function of the RNA.

2. Expression Platform Domains

Expression platform domains are a part of riboswitches that affect expression of the RNA molecule that contains the riboswitch. Expression platform domains generally have at least one portion that can interact, such as by forming a stem structure, with a portion of the linked aptamer domain. This stem structure will either form or be disrupted upon binding of the trigger molecule. The stem structure generally either is, or prevents formation of, an expression regulatory structure. An expression regulatory structure is a structure that allows, prevents, enhances or inhibits expression of an RNA molecule containing the structure. Examples include Shine-Dalgarno sequences, initiation codons, transcription terminators, and stability and processing signals.

B. Trigger Molecules

Trigger molecules are molecules and compounds that can activate a riboswitch. This includes the natural or normal trigger molecule for the riboswitch and other compounds that can activate the riboswitch. Natural or normal trigger molecules are the trigger molecule for a given riboswitch in nature or, in the case of some non-natural riboswitches, the trigger molecule for which the riboswitch was designed or with which the riboswitch was selected (as in, for example, in vitro selection or in vitro evolution techniques). Non-natural trigger molecules can be referred to as non-natural trigger molecules.

C. Compounds

Also disclosed are compounds, and compositions containing such compounds, that can activate, deactivate or block a riboswitch. Riboswitches function to control gene expression through the binding or removal of a trigger molecule. Compounds can be used to activate, deactivate or block a riboswitch. The trigger molecule for a riboswitch (as well as other activating compounds) can be used to activate a riboswitch. Compounds other than the trigger molecule generally can be used to deactivate or block a riboswitch. Riboswitches can also be deactivated by, for example, removing trigger molecules from the presence of the riboswitch. A riboswitch can be blocked by, for example, binding of an analog of the trigger molecule that does not activate the riboswitch.

Also disclosed are compounds for altering expression of an RNA molecule, or of a gene encoding an RNA molecule, where the RNA molecule includes a riboswitch. This can be accomplished by bringing a compound into contact with the RNA molecule. Riboswitches function to control gene expression through the binding or removal of a trigger molecule. Thus, subjecting an RNA molecule of interest that includes a riboswitch to conditions that activate, deactivate or block the riboswitch can be used to alter expression of the RNA. Expression can be altered as a result of, for example, termination of transcription or blocking of ribosome binding to the RNA. Binding of a trigger molecule can, depending on the nature of the riboswitch, reduce or prevent expression of the RNA molecule or promote or increase expression of the RNA molecule.

Also disclosed are compounds for regulating expression of an RNA molecule, or of a gene encoding an RNA molecule. Also disclosed are compounds for regulating expression of a naturally occurring gene or RNA that contains a riboswitch by activating, deactivating or blocking the riboswitch. If the gene is essential for survival of a cell or organism that harbors it, activating, deactivating or blocking the riboswitch can in death, stasis or debilitation of the cell or organism.

Also disclosed are compounds for regulating expression of an isolated, engineered or recombinant gene or RNA that contains a riboswitch by activating, deactivating or blocking the riboswitch. If the gene encodes a desired expression product, activating or deactivating the riboswitch can be used to induce expression of the gene and thus result in production of the expression product. If the gene encodes an inducer or repressor of gene expression or of another cellular process, activation, deactivation or blocking of the riboswitch can result in induction, repression, or de-repression of other, regulated genes or cellular processes. Many such secondary regulatory effects are known and can be adapted for use with riboswitches. An advantage of riboswitches as the primary control for such regulation is that riboswitch trigger molecules can be small, non-antigenic molecules.

Also disclosed are methods of identifying compounds that activate, deactivate or block a riboswitch. For examples, compounds that activate a riboswitch can be identified by bringing into contact a test compound and a riboswitch and assessing activation of the riboswitch. If the riboswitch is activated, the test compound is identified as a compound that activates the riboswitch. Activation of a riboswitch can be assessed in any suitable manner. For example, the riboswitch can be linked to a reporter RNA and expression, expression level, or change in expression level of the reporter RNA can be measured in the presence and absence of the test compound. As another example, the riboswitch can include a conformation dependent label, the signal from which changes depending on the activation state of the riboswitch. Such a riboswitch preferably uses an aptamer domain from or derived from a naturally occurring riboswitch. As can be seen, assessment of activation of a riboswitch can be performed with the use of a control assay or measurement or without the use of a control assay or measurement. Methods for identifying compounds that deactivate a riboswitch can be performed in analogous ways.

Identification of compounds that block a riboswitch can be accomplished in any suitable manner. For example, an assay can be performed for assessing activation or deactivation of a riboswitch in the presence of a compound known to activate or deactivate the riboswitch and in the presence of a test compound. If activation or deactivation is not observed as would be observed in the absence of the test compound, then the test compound is identified as a compound that blocks activation or deactivation of the riboswitch.

Also disclosed are compounds made by identifying a compound that activates, deactivates or blocks a riboswitch and manufacturing the identified compound. This can be accomplished by, for example, combining compound identification methods as disclosed elsewhere herein with methods for manufacturing the identified compounds. For example, compounds can be made by bringing into contact a test compound and a riboswitch, assessing activation of the riboswitch, and, if the riboswitch is activated by the test compound, manufacturing the test compound that activates the riboswitch as the compound.

Also disclosed are compounds made by checking activation, deactivation or blocking of a riboswitch by a compound and manufacturing the checked compound. This can be accomplished by, for example, combining compound activation, deactivation or blocking assessment methods as disclosed elsewhere herein with methods for manufacturing the checked compounds. For example, compounds can be made by bringing into contact a test compound and a riboswitch, assessing activation of the riboswitch, and, if the riboswitch is activated by the test compound, manufacturing the test compound that activates the riboswitch as the compound. Checking compounds for their ability to activate, deactivate or block a riboswitch refers to both identification of compounds previously unknown to activate, deactivate or block a riboswitch and to assessing the ability of a compound to activate, deactivate or block a riboswitch where the compound was already known to activate, deactivate or block the riboswitch.

Specific compounds that can be used to activate riboswitches are also disclosed. Compounds useful with guanine-responsive riboswitches (and riboswitches derived from guanine-responsive riboswitches) include compounds having the formula

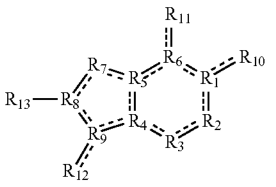

where the compound can bind a guanine-responsive riboswitch or derivative thereof, where, when the compound is bound to a guanine-responsive riboswitch or derivative, $R_7$ serves as a hydrogen bond acceptor, $R_{10}$ serves as a hydrogen bond donor, $R_{11}$ serves as a hydrogen bond acceptor, $R_{12}$ serves as a hydrogen bond donor, where $R_{13}$ is H, $H_2$ or is not present, where $R_1$, $R_2$, $R_3$, $R_4$, $R_5$, $R_6$, $R_8$, and $R_9$ are each independently C, N, O, or S, and where ⎓ each independently represent a single or double bond.

Every compound within the above definition is intended to be and should be considered to be specifically disclosed herein. Further, every subgroup that can be identified within the above definition is intended to be and should be considered to be specifically disclosed herein. As a result, it is specifically contemplated that any compound, or subgroup of compounds can be either specifically included for or excluded from use or included in or excluded from a list of compounds. For example, as one option, a group of compounds is contemplated where each compound is as defined above but is not guanine, hypoxanthine, xanthine, or $N^2$-methylguanine. As another example, a group of compounds is contemplated where each compound is as defined above and is able to activate a guanine-responsive riboswitch.

Compounds useful with adenine-responsive riboswitches (and riboswitches derived from adenine-responsive riboswitches) include compounds having the formula

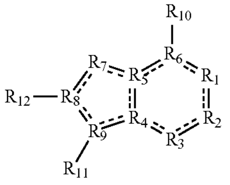

where the compound can bind an adenine-responsive riboswitch or derivative thereof, where, when the compound is bound to an adenine-responsive riboswitch or derivative, $R_1$, $R_3$ and $R_7$ serve as hydrogen bond acceptors, and $R_{10}$ and $R_{11}$ serve as hydrogen bond donors, where $R_{12}$ is H, $H_2$ or is not present, where $R_1$, $R_2$, $R_3$, $R_4$, $R_5$, $R_6$, $R_8$, and $R_9$ are each independently C, N, O, or S, and where ⎓ each independently represent a single or double bond.

Every compound within the above definition is intended to be and should be considered to be specifically disclosed herein. Further, every subgroup that can be identified within the above definition is intended to be and should be considered to be specifically disclosed herein. As a result, it is specifically contemplated that any compound, or subgroup of compounds can be either specifically included for or excluded from use or included in or excluded from a list of compounds. For example, as one option, a group of compounds is contemplated where each compound is as defined above but is not adenine, 2,6-diaminopurine, or 2-amino purine. As another example, a group of compounds is contemplated where each compound is as defined above and is able to activate an adenine-responsive riboswitch.

Compounds useful with lysine-responsive riboswitches (and riboswitches derived from lysine-responsive riboswitches) include compounds having the formula

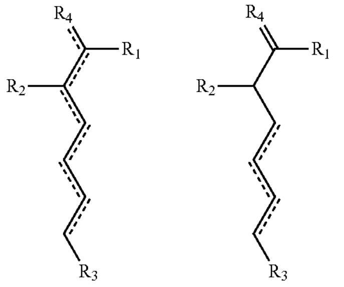

where the compound can bind a lysine-responsive riboswitch or derivative thereof, where $R_2$ and $R_3$ are each positively charged, where $R_1$ is negatively charged, where $R_4$ is C, N, O, or S, and where ⎓ each independently represent a single or double bond. Also contemplated are compounds as defined above where $R_2$ and $R_3$ are each $NH_3^+$ and where $R_1$ is $O^-$.

Every compound within the above definition is intended to be and should be considered to be specifically disclosed herein. Further, every subgroup that can be identified within the above definition is intended to be and should be considered to be specifically disclosed herein. As a result, it is specifically contemplated that any compound, or subgroup of compounds can be either specifically included for or excluded from use or included in or excluded from a list of compounds. For example, as one option, a group of compounds is contemplated where each compound is as defined above but is not lysine. As another example, a group of compounds is contemplated where each compound is as defined above and is able to activate a lysine-responsive riboswitch.

Compounds useful with TPP-responsive riboswitches (and riboswitches derived from lysine-responsive riboswitches) include compounds having the formula

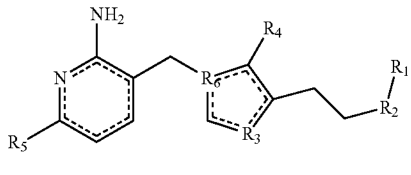

where the compound can bind a TPP-responsive riboswitch or derivative thereof, where $R_1$ is positively charged, where $R_2$ and $R_3$ are each independently C, O, or S, where $R_4$ is $CH_3$, $NH_2$, OH, SH, H or not present, where $R_5$ is $CH_3$, $NH_2$, OH, SH, or H, where $R_6$ is C or N, and where ⎓ each independently represent a single or double bond. Also contemplated are compounds as defined above where $R_1$ is phosphate, diphosphate or triphosphate.

Every compound within the above definition is intended to be and should be considered to be specifically disclosed herein. Further, every subgroup that can be identified within the above definition is intended to be and should be considered to be specifically disclosed herein. As a result, it is specifically contemplated that any compound, or subgroup of compounds can be either specifically included for or excluded from use or included in or excluded from a list of compounds. For example, as one option, a group of compounds is contemplated where each compound is as defined above but is not TPP, TP or thiamine. As another example, a group of compounds is contemplated where each compound is as defined above and is able to activate a TPP-responsive riboswitch.

D. Constructs, Vectors and Expression Systems

The disclosed riboswitches can be used in with any suitable expression system. Recombinant expression is usefully accomplished using a vector, such as a plasmid. The vector can include a promoter operably linked to riboswitch-encoding sequence and RNA to be expression (e.g., RNA encoding a protein). The vector can also include other elements required for transcription and translation. As used herein, vector refers to any carrier containing exogenous DNA. Thus, vectors are agents that transport the exogenous nucleic acid into a cell without degradation and include a promoter yielding expression of the nucleic acid in the cells into which it is delivered. Vectors include but are not limited to plasmids, viral nucleic acids, viruses, phage nucleic acids, phages, cosmids, and artificial chromosomes. A variety of prokaryotic and eukaryotic expression vectors suitable for carrying riboswitch-regulated constructs can be produced. Such expression vectors include, for example, pET, pET3d, pCR2.1, pBAD, pUC, and yeast vectors. The vectors can be used, for example, in a variety of in vivo and in vitro situation.

Viral vectors include adenovirus, adeno-associated virus, herpes virus, vaccinia virus, polio virus, AIDS virus, neuronal trophic virus, Sindbis and other RNA viruses, including these viruses with the HIV backbone. Also useful are any viral families which share the properties of these viruses which make them suitable for use as vectors. Retroviral vectors, which are described in Verma (1985), include Murine Maloney Leukemia virus, MMLV, and retroviruses that express the desirable properties of MMLV as a vector. Typically, viral vectors contain, nonstructural early genes, structural late genes, an RNA polymerase III transcript, inverted terminal repeats necessary for replication and encapsidation, and promoters to control the transcription and replication of the viral genome. When engineered as vectors, viruses typically have one or more of the early genes removed and a gene or gene/promotor cassette is inserted into the viral genome in place of the removed viral DNA.

A "promoter" is generally a sequence or sequences of DNA that function when in a relatively fixed location in regard to the transcription start site. A "promoter" contains core elements required for basic interaction of RNA polymerase and transcription factors and can contain upstream elements and response elements.

"Enhancer" generally refers to a sequence of DNA that functions at no fixed distance from the transcription start site and can be either 5' (Laimins, 1981) or 3' (Lusky et al., 1983) to the transcription unit. Furthermore, enhancers can be within an intron (Banerji et al., 1983) as well as within the coding sequence itself (Osborne et al., 1984). They are usually between 10 and 300 by in length, and they function in cis. Enhancers function to increase transcription from nearby promoters. Enhancers, like promoters, also often contain response elements that mediate the regulation of transcription. Enhancers often determine the regulation of expression.

Expression vectors used in eukaryotic host cells (yeast, fungi, insect, plant, animal, human or nucleated cells) can also contain sequences necessary for the termination of transcription which can affect mRNA expression. These regions are transcribed as polyadenylated segments in the untranslated portion of the mRNA encoding tissue factor protein. The 3' untranslated regions also include transcription termination sites. It is preferred that the transcription unit also contain a polyadenylation region. One benefit of this region is that it increases the likelihood that the transcribed unit will be processed and transported like mRNA. The identification and use of polyadenylation signals in expression constructs is well established. It is preferred that homologous polyadenylation signals be used in the transgene constructs.

The vector can include nucleic acid sequence encoding a marker product. This marker product is used to determine if the gene has been delivered to the cell and once delivered is being expressed. Preferred marker genes are the *E. Coli* lacZ gene which encodes β-galactosidase and green fluorescent protein.

In some embodiments the marker can be a selectable marker. When such selectable markers are successfully transferred into a host cell, the transformed host cell can survive if placed under selective pressure. There are two widely used distinct categories of selective regimes. The first category is based on a cell's metabolism and the use of a mutant cell line which lacks the ability to grow independent of a supplemented media. The second category is dominant selection which refers to a selection scheme used in any cell type and does not require the use of a mutant cell line. These schemes typically use a drug to arrest growth of a host cell. Those cells which have a novel gene would express a protein conveying drug resistance and would survive the selection. Examples of such dominant selection use the drugs neomycin, (Southern and Berg,1982), mycophenolic acid, (Mulligan and Berg, 1980) or hygromycin (Sugden et al., 1985).

Gene transfer can be obtained using direct transfer of genetic material, in but not limited to, plasmids, viral vectors, viral nucleic acids, phage nucleic acids, phages, cosmids, and artificial chromosomes, or via transfer of genetic material in cells or carriers such as cationic liposomes. Such methods are well known in the art and readily adaptable for use in the method described herein. Transfer vectors can be any nucleotide construction used to deliver genes into cells (e.g., a plasmid), or as part of a general strategy to deliver genes, e.g., as part of recombinant retrovirus or adenovirus (Ram et al. Cancer Res. 53:83-88, (1993)). Appropriate means for transfection, including viral vectors, chemical transfectants, or physico-mechanical methods such as electroporation and direct diffusion of DNA, are described by, for example, Wolff, J. A., et al., Science, 247, 1465-1468, (1990); and Wolff, J. A. Nature, 352, 815-818, (1991).

1. Viral Vectors

Preferred viral vectors are Adenovirus, Adeno-associated virus, Herpes virus, Vaccinia virus, Polio virus, AIDS virus, neuronal trophic virus, Sindbis and other RNA viruses, including these viruses with the HIV backbone. Also preferred are any viral families which share the properties of these viruses which make them suitable for use as vectors. Preferred retroviruses include Murine Maloney Leukemia virus, MMLV, and retroviruses that express the desirable properties of MMLV as a vector. Retroviral vectors are able to carry a larger genetic payload, i.e., a transgene or marker gene, than other viral vectors, and for this reason are a commonly used vector. However, they are not useful in non-proliferating cells. Adenovirus vectors are relatively stable and easy to work with, have high titers, and can be delivered in aerosol formulation, and can transfect non-dividing cells. Pox viral vectors are large and have several sites for inserting genes, they are thermostable and can be stored at room temperature. A preferred embodiment is a viral vector which has been engineered so as to suppress the immune response of the host organism, elicited by the viral antigens. Preferred vectors of this type will carry coding regions for Interleukin 8 or 10.

Viral vectors have higher transaction (ability to introduce genes) abilities than do most chemical or physical methods to introduce genes into cells. Typically, viral vectors contain, nonstructural early genes, structural late genes, an RNA polymerase III transcript, inverted terminal repeats necessary for replication and encapsidation, and promoters to control the transcription and replication of the viral genome. When engineered as vectors, viruses typically have one or more of the early genes removed and a gene or gene/promotor cassette is inserted into the viral genome in place of the removed viral DNA. Constructs of this type can carry up to about 8 kb of foreign genetic material. The necessary functions of the removed early genes are typically supplied by cell lines which have been engineered to express the gene products of the early genes in trans.

i. Retroviral Vectors

A retrovirus is an animal virus belonging to the virus family of Retroviridae, including any types, subfamilies, genus, or tropisms. Retroviral vectors, in general, are described by Verma, I.M., Retroviral vectors for gene transfer. In Microbiology-1985, American Society for Microbiology, pp. 229-232, Washington, (1985), which is incorporated by reference herein. Examples of methods for using retroviral vectors for gene therapy are described in U.S. Pat. Nos. 4,868,116 and 4,980,286; PCT applications WO 90/02806 and WO 89/07136; and Mulligan, (Science 260:926-932 (1993)); the teachings of which are incorporated herein by reference.

A retrovirus is essentially a package which has packed into it nucleic acid cargo. The nucleic acid cargo carries with it a packaging signal, which ensures that the replicated daughter molecules will be efficiently packaged within the package coat. In addition to the package signal, there are a number of molecules which are needed in cis, for the replication, and packaging of the replicated virus. Typically a retroviral genome, contains the gag, pol, and env genes which are involved in the making of the protein coat. It is the gag, pol, and env genes which are typically replaced by the foreign DNA that it is to be transferred to the target cell. Retrovirus vectors typically contain a packaging signal for incorporation into the package coat, a sequence which signals the start of the gag transcription unit, elements necessary for reverse transcription, including a primer binding site to bind the tRNA primer of reverse transcription, terminal repeat sequences that guide the switch of RNA strands during DNA synthesis, a purine rich sequence 5' to the 3' LTR that serve as the priming site for the synthesis of the second strand of DNA synthesis, and specific sequences near the ends of the LTRs that enable the insertion of the DNA state of the retrovirus to insert into the host genome. The removal of the gag, pol, and env genes allows for about 8 kb of foreign sequence to be inserted into the viral genome, become reverse transcribed , and upon replication be packaged into a new retroviral particle. This amount of nucleic acid is sufficient for the delivery of a one to many genes depending on the size of each transcript. It is preferable to include either positive or negative selectable markers along with other genes in the insert.

Since the replication machinery and packaging proteins in most retroviral vectors have been removed (gag, pol, and env), the vectors are typically generated by placing them into a packaging cell line. A packaging cell line is a cell line which has been transfected or transformed with a retrovirus that contains the replication and packaging machinery, but lacks any packaging signal. When the vector carrying the DNA of choice is transfected into these cell lines, the vector containing the gene of interest is replicated and packaged into new retroviral particles, by the machinery provided in cis by the helper cell. The genomes for the machinery are not packaged because they lack the necessary signals.

ii. Adenoviral Vectors

The construction of replication-defective adenoviruses has been described (Berkner et al., J. Virology 61:1213-1220 (1987); Massie et al., Mol. Cell. Biol. 6:2872-2883 (1986); Haj-Ahmad et al., J. Virology 57:267-274 (1986); Davidson et al., J. Virology 61:1226-1239 (1987); Zhang "Generation and identification of recombinant adenovirus by liposome-mediated transfection and PCR analysis" BioTechniques 15:868-872 (1993)). The benefit of the use of these viruses as vectors is that they are limited in the extent to which they can spread to other cell types, since they can replicate within an initial infected cell, but are unable to form new infectious viral particles. Recombinant adenoviruses have been shown to achieve high efficiency gene transfer after direct, in vivo delivery to airway epithelium, hepatocytes, vascular endothelium, CNS parenchyma and a number of other tissue sites (Morsy, J. Clin. Invest. 92:1580-1586 (1993); Kirshenbaum, J. Clin. Invest. 92:381-387 (1993); Roessler, J. Clin. Invest. 92:1085-1092 (1993); Moullier, Nature Genetics 4:154-159 (1993); La Salle, Science 259:988-990 (1993); Gomez-Foix, J. Biol. Chem. 267:25129-25134 (1992); Rich, Human Gene Therapy 4:461-476 (1993); Zabner, Nature Genetics 6:75-83 (1994); Guzman, Circulation Research 73:1201-1207 (1993); Bout, Human Gene Therapy 5:3-10 (1994); Zabner, Cell 75:207-216 (1993); Caillaud, Eur. J. Neuroscience 5:1287-1291 (1993); and Ragot, J. Gen. Virology 74:501-507 (1993)). Recombinant adenoviruses achieve gene transduction by binding to specific cell surface receptors, after which the virus is internalized by receptor-mediated endocytosis, in the same manner as wild type or replication-defective adenovirus (Chardonnet and Dales, Virology 40:462-477 (1970); Brown and Burlingham, J. Virology 12:386-396 (1973); Svensson and Persson, J. Virology 55:442-449 (1985); Seth, et al., J. Virol. 51:650-655 (1984); Seth, et al., Mol. Cell. Biol. 4:1528-1533 (1984); Varga et al., J. Virology 65:6061-6070 (1991); Wickham et al., Cell 73:309-319 (1993)).

A preferred viral vector is one based on an adenovirus which has had the E1 gene removed and these virons are generated in a cell line such as the human 293 cell line. In another preferred embodiment both the E1 and E3 genes are removed from the adenovirus genome.

Another type of viral vector is based on an adeno-associated virus (AAV). This defective parvovirus is a preferred vector because it can infect many cell types and is nonpathogenic to humans. AAV type vectors can transport about 4 to 5 kb and wild type AAV is known to stably insert into chromosome 19. Vectors which contain this site specific integration property are preferred. An especially preferred embodiment of this type of vector is the P4.1 C vector produced by Avigen, San Francisco, Calif., which can contain the herpes simplex virus thymidine kinase gene, HSV-tk, and/or a marker gene, such as the gene encoding the green fluorescent protein, GFP.

The inserted genes in viral and retroviral usually contain promoters, and/or enhancers to help control the expression of the desired gene product. A promoter is generally a sequence or sequences of DNA that function when in a relatively fixed location in regard to the transcription start site. A promoter contains core elements required for basic interaction of RNA polymerase and transcription factors, and can contain upstream elements and response elements.

2. Viral Promoters and Enhancers

Preferred promoters controlling transcription from vectors in mammalian host cells can be obtained from various sources, for example, the genomes of viruses such as: polyoma, Simian Virus 40 (SV40), adenovirus, retroviruses, hepatitis-B virus and most preferably cytomegalovirus, or from heterologous mammalian promoters, e.g. beta actin promoter. The early and late promoters of the SV40 virus are conveniently obtained as an SV40 restriction fragment which also contains the SV40 viral origin of replication (Fiers et al., Nature, 273: 113 (1978)). The immediate early promoter of the human cytomegalovirus is conveniently obtained as a HindIII E restriction fragment (Greenway, P. J. et al., Gene 18: 355-360 (1982)). Of course, promoters from the host cell or related species also are useful herein.

Enhancer generally refers to a sequence of DNA that functions at no fixed distance from the transcription start site and can be either 5' (Laimins, L. et al., Proc. Natl. Acad. Sci. 78: 993 (1981)) or 3' (Lusky, M. L., et al., Mol. Cell Bio. 3: 1108 (1983)) to the transcription unit. Furthermore, enhancers can be within an intron (Banerji, J. L. et al., Cell 33: 729 (1983)) as well as within the coding sequence itself (Osborne, T. F., et al., Mol. Cell Bio. 4: 1293 (1984)). They are usually between 10 and 300 by in length, and they function in cis. Enhancers function to increase transcription from nearby promoters. Enhancers also often contain response elements that mediate the regulation of transcription. Promoters can also contain response elements that mediate the regulation of transcription. Enhancers often determine the regulation of expression of a gene. While many enhancer sequences are now known from mammalian genes (globin, elastase, albumin, a-fetoprotein and insulin), typically one will use an enhancer from a eukaryotic cell virus. Preferred examples are the SV40 enhancer on the late side of the replication origin (bp 100-270), the cytomegalovirus early promoter enhancer, the polyoma enhancer on the late side of the replication origin, and adenovirus enhancers.

The promotor and/or enhancer can be specifically activated either by light or specific chemical events which trigger their function. Systems can be regulated by reagents such as tetracycline and dexamethasone. There are also ways to enhance viral vector gene expression by exposure to irradiation, such as gamma irradiation, or alkylating chemotherapy drugs.

It is preferred that the promoter and/or enhancer region be active in all eukaryotic cell types. A preferred promoter of this type is the CMV promoter (650 bases). Other preferred promoters are SV40 promoters, cytomegalovirus (full length promoter), and retroviral vector LTF.

It has been shown that all specific regulatory elements can be cloned and used to construct expression vectors that are selectively expressed in specific cell types such as melanoma cells. The glial fibrillary acetic protein (GFAP) promoter has been used to selectively express genes in cells of glial origin.

Expression vectors used in eukaryotic host cells (yeast, fungi, insect, plant, animal, human or nucleated cells) can also contain sequences necessary for the termination of transcription which can affect mRNA expression. These regions are transcribed as polyadenylated segments in the untranslated portion of the mRNA encoding tissue factor protein. The 3' untranslated regions also include transcription termination sites. It is preferred that the transcription unit also contain a polyadenylation region. One benefit of this region is that it increases the likelihood that the transcribed unit will be processed and transported like mRNA. The identification and use of polyadenylation signals in expression constructs is well established. It is preferred that homologous polyadenylation signals be used in the transgene constructs. In a preferred embodiment of the transcription unit, the polyadenylation region is derived from the SV40 early polyadenylation signal and consists of about 400 bases. It is also preferred that the transcribed units contain other standard sequences alone or in combination with the above sequences improve expression from, or stability of, the construct.

3. Markers

The vectors can include nucleic acid sequence encoding a marker product. This marker product is used to determine if the gene has been delivered to the cell and once delivered is being expressed. Preferred marker genes are the *E. Coli* lacZ gene which encodes β-galactosidase and green fluorescent protein.

In some embodiments the marker can be a selectable marker. Examples of suitable selectable markers for mammalian cells are dihydrofolate reductase (DHFR), thymidine kinase, neomycin, neomycin analog G418, hydromycin, and puromycin. When such selectable markers are successfully transferred into a mammalian host cell, the transformed mammalian host cell can survive if placed under selective pressure. There are two widely used distinct categories of selective regimes. The first category is based on a cell's metabolism and the use of a mutant cell line which lacks the ability to grow independent of a supplemented media. Two examples are: CHO $DHFR^-$ cells and mouse $LTK^-$ cells. These cells lack the ability to grow without the addition of such nutrients as thymidine or hypoxanthine. Because these cells lack certain genes necessary for a complete nucleotide synthesis pathway, they cannot survive unless the missing nucleotides are provided in a supplemented media. An alternative to supplementing the media is to introduce an intact DHFR or TK gene into cells lacking the respective genes, thus altering their growth requirements. Individual cells which were not transformed with the DHFR or TK gene will not be capable of survival in non-supplemented media.

The second category is dominant selection which refers to a selection scheme used in any cell type and does not require the use of a mutant cell line. These schemes typically use a drug to arrest growth of a host cell. Those cells which would express a protein conveying drug resistance and would survive the selection. Examples of such dominant selection use the drugs neomycin, (Southern P. and Berg, P., J. Molec. Appl. Genet. 1: 327 (1982)), mycophenolic acid, (Mulligan, R. C. and Berg, P. Science 209: 1422 (1980)) or hygromycin, (Sugden, B. et al., Mol. Cell. Biol. 5: 410-413 (1985)). The three examples employ bacterial genes under eukaryotic control to convey resistance to the appropriate drug G418 or neomycin (geneticin), xgpt (mycophenolic acid) or hygromycin, respectively. Others include the neomycin analog G418 and puramycin.

E. Biosensor Riboswitches

Also disclosed are biosensor riboswitches. Biosensor riboswitches are engineered riboswitches that produce a detectable signal in the presence of their cognate trigger molecule. Useful biosensor riboswitches can be triggered at or above threshold levels of the trigger molecules. Biosensor riboswitches can be designed for use in vivo or in vitro. For example, biosensor riboswitches operably linked to a reporter RNA that encodes a protein that serves as or is involved in producing a signal can be used in vivo by engineering a cell or organism to harbor a nucleic acid construct encoding the riboswitch/reporter RNA. An example of a biosensor riboswitch for use in vitro is a riboswitch that includes a conformation dependent label, the signal from which changes depending on the activation state of the riboswitch. Such a biosensor riboswitch preferably uses an aptamer domain from or derived from a naturally occurring riboswitch.

F. Reporter Proteins and Peptides

For assessing activation of a riboswitch, or for biosensor riboswitches, a reporter protein or peptide can be used. The reporter protein or peptide can be encoded by the RNA the expression of which is regulated by the riboswitch. The examples describe the use of some specific reporter proteins. The use of reporter proteins and peptides is well known and can be adapted easily for use with riboswitches. The reporter proteins can be any protein or peptide that can be detected or that produces a detectable signal. Preferably, the presence of the protein or peptide can be detected using standard techniques (e.g., radioimmunoassay, radio-labeling, immunoassay, assay for enzymatic activity, absorbance, fluorescence, luminescence, and Western blot). More preferably, the level of the reporter protein is easily quantifiable using standard techniques even at low levels. Useful reporter proteins include luciferases, green fluorescent proteins and their derivatives, such as firefly luciferase (FL) from *Photinus pyralis*, and *Renilla luciferase* (RL) from *Renilla reniformis*.

G. Conformation Dependent Labels

Conformation dependent labels refer to all labels that produce a change in fluorescence intensity or wavelength based on a change in the form or conformation of the molecule or compound (such as a riboswitch) with which the label is associated. Examples of conformation dependent labels used in the context of probes and primers include molecular beacons, Amplifluors, FRET probes, cleavable FRET probes, TaqMan probes, scorpion primers, fluorescent triplex oligos including but not limited to triplex molecular beacons or triplex FRET probes, fluorescent water-soluble conjugated polymers, PNA probes and QPNA probes. Such labels, and, in particular, the principles of their function, can be adapted for use with riboswitches. Several types of conformation dependent labels are reviewed in Schweitzer and Kingsmore, Curr. Opin. Biotech. 12:21-27 (2001).

Stem quenched labels, a form of conformation dependent labels, are fluorescent labels positioned on a nucleic acid such that when a stem structure forms a quenching moiety is brought into proximity such that fluorescence from the label is quenched. When the stem is disrupted (such as when a riboswitch containing the label is activated), the quenching moiety is no longer in proximity to the fluorescent label and fluorescence increases. Examples of this effect can be found in molecular beacons, fluorescent triplex oligos, triplex molecular beacons, triplex FRET probes, and QPNA probes, the operational principles of which can be adapted for use with riboswitches.

Stem activated labels, a form of conformation dependent labels, are labels or pairs of labels where fluorescence is increased or altered by formation of a stem structure. Stem activated labels can include an acceptor fluorescent label and a donor moiety such that, when the acceptor and donor are in proximity (when the nucleic acid strands containing the labels form a stem structure), fluorescence resonance energy transfer from the donor to the acceptor causes the acceptor to fluoresce. Stem activated labels are typically pairs of labels positioned on nucleic acid molecules (such as riboswitches) such that the acceptor and donor are brought into proximity when a stem structure is formed in the nucleic acid molecule. If the donor moiety of a stem activated label is itself a fluorescent label, it can release energy as fluorescence (typically at a different wavelength than the fluorescence of the acceptor) when not in proximity to an acceptor (that is, when a stem structure is not formed). When the stem structure forms, the overall effect would then be a reduction of donor fluorescence and an increase in acceptor fluorescence. FRET probes are an example of the use of stem activated labels, the operational principles of which can be adapted for use with riboswitches.

H. Detection Labels

To aid in detection and quantitation of riboswitch activation, deactivation or blocking, or expression of nucleic acids or protein produced upon activation, deactivation or blocking of riboswitches, detection labels can be incorporated into detection probes or detection molecules or directly incorporated into expressed nucleic acids or proteins. As used herein, a detection label is any molecule that can be associated with nucleic acid or protein, directly or indirectly, and which results in a measurable, detectable signal, either directly or indirectly. Many such labels are known to those of skill in the art. Examples of detection labels suitable for use in the disclosed method are radioactive isotopes, fluorescent molecules, phosphorescent molecules, enzymes, antibodies, and ligands.

Examples of suitable fluorescent labels include fluorescein isothiocyanate (FITC), 5,6-carboxymethyl fluorescein, Texas red, nitrobenz-2-oxa-1,3-diazol-4-yl (NBD), coumarin, dansyl chloride, rhodamine, amino-methyl coumarin (AMCA), Eosin, Erythrosin, BODIPY®, Cascade Blue®, Oregon Green®, pyrene, lissamine, xanthenes, acridines, oxazines, phycoerythrin, macrocyclic chelates of lanthanide ions such as quantum dye™, fluorescent energy transfer dyes, such as thiazole orange-ethidium heterodimer, and the cyanine dyes Cy3, Cy3.5, Cy5, Cy5.5 and Cy7. Examples of other specific fluorescent labels include 3-Hydroxypyrene 5,8,10-Tri Sulfonic acid, 5-Hydroxy Tryptamine (5-HT), Acid Fuchsin, Alizarin Complexon, Alizarin Red, Allophycocyanin, Aminocoumarin, Anthroyl Stearate, Astrazon Brilliant Red 4G, Astrazon Orange R, Astrazon Red 6B, Astrazon Yellow 7 GLL, Atabrine, Auramine, Aurophosphine, Aurophosphine G, BAO 9 (Bisaminophenyloxadiazole), BCECF, Berberine Sulphate, Bisbenzamide, Blancophor FFG Solution, Blancophor SV, Bodipy F1, Brilliant Sulphoflavin FF, Calcien Blue, Calcium Green, Calcofluor RW Solution, Calcofluor White, Calcophor White ABT Solution, Calcophor White Standard Solution, Carbostyryl, Cascade Yellow, Catecholamine, Chinacrine, Coriphosphine O, Coumarin-Phalloidin, CY3.1 8, CY5.1 8, CY7, Dans (1-Dimethyl Amino Naphaline 5 Sulphonic Acid), Dansa (Diamino Naphtyl Sulphonic Acid), Dansyl NH-CH3, Diamino Phenyl Oxydiazole (DAO), Dimethylamino-5-Sulphonic acid, Dipyrrometheneboron Difluoride, Diphenyl Brilliant Flavine 7GFF, Dopamine, Erythrosin ITC, Euchrysin, FIF (Formaldehyde Induced Fluorescence), Flazo Orange, Fluo 3, Fluorescamine, Fura-2, Genacryl Brilliant Red B, Genacryl Brilliant Yellow 10GF, Genacryl Pink 3G, Genacryl Yellow 5GF, Gloxalic Acid, Granular Blue, Haematoporphyrin, Indo-1, Intrawhite Cf Liquid, Leucophor PAF, Leucophor SF, Leucophor WS, Lissamine Rhodamine B200 (RD200), Lucifer Yellow CH, Lucifer Yellow VS, Magdala Red, Marina Blue, Maxilon Brilliant Flavin 10 GFF, Maxilon Brilliant Flavin 8 GFF, MPS (Methyl Green Pyronine Stilbene), Mithramycin, NBD Amine, Nitrobenzoxadidole, Noradrenaline, Nuclear Fast Red, Nuclear Yellow, Nylosan Brilliant Flavin EBG, Oxadiazole, Pacific Blue, Pararosaniline (Feulgen), Phorwite AR Solution, Phorwite BKL, Phorwite Rev, Phorwite RPA, Phosphine 3R, Phthalocyanine, Phycoerythrin R, Polyazaindacene Pontochrome Blue Black, Porphyrin, Primuline, Procion Yellow, Pyronine, Pyronine B, Pyrozal Brilliant Flavin 7GF, Quinacrine Mustard, Rhodamine 123, Rhodamine 5 GLD, Rhodamine 6G, Rhodamine B, Rhodamine B 200, Rhodamine B Extra, Rhodamine BB, Rhodamine BG, Rhodamine WT, Serotonin, Sevron Brilliant Red 2B, Sevron Brilliant Red 4G, Sevron Brilliant Red B, Sevron Orange, Sevron Yellow L, SITS (Primuline), SITS (Stilbene Isothiosulphonic acid), Stilbene, Snarf 1, sulpho Rhodamine B Can C, Sulpho Rhodamine G Extra, Tetracycline, Thiazine Red R, Thioflavin S, Thioflavin TCN, Thioflavin 5, Thiolyte, Thiozol Orange, Tinopol CBS, True Blue, Ultralite, Uranine B, Uvitex SFC, Xylene Orange, and XRITC.

Useful fluorescent labels are fluorescein (5-carboxyfluorescein-N-hydroxysuccinimide ester), rhodamine (5,6-tetramethyl rhodamine), and the cyanine dyes Cy3, Cy3.5, Cy5, Cy5.5 and Cy7. The absorption and emission maxima, respectively, for these fluors are: FITC (490 nm; 520 nm), Cy3 (554 nm; 568 nm), Cy3.5 (581 nm; 588 nm), Cy5 (652 nm: 672 nm), Cy5.5 (682 nm; 703 nm) and Cy7 (755 nm; 778 nm), thus allowing their simultaneous detection. Other examples of fluorescein dyes include 6-carboxyfluorescein (6-FAM), 2',4',1,4,-tetrachlorofluorescein (TET), 2',4',5',7',1,4-hexachlorofluorescein (HEX), 2',7'-dimethoxy-4',5'-dichloro-6-carboxyrhodamine (JOE), 2'-chloro-5'-fluoro-7',8'-fused phenyl-1,4-dichloro-6-carboxyfluorescein (NED), and 2'-chloro-7'-phenyl-1,4-dichloro-6-carboxyfluorescein (VIC). Fluorescent labels can be obtained from a variety of commercial sources, including Amersham Pharmacia Biotech, Piscataway, N.J.; Molecular Probes, Eugene, Oreg.; and Research Organics, Cleveland, Ohio.

Additional labels of interest include those that provide for signal only when the probe with which they are associated is specifically bound to a target molecule, where such labels include: "molecular beacons" as described in Tyagi & Kramer, Nature Biotechnology (1996) 14:303 and EP 0 070 685 B1. Other labels of interest include those described in U.S. Pat. No. 5,563,037; WO 97/17471 and WO 97/17076.

Labeled nucleotides are a useful form of detection label for direct incorporation into expressed nucleic acids during synthesis. Examples of detection labels that can be incorporated into nucleic acids include nucleotide analogs such as BrdUrd (5-bromodeoxyuridine, Hoy and Schimke, *Mutation Research* 290:217-230 (1993)), aminoallyldeoxyuridine (Henegariu et al., *Nature Biotechnology* 18:345-348 (2000)), 5-methylcytosine (Sano et al., *Biochim. Biophys. Acta* 951: 157-165 (1988)), bromouridine (Wansick et al., *J. Cell Biology* 122:283-293 (1993)) and nucleotides modified with biotin (Langer et al., *Proc. Natl. Acad. Sci. USA* 78:6633 (1981)) or with suitable haptens such as digoxygenin (Kerkhof, *Anal. Biochem.* 205:359-364 (1992)). Suitable fluorescence-labeled nucleotides are Fluorescein-isothiocyanate-dUTP, Cyanine-3-dUTP and Cyanine-5-dUTP (Yu et al., *Nucleic Acids Res.,* 22:3226-3232 (1994)). A preferred nucleotide analog detection label for DNA is BrdUrd (bromodeoxyuridine, BrdUrd, BrdU, BUdR, Sigma-Aldrich Co). Other useful nucleotide analogs for incorporation of detection label into DNA are AA-dUTP (aminoallyl-deoxyuridine triphosphate, Sigma-Aldrich Co.), and 5-methyl-dCTP (Roche Molecular Biochemicals). A useful nucleotide analog for incorporation of detection label into RNA is biotin-16-UTP (biotin-16-uridine-5'-triphosphate, Roche Molecular Biochemicals). Fluorescein, Cy3, and Cy5 can be linked to dUTP for direct labelling. Cy3.5 and Cy7 are available as avidin or anti-digoxygenin conjugates for secondary detection of biotin- or digoxygenin-labelled probes.

Detection labels that are incorporated into nucleic acid, such as biotin, can be subsequently detected using sensitive methods well-known in the art. For example, biotin can be detected using streptavidin-alkaline phosphatase conjugate (Tropix, Inc.), which is bound to the biotin and subsequently detected by chemiluminescence of suitable substrates (for example, chemiluminescent substrate CSPD: disodium, 3-(4-methoxyspiro-[1,2,-dioxetane-3-2'-(5'-chloro)tricyclo [3.3.1.1$^{3,7}$]decane]-4-yl)phenyl phosphate; Tropix, Inc.). Labels can also be enzymes, such as alkaline phosphatase, soybean peroxidase, horseradish peroxidase and polymerases, that can be detected, for example, with chemical signal amplification or by using a substrate to the enzyme which produces light (for example, a chemiluminescent 1,2-dioxetane substrate) or fluorescent signal.

Molecules that combine two or more of these detection labels are also considered detection labels. Any of the known detection labels can be used with the disclosed probes, tags, molecules and methods to label and detect activated or deactivated riboswitches or nucleic acid or protein produced in the disclosed methods. Methods for detecting and measuring signals generated by detection labels are also known to those of skill in the art. For example, radioactive isotopes can be detected by scintillation counting or direct visualization; fluorescent molecules can be detected with fluorescent spectrophotometers; phosphorescent molecules can be detected with a spectrophotometer or directly visualized with a camera; enzymes can be detected by detection or visualization of the product of a reaction catalyzed by the enzyme; antibodies can be detected by detecting a secondary detection label coupled to the antibody. As used herein, detection molecules are molecules which interact with a compound or composition to be detected and to which one or more detection labels are coupled.

I. Sequence Similarities

It is understood that as discussed herein the use of the terms homology and identity mean the same thing as similarity. Thus, for example, if the use of the word homology is used between two sequences (non-natural sequences, for example) it is understood that this is not necessarily indicating an evolutionary relationship between these two sequences, but rather is looking at the similarity or relatedness between their nucleic acid sequences. Many of the methods for determining homology between two evolutionarily related molecules are routinely applied to any two or more nucleic acids or proteins for the purpose of measuring sequence similarity regardless of whether they are evolutionarily related or not.

In general, it is understood that one way to define any known variants and derivatives or those that might arise, of the disclosed riboswitches, aptamers, expression platforms, genes and proteins herein, is through defining the variants and derivatives in terms of homology to specific known sequences. This identity of particular sequences disclosed herein is also discussed elsewhere herein. In general, variants of riboswitches, aptamers, expression platforms, genes and proteins herein disclosed typically have at least, about 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 percent homology to a stated sequence or a native sequence. Those of skill in the art readily understand how to determine the homology of two proteins or nucleic acids, such as genes. For example, the homology can be calculated after aligning the two sequences so that the homology is at its highest level.

Another way of calculating homology can be performed by published algorithms. Optimal alignment of sequences for comparison can be conducted by the local homology algorithm of Smith and Waterman Adv. Appl. Math. 2: 482 (1981), by the homology alignment algorithm of Needleman and Wunsch, J. MoL Biol. 48: 443 (1970), by the search for similarity method of Pearson and Lipman, Proc. Natl. Acad. Sci. U.S.A. 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection.

The same types of homology can be obtained for nucleic acids by for example the algorithms disclosed in Zuker, M. *Science* 244:48-52, 1989, Jaeger et al. *Proc. Natl. Acad. Sci.*

*USA* 86:7706-7710, 1989, Jaeger et al. *Methods Enzymol.* 183:281-306, 1989 which are herein incorporated by reference for at least material related to nucleic acid alignment. It is understood that any of the methods typically can be used and that in certain instances the results of these various methods can differ, but the skilled artisan understands if identity is found with at least one of these methods, the sequences would be said to have the stated identity.

For example, as used herein, a sequence recited as having a particular percent homology to another sequence refers to sequences that have the recited homology as calculated by any one or more of the calculation methods described above. For example, a first sequence has 80 percent homology, as defined herein, to a second sequence if the first sequence is calculated to have 80 percent homology to the second sequence using the Zuker calculation method even if the first sequence does not have 80 percent homology to the second sequence as calculated by any of the other calculation methods. As another example, a first sequence has 80 percent homology, as defined herein, to a second sequence if the first sequence is calculated to have 80 percent homology to the second sequence using both the Zuker calculation method and the Pearson and Lipman calculation method even if the first sequence does not have 80 percent homology to the second sequence as calculated by the Smith and Waterman calculation method, the Needleman and Wunsch calculation method, the Jaeger calculation methods, or any of the other calculation methods. As yet another example, a first sequence has 80 percent homology, as defined herein, to a second sequence if the first sequence is calculated to have 80 percent homology to the second sequence using each of calculation methods (although, in practice, the different calculation methods will often result in different calculated homology percentages).

J. Hybridization and Selective Hybridization

The term hybridization typically means a sequence driven interaction between at least two nucleic acid molecules, such as a primer or a probe and a riboswitch or a gene. Sequence driven interaction means an interaction that occurs between two nucleotides or nucleotide analogs or nucleotide derivatives in a nucleotide specific manner. For example, G interacting with C or A interacting with T are sequence driven interactions. Typically sequence driven interactions occur on the Watson-Crick face or Hoogsteen face of the nucleotide. The hybridization of two nucleic acids is affected by a number of conditions and parameters known to those of skill in the art. For example, the salt concentrations, pH, and temperature of the reaction all affect whether two nucleic acid molecules will hybridize.

Parameters for selective hybridization between two nucleic acid molecules are well known to those of skill in the art. For example, in some embodiments selective hybridization conditions can be defined as stringent hybridization conditions. For example, stringency of hybridization is controlled by both temperature and salt concentration of either or both of the hybridization and washing steps. For example, the conditions of hybridization to achieve selective hybridization can involve hybridization in high ionic strength solution (6× SSC or 6× SSPE) at a temperature that is about 12-25° C. below the Tm (the melting temperature at which half of the molecules dissociate from their hybridization partners) followed by washing at a combination of temperature and salt concentration chosen so that the washing temperature is about 5° C. to 20° C. below the Tm. The temperature and salt conditions are readily determined empirically in preliminary experiments in which samples of reference DNA immobilized on filters are hybridized to a labeled nucleic acid of interest and then washed under conditions of different stringencies. Hybridization temperatures are typically higher for DNA-RNA and RNA-RNA hybridizations. The conditions can be used as described above to achieve stringency, or as is known in the art (Sambrook et al., Molecular Cloning: A Laboratory Manual, 2nd Ed., Cold Spring Harbor Laboratory, Cold Spring Harbor, N.Y., 1989; Kunkel et al. Methods Enzymol. 1987:154:367, 1987 which is herein incorporated by reference for material at least related to hybridization of nucleic acids). A preferable stringent hybridization condition for a DNA:DNA hybridization can be at about 68° C. (in aqueous solution) in 6× SSC or 6× SSPE followed by washing at 68° C. Stringency of hybridization and washing, if desired, can be reduced accordingly as the degree of complementarity desired is decreased, and further, depending upon the G-C or A-T richness of any area wherein variability is searched for. Likewise, stringency of hybridization and washing, if desired, can be increased accordingly as homology desired is increased, and further, depending upon the G-C or A-T richness of any area wherein high homology is desired, all as known in the art.

Another way to define selective hybridization is by looking at the amount (percentage) of one of the nucleic acids bound to the other nucleic acid. For example, in some embodiments selective hybridization conditions would be when at least about, 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 percent of the limiting nucleic acid is bound to the non-limiting nucleic acid. Typically, the non-limiting nucleic acid is in for example, 10 or 100 or 1000 fold excess. This type of assay can be performed at under conditions where both the limiting and non-limiting nucleic acids are for example, 10 fold or 100 fold or 1000 fold below their $k_d$, or where only one of the nucleic acid molecules is 10 fold or 100 fold or 1000 fold or where one or both nucleic acid molecules are above their $k_d$.

Another way to define selective hybridization is by looking at the percentage of nucleic acid that gets enzymatically manipulated under conditions where hybridization is required to promote the desired enzymatic manipulation. For example, in some embodiments selective hybridization conditions would be when at least about, 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 percent of the nucleic acid is enzymatically manipulated under conditions which promote the enzymatic manipulation, for example if the enzymatic manipulation is DNA extension, then selective hybridization conditions would be when at least about 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 percent of the nucleic acid molecules are extended. Preferred conditions also include those suggested by the manufacturer or indicated in the art as being appropriate for the enzyme performing the manipulation.

Just as with homology, it is understood that there are a variety of methods herein disclosed for determining the level of hybridization between two nucleic acid molecules. It is understood that these methods and conditions can provide different percentages of hybridization between two nucleic acid molecules, but unless otherwise indicated meeting the parameters of any of the methods would be sufficient. For example if 80% hybridization was required and as long as hybridization occurs within the required parameters in any one of these methods it is considered disclosed herein.

It is understood that those of skill in the art understand that if a composition or method meets any one of these criteria for determining hybridization either collectively or singly it is a composition or method that is disclosed herein.

K. Nucleic Acids

There are a variety of molecules disclosed herein that are nucleic acid based, including, for example, riboswitches, aptamers, and nucleic acids that encode riboswitches and aptamers. The disclosed nucleic acids can be made up of for example, nucleotides, nucleotide analogs, or nucleotide substitutes. Non-limiting examples of these and other molecules are discussed herein. It is understood that for example, when a vector is expressed in a cell, that the expressed mRNA will typically be made up of A, C, G, and U. Likewise, it is understood that if a nucleic acid molecule is introduced into a cell or cell environment through for example exogenous delivery, it is advantageous that the nucleic acid molecule be made up of nucleotide analogs that reduce the degradation of the nucleic acid molecule in the cellular environment.

So long as their relevant function is maintained, riboswitches, aptamers, expression platforms and any other oligonucleotides and nucleic acids can be made up of or include modified nucleotides (nucleotide analogs). Many modified nucleotides are known and can be used in oligonucleotides and nucleic acids. A nucleotide analog is a nucleotide which contains some type of modification to either the base, sugar, or phosphate moieties. Modifications to the base moiety would include natural and synthetic modifications of A, C, G, and T/U as well as different purine or pyrimidine bases, such as uracil-5-yl, hypoxanthin-9-yl (I), and 2-aminoadenin-9-yl. A modified base includes but is not limited to 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Additional base modifications can be found for example in U.S. Pat. No. 3,687,808, Englisch et al., Angewandte Chemie, International Edition, 1991, 30, 613, and Sanghvi, Y. S., Chapter 15, Antisense Research and Applications, pages 289-302, Crooke, S. T. and Lebleu, B. ed., CRC Press, 1993. Certain nucleotide analogs, such as 5-substituted pyrimidines, 6-azapyrimidines and N-2, N-6 and 0-6 substituted purines, including 2-aminopropyladenine, 5-propynyluracil and 5-propynylcytosine. 5-methylcytosine can increase the stability of duplex formation. Other modified bases are those that function as universal bases. Universal bases include 3-nitropyrrole and 5-nitroindole. Universal bases substitute for the normal bases but have no bias in base pairing. That is, universal bases can base pair with any other base. Base modifications often can be combined with for example a sugar modification, such as 2'-O-methoxyethyl, to achieve unique properties such as increased duplex stability. There are numerous United States patents such as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; and 5,681,941, which detail and describe a range of base modifications. Each of these patents is herein incorporated by reference in its entirety, and specifically for their description of base modifications, their synthesis, their use, and their incorporation into oligonucleotides and nucleic acids.

Nucleotide analogs can also include modifications of the sugar moiety. Modifications to the sugar moiety would include natural modifications of the ribose and deoxyribose as well as synthetic modifications. Sugar modifications include but are not limited to the following modifications at the 2' position: OH; F; O—, S—, or N-alkyl; O—, S—, or N-alkenyl; O—, S— or N-alkynyl; or O-alkyl-O-alkyl, wherein the alkyl, alkenyl and alkynyl can be substituted or unsubstituted C1 to C10, alkyl or C2 to C10 alkenyl and alkynyl. 2' sugar modifications also include but are not limited to $—O[(CH_2)nO]mCH_3$, $—O(CH_2)nOCH_3$, $—O(CH_2)nNH_2$, $—O(CH_2)nCH_3$, $—O(CH_2)n—ONH_2$, and $—O(CH_2)nON[(CH_2)nCH_3)]_2$, where n and m are from 1 to about 10.

Other modifications at the 2' position include but are not limited to: C1 to C10 lower alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2$ $CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. Similar modifications can also be made at other positions on the sugar, particularly the 3' position of the sugar on the 3' terminal nucleotide or in 2'-5' linked oligonucleotides and the 5' position of 5' terminal nucleotide. Modified sugars would also include those that contain modifications at the bridging ring oxygen, such as $CH_2$ and S. Nucleotide sugar analogs can also have sugar mimetics such as cyclobutyl moieties in place of the pentofuranosyl sugar. There are numerous United States patents that teach the preparation of such modified sugar structures such as U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920, each of which is herein incorporated by reference in its entirety, and specifically for their description of modified sugar structures, their synthesis, their use, and their incorporation into nucleotides, oligonucleotides and nucleic acids.

Nucleotide analogs can also be modified at the phosphate moiety. Modified phosphate moieties include but are not limited to those that can be modified so that the linkage between two nucleotides contains a phosphorothioate, chiral phosphorothioate, phosphorodithioate, phosphotriester, aminoalkylphosphotriester, methyl and other alkyl phosphonates including 3'-alkylene phosphonate and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates. It is understood that these phosphate or modified phosphate linkages between two nucleotides can be through a 3'-5' linkage or a 2'-5' linkage, and the linkage can contain inverted polarity such as 3'-5' to 5'-3' or 2'-5' to 5'-2'. Various salts, mixed salts and free acid forms are also included. Numerous United States patents teach how to make and use nucleotides containing modified phosphates and include but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050, each of which is herein incorporated by reference its entirety, and specifically for their description of modified phosphates, their synthesis, their use, and their incorporation into nucleotides, oligonucleotides and nucleic acids.

It is understood that nucleotide analogs need only contain a single modification, but can also contain multiple modifications within one of the moieties or between different moieties.

Nucleotide substitutes are molecules having similar functional properties to nucleotides, but which do not contain a phosphate moiety, such as peptide nucleic acid (PNA). Nucleotide substitutes are molecules that will recognize and hybridize to (base pair to) complementary nucleic acids in a Watson-Crick or Hoogsteen manner, but which are linked together through a moiety other than a phosphate moiety. Nucleotide substitutes are able to conform to a double helix type structure when interacting with the appropriate target nucleic acid.

Nucleotide substitutes are nucleotides or nucleotide analogs that have had the phosphate moiety and/or sugar moieties replaced. Nucleotide substitutes do not contain a standard phosphorus atom. Substitutes for the phosphate can be for example, short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and CH2 component parts. Numerous United States patents disclose how to make and use these types of phosphate replacements and include but are not limited to U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, each of which is herein incorporated by reference its entirety, and specifically for their description of phosphate replacements, their synthesis, their use, and their incorporation into nucleotides, oligonucleotides and nucleic acids.

It is also understood in a nucleotide substitute that both the sugar and the phosphate moieties of the nucleotide can be replaced, by for example an amide type linkage (aminoethylglycine) (PNA). U.S. Pat. Nos. 5,539,082; 5,714,331; and 5,719,262 teach how to make and use PNA molecules, each of which is herein incorporated by reference. (See also Nielsen et al., *Science* 254:1497-1500 (1991)).

Oligonucleotides and nucleic acids can be comprised of nucleotides and can be made up of different types of nucleotides or the same type of nucleotides. For example, one or more of the nucleotides in an oligonucleotide can be ribonucleotides, 2'-O-methyl ribonucleotides, or a mixture of ribonucleotides and 2'-O-methyl ribonucleotides; about 10% to about 50% of the nucleotides can be ribonucleotides, 2'-O-methyl ribonucleotides, or a mixture of ribonucleotides and 2'-O-methyl ribonucleotides; about 50% or more of the nucleotides can be ribonucleotides, 2'-O-methyl ribonucleotides, or a mixture of ribonucleotides and 2'-O-methyl ribonucleotides; or all of the nucleotides are ribonucleotides, 2'-O-methyl ribonucleotides, or a mixture of ribonucleotides and 2'-O-methyl ribonucleotides. Such oligonucleotides and nucleic acids can be referred to as chimeric oligonucleotides and chimeric nucleic acids.

L. Solid Supports

Solid supports are solid-state substrates or supports with which molecules (such as trigger molecules) and riboswitches (or other components used in, or produced by, the disclosed methods) can be associated. Riboswitches and other molecules can be associated with solid supports directly or indirectly. For example, analytes (e.g., trigger molecules, test compounds) can be bound to the surface of a solid support or associated with capture agents (e.g., compounds or molecules that bind an analyte) immobilized on solid supports. As another example, riboswitches can be bound to the surface of a solid support or associated with probes immobilized on solid supports. An array is a solid support to which multiple riboswitches, probes or other molecules have been associated in an array, grid, or other organized pattern.

Solid-state substrates for use in solid supports can include any solid material with which components can be associated, directly or indirectly. This includes materials such as acrylamide, agarose, cellulose, nitrocellulose, glass, gold, polystyrene, polyethylene vinyl acetate, polypropylene, polymethacrylate, polyethylene, polyethylene oxide, polysilicates, polycarbonates, teflon, fluorocarbons, nylon, silicon rubber, polyanhydrides, polyglycolic acid, polylactic acid, polyorthoesters, functionalized silane, polypropylfumerate, collagen, glycosaminoglycans, and polyamino acids. Solid-state substrates can have any useful form including thin film, membrane, bottles, dishes, fibers, woven fibers, shaped polymers, particles, beads, microparticles, or a combination. Solid-state substrates and solid supports can be porous or non-porous. A chip is a rectangular or square small piece of material. Preferred forms for solid-state substrates are thin films, beads, or chips. A useful form for a solid-state substrate is a microtiter dish. In some embodiments, a multiwell glass slide can be employed.

An array can include a plurality of riboswitches, trigger molecules, other molecules, compounds or probes immobilized at identified or predefined locations on the solid support. Each predefined location on the solid support generally has one type of component (that is, all the components at that location are the same). Alternatively, multiple types of components can be immobilized in the same predefined location on a solid support. Each location will have multiple copies of the given components. The spatial separation of different components on the solid support allows separate detection and identification.

Although useful, it is not required that the solid support be a single unit or structure. A set of riboswitches, trigger molecules, other molecules, compounds and/or probes can be distributed over any number of solid supports. For example, at one extreme, each component can be immobilized in a separate reaction tube or container, or on separate beads or microparticles.

Methods for immobilization of oligonucleotides to solid-state substrates are well established. Oligonucleotides, including address probes and detection probes, can be coupled to substrates using established coupling methods. For example, suitable attachment methods are described by Pease et al., *Proc. Natl. Acad. Sci. USA* 91(11):5022-5026 (1994), and Khrapko et al., *Mol Biol* (*Mosk*) (*USSR*) 25:718-730 (1991). A method for immobilization of 3'-amine oligonucleotides on casein-coated slides is described by Stimpson et al., *Proc. Natl. Acad. Sci. USA* 92:6379-6383 (1995). A useful method of attaching oligonucleotides to solid-state substrates is described by Guo et al., *Nucleic Acids Res.* 22:5456-5465 (1994).

Each of the components (for example, riboswitches, trigger molecules, or other molecules) immobilized on the solid support can be located in a different predefined region of the solid support. The different locations can be different reaction chambers. Each of the different predefined regions can be physically separated from each other of the different regions. The distance between the different predefined regions of the solid support can be either fixed or variable. For example, in an array, each of the components can be arranged at fixed distances from each other, while components associated with beads will not be in a fixed spatial relationship. In particular, the use of multiple solid support units (for example, multiple beads) will result in variable distances.

Components can be associated or immobilized on a solid support at any density. Components can be immobilized to the solid support at a density exceeding 400 different components per cubic centimeter. Arrays of components can have any number of components. For example, an array can have at least 1,000 different components immobilized on the solid support, at least 10,000 different components immobilized on the solid support, at least 100,000 different components immobilized on the solid support, or at least 1,000,000 different components immobilized on the solid support.

M. Kits

The materials described above as well as other materials can be packaged together in any suitable combination as a kit useful for performing, or aiding in the performance of, the disclosed method. It is useful if the kit components in a given kit are designed and adapted for use together in the disclosed method. For example disclosed are kits for detecting compounds, the kit comprising one or more biosensor riboswitches. The kits also can contain reagents and labels for detecting activation of the riboswitches.

N. Mixtures

Disclosed are mixtures formed by performing or preparing to perform the disclosed method. For example, disclosed are mixtures comprising riboswitches and trigger molecules.

Whenever the method involves mixing or bringing into contact compositions or components or reagents, performing the method creates a number of different mixtures. For example, if the method includes 3 mixing steps, after each one of these steps a unique mixture is formed if the steps are performed separately. In addition, a mixture is formed at the completion of all of the steps regardless of how the steps were performed. The present disclosure contemplates these mixtures, obtained by the performance of the disclosed methods as well as mixtures containing any disclosed reagent, composition, or component, for example, disclosed herein.

O. Systems

Disclosed are systems useful for performing, or aiding in the performance of, the disclosed method. Systems generally comprise combinations of articles of manufacture such as structures, machines, devices, and the like, and compositions, compounds, materials, and the like. Such combinations that are disclosed or that are apparent from the disclosure are contemplated. For example, disclosed and contemplated are systems comprising iosensor riboswitches, a solid support and a signal-reading device.

P. Data Structures and Computer Control

Disclosed are data structures used in, generated by, or generated from, the disclosed method. Data structures generally are any form of data, information, and/or objects collected, organized, stored, and/or embodied in a composition or medium. Riboswitch structures and activation measurements stored in electronic form, such as in RAM or on a storage disk, is a type of data structure.

The disclosed method, or any part thereof or preparation therefor, can be controlled, managed, or otherwise assisted by computer control. Such computer control can be accomplished by a computer controlled process or method, can use and/or generate data structures, and can use a computer program. Such computer control, computer controlled processes, data structures, and computer programs are contemplated and should be understood to be disclosed herein.

Methods

Disclosed are methods for activating, deactivating or blocking a riboswitch. Such methods can involve, for example, bringing into contact a riboswitch and a compound or trigger molecule that can activate, deactivate or block the riboswitch. Riboswitches function to control gene expression through the binding or removal of a trigger molecule. Compounds can be used to activate, deactivate or block a riboswitch. The trigger molecule for a riboswitch (as well as other activating compounds) can be used to activate a riboswitch. Compounds other than the trigger molecule generally can be used to deactivate or block a riboswitch. Riboswitches can also be deactivated by, for example, removing trigger molecules from the presence of the riboswitch. Thus, the disclosed method of deactivating a riboswitch can involve, for example, removing a trigger molecule (or other activating compound) from the presence or contact with the riboswitch. A riboswitch can be blocked by, for example, binding of an analog of the trigger molecule that does not activate the riboswitch.

Also disclosed are methods for altering expression of an RNA molecule, or of a gene encoding an RNA molecule, where the RNA molecule includes a riboswitch, by bringing a compound into contact with the RNA molecule. Riboswitches function to control gene expression through the binding or removal of a trigger molecule. Thus, subjecting an RNA molecule of interest that includes a riboswitch to conditions that activate, deactivate or block the riboswitch can be used to alter expression of the RNA. Expression can be altered as a result of, for example, termination of transcription or blocking of ribosome binding to the RNA. Binding of a trigger molecule can, depending on the nature of the riboswitch, reduce or prevent expression of the RNA molecule or promote or increase expression of the RNA molecule.

Also disclosed are methods for regulating expression of an RNA molecule, or of a gene encoding an RNA molecule, by operably linking a riboswitch to the RNA molecule. A riboswitch can be operably linked to an RNA molecule in any suitable manner, including, for example, by physically joining the riboswitch to the RNA molecule or by engineering nucleic acid encoding the RNA molecule to include and encode the riboswitch such that the RNA produced from the engineered nucleic acid has the riboswitch operably linked to the RNA molecule. Subjecting a riboswitch operably linked to an RNA molecule of interest to conditions that activate, deactivate or block the riboswitch can be used to alter expression of the RNA.

Also disclosed are methods for regulating expression of a naturally occurring gene or RNA that contains a riboswitch by activating, deactivating or blocking the riboswitch. If the gene is essential for survival of a cell or organism that harbors it, activating, deactivating or blocking the riboswitch can in death, stasis or debilitation of the cell or organism. For example, activating a naturally occurring riboswitch in a naturally occurring gene that is essential to survival of a microorganism can result in death of the microorganism (if activation of the riboswitch turns off or represses expression). This is one basis for the use of the disclosed compounds and methods for antimicrobial and antibiotic effects.

Also disclosed are methods for regulating expression of an isolated, engineered or recombinant gene or RNA that contains a riboswitch by activating, deactivating or blocking the riboswitch. The gene or RNA can be engineered or can be recombinant in any manner. For example, the riboswitch and coding region of the RNA can be heterologous, the riboswitch can be recombinant or chimeric, or both. If the gene encodes a desired expression product, activating or deactivating the riboswitch can be used to induce expression of the gene and thus result in production of the expression product. If the gene encodes an inducer or repressor of gene expression or of another cellular process, activation, deactivation or blocking of the riboswitch can result in induction, repression, or de-repression of other, regulated genes or cellular processes. Many such secondary regulatory effects are known and can be adapted for use with riboswitches. An advantage of riboswitches as the primary control for such regulation is that riboswitch trigger molecules can be small, non-antigenic molecules.

Also disclosed are methods for altering the regulation of a riboswitch by operably linking an aptamer domain to the expression platform domain of the riboswitch (which is a chimeric riboswitch). The aptamer domain can then mediate regulation of the riboswitch through the action of, for example, a trigger molecule for the aptamer domain. Aptamer domains can be operably linked to expression platform domains of riboswitches in any suitable manner, including, for example, by replacing the normal or natural aptamer domain of the riboswitch with the new aptamer domain. Generally, any compound or condition that can activate, deactivate or block the riboswitch from which the aptamer domain is derived can be used to activate, deactivate or block the chimeric riboswitch.

Also disclosed are methods for inactivating a riboswitch by covalently altering the riboswitch (by, for example, crosslinking parts of the riboswitch or coupling a compound to the riboswitch). Inactivation of a riboswitch in this manner can result from, for example, an alteration that prevents the trigger molecule for the riboswitch from binding, that prevents the change in state of the riboswitch upon binding of the trigger molecule, or that prevents the expression platform domain of the riboswitch from affecting expression upon binding of the trigger molecule.

Also disclosed are methods for selecting, designing or deriving new riboswitches and/or new aptamers that recognize new trigger molecules. Such methods can involve production of a set of aptamer variants in a riboswitch, assessing the activation of the variant riboswitches in the presence of a compound of interest, selecting variant riboswitches that were activated (or, for example, the riboswitches that were the most highly or the most selectively activated), and repeating these steps until a variant riboswitch of a desired activity, specificity, combination of activity and specificity, or other combination of properties results. Also disclosed are riboswitches and aptamer domains produced by these methods.

Techniques for in vitro selection and in vitro evolution of functional nucleic acid molecules are known and can be adapted for use with riboswitches and their components. Useful techniques are described by, for example, A. Roth and R. R. Breaker (2003) Selection in vitro of allosteric ribozymes. In: Methods in Molecular Biology Series—Catalytic Nucleic Acid Protocols (Sioud, M., ed.), Humana, Totowa, N.J.; R. R. Breaker (2002) Engineered Allosteric Ribozymes as Biosensor Components. Curr. Opin. Biotechnol. 13:31-39; G. M. Emilsson and R. R. Breaker (2002) Deoxyribozymes: New Activities and New Applications. Cell. Mol. Life Sci. 59:596-607; Y. Li, R. R. Breaker (2001) In vitro Selection of Kinase and Ligase Deoxyribozymes. Methods 23:179-190; G. A. Soukup, R. R. Breaker (2000) Allosteric Ribozymes. In: Ribozymes: Biology and Biotechnology. R. K. Gaur and G. Krupp eds. Eaton Publishing; G. A. Soukup, R. R. Breaker (2000) Allosteric Nucleic Acid Catalysts. Curr. Opin. Struct. Biol. 10:318-325; G. A. Soukup, R. R. Breaker (1999) Nucleic Acid Molecular Switches. Trends Biotechnol. 17:469-476; R. R. Breaker (1999) In vitro Selection of Self-cleaving Ribozymes and Deoxyribozymes. In: Intracellular Ribozyme Applications: Principles and Protocols. L. Couture, J. Rossi eds. Horizon Scientific Press, Norfolk, England; R. R. Breaker (1997) In vitro Selection of Catalytic Polynucleotides. Chem. Rev. 97:371-390; and references cited therein; each of these publications being specifically incorporated herein by reference for their description of in vitro selections and evolution techniques.

Also disclosed are methods for selecting and identifying compounds that can activate, deactivate or block a riboswitch. Activation of a riboswitch refers to the change in state of the riboswitch upon binding of a trigger molecule. A riboswitch can be activated by compounds other than the trigger molecule and in ways other than binding of a trigger molecule. The term trigger molecule is used herein to refer to molecules and compounds that can activate a riboswitch. This includes the natural or normal trigger molecule for the riboswitch and other compounds that can activate the riboswitch. Natural or normal trigger molecules are the trigger molecule for a given riboswitch in nature or, in the case of some non-natural riboswitches, the trigger molecule for which the riboswitch was designed or with which the riboswitch was selected (as in, for example, in vitro selection or in vitro evolution techniques). Non-natural trigger molecules can be referred to as non-natural trigger molecules.

Deactivation of a riboswitch refers to the change in state of the riboswitch when the trigger molecule is not bound. A riboswitch can be deactivated by binding of compounds other than the trigger molecule and in ways other than removal of the trigger molecule. Blocking of a riboswitch refers to a condition or state of the riboswitch where the presence of the trigger molecule does not activate the riboswitch.

Also disclosed are methods of identifying compounds that activate, deactivate or block a riboswitch. For examples, compounds that activate a riboswitch can be identified by bringing into contact a test compound and a riboswitch and assessing activation of the riboswitch. If the riboswitch is activated, the test compound is identified as a compound that activates the riboswitch. Activation of a riboswitch can be assessed in any suitable manner. For example, the riboswitch can be linked to a reporter RNA and expression, expression level, or change in expression level of the reporter RNA can be measured in the presence and absence of the test compound. As another example, the riboswitch can include a conformation dependent label, the signal from which changes depending on the activation state of the riboswitch. Such a riboswitch preferably uses an aptamer domain from or derived from a naturally occurring riboswitch. As can be seen, assessment of activation of a riboswitch can be performed with the use of a control assay or measurement or without the use of a control assay or measurement. Methods for identifying compounds that deactivate a riboswitch can be performed in analogous ways.

Identification of compounds that block a riboswitch can be accomplished in any suitable manner. For example, an assay can be performed for assessing activation or deactivation of a riboswitch in the presence of a compound known to activate or deactivate the riboswitch and in the presence of a test compound. If activation or deactivation is not observed as would be observed in the absence of the test compound, then the test compound is identified as a compound that blocks activation or deactivation of the riboswitch.

Also disclosed are methods of detecting compounds using biosensor riboswitches. The method can include bringing into contact a test sample and a biosensor riboswitch and assessing the activation of the biosensor riboswitch. Activation of the biosensor riboswitch indicates the presence of the trigger molecule for the biosensor riboswitch in the test sample. Biosensor riboswitches are engineered riboswitches that produce a detectable signal in the presence of their cognate trigger molecule. Useful biosensor riboswitches can be triggered at or above threshold levels of the trigger molecules. Biosensor riboswitches can be designed for use in vivo or in vitro. For example, biosensor riboswitches operably linked to a reporter RNA that encodes a protein that serves as or is involved in producing a signal can be used in vivo by engineering a cell or organism to harbor a nucleic acid construct encoding the riboswitch/reporter RNA. An example of a biosensor riboswitch for use in vitro is a riboswitch that includes a conformation dependent label, the signal from which changes depending on the activation state of the riboswitch. Such a biosensor riboswitch preferably uses an aptamer domain from or derived from a naturally occurring riboswitch.

Biosensor ribsowitches can be used to monitor changing conditions because riboswitch activation is reversible when the concentration of the trigger molecule falls and so the signal can vary as concentration of the trigger molecule varies. The range of concentration of trigger molecules that can be detected can be varied by engineering riboswitches having different dissociation constants for the trigger molecule. This can easily be accomplished by, for example, "degrading" the sensitivity of a riboswitch having high affinity for the trigger molecule. A range of concentrations can be monitored by using multiple biosensor riboswitches of different sensitivities in the same sensor or assay.

Also disclosed are compounds made by identifying a compound that activates, deactivates or blocks a riboswitch and manufacturing the identified compound. This can be accomplished by, for example, combining compound identification methods as disclosed elsewhere herein with methods for manufacturing the identified compounds.

For example, compounds can be made by bringing into contact a test compound and a riboswitch, assessing activation of the riboswitch, and, if the riboswitch is activated by the test compound, manufacturing the test compound that activates the riboswitch as the compound.

Also disclosed are compounds made by checking activation, deactivation or blocking of a riboswitch by a compound and manufacturing the checked compound. This can be accomplished by, for example, combining compound activation, deactivation or blocking assessment methods as disclosed elsewhere herein with methods for manufacturing the checked compounds. For example, compounds can be made by bringing into contact a test compound and a riboswitch, assessing activation of the riboswitch, and, if the riboswitch is activated by the test compound, manufacturing the test compound that activates the riboswitch as the compound. Checking compounds for their ability to activate, deactivate or block a riboswitch refers to both identification of compounds previously unknown to activate, deactivate or block a riboswitch and to assessing the ability of a compound to activate, deactivate or block a riboswitch where the compound was already known to activate, deactivate or block the riboswitch.

Disclosed is a method of detecting a compound of interest, the method comprising bringing into contact a sample and a riboswitch, wherein the riboswitch is activated by the compound of interest, wherein the riboswitch produces a signal when activated by the compound of interest, wherein the riboswitch produces a signal when the sample contains the compound of interest. The riboswitch can change conformation when activated by the compound of interest, wherein the change in conformation produces a signal via a conformation dependent label. The riboswitch can change conformation when activated by the compound of interest, wherein the change in conformation causes a change in expression of an RNA linked to the riboswitch, wherein the change in expression produces a signal. The signal can be produced by a reporter protein expressed from the RNA linked to the riboswitch.

Disclosed is a method comprising (a) testing a compound for inhibition of gene expression of a gene encoding an RNA comprising a riboswitch, wherein the inhibition is via the riboswitch, and (b) inhibiting gene expression by bringing into contact a cell and a compound that inhibited gene expression in step (a), wherein the cell comprises a gene encoding an RNA comprising a riboswitch, wherein the compound inhibits expression of the gene by binding to the riboswitch.

Also disclosed is a method of identifying riboswitches, the method comprising assessing in-line spontaneous cleavage of an RNA molecule in the presence and absence of a compound, wherein the RNA molecule is encoded by a gene regulated by the compound, wherein a change in the pattern of in-line spontaneous cleavage of the RNA molecule indicates a riboswitch.

A. Identification of Antimicrobial Compounds

Riboswitches are a new class of structured RNAs that have evolved for the purpose of binding small organic molecules. The natural binding pocket of riboswitches can be targeted with metabolite analogs or by compounds that mimic the shape-space of the natural metabolite. Riboswitches are: (1) found in numerous Gram-positive and Gram-negative bacteria including *Bacillus anthracis*, (2) fundamental regulators of gene expression in these bacteria, (3) present in multiple copies that would be unlikely to evolve simultaneous resistance, and (4) not yet proven to exist in humans. This combination of features make riboswitches attractive targets for new antimicrobial compounds. Further, the small molecule ligands of riboswitches provide useful sites for derivitization to produce drug candidates.

Once a class of riboswitch has been identified and its potential as a drug target assessed (by, for example, determining how many genes in a target organism are regulated by that class of riboswitch), candidate molecules can be identified. The following provides an illustration of this using the SAM riboswitch (see Example 7).

SAM analogs that substitute the reactive methyl and sulfonium ion center with stable sulfur-based linkages (YBD-2 and YBD3) are recognized with adequate affinity (low to mid-nanomolar range) by the riboswitch to serve as a platform for synthesis of additional SAM analogs. In addition, a wider range of linkage analogs (N- and C-based linkages) can be synthesized and tested to provide the optimal platform upon which to make amino acid and nucleoside derivations.

Sulfoxide and sulfone derivatives of SAM can be used to generate analogs. Established synthetic protocols described in Ronald T. Borchardt and Yih Shiong Wu, Potential inhibitor of S-adenosylmethionine-dependent methyltransferase. 1. Modification of the amino acid portion of S-adenosylhomocysteine. J. Med. Chem. 17, 862-868, 1974, can be used, for example. These and other analogs can be synthesized and assayed for binding sequentially or in small groups. Additional SAM analogs can be designed during the progression of compound identification based on the recognition determinants that are established in each round. Simple binding assays can be conducted on *B. subtilis* and *B. anthracis* riboswitch RNAs as described elsewhere herein. More advanced assays can also be used.

The most promising SAM analog lead compounds must enter bacterial cells and bind riboswitches while remaining metabolically inert. In addition, useful SAM analogs must be bound tightly by the riboswitch, but must also fail to compete for SAM in the active sites of protein enzymes, or there is a risk of generating an undesirable toxic effect in the patient's cells. As a preliminary assessment of these issues, compounds can be tested for their ability to disrupt *B. subtilis* growth, but fail to affect *E. coli* cultures (which use SAM but lack SAM riboswitches). To screen for lead compound candidates, parallel bacterial cultures can be grown as follows:

1. *B. subtilis* can be cultured in glucose minimal media in the absence of exogenously supplied SAM analogs.

2. *B. subtilis* can be cultured in glucose minimal media in the presence of exogenously supplied SAM analogs (high doses can be selected, to be followed by repeated experiments designed to test a concentration range of the putative drug compound).

3. *E. coli* can be cultured in glucose minimal media in the presence of exogenously supplied SAM analogs (high doses will be selected, to be followed by repeated experiments designed to test a concentration range of the putative drug compound).

Fitness of the various cultures can be compared by measurement of cellular doubling times. A range of concentrations for the drug compounds can be tested using cultures grown in microtiter plates and analyzed using a microplate reader from another laboratory. Culture 1 is expected to grow well. Drugs that inhibit culture 2 may or may not inhibit growth of culture 3. Drugs that similarly inhibit both culture 2 and culture 3 upon exposure to a wide range of drug concentrations can reflect general toxicity induced by the exogenous compound (i.e., inhibition of many different cellular processes, in addition or in place of riboswitch inhibition). Successful drug candidates identified in this screen will inhibit *E. coli* only at very high doses, if at all, and will inhibit *B. subtilis* at much (>10-fold) lower concentrations.

As derivization points on SAM are identified, efficient identification of lead drug compounds will require larger-scale screening of appropriate SAM analogs or generic chemical libraries. A high-throughput screen can be created by one or two different methods using nucleic acid engineering principles. Adaptation of both fluorescent sensor designs outlined below to formats that are compatible with high-throughput screening assays can be accommodated by using immobilization methods or solution-based methods.

One way to create a reporter is to add a third function to the riboswitch by adding a domain that catalyzes the release of a fluorescent tag upon SAM binding to the riboswitch domain. In the final reporter construct, this catalytic domain can be linked to the yitJ SAM riboswitch through a communication module that relays the ligand binding event by allowing the correct folding of the catalytic domain for generating the fluorescent signal. This can be accomplished as outlined below.

Figure 10:
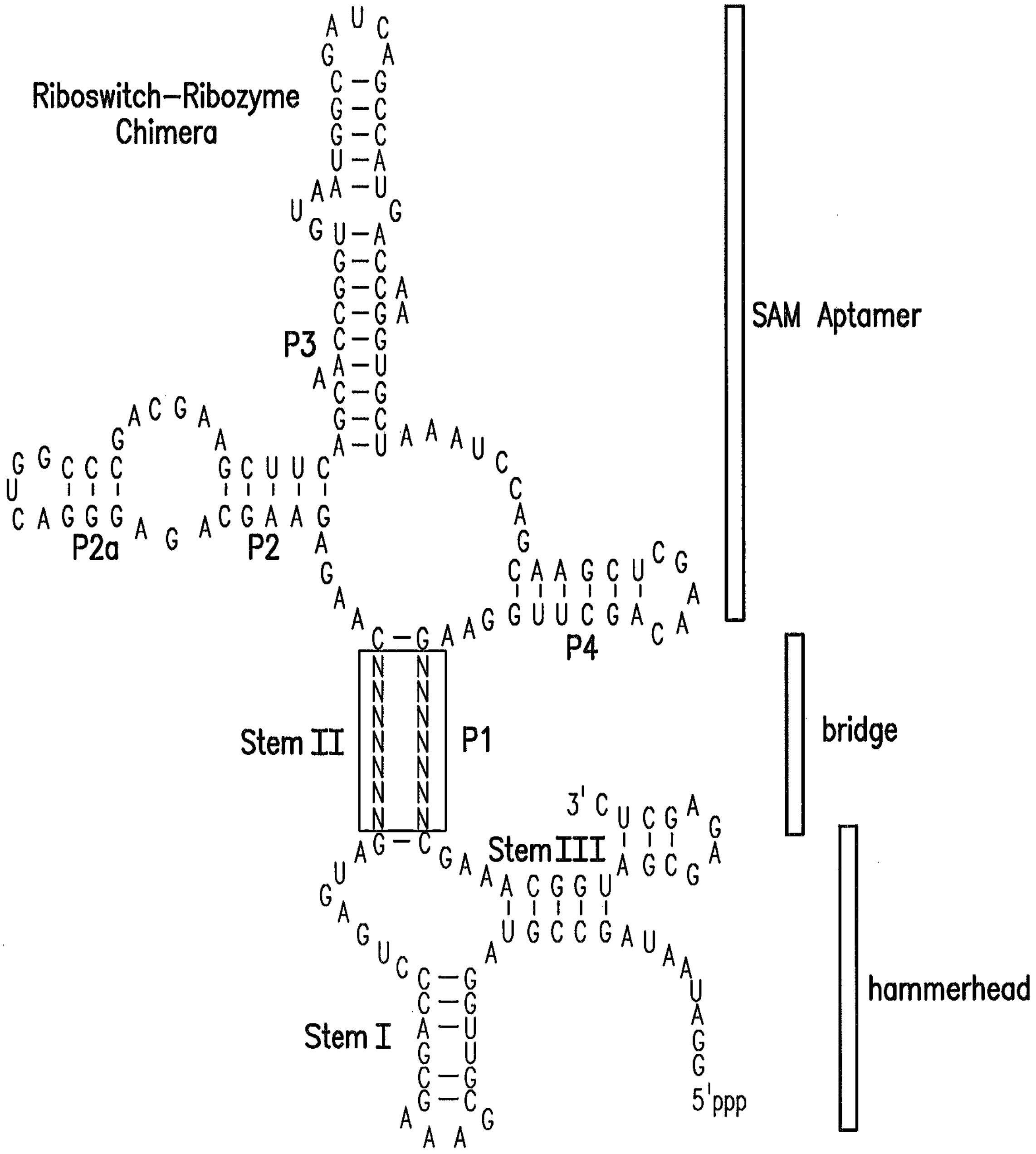
FIG. 10 shows a construct for the selection of SAM-responsive ribozymes (SEQ ID NO:5). The hammerhead self-cleaving ribozyme and the SAM aptamer both require proper formation of the bridge domain to exhibit function. Therefore, the selection is expected to permit ribozyme function only when SAM or another binding-competent analog is present.
Figure 11A:
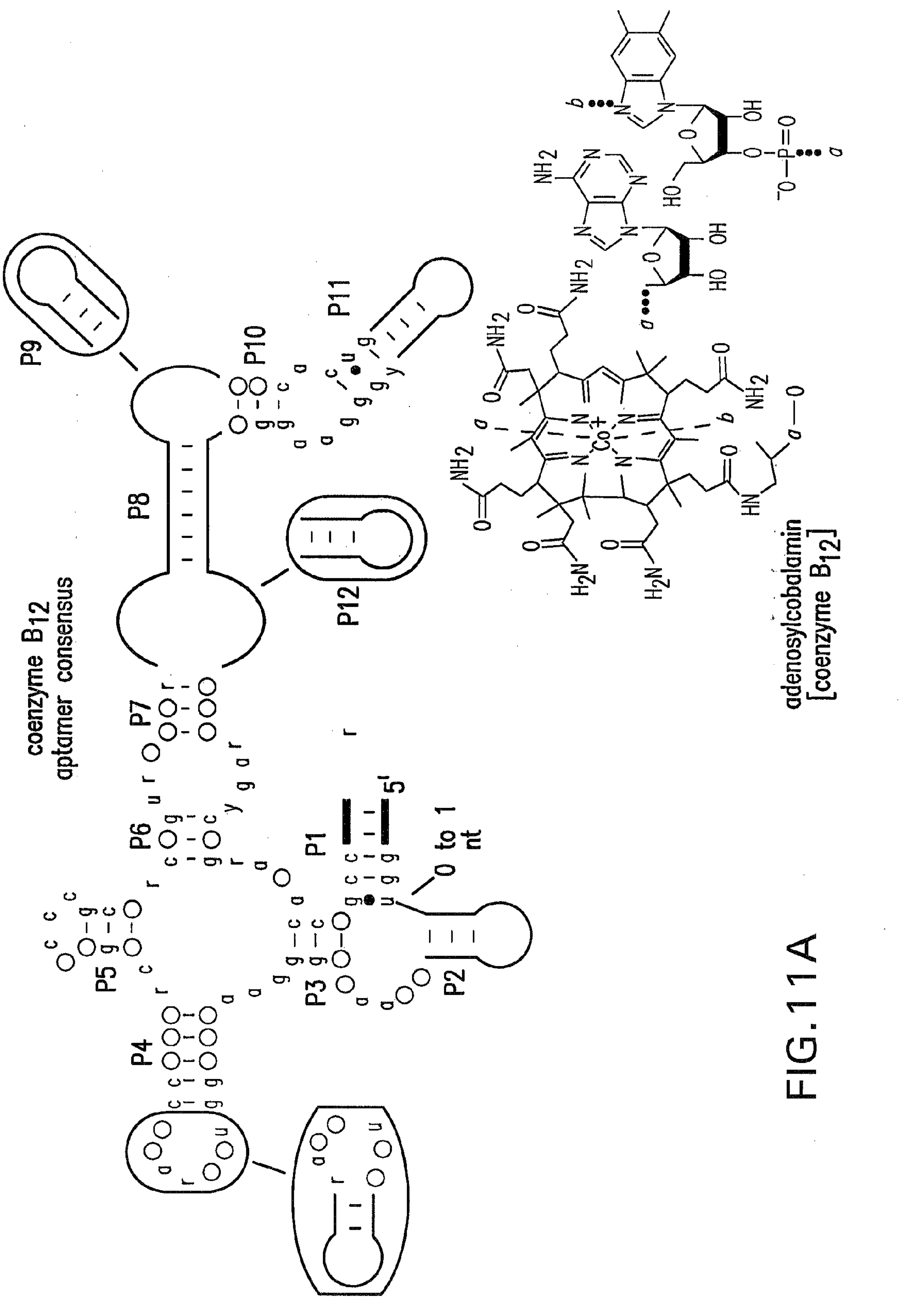
FIGS. 11A (SEQ ID NO:6 and SEQ ID NOs:378-382), 11B (SEQ ID NO:7 and SEQ ID NOs:383-385), 11C (SEQ ID NO:8 and SEQ ID NOs:386-387), 11D (SEQ ID NO:9 and SEQ ID NOs:388-389), 11E (SEQ ID NO:10), 11F (SEQ ID NO:11) and 11G (SEQ ID NO:12 and SEQ ID NOs:390-397) show consensus sequences and putative secondary structures were derived by phylogenetic and biochemical analyses as described for each riboswitch (see references). Nucleotides identified by a lower case a, c, t, or g, are conserved in greater than 90% of the representative sequences, open circles identify nucleotide positions of variable sequence, and lines identify elements that are variable in sequence and length. Models are described as follows: 11A) coenzyme B12 aptamer (Example 1); 11B) TPP aptamer (Example 2); 11C) FMN aptamer (Example 3); 11D) SAM aptamer (Example 7); 11E) guanine aptamer (Example 6); 11F) adenine aptamer (Example 8); and 11G) lysine aptamer Example 5). Letters R and Y represent purine and pyrimidine bases, respectively; K designates G or U; W designates A or U; H designates A, C, or U; D designates G, A, or U; N represents any of the four bases.
Figure 11B:
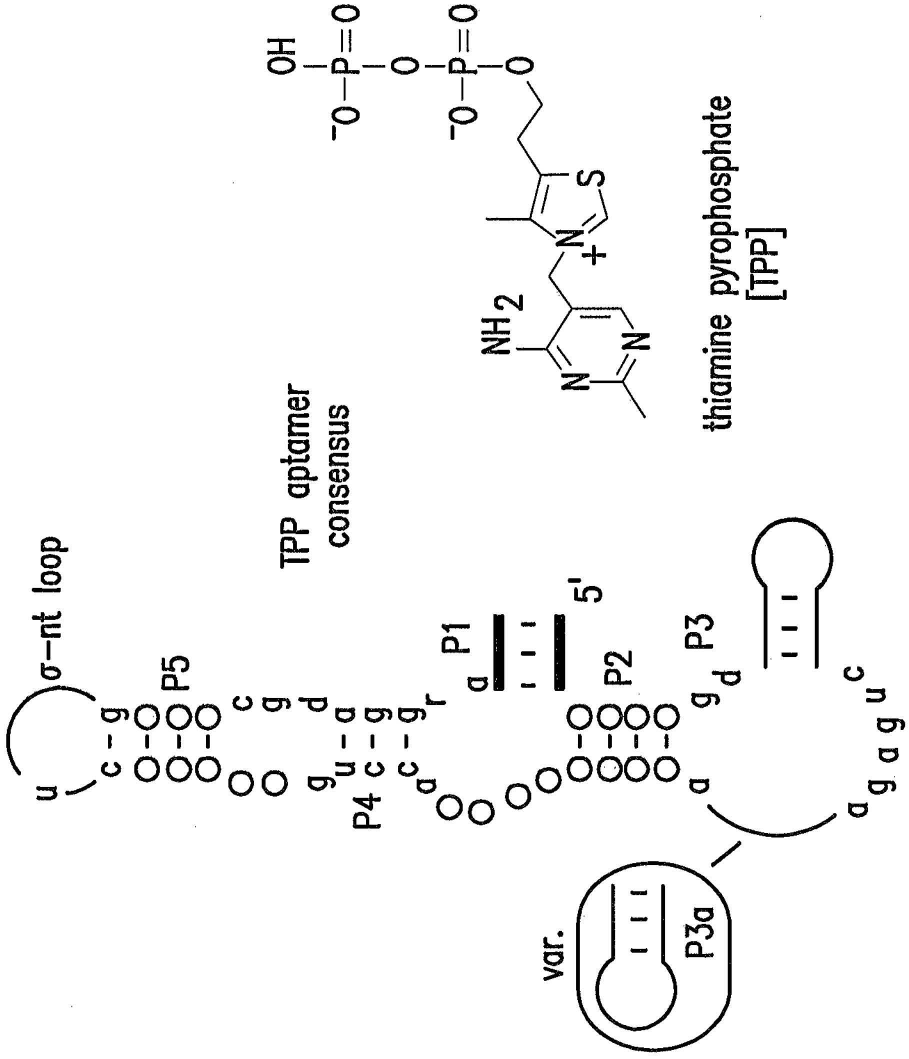
Figure 11C:
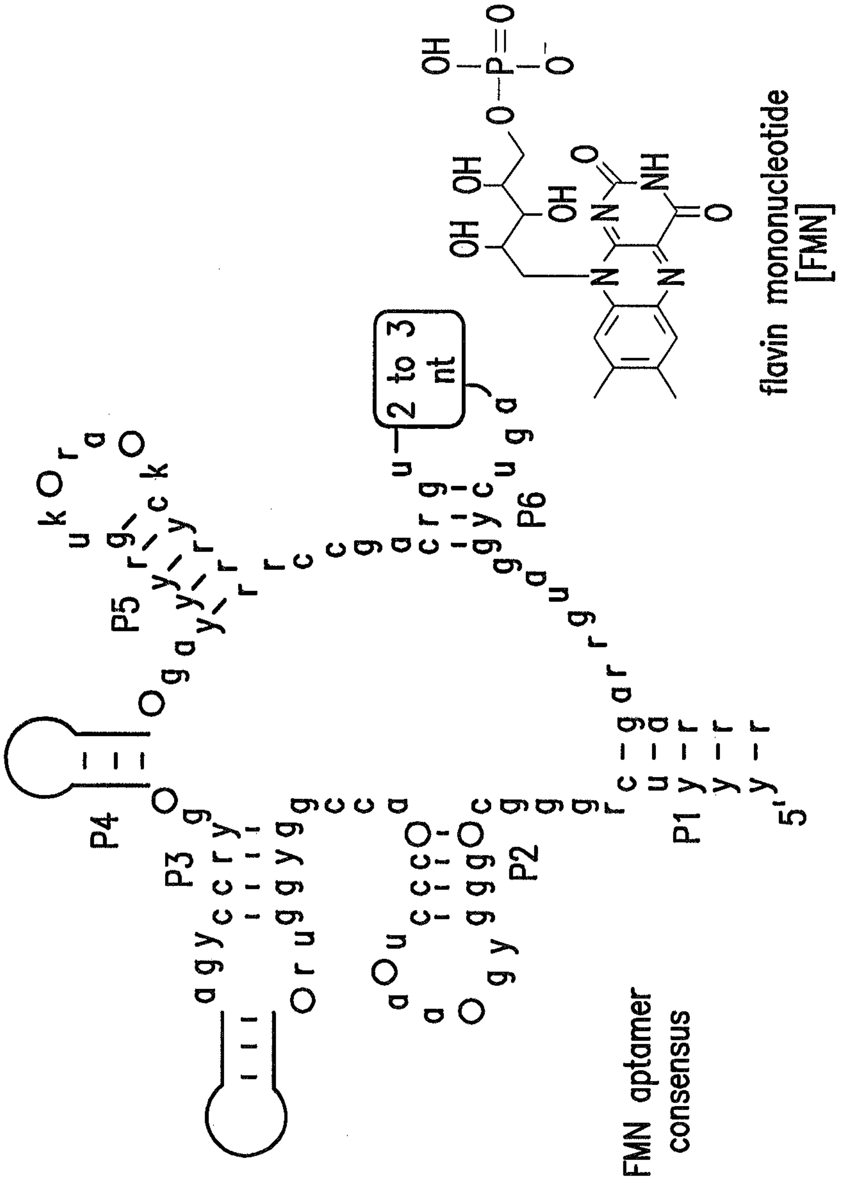
Figure 11D:
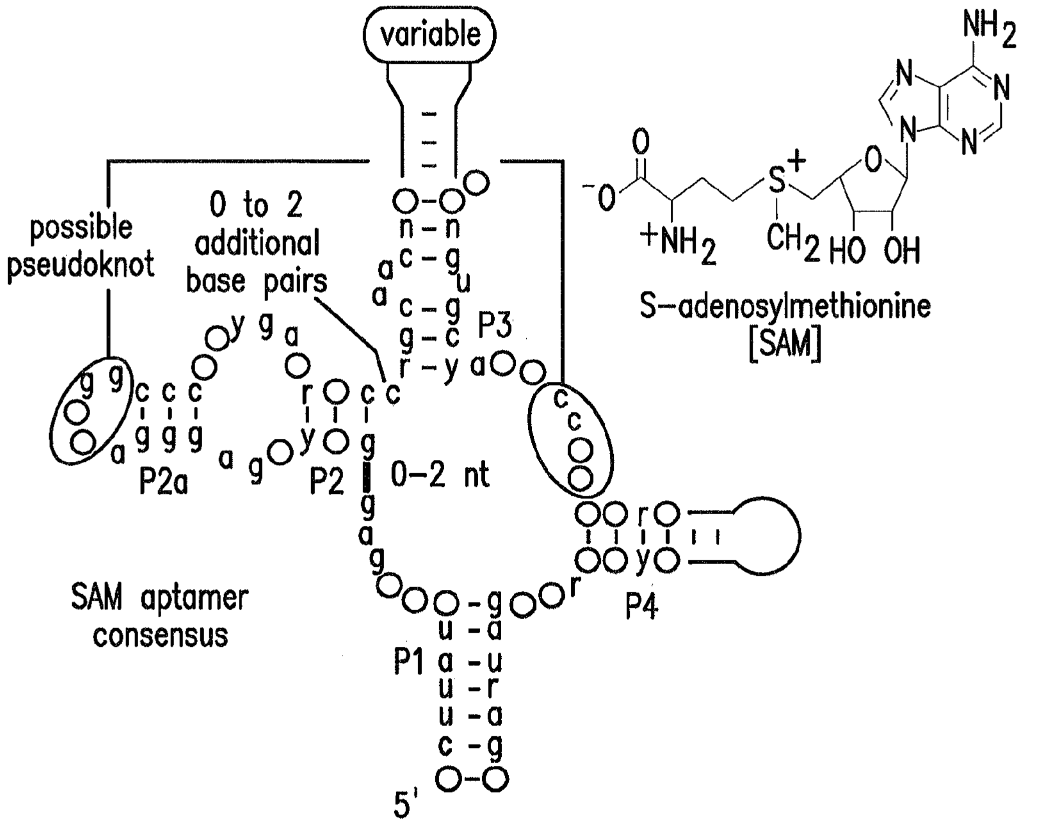
Figure 11E:
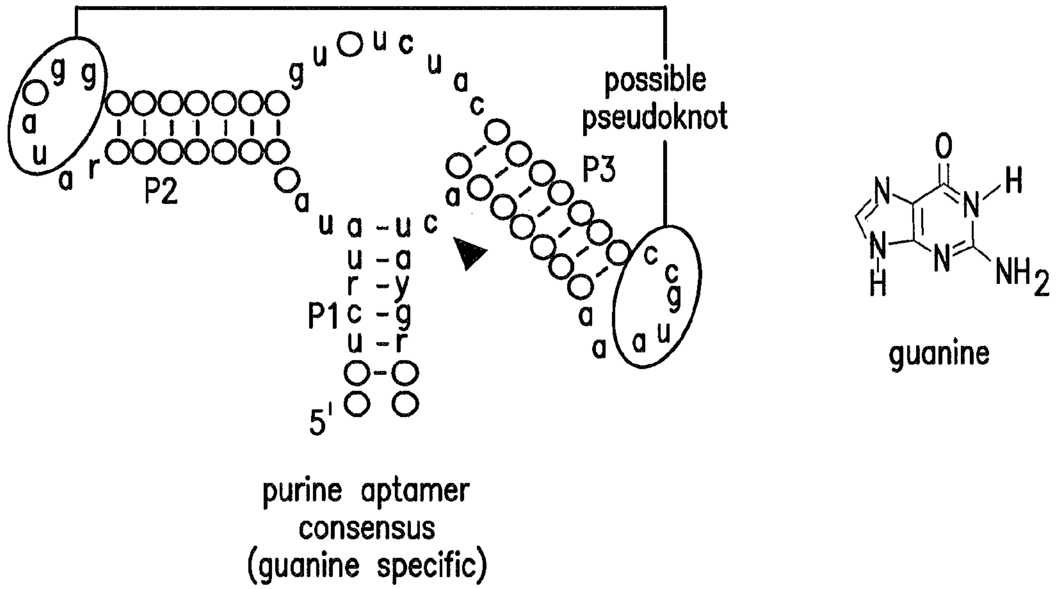
Figure 11F:
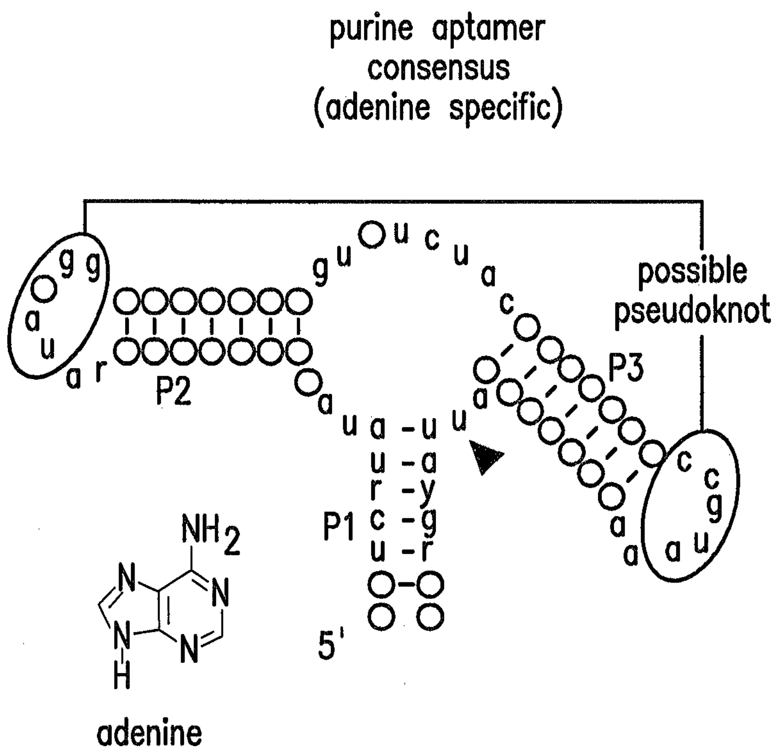
Figure 11G:
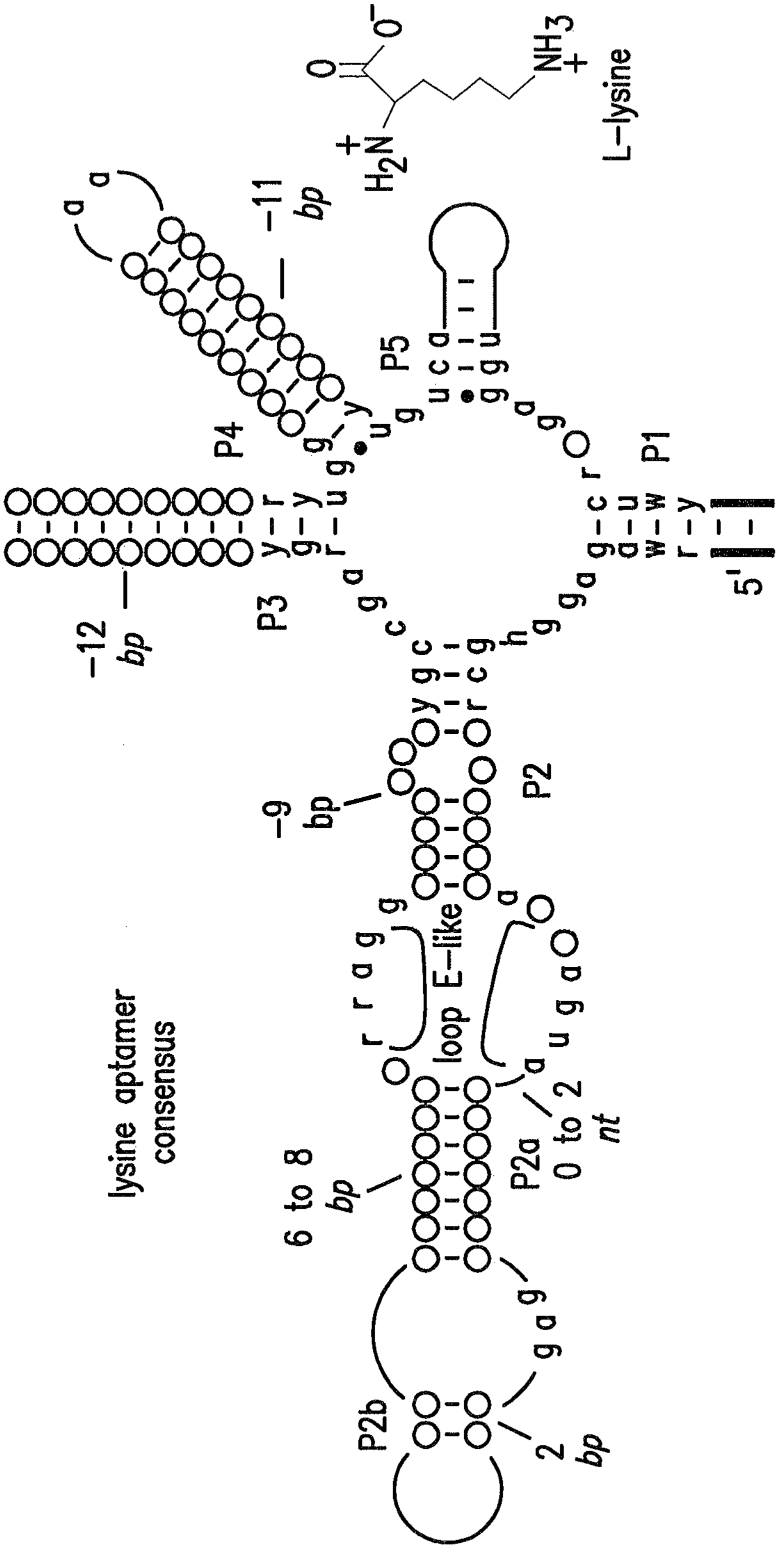

SAM RiboReporter Pool Design: A DNA template for in vitro transcription to RNA (FIG. 10) has been constructed by PCR amplification using the appropriate DNA template and primer sequences. In this construct, stem II of the hammerhead (stem P1 of the SAM aptamer) has been randomized to present more than 250 million possible sequence combinations, wherein some inevitably will permit function of the ribozyme only when the aptamer is occupied by SAM or a related high-affinity analog. Each molecule in the population of constructs is identical in sequence except at the random domain where multiple copies of every possible combination of sequence will be represented in the population.

SAM RiboReporter Selection: The in vitro selection protocol can be a repetitive iteration of the following steps:

1. Transcribe RNA in vitro by standard methods. Include [$\alpha$-$^{32}$P] UTP to incorporate radioactivity throughout the RNA.

2. Purify full length RNA on denaturing PAGE by standard methods.

3. Incubate full length RNA (~100 pmoles) in negative selection buffer containing sufficient magnesium for catalytic activity (20 mM) but no SAM. Incubate 4 h at room temperature (~23° C.), with thermocycling or alkaline denaturation as needed to preclude the emergence of selfish molecules.

4. Purify full length RNA on denaturing PAGE and discard RNAs that react in the absence of SAM.

5. Incubate in positive selection buffer containing 20 mM $Mg^{2+}$ and SAM (pH 7.5 at 23° C.). Incubate 20 min at room temperature.

6. Purify cleaved RNA on denaturing PAGE to recover switches that bound SAM and allowed self-cleavage of the RNA.

7. Reverse transcribe RNA to DNA.

8. PCR amplify DNA with primers that reintroduced cleaved portion of RNA.

The concentration of SAM in step 4 can be 100 μM initially and can be reduced as the selection proceeds. The progress of recovering successful communication modules can be assessed by the amount of cleavage observed on the purification gel in step 6. The selection endpoint can be either when the population approaches 100% cleavage in 10 nM SAM (conditions for maximal activity of the parental ribozyme and riboswitch) or when the population approaches a plateau in activity that does not improve over multiple rounds. The end population can then be sequenced. Individual communication module clones can be assayed for generation of a fluorescent signal in the screening construct in the presence of SAM.

A fluorescent signal can also be generated by riboswitch-mediated triggering of a molecular beacon. In this design, riboswitch conformational changes cause a folded molecular beacon tagged with both a fluor and a quencher to unfold and force the fluor away from the quencher by forming a helix with the riboswitch. This mechanism is easy to adapt to existing riboswitches, as this method can take advantage of the ligand-mediated formation of terminator and anti-terminator stems that are involved in transcription control.

To use riboswitches to report ligand binding by binding a molecular beacon, the appropriate construct must be determined empirically. The optimum length and nucleotide composition of the molecular beacon and its binding site on the riboswitch can be tested systematically to result in the highest signal-to-noise ratio. The validity of the assay can be determined by comparing apparent relative binding affinities of different SAM analogs to a molecular beacon-coupled riboswitch (determined by rate of fluorescent signal generation) to the binding constants determined by standard in-line probing.

EXAMPLES

A. Example 1

Coenzyme $B_{12}$ (AdoCbl) Riboswitches

The example described testing and analysis of a riboswitch that controls gene expression by binding coenzyme $B_{12}$.

1. Methods i. Chemicals and Oligonucleotides

Coenzyme $B_{12}$ (5'-deoxy-5'-adenosylcobalamin or "AdoCbl") and its analogs methylcobalamin, cobinamide dicyanide, and cyannocobalamin were purchased from Sigma. Tritiated AdoCbl was prepared as described previously (Brown and Zou, Thermolysis of coenzymes $B_{12}$ at physiological temperatures: activation parameters for cobalt-carbon bond homolysis and a quantitative analysis of the perturbation of the homolysis equilibrium by the ribonucleoside triphosphate reductase from *Lactobacillus leichmannii*. J. Inorg. Biochem. 77, 185-195 (1999)). For information regarding the AdoCbl analogs $B^6$,$N^6$-dimethyl-AdoCbl, $N^6$-methyl-AdoCbl, $N^1$-methyl-AdoCbl, 3-deaza-AdoCbl, PurCbl, 2'-deoxy-AdoCbl and 13-epi-AdoCbl, see Toraya, In: Chemistry and Biochemistry of $B_{12}$. Banerjee, R. Ed. (Wiley, New York) pp. 783-809 (1999).

DNA oligonucleotides were synthesized by the Keck Foundation Biotechnology Resource Center at Yale University. DNAs were purified by denaturing (8 M urea) PAGE and isolated from the gel by crush/soaking in 10 mM Tris-HCl (pH 7.5 at 23° C.), 200 mM NaCl and 1 mM EDTA. The DNA was recovered from the solution by precipitation with ethanol, resuspended in water and stored at −20° C. until use.

ii. RNA Structure Analysis by In-Line Probing

Precursor mRNA leader molecules were prepared by in vitro transcription from templates generated by PCR (see In vivo Expression Constructs and Assays section below) and 5' $^{32}$p-labeled using methods described previously (Soukup and Breaker, Allosteric nucleic acid catalysts. Curr. Opin. Struct. Biol. 10, 3t8-325 (2000)). Approximately 20 nM of labeled RNA precursor was incubated as described in the brief description of FIG. 1. Accompanying digestions were carried out using reaction conditions similar to those described previously (Soukup and Breaker, Relationship between internucleotide linkage geometry and the stability of P,-NA. RNA 5, 1308-1325 (1999)). To prevent light-induced degradation of ligands, incubations were protected from exposure to light by wrapping each tube with aluminum foil.

iii. Equilibrium Dialysis Assays

Each equilibrium dialysis experiment was conducted using a Dispo-Equilibium Dialyzer (ED-1, Harvard Bioscience) apparatus, wherein two chambers (a and b) each contained 25 μL of equilibration buffer (50 mM Tris-HCl [pH 8.3 at 25° C.], 20 mM $MgCl_2$). The chambers were separated by a dialysis membrane with a 5,000 Dalton molecular weight cut-off In each experiment (I-IV, boxed), 100 pmoles of $^3$H-AdoCbl were included in chamber a, and other additives were included as designated (+) for each chamber. In each step, equilibrations were allows to proceed for 10 hrs at 25° C. before samples were quantitated or before subsequent manipulations were carried out. Quantitation was achieved by liquid scintillation counting using 5 or 10 μL of solution from each chamber.

Dialysis samples were protected from exposure to light by wrapping each apparatus with aluminum foil.

iv. In Vivo Expression Constructs and Assays

*E. coli* K-12 strain was used for all btuB-lacZ expression assays and Top10 cells (Invitrogen) were used for plasmid preparation. A DNA (nucleotides −70 to 450) encompassing the btuB leader sequence was amplified as an EcoRI-BamHI fragment by colony PCR from *E. coli* strain MC4100 (a gift from S. Gottesman, NIH). The wild-type construct and mutant constructs were inserted into plasmid pRS414 (a gift from R. Simons, UCLA; Simons et al., Improved single and multicopy lac-based cloning vectors for protein and operon fusions. Gene 53, 85-96 (1987)), in frame with the 9$^{th}$ codon of lacZ (β-galactosidase). Mutant constructs were generated by a three-step PCR strategy wherein regions upstream and down stream of the mutation site were amplified separately with the appropriate DNA primers that introduced the desired sequence changes. The resulting fragments were purified by agarose gel electrophoresis, and then combined and amplified by PCR using primers that correspond to the ends of the full-length construct. The resulting constructs were cloned and sequenced. Constructs whose sequence was confirmed were used for expression analysis and were used as templates for subsequent preparation of PCR-derived DNAs for in vitro transcription.

The in-frame fusions between various btuB leader sequences and lacZ generated as described above were used to determine the levels of expression by employing a/3-galactosidase assay adapted from that described by Miller, In: A Short Course in Bacterial Genetics (Cold Spring Harbor Laboratory Press, Cold Spring Harbor, N.Y.,) p. 72 (1992).

2. Results

Figure 1B:
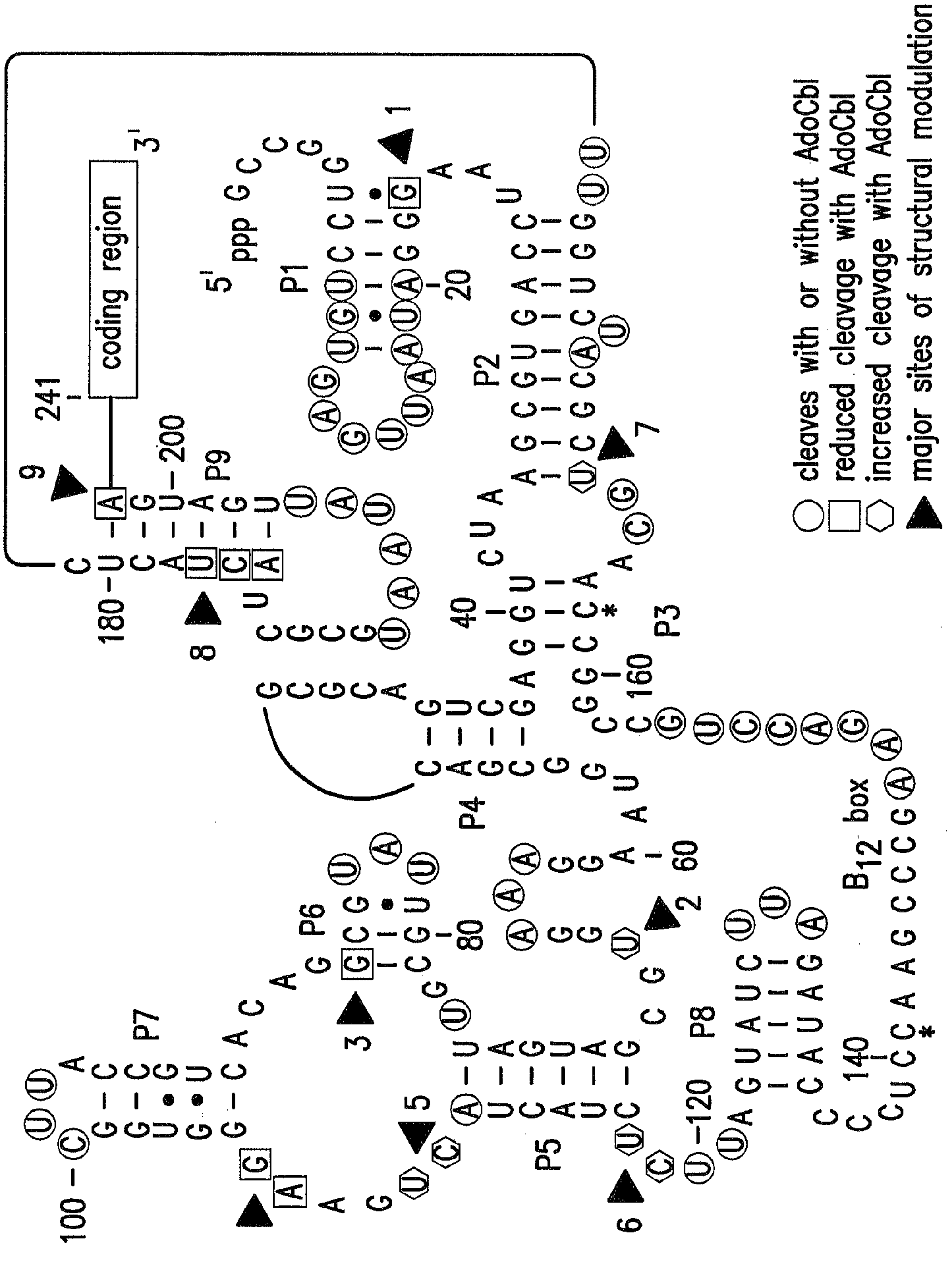

Metabolite-dependent conformational changes in the 202-nucleotide leader sequence of the btuB mRNA. FIG. 1A: Separation of spontaneous RNA-cleavage products of the btuB leader using denaturing 10% polyacrylamide gel electrophoresis (PAGE). 5'-32p-labeled mRNA leader molecules (arrow) were incubated for 41 hr at 25° C. in 20 mM $MgCl_2$, 50 mM Tris-HCl (pH 8.3 at 25° C.) in the presence (+) or absence (−) of 20 μM of AdoCbl. Lanes containing RNAs that have undergone no reaction, partial digest with alkali, and partial digest with RNase T1 (G-specific cleavage) are identified by NR, $^-$OH, and T1, respectively. The location of product bands corresponding to cleavage after selected guanosine residues are identified by filled arrowheads. Arrowheads labeled 1 through 8 identify eight of the nine locations that exhibit effector-induced structure modulation, which experience an increase or decrease in the rate of spontaneous RNA cleavage. The image was generated using a phosphorimager (Molecular Dynamics), and cleavage yields were quantitated by using ImageQuant software. FIG. 1B: Sequence and secondary-structure model for the 202-nucleotide leader sequence of btuB mRNA in the presence of AdoCbl. Putative base-paired elements are designated P1 through P9. Complementary nucleotides in the loops of P4 and P9 that have the potential to form a pseudoknot are juxtaposed. Nine specific sites of structure modulation are identified by light blue arrowheads. The asterisks demark the boundaries of the $B_{12}$ box (nucleotides 141-162). The coding region and the 38 nucleotides that reside immediately 5' of the start codon (nucleotides 241-243) were not included in the 202-nucleotide fragment. The 315-nucleotide fragment includes the 202-nucleotide fragment, the remaining 38 nucleotides of the leader sequence, and the first 75 nucleotides of the coding region.

Figure 2A:
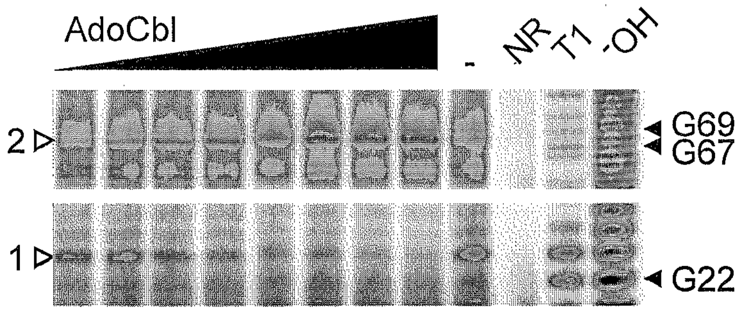
FIGS. 2A and 2B show the btuB mRNA leader forms a saturable binding site for AdoCbl.
Figure 2B:
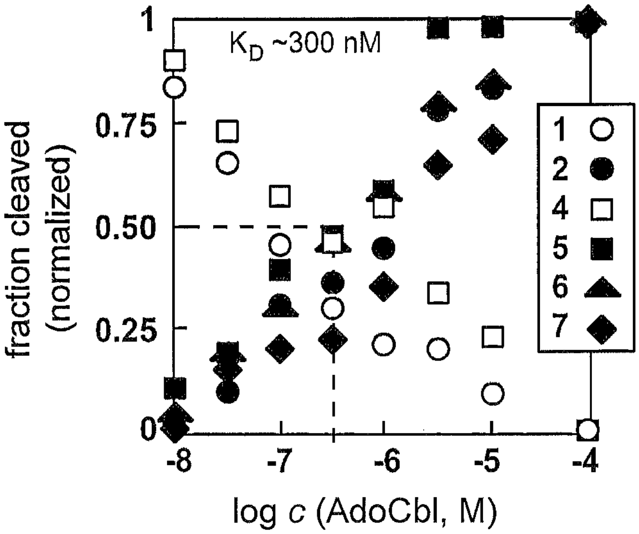

The btuB mRNA leader forms a saturable binding site for AdoCbl. FIG. 2A: The dependence of spontaneous cleavage of btuB mRNA leader on the concentration of AdoCbl effector as represented by site 1 (G23) and site 2 (U68). 5'-$^{32}$P-labeled mRNA leader molecules were incubated, separated, and analyzed as described in the in the legend to FIG. 1A, and include identical control and marker lanes as indicated. Incubations contained concentrations of AdoCbl ranging from 10 nM to 100 μM (lanes 1 though 8) or did not include AdoCbl (−). FIG. 2B: Composite plot of the fraction of RNA cleaved at six locations along the mRNA leader versus the logarithm of the concentration (c) of AdoCbl. Fraction cleaved values were normalized relative to the highest and lowest cleavage values measured for each location, including the values obtained upon incubation in the absence of AdoCbl. The inset defines the symbols used for each of six sites, while the remaining three sites were excluded from the analysis due to weak or obscured cleavage bands. Filled and open symbols represent increasing and decreasing cleavage yields, respectively, upon increasing the concentration of AdoCbl. The dashed line reflects a $K_D$ of ~300 nM, as predicted by the concentration needed to generate half-maximal structural modulation. Data plotted were derived from a single PAGE analysis, of which two representative sections are depicted in FIG. 2A.

Figure 3:
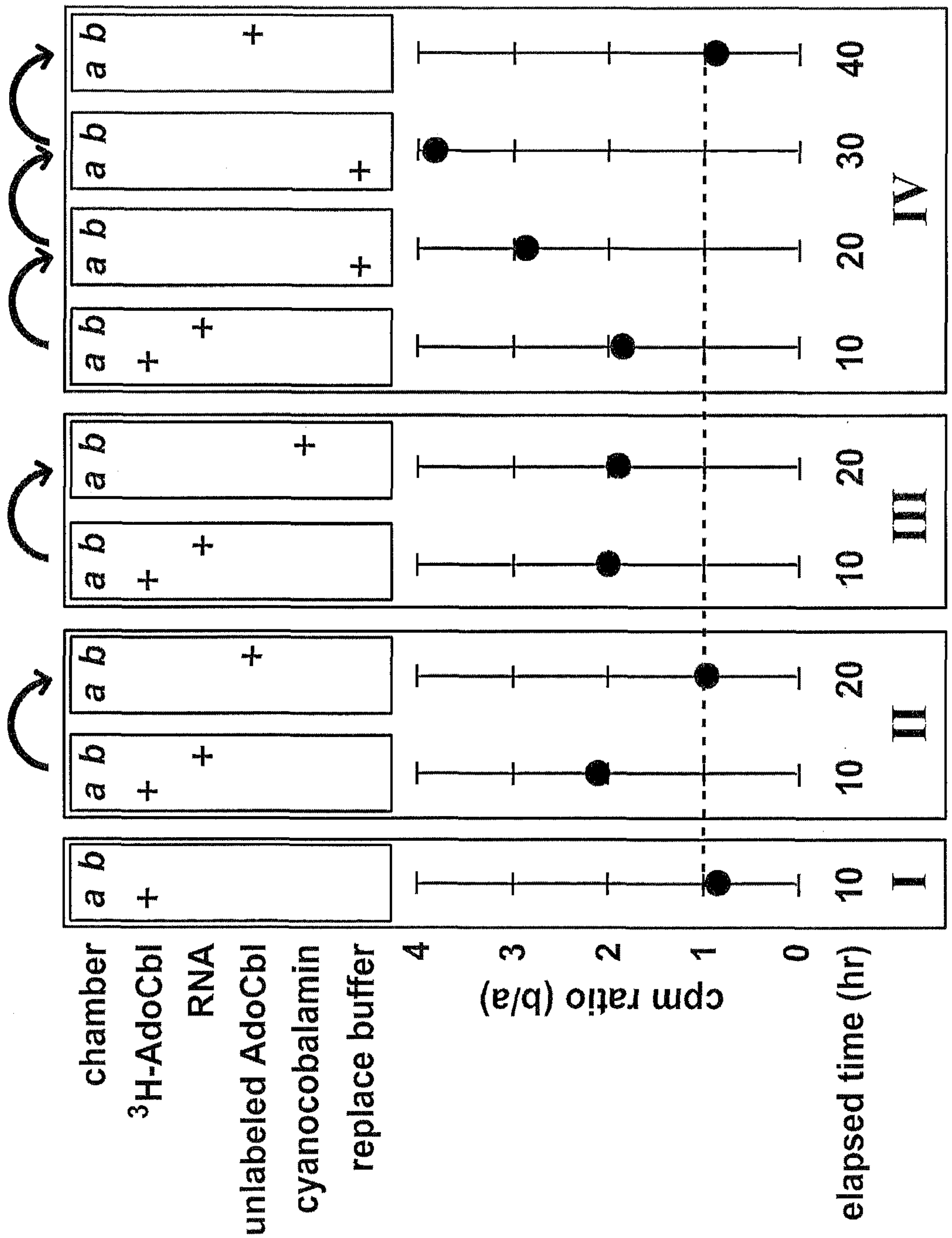
FIG. 3 shows the 202-nucleotide mRNA leader causes an unequal distribution of AdoCbl in an equilibrium dialysis apparatus. I: Equilibration of tritiated effector was conducted in the absence of RNA. II: (step 1) Equilibration was conducted as in I, but with 200 pmoles of mRNA leader added to chamber b; (step 2) 5,000 pmoles of unlabeled AdoCbl was added to chamber b. III: Equilibrations were conducted as described in II, but wherein 5,000 pmoles of cyanocobalamin was added to chamber b. IV: (step 1) Equilibration was initiated as described in step 1 of II; (steps 2 and 3) the solution in chamber a was replaced with 25 μL of fresh equilibration buffer; (step 4) 5,000 pmoles of unlabeled AdoCbl was added to chamber b. The cpm ratio is the ratio of counts detected in chamber b relative to that of a. The dashed line represents a cpm ratio of 1, which is expected if equal distribution of tritium is established.

The 202-nucleotide mRNA leader causes an unequal distribution of AdoCbl in an equilibrium dialysis apparatus. FIG. 3(I): Equilibration of tritiated effector was conducted in the absence of RNA. FIG. 3(II): (step 1) Equilibration was conducted as in I, but with 200 pmoles of mRNA leader added to chamber b; (step 2) 5,000 pmoles of unlabeled AdoCbl was added to chamber b. FIG. 3(III): Equilibrations were conducted as described in II, but wherein 5,000 pmoles of cyanocobalamin was added to chamber b. IV: (step 1) Equilibration was initiated as described in step 1 of II; (steps 2 and 3) the solution in chamber a was replaced with 25 μL of fresh equilibration buffer; (step 4) 5,000 pmoles of unlabeled AdoCbl was added to chamber b. The cpm ratio is the ratio of counts detected in chamber b relative to that of a. The dashed line represents a cpm ratio of 1, which is expected if equal distribution of tritium is established.

Figure 4B:
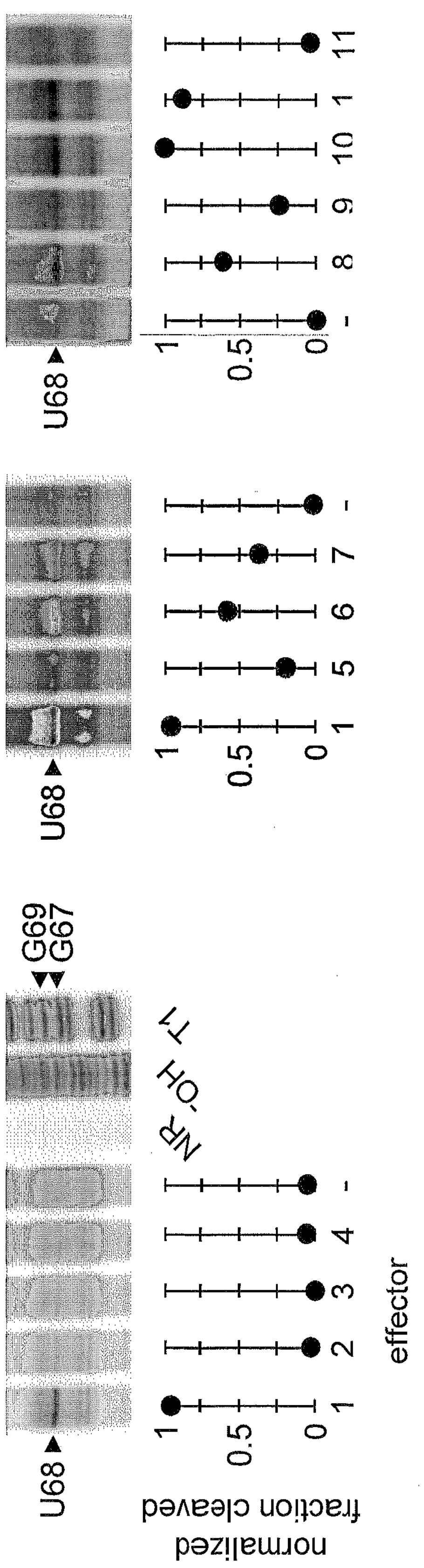

Selective molecular recognition of effectors by the btuB mRNA leader. FIG. 4A shows a chemical structure of AdoCbl (1) and various effector analogs (2 through 11). FIG. 4B: Determination of analog binding by monitoring modulation of spontaneous cleavage of the 202-nucleotide btuB RNA leader. 5'-$^{32}$P-labeled mRNA leader molecules were incubated, separated, and analyzed as described in the legend to FIG. 1A, and include identical control and marker lanes as indicated. The sections of three PAGE analyses encompassing site 2 (U68) are depicted. Below each image is plotted the amount of RNA cleaved (normalized with relation to the lowest and highest levels of cleavage at U68 in each gel) for each effector as indicated, or for no effector (−). The compound 11 (13-epi-AdoCbl) is an epimer of AdoCbl wherein the configuration at C13 is inverted, so that the e propionamide side chain is above the plane of the corrin ring; see Brown et al., Conformational studies of 5'-deoxyadenosyl-13-epicobalamin, a coenzymatically active structural analog of coenzyme $B_{12}$. Polyhedron 17, 2213 (1998).

Figure 5A:
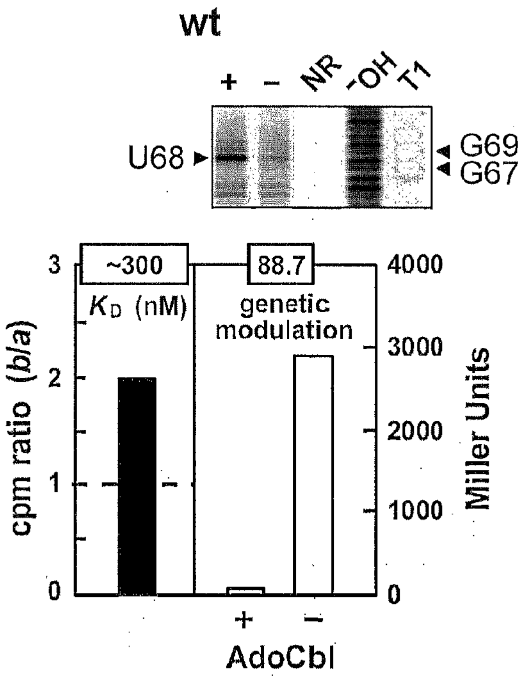
FIGS. 5A, 5B, 5C, 5D, 5E and 5F show mutations in the mRNA leader and their effects on AdoCbl binding and genetic control.
Figure 5B:
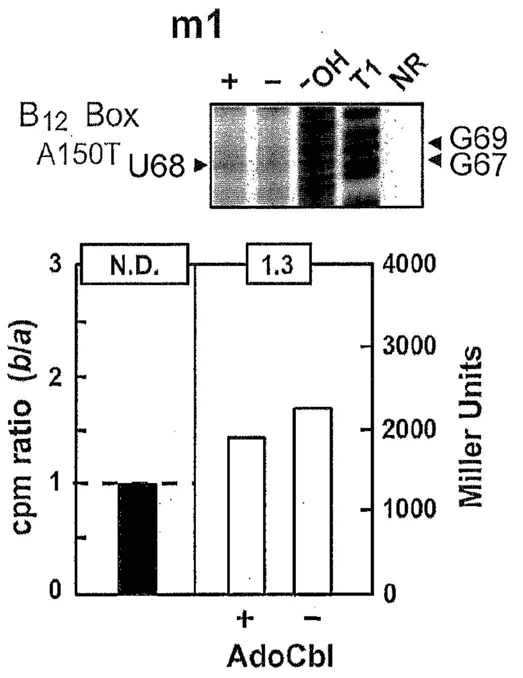
Figure 5C:
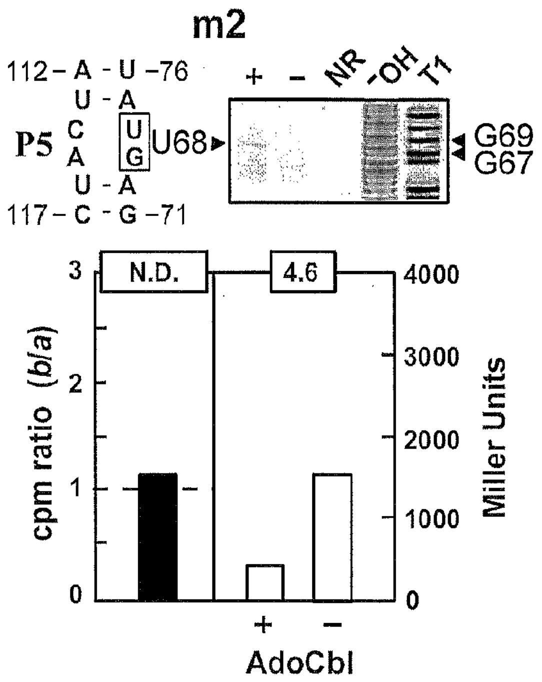

Mutations in the mRNA leader and their effects on AdoCbl binding and genetic control. FIG. 5A: Sequence of the putative P5 element of the wild-type 202-nucleotide btuB leader exhibits AdoCbl-dependent modulation of structure as indicated by the observed increase in spontaneous RNA cleavage at position U68 (10% denaturing PAGE gel). Assays were conducted in the absence (−) or presence (+) of 5 μM AdoCbl. The remaining lanes are as described in the legend to FIG. 1A. The composite bar graph reflects the ability of the RNA to shift the equilibrium of AdoCbl in an equilibrium dialysis apparatus and the ability of a reporter gene (see Experimental Procedures) to be regulated by AdoCbl addition to a bacterial culture. (Left) Plotted is the cpm ratio derived by equilibrium dialysis, wherein chamber b contains the RNA. Details of the equilibrium dialysis experiments are described in the brief description of FIG. 3. (Right) Plotted are the expression levels of β-galactosidase as determined from cells grown in the absence (−) or presence (+) of 5 μM AdoCbl. Boxed numbers on the left and right, respectively, reflect the approximate $K_D$ and the fold repression of β-galactosidase activity in the presence of AdoCbl. N.D. designates not determined. FIGS. 5B-5F: Sequences and performance characteristics of various mutant leader sequences as indicated. Constructs were created as described in the Experimental Procedures section.

i. Metabolite-Induced Structure Modulation of a Messenger RNA.

To assess whether the btuB leader sequence alone is sufficient for sensing and responding to a metabolite, a molecular probing strategy was employed that relies on the structure-dependent spontaneous cleavage of RNA (Soukup and Breaker, Relationship between internucleotide linkage geometry and the stability of P,-NA. RNA 5, 1308-1325 (1999); Soukup et al., Generating new ligand-binding RNAs by affinity maturation and disintegration of allosteric ribozymes. RNA 7, 524-536 (2001)). The principal mechanism by which an RNA phosphodiester linkage is spontaneously cleaved involves an internal nucleophilic attack by the 2'-oxygen on the adjacent phosphorus center. Since the precise "in-line" positioning of the U-oxygen, phosphorus, and 5'-oxygen atoms of a given RNA linkage is essential for a productive nucleophilic attack to occur (Soukup and Breaker, Relationship between internucleotide linkage geometry and the stability of P,-NA. RNA 5, 1308-1325 (1999); Soukup et al., Generating new ligand-binding RNAs by affinity maturation and disintegration of allosteric ribozymes. RNA 7, 524-536 (2001); Westheimer, Pseudo-rotation in the hydrolysis of phosphate esters. Acc. Chem. Res. 1, 70-78 (1968); Usher, On the mechanism of ribonuclease action. Proc. Natl. Acad. USA 62, 661-667 (1969); Usher and McHale, Hydrolytic stability of helical RNA: a selective advantage for the natural 3',5'-bond. Proc. Natl. Acad. USA 73, 1149-1153 (1976); Dock-Bregeon and Moras, Conformational changes and dynamics of tRNAs: evidence from hydrolysis patterns. Cold Spring Harbor Symp. Quant. Biol. 52, 113-121 (1987)), the rate at which spontaneous cleavage occurs at a given linkage is highly dependent upon the secondary and tertiary structure of the RNA. Specifically, RNA linkages that are formed by nucleotides involved in stable base-paired structures rarely undergo spontaneous cleavage because they rarely adopt an in-line conformation, while nucleotides located in relatively unstructured regions or in tertiary-structured regions experience far greater levels of spontaneous cleavage. Thus, probing of an RNA receptor in the absence and presence of its ligand can be used to provide evidence for RNA structural models and even to determine the dissociation constant for a given RNA-ligand interaction (Soukup and Breaker, Relationship between internucleotide linkage geometry and the stability of P,-NA. RNA 5, 1308-1325 (1999); Soukup et al., Generating new ligand-binding RNAs by affinity maturation and disintegration of allosteric ribozymes. RNA 7, 524-536 (2001)).

A preparation of RNAs that encompass nucleotides 1 through 202 of the 5'-untranslated region of the btuB mRNA (Nou and Kadner, Adenosylcobalamin inhibits ribosome binding to btuB RNA. Proc. Nail. Acad. Sci. USA 97, 7190-7195 (2000); Lundrigan et al., Transcribed sequences of the *Escherichia coli* btuB gene control its expression and regulation by vitamin $B_{12}$ Proc. Natl. Acad. USA 88, 1479-1483 (1991)) was subjected to in-line probing (FIG. 1). In the absence of the putative AdoCbl effector, the RNA exhibits a distinct pattern of cleavage products that is indicative of a well ordered conformational state, which has a mixture of stable structural elements interspersed with regions that are mostly unstructured (FIG. 1A). In the presence of AdoCbl, the pattern of cleavage changes at eight locations, while a ninth position of structural modulation (FIG. 1B) is observed when a longer portion of the mRNA is used. Specifically, metabolite-induced structural modulation at nucleotide 202 (FIG. 1B, position 9) was observed by using in-line probing of a fragment that encompasses nucleotides 1 through 315 of the btuB mRNA (Nou and Kadner, Adenosylcobalamin inhibits ribosome binding to btuB RNA. Proc. Nail. Acad. Sci. USA 97, 7190-7195 (2000)). Positions 1, 3, 4, 8, and 9 undergo an effector-dependent dampening of spontaneous cleavage while the remaining sites experience the reverse effect. A similar pattern of metabolite-modulated RNA cleavage was observed with the analogous 206-nucleotide btuB leader RNA of *S. typhimurium* (Wei et al., Res. Microbiol. 143, 459 (1992)).

These effector-modulated sites are mapped on a secondary-structure model that was generated by using a combination of computational and RNA probing data. An RNA secondary-structure prediction algorithm (Zuker et al., Algorithms and thermodynamics for RNA secondary structure prediction: a practical guide. In RNA Biochemistry and Biotechnology (eds. Barciszewski, J., and Clark, B. F. C.) pp. 11-43 (NATO ASI Series, Kluwer Academic Publishers) (1999)) supports a model wherein nine base-paired elements are formed. The in-line probing data and preliminary mutational analyses are consistent with eight of these pairing interactions (P1-P4 and P6-P9), while an alternative pairing interaction (P5) is supported (see below). The majority of these putative base-paired elements appear to remain intact upon effector-induced modulation, with the notable exception of P9. The importance of this structural element in the modulation of ribosome binding and translation has been previously established by mutational analysis (Nou and Kadner, Adenosylcobalamin inhibits ribosome binding to btuB RNA. Proc. Nail. Acad. Sci. USA 97, 7190-7195 (2000)). Metabolite-dependent formation of the P9 stem-loop structure appears to be critical for the down-regulation of mRNA translation. Consistent with this hypothesis is the observed increase in structure formation in this location upon the addition of AdoCbl (FIG. 1B, decreased cleavage at positions 8 and 9).

ii. A Saturable Metabolite-Binding Site is Formed by a Messenger RNA.

If the structural alteration of the mRNA leader is induced selectively by AdoCbl (as opposed to modulation by a non-specific effect) then the RNA should exhibit characteristics of a typical receptor-ligand interaction. Thus, a plot of the relative extents of structural modulation at each site is expected to yield an apparent dissociation constant (apparent KD) for the effector, which reflects the concentration of effector needed to convert half of the RNAs into their altered structural state. Furthermore, if a single binding event brings about the global structural changes that are observed, then the individual Kr) values calculated for each modulation site should converge on a single value, while these values are likely to vary if the structural modulation results from non-specific effects.

Indeed, the levels of spontaneous RNA cleavage were found to correlate with the concentrations of AdoCbl added to the in-line probing mixtures (FIG. 2A). Examination of the dependency of the six most prominent sites of modulation on effector concentration reveals similar apparent $K_D$ values of approximately 300 nM at 25° C. (FIG. 2B). This value is comparable to an apparent $K_D$ value derived from a previous assay that examined the AdoCbl-dependent binding of ribosomes to the btuB mRNA (Nou and Kadner, Adenosylcobalamin inhibits ribosome binding to btuB RNA. Proc. Nail. Acad. Sci. USA 97, 7190-7195 (2000)). Moreover, the fact that structural modulation occurs over a broad range of concentrations of AdoCbl suggests that this RNA is not likely to make use of cooperative binding of multiple effectors, which would result in a more substantial response to small changes in effector concentration. Together, these observations indicate that the mRNA leader undergoes a substantial change in conformation and forms a high-affinity binding pocket for AdoCbl.

To provide further support for this conclusion, equilibrium dialysis was used to determine whether the RNA could selectively generate an unequal distribution of tritiated AdoCbl (3H-AdoCbl) when incubated in a two-chamber dialysis system. As expected, addition of 3H-AdoCbl to chamber a of an equilibrium dialysis assembly results in near equal distribution of tritium (cpm ratio ~1) between chambers a and b upon incubation (FIG. 3, experiment I). However, the addition of the 202-nucleotide mRNA leader to chamber b causes a shift in the equilibrium of 3H-AdoCbl (cpm ratio ~2) in favor of chamber b (FIG. 3, experiments II and III). Importantly, the subsequent addition of an excess of unlabeled AdoCbl restores equal distribution of tritium between the two chambers, while the addition of an excess of cyanocobalamin (vitamin $B_{12}$, an analog of AdoCbl) does not restore the ratio of tritium to unity. Excess unlabeled AdoCbl is expected to restore equal distribution by serving to occupy the vast majority of the binding sites formed by the btuB RNA. In contrast, cyanocobalamin is known to be incapable of serving as a regulatory effector for btuB expression in *E. coli* (Nou and Kadner, Adenosylcobalamin inhibits ribosome binding to btuB RNA. Proc. Nail. Acad. Sci. USA 97, 7190-7195 (2000); Lundrigan and Kadner, Altered cobalamin metabolism in *Escherichia coli* btuR mutants affects btuB gene regulation. J. Bacteriol. 171, 154-161 (1989)), and thus should be ignored as an effector by the RNA. These findings are consistent with the conclusion that the RNA directly binds AdoCbl and indicate that the RNA forms a selective binding pocket that excludes certain analog compounds.

Assuming that a 1:1 complex is formed between effector and RNA, it was expected that equilibrium dialysis would produce a cpm ratio of far greater than 2 under the assay conditions (2-fold excess RNA over 3H-AdoCbl and concentrations of RNA and effector in excess of the apparent KD). Since there should be an excess of binding sites, the majority of the tritium should be shifted to chamber b upon equilibration. However, the data suggest that −70% of the tritium in the sample used is not in the form of 3H-AdoCbl. For example, successive replacement of the buffer in chamber a (which removes unshifted tritium from the equilibrium dialysis system) results in increasing values for the cpm ratio (FIG. 3; experiment IV). In addition, the tritium that remains in chamber a upon equilibration with RNA in chamber b cannot be induced to yield an unequal distribution of tritium by btuB RNA in a subsequent equilibrium dialysis experiment (data not shown). The source of this unbound tritium is most likely from light-mediated degradation of AdoCbl, which is highly unstable under ambient light conditions. Mass spectrum analysis of 3H-AdoCbl reveals that the sample is almost entirely intact in the absence of light exposure, but yields −70% degradation upon exposure to light for a time of about 20 sec) that is typically experienced by a sample when establishing an equilibrium dialysis experiment.

iii. The btuB mRNA Leader Selectively Binds AdoCbl.

To-provide selectivity for the genetic response, the btuB mRNA leader must form a precise binding pocket for AdoCbl in order to preclude the genetic switch from being triggered by other metabolites. To explore the molecular recognition capabilities of this RNA, the binding affinity of AdoCbl relative to 10 analogs was indirectly determined (FIG. 4A). This was achieved by determining the extent of spontaneous cleavage at site 2 (nucleotide U68) upon incubation in the presence of AdoCbl or of various analogs (FIG. 4B). It was found that the RNA fails to undergo structural modulation when cobalamin compounds lack the 5'-deoxy-5'-adenosyl moiety. The importance of individual functional groups on this moiety is revealed by the function of other analogs. In summary, modifications at the N1, N3, and N6 positions of the adenine ring cause significant disruption of binding, while the 2"-hydroxyl group of the adjoining ribose moiety is not an important molecular recognition element. Interestingly, a change in the stereochemistry at position 13 of the corrin ring (compound 11) renders the molecule inactive as a regulatory effector in this in vitro assay and also inside cells. These findings indicate that the btuB mRNA leader forms a binding pocket for AdoCbl and that the RNA makes numerous contacts with the effector to ensure high molecular specificity.

iv. Disruption of Metabolite-RNA Binding has Consequences for Genetic Control.

The presence of AdoCbl causes reductions in ribosome binding and translation efficiency of the btuB mRNA (Nou and Kadner, Adenosylcobalamin inhibits ribosome binding to btuB RNA. Proc. Nail. Acad. Sci. USA 97, 7190-7195 (2000)). The results indicate that this genetic control process is mediated by the selective binding of AdoCbl to the btuB mRNA. The effector-binding function of mutant RNA leaders in vitro was compared with their ability to support effector-induced genetic control inside cells. As expected, the wild-type mRNA leader exhibits effector-induced structure modulation, induces an unequal distribution of $^3$H-AdoCbl in an equilibrium dialysis system, and permits down regulation of a reporter gene in *E. coli* cells treated with AdoCbl and harboring the appropriate reporter construct (summarized in FIG. 5A). However, the introduction of a single mutation (A150T) in the evolutionarily conserved "$B_{12}$ box" (Nou and Kadner, Adenosylcobalamin inhibits ribosome binding to btuB RNA. Proc. Nail. Acad. Sci. USA 97, 7190-7195 (2000)) completely eliminates the in vitro effector-binding and in vivo gene-control functions of this construct, termed "m1" (FIG. 5B), which is consistent with the necessity of effector binding for genetic control.

Figure 5D:
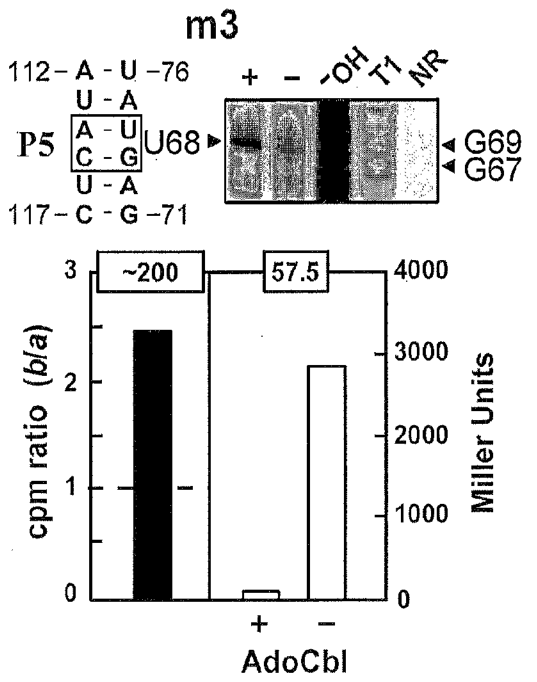
Figure 5E:
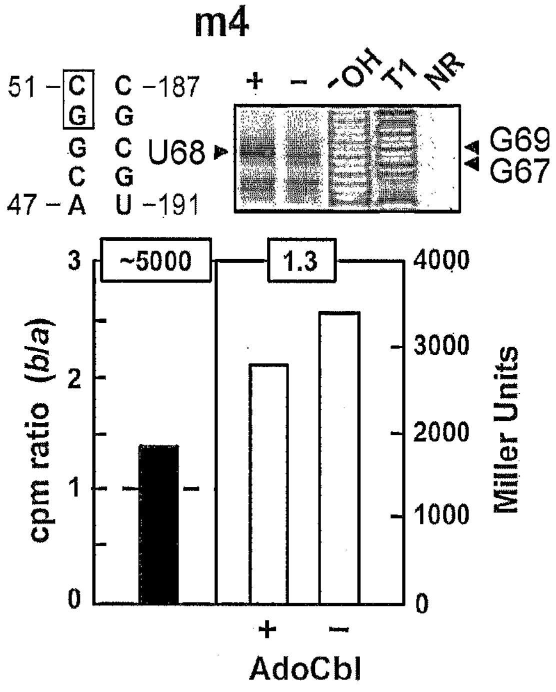
Figure 5F:
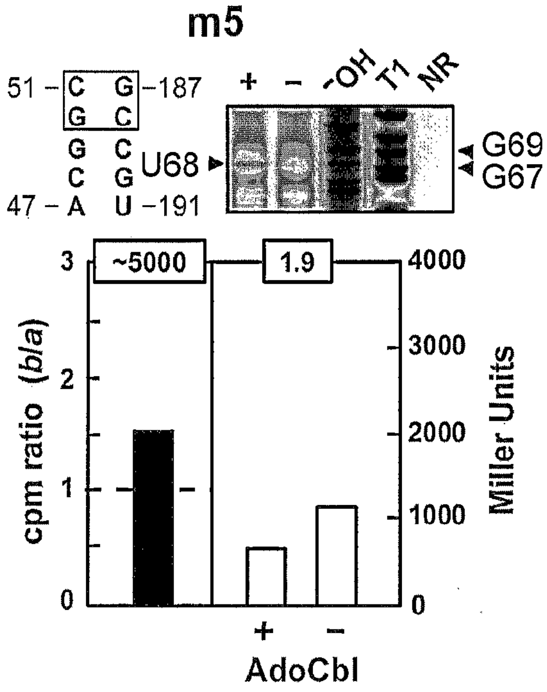

Mutations that disrupt (U73G, G74U) and subsequently restore (U73G, G74U, C114A, A115C) the predicted P5 stem element were examined. The disrupted stem in construct m2 causes a reduction of AdoCbl binding affinity in vitro and a corresponding reduction of genetic control in cell assays (FIG. 5C), while restoration of the P5 stem element (construct m3) results in near wild-type functions for binding and genetic control (FIG. 5D). This indicates that the P5 stem is an important structural element for function of the RNA. Interestingly, potentially disruptive (m4) and restorative (m5) mutations in a possible pseudoknot structure between the P4 and P9 loops (FIG. 1B) both result in a reduction in binding affinity ($K_D$~5 μM). If a pseudoknot is being formed, this structure might require a specific sequence for proper function. Although these RNAs maintain diminished but detectable levels of effector binding, neither exhibits genetic control upon the addition of AdoCbl to bacterial cultures harboring the corresponding reporter constructs. The loss in binding affinity likely is sufficient to place these mutant RNAs out of the physiological range for effector concentration, as the cells still retain their natural btuB gene whose regulatory system continues to control the import of AdoCbl. The findings support the hypothesis that mRNAs have the structural and functional sophistication needed to perform precision genetic control in the absence of protein regulatory elements.

v. Analysis

Genetic control by mRNAs that directly sense the concentrations of metabolites is a newly established paradigm for monitoring the status of cellular metabolism. Although sensing of aminoacyl tRNAs in prokaryotes also appears to be achieved by direct binding of tRNAs to the 5'-untranslated region of their corresponding aminoacyl tRNA synthetases (Henkin, tRNA-directed transcription antitermination. Mol. Microbiol. 3, 381-387 (1994)), binding appears to be mediated by Watson/Crick base pairing. In the case of btuB the mRNA directly binds the Ado-Cbl effector and becomes resistant to translation initiation, presumably by preventing ribosome binding (Nou and Kadner, Adenosylcobalamin inhibits ribosome binding to btuB RNA. Proc. Nail. Acad. Sci. USA 97, 7190-7195 (2000)). If no protein receptors are required for molecular recognition or for modulating gene expression, then this simple "riboswitch" mechanism is most economical in its architecture. Given the organizational simplicity of the btuB genetic control components compared to analogous systems that involve proteins, it is likely that mRNAs could be more easily engineered to respond directly to natural and non-biological regulatory effectors.

It is possible that variations of this mechanism involving direct contacts between metabolite and mRNA are far more widespread in genetic circuitry. For example, the *S. typhimurium* cob operon, which encodes proteins in the biosynthetic pathway for the AdoCbl coenzyme, carries $B_{12}$ box and other regulatory structures in its leader domain (Ravnum and Andersson, An adenosyl-cobalamin (coenzyme-$B_{12}$)-repressed translational enhancer in the cob mRNA of *Salmonella typhimurium*. Mol. Microbiol. 39, 1585-1594 (2001)). It has been noted (White III, Coenzymes as fossils of an earlier metabolic state. J. Mol. Evol. 7, 101-104 (1976)) that these two coenzymes and FMN, which is another potential riboswitch effector (Gelfand et al., A conserved RNA structure element involved in the regulation of bacterial riboflavin synthesis genes. Trends Genetics 15, 439-442 (1999)), possibly are molecular fossils of an ancient metabolic state that was run entirely by RNA. If true, then mechanisms involving metabolite sensing by mRNA might be one of the oldest forms of genetic control in existence.

B. Example 2

Thiamine Pyrophosphate (TTP) Riboswitches

The example described testing and analysis of a riboswitch that controls gene expression by binding thiamine pyrophosphate.

1. Chemicals and Oligonucleotides

TPP, thiamine monophosphate (TP), thiamine, oxythiamine, amprolium, and benfotiamine were purchased from Sigma. Thiamine disulfide and 4-methyl-5-β-hydroxyethylthiazole (THZ) were purchased from TCI America. $^3$H-labeled thiamine was purchased from American Radiolabeled Chemicals, Inc. (10 Ci $mmol^{-1}$). Synthetic DNAs were synthesized by the Keck Foundation Biotechnology Resource Center at Yale University. DNAs were purified by denaturing (8 M urea) polyacrylamide gel electrophoresis (PAGE) and isolated from the gel by crush-soaking in 10 mM Tris-HCl (pH 7.5 at 23° C.), 200 mM NaCl and 1 mM EDTA. The DNA was recovered by precipitation with ethanol.

2. Construction of *E. coli* thiM- and *E. coli* thiC-lacZ Fusions

Nucleotides −83 to 238 of the *E. coli* thiCEFGH operon (Vander Horn et al., Structural genes for thiamine biosynthetic enzymes (thiCEFGH) in *Echerichia coli* K-12. *J. Bacteriology* 175, 982-992 (1993)), was amplified by PCR from *E. coli* strain MC4100 (obtained from S. Gottesman, NIH) as a EcoR1-BglII fragment. The DNA was ligated into EcoR1- and BamH1-digested pRS414 plasmid DNA, which contains a promoterless copy of lacZ (obtained from R. Simons, UCLA; Simons et al., Improved single and multicopy lac-based cloning vectors for protein and operon fusions *Gene* 53, 85-96 (1987)), resulting in the in-frame fusion of the $9^{th}$ codon of lacZ to the $9^{th}$ codon of thiC. Similarly, the regulatory region of thiM (nucleotides −67 to 163) was amplified by PCR as a EcoR1-BamH1 fragment and inserted into plasmid pRS414, wherein the $6^{th}$ codon of thiM resides in-frame with the $9^{th}$ codon of lacZ. The plasmids were transformed into Top 10 cells (Invitrogen) for all subsequent manipulations. All site-directed mutations were introduced into the thiC and thiM regulatory regions using the QuikChange site-directed mutagenesis kit (Stratagene) and the appropriate mutagenic DNA primers. All mutations were confirmed by DNA sequencing (USB Thermosequenase).

3. Thiamine-Repression β-Galactosidase Assays

*E. coli* cells (Top 10; Invitrogen) that contained in-frame lacZ fusions to thiC or thiM mRNA leader sequences, were grown in M9 glucose minimal media (plus 50 μg/ml Vitamin assay Casamino acids; Difco) to mid-exponential phase. The cultures were either grown with or without added thiamine (100 μM). Aliqouts (1 mL) were removed for β-galactosidase enzyme assays, which were conducted in a manner similar to that described by Miller (Miller, In: *A Short Course in Bacterial Genetics* Cold Spring Harbor Laboratory Press, Cold Spring Harbor, N.Y., p. 72. (1992)). All assays were repeated twice and in duplicate, with Miller unit values reflecting the average of these analyses.

4. In Vitro Transcription

Templates for in vitro transcription of the fragments of thiC and thiM mRNA leaders were generated by PCR using the appropriate DNA primers and plasmids pRS4l4thiC or pRS4l4thiM, respectively. The dinucleotide sequence GG was introduced into the DNA constructs (corresponding to the 5' terminus of each RNA construct) at this step to facilitate transcription by T7 RNA polymerase. RNAs were prepared by in vitro transcription and were 5' $^{32}$P-labeled as described previously (Seetharaman et al., Immobilized riboswitches for the analysis of complex chemical and biological mixtures. *Nature Biotechnol.* 19, 336-341 (2001)).

5. In-Line Probing of RNA

Determination of apparent $K_D$ values for each construct was achieved by conducting in-line probing of RNA constructs wherein the concentration of the ligand was varied between 10 nM and 100 μM, or up to 10 mM for weakly binding ligands. Specifically, TPP-dependent modulation of the spontaneous cleavage of RNA constructs was visualized by polyacrylamide gel electrophoresis (PAGE). 5' $^{32}$P-labeled RNAs (20 nM) were incubated for approximately 40 hr at 25° C. in 20 mM $MgCl_2$, 50 mM Tris-HCl (pH 8.3 at 25° C.) in the presence (+) or absence (−) of 100 μM TPP. Some RNAs were subjected to no reaction, partial digestion with alkali, or partial digestion with RNase T1 (G-specific cleavage) (see FIG. 6*a*). Composite plots of the fraction of RNA cleaved at specific sites versus the logarithm of the concentration of ligand (e.g. FIG. 7*a*) were generated to provide an estimate of the apparent $K_D$. Fraction cleaved values were normalized relative to the highest and lowest cleavage values measured for each site.

6. Equilibrium Dialysis

Equilibrium dialysis assays were conducted using a DispoEquilibrium Dialyzer (ED-1, Harvard Bioscience), wherein chambers a and b were separated by a 5,000 Dalton molecular weight cut-off membrane. Equilibration was initiated by the addition of 25 μL of equilibration buffer [50 mM Tris-HCl (pH 8.3 at 25° C.), 20 mM $MgCl_2$, mM KCl], containing 100 nM $^3$H-thiamine and by the addition of an equal volume of equilibration buffer either without or with 20 μM RNA as indicated to chamber b. Equilibrations were allowed to proceed for 10 hr at 23° C., and aliquots were removed from each chamber and quantitated by using a liquid scintillation counter.

7. Results i. Metabolite Binding by mRNAs.

Figure 6A:
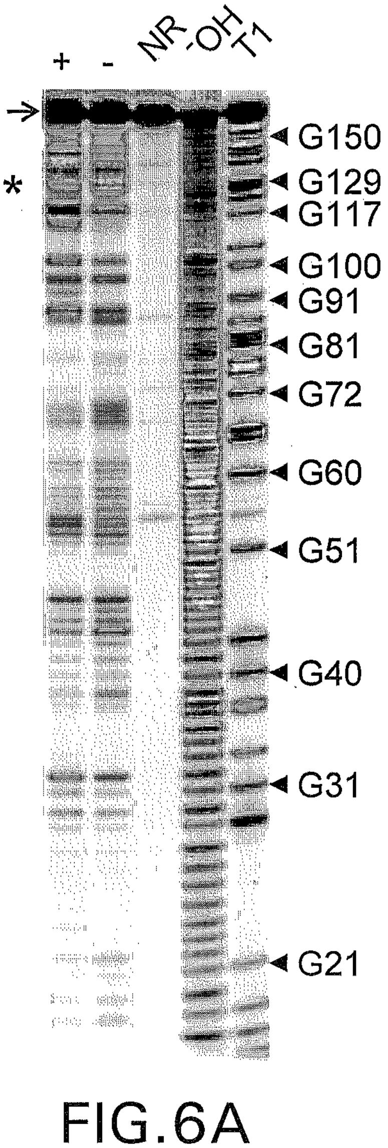
FIGS. 6A, 6B, 6C and 6D show metabolite binding by mRNAs.

FIG. 6A shows TPP-dependent modulation of the spontaneous cleavage of 165 thiM RNA was visualized by polyacrylamide gel electrophoresis (PAGE). 5' $^{32}$P-labeled RNAs (arrow, 20 nM) were incubated for approximately 40 hr at 25° C. in 20 mM $MgCl_2$, 50 mM Tris-HCl (pH 8.3 at 25° C.) in the presence (+) or absence (−) of 100 μM TPP. NR, $^{-}$OH and T1 represent RNAs subjected to no reaction, partial digestion with alkali, or partial digestion with RNase Tl (G-specific cleavage), respectively. Product bands representing cleavage after selected G residues are numbered and identified by filled arrowheads. The asterisk identifies modulation of RNA structure involving the Shine-Dalgarno (SD) sequence. Gel separations were analyzed using a phosphorimager (Molecular Dynamics) and quantitated using ImageQuant software.

Figure 6C:
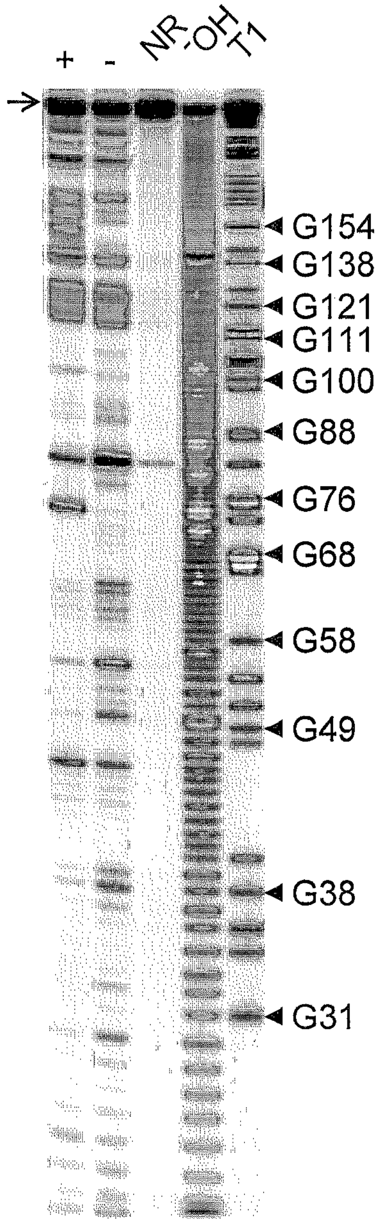
Figure 6B:
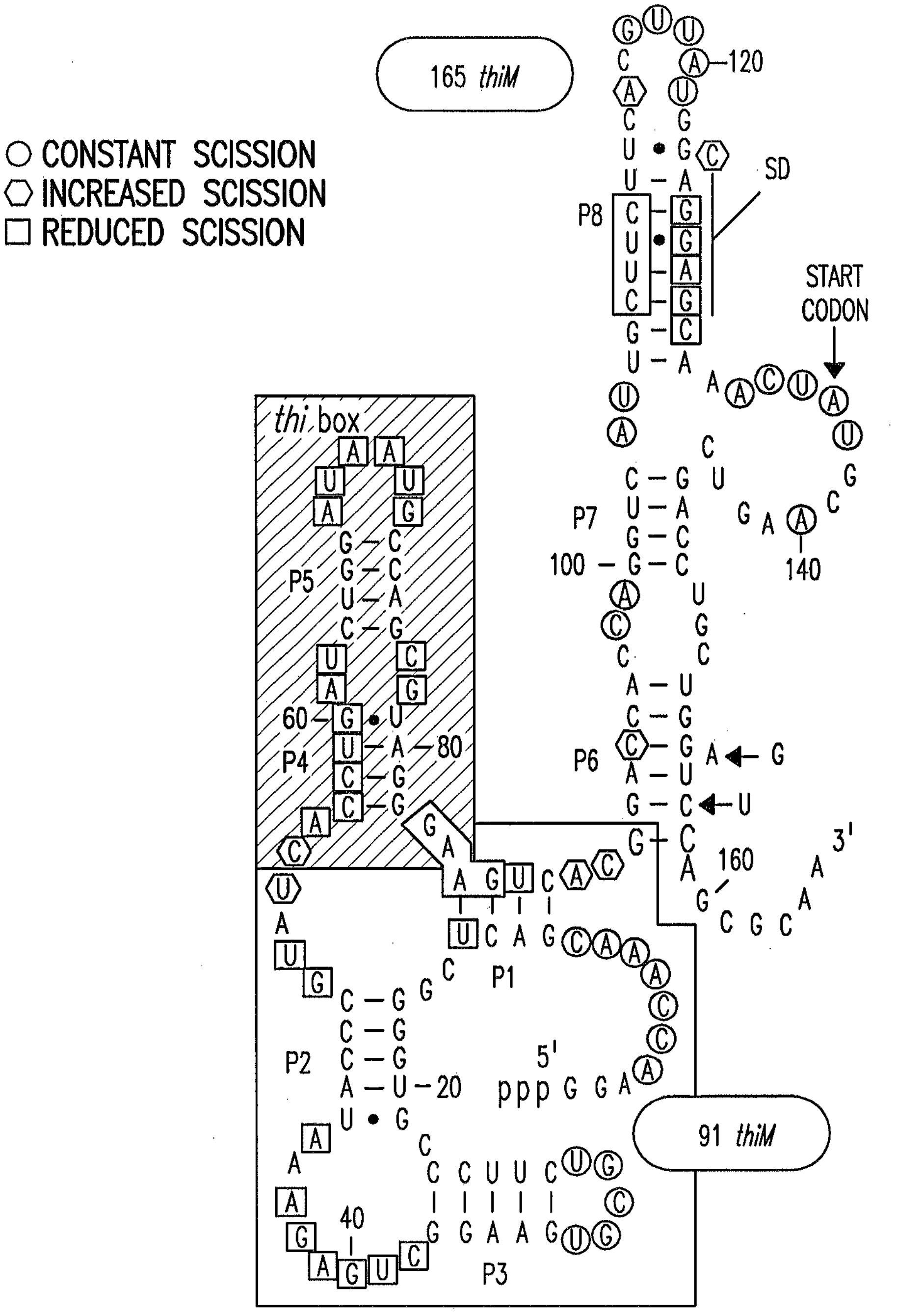

FIG. 6B shows a secondary-structure model of 165 thiM as predicted by computer modeling (Zuker et al., Algorithms and thermodynamics for RNA secondary structure prediction: a practical guide. In *RNA Biochemistry and Biotechnology* (eds. Barciszewski J. & Clark, B.F.C.) 11-43 (NATO ASI Series, Kluwer Academic Publishers, 1999); Mathews et al., Expanded sequence dependence of thermodynamic parameters improves prediction of RNA secondary structure. *J. Mol. Biol.* 288, 911-940 (1999)) and by the structure probing data depicted in FIG. 6A. Spontaneous cleavage characteristics are as noted in the inset. Unmarked nucleotides exhibit a constant but low level of degradation. The truncated 91 thiM RNA is boxed and the thi box element (Miranda-Rios et al., A conserved RNA structure (thi box) is involved in regulation of thiamin biosynthetic gene expression in bacteria. *Proc. Natl. Acad. Sci. USA* 98, 9736-9741 (2001)) is shaded. Nucleotides enclosed in boxes identify an alternative pairing, designated P8*. The RNA carries two mutations (G156A and U157C) relative to wild type that were introduced in a non-essential portion of the construct to form a restriction site for cloning, while all RNAs carry two 5'-terminal G residues to facilitate in vitro transcription.

Figure 6D:
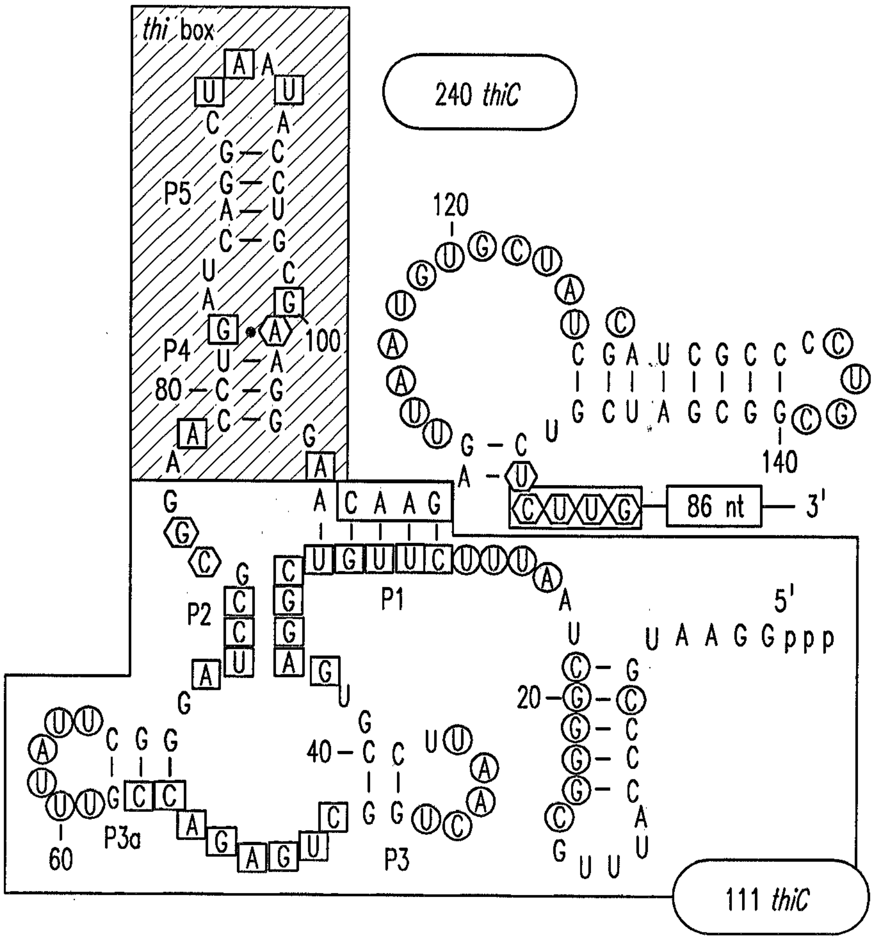
Figure 7A:
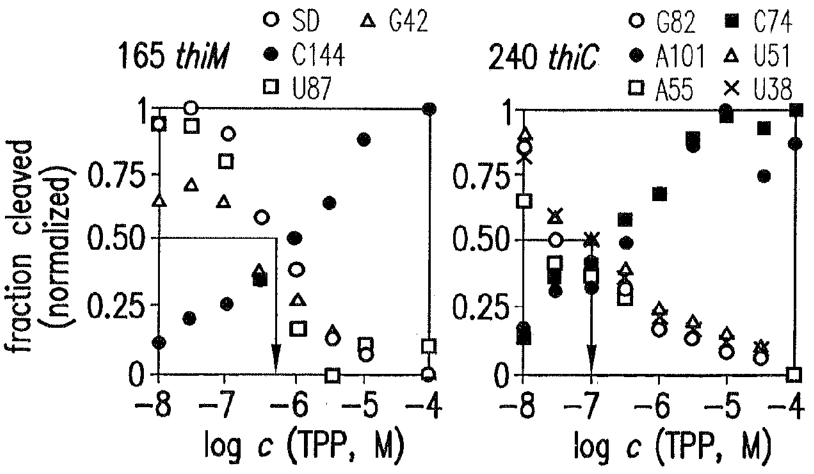
FIGS. 7A, 7B and 7C show the thiM and thiC mRNA leaders serve as high-affinity metabolite receptors.
Figure 7B:
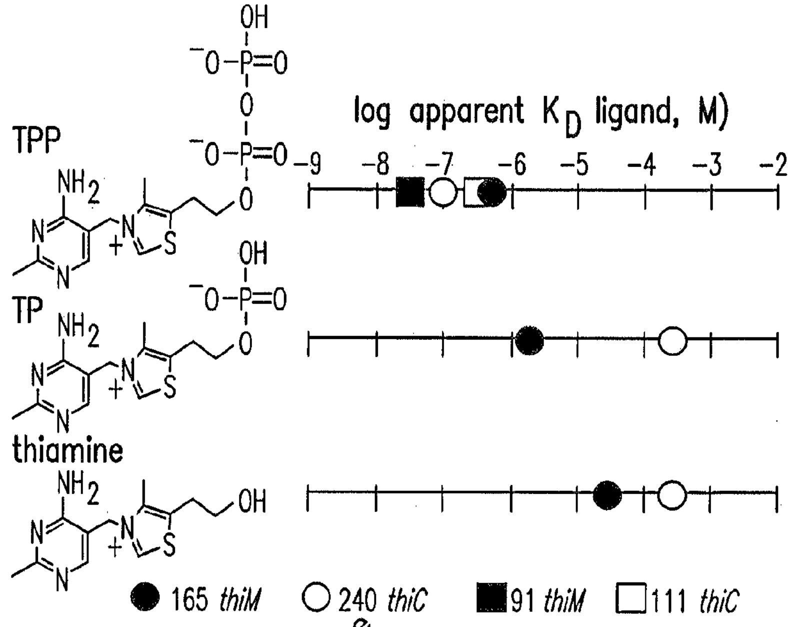
Figure 7C:
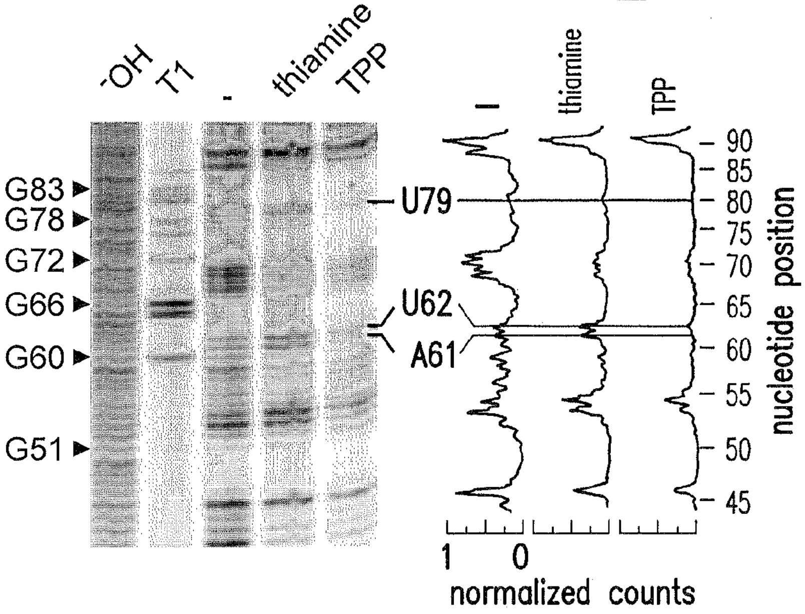

FIG. 6C shows TPP-dependent modulation of the spontaneous cleavage of 240 thiC RNA. Reactions were conducted and analyzed as described in above for FIG. 6A. FIG. 6D shows a secondary-structure model of 240 thiC. Base-paired elements that are similar to those of thiM are labeled P1 through P5. The truncated RNA 111 thiC is boxed. Nucleotides enclosed in boxes identify an alternative pairing.

ii. The thiM and thiC mRNA Leaders Serve as High-Affinity Metabolite Receptors. FIG. 7A shows the extent of spontaneous modulation of RNA cleavage at several sites within 165 thiM (left) and 240 thiC (right) plotted for different concentrations (c) of TPP. Arrows reflect the estimated concentration of TPP needed to attain half maximal modulation of RNA (apparent $K_D$). FIG. 7B shows the logarithm of the apparent $K_D$ values plotted for both RNAs with TPP, TP and thiamine as indicated. The boxed data was generated using TPP with the truncated RNAs 91 thiM and 111 thiC. FIG. 7C shows that patterns of spontaneous cleavage of 165 thiM differ between thiamine and TPP ligands as depicted by PAGE analysis (left) and as reflected by graphs (right) representing the relative phosphorimager counts for the three lanes as indicated. Details for the RNA probing analysis are similar to those described above in connection with FIG. 6A. The graphs were generated by ImageQuant software.

iii. High Sensitivity and Selectivity of mRNA Leaders for Metabolite Binding.

Figure 8A:
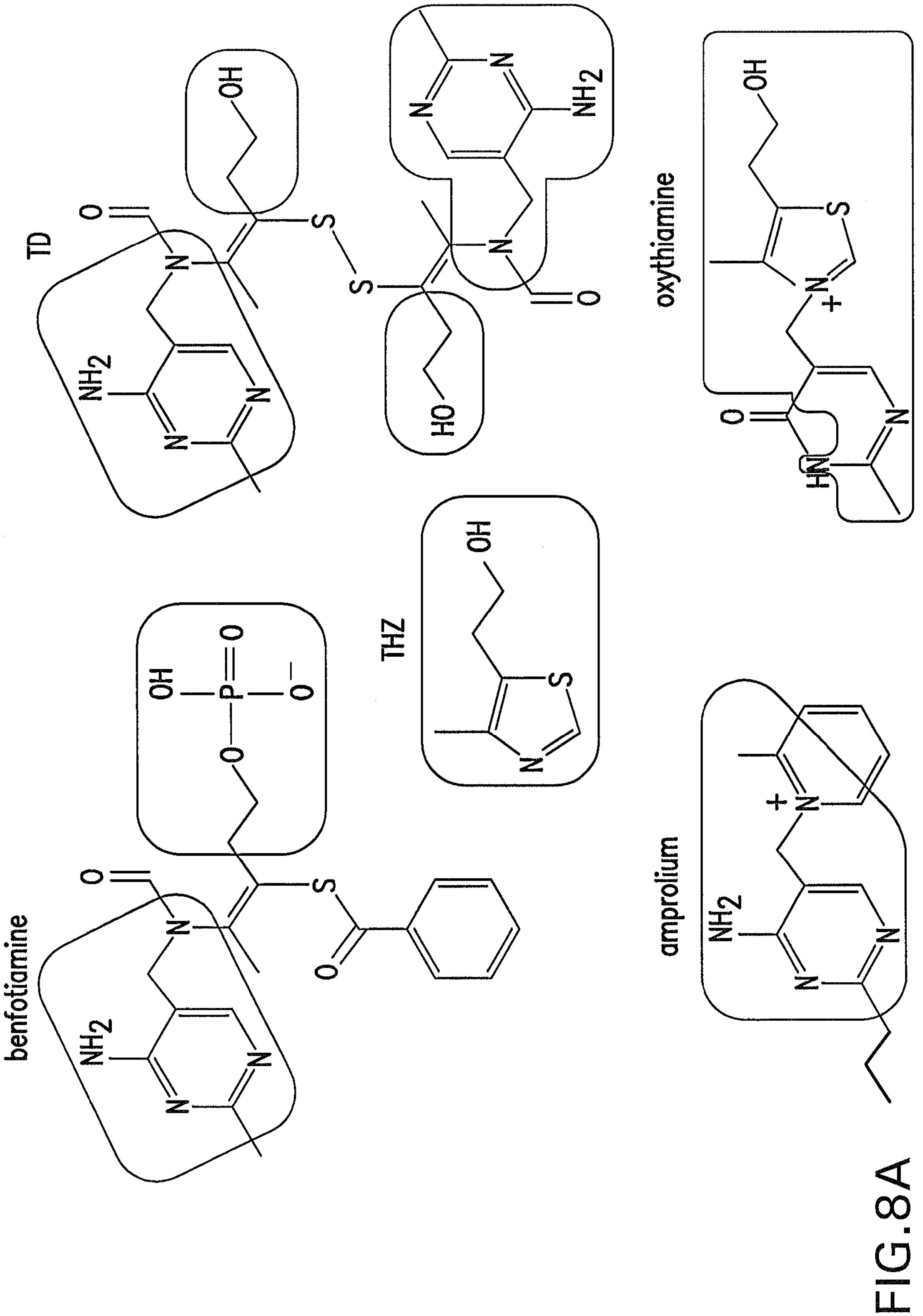
FIGS. 8A, 8B, 8C and 8D show high sensitivity and selectivity of mRNA leaders for metabolite binding.
Figure 8B:
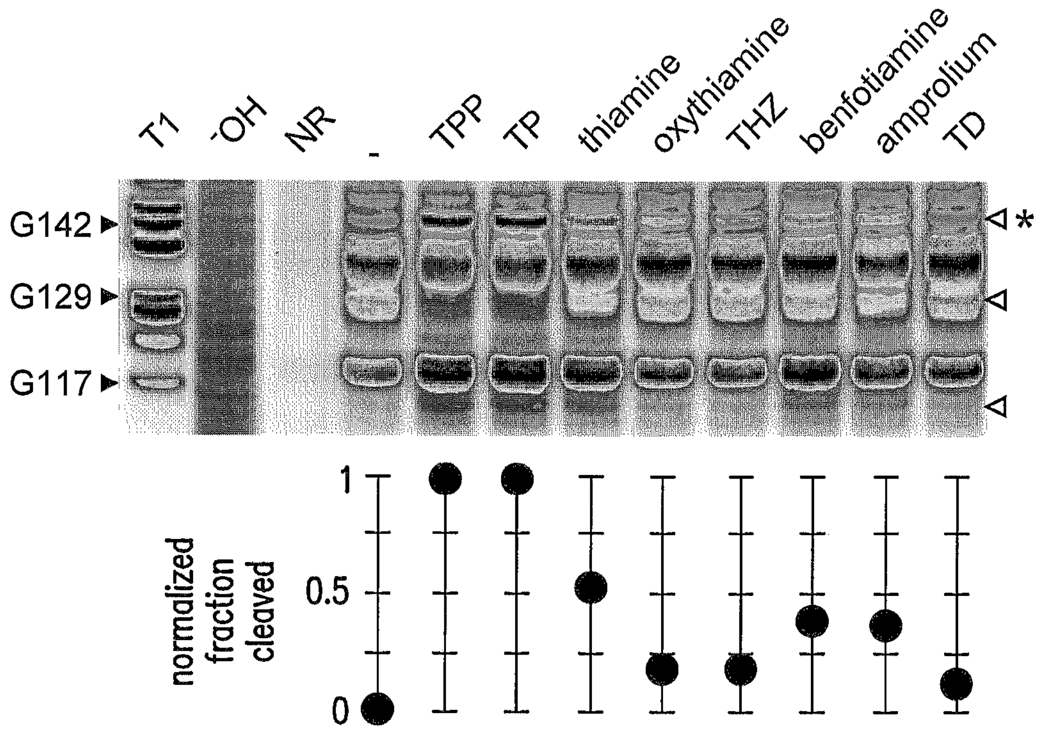
Figure 8D:
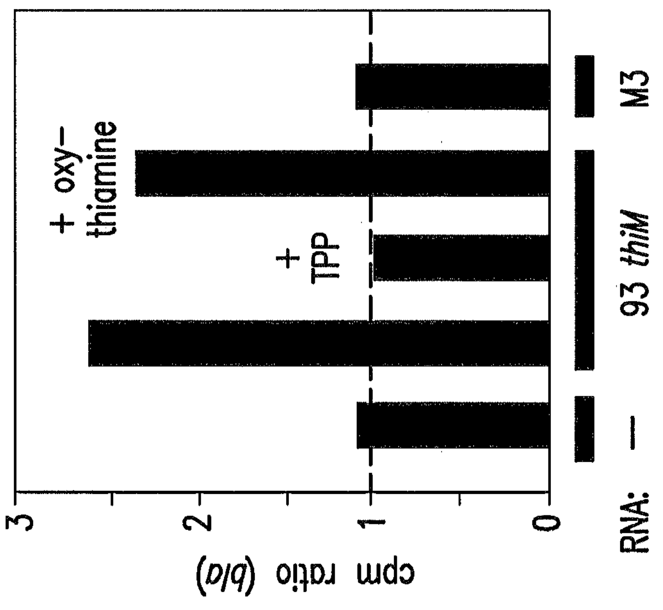
Figure 8C:
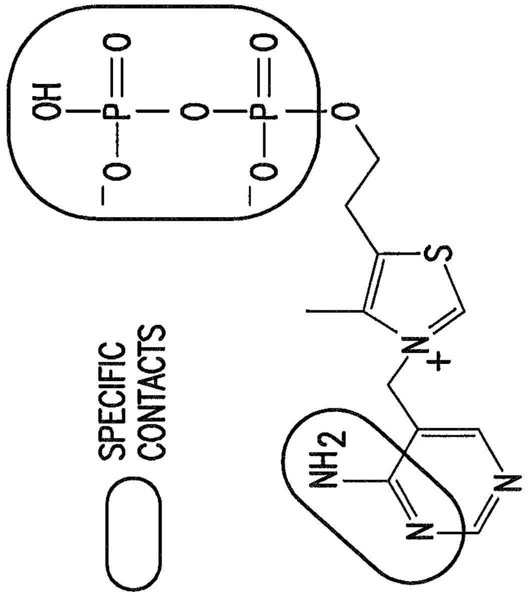

FIG. 8A shows chemical structures of several analogues of thiamine. TD is thiamine disulfide and THZ is 4-methyl-5-β-hydroxyethylthiazole. FIG. 8B shows PAGE analysis of 165 thiM RNA structure probing using TPP and various chemical analogues (40 μM each) as indicated. Locations of significant structural modulation within the RNA spanning nucleotides ~113 to ~150 are indicated by open arrowheads. The asterisk identifies the site (C144) used to compare the normalized fraction of RNA that is cleaved (bottom) in the presence of specific compounds. Details for the RNA probing analysis are similar to those described above in connection with FIG. 6A. FIG. 8C shows a summary of the features of TPP that are critical for molecular recognition. FIG. 8D shows equilibrium dialysis using $^3$H-thiamine as a tracer. Plotted are the ratios for tritium distribution in a two-chamber system (a and b) that were established upon equilibration in the presence of the RNA constructs in chamber b as indicated (see below for a description of the non-TPP-binding mutant M3). 100 μM TPP or oxythiamine were added to chamber a, as denoted, upon the start of equilibration.

iv. Mutational Analysis of the Structure and Function of the thiM Riboswitch.

Figure 9A:
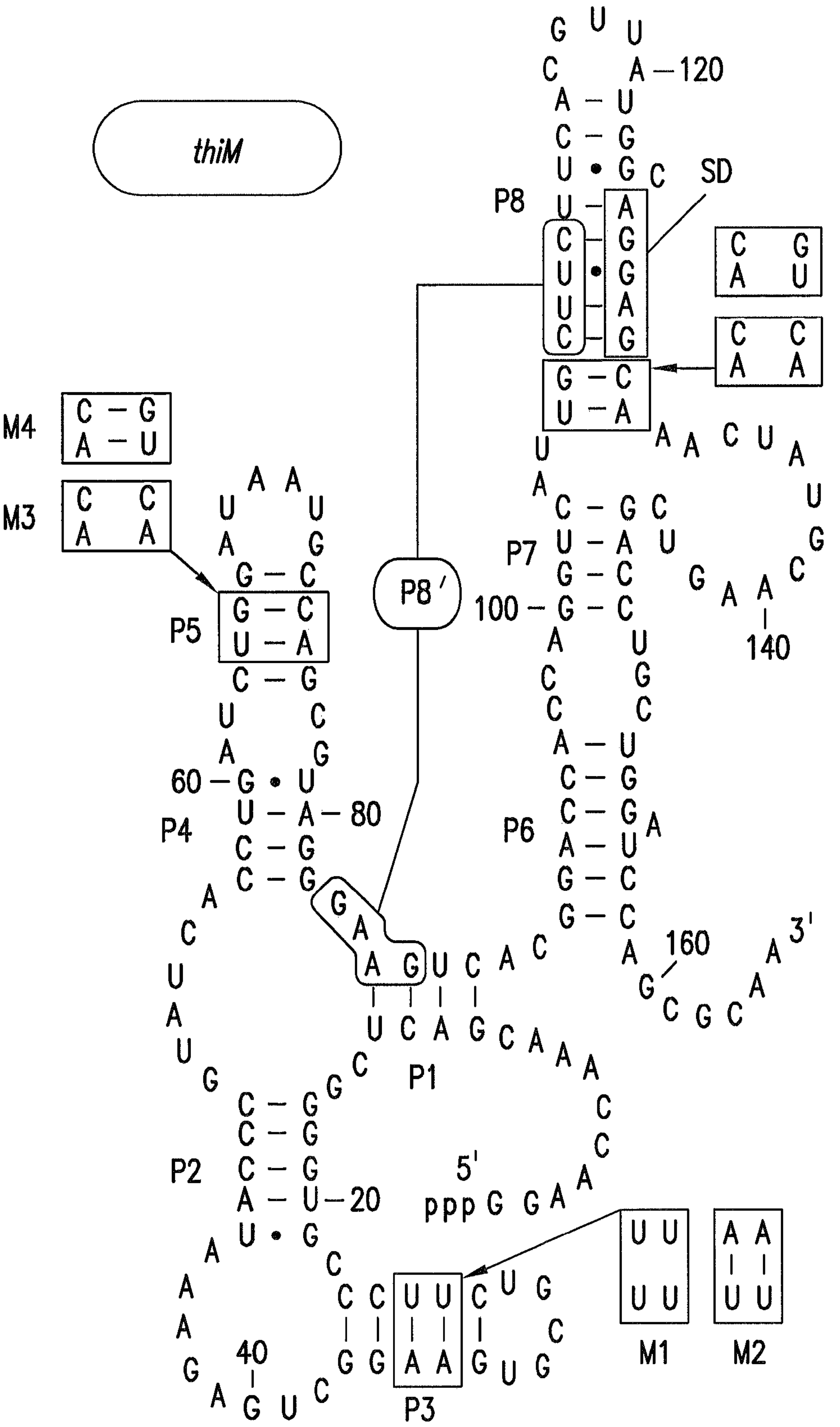
Figure 9B:
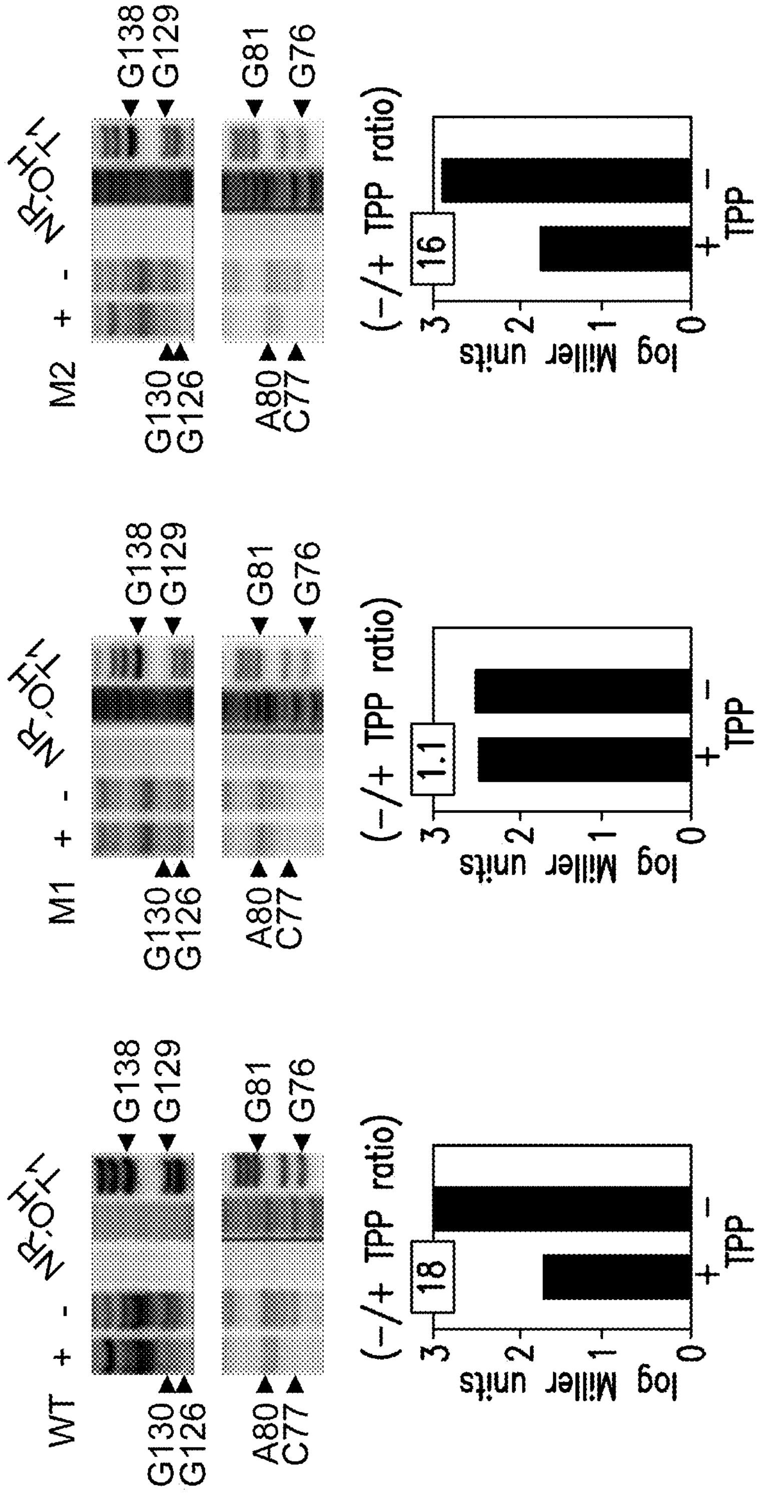
Figure 9D:
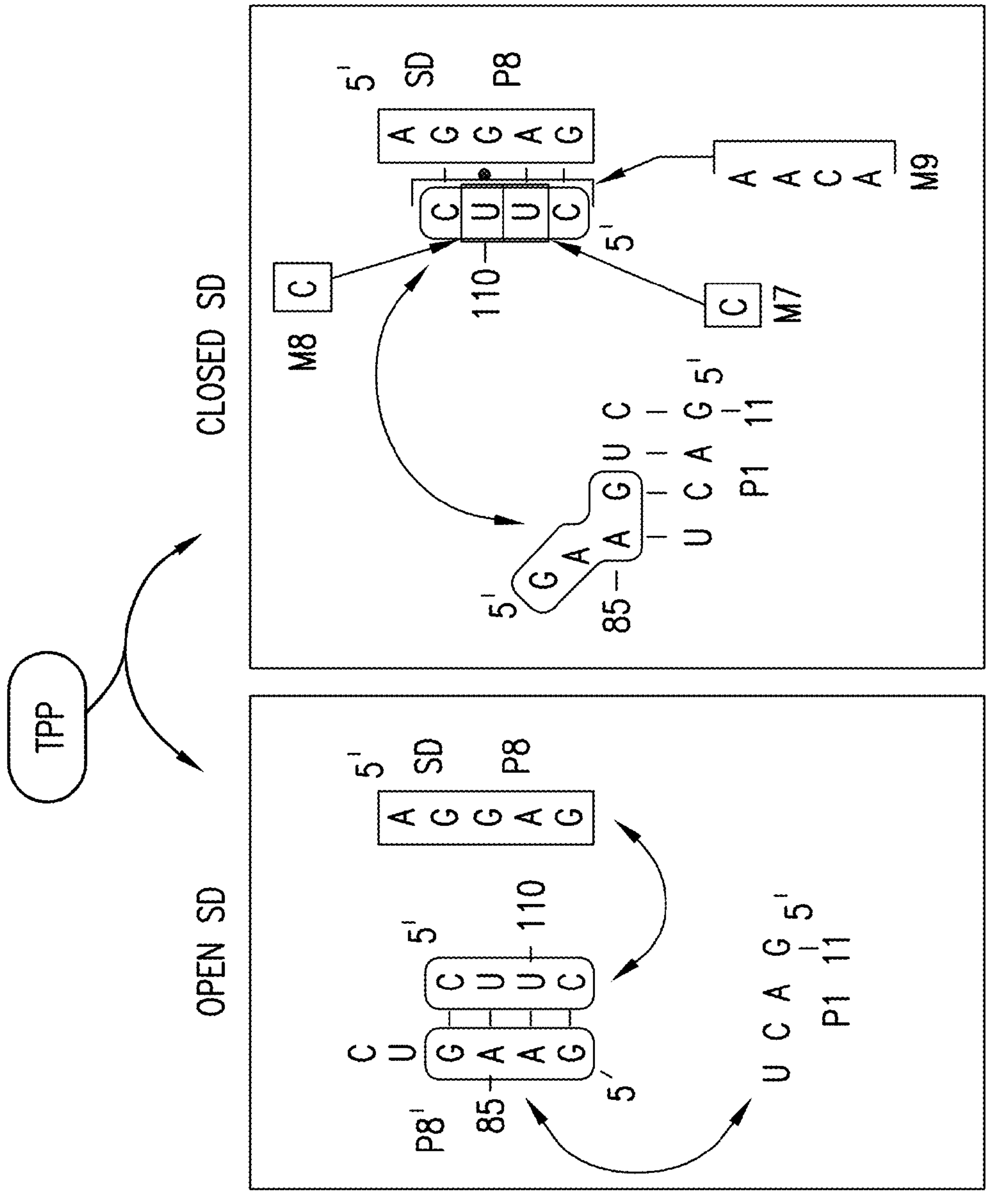

FIG. 9A shows mutations present in constructs M1 through M8 relative to the 165 thiM RNA. P8* is a putative base-paired element between portions (shaded) of the P1 and P8 stems. FIGS. 9B and 9C show in vitro ligand-binding and genetic control functions of the wild-type (WT), M1 and M2 RNAs as reflected by PAGE analysis of in-line probing experiments (10 μM TPP) and by β-galactosidase expression assays. Labels on PAGE gels are as described above in connection with FIG. 6A. Bars represent the levels of gene expression in the presence (+) and the absence (−) of TPP in the culture medium. FIG. 9D is a summary of similar analyses of WT through M9 is presented in table form. The SD status “n.d.” (not determined) indicates either that the level of spontaneous cleavage detected in the absence and presence of TPP is near the limit of detection (M6, M7 and M8) or that the region adopts an atypical structure (M9) compared to WT.

8. Discussion

β-galactosidase fusion constructs were prepared that encompass the 5'-untranslated region of thiM and thiC mRNAs of *E. coli*, which includes a previously identified “thi box” domain whose sequence and potential secondary structure are conserved in several species of bacteria and archaea (Miranda-Rios et al., A conserved RNA structure (thi box) is involved in regulation of thiamin biosynthetic gene expression in bacteria. *Proc. Natl. Acad. Sci. USA* 98, 9736-9741 (2001)). The thiM and thiC translational fusion constructs exhibit thiamine-dependent suppression of β-galactosidase activity of 18- and 110-fold, respectively, when host cells are grown in a minimal medium that otherwise lacks a source of thiamine. A transcriptional fusion containing the thiM leader is not subject to suppression by thiamine, but a similar fusion with thiC leader yields a 16-fold modulation with thiamine, suggesting that a significant portion of genetic control observed with thiC occurs at the level of transcription.

These constructs were used to prepare DNA templates by PCR for in vitro transcription of RNA fragments. The resulting RNAs were subjected to a structure-probing process (see Example 1) to reveal whether the RNAs undergo structure modulation upon binding of ligands. Internucleotide linkages in unstructured regions are more likely to undergo spontaneous cleavage compared to linkages that reside in highly structured regions of an RNA (Soukup & Breaker, Relationship between internucleotide linkage geometry and the stability of RNA. RNA 5, 1308-1325 (1999)). The 165-nucleotide thiM RNA fragment (165 thiM) has a distinct pattern of cleavage products that is generated when the RNA is incubated for an extended period in the absence of TPP (FIG. 6A). Upon addition of 100 μM TPP, 165 thiM undergoes substantial structural alteration as many internucleotide linkages in the region spanning positions 39 through 80 exhibit a reduction in spontaneous cleavage. This indicates that TPP binds to the RNA and stabilizes a defined structure within this region, resulting in a lower rate of fragmentation.

The fragmentation patterns are largely congruent with potential base-paired and bulge structures that are identified by a secondary-structure prediction algorithm (Zuker et al., Algorithms and thermodynamics for RNA secondary structure prediction: a practical guide. In *RNA Biochemistry and Biotechnology* (eds. Barciszewski J. & Clark, B.F.C.) 11-43 (NATO ASI Series, Kluwer Academic Publishers, 1999); Mathews et al., Expanded sequence dependence of thermodynamic parameters improves prediction of RNA secondary structure. *J. Mol. Biol.* 288, 911-940 (1999)). Most linkages that experience a ligand-induced reduction of cleavage are encompassed by the thi box and nucleotides that reside immediately 5' relative to this domain (FIG. 6B). Other linkages that undergo cleavage, but that are not modulated by TPP, are predicted to reside in bulges or in the loops of hairpins. Predicted base-paired structures labeled P2 through P7 encompass linkages that exhibit the lowest levels of spontaneous cleavage, implying that they remain structured in both the presence and absence of TPP. Interestingly, nucleotides 126 through 130 encompass the only region apart from those described above that become more structured upon TPP addition. These nucleotides correspond to the Shine-Dalgarno (SD) sequence, which is required for efficient translation of mRNAs in prokaryotes. These findings are consistent with a genetic control mechanism wherein the thiM RNA binds to TPP and forms a complex wherein the ribosome cannot gain access to the SD sequence.

Similarly, structure probing was used to examine the mRNA leader for thiC. The 240 thiC RNA also exhibits extensive modulation of its pattern of spontaneous cleavage, and again the majority of the changing pattern is located in the thi box and in the region located immediately upstream of this domain (FIG. 6C). These regions of highest structure modulation in thiM and thiC can be folded into similar secondary structures (FIG. 6D), and carry several common sequence elements within and adjacent to the thi box domain. Thus, the structures of thiM and thiC spanning stems P1 through P5 comprise TPP-binding motifs that are analogous to aptamers, which are engineered ligand-binding RNAs (Osborne & Ellington, Nucleic acid selection and the challenge of combinatorial chemistry. *Chem. Rev.* 97, 349-370 (1997); Hermann & Patel, Adaptive recognition by nucleic acid aptamers. *Science* 287, 820-825 (2000); Gold et al., Diversity of oligonucleotide functions. *Annu. Rev. Biochem.* 64, 763-797

(1995)). Nucleotides residing 3' relative to this natural TPP aptamer are involved in converting the metabolite binding event into a genetic response.

The sensitivity of metabolite detection by these mRNAs was assessed by establishing apparent dissociation constant (apparent $K_D$) values for TPP, thiamine, and thiamine monophosphate (TP). Values were generated by monitoring the extent of spontaneous cleavage at several ligand-sensitive sites within the RNA under a range of ligand concentrations. For example, probing of a trace amount of 165 thiM RNA under TPP concentrations ranging from zero to 100 μM (or up to 10 mM with certain analogues) reveals that half-maximal modulation of RNA structure occurs when approximately 600 nM TPP is present (FIG. 7A), which reflects an apparent $K_D$ of 600 nM. Likewise, probing of 240 thiC reveals an apparent $K_D$ of 100 nM. Both 165 thiM and 240 thiC RNAs appear to bind TPP more avidly than TP or thiamine, with thiC exhibiting more than 1,000-fold discrimination against TP and thiamine (FIG. 7B). The fact that TPP is the strongest modulator of RNA structure is consistent with genetic observations in *Salmonella typhimurium* that TPP synthesis is required for regulation of expression of thiamine biosynthesis genes (Webb et al., Thiamine pyrophosphate (TPP) negatively regulates transcription of some thi genes of *Salmonella typhimurium. J. Bacteriol.* 178, 2533-2538 (1996)). The differential specificity achieved by the RNAs, which is a phenomenon that is commonly observed for receptor-ligand systems made of protein, indicates that these ligand-binding RNAs would be receptive to specificity changes (through, for example, natural or artificial evolutionary forces).

The actual $K_D$ values for RNA-ligand interactions might be different inside cells where physiological conditions of $Mg^{2+}$ and other agents that can influence RNA structure will not match those of the in vitro assays. Also, the nature of the RNA construct can be a source of an altered $K_D$. For example, the minimized 91 thiM construct (FIG. 6A), which largely encompasses only the putative natural aptamer, retains the ability to bind TPP and exhibits an apparent $K_D$ that is improved by approximately 20 fold compared to the longer construct (FIG. 7B). Thus, the affinity for TPP might vary as the nascent RNA transcript emerges from the active site of RNA polymerase or the ribosome. Furthermore, this result demonstrates that the 91 thiM aptamer domain can be separated from RNA components (collectively termed the "expression platform") that are directly controlling gene expression. This modular construction, involving the physical and functional separation of aptamer and expression platform domains allows the generation of TPP-controlled RNAs by rational RNA engineering strategies (or through evolutionary processes).

Spontaneous cleavage at several linkages within the thi box domain of 165 thiM specifically correlate with the type of ligand used. Although TPP reduces spontaneous cleavage of 165 thiM at nucleotides A61, U62 and to a smaller extent at U79, these same sites retain an elevated level of cleavage when thiamine is present near its saturating concentration (FIG. 7C). These nucleotides cluster at an internal bulge within the thi box domain, and appear to contribute to the binding site for the phosphate groups of TPP.

The structural modulation of 165 thiM was further examined in the presence of several analogues that carry certain structural features of thiamine (FIG. 8A). Thiamine and its phosphorylated derivatives TP and TPP induce modulation as expected (FIG. 8B). However, oxythiamine and other thiamine analogues with less similarity to TPP fail to induce structure modulation. The performance of this sampling of analogues indicates that the RNA makes specific contacts to distal parts of its ligand and that both the purine and phosphate groups carry important elements for molecular recognition (FIG. 8C). Similar results are obtained by using equilibrium dialysis assays (FIG. 8D). For example, the addition of 91 thiM RNA to chamber b of an equilibrium dialysis assembly causes a shift in the distribution of $^3$H-thiamine in favor of chamber b, unless an excess of unlabeled TPP is also included. However, the presence of oxythiamine does not significantly restore the tritium distribution to unity, which is expected because probing data indicate that it is not able to bind the RNA. These findings indicate that the aptamer domain of the TPP riboswitch is highly selective for its target ligand.

The secondary structure model for 165 thiM RNA was examined in greater detail by generating and testing a series of variant constructs (FIG. 9A). For example, variant M1 carries a mutation that disrupts the predicted P3 pairing element. This mutation causes a loss of TPP binding (FIG. 9B, e.g. see position C77) and a loss of genetic control of the corresponding β-galactosidase fusion construct (FIG. 9C, graph). Re-establishment of base pairing in the double-mutant construct M2 restores both TPP binding and genetic control. Similarly, disruptive and restorative mutations encompassed by constructs M3 through M6 are consistent with the formation of stems P5 and P8. Upon the addition of TPP, the SD element of both the WT and M2 constructs becomes sequestered in a structure that precludes a high level of spontaneous cleavage. In contrast, the M1 construct does not exhibit SD modulation (FIGS. 9B and 9C, nucleotides 126-130). These results are consistent with the genetic switch being turned off by a mechanism whereby TPP binding ultimately promotes the stable formation of P8, which reduces access to the SD by the ribosome.

The partner of the SD sequence in P8 (nucleotides 108 to 111) remains resistant to spontaneous cleavage both in the presence and absence of TPP (FIG. 6A). This is consistent with the formation of P8, upon addition of TPP, due to the displacement of an alternative structure that otherwise prevents this anti-SD element from forming P8. Furthermore, nucleotides 83 through 86 are complementary to the anti-SD element and this region also resists spontaneous cleavage in the presence and absence of TPP. A mechanism by which genetic control could result, which is tested as described below, is via the mutually exclusive formation of P8* in the 'On' state versus the simultaneous formation of P1 and P8 in the metabolite-bound 'Off' state (FIG. 9D).

Constructs M7 through M9 were tested in an assessment of this mechanism. Construct M7 carries a U109C mutation in the anti-SD sequence that is designed to destabilize the P8 interaction while simultaneously destabilizing the P8* interaction. M7 retains TPP binding function and exhibits a significant level of genetic modulation (FIG. 9C, box), which is expected if the mutation does not disrupt the relative distribution of mRNAs between the 'On' and 'Off' states. In comparison, M8 (U110C) retains TPP binding, exhibits a dramatic reduction in the level of reporter expression, and loses nearly all genetic modulation. In addition, M8 no longer exhibits detectable spontaneous cleavage in the SD sequence, which is consistent with the thermodynamic balance between P8 and P8* formation being shifted decidedly in favor of P8 in this RNA variant. Construct M9, which carries four mutations in the anti-SD element, has a significantly different pattern of spontaneous cleavage in the SD region. M9 fails to reduce gene expression upon thiamine addition to cells, despite the fact that the construct retains TPP binding in vitro. It is evident from these data that TPP binding restricts the structural freedom of the SD element in the appropriate RNA variants, and that this correlates with genetic control.

C. Example 3

Metabolite-Binding Riboswitches

1. Introduction

Modern organisms must coordinate the expression of many hundreds of genes in response to metabolic demands and environmental changes. Each gene product must be regulated temporally, quantitatively, and oftentimes spatially. Additionally, genetic control processes must be dynamic, rapid, and selectively responsive to the specific conditions undergoing change. Therefore, organisms require sentries of genetic regulatory factors that continuously quantify a multitude of environmental signals. Upon measurement of a particular signal, which may be one of many possible biochemical or physical cues, these regulatory factors must modulate expression of a specific subset of the organism's genes.

It has generally been assumed that proteins are the obligate sensors of these signals because proteins are a proven medium for forming highly responsive sensors. However, it was discovered that mRNAs also are capable of acting as direct sensors of chemical and physical conditions for the purpose of genetic control. Classes of mRNA domains, collectively referred to as 'riboswitches', serve as RNA genetic control elements that sense the concentrations of specific metabolites by directly binding the target compound. Riboswitches that have been discovered are responsible for sensing metabolites that are critical for fundamental biochemical processes including adenosylcobalamin (AdoCbl) (see Example 1), thiamine pyrophosphate (TPP) (see Example 2), flavin mononucleotide (FMN), S-adenosylmethionine (SAM) (see Example 7), lysine (see Example 5), guanine (see Example 6), and adenine (see Example 8). Upon interaction with the appropriate small molecule ligand, riboswitch mRNAs undergo a structural reorganization that results in the modulation of genes that they encode. To date, all riboswitches that have been examined in detail cause genetic repression upon binding their target ligand, although riboswitches that activate gene expression upon ligand binding can be produced (and will likely be found in nature).

In each instance, riboswitch domains have been subjected to a battery of biochemical and genetic analyses in order to convincingly demonstrate that direct interaction of small organic metabolites with mRNA receptors leads to a corresponding alteration in genetic expression. This example provides a brief summary of these efforts and of some of the general characteristics that are exhibited by riboswitches. Using these discoveries and the principles of riboswitch operation described in this example and elsewhere herein, those of skill in the art can use and adapt riboswitches for many purposes including use as genetic tools and as targets for development of antimicrobials.

2. General Organization of Riboswitch RNAs

Bacterial riboswitch RNAs are genetic control elements that are located primarily within the 5'-untranslated region (5'-UTR) of the main coding region of a particular mRNA. Structural probing studies (discussed further below) revealed that riboswitch elements are generally composed of two domains: a natural aptamer (T. Hermann, D. J. Patel, *Science* 2000, 287, 820; L. Gold, et al., *Annual Review of Biochemistry* 1995, 64, 763) that serves as the ligand-binding domain (referred to herein as the aptamer domain), and an 'expression platform' that interfaces with RNA elements that are involved in gene expression (e.g. Shine-Dalgarno (SD) elements; transcription terminator stems). These conclusions are drawn from the observation that aptamer domains synthesized in vitro bind the appropriate ligand in the absence of the expression platform (see Examples 2 and 6). Moreover, structural probing investigations suggest that the aptamer domain of most riboswitches adopts a particular secondary- and tertiary-structure fold when examined independently, that is essentially identical to the aptamer structure when examined in the context of the entire 5' leader RNA. This implies that, in many cases, the aptamer domain is a modular unit that folds independently of the expression platform (see Examples 2 and 6).

Ultimately, the ligand-bound or unbound status of the aptamer domain is interpreted through the expression platform, which is responsible for exerting an influence upon gene expression. The view of a riboswitch as a modular element is further supported by the fact that aptamer domains are highly conserved amongst various organisms (and even between kingdoms as is observed for the TPP riboswitch, whereas the expression platform varies in sequence, structure, and in the mechanism by which expression of the appended open reading frame is controlled. For example, ligand binding to the TPP riboswitch of the tenA mRNA of *B. subtilis* causes transcription termination. This expression platform is distinct in sequence and structure compared to the expression platform of the TPP riboswitch in the thiM mRNA from *E. coli*, wherein TPP binding causes inhibition of translation by a SD blocking mechanism (see Example 2). The TPP aptamer domain is easily recognizable and of near identical functional character between these two transcriptional units, but the genetic control mechanisms and the expression platforms that carry them out are very different.

Aptamer domains for riboswitch RNAs typically range from ~70 to 170 nt in length (FIG. 11). This observation was somewhat unexpected given that in vitro evolution experiments identified a wide variety of small molecule-binding aptamers, which are considerably shorter in length and structural intricacy (T. Hermann, D. J. Patel, *Science* 2000, 287, 820; L. Gold, et al., *Annual Review of Biochemistry* 1995, 64, 763; M. Famulok, *Current Opinion in Structural Biology* 1999, 9, 324). The substantial increase in complexity and information content of the natural aptamer sequences relative to artificial aptamers is most likely required to form RNA receptors that function with high affinity and selectivity. Apparent $K_D$ values for the ligand-riboswitch complexes range from low nanomolar to low micromolar. It is also worth noting that some aptamer domains, when isolated from the appended expression platform, exhibit improved affinity for the target ligand over that of the intact riboswitch (~10 to 100-fold) (see Example 2). This likely represents an energetic cost in sampling the multiple distinct RNA conformations required by a fully intact riboswitch RNA, which is reflected by a loss in ligand affinity. Since the aptamer domain must serve as a molecular switch, this might also add to the functional demands on natural aptamers that might help rationalize their more sophisticated structures.

3. Riboswitch Regulation of Transcription Termination in Bacteria

Bacteria primarily make use of two methods for termination of transcription. Certain genes incorporate a termination signal that is dependent upon the Rho protein (J. P. Richardson, *Biochimica et Biophysica Acta* 2002, 1577, 251), while others make use of Rho-independent terminators (intrinsic terminators) to destabilize the transcription elongation complex (I. Gusarov, E. Nudler, *Molecular Cell* 1999, 3, 495; E. Nudler, M. E. Gottesman, *Genes to Cells* 2002, 7, 755). The latter RNA elements are composed of a GC-rich stem-loop followed by a stretch of 6-9 uridyl residues. Intrinsic terminators are widespread throughout bacterial genomes (F. Lillo, et al., *Bioinformatics* 2002, 18, 971), and are typically located at the 3'-termini of genes or operons. Interestingly, an increasing number of examples are being observed for intrinsic terminators located within 5'-UTRs.

Amongst the wide variety of genetic regulatory strategies employed by bacteria there is a growing class of examples wherein RNA polymerase responds to a termination signal within the 5'-UTR in a regulated fashion (T. M. Henkin, *Current Opinion in Microbiology* 2000, 3, 149). During certain conditions the RNA polymerase complex is directed by external signals either to perceive or to ignore the termination signal. Although transcription initiation might occur without regulation, control over mRNA synthesis (and of gene expression) is ultimately dictated by regulation of the intrinsic terminator. Generally, one of at least two mutually exclusive mRNA conformations results in the formation or disruption of the RNA structure that signals transcription termination. A trans-acting factor, which in some instances is a RNA (F. J. Grundy, et al., *Proceedings of the National Academy of Sciences of the United States of America* 2002, 99, 11121; T. M. Henkin, C. Yanofsky, *Bioessays* 2002, 24, 700) and in others is a protein (J. Stulke, *Archives of Microbiology* 2002, 177, 433), is generally required for receiving a particular intracellular signal and subsequently stabilizing one of the RNA conformations. Riboswitches offer a direct link between RNA structure modulation and the metabolite signals that are interpreted by the genetic control machinery. A brief overview of the FMN riboswitch from a *B. subtilis* mRNA is provided below to illustrate this mechanism.

i. A Natural Aptamer for FMN

A highly conserved RNA domain, referred to as the RFN element, was identified in bacterial genes involved in the biosynthesis and transport of riboflavin and FMN (M. S. Gelfand, et al., *Trends in Genetics* 1999, 15, 439; A. G. Vitreschak, et al., *Nucleic Acids Research* 2002, 30, 3141). This element is required for genetic manipulation of the ribDEAHT operon (hereafter, 'ribD') of *B. subtilis*, as mutations resulted in a loss of FMN-mediated regulation (Y. V. Kil, et al., *Molecular & General Genetics* 1992, 233, 483; V. N. Mironov, et al., *Molecular & General Genetics* 1994, 242, 201). These data led to the proposal that either a protein-based FMN sensor, or FMN itself (G. D. Stormo, Y. Ji, *Proceedings of the National Academy of Sciences of the United States of America* 2001, 98, 9465) interacts with the RFN element in order to repress ribD gene expression. However, there was no understanding of how such interactions would take place or the mechanism by which expression would be affected. Although RNA sequences that specifically bind FMN had been identified through directed evolution experimentation (C. T. Lauhon, J. W. Szostak, *Journal of the American Chemical Society* 1995, 117, 1246, M. Roychowdhury-Saha, et al., *Biochemistry* 2002, 41, 2492), they exhibit no obvious resemblances to the RFN element.

a. Structural Probing Reveals FMN-Mediated RNA Structure Modulation

Each internucleotide linkage in a RNA polymer is susceptible to spontaneous hydrolysis by an $S_N2$-like mechanism, wherein the 2' oxygen attacks the adjacent phosphorus center, leading to chain cleavage. This reaction requires a 180° orientation between the attacking nucleophile, the phosphorus center, and the 5'-oxygen leaving group (in-line conformation) (G. A. Soukup, R. R. Breaker, *RNA* 1999, 5, 1308; V. Tereshko, et al., *RNA* 2001, 7, 405). Nucleotides that are base-paired, or otherwise structurally constrained, are typically incapable of adopting this configuration and therefore display low rates of spontaneous cleavage. In contrast, nucleotides that are structurally unrestrained exhibit much higher rates of spontaneous cleavage. These observations have been exploited in a structural probing method, referred to as "in-line probing", which establishes the relative rates of spontaneous cleavage for a given RNA polymer and correlates this with secondary- and tertiary-structure models (V. Tereshko, et al., *RNA* 2001, 7, 405).

To assess whether the RFN element of ribD was responsive to FMN, a fragment of the corresponding 5'-UTR was 5'-$^{32}$P labeled and incubated in the absence and presence of FMN, and the resulting fragments were analyzed by polyacrylamide gel electrophoresis (PAGE). Interestingly, patterns differ between reactions with and without FMN, signifying that there is a structural rearrangement of the RNA upon FMN binding to ribD. The spontaneous cleavages of certain nucleotide positions located within inter-helical regions of the RFN element become significantly reduced in the presence of FMN, suggesting that these nucleotides are involved in forming an FMN-RNA complex, which forces structural constraints upon the RNA (FIG. 12). It is this type of structural modulation that can be harnessed by the expression platform for allosteric modulation of gene expression.

Additional evidence for direct binding of FMN by the ribD RFN element was generated by enzymatic probing. Oligonucleotides predicted to anneal with the RFN element were added to ribD transcripts in the presence and absence of FMN, and the resulting mixtures was digested with RNase H (which specifically cleaves RNA:DNA heteroduplexes) and analyzed by PAGE (A. S. Mironov, et al., *Cell* 2002, 111, 747). A significant portion of transcripts bind certain oligonucleotides in the absence of FMN, but not in the presence of FMN, indicating that FMN stabilizes a structural rearrangement of ribD transcripts that in turn prevents annealing of the oligonucleotide.

b. Affinity and Specificity of the FMN-ribD Complex

If the RFN element serves as an aptamer for FMN, it should exhibit characteristics of a saturable receptor that has some ability to discriminate against related ligands. To obtain values for apparent dissociation constant (apparent $K_D$) for FMN, in-line probing assays were repeated with trace amounts of ribD RNA and increasing concentrations of FMN; the ligand concentration that correlates with half-maximal modulation of RNA structure should reflect the apparent $K_D$. These experiments indicate that the ribD RNA contains a saturable ligand-binding site that exhibits an apparent $K_D$ of ~5 nM. Furthermore, the RNA discriminates against the dephosphorylated form of FMN (riboflavin) by approximately three orders of magnitude. This exceptional ligand specificity of the ribD mRNA is surprising since the aptamer must generate a binding pocket for FMN that makes productive interactions with a phosphate group.

ii. FMN-Induced Transcription Termination a. In Vitro Transcription Termination Mediated by an FMN Riboswitch The relative amounts of the major transcription products for the ribD leader region were examined by in vitro transcription using T7 RNA polymerase or *Bacillus subtilis* RNA polymerase. The ribD leader region contains a classical intrinsic terminator just upstream of the ribD coding region. Interestingly, transcripts that terminated at the intrinsic terminator are specifically induced by FMN, in the absence of additional protein factors. Furthermore, mutations in the RFN element abrogate this phenomenon. The left-half of the terminator sequence forms alternative base-pairing interactions with a portion of the RFN element, thereby forming an antiterminator element. Sequence alterations of the intrinsic terminator eliminate FMN-induced termination while alterations in the antiterminator result in constitutive termination. Taken together, these observations are consistent with a mechanistic model wherein FMN directly interacts with ribD transcripts during conditions of excess FMN. Complex formation subsequently induces transcription termination within the 5'-UTR (FIG. 12), which precludes gene expression by preventing the ORF from being transcribed. During conditions of limiting FMN, an antiterminator structure is formed within the ribD nascent transcript, which allows for synthesis of the downstream genes.

b. FMN-Mediated Control of Transcription Termination In Vivo

The molecular details of riboswitch-mediated transcription termination are likely to be more complex than this rather simplistic model implies. For example, given that the 'decision' to form the terminator or antiterminator conformation occurs only once during transcription, the regulatory mechanism is likely to rely on precise transcriptional kinetics as well as the appropriate RNA folding pathways. Moreover, the kinetics of FMN interacting with the RNA receptor is likely a critical factor. Although the affinity that the RNA has for FMN is exceptionally strong compared to engineered aptamers, it is possible that the kinetics of ligand association might be the more important determinant of genetic regulation. Indeed, all of these parameters are likely to conspire together in order to exert appropriate control over the intrinsic terminator. In adapting and designing riboswitches for use as described herein, the impact of transcription speed should be taken into account.

iii. Control of Transcription Termination by other Riboswitches

Intrinsic terminators can be identified via computer-assisted search algorithms (F.

Lillo, et al., 2002, 18, 971). Using such bioinformatic analyses, a subset of riboswitch RNAs that are predicted to contain an intrinsic terminator and an alternate antiterminator structural element can be identified (M. Mandal, et al., *Cell* 2003, 113; A. G. Vitreschak, et al., *Nucleic Acids Research* 2002, 30, 3141; F. J. Grundy, T. M. Henkin, *Molecular Microbiology* 1998, 30, 737; S. Kochhar, H. Paulus, *Microbiology* 1996, 142, 1635; D. A. Rodionov, et al., *Journal of Biological Chemistry* 2002, 277, 48949). Therefore, the results described above for the FMN riboswitch are indicative of the mechanisms used by many other riboswitch RNAs. Indeed, SAM- and TPP-dependent riboswitches have been demonstrated to exert control over termination via formation of mutually exclusive intrinsic terminator and antiterminator structures (see, e.g., Example 7). Furthermore, mutations that disrupt and subsequently restore helices within the SAM riboswitch aptamer result in loss and restoration, respectively, of SAM binding. Concurrently, these mutations also result in disruption or restoration of SAM-induced transcription termination in accordance with ligand-binding function. Riboswitches can be adapted and designed to exert control over transcription termination signals that differ appreciably from classical intrinsic terminators according to principles described herein. As described elsewhere herein, expression platform domains having expression-controling stem structures can be matched to aptamer domains by designing the P1 stem of the aptamer domain such that the control strand (P1b) of the aptamer can form a stem structure with the regulated strand (P1c) of the expression platform.

4. Riboswitch Regulation of Translation Initiation in Bacteria

An alternative mechanism of genetic control by riboswitches is the modulation of translation initiation. Unlike transcription termination, the entire mRNA would be synthesized by RNA polymerase, but expression would be prevented by the riboswitch until the metabolite concentration reached a certain level. In most instances, it was observed that riboswitches prevent translation initiation in the presence of high concentrations of target metabolite. However, riboswitches can be designed and adapted such thatallosteric modulation of riboswitch structures could lead to translation activation. The regulatory mechanism of translation control is briefly described below for a TPP riboswitch from *E. coli.* i. A Natural Aptamer for TPP

A conserved RNA element, referred to as the thi box, was identified within 5'-UTRs of mRNAs that are responsible for thiamine biosynthesis and transport (D. A. Rodionov, et al., *Journal of Biological Chemistry* 2002, 277, 48949; J. Miranda-Rios, M. Navarro, M. Soberon, *Proceedings of the National Academy of Sciences of the United States of America* 2001, 98, 9736.). Genetic experiments confirmed that this structural element was required for thiamine-dependent regulation of *Rhizobium meliloti* thiamine biosynthesis genes (J. Miranda-Rios, M. Navarro, M. Soberon, *Proceedings of the National Academy of Sciences of the United States of America* 2001, 98, 9736), yet no regulatory factor had been identified through classical genetic experimentation. Therefore, it was possible that the thi box might serve as a portion of a riboswitch that responds to thiamine or its derivatives.

In *E. coli*, thiamine biosynthesis and transport genes are primarily located within three operons and four single genes (T. P. Begley, et al., *Archives of Microbiology* 1999, 171, 293), wherein each operon is preceded by a thi element. To begin to assess the regulatory properties of these sequences, the leader regions for the thiMD and thiCEFSGH operons were utilized to construct transcriptional and translational fusions to a lacZ reporter gene (see Example 2). Addition of exogenous thiamine results in repression of the lacZ reporter gene in *E. coli*. Results from these data demonstrate that the thiM gene is regulated primarily at the level of translation while the thiC leader region confers both transcriptional and translational regulation to the lacZ reporter.

a. Direct Binding of Thiamine Pyrophosphate by *E. coli* mRNAs

Figure 13B:
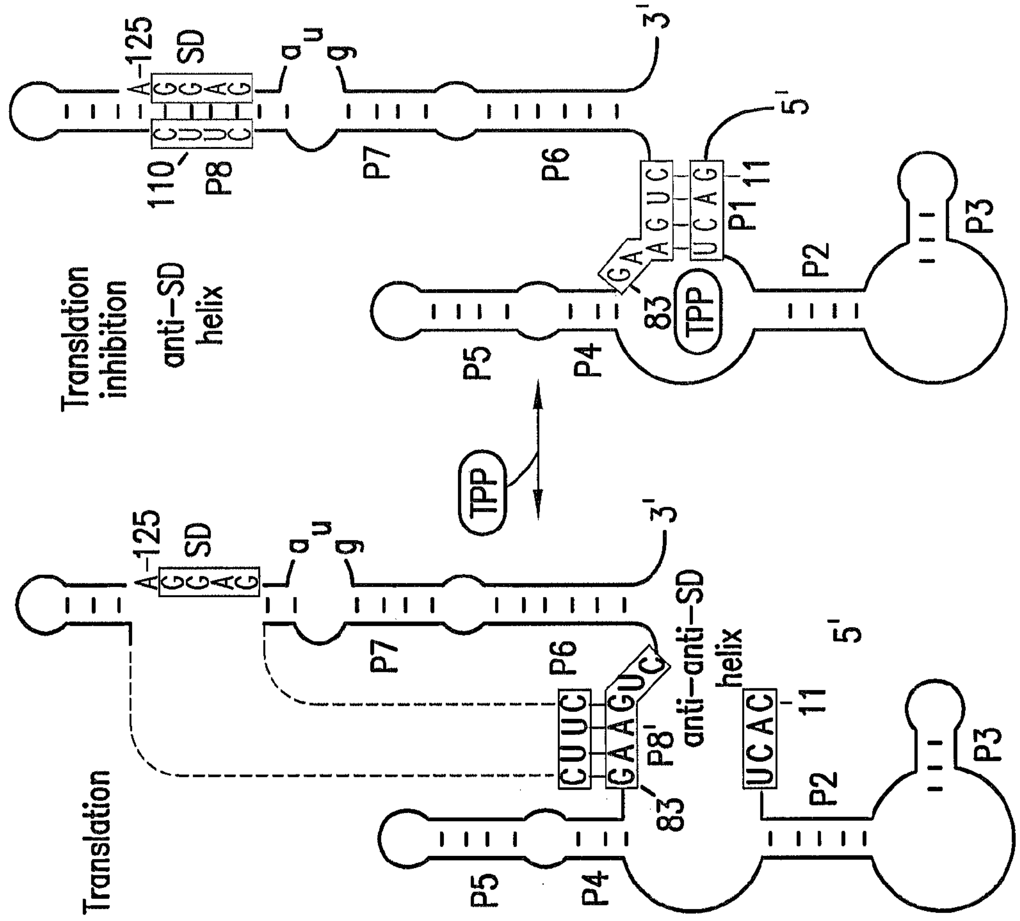
FIG. 13B shows a model for the mechanism of thiM regulation. In the absence of TPP, the anti-SD sequence interacts with part of aptamer domain to form anti-anti-SD. As TPP is increased, aptamer-TPP complexes are formed and the anti-SD favors pairing with the SD.
Figure 13A:
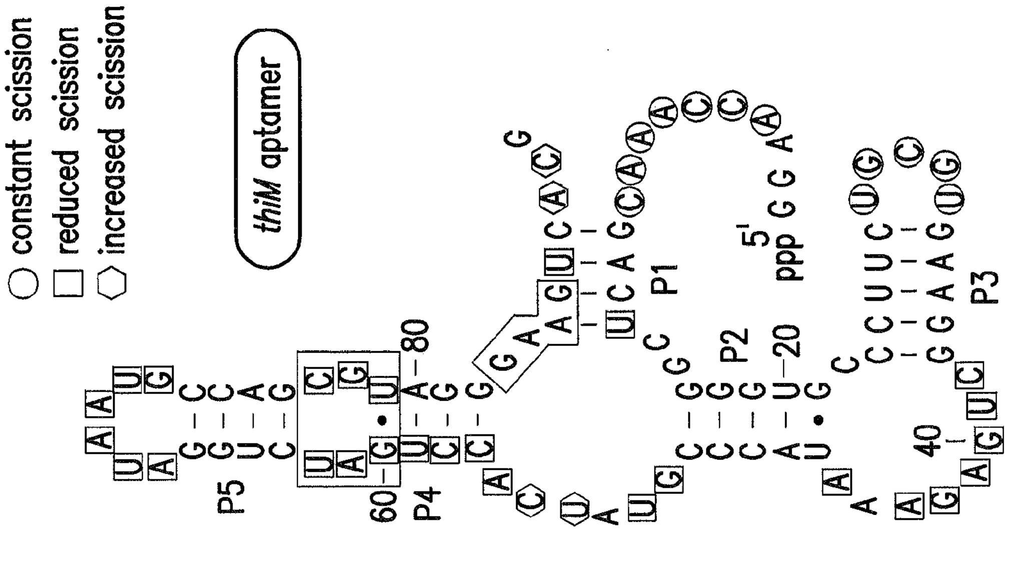
FIGS. 13A (residues 1-91 of SEQ ID NO:2), 13B and 13C show the regulation of the *E. coli* thiM mRNA by TPP.

As described above for the FMN aptamer, direct binding of TPP to the thiM and thiC leaders was demonstrated by in-line probing assays (see Example 2). The addition of thiamine, thiamine monophosphate (TP), or the pyrophosphate derivative (TPP) leads to structural rearrangement of the thiM RNA, particularly in the region encompassing the thi element (FIG. 13). Significantly, TPP, which is the bioactive form of thiamine, exhibits the best affinity between the ligands, with an apparent $K_D$ of 500 nM, while TP and thiamine associate to thiM with apparent $K_D$ values of 3 μM and 40 μM, respectively. In-line probing assays of RNAs resembling the thiC leader region reveal even more dramatic discrimination between thiamine and its phosphorylated forms, exhibiting greater than a 1,000-fold difference between binding of thiamine and TPP. These data are consistent with genetic experiments that suggested that TPP synthesis was required for regulation (E. Webb, et al., *Journal of Bacteriology* 1996, 178, 2533; E. Webb, D. Downs, *Journal of Biological Chemistry* 1997, 272, 15702). Also, this system provides another example of a natural RNA aptamer that makes productive contacts to phosphate groups.

b. Confirmation of TPP Binding by Equilibrium Dialysis

RNAs resembling the thiM leader region were synthesized and placed into one side of a two-chamber equilibrium dialysis apparatus, in which the compartments are separated by a 3000-dalton molecular-weight-cut-off dialysis membrane. $^3$H-thiamine was preferentially retained within the thiM-containing chamber when allowed to equilibrate between chambers (see Example 2). This effect could be eliminated by providing excess unlabeled thiamine, but could not be reversed when supplemented with oxythiamine, a close chemical analog of thiamine. Additionally, a mutated version of thiM was unable to shift $^3$H-thiamine to the RNA-containing chamber. Together, these data are indicative of the formation of stable thiM:thiamine complexes, wherein the sequence of the RNA and the chemical form of the ligand are critical for maximal binding affinity.

ii. Binding of Thiamine Derivatives Correlates with Structural Modulation

Close inspection of in-line probing data for thiM reveal two surprising patterns of structural modulation. First, the relative rates of spontaneous fragmentation between reactions containing either thiamine or TPP differ within an internal loop of the thi element (FIG. 13). Nucleotides in this region adopt an increase in structural order in the presence of TPP but not with thiamine, implying this region is somehow involved in formation of a pyrophosphate-recognition pocket. Secondly, the region of the SD sequence is the only portion outside of the thi element that becomes structurally modulated in the presence of TPP.

Specifically, the SD sequence exhibits a significant decrease in spontaneous cleavage relative to reactions lacking TPP, suggesting that the SD is converted into a more structurally constrained form upon binding of TPP. This idea is consistent with a mechanism (FIG. 13) whereby in the absence of TPP the SD has a significant degree of single-stranded character and is accessible for translation initiation. An anti-SD sequence is proposed to interact with an anti-anti-SD sequence within the TPP aptamer under these conditions. In contrast, during conditions of excess TPP, a TPP-RNA complex is formed that disrupts the base pairing of the anti-SD sequence, which is then free to interact directly with the SD and decrease the single-stranded character of the region, hence decreasing efficiency of translation initiation. Preliminary site-directed mutagenesis of the thiM mRNA supports this overall model (see Example 2). Specifically, mutations that disrupt TPP binding also disrupt regulation of translation for thiM-lacZ fusions, while mutations that alter the anti-SD sequence affect regulation but do not affect TPP binding. Thus, binding of thiamine correlates with both the structural accessibility of the SD and the translation efficiency in vivo.

iii. Control of Translation Initiation by other Riboswitches

Bioinformatics analyses are consistent with molecular mechanisms similar to that of thiM also being recurrent amongst riboswitch RNAs. Specifically, anti-SD and anti-anti-SD structures have been proposed for several riboswitch classes, including FMN (A. G. Vitreschak, et al., *Nucleic Acids Research* 2002, 30, 3141), lysine, TPP (D. A. Rodionov, et al., *Journal of Biological Chemistry* 2002, 277, 48949), coenzyme $B_{12}$ (see Example 1) and SAM. In general, riboswitches from Gram-negative organisms seem to favor expression platforms that exert control over translation, while riboswitches from Gram-positive bacteria appear to predominately use expression platforms that control transcription termination. The latter can reflect a greater reliance upon multigene transcriptional units in Gram-positive organisms, which might be more efficient to preclude transcription of long operons when the gene products are unnecessary.

Biochemical evidence for riboswitch-mediated control over translation initiation has also been obtained for FMN and AdoCb1 riboswitches (see Example 1). FMN binding to a riboswitch that regulates the *B. subtilis* ypaA gene results in alteration of the SD structural context, similar to what was observed for thiM. Interestingly, this genetic control element has also been proposed to regulate ypaA transcription (J. M. Lee, et al., *Journal of Bacteriology* 2001, 183, 7371), although the leader region does not contain an obvious intrinsic terminator structure. Binding of AdoCb1 to the *E. coli* btuB riboswitch has also been demonstrated to correlate with regulation of translation in vivo.

Certain riboswitch RNAs exert control over transcription and translation using the same RNA sequence. For this class of riboswitches, the SD sequence is contained within an intrinsic terminator. Therefore, the formation of the terminator structure also enacts formation of a SD-sequestering structure. In total, all of these observations suggest that although the thiM and ribD riboswitches represent useful paradigms for riboswitch-mediated control of translation and transcription, respectively, there are likely to be a wide variety of molecular mechanisms utilized by riboswitch RNAs for control of gene expression. Indeed, TPP riboswitches that must be employing different mechanisms of control have been identified in several plant and fungal species (see Example 4). The placement of these RNAs near splice sites in some instances and in the 3'-UTR in others indicate TPP-responsive control over splicing and mRNA stability or expression, respectively.

5. Early Origins?

The FMN, TPP, lysine and AdoCb1 riboswitch RNAs are widespread among evolutionarily distant microorganisms, implying an ancient origin for these RNA genetic elements (A. G. Vitreschak, et al., *Nucleic Acids Research* 2002, 30, 3141; D. A. Rodionov, et al., *Journal of Biological Chemistry* 2002, 277, 48949; D. A. Rodionov, et al., *Journal of Biological Chemistry* 2002, 277, 48949). SAM, guanine, and adenine riboswitches are also represented in numerous different genera, although they appear to be primarily limited to Gram-positive bacteria, with a few Gram-negative bacteria as exceptions (see Example 6). In all instances, the structural and sequence conservation of riboswitch classes is limited to the aptamer domain (FIG. 11). This is not unexpected given that the aptamer RNA must preserve its capability to bind the target chemical, which has not been significantly modified through evolution. In contrast, there is considerable sequence and structural diversity between expression platforms, even between riboswitches of the same class and within the same organism. Together, these data hint that the ligand-binding properties of riboswitch aptamer domains have been maintained throughout expansive evolutionary timescales.

Furthermore, the ligands for riboswitch RNAs have been proposed to be functional relics from a hypothetical RNA-based world, in which RNA polymers provided all the necessary catalytic and genomic content for some of the earliest self-replicating organisms (H. B. White, 3rd, *Journal of Molecular Evolution* 1976, 7, 101; G. F. Joyce, *Nature* 2002, 418, 214). Therefore it is tempting to speculate that as cofactor-binding RNAs the aptamer domains from riboswitches may have been useful in the context of an RNA-based world for some of the earliest forms of genetic control, for allosteric modulation of ribozymes, or as part of ribozymes that utilized the ligands as catalytic cofactors.

6. Riboswitches as Drug Targets and Genetic Tools

Riboswitches are utilized for control of numerous genes involved in the biosynthesis and transport of prokaryotic enzymatic cofactors. At least 69 genes, which represents nearly 2% of *Bacillus subtilis* total genomic content, is under control of riboswitch RNAs (Table 1), exemplifying the extensive use of riboswitch RNAs for genetic control in prokaryotes. (M. Mandal, et al., Cell 2003, 113). Many riboswitch-mediated genes are expected to be essential under most growth conditions. Interference with riboswitch function is then predicted to result in dramatic destabilization of vital metabolic pathways and perhaps, cessation of growth. Therefore, it seems likely that compounds that closely resemble the target metabolites will bind to riboswitch RNAs and cause a decrease in gene expression. If this analog-induced disruption of gene expression is sufficient, then such compounds might be candidates for antimicrobial applications.

TABLE 1

Distribution of known riboswitch classes in *Bacillus subtilis*. Gene nomenclature is derived from the SubtiList database except for metI and metC, which are recent designations (S. Auger, et al., *Microbiology* 2002, 148, 507). Functional roles for ypaA (R. A. Kreneva, et al., *Genetika* 2000, 36, 1166), yuaJ (D. A. Rodionov, et al., Journal of Biological Chemistry 2002, 277, 48949), ykrTS (B. A. Murphy, et al., *Journal of Bacteriology* 2002, 184, 2314), and ykrWXYZ (B. A. Murphy, et al., *Journal of Bacteriology* 2002, 184, 2314.), have recently been proposed.

| Ligand | Transcriptional Unit | Predicted Gene Function(s) |
|---|---|---|
| Lysine | lysC | Aspartokinase II |
| Flavin | ypaA | Putative flavin transporter |
| mononucleotide | ribD-ribE-ribBA-ribH | Riboflavin biosynthesis |
| Adenosylcobalamin | yvrC-yvrB-yvrA-yvqK | Unknown; similar to iron transport proteins |
| Thiamine pyrophosphate | thiC | Biosynthesis of thiamine pyrimidine moiety |
| | tenA1-thiX1-thiY1-thiz1-thiE2-thiO-thiS-thiG-thiF-thiD | Thiamine biosynthesis |
| | ykoF-ykoE-ykoD-ykoC | Unknown |
| | yuaJ | Unknown; putative thiamine transporter |
| | ylmB | Similar to acetylornithine deacetylase |
| Guanine | yxjA | Similar to pyrimidine nucleoside transport |
| | xpt-pbuX | Xanthine permease |
| | pbuG | Hypoxanthine/Guanine permease |
| | purE-purK-purB-purC-purS-purQ-purL-purF-purM-purN-purH-purD | Purine biosynthesis |
| Adenine | ydhL | Unknown |
| S-adenosylmethionine | yitJ | Putative methylene tetrahydrafolate reductase |
| | metI-metC | Methionine biosynthesis |
| | ykrT-ykrS | 5' methylthioadenosine recycling pathway |
| | ykrW-ykrX-ykrY-ykrZ | 5' methylthioadenosine recycling pathway |
| | cysH-cysP-sat-cysC-ylnD-ylnE-ylnF | Cysteine biosynthesis |
| | yoaD-yoaC-yoaB | Unkown |
| | metE | Methionine synthase, $B_{12}$-independent |
| | metK | S-adenosylmethionine synthetase |
| | yusC-yusB-yusA | Unknown ABC transporter |
| | yxjG | Unknown |
| | yxjH | Unknown |

There is clear precedence for the targeting of RNAs with small molecule drugs (G. J. Zaman, et al., *Nucleic Acids Research* 2002, 30, 62), the most obvious example being that of ribosomal RNA. Several other bacterial-specific RNAs have been explored as candidates for small molecule drug interaction; however, the approach relies upon screening large chemical libraries for those chemicals that fortuitously interact with the RNA of interest, even though the RNA itself does not naturally form a binding pocket for small organic molecules. Riboswitch RNAs therefore exhibit an advantage in antimicrobial development given that they serve as a receptor for small molecule ligands, much like their protein receptor counterparts.

In addition to their use as targets for chemical inhibition, understanding of the mechanisms utilized by natural riboswitch RNAs allows adaptation of riboswitches and development of new riboswitches as novel genetic control elements. Numerous aptamer RNA sequences have been identified that interact with a wide variety of small organic molecules (M. Famulok, *Current Opinion in Structural Biology* 1999, 9, 324). Engineered riboswitches can be generated that respond to non-biological, or otherwise metabolically inert, compounds. Such genetic control elements can be used for a variety of expression control and molecular detection applications.

D. Example 4

Eukaryotic Riboswitches

1. Abstract

Genetic control by metabolite-binding mRNAs is wide spread in prokaryotes. These "riboswitches" are typically located in non-coding regions of mRNA, where they selectively bind their target compound and subsequently modulate gene expression. Disclosed are mRNA elements that have been identified in fungi and in plants that match the consensus sequence and structure of thiamine pyrophosphate-binding domains of prokaryotes. In *Arabidopsis*, the consensus motif resides in the 3'-UTR of a thiamine biosynthetic gene, and the isolated RNA domain binds the corresponding coenzyme in vitro. These results suggest that metabolite-binding mRNAs possibly are involved in eukaryotic gene regulation and that some riboswitches might be representatives of an ancient form of genetic control.

2. Introduction

Riboswitches are genetic control elements that can be found in the 5'-untranslated region of certain messenger RNAs of prokaryotes (see Examples 1-3). These genetic switches exhibit two surprising properties. First, the mRNA is able to form a highly selective binding site for the target metabolite without the aid of proteins. Second, metabolite binding brings about an allosteric reorganization of RNA structure that leads to alterations in genetic expression. Unlike many other genetic control systems, riboswitches do not require metabolite-binding proteins to serve as sensors, and thus offer a direct link between the genetic information that is encoded by an mRNA and its chemical surroundings.

A number of distinct types of riboswitches have been confirmed by biochemical and genetic analyses. For example, a coenzyme $B_{12}$-binding RNA has been shown (Example 1) to control expression of the *Escherichia coli* btuB gene, which encodes a cobalamin transport protein. Riboswitches triggered by thiamine pyrophosphate (TPP) have been shown to control operons in *E. coli* (Example 3) and *Bacillus subtilis* (Example 6) that are responsible for biosynthesis of this coenzyme. In addition, the RFN element, which frequently is found in the 5'-untranslated region of genes responsible for the biosynthesis or import of riboflavin and FMN, serves as the receptor portion of FMN-dependent riboswitches in *Bacillus subtilis* (see Examples 3 and 6). Recently, it has been determined that certain S-box motifs that are located in the 5'-UTRs of numerous genes in *B. subtilis* bind the coenzyme S-adenosylmethionine (SAM) with high affinity and precision. These findings indicate that riboswitches are used to recognize a diverse collection of metabolites and that direct sensing of small molecules by mRNAs is an important form of genetic control for certain organisms. Disclosed herein, is evidence that metabolite-binding domains are embedded in certain mRNAs of eukaryotes, indicating that higher organisms might also exploit riboswitches for genetic control.

3. Results

Disclosed are many RNA elements that have been identified in prokaryotes that exhibit sequence similarity to the $B_{12}$- and SAM-dependent riboswitches. Given the relatively large size and sequence complexity of these RNA motifs, it is unlikely that numerous evolutionary reinventions of the same elements would have occurred. Furthermore, the metabolite triggers of these genetic switches are predicted to have been present in a time before the emergence of proteins (White, 1976; Benner et al., 1989; Jeffares et al., 1998). This is consistent with the known classes of metabolite-sensing RNAs having originated in the ancient RNA world, which is believed to be a time before the emergence of proteins and when metabolism was guided entirely by RNA (Joyce, 2002).

Figure 14A:
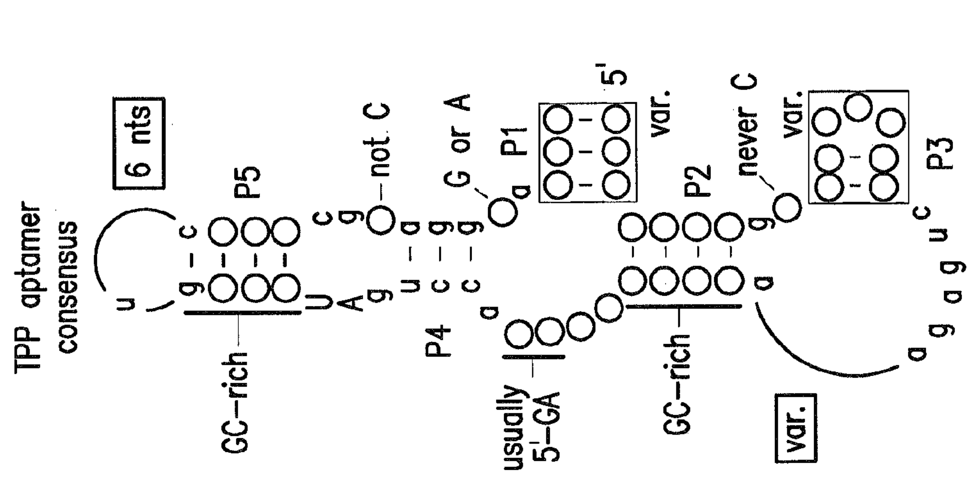
FIGS. 14A, 14B and 14C show putative eukaryote riboswitches.
Figure 14B:
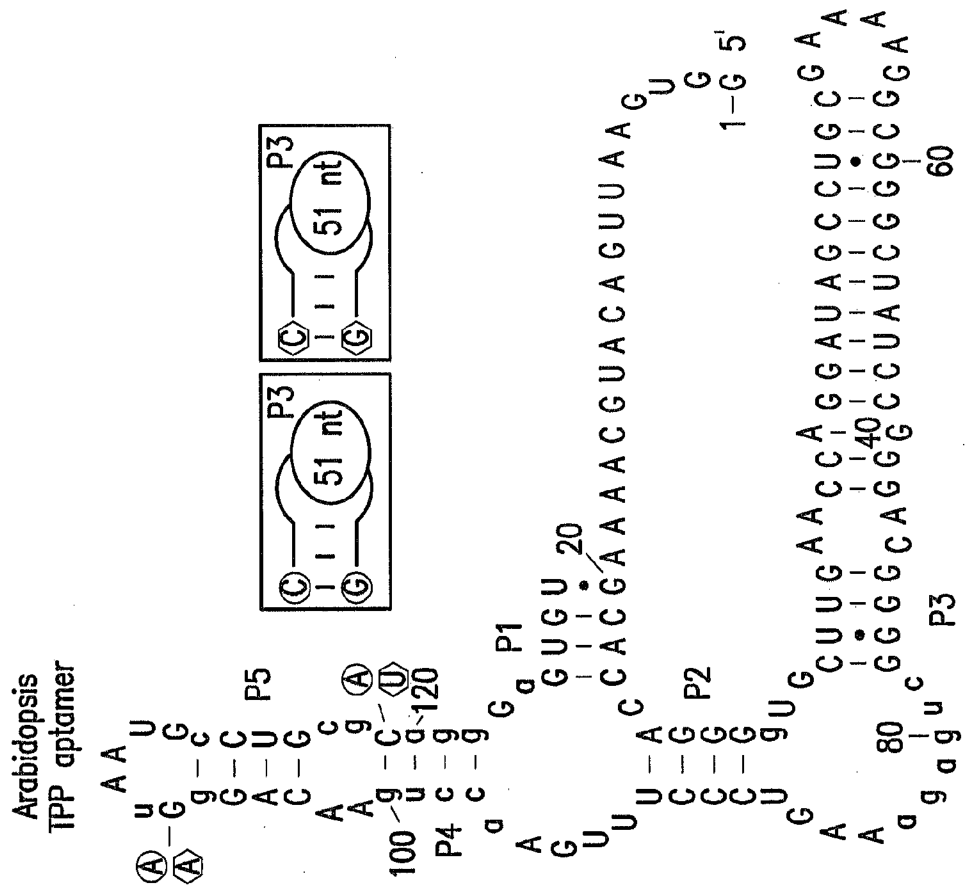
Figure 14C:
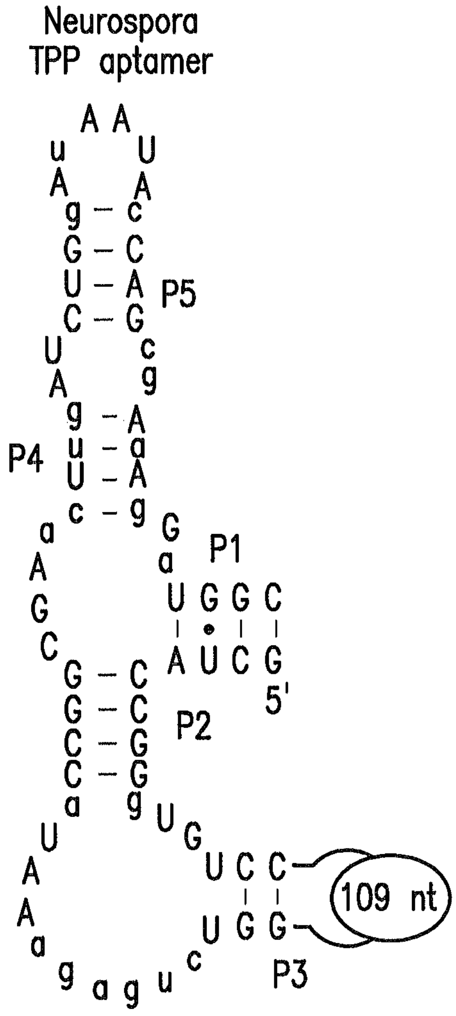

If the present-day riboswitches are of ancient origin, then eukaryotes might possess RNA genetic switches that are descendent from the last common ancestor of modern cells. Disclosed herein several eukaryotes carry RNA domains that conform to the consensus sequence and structure of the metabolite-binding domain of the TPP riboswitch class (FIG. 14A) (The mRNAs that carry the TPP-binding domains encode for a protein that is homologous to the thiC protein of *E. coli*. This protein enzyme catalyzes the conversion of 5-aminoimidazole ribotide (AIR) to hydroxymethyl pyrimidine phosphate (HMP-P), which is a key biosynthetic step in the synthesis of thiamine and ultimately TPP (Vander Horn et al., 1993; Begley et al., 1999)). For example, a putative thiamine biosynthesis gene of *Arabidopsis thaliana* carries an RNA element (FIG. 14B) in its 3'-UTR that conforms to the consensus TPP-binding domain. Similar RNA elements are found in rice (*Oriza sativa*) and bluegrass (*Poa secunda*). RNA elements that conform to the TPP-binding sequence and structure are also present in fungi such as *Neurospora crassa* (FIG. 14C) and *Fusarium oxysporum*. As with plants, the riboswitch homologs in fungi are located in genes that have been implicated in the biosynthesis of thiamine, suggesting that in each case their role is to maintain required coenzyme levels by modulating expression of the appropriate biosynthetic genes. A sequence alignment of the homologous domains found in eukaryotes compared to that of the gram negative bacterium *E. coli* (thiC and thiM) and the gram positive bacterium *Chlostridium acetobutylicum* (thiC) is depicted in FIG. 15.

Figure 16A:
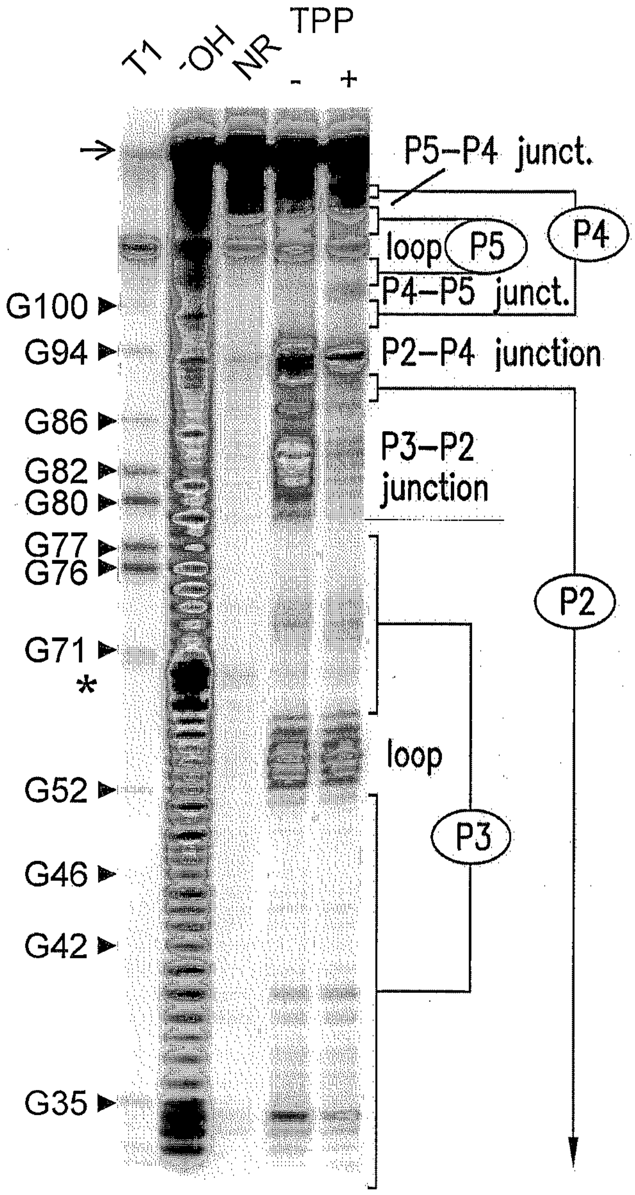
FIGS. 16A and 16B show the structural probing of the putative TPP-riboswitch from Arabidopsis.
Figure 16B:
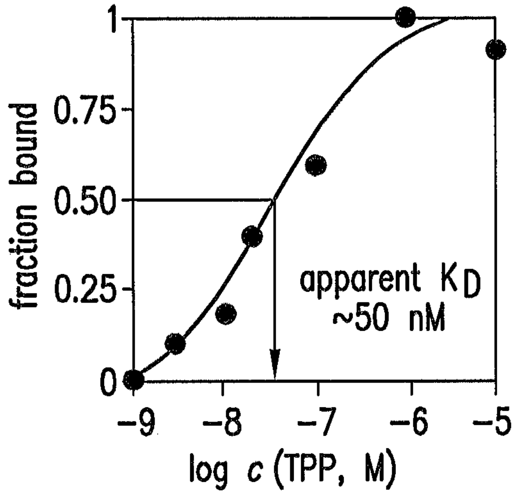

The RNA element corresponding to the consensus TPP-binding domain of *A. thaliana* (FIG. 14A) was generated by in vitro transcription of a synthetic DNA template and the RNA was subjected to "in-line probing" (FIG. 16A). This method relies on the spontaneous breakdown of RNA phosphodiester linkages, whose pattern of cleavage can be used to reveal the structural and functional features of ligand-binding RNAs (see Examples 1-3). Indeed, the riboswitch-like element exhibits TPP-dependent structural modulation and has a fragmentation pattern that is consistent with the predicted secondary structure of TPP riboswitches from bacteria (see Examples 2 and 3). In addition, this structure-probing method has been used herein to establish that the RNA binds TPP with an apparent dissociation constant ($K_D$) of ~50 nM (FIG. 16B), which is similar to that determined previously for an *E. coli* riboswitch variant. Similarly, it has been demonstrated that the sequence elements of fungi that correspond to the TPP riboswitch consensus also bind TPP with high affinity.

Figure 17:
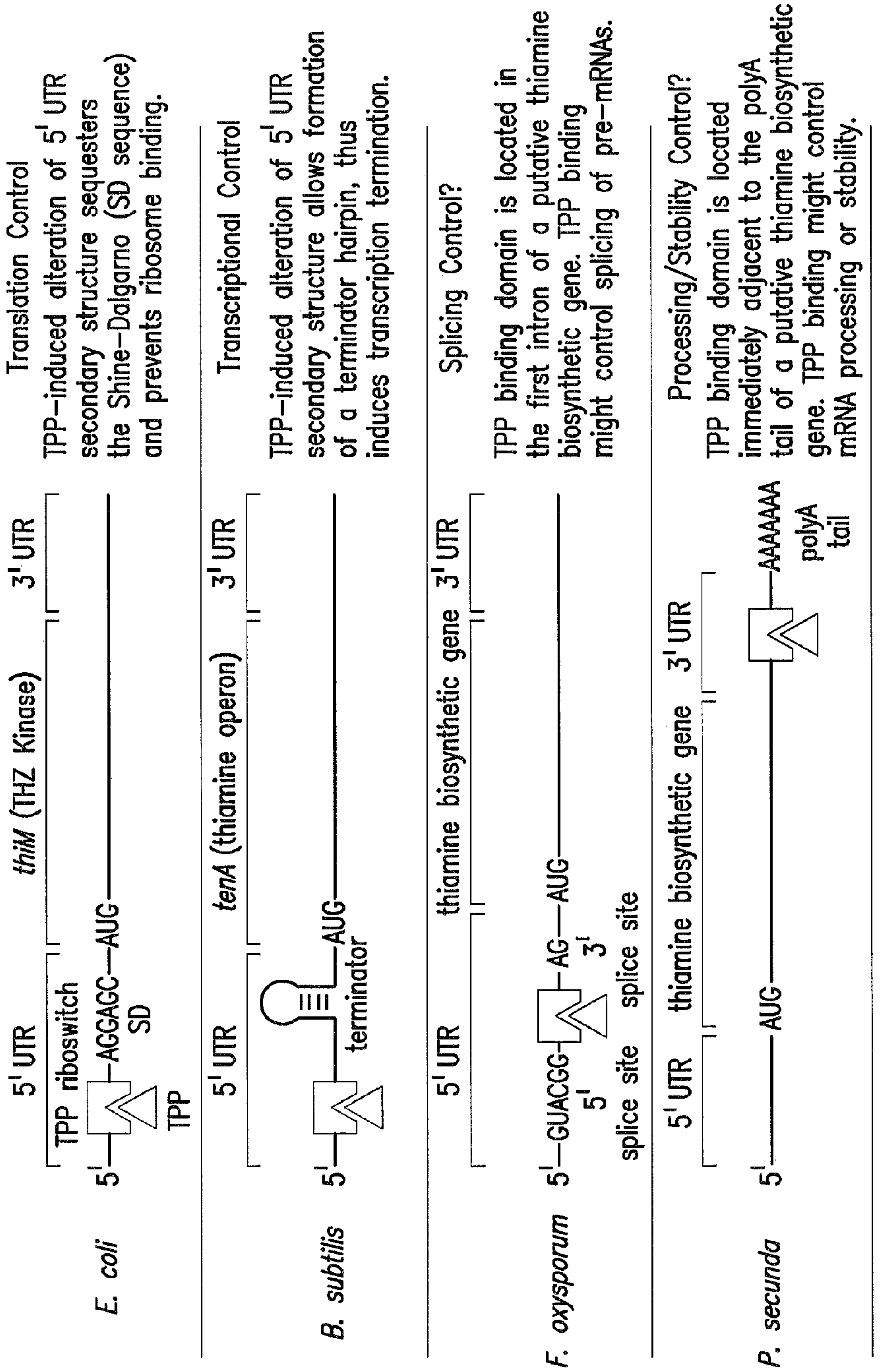
FIG. 17 shows genetic structures thiamine biosynthetic genes and possible mechanisms of riboswitch control. The location and mechanism of the *E. coli* and *B. subtilis* riboswitches are detailed in Examples 2 and 6. The putative TPP riboswitch from *P. secunda* resides immediately upstream from the polyA tail in the cDNA clone of the THIC gene. The putative TPP riboswitch domain in *F. oxysporum* is located in a 5'-UTR intron of the STI35 gene according to the genomic sequence but is absent in the cDNA clone.

Sequestering of the ribosome binding site and transcription termination are demonstrated mechanisms for TPP riboswitches in *E. coli* (FIG. 17). Since the TPP-binding element in plants is located immediately upstream from the polyA tail, it is possible that metabolite binding might regulate mRNA processing and stability. Alternatively, a consensus TPP-binding sequence (FIG. 14C) identified in the fungal genome of *N. crassa* resides in an intron, suggesting that RNA splicing might also be guided by metabolite-binding pre-mRNAs. In prokaryotes, ligand binding typically brings about allosteric changes in the Watson-Crick base pairing arrangements near gene control elements such as transcription terminators and ribosome binding sites. Likewise, secondary structure rearrangements by metabolite-binding riboswitches can be used to modulate a greater variety of RNA processing, transport and expression pathways in eukaryotes.

Although it is likely that TPP-binding domains and those for coenzyme $B_{12}$, FMN, and SAM are of ancient origin, it is possible that other examples of metabolite-binding mRNAs have emerged more recently in evolution. These newer riboswitches would be more narrowly distributed across the phylogenetic landscape, so efforts to search for new riboswitches that are triggered by compounds that are not ancient and universally distributed will be difficult. Regardless of the scope of riboswitch use in modern organisms, both natural and engineered riboswitches could have significant utility. Given the central role that known riboswitches serve in modulating the concentration of key coenzymes, these RNAs can serve as new targets for drug discovery efforts. Therefore, reverse engineering of natural riboswitches can be used to establish a conceptual basis for creating designer riboswitches for the purposeful control of eukaryotic genes.

E. Example 5

Lysine Riboswitches

The precise control of gene expression in response to changes in the chemical and physical environment of cells requires selective interactions between biochemical sensor elements and the molecules that carry or interpret genetic information. Most known genetic factors that respond to such environmental changes are proteins (Ptashne and Gann 2002). However, a number of studies (e.g. see Examples 1-3 and 6-8) have demonstrated that natural RNA molecules can also recognize small organic compounds and harness allosteric changes to control the expression of adjacent genes. These metabolite-binding RNA domains, termed riboswitches, typically are embedded within the 5'-UTRs of mRNAs and control the expression of proteins involved in the biosynthesis or import of the target compound. Riboswitches also play an important role in controlling fundamental metabolic pathways in bacteria involved in sulfur metabolism, and in the biosynthesis of various coenzymes and purines (see Example 6). Furthermore, riboswitches are phylogenetically widespread amongst eubacterial organisms, and both sequence and biochemical data suggest that riboswitches are also present in the genes of eukaryotes (see Example 4).

These observations indicate that riboswitches likely comprise a widely used mechanism of genetic control in living systems. Transcription of the lysC gene of *B. subtilis* is repressed by high concentrations of lysine (Kochhar, S., and Paulus, H. 1996, *Microbiol.* 142:1635-1639; Mäder, U., et al., 2002, *J. Bacteriol.* 184:4288-4295; Patte, J. C. 1996. Biosynthesis of lysine and threonine. In: *Escherichia coli* and *Salmonella: Cellular and Molecular Biology*, F. C. Neidhardt, et al., eds., Vol. 1, pp. 528-541. ASM Press, Washington, D.C.; Patte, J.-C., et al., 1998, *FEMS Microbiol. Lett.* 169:165-170), but that no protein factor had been identified that served as the genetic regulator (Liao, H.-H., and Hseu, T.-H. 1998, *FEMS Microbiol. Lett.* 168:31-36). The lysC gene encodes aspartokinase II, which catalyzes the first step in the metabolic pathway that converts L-aspartic acid into L-lysine (Belitsky, B. R. 2002. Biosynthesis of amino acids of the glutamate and aspartate families, alanine, and polyamines. In: *Bacillus subtilis* and its *Closest Relatives: from Genes to Cells*. A. L. Sonenshein, J. A. Hoch, and R. Losick, eds., ASM Press, Washington, D.C.). Interestingly, several efforts have been successful in generating mutants that exhibit constitutive expression of the aspartokinase II enzyme, and all mutations map to the 5'-UTR of the lysC mRNA (Boy, E., et al., 1979. *Biochimie* 61:1151-1160; Lu, Y., et al., 1991, *J. Gen. Microbiol.* 137:1135-1141; Lu, Y., et al., 1992, *FEMS Microbiol. Lett.* 92:23-27). Furthermore, a significant level of sequence similarity was identified between the *B. subtilis* and *E. coli* lysC 5'-UTRs (Patte, J.-C., et al., 1998, *FEMS Microbiol. Lett.* 169:165-170.). These characteristics are consistent with a lysine-responsive riboswitch serving as the genetic control element for this gene.

1. Materials and Methods i. Chemicals and Oligonucleotides

L-lysine, all analogs with the exception of L-α-homolysine (compound 6, FIG. 20A), tritiated lysine (L-Lysine-[4,5-$^3$H (N)]), and the four dipeptides were purchased from Sigma. A protocol adapted from that reported previously (Dong, Z. 1992, *Tetrahedron Lett.* 33:7725-7726) was used to synthesize L-α-homolysine. Purity and integrity of synthetic L-α-homolysine was confirmed by TLC and NMR.

DNA oligonucleotides were synthesized by the HHMI Keck Foundation Biotechnology Resource Center at Yale University, purified by denaturing PAGE and eluted from the gel by crush-soaking in 10 mM Tris-HCl (pH 7.5 at 23° C.), 200 mM NaCl, and 1 mM EDTA. Oligonucleotides were recovered from solution by precipitation with ethanol.

ii. Phylogenetic Analyses

L box domains were identified by sequence similarity to the *B. subtilis* lysC 5'-UTR. Ultimately, the program was used to search for degenerate matches to the pattern (WAGAGGNGC [10] A [3] RKTA [50] RRGR [10] CCGARR [40] GG [13] VAA [13] YTGTCA [36] TGRWG [2] CTWY) (SEQ ID NO:376), however, less complete versions of this pattern were used with iterative refinements to identify the consensus sequence and structure of the L box motif. Bracketed numbers are variable gaps with constrained maximum lengths denoted. Nucleotide notations are as follows: Y=pyrimidine; R=purine; W=A or T; K=G or T; V=A, G or C. Up to six violations of this pattern were permitted when forming the phylogeny depicted in FIG. 18.

iii. In-line Probing of RNA Constructs

The *B. subtilis* 315 lysC, 237 lysC and 179 lysC RNAs were prepared by in vitro transcription using T7 RNA polymerase and the appropriate PCR DNA templates. RNA transcripts were dephosphorylated and subsequently 5' $^{32}$P-labeled using a protocol similar to that described previously (Seetharaman, S. et al., 2001, *Nature Biotechnol.* 19, 336-341). Labeled precursor RNAs (~2 nM) were subjected to in-line probing using conditions similar to those described in Examples 1 and 2. Reactions (10 μL) were incubated for 40 hr at 25° C. in a buffer containing 50 mM Tris (pH 8.5 at 25° C.), 20 mM $MgCl_2$ and 100 mM KCl in the presence or absence of L-lysine or various analogs as indicated for each experiment. Denaturing 10% PAGE was used to separate spontaneous cleavage products, which were detected and quantitated by using a Molecular Dynamics PhosphorImager and ImageQuaNT software.

iv. Equilibrium Dialysis and Scatchard Analyses

Equilibrium dialysis assays were conducted using a DispoEquilibrium Dialyzer (ED-1, Harvard Bioscience), wherein two chambers a and b were separated by a 5,000 MWCO membrane. The final composition of buffer included 50 mM Tris-HCl (pH 8.5 at 25° C.), 20 mM $MgCl_2$ and 100 mM KCl (30 μL delivered to each chamber). Assays were initiated by the addition of $^3$H-lysine (50 nM initial concentration prior to equilibration; 40 Ci $mmol^{-1}$; 15,000 cpm) to chamber a. When present, RNA (179 lysC) was introduced into chamber b to yield a concentration of 10 μM. After 10 hr of equilibration at 25° C., a 3-μl aliquot from each chamber was removed for quantitation by liquid scintillation counter. Competition assays were established by delivering an additional 3 μL of buffer to a and an equivalent volume of buffer containing 50 μM unlabeled L-lysine, D-lysine, L-ornitihine, or L-lysine hydroxamate as indicated to b. After 10 hr of additional incubation at 25° C., 3-μl aliquots were again drawn for quantitation of tritium distribution.

Scatchard data points were generated as described above with the following exceptions. RNA was added to chamber b to yield a concentration of 1 μM RNA and equilibration of the dialysis mixtures proceeded for 20 hr. In addition, $^3$H-lysine concentrations were varied from 50 nM to 2.5 μM. Calculation of points on the Scatchard plot from the equilibrium dialysis data was carried out as described elsewhere herein.

v. In vitro Transcription Termination Assays

Transcription termination assays were conducted using a method of single-round transcription adapted from that described previously (Landick, R., et al., 1996, *Methods Enzymol.* 274:334-353). The template for lysC 5'-UTR transcription was altered (C6G of the RNA) such that the first C residue of the nascent RNA is not encountered until position 17. Polymerization was initiated by the addition of a mixture of ApA dinucleotide (1.35 μM), GTP and UTP (2.5 μM each) plus unlabeled ATP (1 μM) and [α-$^{32}$P]-ATP (4 μCi), which was incubated for 10 min. Halted complexes are restarted by the addition of 150 μM each of the four NTPs, and heparin (0.1 mg $mL^{-1}$) is simultaneously added to prevent polymerases from initiating transcription on new templates. Transcription mixtures also contained 20 mM Tris-HCl (pH 8.0 at 23° C.), 20 mM NaCl, 14 mM $MgCl_2$, 0.1 mM EDTA, 0.01 mg/mL BSA, 1% v/v glycerol, 4 pmoles DNA template, 0.045 U $\mu L^{-1}$ *E. coli* RNA polymerase (Epicenter, Madison, Wis.), and 10 mM of L-lysine or the lysine analog as indicated for each experiment. Reactions were incubated for an additional 20 min at 37° C. and the products were examined by denaturing 6% PAGE followed by analysis using a PhosphorImager.

vi. In vivo Analysis of lysC Genetic Variants

Fusions of the lysC 5'-UTR with a lacZ reporter gene were used to assess the function of the lysine riboswitch in vivo using methods similar to those described elsewhere herein. Briefly, the lysC 5'-UTR, comprising the promoter and the first 315 nucleotides of the transcription template, was prepared as an EcoRI-BamHI fragment by PCR. Sequence variants M1 through M3, G39A, and G40A were generated by PCR amplification of the wild-type construct using primers that carried the desired mutations. The PCR products were cloned into pDG1661 immediately upstream of the lacZ reporter gene and the integrity of the resulting clones were confirmed by sequencing. Transformations of pDG1661 variants into *B. subtilis* strain 1A40 (obtained from the *Bacillus* Genetic Stock Center, Columbus, Ohio) were performed and the correct transformants were identified by selecting for chloramphenicol resistance and screening for spectinomycin sensitivity.

Cells were grown with shaking at 37° C. either in rich medium (2XYT broth or tryptose blood agar base) or defined medium (0.5% w/v glucose, 2 g $L^{-1}$ $(NH_4)_2SO_4$, 18.3 g $L^{-1}$ $K_2HPO_4.3H_2O$, 6 g $L^{-1}$ $KH_2PO_4$, 1 g $L^{-1}$ sodium citrate, 0.2 g $L^{-1}$ $MgSO_4.7H_2O$, 5 μM $MnCl_2$, and 5 μM $CaCl_2$. Methionine, lysine, and tryptophan were added to 50 μg $mL^{-1}$ for routine growth. Growth under lysine-limiting conditions was established by incubation under routine growth conditions in defined medium to an $A_{595}$ of 0.1, at which time the cells were pelleted by centrifugation, resuspended in minimal medium, split into five aliquots, and supplemented with five different media types as defined in the legend to FIG. 22C. Cultures were incubated for an additional 3 hr before performing β-galactosidase assays.

2. Results i. The L Box: a Conserved mRNA Element that is Important for Genetic Control Riboswitches are typically formed by close juxtaposition of a metabolite-binding 'aptamer' domain and an 'expression platform' that interfaces with mRNA elements necessary for gene expression. Although the RNA sequences and structural components that serve as the expression platform change significantly throughout evolution, the aptamer domain largely retains the sequence composition of its ligand-binding core along with the major secondary-structure features. This permits the use of phylogenetic analyses to identify related RNA domains and to establish a consensus sequence and structure for a given class of riboswitches.

Figure 18A:
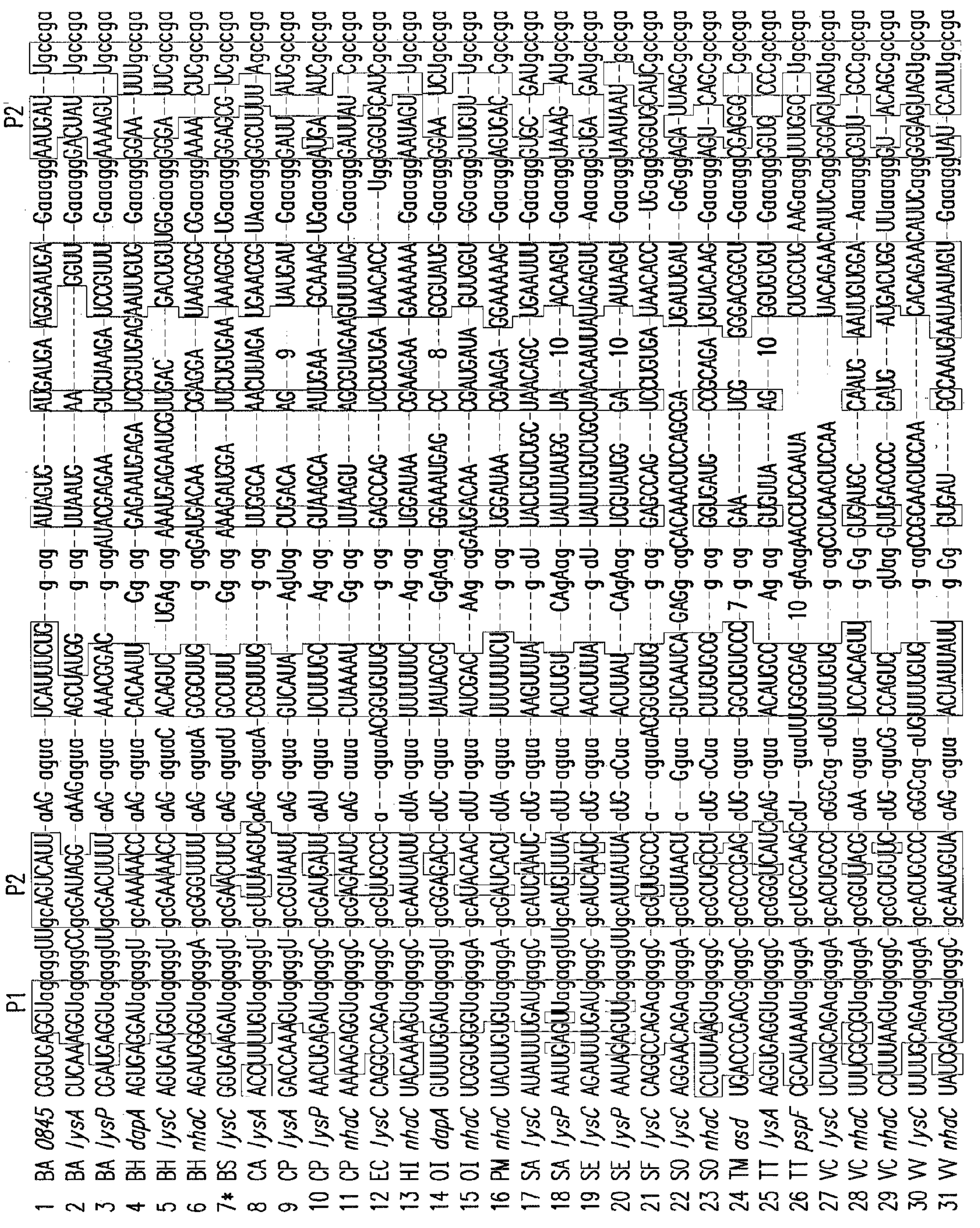
Figure 19A:
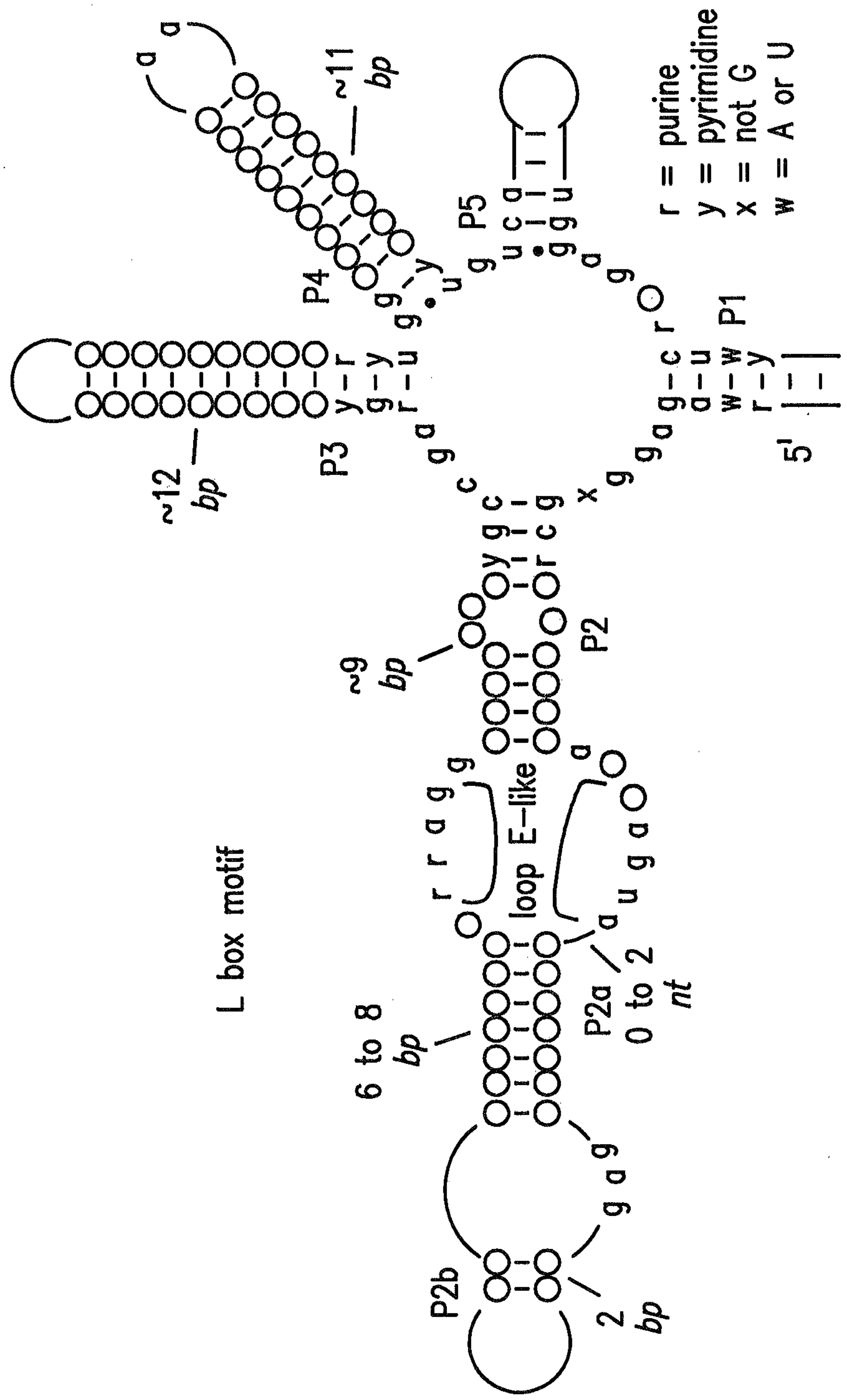
FIGS. 19A (SEQ ID NO:60 and SEQ ID NOs:400-408), 19B and 19C (SEQ ID NO:61) show the consensus L box motif from the lysC 5'-UTR of *B. subtilis* undergoes allosteric rearrangement in the presence of L-lysine. (A) Consensus sequence and structure of the L box domain as derived using a phylogeny of 31 representative sequences from prokaryotic and archaeal organisms (FIG. 18) BA 0845, BA lysA, BA lysP, BH dapA, BH lysC, BH nhaC, BS lysC, BX lysC, CA lysA, CP lysA, CP lysP, EC lysC, HI nhaC, OI dapA, OI nhaC, PM nhaC, SA lysC, SA lysP, SE lysC, SE lysP, SF lysC, SO lysC, SO nhaC, TM asd, TT lysA, TT pspF, VC lysC, VC nhaC, VC nhaC, VV lysC, VV nhaC, which are represented by SEQ ID NOs:29-59, respectively. Nucleotides depicted a lower case a, c, t, or g, are present in at least 80% of the representatives, open circles identify nucleotide positions of variable identity, and dashed lines denote variable nucleotide identity and chain length.

Beginning with the sequence homology reported to exist between the lysC 5'-UTRs of three bacterial species (Patte, J.-C., et al., 1998, *FEMS Microbiol. Lett.* 169:165-170), the number of representatives was expanded using an algorithm that searches for related sequences and secondary structures (e.g. see Examples 4 and 6). 31 representatives of this RNA domain, termed the "L box", in the 5'-UTRs of lysC homologs and other genes related to lysine biosynthesis from a number of Gram-positive and Gram-negative organisms were identified (FIG. 18). The sequence alignment reveals that the RNA forms a five-stem junction wherein major base-paired domains are interspersed with 56 highly conserved nucleotides (FIG. 19A). Furthermore, the base-paired elements P2, P2a, P2b, P3 and P4 each appear to conform to specific length restrictions, suggesting that they are integral participants in the formation of a highly structured RNA. It was also noticed that conserved sequences in the junction between stems P2 and P2a conform to a "loop E" motif, which is an RNA element that occurs frequently in other highly-structured RNAs (e.g. see Leonitis, N. B., and Westhof, E. 1998, *J. Mol. Biol.* 283:571-583).

Figure 19B:
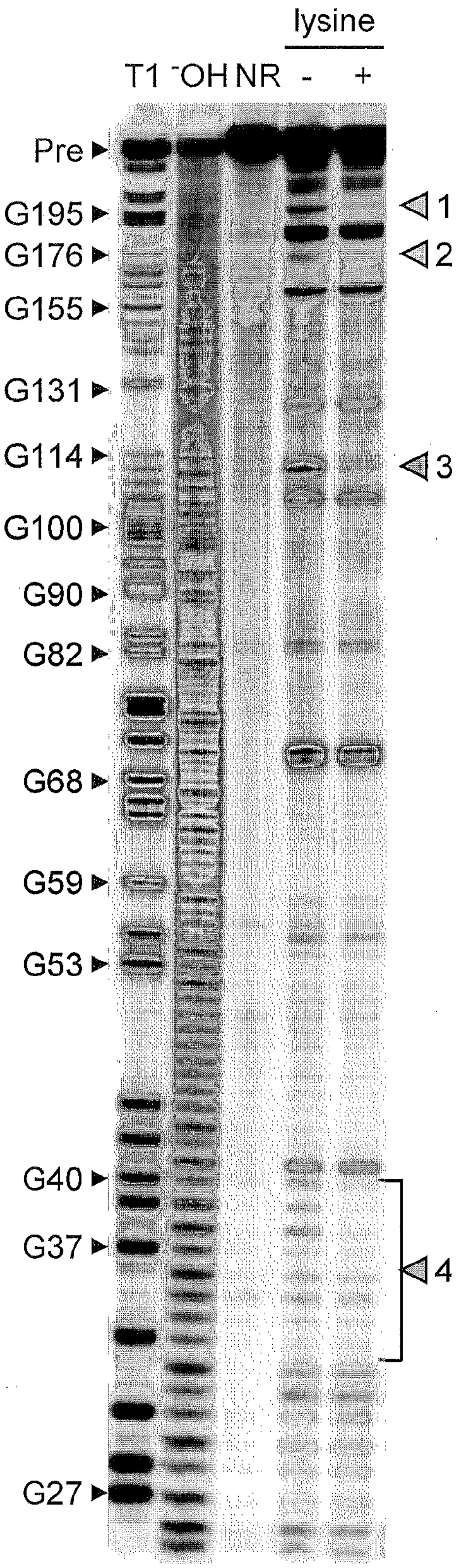
FIG. 19B shows sequence, secondary structure model, and lysine-induced structural modulation of the lysC 5'-UTR of *B. subtilis*. An additional 94 nucleotides (not depicted) reside between nucleotide 237 and the AUG start codon. Structural modulation sites (nucleotides enclosed in squares) were established using 237 lysC RNA by monitoring spontaneous RNA cleavage as depicted in C.
Figure 19C:
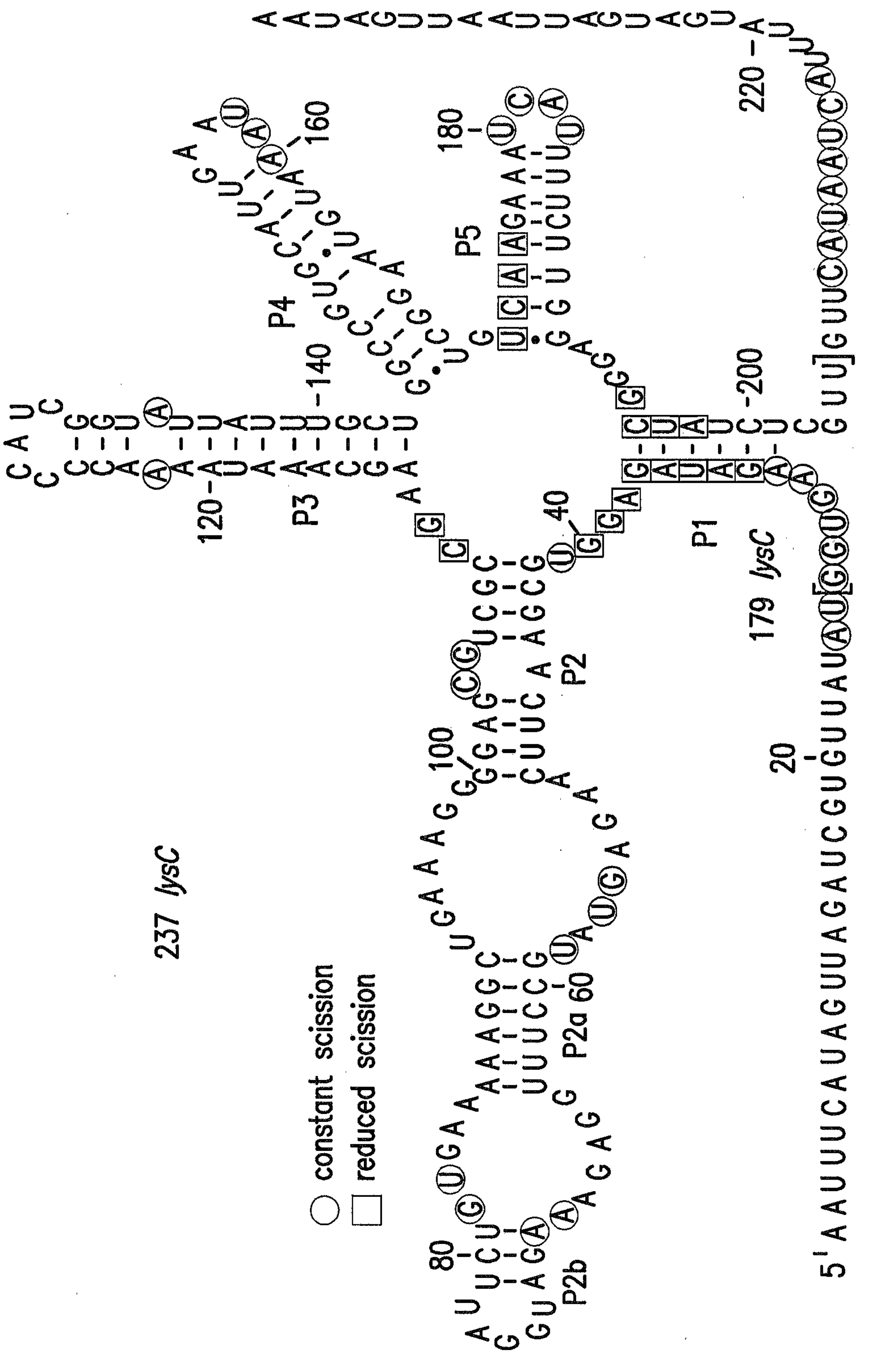
FIG. 19C shows in-line probing of the 237 lysC RNA reveals lysine-induced modulation of RNA structure. Patterns of spontaneous cleavage, revealed by product separation using denaturing 10% polyacrylamide gel electrophoresis (PAGE), are altered at four major sites (denoted 1 through 4) in the presence (+) of 10 μM L-lysine (L) relative to that observed in the absence (−) of lysine. T1, $^{-}$OH and NR represent partial digest with RNase T1, partial digest with alkali, and no reaction, respectively. Selected bands in the T1 lane (G-specific cleavage) are identified by nucleotide position. See Methods for experimental details.

The L box domain of the *B. subtilis* lysC mRNA resides immediately upstream from a putative transcription terminator stem (Kochhar, S., and Paulus, H. 1996, *Microbiol.* 142: 1635-1639; Patte, J.-C., et al., 1998, *FEMS Microbiol. Lett.* 169:165-170). In several other riboswitches with similar arrangements (e.g. Examples 3 and 6), the 5'-UTR can be trimmed to separate the minimal aptamer domain from the adjacent expression platform. An RNA fragment (237 lysC, FIG. 19B), encompassing nucleotides 1 through 237 of the lysC 5'-UTR, was generated and examined for allosteric function. This construct, which excludes the putative transcription terminator stem, was subjected to structural analysis by in-line probing (Soukup, G. A. and Breaker, R. R. 1999, *RNA* 5:1308-1325) to determine whether the presence of lysine alters RNA structure. It was observed that 237 lysC exhibits a pattern of spontaneous RNA cleavage (FIG. 19C) that is consistent with the secondary structure model of the L box motif constructed from phylogenetic sequence data. Furthermore, it was found that the addition of 10 μM L-lysine causes significant changes in the cleavage pattern at four locations along the RNA chain, indicating that allosteric modulation of the 5'-UTR fragment is occurring. In addition, the same pattern of spontaneous cleavage and amino acid-dependent structural modulation was observed when using the 179 lysC RNA construct, which encompasses only the most highly-conserved portion of the L-box motif (nucleotides 27 through 205 of the lysC 5'-UTR).

Figure 20A:
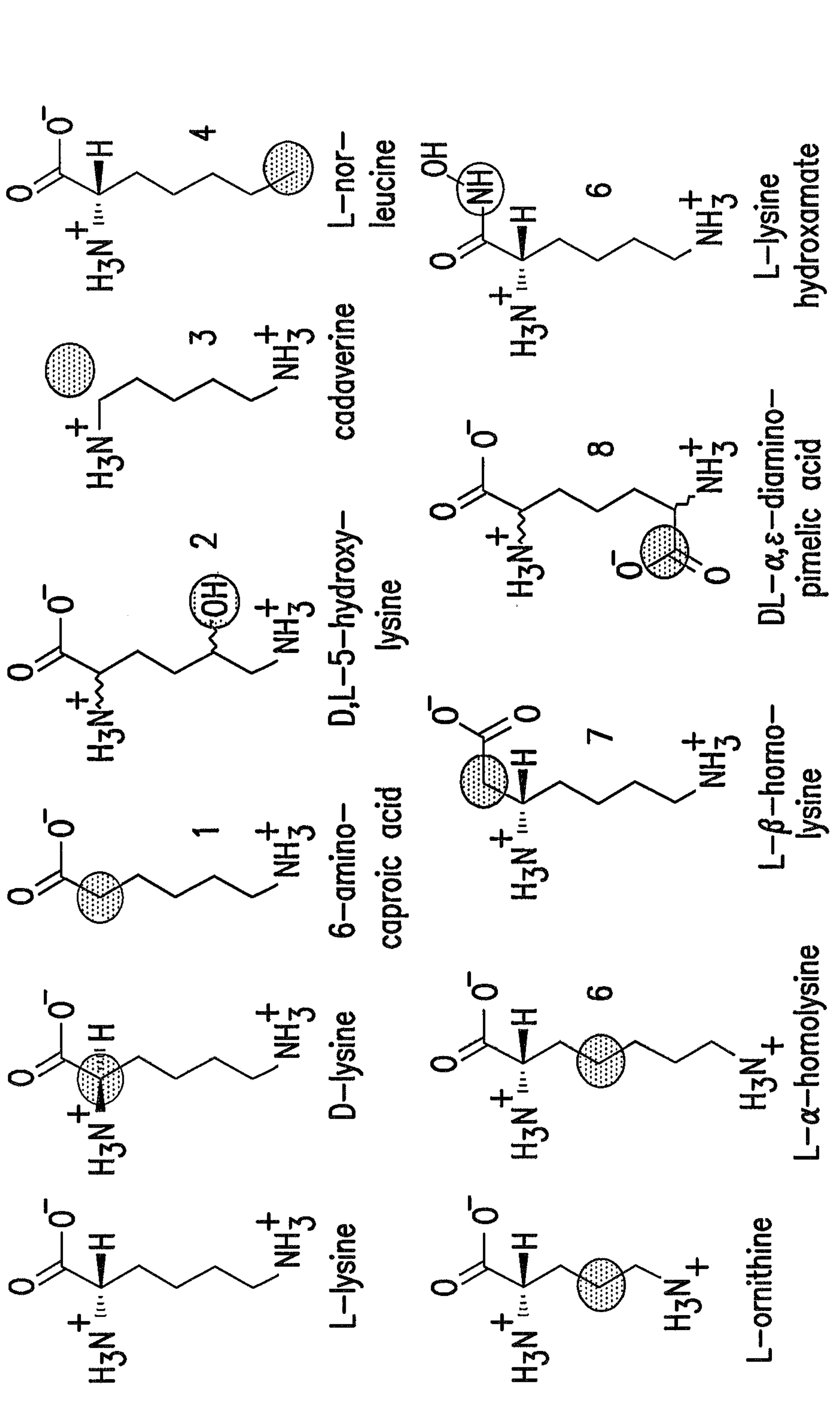
FIGS. 20A, 20B, 20C, 20D and 20E show the molecular recognition characteristics of the lysine aptamer and the use of caged lysine.
Figure 20B:
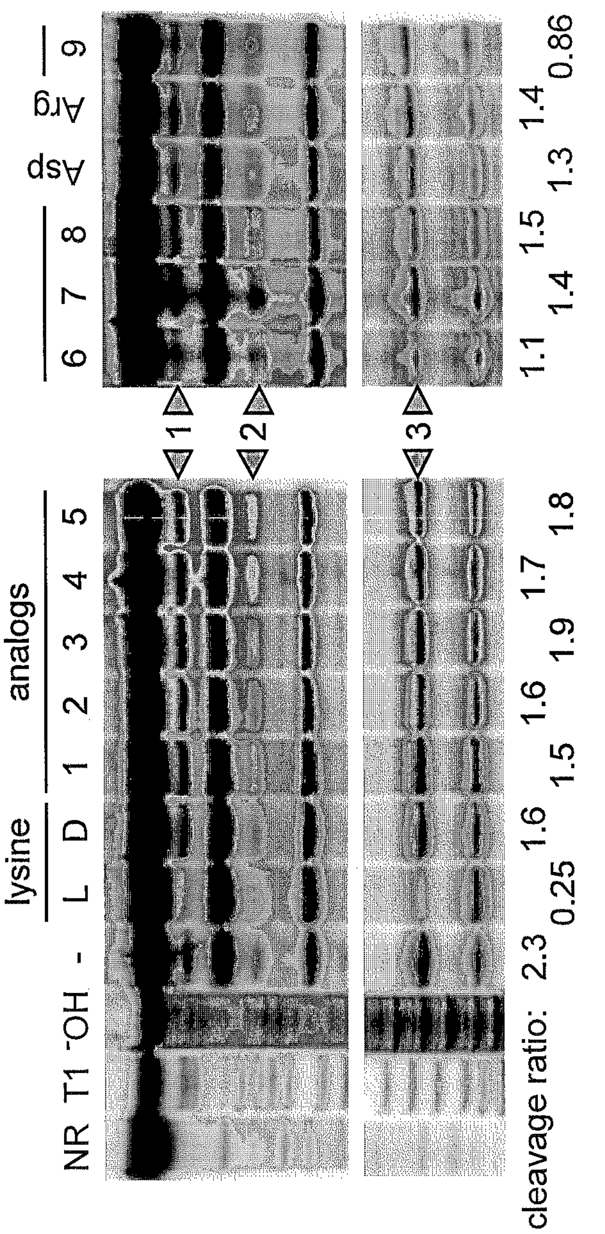

A reduction of spontaneous cleavage is observed in each of the four sites of metabolite-induced structural modulation. In most instances, a reduction in spontaneous cleavage is due to the nucleotides becoming more ordered in the complex formed between RNA and its ligand (Soukup, G. A. and Breaker, R. R. 1999, *RNA* 5:1308-1325). Interestingly, these four groups of nucleotides are located at the center of the 5-stem junction of the L box secondary structure model (FIG. 19B), implying that these nucleotides are directly involved in recognizing the amino acid target. Similar patterns of ligand-induced structural modulation have been observed with the aptamer domains of other riboswitches (see Examples 2, 3 and 6).

ii. The Lysine Aptamer Exhibits High Specificity for L-Lysine and Discriminates Against Closely-Related Analogs Riboswitches, like their counterpart genetic factors made of protein, must exhibit sufficient specificity and affinity for their target metabolite in order to achieve precision genetic control. To examine the molecular recognition characteristics of the lysC L box domain, a series of in-line probing assays were performed using various analogs of lysine at 100 μM. The properties of a lysine analog collection were examined, wherein each compound carries minimal chemical changes relative to L-lysine (FIG. 20A). Nearly every chemical alteration to the amino acid renders the compound incapable of causing a structural modulation of the 179 lysC RNA (FIG. 20B). Perhaps most striking is that the RNA does not undergo structural modulation in the presence of D-lysine, which differs from L-lysine by the stereochemical configuration at a single carbon center.

The absence of significant structural modulation in the presence of D-lysine and of other analogs indicates that at least three points of contact are being made between the RNA and its amino acid target. Specifically, the observation that analogs 1, 3, and 4 fail to induce structural modulation is consistent with contacts being made to the amino and carboxy groups of the chain atoms, and to the amino group of the side chain, respectively. Moreover, the failures of compounds 2, 5, 6, 7 and 8 to induce conformational change in the RNA indicate that the aptamer forms a highly discriminating binding pocket that can measure the length and the integrity of the alkyl side chain. This high level of molecular discrimination is of particular biological significance, as a genetic switch for lysine most likely must respond exclusively to L-lysine and not closely related natural compounds.

Figure 20C:
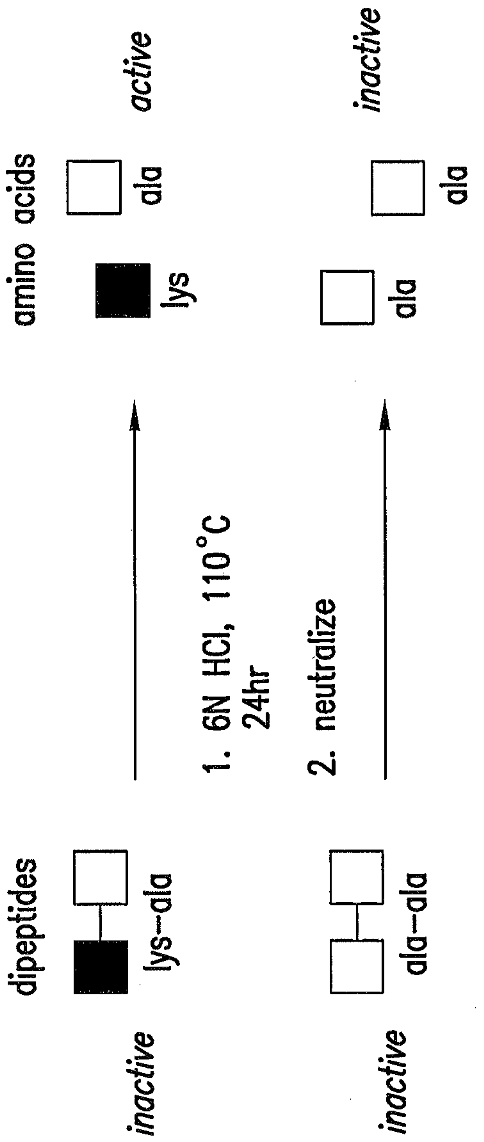
Figure 20D:
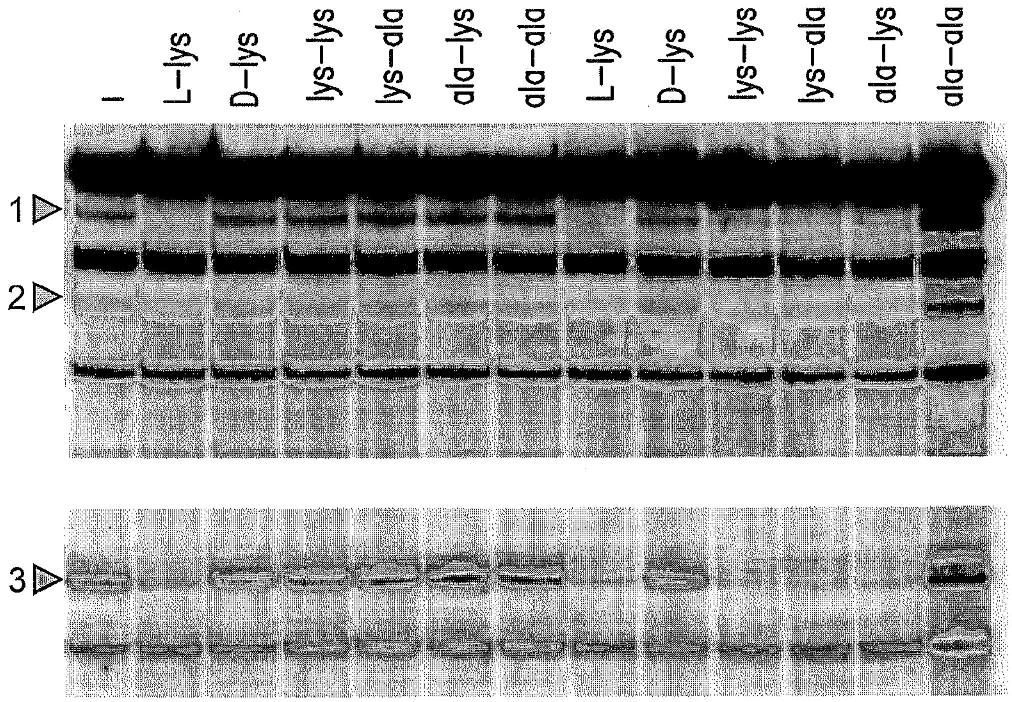

Similarly, the allosteric response of the 179 lysC RNA to various dipeptides and acid-hydrolyzed dipeptides was examined. It was hypothesized that dipeptides should not trigger allosteric modulation of RNA structure, but that acid-mediated hydrolysis of dipeptides (FIG. 20C) carrying at least 1 lysyl residue should become active. As predicted, 179 lysC does not undergo allosteric modulation upon the addition of the dipeptides lys-lys, lys-ala, ala-lys, or ala-ala (FIG. 20D). However, the three dipeptides that carry at least one lysyl residue induce structural modulation of RNA upon pre-treatment of the dipeptides with 6 N HCl at 115° C. for 23 hr, followed by evaporation and neutralization. The extent of structural modulation (FIG. 20E) indicates that the samples containing the hydrolyzed lysine-containing dipeptides fully saturate the lysC aptamer, which is in accordance with the acid-mediated release of saturating amounts (greater than 1 μM; see below) of L-lysine.

Figure 20E:
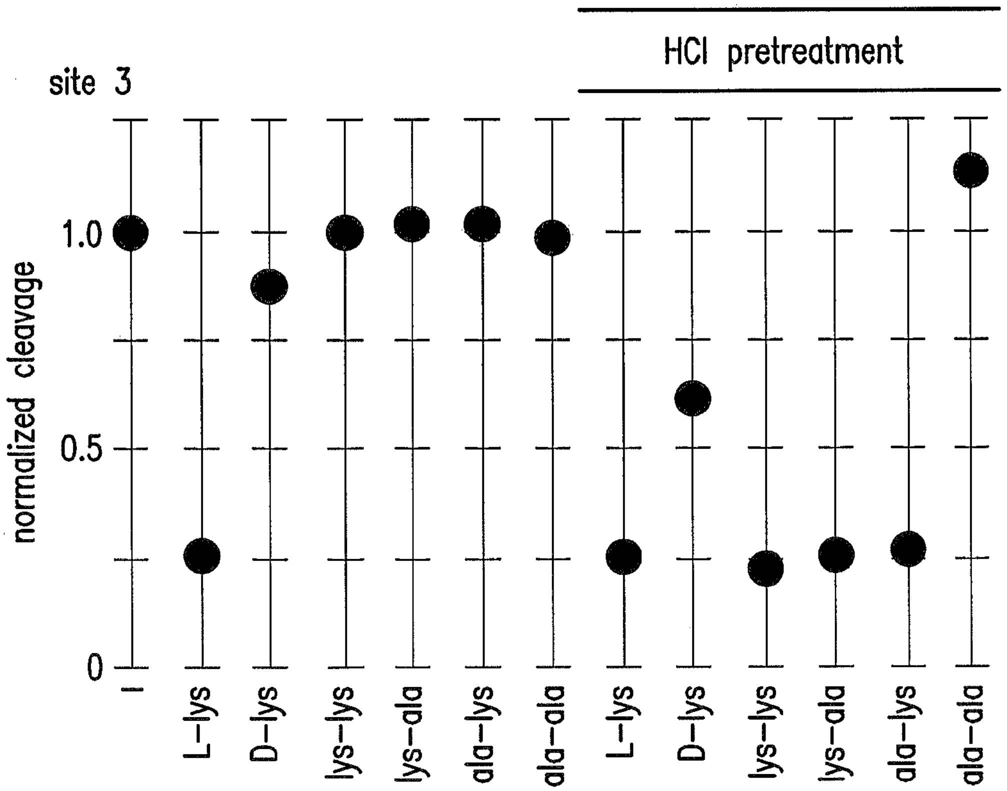

It was also observed that an intermediate level of structural modulation occurs when D-lysine is pre-treated with HCl. Interestingly, the published rate of epimerization between D- and L-lysine (Engel, M. H., and Hare, P. E. 1982. Racemization rates of the basic amino acids. *Year Book Carnegie Inst. Washington* 81:422-425) is sufficient to account for the approximately 1 μM of L-lysine that is needed to produce half-maximal structural modulation (FIG. 20E). These results are consistent with lysine acting as the molecular ligand for the lysC aptamer, and that RNA conformational changes are not due to unknown contaminants of the commercial L-lysine preparation.

iii. Binding Affinity and Stoichiometry of the *B. subtilis* L-Lysine Aptamer

Figure 21A:
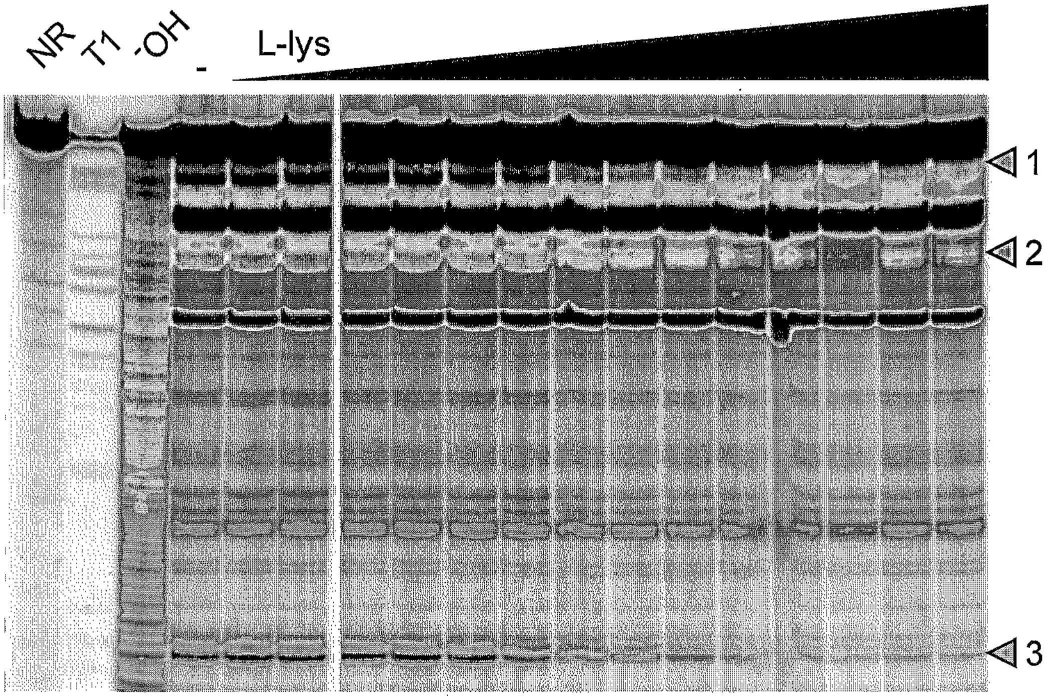
FIGS. 21A, 21B, 21C and 21D show determination of the dissociation constant and stoichiometry for L-lysine binding to the 179 lysC RNA.
Figure 21B:
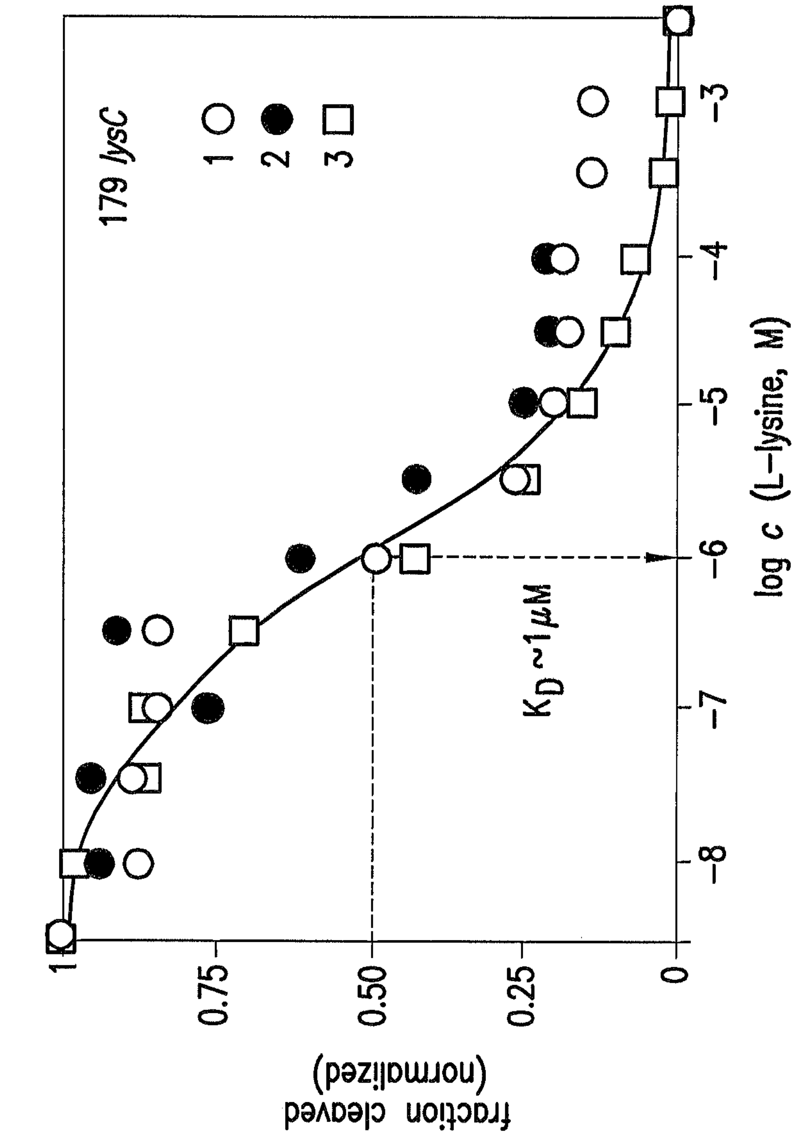

An approximation of the dissociation constant ($K_D$) was made by conducting in-line probing assays with 179 lysC using various concentrations of L-lysine (FIG. 21A). The sites of structural modulation exhibit progressively lower levels of spontaneous cleavage in response to increasing concentrations of ligand. A plot of the extent of RNA cleavage versus concentration of L-lysine (FIG. 21B) indicates that half-maximal structural modulation occurs when approximately 1 μM amino acid is present in the mixture, thus reflecting the apparent $K_D$ of the 179 lysC for its target ligand.

The apparent $K_D$ value for a longer construct that encompasses structural elements predicted to be involved in transcription termination exhibits a significantly poorer affinity for L-lysine. Specifically, an RNA construct encompassing nucleotides 1 through 315 of the lysC 5'-UTR was found by in-line probing to exhibit an apparent $K_D$ of ~500 μM. Similar differences in ligand affinities for other riboswitches have been observed, wherein the minimized aptamer binds more tightly its cognate ligand compared to the same aptamer in the context of the complete riboswitch (aptamer plus the adjoining expression platform). This is most likely due to the presence of competing secondary or tertiary structures that might be important for the function of the riboswitch as a genetic control element, but that reduce ligand binding affinity by reducing pre-organization of the aptamer domain.

Figure 21C:
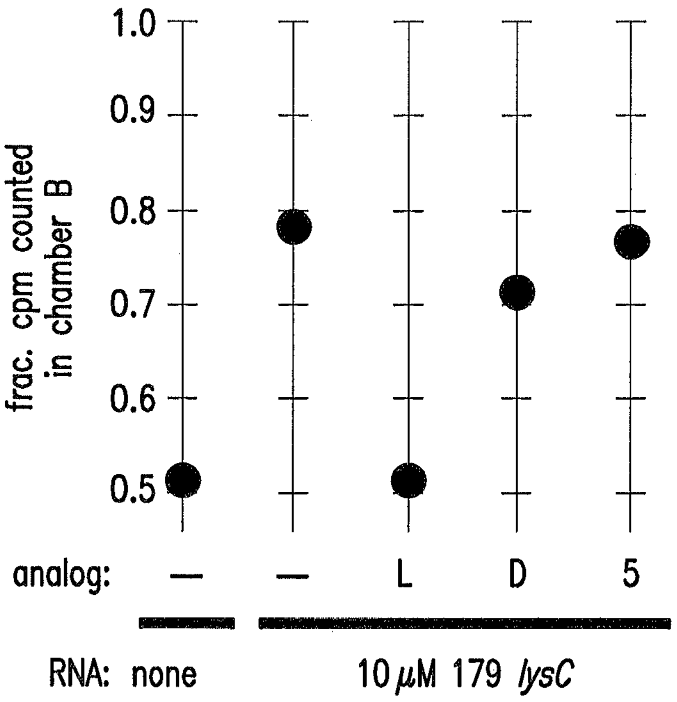

Equilibrium dialysis also was used to examine the affinity and specificity of the 179 lysC aptamer for its target (FIG. 21C). In the absence of RNA, tritiated L-lysine is expected to distribute equally between the two chambers (a and b) of an equilibrium dialysis apparatus. However, the addition of excess aptamer to one chamber of the system should shift the distribution of tritium towards this chamber as a result of complex formation. This asymmetric distribution of tritium is expected to be restored to unity by the addition of a large excess of unlabeled competitor ligand, which displaces the bulk of the tritiated lysine from the RNA. As expected, the fraction of tritiated L-lysine in chamber b of the equilibrium dialysis apparatus is ~0.5 in the absence of RNA (FIG. 21C) after a 10 hr incubation. This fraction is altered to ~0.8 after incubation when a 200-fold excess of 179 lysC (10 μM) is added to chamber b, while this symmetric distribution of tritium is restored upon incubation for an additional 10 hours after the introduction of excess (50 μM) unlabeled L-lysine. Furthermore, D-lysine and L-ornitihine do not restore equal distribution of tritium, which is consistent with their failure to modulate RNA structure as determined by in-line probing.

Figure 21D:
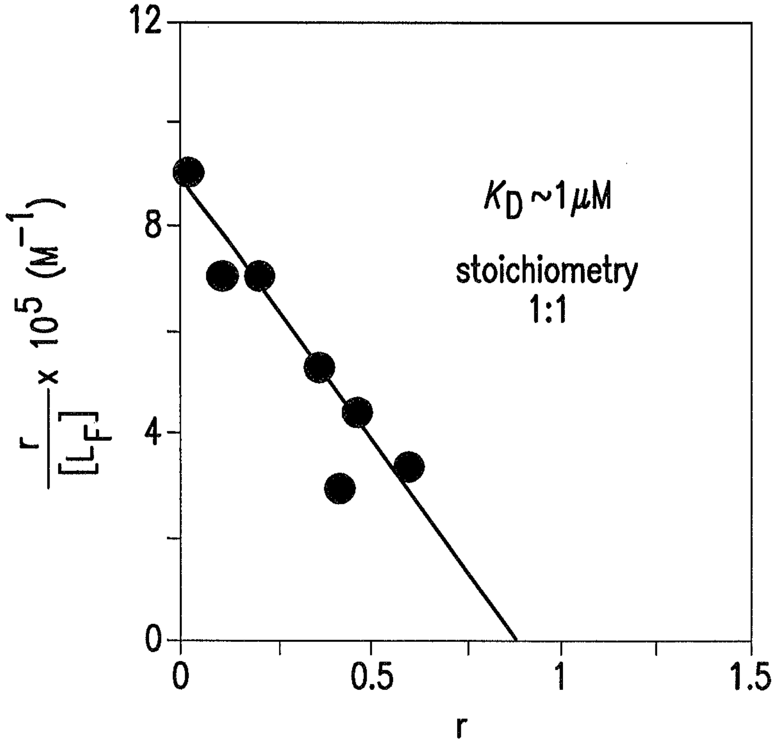
Figure 22A:
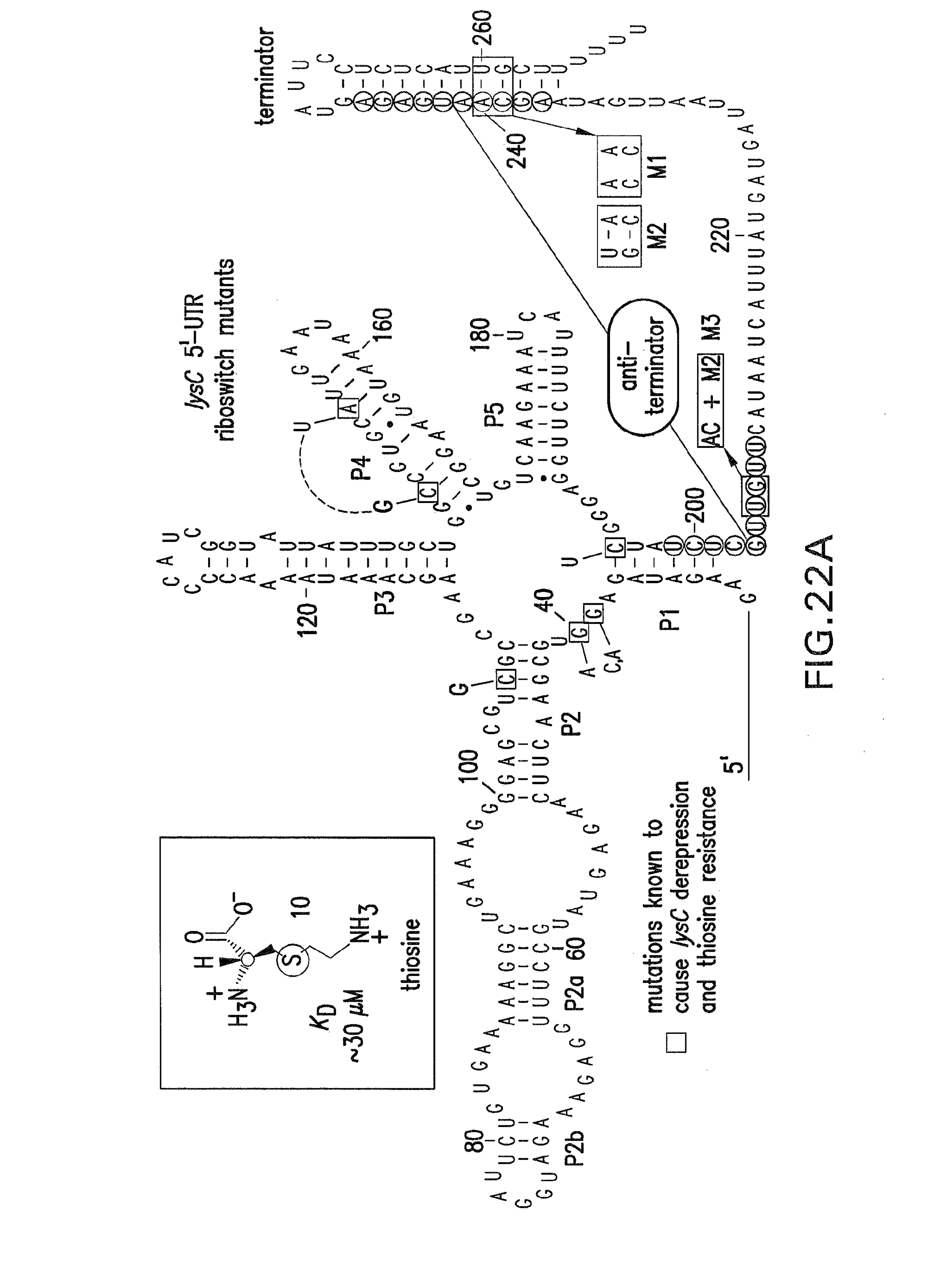
FIGS. 22A, 22B and 22C show the *B. subtilis* lysC riboswitch and its mechanism for metabolite-induced transcription termination.

A Scatchard plot also was created by using data from a series of equilibrium dialysis experiments conducted under various concentrations of tritiated L-lysine (FIG. 21D). The slope of the resulting line indicates that the 179 lysC RNA binds to L-lysine with an apparent $K_D$ of ~1 μM, which is consistent with that observed by using in-line probing. Furthermore, the x intercept of the line occurs near an r value of 1, which demonstrates that the RNA forms a 1:1 complex with its ligand.

iv. The Lysine Aptamer and Adjacent Sequences Function as an Amino Acid-Dependent Riboswitch With a number of riboswitches examined to date, there is a discernable set of structures residing immediately downstream of the aptamer domain that serve to control gene expression in response to ligand binding. Typically, the structure of this “expression platform” is modulated by metabolite binding to the aptamer domain. The alternative structure subsequently leads to modulation of transcription or translation processes. For example, the TPP riboswitch on the thiM mRNA of *E. coli* carries an expression platform that appears to preclude ribosome binding to the Shine-Dalgarno sequence of the adjacent coding region (see Example 2). Similarly, the expression platforms of various riboswitches from *B. subtilis* undergo ligand-induced formation of a stem-loop structure that induces transcription termination (e.g. Examples 3, 6 and 7). It has been reported that the lysC mRNA undergoes transcription termination in cultured *B. subtilis* cells grown in the presence of excess L-lysine (Kochhar, S., and Paulus, H. 1996, *Microbiol.* 142:1635-1639.). It was observed herein that a sequence domain that participates in forming the P1 stem of the lysC aptamer is complementary to a portion of the putative terminator hairpin that resides ~30 nucleotides downstream (FIG. 22A). This architecture is similar to that of several other riboswitches, some of which exhibit termination of transcription in vitro upon addition of the corresponding ligand as cited above. Therefore, the lysC leader sequence appears to serve as a L-lysine-specific riboswitch that induces transcription termination by modulating the formation of a terminator stem.

Figures 22B, 22C:
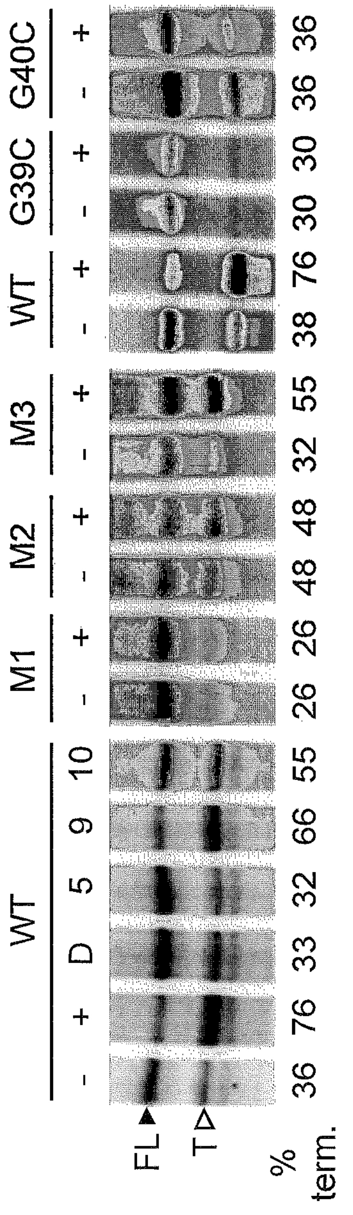

In vitro transcription assays were conducted in the absence and presence of L-lysine and several analogs (FIG. 22B, left). In the absence of added ligand, single-round transcription in vitro using *E. coli* RNA polymerase produces terminated product corresponding to ~36% of the total transcription yield. In contrast, the amount of terminated product increases to ~76% when 10 mM L-lysine is present during in vitro transcription. Neither D-lysine nor L-ornithine induce termination, which is consistent with the fact that these compounds are not recognized by the lysine aptamer domain and thus are not expected to trigger transcription termination.

The configuration of the expression platform for the lysC gene in *B. subtilis* strongly implicates a transcription termination mechanism, wherein the binding of L-lysine is expected to stabilize the P1 stem, thus permitting formation of the terminator hairpin (FIG. 22A). This proposed mechanism was examined by placing mutations within the critical pairing elements and by assessing lysine-induced transcription termination (FIG. 22B, center). Specifically, variant M1 carries two mutations that disrupt the formation of the terminator stem. This variant loses lysine-dependent modulation of transcription termination, and produces greater transcriptional read-through relative to the wild-type construct. M2 carries a total of four mutations that compensate for the disruption of the terminator stem, but that cause disruption of the anti-terminator stem. This construct also loses lysine-dependent modulation, whereas the amount of the terminated product expectedly becomes greater. Finally, the six-nucleotide variant M3 that carries the same mutations as M2 plus two additional mutations to restore the anti-terminator base-pairing potential results in near wild-type performance with regards to lysine-mediated modulation of transcription termination. These findings are consistent with a riboswitch mechanism wherein lysine binding precludes formation of an anti-terminator stem, thus increasing transcription termination by formation of an intrinsic terminator structure.

v. Evidence that Riboswitches Serve as Antibiotics Targets

Unlike other lysine analogs, both L-lysine hydroxymate and the antimicrobial compound thiosine (S-(2-aminoethyl)-L-cysteine; FIG. 22A, inset) cause an increase in transcription termination (FIG. 22B, left). These two compounds exhibit the best apparent $K_D$ values of any of the analogs tested, with values for L-lysine hydroxymate and thiosine of ~100 μM and ~30 μM, respectively (data not shown). In previous studies, a series of mutants were identified in *B. subtilis* (Vold, B., et al., 1975, *J. Bacteriol.* 121:970-974; Lu, Y., et al., 1992, *FEMS Microbiol. Lett.* 92:23-27) and *E. coli* (Patte, J.-C., et al., 1998, *FEMS Microbiol. Lett.* 169:165-170) that cause resistance to thiosine and cause derepression of lysC expression. These mutations all map to the lysine aptamer domain (see FIG. 22A for select *B. isubilis* mutants), and all appear to cause disruptions in the conserved elements or the base-pairing integrity of the structure.

The functional integrity of two thiosine-resistant mutants (G39A and G40A) was examined by equilibrium dialysis and by in line probing, and both mutants fail to exhibit lysine-binding activity. Furthermore, RNA constructs that carry mutations in the otherwise conserved P1-P2 junction fail to undergo lysine-dependent transcription termination in vitro (FIG. 22B, right). These findings suggest that the antimicrobial action of thiosine might at least partially be due to direct binding of the analog to the lysine riboswitch, causing repression of aspartokinase expression to a level that is deleterious to cell growth.

The function of the wild-type 5'-UTR of lysC and of the two thiosine-resistant mutants were also examined in vivo by fusion to a lacZ reporter gene. The wild-type riboswitch domain exhibits ligand-dependent modulation upon addition of L-lysine, whereas the G39A and G40A mutants fail to regulate β-galactosidase expression (FIG. 22C, medium II versus III). In contrast, lysine hydroxymate fails to repress expression of the reporter gene in vivo (medium IV), indicating that this compound might not attain a sufficiently high concentration inside cells to trigger transcription termination. As with lysine, thiosine also represses β-galactosidase expression for the wild-type construct, but not the two derepression mutants (medium V). This latter observation is consistent with the antimicrobial action of thiosine being due largely to its function as an effector for the lysine riboswitch.

3. Conclusions

The first mutants that caused deregulation of lysine biosynthesis in *B. subtilis* were identified nearly three decades ago (Vold, B., et al., 1975, *J. Bacteriol.* 121:970-974), however, the mechanism of genetic regulation has remained unresolved. Disclosed herein, it was demonstrated that the 5'-UTR of the lysC mRNA from *B. subtilis* serves as a riboswitch that responds to the amino acid lysine. The derepressed mutants isolated in the original study cause disruption of the aptamer domain of the riboswitch, such that the ligand is no longer bound by the RNA. Furthermore, in vivo expression studies using mutant lysC fragment-reporter gene fusions indicate that these riboswitch mutations most likely cause unregulated over-expression of aspartokinase, which catalyzes the first step in the biosynthetic pathway to lysine and several other amino acids.

Bacteria use various mechanisms to respond genetically to amino acid concentrations. Two of the more prominent mechanisms, translation-mediated transcription attenuation and T box-dependent mechanisms (Henkin, T. M., and Yanofsky, C. 2002, *BioEssays* 24:700-707), both sense the presence of non-aminoacylated tRNAs. Indeed, 18 of the 20 common amino acids in *B. subtilis* appear to be detected indirectly through the use of T box elements. Interestingly, there is no known $tRNA^{lys}$-dependent T-box in any organism, and presumably the lysine riboswitch described herein serves as the genetic sensor for this amino acid in the absence of a corresponding T box. Moreover, the genetic distribution of lysine riboswitches affiliated with the nhaC gene from several organisms indicates that this RNA genetic element might be a key regulator of cellular pH.

Since the lysC mRNA functions as receptor for L-lysine, the Lys riboswitch can serve as a drug target. (See other examples, Hesselberth, J. R., and Ellington, A. D. 2002, *Nature Struct. Biol.* 9:891-893; Sudarsan, N., et al., 2003, *RNA* 9:644-647). The lysine riboswitch, and perhaps other classes of riboswitches as well, can be targeted by analogs that selectively bind to the riboswitch and induce genetic modulation. In *B. subtilis*, an analog of lysine that triggers the riboswitch would be expected to function as an antimicrobial agent, because the reduction of aspartokinase expression should induce starvation for lysine and other critical metabolites. The finding that thiosine binds to the lysine aptamer in vitro, and causes down regulation of a reporter construct fused to the wild-type riboswitch, provides support for the view that riboswitches are a newly recognized class of targets for drug discovery.

Recent discoveries have been elucidating the roles of small RNAs in guiding gene expression in a wide range of organisms (for a review see Gottesman, S. 2002, *Genes Dev.* 16:2829-2842). It is apparent that small RNAs, including riboswitch domains embedded within mRNAs, can control gene expression by a wide range of mechanisms. Unlike other RNA genetic control elements, riboswitches directly bind to metabolites and control the expression of genes that are involved in the import and biosynthesis of a number of fundamental metabolites. Riboswitches examined previously respond to compounds that are chemically related to nucleotides. However, the existence of a class of riboswitches that responds to a small amino acid with high selectivity serves as proof that natural RNA switches can detect and respond to a greater range of metabolite classes.

F. Example 6

Guanine and Other Riboswitches in *Bacillus subtilis* and Other Bacteria

1. Summary

Riboswitches are metabolite-binding domains within certain messenger RNAs that serve as precision sensors for their corresponding targets. Allosteric rearrangement of mRNA structure is mediated by ligand binding, and this results in modulation of gene expression. A class of riboswitches that selectively recognizes guanine and becomes saturated at concentrations as low as 5 nM are disclosed herein. In *Bacillus subtilis*, this mRNA motif is located on at least five separate transcriptional units that together encode 17 genes that are mostly involved in purine transport and purine nucleotide biosynthesis. These findings provide further examples of mRNAs that sense metabolites and that control gene expression without the need for protein factors. Furthermore, it is now apparent that riboswitches contribute to the regulation of numerous fundamental metabolic pathways in certain bacteria.

2. Introduction

It is widely understood that the interplay of protein factors and nucleic acids guide the complex regulatory networks for genetic expression in modern cells. In most instances, protein factors appear to be well-suited agents for maintaining genetic expression networks. Proteins can adopt complex shapes and carry out a variety of functions that permit living systems to sense accurately their chemical and physical environments. Protein factors that respond to metabolites typically act by binding DNA to modulate transcription initiation (e.g. the lac repressor protein; Matthews, K. S., and Nichols, J. C., 1998, Prog. Nucleic Acids Res. Mol. Biol. 58, 127-164) or by binding RNA to control either transcription termination (e.g. the PyrR protein; Switzer, R. L., et al., 1999, Prog. Nucleic Acids Res. Mol. Biol. 62, 329-367) or translation (e.g. the TRAP protein; Babitzke, P., and Gollnick, P., 2001, J. Bacteriol. 183, 5795-5802). Protein factors respond to environmental stimuli by various mechanisms such as allosteric modulation or post-translational modification, and are adept at exploiting these mechanisms to serve as highly responsive genetic switches (e.g. see Ptashne, M., and Gann, A. (2002). Genes and Signals. Cold Spring Harbor Laboratory Press, Cold Spring Harbor, N.Y.).

In addition to the widespread participation of protein factors in genetic control, it is also known that RNA can take an active role in genetic regulation. Recent studies have begun to reveal the substantial role that small non-coding RNAs play in selectively targeting mRNAs for destruction, which results in down-regulation of gene expression (e.g. see Hannon, G. J. 2002, Nature 418, 244-251and references therein). This process of RNA interference takes advantage of the ability of short RNAs to recognize the intended mRNA target selectively via Watson-Crick base complementation, after which the bound mRNAs are destroyed by the action of proteins. RNAs are ideal agents for molecular recognition in this system because it is far easier to generate new target-specific RNA factors through evolutionary processes than it would be to generate protein factors with novel but highly specific RNA binding sites.

Many studies have now confirmed that the complex three-dimensional shapes that some RNA molecules can mimic protein receptors and antibodies in their ability to selectively bind proteins or even small molecules (Gold, L., et al., 1995, Annu Rev. Biochem. 64, 763-797; Hermann, T., and Patel, D., 2000, Science 287, 820-825). Furthermore, RNAs exhibit sufficient structural complexity to permit the formation of allosteric domains that undergo structural and functional modulation upon ligand binding (Soukup, G. A., and Breaker, R. R., 1999a, Proc. Natl. Acad. Sci. USA 96, 3584-3589; Seetharaman, S. et al., 2001, Nature Biotechnol. 19, 336-341). Natural RNAs also are capable of binding nucleotides, as demonstrated by the group I self-splicing RNA, which binds guanosine or its phosphorylated derivatives (McConnell, T. S., et al., 1993, Proc. Natl. Acad. Sci. USA 90, 8362-8366). More recently, evidence has been provided which indicates that direct binding of ATP by an RNA is essential for packaging DNA into a viral capsid (Shu, D., and Guo, P., 2003, J. Biol. Chem. 278, 7119-7125.).

The known riboswitches bind their target metabolites with high affinity and precision, which are essential characteristics for any type of molecular switch that can permit accurate and sensitive genetic control. For example, a recently identified riboswitch that responds to the coenzyme S-adenosylmethionine (SAM) binds it target with a dissociation constant ($K_D$) of ~4 nM (see Example 7). Furthermore, the riboswitch can discriminate ~100-fold against S-adenosylhomocysteine, which is a natural metabolite that differs from SAM by a single methyl group and an associated positive charge. Disclosed herein (Example 1) genetic control involving riboswitches is a widespread phenomenon with regard to its biological distribution and the target molecules that are being monitored. The observations that certain mRNAs from Archaeal organisms carry riboswitch-like domains (Stormo, G. D., and Ji., Y., 2001, Proc. Natl. Acad. Sci. USA 98, 9465-9467; Rodionov, D. A., et al., 2002, J. Biol. Chem. 277, 48949-48959) and that several mRNAs from fungi and plants bind thiamine pyrophosphate (TPP) (Sudarsan, N., et al., 2003, *RNA* 9:644-647).

The genetic regulation of purine transport and purine biosynthesis pathways in bacteria, which are fundamental to the metabolic maintenance of nucleotides and nucleic acids (Switzer, R. L., et al., 2002, A. L. Sonenshein, et al., eds., ASM Press, Washington, pp. 255-269), were analyzed for the presence of riboswitches. In *B. subtilis*, numerous genes are involved in the biosynthesis of purines (pur operon with 12 genes; Ebbole, D. J., and Zalkin, H. 1987, J. Biol. Chem. 262, 8274-8287) and in the salvage of purine bases from degraded nucleic acids. The involvement of a regulatory protein factor has been proposed to participate in the control of the xpt-pbuX operon that encodes a xanthine phosphoribosyltransferase and a xanthine-specific purine permease, respectively (Christiansen, L. C., et al., 1997, J. Bacteriol. 179, 2540-2550). Although the protein factor PurR is known to serve as a repressor of transcription in the presence of elevated adenine concentrations (Weng, M., et al., 1995, Proc. Natl. Acad. Sci. USA 92, 7455-7459), no protein with corresponding function has been identified in *B. subtilis* that responds to guanine Disclosed herein the xpt-pbuX operon is controlled by a riboswitch that exhibits high affinity and high selectivity for guanine This newfound class of riboswitches is present in the 5'-untranslated region (5'-UTR) of five transcriptional units in *B. subtilis,* including that of the 12-gene pur operon. Thus, direct binding of guanine by mRNAs serves as a critical determinant of metabolic homeostasis for purine metabolism in certain bacteria. Furthermore, it was determined that the known classes of riboswitches, which respond to seven distinct target molecules, appear to control at least 68 genes in *Bacillus subtilis* that are of fundamental importance to central metabolic pathways. These findings indicate that riboswitches play a substantial role in metabolic regulation in living systems that direct interaction between small metabolites and RNA is a significant and widespread form of genetic regulation in bacteria.

3. Experimental Procedures i. Chemicals and Oligonucleotides

Guanine and its analogs xanthine, hypoxanthine, adenine, guanosine, 7-methylguanine, $N^2$-methylguanine, 1-methylxanthine, 3-methylxanthine, 8-methylxanthine, 2-aminopurine, 2,6-diaminopurine, allopurinol, 2-amino-6-mercaptopurine, lumazine, and guanine-8-$^3$H hydrochloride were purchased from Sigma. Inosine, uric acid, 2-amino-6-bromopurine, O-methyl guanine and pterin were purchased from Aldrich.

DNA oligonucleotides were synthesized by the Keck Foundation Biotechnology Resource Center at Yale University, purified by denaturing PAGE and eluted from the gel by crush-soaking in 10 mM Tris-HCl (pH 7.5 at 23° C.), 200 mM NaCl, and 1 mM EDTA. Oligonucleotides were recovered from solution by precipitation with ethanol.

ii. Phylogenetic Analyses

G box domains were identified by sequence similarity to the xpt-pbuX 5'-UTR by conducting a BLASTN search of Genbank using default parameters. These hits were expanded by searching for degenerate matches to the pattern (<<<<[2] TA [6]<<<[2]ATNNGG [2]>>>[5]GTNTCTAC [3]<<<<< [3]CCNNNAA [3]>>>>>[5]>>>>) (SEQ ID NO:377). Angled brackets indicate base pairing. Bracketed numbers are variable gaps with constrained maximum lengths denoted. A total of four violations of this pattern were permitted when forming the phylogeny depicted in FIG. 23. It is important in this instance to note that only the BS3-xpt domain (that of the xpt-pbuX leader) has been shown to bind guanine. It was demonstrated that the molecular specificity of the VV1 representative is for adenine and not guanine (unpublished data). Given the possible trivial means by which a guanine-binding RNA aptamer might be altered to bind adenine (e.g. a C to U change if the C residue is used by the aptamer to make a Watson-Crick-pairing interaction with guanine), it cannot be ruled out that other representatives also have altered molecular recognition.

iii. In-line Probing of RNA Constructs

The *B. subtilis* 201 xpt leader and truncated 93 xpt aptamer RNAs were prepared by in vitro transcription using T7 RNA polymerase and the appropriate PCR DNA templates, and were subsequently 5' $^{32}$P-labeled using a protocol similar to that described previously (Seetharaman, S. et al., 2001, Nature Biotechnol. 19, 336-341). Labeled precursor RNAs (~2 nM) were subjected to in-line probing using conditions similar to those described in Example 2. Reactions (10 μL) were incubated for 40 hr at 25° C. in a buffer containing 50 mM Tris (pH 8.5 at 25° C.), 20 mM $MgCl_2$ and 100 mM KCl in the presence or absence of purines as indicated for each experiment. Purine concentrations ranging from 1 nM to 10 μM were typically employed but ranged as high as 300 μM for poor-binding ligands. Denaturing 10% PAGE was used to separate spontaneous cleavage products and a Molecular Dynamics PhosphorImager was used to view the results. Quantitation of spontaneous cleavage yields was achieved by using ImageQuaNT software. Since concentrations of RNA below 2 nM for in-line probing cannot be used easily due to insufficient levels of signal, apparent $K_D$ values near this concentration reflect the maximum possible value.

iv. Equilibrium Dialysis

Equilibrium dialysis assays were conducted using a DispoEquilibrium Dialyzer (ED-1, Harvard Bioscience), wherein two chambers a and b were separated by a 5,000 MWCO membrane. The final composition of buffer included 50 mM Tris-HCl (pH 8.5 at 25° C.), 20 mM $MgCl_2$ and 100 mM KCl (30 μL delivered to each chamber). Chamber a also contained 100 nM $^3$H-guanine, while chamber b also contained 300 nM of xpt RNA constructs as indicated for each experiment. After 10 hr of equilibration at 25° C., a 5 μl aliquot from each chamber was removed for quantitation by liquid scintillation counter. When appropriate, an additional 5 μL of buffer was added to a and an equivalent volume of buffer containing 500 nM unlabeled purine was added to b. After an additional 10 hr incubation at 25° C., 5 μl aliquots were again drawn for quantitation of tritium distribution.

v. Construction of xpt-lacZ Fusions

Genetic manipulations were conducted using approaches similar to those described elsewhere herein. Briefly, a DNA construct encompassing nt −121 to +197 relative to the transcription start site of the xpt-pbuX operon from *B. subtilis* strain 1A40 (Bacillus Genetic Stock Center, Columbus, Ohio) was PCR amplified as an EcoR1-BamH1 fragment. The product was cloned into pDG1661 at a site directly upstream of the lacZ reporter gene. Mutants were created within the engineered pDG1661 by using the appropriate primers and the QuickChange Site-directed mutagenesis kit (Stratagene). Plasmid variants were integrated into the amyE locus of strain 1A40. Transformants were selected for chloramphenicol (5 μg $ml^{-1}$) resistance and screened for sensitivity to spectinomycin (100 μg $ml^{-1}$). The integrity of each construct was confirmed by sequencing.

vi. Guanine-mediated Modulation of β-galactosidase Expression

*B. subtilis* cells were grown with shaking at 37° C. in minimal media containing 0.4% w/v glucose, 20 g $L^{-1}$ $(NH_4)_2SO_4$, 25 g $L^{-1}$ $K_2HPO_4.3H_2O$, 6 g $L^{-1}$ $KH_2PO_4$, 1 g $L^{-1}$ sodium citrate, 0.2 g $L^{-1}$ $MgSO_4.7H_2O$, 0.2% glutamate, 5 μg $ml^{-1}$ chloramphenicol, 50 μg $ml^{-1}$ L-tryptophan, 50 μg $m^{-1}$ L-lysine and 50 μg $ml^{-1}$ L-methionine. Purines were added at a final concentration of 0.5 mg $ml^{-1}$. Cells at mid exponential stage ($A_{595}$ of ~0.1) were harvested by centrifugation and resuspended in minimal media in the absence or presence of a purine (0.5 mg $mL^{-1}$) as indicated for each experiment. Although the poor solubility of guanine causes the formation of a detectable level of precipitate at this concentration, no adverse affects of cell growth were observed. Unless otherwise specified, cells were incubated for an additional 3 hrs before performing β-galactosidase assays. Data presented in FIG. 28C was generated as described above with the exception that β-galactosidase assays were performed at the times indicated.

4. Results and Discussion i. A Conserved Domain in the 5'-UTR of Several *B. subtilis* mRNAs.

The xpt-pbuX operon is regulated by guanine, hypoxanthine, and xanthine. These purine compounds share chemical similarity and are adjacent to each other in the pathways of purine salvage. In contrast to the pur operon, regulation of the xpt-pbuX operon remains unaffected by adenine in a strain wherein adenine deaminase is inactive (Christiansen, L. C., et al., 1997, J. Bacteriol. 179, 2540-2550). These observations had fostered speculation that an unidentified protein factor might be involved in guanine recognition (Ebbole, D. J., and Zalkin, H. 1987, J. Biol. Chem. 262, 8274-8287), however, such a genetic factor has not been identified. Moreover, the 5'-UTR of the xpt-pbuX mRNA is rather large (185 nucleotides), which could be sufficient to accommodate a riboswitch domain.

Riboswitches are typically composed of two functional domains: an aptamer that selectively binds its target metabolite and an expression platform that responds to metabolite binding and controls gene expression by allosteric means. The most conserved portion of known riboswitches is the aptamer domain, whereas the adjoining expression platform can vary widely in sequence and in secondary structure. The high sequence conservation of the aptamer is due to the fact that the RNA must retain its ability to form a receptor for a chemical that does not change through evolution. In contrast, the expression platform can form one of a great diversity of structures that permit genetic control in response to ligand binding by the aptamer domain. This evolutionary conservation was exploited to conduct a database search for xpt-pbuX 5'-UTR sequences that are present in other *B. subtilis* genes and also in other bacterial species. Five transcriptional units within *B. subtilis* that closely correspond in sequence and predicted secondary structure with nucleotides 14 through 82 of the xpt-pbuX 5'-UTR (FIG. 23) were identified. A total of 32 representatives of this domain were identified amongst several Gram-positive and Gram-negative bacteria. Other members can exist as well.

Figure 24A:
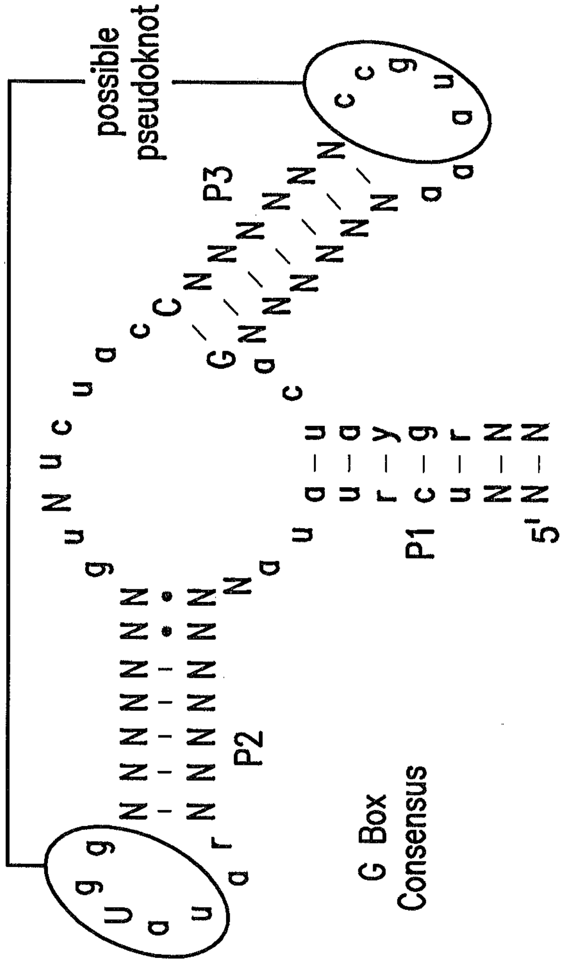
FIGS. 24A, 24B and 24C show the G box RNA of the xpt-pbuX mRNA in *B. subtilis* responds allosterically to guanine

From this representative set of RNAs, a consensus sequence and secondary structure for the conserved RNA motif termed the "G box" (FIG. 24A) were identified. The secondary structure of the G box is composed of a three-stem (P1 through P3) junction, wherein significant sequence conservation occurs within P1 and in the unpaired regions. Furthermore, it was found that stems P2 and P3 both favor seven base pairs in length with one- or two-base mismatches permitted. This unusual conservation of stem length implies that these structural elements establish distance and orientation constraints of their stem-loop sequences relative to the three-stem junction. Some base-pairing potential exists between the two stem-loop sequences, which might permit the formation of a pseudoknot. These characteristics indicate that G-box domains most likely use conserved secondary- and tertiary-structure elements to adopt a precise three-dimensional fold.

ii. The G box RNA from the xpt-pbuX 5'-UTR of *B. subtilis* Binds Guanine

Figure 24B:
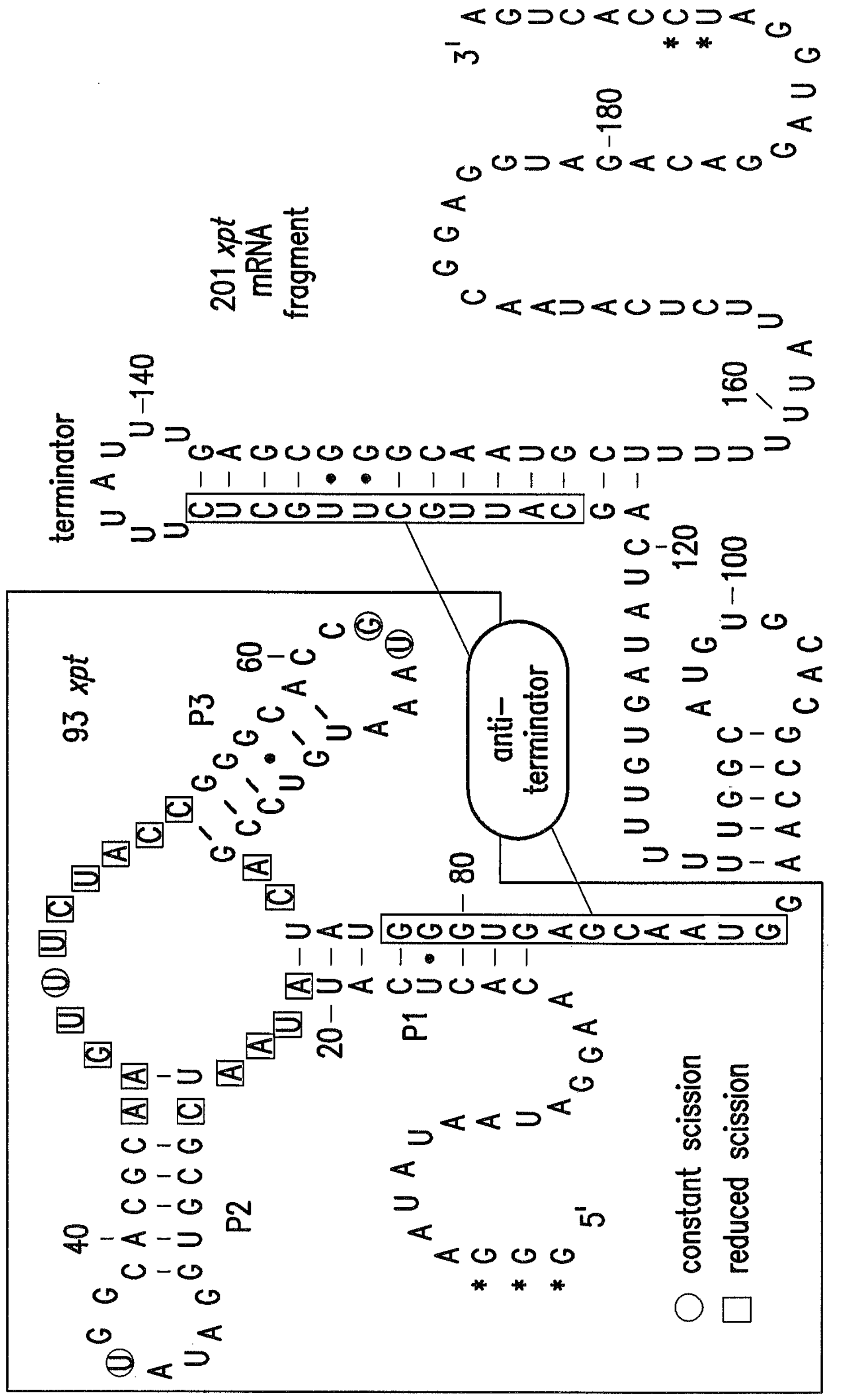

Two RNA constructs based on the xpt-pbuX 5'-UTR of *B. subtilis* were prepared to examine whether the mRNA selectively binds guanine or its closest analogs. A double-stranded DNA template corresponding to the entire 5' UTR and the first four codons of the xpt-pbuX mRNA was generated by PCR using primers that introduced a promoter sequence for T7 RNA polymerase and several nucleotide additions and mutations that permit further manipulation (FIG. 24B; see also Experimental Procedures). A truncated form of this construct also was created by PCR that encompasses the 5' half of the UTR. Upon transcription, the shorter DNA template generates a 93-nucleotide transcript termed 93 xpt, while the longer template produces a 201-nucleotide transcript termed 201 xpt.

Figure 24C:
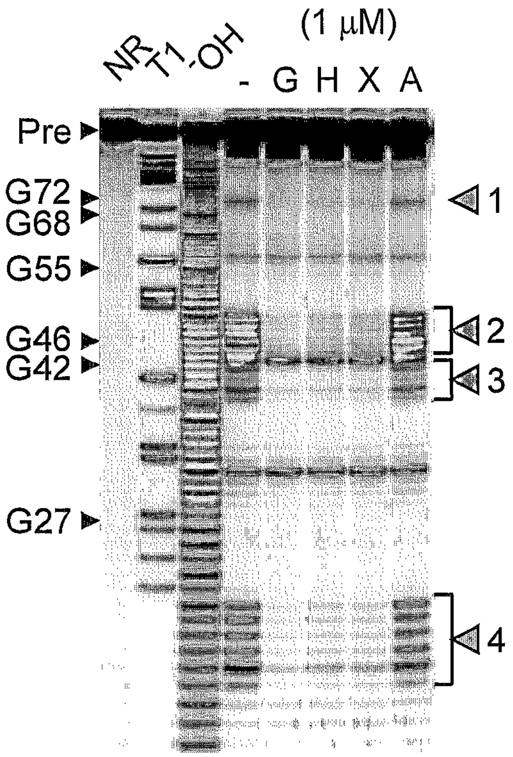

These precursor RNAs were 5' $^{32}P$-labeled and subjected to an in-line probing assay (e.g. see Example 1) wherein the spontaneous cleavage of RNA linkages within an aptamer is monitored in the presence and absence of its corresponding ligand. It was found that the patterns of spontaneous cleavage of the 93 xpt (FIG. 24C) and the 201 xpt (FIG. 25A) RNAs undergo significant alteration upon addition of guanine at a concentration of 1 μM. Both hypoxanthine and xanthine also induce modulation of spontaneous cleavage at this concentration. Specifically, four major regions exhibit ligand-mediated reduction in spontaneous cleavage (FIGS. 24B and 24C). However, the presence of 1 μM adenine (and as much as 1 mM) does not alter the pattern of RNA cleavage products. These results indicate that the G box domain in the 5' UTR of the *B. subtilis* xpt-pbuX mRNA serves as an aptamer for guanine and related purines, and that this aptamer undergoes significant structural modulation upon ligand binding. In the context of a riboswitch, this allosteric function could be harnessed by the mRNA to modulate structural elements that regulate gene expression.

Figure 25A:
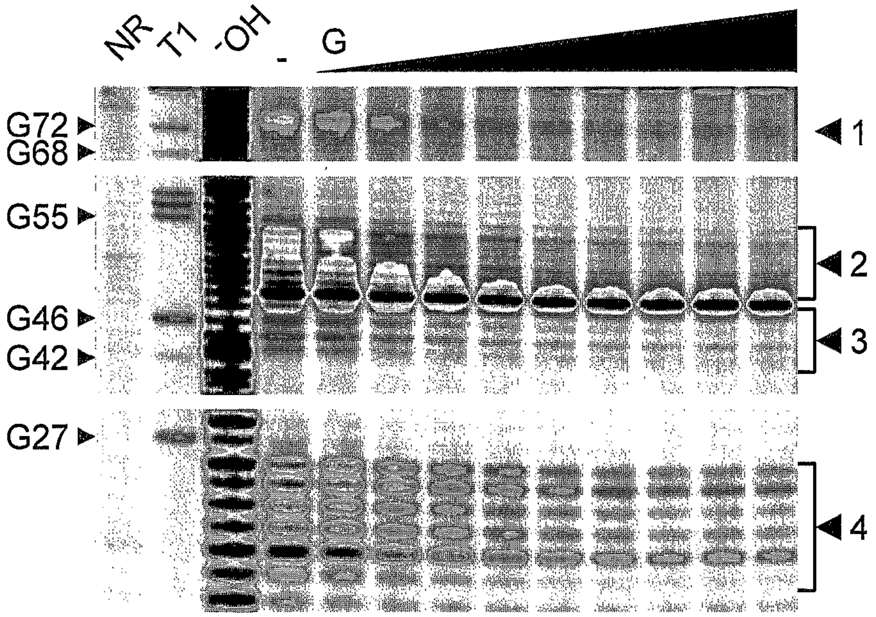
FIGS. 25A and 25B show the 201 xpt mRNA Leader Binds Guanine with High Affinity.
Figure 25B:
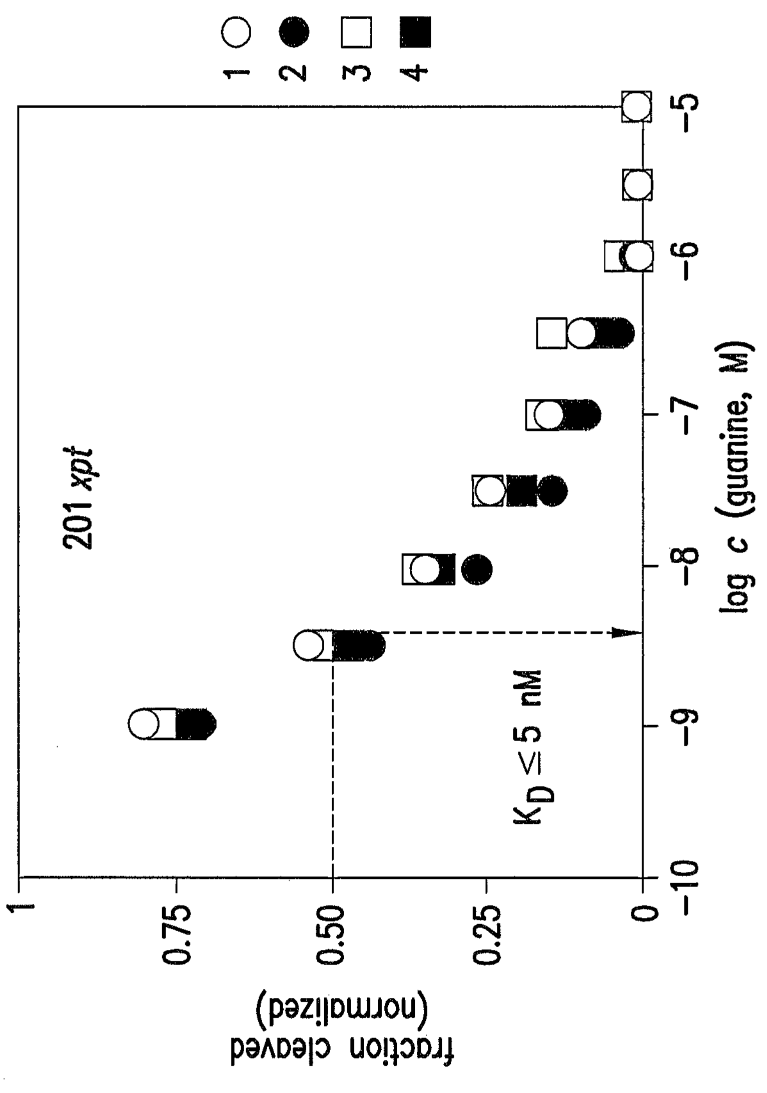

In a preliminary assessment of the affinity that the guanine aptamer has for its target, in-line probing with 201 xpt in the presence of various concentrations of guanine was conducted. As expected, increasing concentrations provided progressively decreasing amounts of spontaneous cleavage at the four major sites of structural modulation (FIG. 25A). Half-maximum levels of modulation were observed when a concentration of ~5 nM guanine is used for in-line probing (FIG. 25B). Although this implies that the $K_D$ for 201 xpt under these conditions is ~5 nM, it is important to note that the actual value might be somewhat lower because of the limitations of the in-line probing assay (see Experimental Procedures). In addition, the $K_D$ was determined under non-physiological conditions (e.g. high $Mg^{2+}$ and elevated pH), and so the binding affinity might be somewhat different in vivo. However, using this number for comparison, the affinity of the 201 xpt RNA for guanine is more than 10,000-fold greater than that of the *Tetrahymena* group I ribozyme for its guanosine monophosphate substrate (McConnell, T. S., et al., 1993, Proc. Natl. Acad. Sci. USA 90, 8362-8366). This difference most likely reflects the relative differences in concentrations of the two compounds that the RNAs experience inside their respective cellular environments.

iii. The Guanine Aptamer Discriminates Against Many Purine Analogs

To maintain precise metabolic homeostasis, the cell must be able to sense the concentration of its target metabolite, but also must prevent regulatory cross talk with other compounds that otherwise might inadvertently trigger genetic modulation. Indeed, a hallmark of other riboswitches is the ability to discriminate between closely related metabolites. For example, the FMN and TPP riboswitches discriminate against the unphosphorylated coenzyme precursors thiamine and riboflavin by ~1,000 fold (see Examples 2 and 3).

Figure 26A:
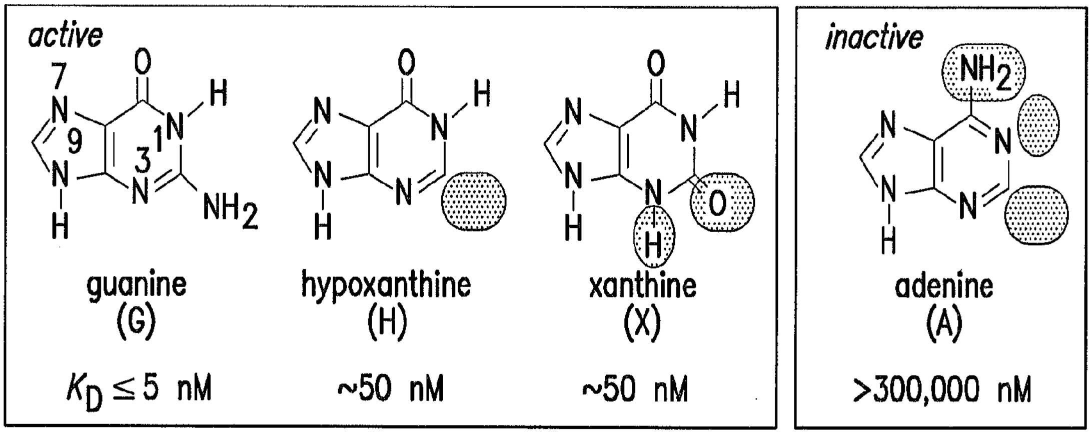
FIGS. 26A, 26B and 26C show a molecular discrimination by the guanine-binding aptamer of the xpt-pbuX mRNA.

This requirement for obligate molecular discrimination against related metabolites is expected to be extreme with guanine riboswitches, as there are numerous purine nucleosides and nucleotides, purine bases, and purine-like compounds that are present in the cell. Using the in-line probing strategy described in FIG. 25, the apparent $K_D$ values of the 93 xpt RNA were established for a variety of purines and purine analogs. Hypoxanthine and xanthine exhibit $K_D$ values that are closest to the value determined for guanine, while adenine has a $K_D$ value in excess of 300 μM (FIG. 26A).

These results are consistent with the observation that adenine does not significantly repress expression of the xpt-pbuX operon as do the other purines (Christiansen, L. C., et al., 1997, J. Bacteriol. 179, 2540-2550). However, it is not clear whether hypoxanthine and xanthine might repress gene expression by directly binding a guanine riboswitch, or whether they might first be converted into guanine before influencing genetic control.

Figure 26C:
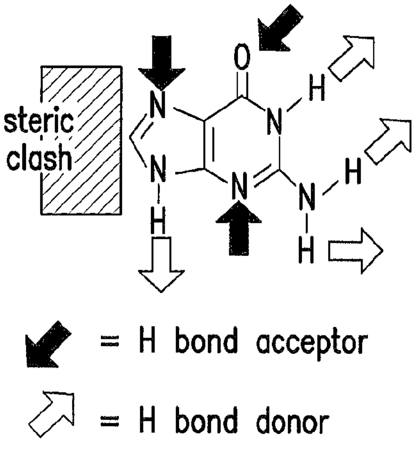
Figure 26B:
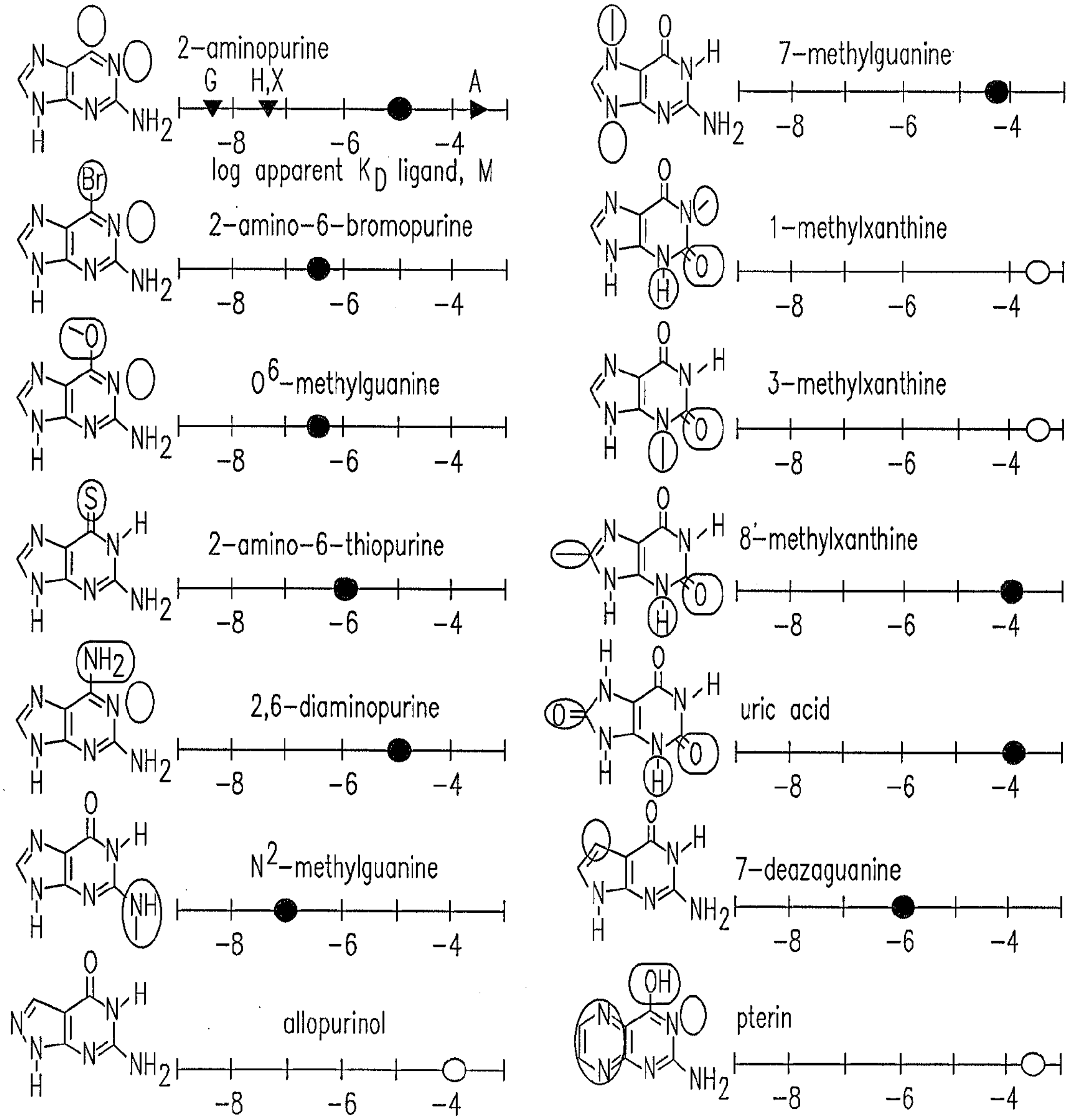

It was found that alteration of every functionalized position on the guanine heterocycle causes a substantial loss of binding affinity (FIG. 26B, FIG. 27). For example, the oxygen atom at position 6 of guanine is a significant determinant of molecular recognition, as demonstrated by the losses in apparent $K_D$ for 2-aminopurine (>10,000-fold loss), 2-amino-6-bromopurine (~1,000 fold), and $O^6$-methylguanine (>100 fold). Most molecular interactions could be explained by invoking hydrogen-bonding contacts between the RNA and guanine with the exception of the molecular interaction at C8. Here, presumably the RNA structure creates a steric clash with analogs that carry additional bulk, such as 8-methylxanthine (>10,000 fold) and uric acid (>10,000 fold).

A summary of the likely molecular recognition features that the guanine aptamer requires for maximum affinity is depicted in FIG. 26C. However, the likely possibility that significant binding affinity could be derived through base stacking was not examined. The presence of so many productive contacts between the RNA and all faces of guanine suggest that the ligand is most likely entirely engulfed by the aptamer's structure. This would also explain why the RNA is capable of generating recognition via steric occlusion of bulkier compounds such as uric acid. In certain biological environments, for example, uric acid can build up to high concentrations that permit crystallization. In such environments, a bacterium would require a high level of discrimination to prevent undesirable repression of guanine-regulated genes. In light of such molecular recognition challenges, it is not surprising that an RNA genetic switch would evolve extensive molecular contacts with its target compound.

iv. Confirmation of Guanine Aptamer Function by Equilibrium Dialysis

Figure 27A:
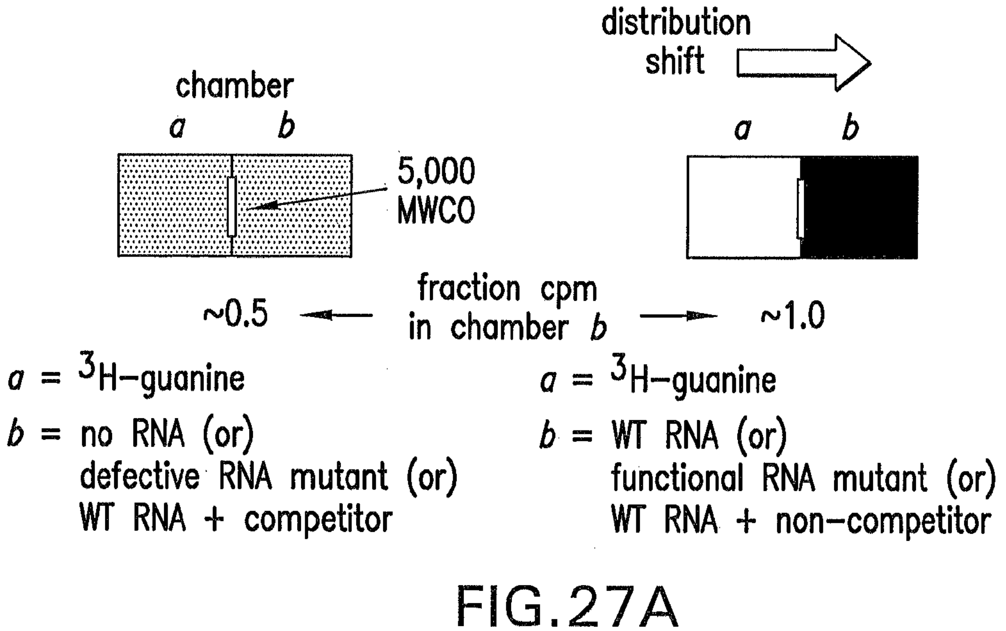
FIGS. 27A and 27B show confirmation of guanine binding specificity by equilibrium dialysis.
Figure 27B:
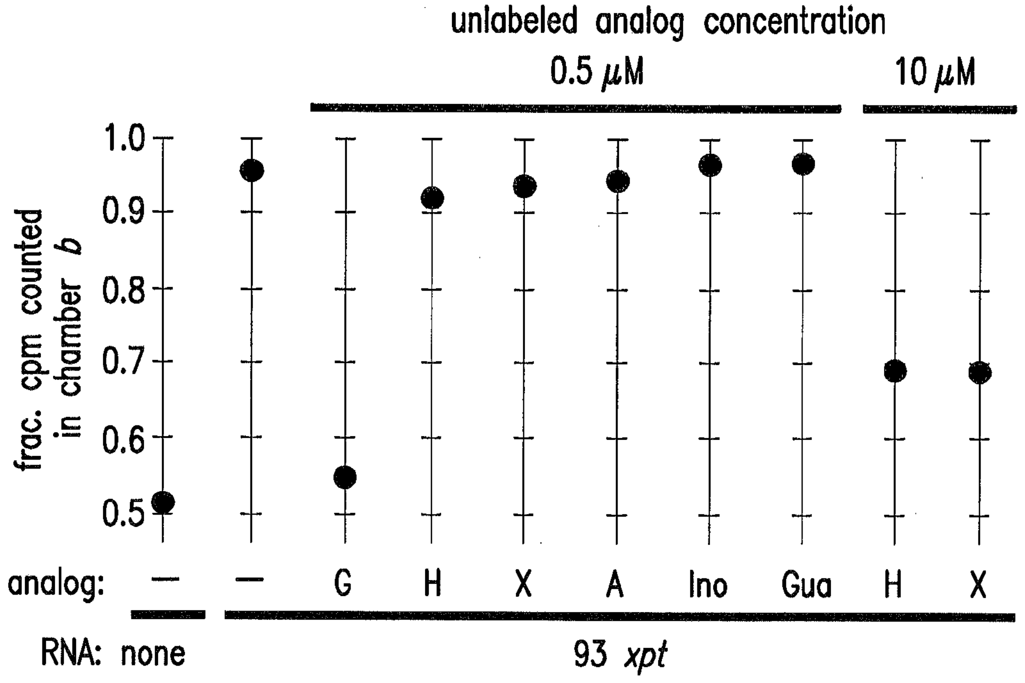

Equilibrium dialysis was used to provide further evidence that the G box RNA from the xpt-pbuX operon binds guanine preferentially over other purines and purine analogs. A substantial shift in tritiated guanine is expected to occur in a two-chamber dialysis apparatus when an excess of functional RNA is added to one chamber (FIG. 27A). Furthermore, this shifted equilibrium should return to unity upon addition of an excess of unlabeled competitor ligand. As expected, it was observed that greater than 90% of tritiated guanine co-localizes with 93 xpt RNA, and subsequently redistributes when an excess of unlabeled guanine is introduced. In contrast, the presence of excess unlabeled analogs has no effect on co-localization of $^3$H-guanine and the RNA (FIG. 27B). Even the nucleoside guanosine (9-ribosylguanine) fails to restore equal distribution of guanine between the two chambers, which is consistent with the RNA folding to form a tight pocket for the base alone.

Both in-line probing and equilibrium dialysis data indicate that this natural aptamer binds guanine with high affinity and specificity. In a previous study, in vitro evolution was used to isolate a purine-binding aptamer from a pool of random-sequence RNAs (Kiga, D., et al., 1998, Nucleic Acids Res. 26, 1755-1760). This engineered aptamer exhibits a $K_D$ of 1.3 μM for guanine, and shows only a 2- to 3-fold discrimination against hypoxanthine and xanthine. The lower specificity and affinity of this aptamer for selected purines is due to the fact that only the N1, N7 and O6 positions are important for molecular recognition. In contrast, the G box RNA appears to make productive contacts with all available functional groups on guanine, presumably through hydrogen bonding (FIG. 26C).

v. Aptamer Mutations Affect Guanine Binding and Genetic Control

Figure 28A:
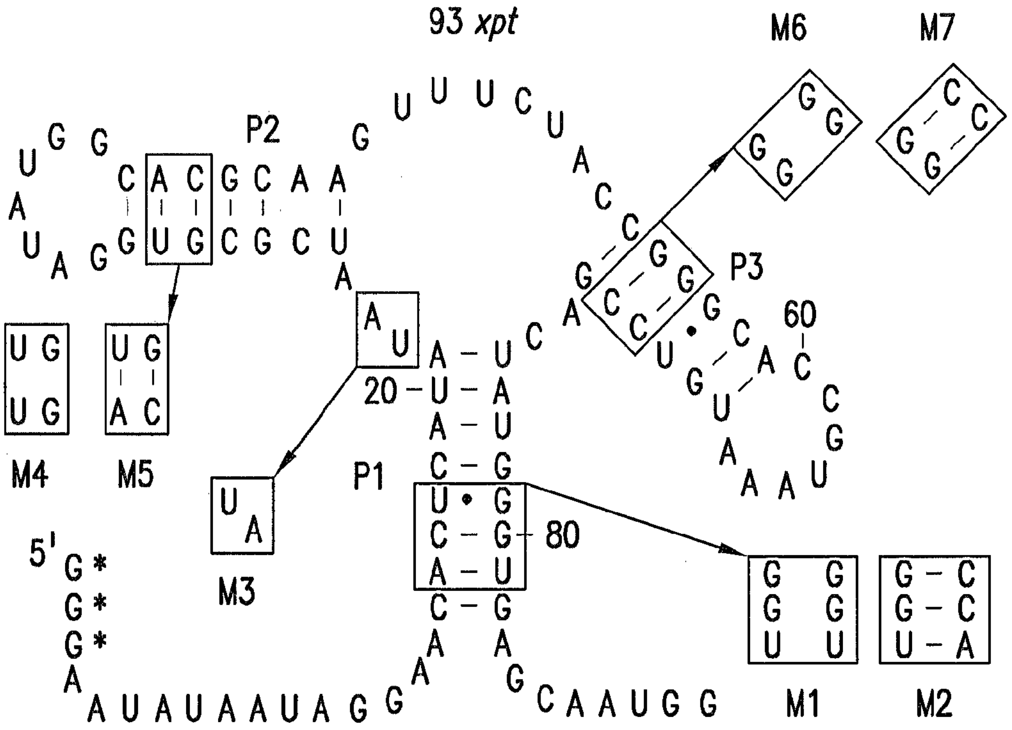
FIGS. 28A, 28B, 28C and 28D show the binding and genetic control functions of variant guanine riboswitches.
Figure 28B:
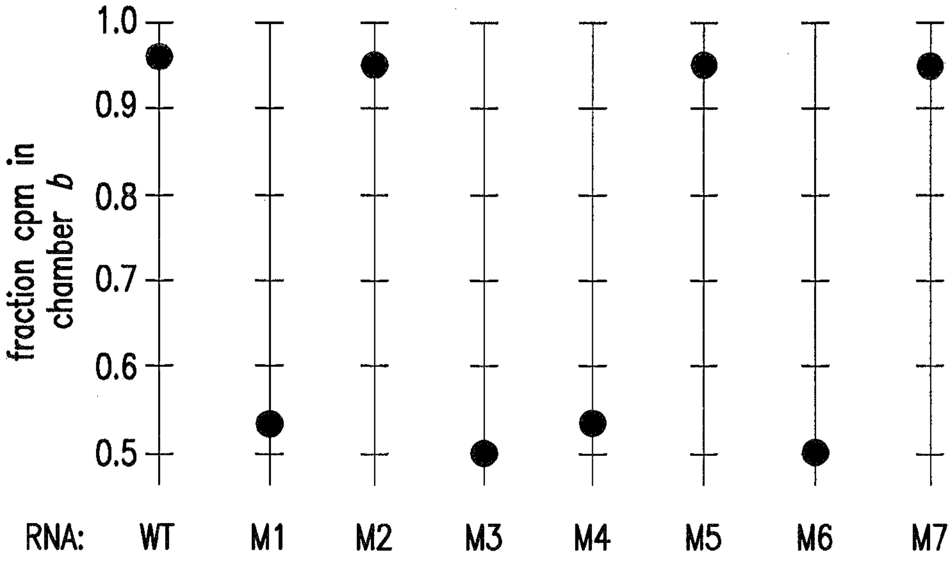

A variety of mutations were introduced into the G box domain to examine the importance of several structural elements and conserved nucleotides (FIG. 28A). The influence of these mutations on guanine binding was determined in the context of the 93 xpt RNA by using equilibrium dialysis. Mutations that independently disrupt the three stems (M1, M4 and M6) cause a loss of binding function, as does a variant RNA (M3) that carries two mutations in the central junction (FIG. 28B). In contrast, the effects of the disruptive stem mutations are largely reversed by making compensatory mutations (M2, M5 and M7) that restore base pairing. These results are consistent with the phylogenetic analysis (FIG. 23), which indicates that stem structure is important but that the precise sequence composition of these elements is of less importance.

Figure 28C:
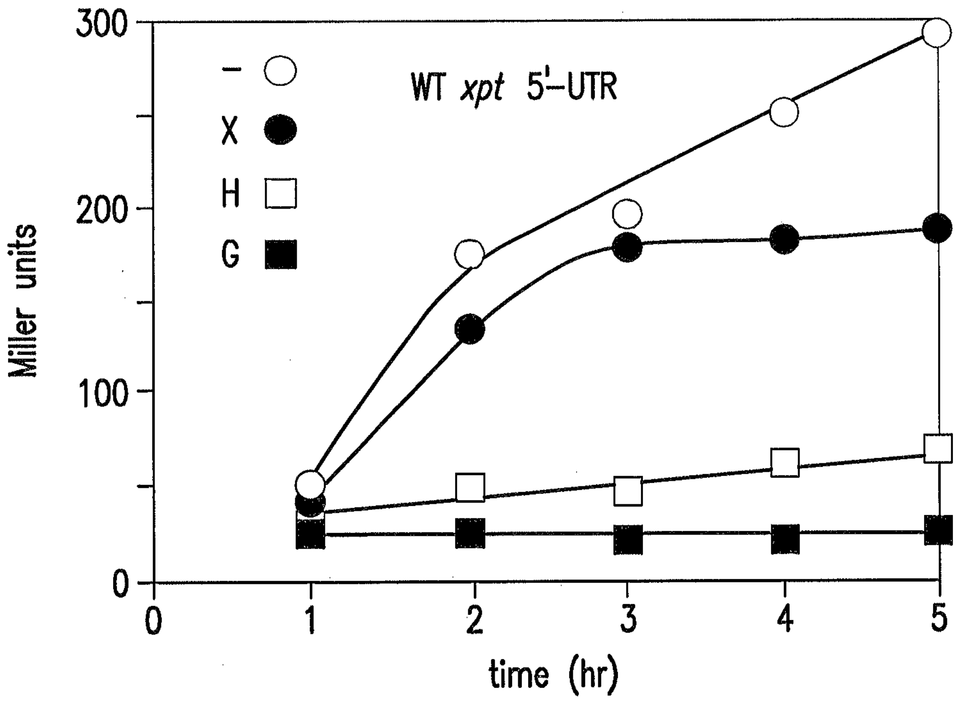

Binding function of variant aptamers in vitro also correlates with genetic control in vivo. The results disclosed herein confirmed earlier findings that a reporter gene carrying the 5'-UTR of the xpt-pbuX mRNA is repressed by guanine, and to a lesser extent by hypoxanthine and xanthine (Christiansen, L. C., et al., 1997, J. Bacteriol. 179, 2540-2550). Specifically, transcriptional fusions were created between a β-galactosidase reporter gene and variant xpt-pbuX5"-UTR sequences carrying the mutations described in FIG. 28A. *B. subtilis* chromosomal transformants using the wild-type sequence exhibit the expected levels of genetic modulation (FIG. 28C). Although the xtp aptamer exhibits dissociation constants for xanthine and hypoxanthine that are essentially identical in vitro, the differences in genetic modulation by these compounds in vivo might be due to differences in their cellular concentrations.

Figure 28D:
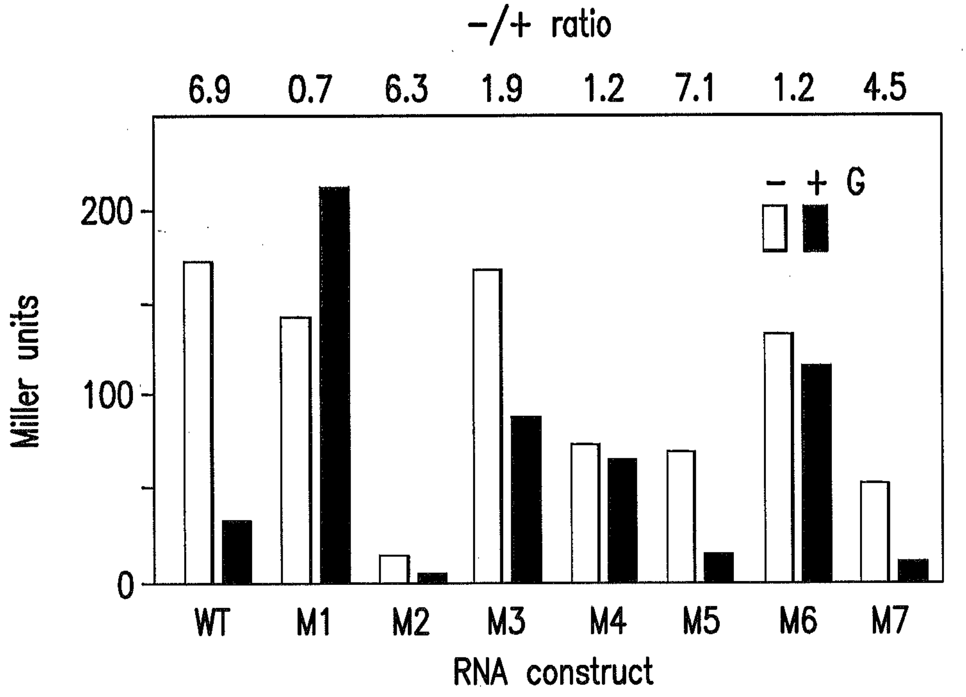

Aptamer variants with impaired guanine binding in vitro also exhibit a loss of β-galactosidase repression (FIG. 28D). Furthermore, restoration of base pairing in stems P1 through P3 results in restored genetic control. The M2 variant is of particular interest because it not only exhibits restored genetic control, but also provides modest expression of β-galactosidase in the absence of guanine Riboswitch function requires the action of an aptamer for molecular sensing as well as an expression platform that transduces RNA-ligand complex formation into a genetic response. Examples of TPP and FMN riboswitches (see Examples 2 and 3) appear to function by differential formation of terminator and antiterminator structures. Such ligand-induced formation of transcription anti-termination structures also appears to be the basis of expression platform mechanisms used by numerous SAM riboswitches (see Example 7). Construct M2 carries three mutations within the putative anti-terminator structure of the xpt-pbuX leader, and thus is expected to exhibit an overall reduction of reporter gene expression because these mutations should bias structure folding towards terminator stem formation.

The results of these mutational and functional analyses confirm the major features of the secondary structure model (P1 though P3) and demonstrate that they are critical for metabolite binding. Furthermore, the correlation between ligand binding and genetic control indicates that the G box and adjacent nucleotides of the xpt-pbuX leader sequence operate in concert to function as a guanine-dependent riboswitch, most likely by operating via allosteric control of transcription termination.

vi. Riboswitches Control Fundamental Biochemical Pathways

Figure 23:
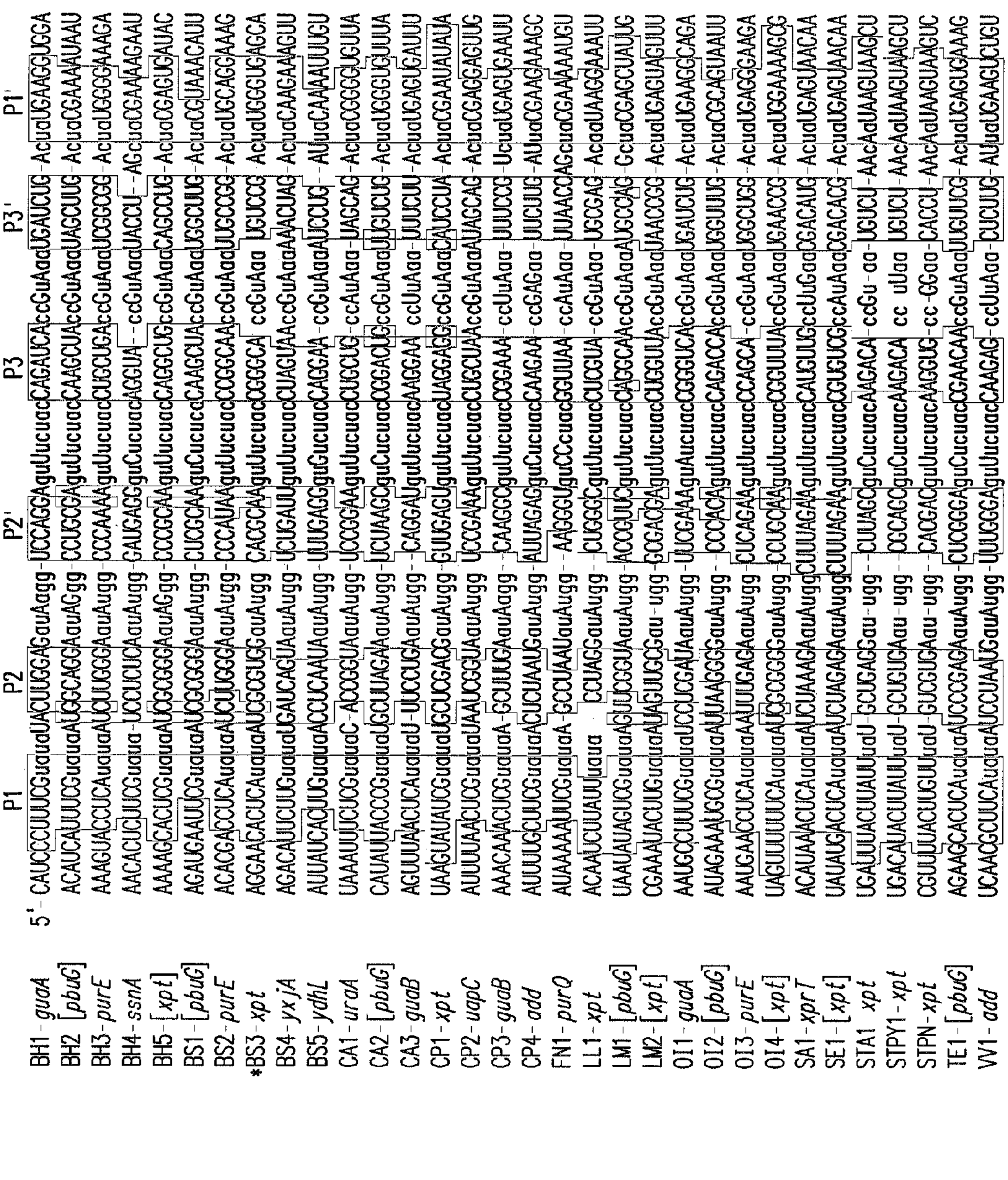
FIG. 23 shows that a highly conserved domain is present in the 5'-UTR of certain gram-positive and gram-negative bacterial mRNAs. Depicted is an alignment of 32 representative mRNA domains from bacteria that conform to the G box consensus sequence BH1-guaA, BH2-[pbuG], BH3-purE, BH4-ssnA, BH5-[xpt], BS1-[pbuG], BS2-purE, BS3-xpt, BS4-yxjA, BS5-ydhL, CA1-uraA, CA2-[pbuG], CA3-guaB, CP1-xpt, CP2-uapC, CP3-guaB, CP4-add, FN1-purQ, LL1-xpt, LM1-[pbuG], LM2-[xpt], OI1-guaA, OI2-[pbuG], OI3-purE, OI4-[xpt], SA1-xpr, TSE1-[xpt], STA1-xpt, STPY1-xpt, STPN-xpt, TE1-[pbuG], VV1-add, which are represented by SEQ ID NOs:63-94 respectively. Enclosed and enumerated regions identify base-pairing potential of stems P1, P2, and P3, respectively. Nucleotides shown as lower case letters are conserved in greater than 90% of the examples. The asterisk identifies the representative (xpt-pbuX 5'-UTR) that was examined in this study. It is important to note that three representatives (BS5, CP4 and VV1) that carry a C to U mutation in the conserved core (in the P3-P1 junction) appear to be adenine-specific riboswitches (unpublished observations). Gene names are as annotated in GenBank, the SubtiList database, or based on protein similarity searches (brackets). Organisms abbreviations are as follows: *Bacillus halodurans* (BH), *Bacillus subtilis* (BS), *Clostridium acetobutylicum* (CA), *Clostridium perfringens* (CP), *Fusobacterium nucleatum* (FN), *Lactococcus lactis* (LL), *Listeria monocytogenes* (LM), *Oceanobacillus iheyensis* (OI), *Staphylococcus aureus* (SA), *Staphylococcus epidermidis* (SE), *Streptococcus agalactiae* (STA), *Streptococcus pyogenes* (STPY), *Streptococcus pneumoniae* (STPN), *Thermoanaerobacter tengcongensis* (TE), and *Vibrio vulnificus* (VV).

Our findings indicate that the G box RNA of the xpt-pbuX operon is a key structural element of a guanine-sensing riboswitch that exhibits extraordinary affinity and selectivity for its target. In *B. subtilis*, this general riboswitch motif appears to control at least five transcriptional units (FIG. 23). Although the precise function of several of the gene products in this newly identified regulon have not been clearly defined, the known genes from *B. subtilis* and from other organisms are mostly related to purine metabolism. Based on the results disclosed herein, it is likely the G box domain within the 5'-UTR of this large pur operon is responsible for guanine-dependent riboswitch regulation, and that the genetic regulatory mechanism might be similar to that proposed herein for the xpt-pbuX operon.

Figure 29A:
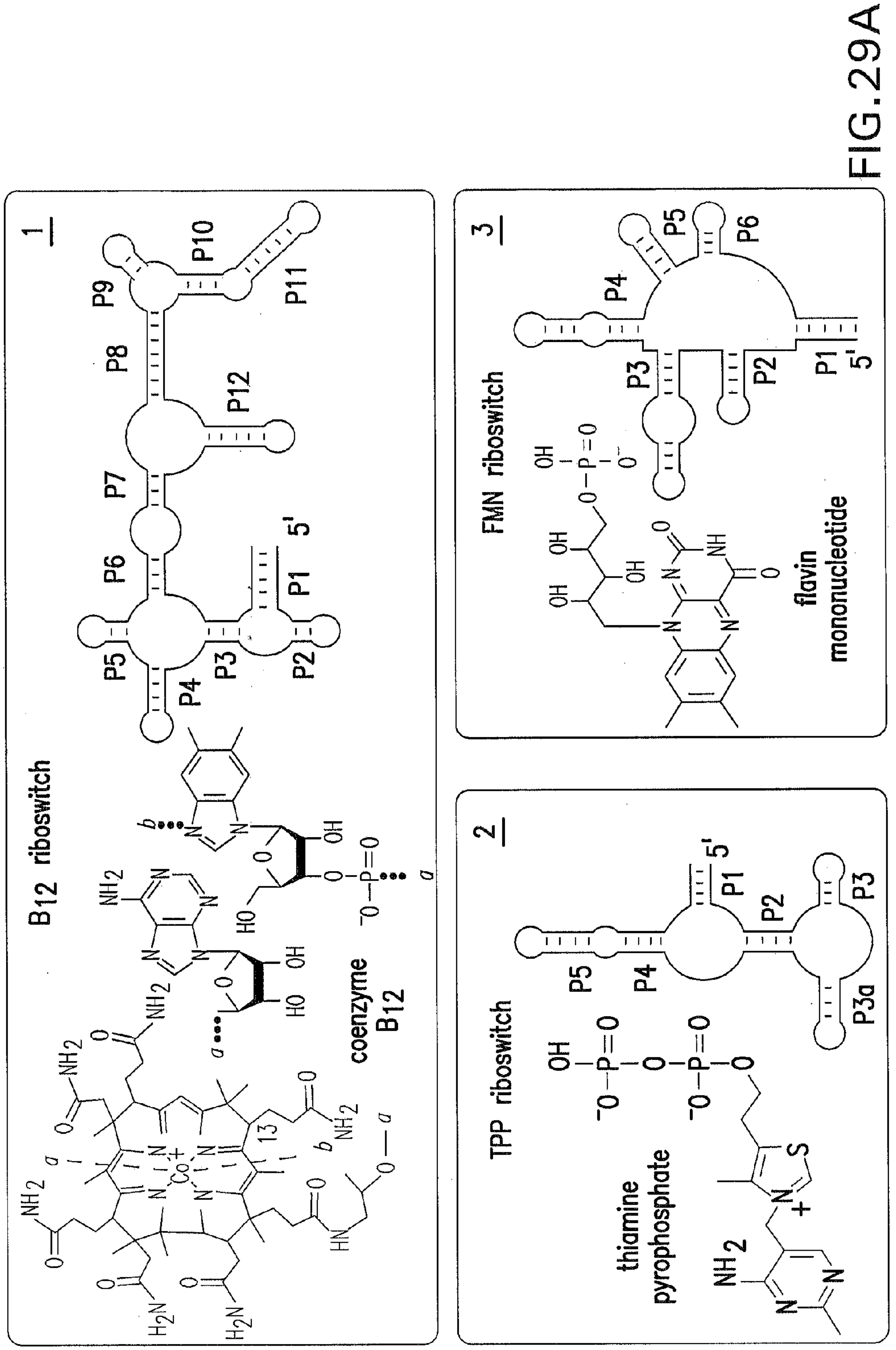
FIGS. 29A, 29B and 29C show that riboswitches participate in fundamental genetic control.
Figure 29B:
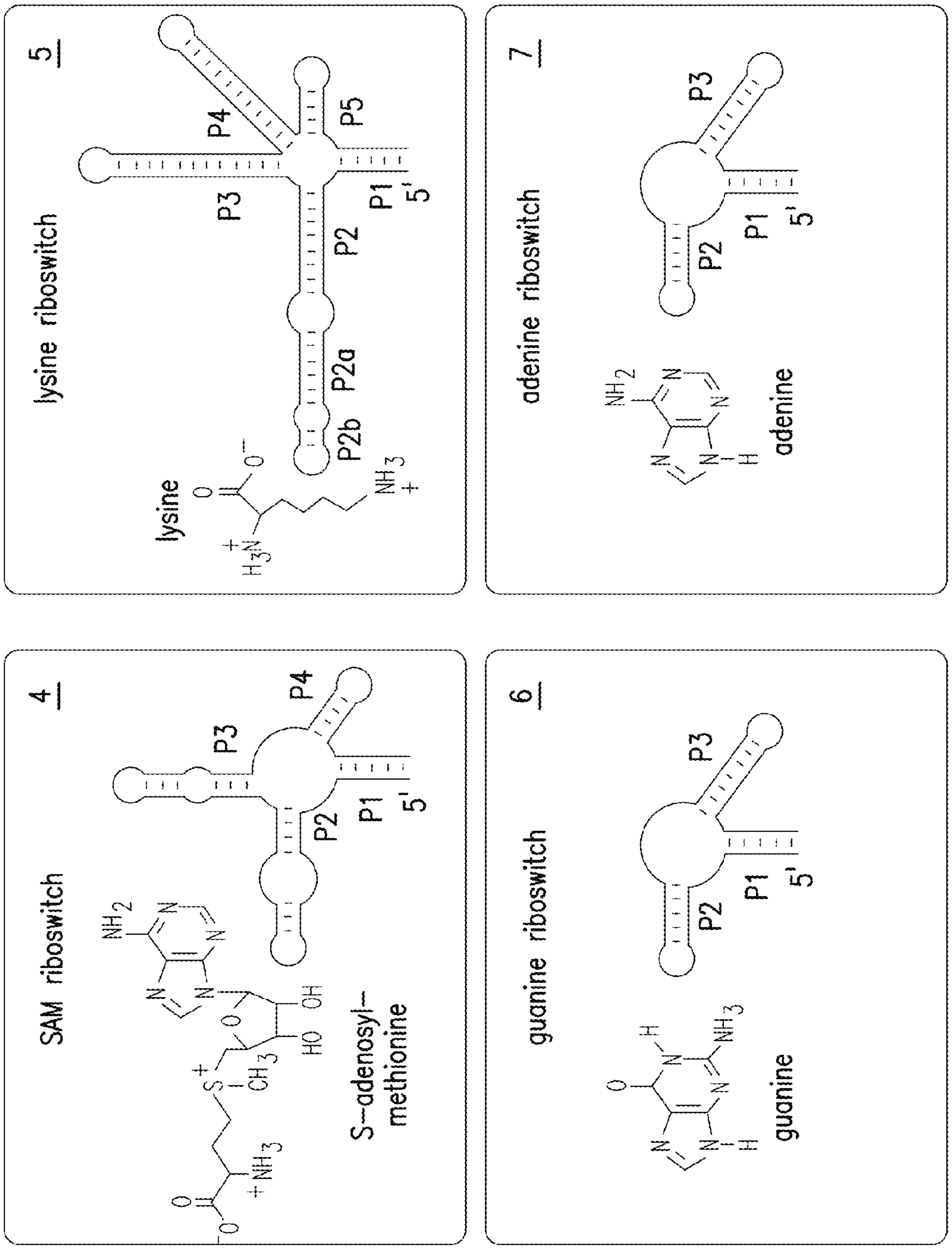
Figure 29C:
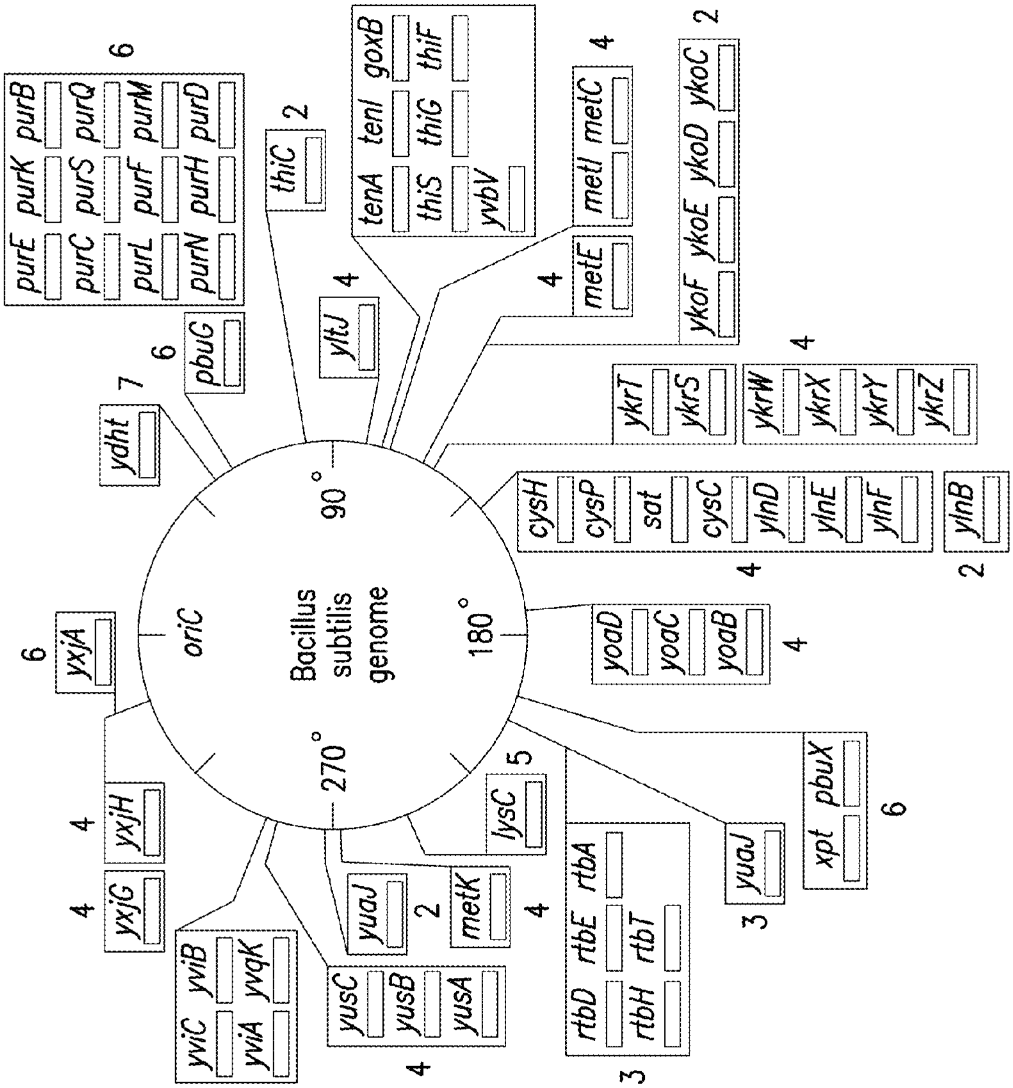

The distribution of G box domains in *B. subtilis* and other bacteria suggests that this class of metabolite-binding RNAs controls a regulon that is essential for cell survival. In *B. subtilis*, guanine riboswitches (or related adenine-dependent riboswitches—see the legend to FIG. 23) appear to provide at least some contribution to the genetic regulation of 17 genes. The discovery of guanine-dependent riboswitches adds to a growing list of similar metabolite-sensing RNAs. For example, a class of riboswitches that responds to SAM (McDaniel, B. A. M., et al., 2003, Proc. Natl. Acad. Sci. USA 100, 3083-3088; Epshtein, V., et al., 2003, Proc. Natl. Acad. Sci. USA 100, 5052-5056) controls a regulon of as many as 26 genes that are involved in coenzyme biosynthesis, amino acid metabolism, and sulfur metabolism. When included with genes that are controlled by other riboswitch classes, at least 68 genes (nearly 2% of its total genetic complement) are under riboswitch control (FIG. 29).

Riboswitches for ligands such as guanine and SAM apparently are serving as master control molecules whose concentrations are being monitored to ensure homeostasis of a much wider set of metabolic pathways. Riboswitches also seem to permit metabolite surveillance and genetic control with the same level of precision and efficiency as that exhibited by protein factors. Therefore, these RNA switches could have emerged late in the evolution of modern biochemical architectures because they are functionally comparable to genetic switches made of protein. However, given their fundamental role in metabolic maintenance and the widespread phylogenetic distribution of certain riboswitches, it is consistent that aptamer domains similar to these might have been the primary mechanism by which RNA-world organisms detected metabolites and controlled biochemical pathways before the emergence of proteins.

5. Conclusions

This demonstration that guanine is sensed by metabolite-binding mRNAs expands the known classes of riboswitches, and provides additional evidence that certain bacterial RNAs are responsible for monitoring the concentrations of critical coenzymes and other compounds that are fundamental to all living systems. Phylogenetic analyses and biochemical data indicate that many bacteria and, in some instances, eukaryotes (Sudarsan, N., et al., 2003, RNA 9:644-647) entrust riboswitches to sense essential metabolites and mediate genetic control. Although protein factors undoubtedly could be used to carry out these important regulatory tasks, based on the disclosure herein, highly structured RNAs are well suited for this role. If RNA polymers were a poorly suited medium for generating metabolite receptors with high affinity and precision, then one would expect that evolution would have long ago replaced them by protein factors.

Disclosed herein it is consistent (e.g. see Examples 1 and 2) that riboswitches are derivatives of an ancient genetic control system that monitored metabolic and environmental signals before the evolutionary emergence of proteins. Interestingly, each of the metabolite targets of riboswitches has been proposed to come from an RNA world (White, H. B. III., 1976, J. Mol. Evol. 7, 101-104; Benner, S. A., et al., 1989, Proc. Natl. Acad. Sci. USA 86, 7054-7058; Jeffares, D. C., et al., 1998, J. Mol. Evol. 46, 18-36; Jadhav, V. R., and Yams, M., 2002, Biochimie 84, 877-888). The identification of guanine as a trigger for riboswitches is consistent with metabolite sensing RNAs having originated very early in evolution. Also disclosed herein is another class of riboswitches that responds to the amino acid lysine (FIG. 29). Although all riboswitches could be more recent evolutionary inventions, even the origin of the lysine riboswitch might date from before the last common ancestor and back to a time when living systems were transitioning from a pure RNA world to a more modern metabolic state that made use of encoded protein synthesis.

G. Example 7

S-adenosylmethionine Riboswitches

Riboswitches are metabolite-binding RNA structures that serve as genetic control elements for certain messenger RNAs. These RNA switches have been identified in all three kingdoms of life and are typically responsible for the control of genes whose protein products are involved in the biosynthesis, transport, or utilization of the target metabolite. Disclosed herein, is a highly conserved RNA domain found in bacteria serves as a riboswitch that responds to the coenzyme S-adenosylmethionine (SAM) with remarkably high affinity and specificity. SAM riboswitches undergo structural reorganization upon introduction of SAM, and these allosteric changes regulate the expression of 26 genes in Bacillus subtilis. This and related findings indicate that direct interaction between small metabolites and allosteric mRNAs is a significant and widespread form of genetic regulation in bacteria.

1. Results i. Identification of a SAM-Responsive riboswitch

Each of the compounds sensed by previously identified riboswitches (coenzyme $B_{12}$, TPP, FMN) is used as a coenzyme by modern protein enzymes. Interestingly, these coenzymes have significant structural similarity to RNA, which has been used to support speculation that they might also have been used as coenzymes by ancient ribozymes in an RNA world (S. A. Benner, et al., *Proc. Natl. Acad. Sci. USA* 86, 7054 (1989); H. B. White III, *J. Mol. Evol.* 7, 101 (1976); D. C. Jeffares, et al., *J. Mol. Evol.* 46, 18 (1998). If modern riboswitches are direct descendents of RNA control systems that originated in the RNA world, then the metabolites they sense and the metabolic pathways that they control will be of fundamental importance to modern biochemical processes. To further assess this hypothesis, a search for additional riboswitches, to determine their biochemical characteristics, and to establish their role in genetic control on a genome-wide level was performed.

Figure 30A:
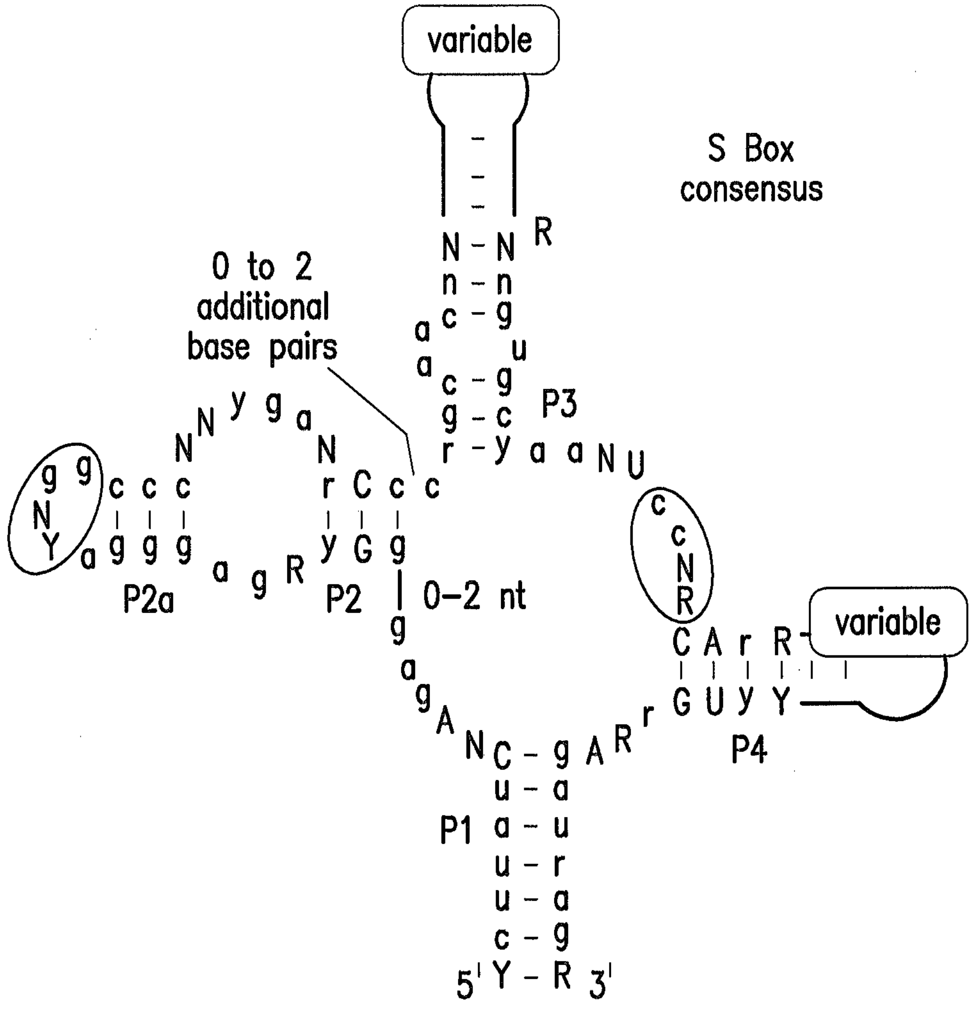
FIGS. 30A, 30B and 30C show the S Box is a structured RNA domain that binds SAM. (A) Consensus sequence and secondary-structure model of the S box domain derived from 107 bacterial representatives (SEQ ID NO:98 and SEQ ID NOs:409-410). Lower case letter and capital letter positions identify nucleotides whose identity as depicted is conserved in greater than 90% or 80% of the representative S box RNAs, respectively. R, Y, and N represent purine, pyrimidine, and any nucleotide, respectively. P1 through P4 identify conserved base pairing. Enclosed nucleotides identify a putative pseudoknot interaction.
Figure 30B:
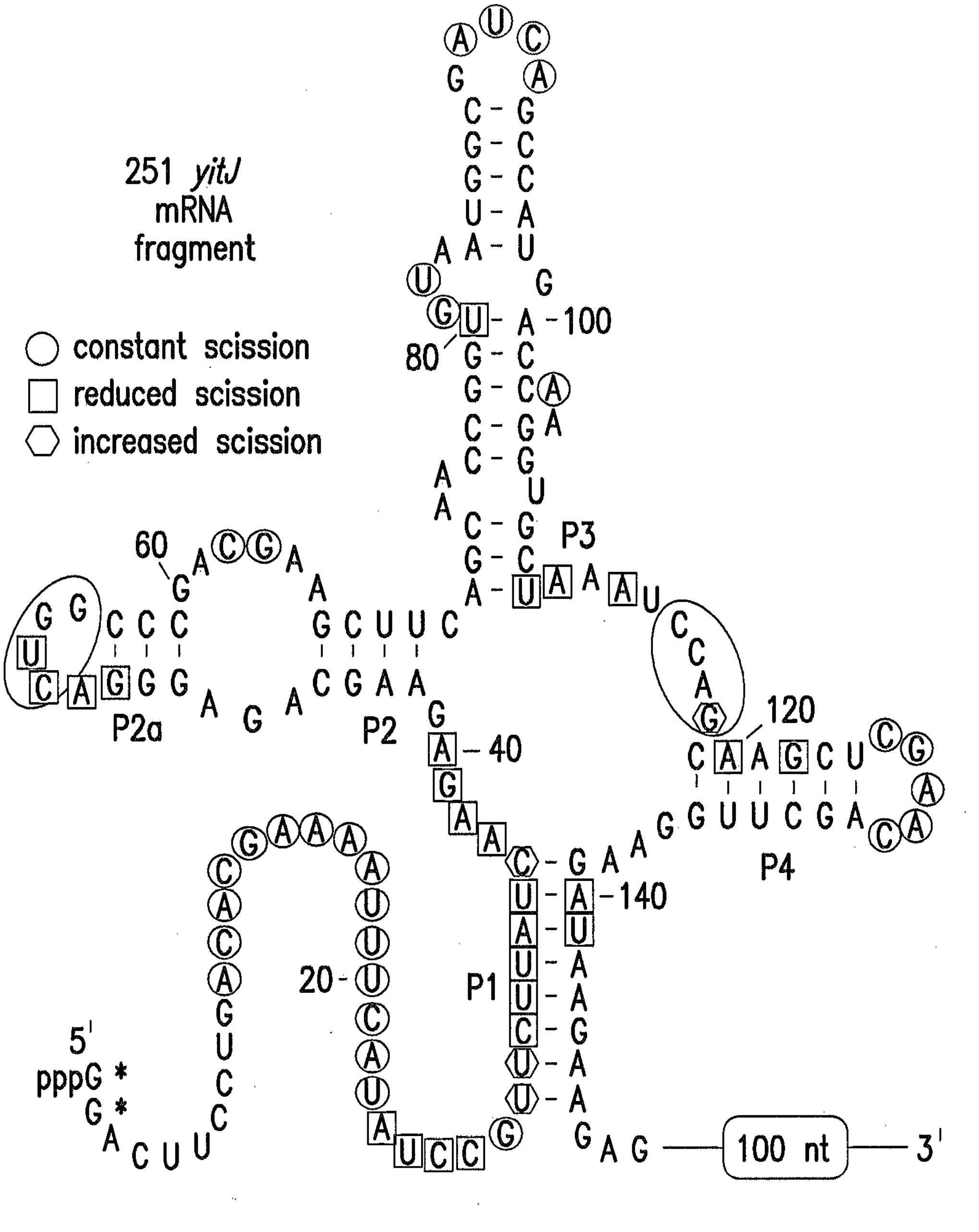

In this effort the S box was examined (F. J. Grundy, T. M. Henkin, *Mol. Microbiol.* 30, 737 (1998)), which is a highly conserved sequence domain (FIG. 30A) that is located within the 5'-untranslated region (5'-UTR) of certain messenger RNAs in Gram-positive bacteria. Both genetic and sequence analyses suggest that the S box domain serves as a genetic control element for a regulon composed of 11 transcriptional units. These mRNAs encode as many as 26 different genes in *B. subtilis* that are involved in sulfur metabolism, methionine biosynthesis, cysteine biosynthesis, and SAM biosynthesis. However, the nature of the putative regulatory factor and the metabolite to which it responds had not been established (T. M. Henkin, *Curr. Opin. Microbiol.* 3, 149 (2000); F. J. Grundy, T. M. Henkin, *Frontiers Biosci.* 8, D20 (2003)). An RNA construct corresponding to the first 251 nucleotides of the yitJ mRNA of *B. subtilis* (FIG. 30*b*) was prepared by in vitro transcription (G. A. Soukup, R. R. Breaker, RNA 5, 1308 (1999)). The yitJ gene product is a putative methylene tetrahydrofolate reductase—an enzyme proposed to be involved in methionine biosynthesis (F. J. Grundy, T. M. Henkin, *Mol. Microbiol.* 30, 737 (1998). The 251 yitJ RNA was subjected to "in-line probing", which reveals locations of structured and unstructured portions of RNA polymers by relying on the variability in rates of spontaneous RNA phosphodiester cleavage caused by differences in structural context. In-line probing can also reveal nucleotides participating in metabolite-induced structural modulation (see Examples 1-3).

Figure 30C:
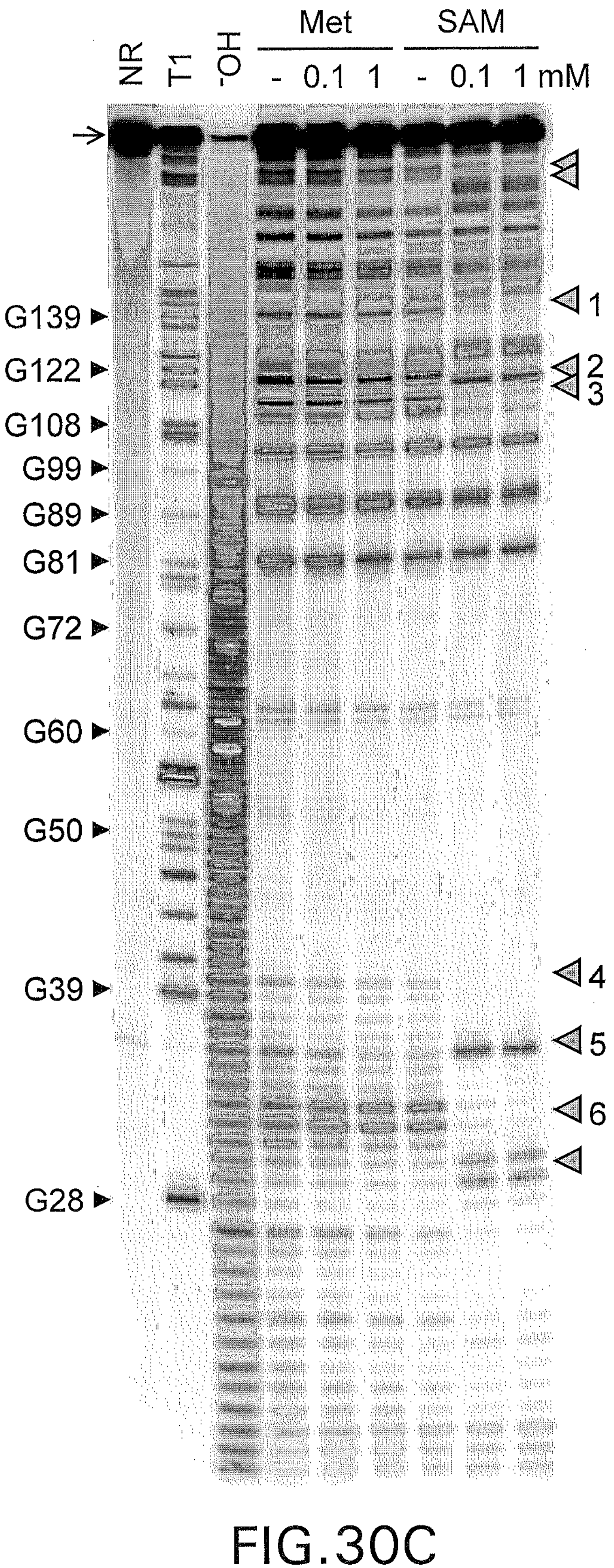

Whether the 251 yitJ RNA might bind S-adenosylmethionine (SAM) was analyzed. Indeed, upon separation by polyacrylamide gel electrophoresis (PAGE), the pattern of spontaneous RNA cleavage products (FIG. 30*c*) was indicative of a highly structured RNA element that undergoes conformational modulation upon introduction of SAM to a final concentration of either 0.1 mM or 1 mM. In contrast, no structural modulation was evident upon the introduction of methionine at the same concentrations, suggesting that the RNA might require both the methionine and 5'-deoxyadenosyl moieties of SAM to induce structural reorganization. The locations of the ligand-induced modulations (FIG. 30*b*) indicated that the conserved core of the S box RNA serves as a natural aptamer (L. Gold, et al., *Annu. Rev. Biochem.* 64, 763 (1995)). for SAM. Similar results were observed with 124 yitJ, which encompasses nucleotides 28 through 149 of the mRNA leader plus two G residues at the 5' terminus.

ii. Molecular Recognition by a SAM-Dependent Riboswitch

Figure 31A:
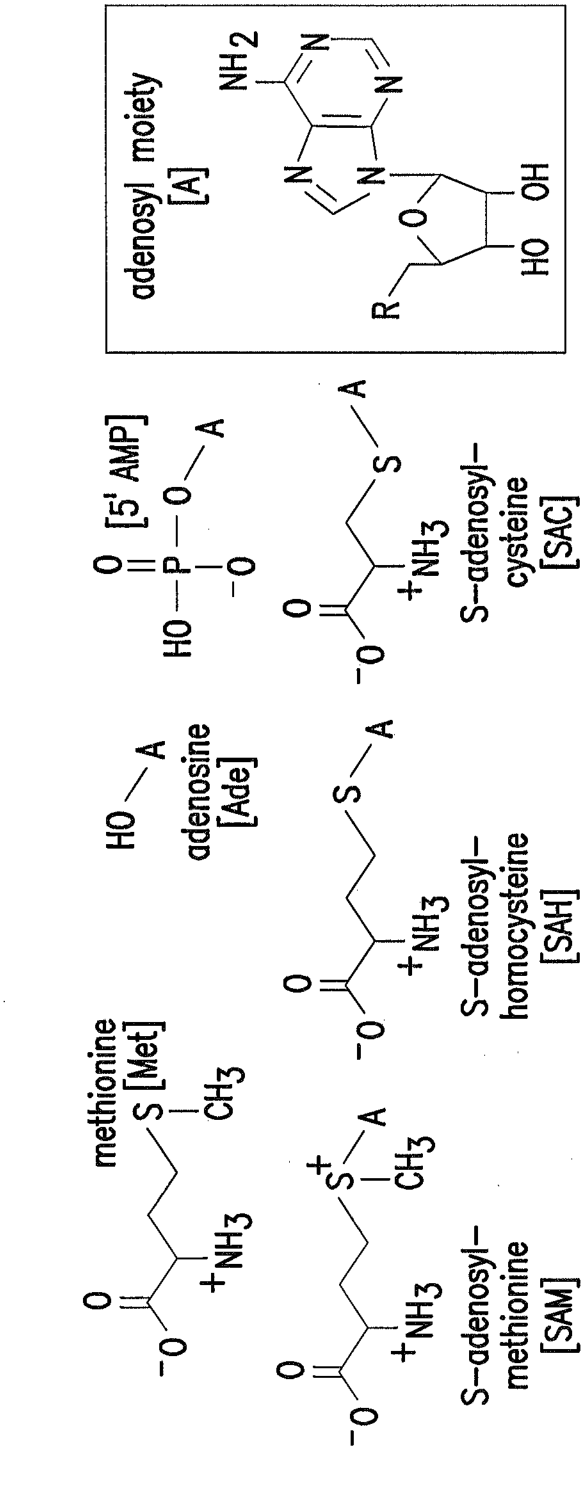
FIGS. 31A, 31B and 31C show the binding affinity and molecular discrimination by a SAM-binding RNA.

A genetic switch that responds to metabolites must be able to bind its target with a dissociation constant ($K_D$) that is relevant to physiological concentrations. Furthermore, the metabolite receptor must be able to discriminate precisely against closely related compounds that are likely to occur in the same milieu, or risk undesirable modulation of gene expression. Therefore, the affinity of the yitJ RNA for SAM was assessed, and the ability of the RNA to discriminate against biologically relevant compounds that are structurally similar to this target (FIG. 31*a*).

Figure 31B:
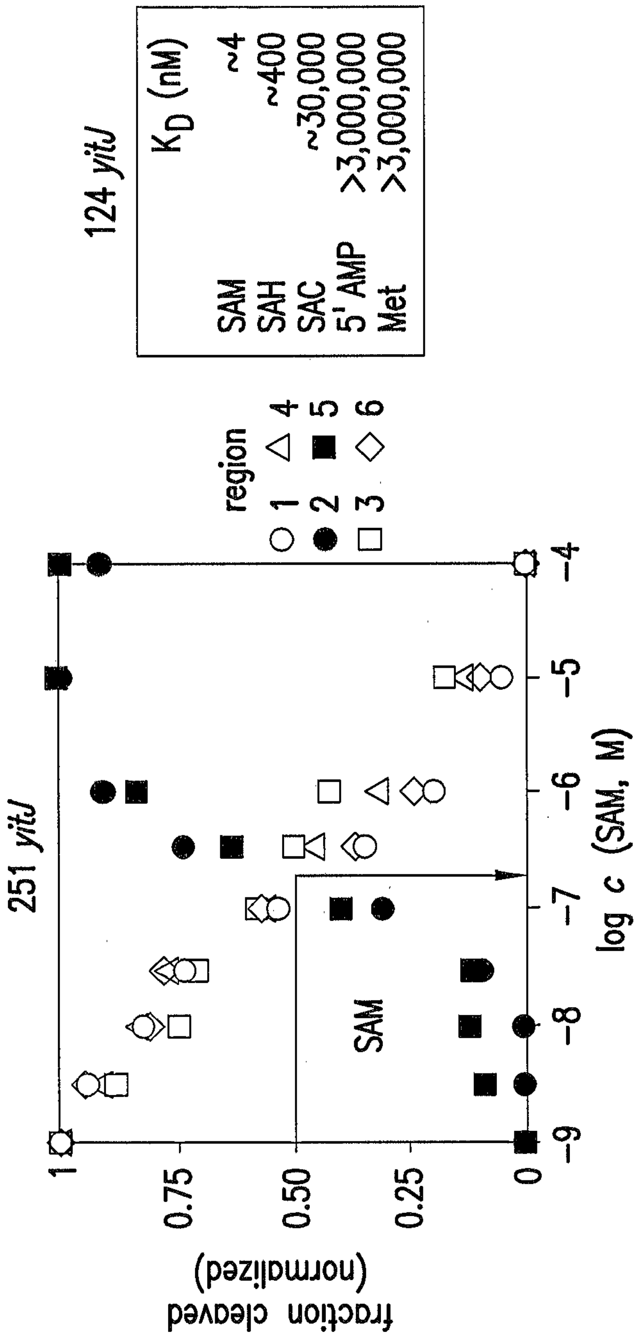

The $K_D$ of 251 yitJ for SAM was determined by using in-line probing to monitor the extent of structural modulation over a range of ligand concentrations (FIG. 31*b*, left). Although the $K_D$ of 251 yitJ for SAM is ~200 nM, the minimized aptamer domain represented by 124 yitJ exhibits a $K_D$ of ~4 nM under the disclosed assay conditions. Such improvements in binding affinity by minimized aptamer domains have been observed (see Example 2). This most likely reflects greater structural preorganization of the ligand binding form of the aptamer domain due to the elimination of the adjoining expression platform, which otherwise would permit alternative folding to occur. Tight binding was also observed when the 124 yitJ was interrogated by using a Scatchard analysis with tritiated SAM. The assessment of binding affinity indicated that the $K_D$ for the 124 yitJ aptamer is more than 1000-fold improved compared to that reported recently for a related RNA (McDaniel, B. et al., *Proc. Natl. Acad. Sci. USA* 100, 3083-3088 (2003)). Normal concentrations of SAM in bacteria are typically in the low micromolar range (McDaniel, B. et al., *Proc. Natl. Acad. Sci. USA* 100, 3083-3088 (2003)), however, most of this coenzyme pool is probably bound by enzymes. Therefore the low $K_D$ exhibited by this riboswitch might be needed to sense the concentration of free SAM.

Figure 31C:
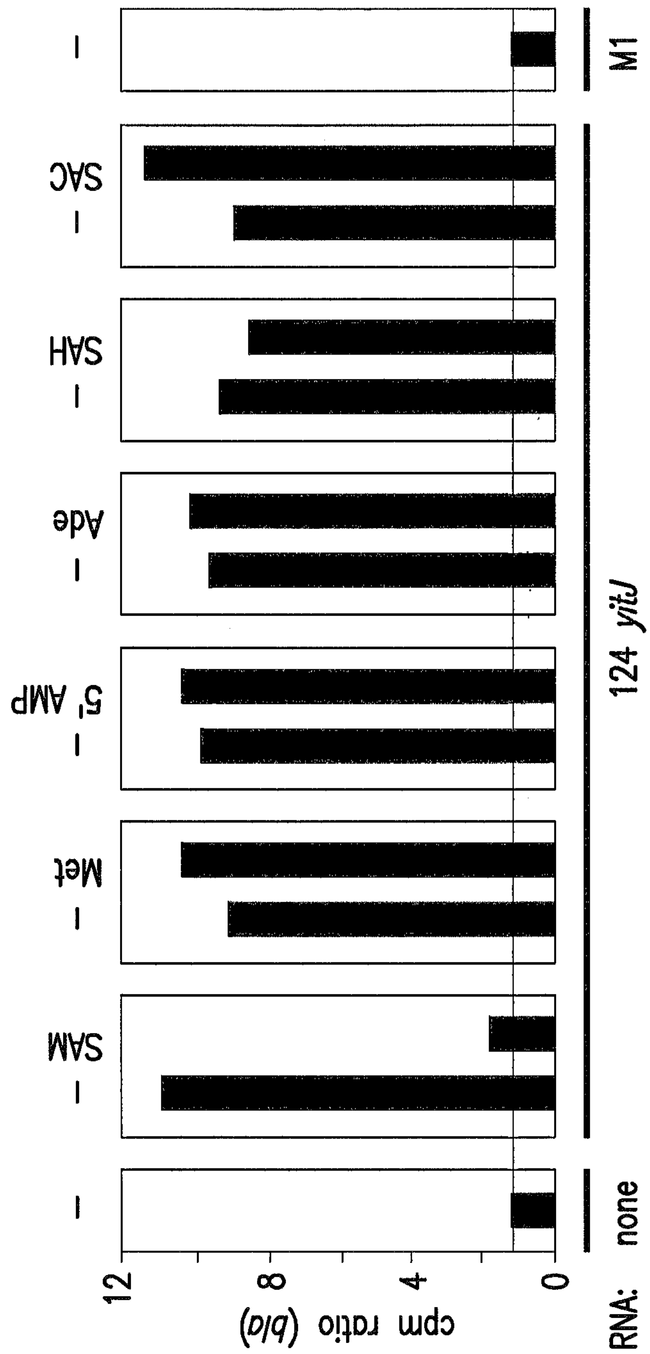

As expected, the 124 yitJ RNA achieves a high level of molecular discrimination against analogs of SAM. For example, the RNA exhibits ~100-fold discrimination against SAH (FIG. 31*b*, right), which is produced upon utilization of SAM as a coenzyme for methylation reactions (F. Takusagawa, et al., In: *Comprehensive Biological Catalysis*, M. Sinnott, ed., Academic Press, Vol. 1, pp. 1-30 (1998)). Thus, the aptamer must form a binding pocket for SAM that can sense the absence of a single methyl group and an associated loss of positive charge. Similarly, the RNA discriminates nearly 10,000 fold against SAC, which is another biological compound that differs from SAH by the absence of a single methylene group. This pattern of molecular discrimination was confirmed by using equilibrium dialysis (FIG. 31*c*).

iii. SAM Binding by an mRNA is Required for Genetic Regulation

Figure 32A:
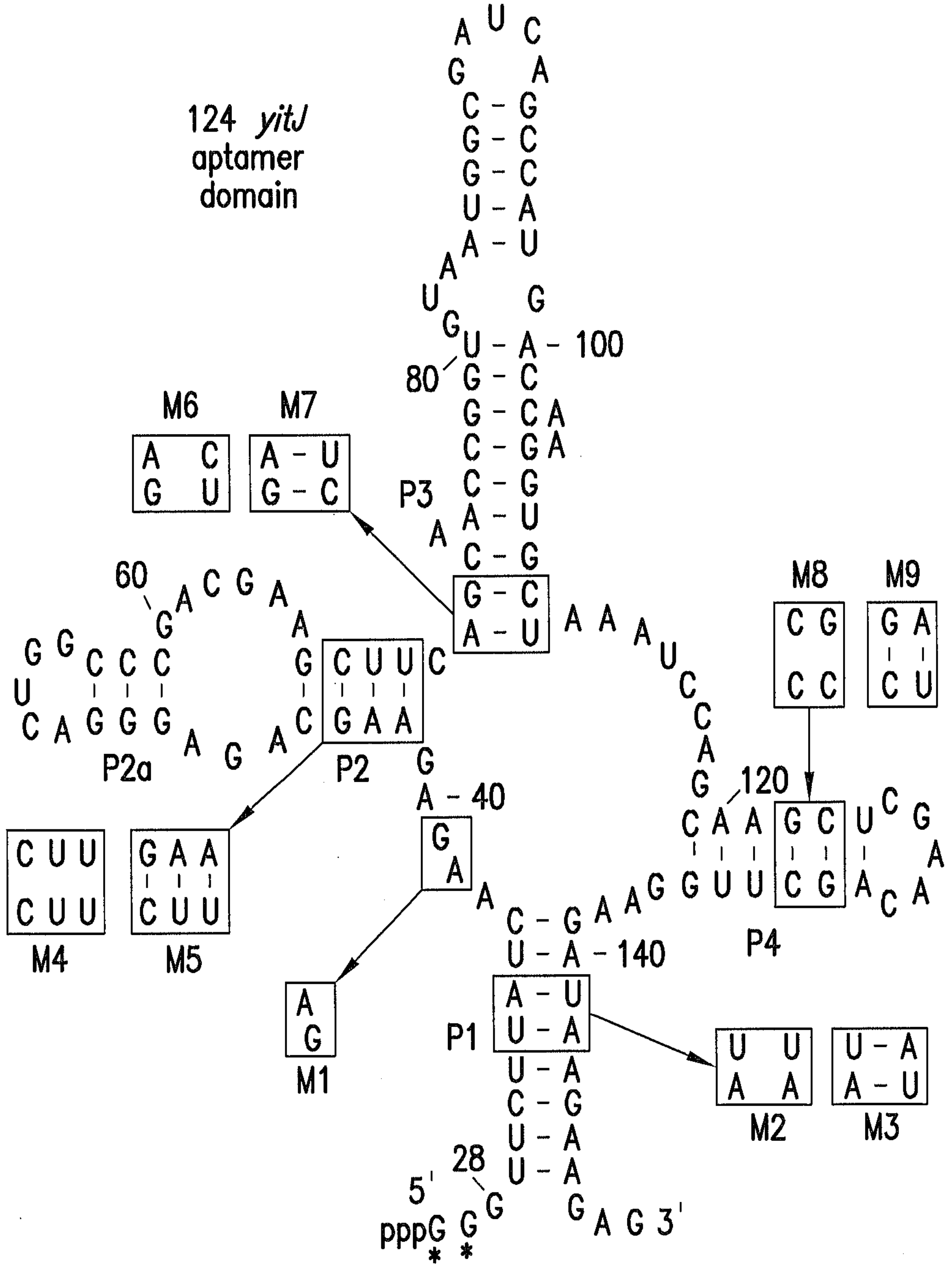
FIGS. 32A, 32B and 32C show the effects of RNA mutations on SAM binding and genetic control.
Figure 32B:
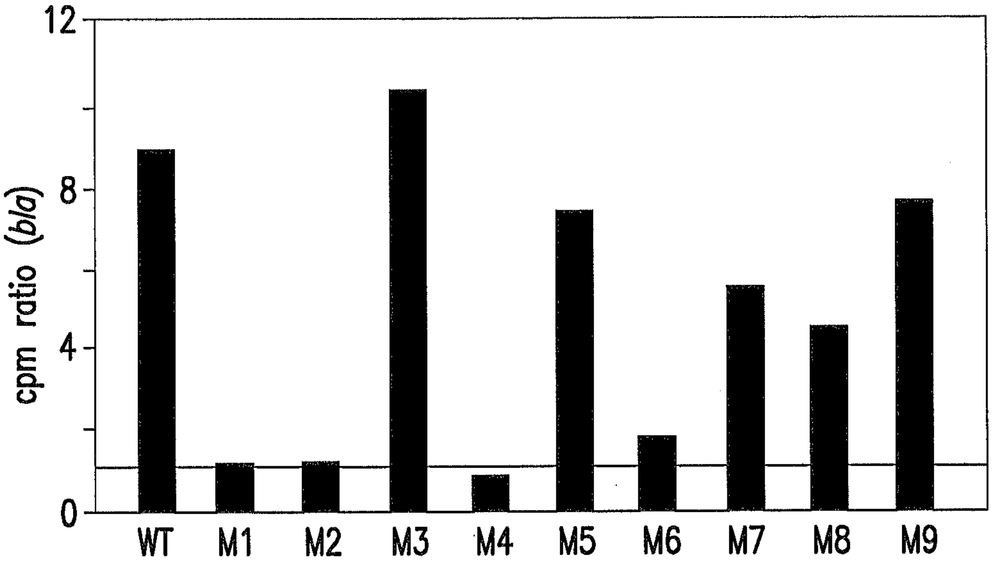

The secondary structure model for the SAM-binding aptamer domain was established using phylogenetic data (F. J. Grundy, T. M. Henkin, *Mol. Microbiol.* 30, 737 (1998)). To provide further support for this model, the influence of disruptive and compensatory mutations (FIG. 32*a*) on the binding function of the 124 yitJ RNA, and on SAM-mediated genetic control of a lacZ reporter gene when fused with variant riboswitches based on these mutant aptamers was examined. Mutations that alter the conserved core of the aptamer (M1) or that disrupt base pairing in each of the four major base-paired regions (M2, M4, M6 and M8) largely result in a loss of SAM binding function as determined by equilibrium dialysis (FIG. 32*b*). Compensatory mutations that restore base pairing in these stems (M3, M5, M7, M9) restore at least partial binding activity.

Figure 32C:
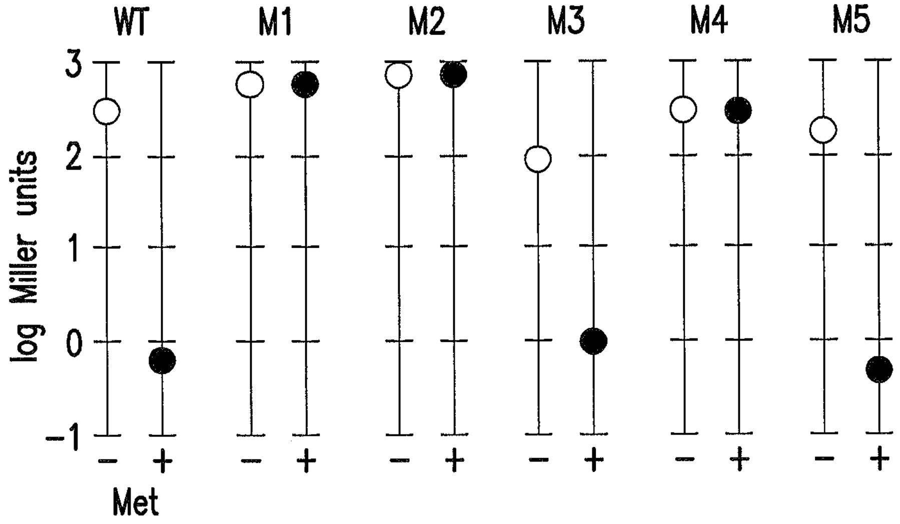

It has been shown (F. J. Grundy, T. M. Henkin, *Mol. Microbiol.* 30, 737 (1998)) that a growth medium rich in methionine leads to repression of *B. subtilis* genes that carry the S box domain. This is most likely due to the ability of the cell to convert methionine into an ample supply of SAM. Disclosed herein in all cases tested, the binding function of the mutant correlates with their ability to down regulate an appended reporter gene when presented with excess methionine in otherwise minimal growth media (FIG. 32*c*). These findings are consistent with SAM binding to the mRNA being necessary for the genetic regulation of S box mRNAs.

iv. SAM Riboswitches Control Gene Expression by Transcription Termination in *B. subtilis*

Disclosed herein bacterial riboswitches can control gene expression by modulating either transcription termination or translation initiation (see Examples 2 and 3), while several putative riboswitches in eukaryotes might use one of several different mechanisms. In *B. subtilis*, the SAM-binding aptamer domains typically reside immediately upstream from a putative transcription terminator hairpin (F. J. Grundy, T. M. Henkin, *Mol. Microbiol.* 30, 737 (1998)), which implies that SAM binding most likely induces transcription termination as described previously for FMN- and TPP-dependent riboswitches (see Example 3).

Figure 33A:
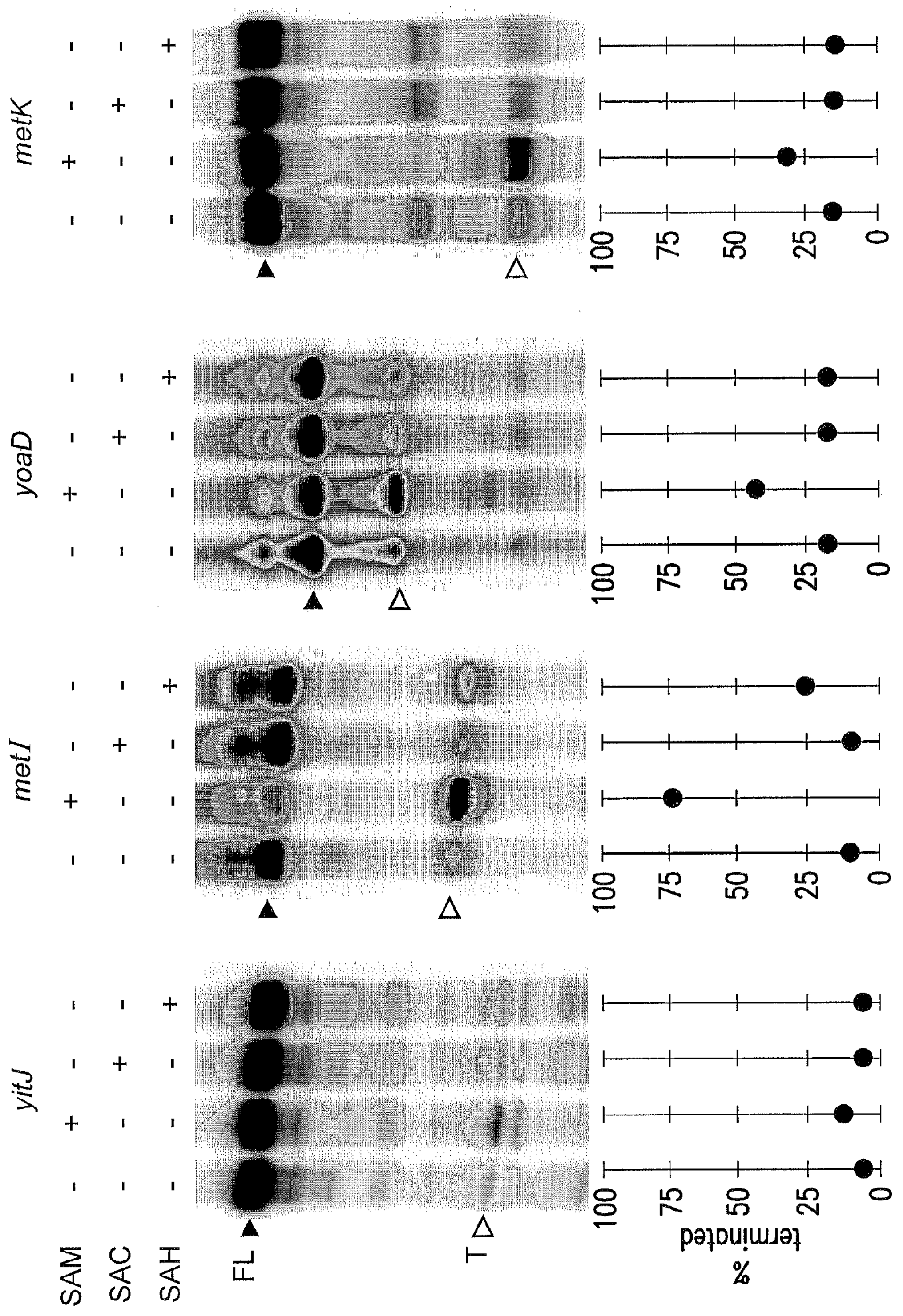
FIGS. 33A, 33B, 33C and 33D show metabolite-induced transcription termination of several mRNAs that carry a SAM riboswitch.

In vitro transcription in the absence or presence of SAM using 11 DNA templates corresponding to the mRNA leader sequences of the S box regulon was performed. These assays were simplified by using T7 RNA polymerase instead of the native *B. subtilis* RNA polymerase. It was observed that an FMN-dependent riboswitch induces transcription termination even when T7 RNA polymerase is used as a surrogate for the bacterial polymerase (see Example 3). In this study, it was found that the yitJ, yoaD and metK leader constructs exhibit modest transcription termination upon the addition of SAM. More dramatically, the termination product from the metI leader construct increases from ~12% to nearly 75% upon introduction of SAM (FIG. 33*a*). In all instances, little or no modulation of transcription termination occurs when the analogs SAH or SAC are added to the reaction. The remaining seven S-box representatives did not exhibit significant modulation with T7 RNA polymerase, presumably because it serves as an imperfect substitute for the native polymerase. Indeed, SAM-dependent transcription termination is observed with many of these mRNA leader sequences when *E. coli* or *B. subtilis* polymerases are used in the assay (McDaniel, B. et al., *Proc. Natl. Acad. Sci. USA* 100, 3083-3088 (2003)).

Figure 33B:
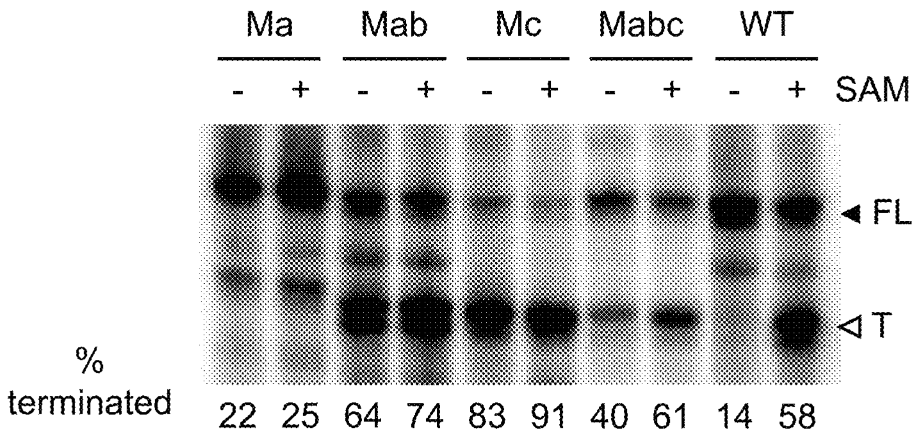
Figure 33C:
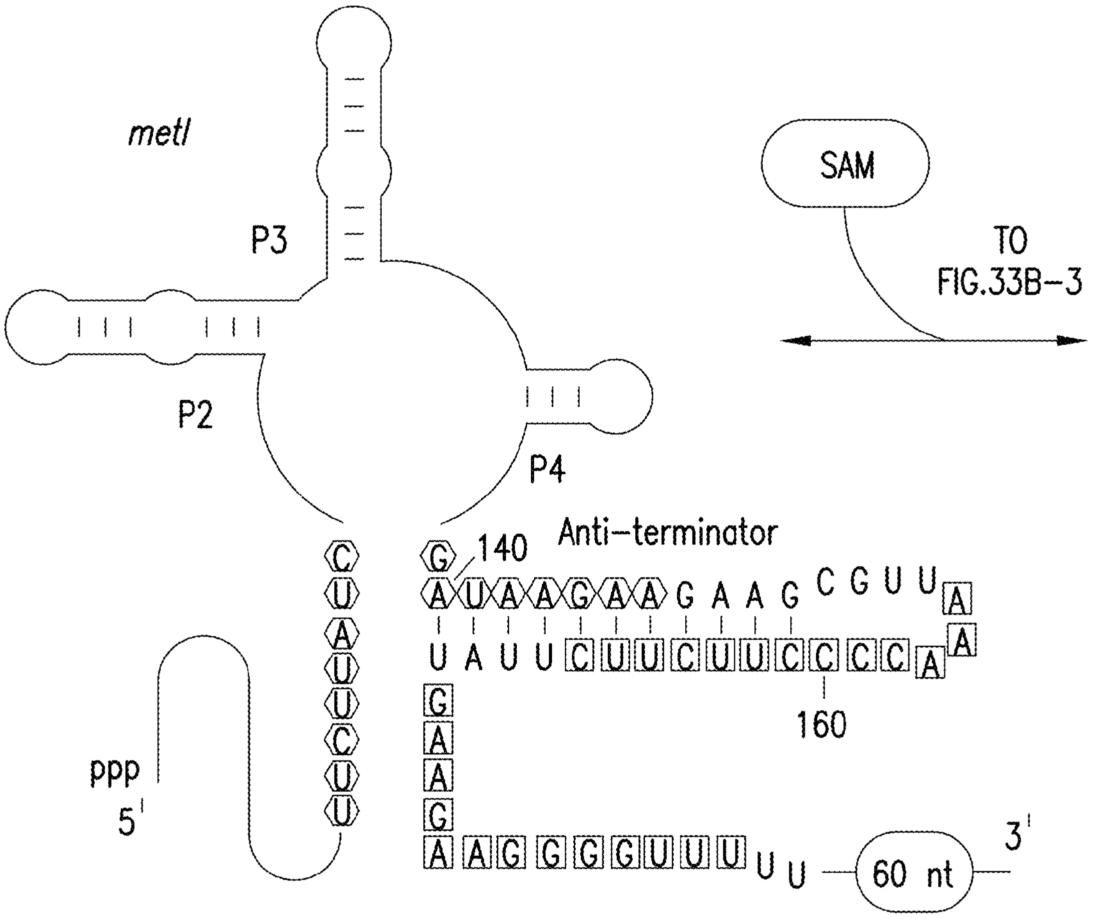
Figure 33D:
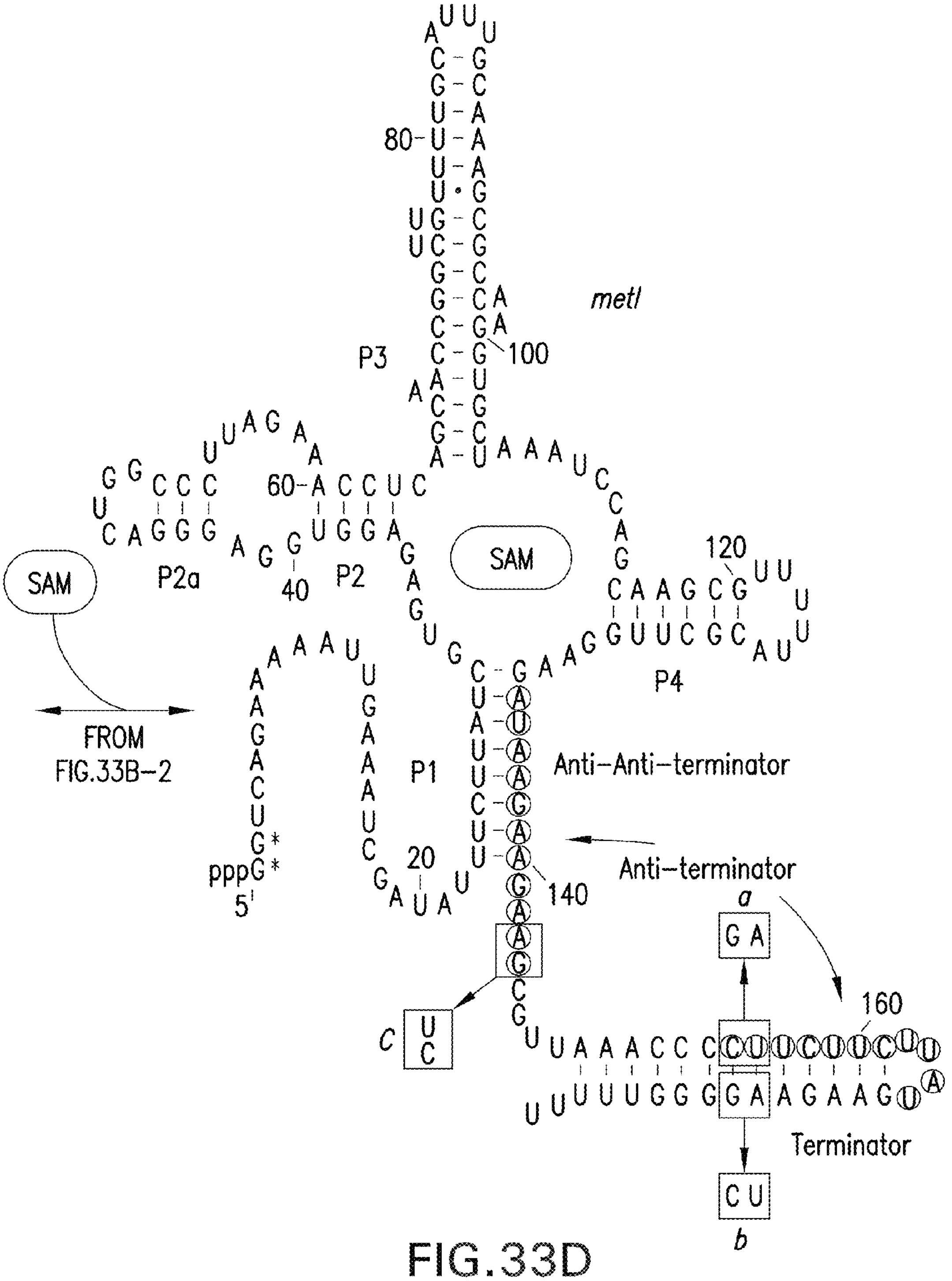
Figure 34A:
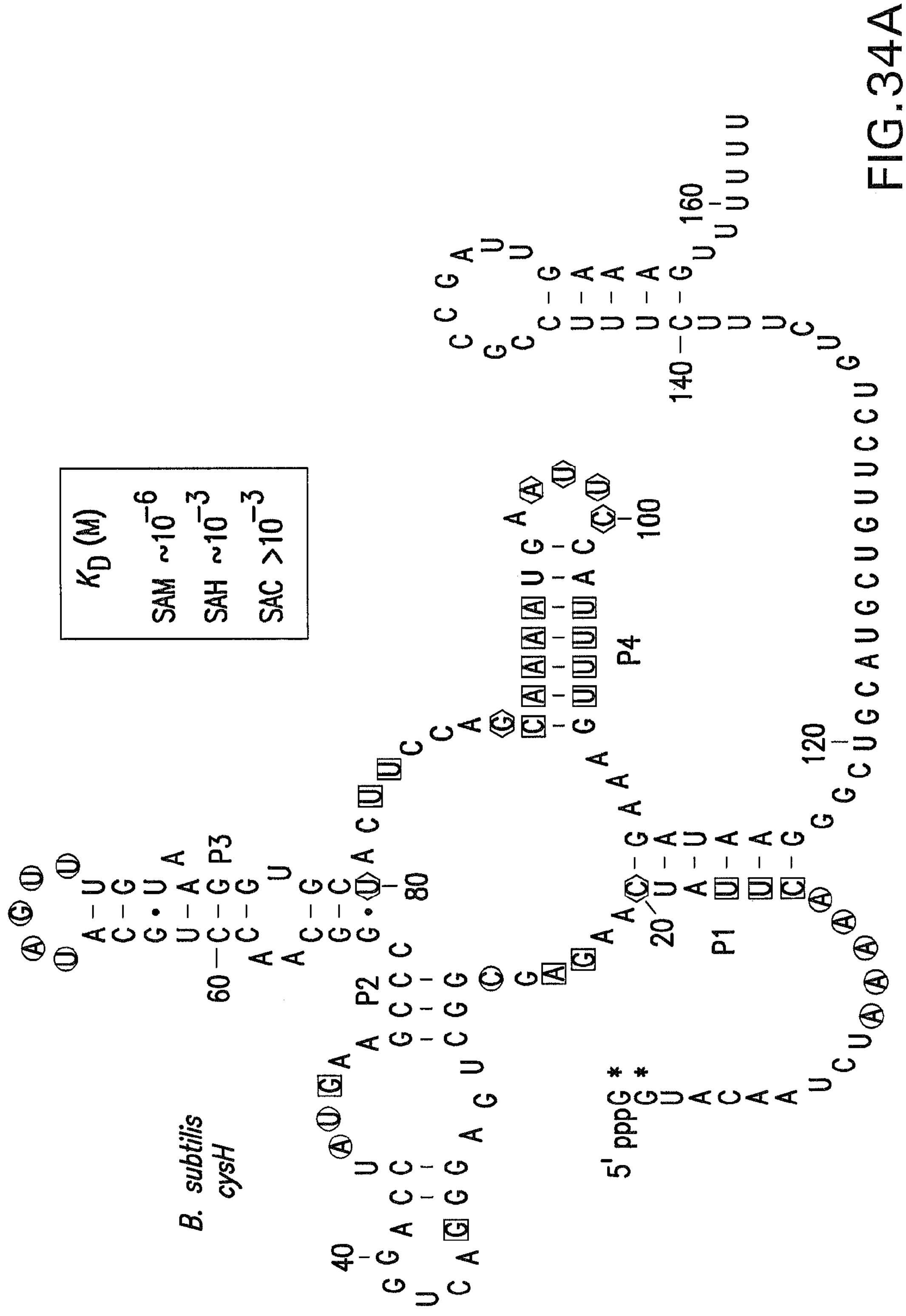
FIGS. 34A and 34B show *Bacilli* species *subtilis* and anthrasis bind SAM with different affinities.
Figure 34B:
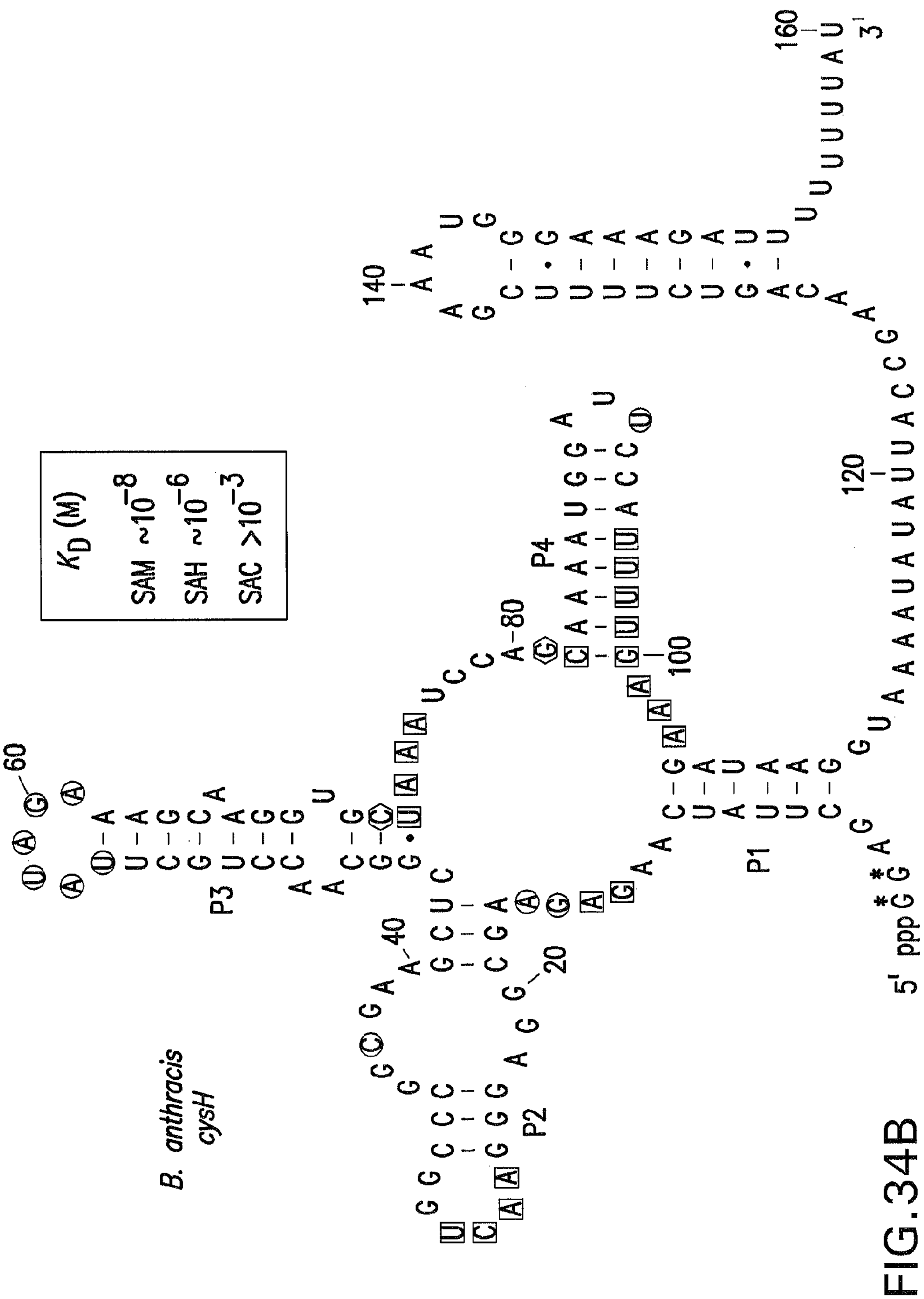

The mechanism of SAM-induced termination (FIG. 33*b*) most likely involves the ligand-mediated formation of alternative hairpin structures that permit transcriptional read-through (anti-terminator formation without SAM) or that cause termination (terminator formation with SAM). This mechanism was examined by generating several mutant metI constructs that carry disruptive or compensatory changes in the expression platform (FIG. 33*b*). SAM causes an additional ~20% yield in transcription termination in a mutant (Mabc) that carries six mutations relative to the wild-type metI riboswitch, which retains proper terminator and anti-terminator base complementation. However, incomplete representation of these six mutations that do not permit normal pairing interactions to occur permits little or no SAM-mediated transcription modulation. Furthermore, mutations that disrupt terminator stem formation (Ma) yield lower levels of termination, while mutations that disrupt anti-terminator stem formation (Mab, Mc) yield higher levels of termination (FIG. 33*b*). These findings indicate that the RNA structural modulation induced by SAM binding mediates genetic control by sequestering an anti-terminator sequence, and thus favors the formation of a transcriptional terminator hairpin.

v. Riboswitches Control Multiple Genes that are Involved in Fundamental Biochemical Pathways The 11 transcriptional units that comprise the regulon controlled by SAM riboswitches (F. J. Grundy, T. M. Henkin, *Mol. Microbiol.* 30, 737 (1998)) appear to encompass at least 26 genes that are central to sulfur metabolism, amino acid metabolism, and SAM biosynthesis. Although all 11 transcriptional units from *B. subtilis* carry a consensus S box element, a recent report indicates that gene expression from one of these (cysH) is not modulated by addition of methionine to the medium, as are other S box RNAs (M. C. Mansilla, et al., *J. Bacteriol.* 182, 5885 (2000)). The aptamer domain from *B. subtilis* cysH does bind SAM with an affinity that is more than 2 orders of magnitude poorer than that of yitJ from the same organism (FIG. 34*a*). However, the cysH homolog from *B. anthracis* exhibits a $K_D$ that matches that of yitJ (FIG. 34*b*), implying that the *B. subtilis* cysH aptamer has suffered one or more mutations that have somewhat degraded binding affinity.

2. Conclusion

Current biochemical and bioinformatics data indicate that *B. subtilis* has at least 68 genes (nearly 2% of its total genetic complement) under riboswitch control. Moreover, each of these mRNAs is responding to biological compounds that are universal in biology. The fact that genetic control elements for fundamental metabolic processes are formed by RNA indicates that this polymer has the structural sophistication needed to precisely monitor chemical environments and transduce metabolite binding events into genetic responses. A more detailed analysis of riboswitch structures at the atomic level would be of great utility in determining how metabolite binding promotes allosteric reorganization RNA genetic switches.

Riboswitches for ligands such as SAM and guanine appear to be serving as master control molecules whose concentrations are being monitored to ensure homeostasis of a much wider set of metabolic pathways. Riboswitches seem to permit metabolite surveillance and genetic control with the same level of precision and efficiency as that exhibited by protein factors, and thus could have emerged late in the evolution of modern biochemical architectures.

3. Methods i. DNA Oligonucleotides and Chemicals

Synthetic DNAs were purchased from The Keck Foundation Biotechnology Resource Center at Yale University. Preparation of RNAs by in vitro transcription was conducted (Seetharaman, S., et al., *Nat. Biotechnol.* 19, 336-341 (2001)) and the products were purified as described in Example 2. SAM, various analogs of SAM, and S-adenosyl-L-methionine-methyl-$^3$H ($^3$H-SAM) were purchased from Sigma.

ii. DNA Constructs

A yitJ DNA construct encompassing nucleotides −380 to +15 relative to the translation start site was prepared using primers that generated EcoRI and BamH1 restriction sites upon PCR amplification of *B. subtilis* chromosomal DNA (strain 168). The product was cloned into pDG1661 (ref 26; *Bacillus* Genetic Stock Center, Columbus, Ohio) using these restriction sites, which places the riboswitch immediately upstream of the lacZ reporter gene. Mutants were created by using the appropriate mutagenic primers and the QuickChange site-directed mutagenesis kit (Stratagene). All sequences were confirmed by sequencing.

iii. In vivo Analysis of Riboswitch Function

*B. subtilis* strain 1A234 was obtained from the *Bacillus* Genetic Stock Center, Columbus, Ohio. Cells were grown with shaking at 37° C. either in rich media (2XYT broth or tryptose blood agar base) or defined media (0.5% w/v glucose, 20 g $L^{-1}$ $(NH_4)_2SO_4$, 183 g $L^{-1}$ $K_2HPO_4.3H_2O$, 60 g $L^{-1}$ $KH_2PO_4$, 10 g $L^{-1}$ sodium citrate, 2 g $L^{-1}$ $MgSO_4.7H_2O$, 5 μM $MgCl_2$, 50 μg $L^{-1}$ tryptophan, and 50 μg $L^{-1}$ glutamate. Methionine was added to 50 μg $L^{-1}$ for routine growth. Growth under methionine-limiting conditions was established by incubation under routine growth conditions to an $A_{595}$ of 0.1, at which time the cells were pelleted by centrifugation, resuspended in minimal media, split into two aliquots, and supplemented with either 50 μg $L^{-1}$(+ methionine) or 0.75 μg $L^{-1}$ (− methionine) (FIG. 32*c*). Cultures were incubated for an additional 3 hr before performing βassays. Transformations of pDG1661 variants (see DNA constructs) into *B. subtilis* were performed as described elsewhere (H. Jarmer, et al., *FEMS Microbiol. Lett.* 206, 197 (2002)). The correct transformants were identified by selecting for chloramphenicol (5 μg $mL^{-1}$) resistance and screening for spectinomycin (100 μg $mL^{-1}$) sensitivity. Proper site-specific genomic insertion by double cross-over recombination was confirmed by PCR using amyE-specific primers.

iv. In vitro Transcription Termination Assays

Transcription reactions (10 μL) containing ~30 pmoles of specific template DNA, 200 μM each NTP, 5 μCi [α-$^{32}$P]UTP (1 Ci=37 GBq) and 50 units of T7 RNA polymerase (New England Biolabs) were incubated in the presence of 50 mM Tris-HCl (pH 7.5 at 23° C.), 15 mM $MgCl_2$, 2 mM spermidine, 5 mM DTT at 37° C. for 2 hr. SAM and its analogs were added to a final concentration of 50 μM. Transcription templates were generated for all 11 riboswitch domains in the S box regulon of *B. subtilis* by using PCR with corresponding primers that in each case produced transcripts beginning with GG, encompassing the putative natural transcription start (F. J. Grundy, T. M. Henkin, *Mol. Microbiol.* 30, 737 (1998)), and including the first 13 codons of the adjoining open reading frame. Transcription products were separated by denaturing 6% PAGE and visualized by PhosphorImager. Termination yields were approximated by determining the ratio of RNAs in the termination band relative to the combined terminated and full-length RNAs.

H. Example 8

Adenine Riboswitches

A class of riboswitches that recognizes guanine and discriminates against most other purine analogs was recently identified (see Example 6). Representative RNAs that carry the consensus sequence and structural features of guanine riboswitches are located in the 5'-untranslated region (UTR) of numerous genes of prokaryotes, where they control expression of proteins involved in purine salvage and biosynthesis. This example shows that three representatives of this phylogenetic collection bind adenine with values for apparent dissociation constant (apparent $K_D$) that are several orders of magnitude better than for guanine. The preference for adenine is due to a single nucleotide substitution in the core of the riboswitch, wherein each representative most likely recognizes its corresponding ligand by forming a Watson/Crick base pair. In addition, the adenine-specific riboswitch associated with the ydhL gene of *Bacillus subtilis* functions as a genetic 'ON' switch, wherein adenine binding causes a structural rearrangement that precludes formation of an intrinsic transcription terminator stem.

Guanine-sensing riboswitches are a class of RNA genetic control elements that modulate gene expression in response to changing concentrations of this compound (see Example 6). This is one of a number of classes of metabolite-binding riboswitches that regulate gene expression in response to various fundamental compounds such as lysine and the coenzymes FMN, SAM, $B_{12}$ and TPP (thiamin pyrophosphate) (see Example 6). Typically, each riboswitch is composed of two functional domains, an aptamer and an expression platform, that function together as a transducer of chemical signals into altered patterns of gene expression. The aptamer serves as a specific receptor for the target metabolite, wherein ligand binding brings about allosteric changes in both the aptamer and expression platform domains.

Detailed examinations of the ligand specificities for the natural aptamers from guanine- and lysine-specific riboswitches have been conducted (see Example 6), and less comprehensive examinations of the FMN, SAM, $B_{12}$ and TPP aptamers have been conducted (see Examples 1-3). In each case, the RNAs exhibit high levels of molecular discrimination by disfavoring the binding of even closely related metabolite analogs. This characteristic of high molecular discrimination is a hallmark of enzymes and receptors, including genetic regulatory factors, which need to carry out biological processes with great precision in the presence of complex chemical mixtures.

The molecular recognition characteristics of guanine riboswitches are distinguished by the fact that nearly every position around the purine heterocycle appears to be critical for high affinity binding by the aptamer. Thus, the arrangement of the binding pocket permits the riboswitch to control gene expression in response to changing guanine concentrations, but prevents modulation of gene expression in response to increasing concentrations of adenine (see Example 6; Cristiansen, L. C., et al., *J. Bacteriol.* 179, 2540-1550 (1997)). However, it is likely that receptors made of RNA, like their protein counterparts, could acquire altered molecular recognition characteristics as a result of natural selection. This would permit riboswitches to emerge through evolution that selectively sense and respond to metabolites that are proximal in metabolic pathways.

This example confirms the existence of a variant class of riboswitches that responds to adenine. These riboswitches carry an aptamer domain that corresponds closely in sequence and secondary structure to the guanine aptamer described recently (see Example 6). However, each representative of the adenine sub-class of riboswitches carries a C to U mutation in the conserved core of the aptamer, indicating that this residue is involved in metabolite recognition. The results indicate that the identity of this single nucleotide determines the binding specificity between guanine and adenine, which provides an example of how complex riboswitch structures could mutate to recognize new metabolite targets.

1. Results i. Phylogenetic Comparison Between Riboswitch Domains

Figure 35A:
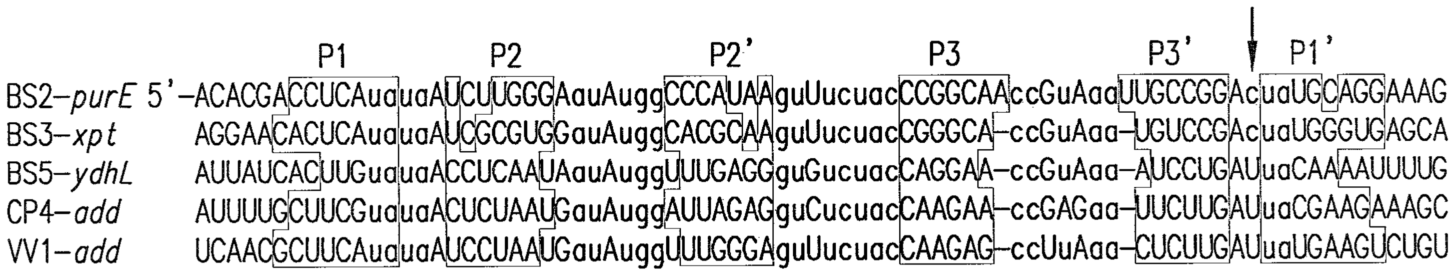
FIGS. 35A, 35B and 35C show guanine- and adenine-specific riboswitches.

A comparative sequence strategy was used to identify a series of intergenic regions from a number of prokaryotic species that carry a conserved sequence element termed the "G box" (see Example 6). *B. subtilis* carries at least five of these motifs, which were also identified using genetics techniques (Johansen, L. E., et al., *J. Bacteriol.* 185, 5200-5209). Each representative of the phylogeny has three potential base-paired elements (P1 through P3) and as many as 24 nucleotides that are conserved in greater than 90% of the examples identified to date. A subset of this phylogeny with features common to the G box motif highlighted is presented herein (FIG. 35A). When selected representatives are examined in greater detail, they are encompassed by the mRNA transcript of the gene immediately downstream, and thus are present as RNA elements located in the 5'-UTR of certain mRNAs.

Figure 35B:
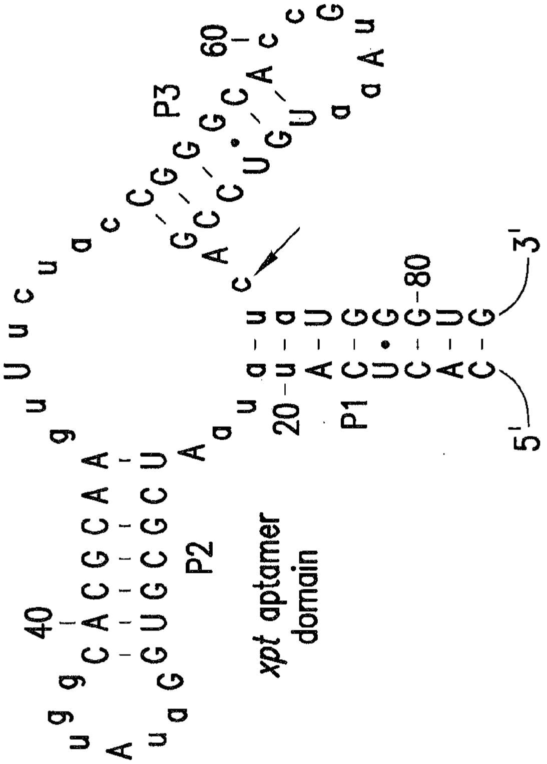
Figure 35C:
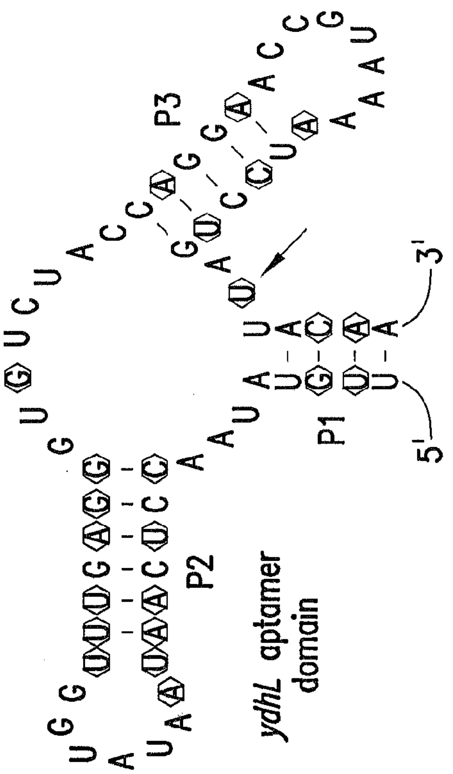

Several notable differences present in the guanine-binding domain of xpt (FIG. 35B) relative to the RNA from ydhL (FIG. 35C) were identified. First, among the 23 sequence variations in ydhL compared to xpt, 20 reside within base-paired elements and most of these changes permit base pairing to be retained. This strongly indicates that the overall secondary structure between the two RNAs is similar. Second, the remaining three mutations reside in unpaired regions, such that two (corresponding to positions 31 and 48 relative to xpt) reside at locations that are known to be variable. These mutations do not impact significantly the structure and function of the RNA. Third, the remaining mutation is a C to U change at position 74 relative to xpt, which otherwise corresponds to a strictly conserved nucleotide of the three-stem junction. Given the location of this mutation, this change might alter the molecular recognition characteristics of the ydhL aptamer.

ii. Variant G Box RNAs Selectively Bind Adenine

It had been established (see Example 6) that the xpt aptamer makes numerous contacts with its ligand, and that as many as seven hydrogen bonds might be involved in forming the RNA-ligand complex. Furthermore, there is evidence that steric clashes also likely aid in restricting the range of metabolites that can be bound by the RNA. This array of contacts can only be established by forming multiple interactions between the various sides of guanine and distal parts of the RNA.

An intriguing hypothesis is the possibility that the C residue at position 74 of xpt could conceivably be forming a Watson/Crick base pair with guanine, thus forming three of these hydrogen bonds. Since a U mutation resides in the corresponding position in *B.* subtilis ydhL and two RNAs from *C. perfringens* and *V. vulnificus*, we believe that these RNAs might serve as adenine-responsive riboswitches. This hypothesis was further supported by recognition that the latter two genes (add) encode adenine deaminase enzymes. It seems reasonable that adenine should be the metabolite whose concentration is being monitored to determine the expression levels of adenine deaminase.

Figure 36A:
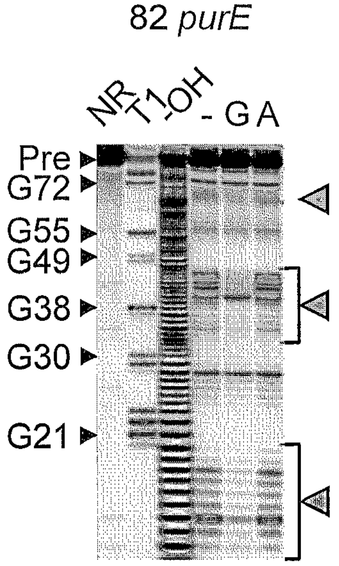
FIGS. 36A, 36B, 36C, 36D and 36E show the ligand specificity of five G box RNAs. (A through E) In-line probing assays for the conserved aptamer domains as labeled. NR, T1 and $^-$OH identify marker lanes wherein precursor RNAs (Pre) were not incubated, or were partially digested with RNase T1 or alkali, respectively. Selected bands corresponding to RNase T1 digestion (cleavage 3' relative to guanidyl residues) are labeled for each RNA. RNAs were incubated for 40 hr in the absence of ligand (−), or in the presence of 1 μM guanine (G) or adenine (A). Large arrowheads identify sites of substantial change in cleavage pattern that is due to the addition of a particular ligand. See Methods for additional details.
Figure 36B:
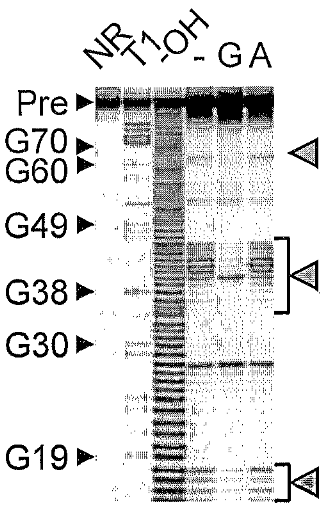
Figure 36C:
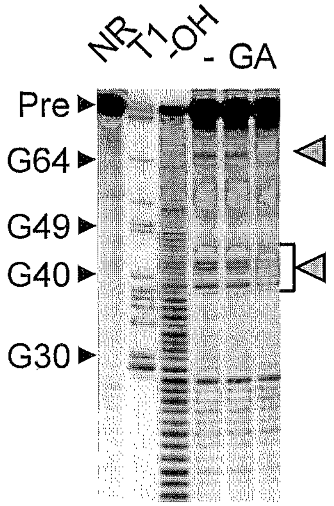
Figure 36D:
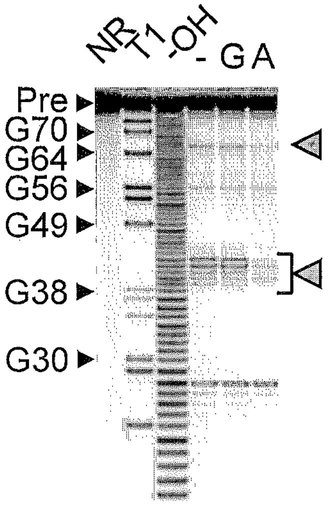
Figure 36E:
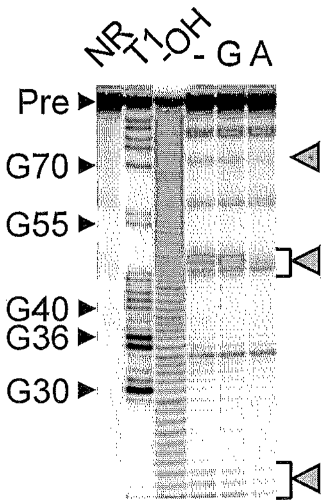

The ligand specificity of five G box RNAs (FIG. 35A) was examined by using in-line probing (. Soukup, G. A. & Breaker, R. R. *RNA* 5, 1308-1325 (1999); Soukup, G. A., DeRose, E. C., *RNA* 7, 524-536 (2001)). In this assay, the spontaneous cleavage of RNA is monitored in the absence of ligand, or in the presence of guanine or adenine. As predicted previously (see Example 6), the purE RNA (FIG. 36A) exhibits changes in the pattern of spontaneous cleavage products in the presence of guanine that correspond to that observed for the xpt RNA (FIG. 36B). These results confirm that the purE RNA, like the xpt RNA, responds allosterically to guanine and not to adenine when incubated in the presence of the concentrations of ligand tested.

In contrast, all three RNAs that carry the C to U mutation in the junction between P1 and P3 (corresponding to C74 of xpt) do not respond to guanine, but exhibit structural modulation only when incubated in the presence of adenine. Furthermore, the patterns of spontaneous cleavage for the adenine-specific aptamers are consistent with the secondary-structure model proposed for G box RNAs (FIG. 35). These results indicate that certain variants of the G box class of RNAs serve as sensors of adenine. Furthermore, these findings are consistent with the hypothesis that, when located in their natural settings, the ydhL RNA from *B. subtilis* and the two add RNAs from *C. perfringens* and *V. vulnificus* serve as adenine-specific riboswitches.

iii. The ydhL Aptamer Binds Adenine with High Affinity and Selectivity

Figure 37A:
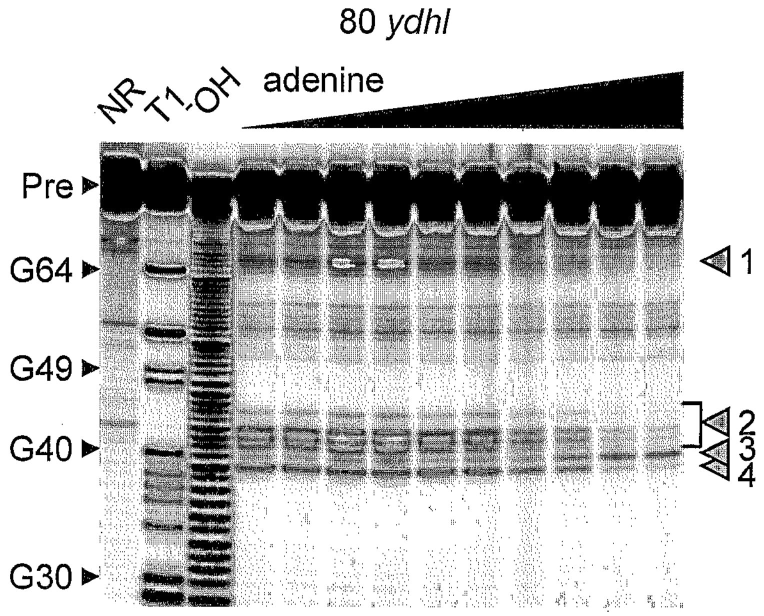
FIGS. 37A and 37B show the binding affinity of the ydhL aptamer for adenine.

Another characteristic of riboswitches is the aptamer domains exhibit tight binding for their corresponding target compound, and they discriminate against analogs, in some cases, by orders of magnitude in apparent $K_D$. For example, the guanine riboswitch from *B. subtilis* xpt exhibits an apparent $K_D$ for guanine of ~5 nM, but binds adenine with an apparent $K_D$ that is at least 100,000-fold poorer. In-line probing assays were used to determine the binding affinities of the *B. subtilis* 80 ydhL RNA for these two purines. As expected, the RNA exhibits progressively changing patterns of spontaneous RNA cleavage fragments in the presence of increasing concentrations of adenine (FIG. 37A), but the pattern remains unchanged with increasing guanine concentrations as high as 10 μM (see below).

Figure 37B:
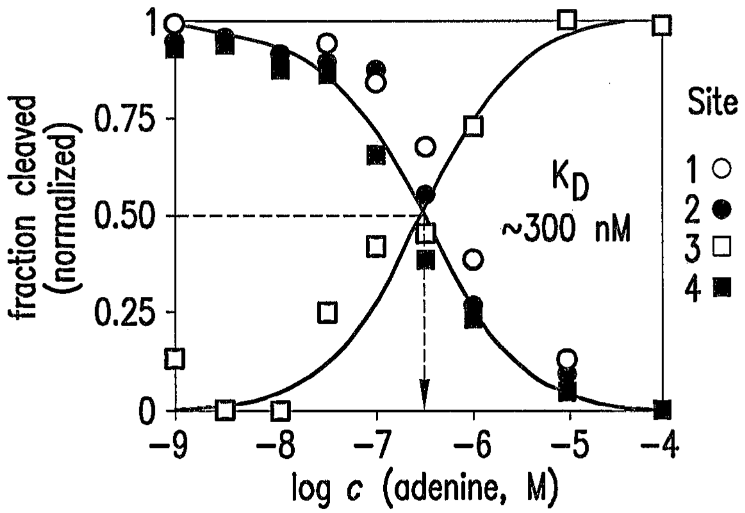

The bands corresponding to spontaneous cleavage fragments that undergo change with increasing adenine concentrations were grouped into four sites and the extent of cleavage relative to the total RNA present were quantitated. This data was used to generate a plot (FIG. 37B) that provides an estimate of the apparent $K_D$ for ligand binding. In this instance, half-maximal decrease in spontaneous cleavage at sites 1, 2 and 4, and the corresponding half-maximal increase in spontaneous cleavage at site 3 occurs when approximately 300 nM adenine is present in the in-line probing assay. Thus, the ydhL aptamer binds adenine with an apparent $K_D$ that is similar to those exhibited by other classes of riboswitches.

Figure 38A:
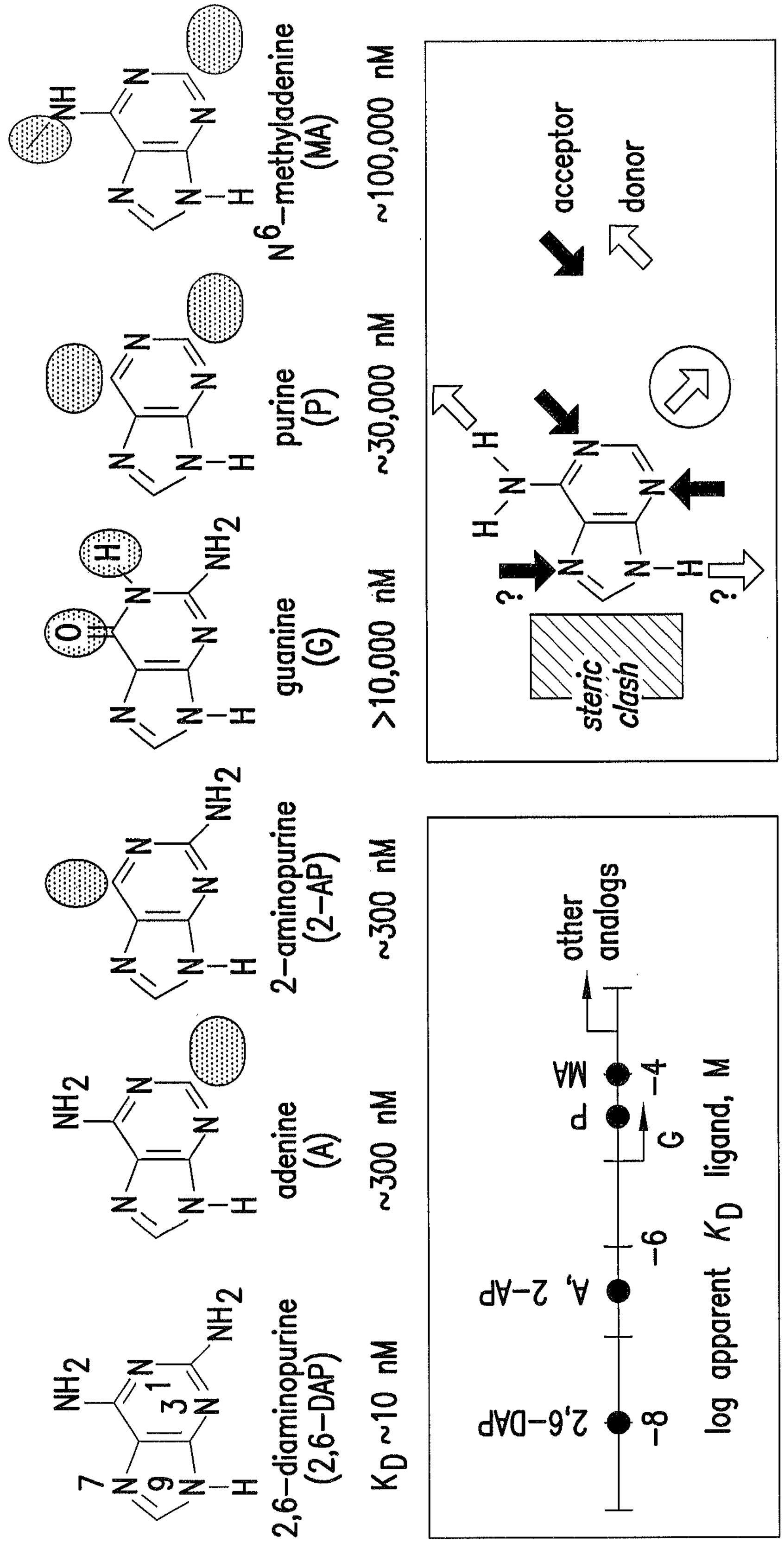

The molecular recognition characteristics of 80 ydhL were further examined by using the same in-line probing strategy with a variety of analogs. For example, a series of purine analogs that are close chemical variants to adenine exhibit measurable binding to the RNA (FIG. 38A). The ligands with measurable binding, 2,6-DAP, A and 2-AP, P, MA (listed in order of decreasing affinity), are all close analogs of adenine. Furthermore, the relative affinities of the RNA for various ligands provide some indication of the contact points that the aptamer likely uses to establish molecular recognition (FIG. 38A, bottom right). This model is consistent with the finding that a series of purine analogs fail to exhibit measurable binding to the 80 ydhL RNA (FIG. 38B).

The collection of purines that are recognized by 80 ydhL indicate that only the Watson/Crick base-pairing face of the purine ligand is recognized differently by the ydhL aptamer compared to the xpt aptamer. For example, modification at the C8 position (8-chloroadenine) prevents ligand binding, which implies that a steric clash between certain purines and 80 ydhL as was observed for the xpt aptamer (see Example 6). Interestingly, the fact that 2,6-DAP, and not adenine, is the tightest-binding ligand provides insight into the similarities between the ydhL and xpt aptamers. This observation suggests that the 80 ydhL RNA retains at least one of the two hydrogen bond acceptor contacts that were proposed to exist in the xpt aptamer. Thus, the molecular recognition characteristics of these RNAs are consistent with the ydhL RNA differing in molecular recognition from xpt with a pattern that can be explained by a change from a Watson/Crick guanine-C base pair in xpt to a Watson/Crick adenine-U base pair in ydhL.

iv. Swapping Ligand Specificity of G Box RNAs by Molecular Engineering

The idea that the xpt and ydhL RNAs might be deriving their specificity for guanine or adenine by a Watson/Crick base pairing interaction was examined in greater detail by using a molecular engineering approach. A similar approach was used previously (Wilson, K. S. & von Hippel, P. H. *Proc. Natl. Acad. Sci. USA* 92, 8793-8797) to change the ligand-rescue specificity of an abasic hammerhead ribozyme construct from guanine to adenine. Both wild-type (93 xpt and 80 ydhL) and mutant (93 xpt C to U and 80 ydhL U to C) forms of G box aptamers were generated and tested for binding activity with guanine and adenine (FIG. 39). The mutations correspond to nucleotide position 74 relative to the xpt sequence (FIG. 35B), which is suspected to be the determinant of molecular discrimination between guanine and adenine.

Figure 39A:
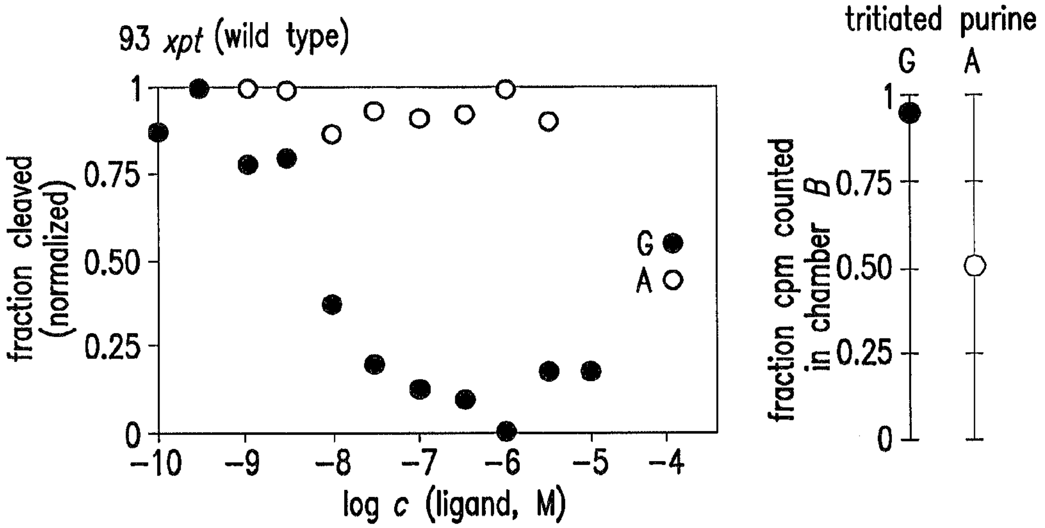
FIGS. 39A, 39B, 39C and 39D show interconversion of guanine- and adenine-specific aptamers.
Figure 39B:
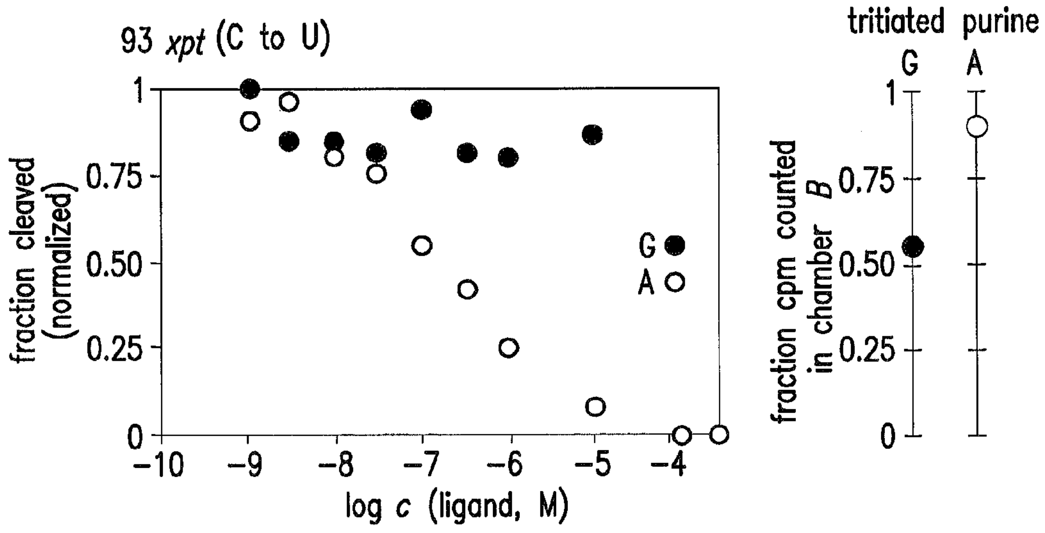
Figure 39C:
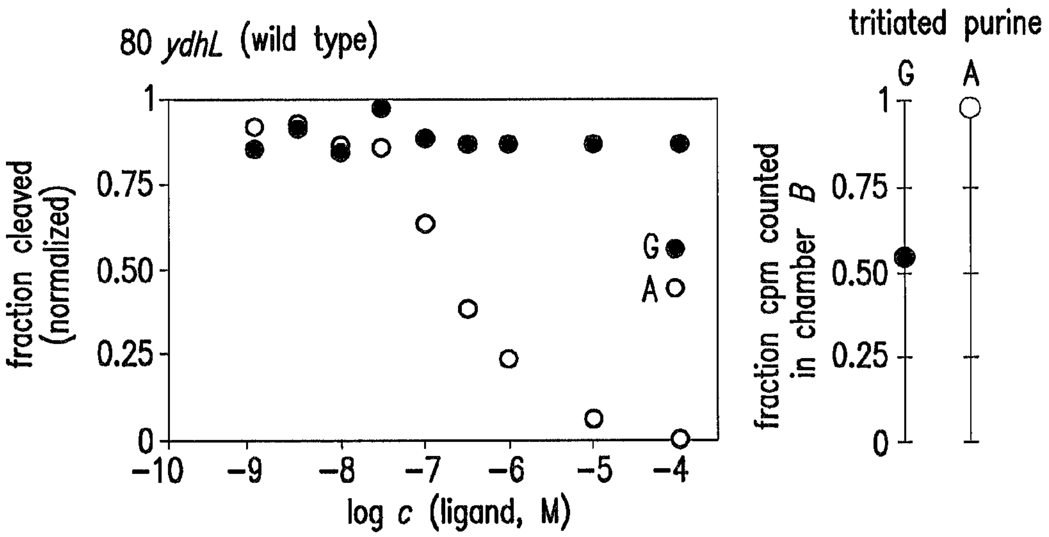
Figure 39D:
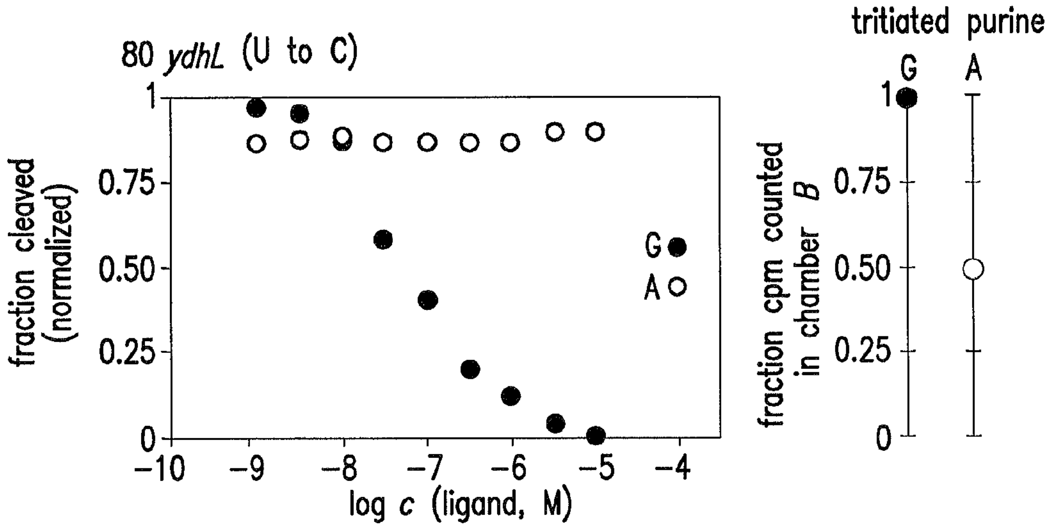

As observed previously (see Example 6), the aptamer based on xpt exhibits structural modulation only when incubated in the presence of guanine, and is able to shift the distribution of tritiated guanine (but not adenine) in an equilibrium dialysis assay (FIG. 39A). However, the 93 xpt RNA that carries a single C to U mutation at position 74 no longer is responsive to guanine, but exhibits structural modulation and binding activity during equilibrium dialysis only in the presence of adenine (FIG. 39B). In contrast, the wild-type 80 ydhL RNA is specific for adenine (FIG. 39C), while the corresponding U to C mutation at this critical nucleotide position alters binding specificity to guanine (FIG. 39D). Therefore, the primary determinant of the base specificity of G box aptamers is the C or U residue that is present in the junction between stems P1 and P3, and that this base most likely forms a conventional Watson-Crick base pair with its target ligand.

v. Mechanism of Genetic Control by the ydhL Adenine Riboswitch from *B. subtilis*

In most instances, riboswitches control gene expression in prokaryotes by allosteric interconversion between alternate base-paired structures. For example, a TPP riboswitch from the thiM gene of *E. coli* makes use of alternate base pairing to sequester the Shine-Dalgarno sequence of the mRNA in the presence of ligand, presumably resulting in reduced translation initiation (see Example 2). In contrast, TPP riboswitches from *B. subtilis* harness ligand-binding events to alter base-pairing patterns and form intrinsic terminator stems that cause transcription elongation to abort (Gusarov, I & Nudler, E. *Mol. Cell.* 4, 495-504 (1999); Mironov, A. S. et al. *Cell* 111, 747-756 (2002)). Similarly, metabolite-mediated formation of transcription terminator stems is a mechanism used by certain examples of riboswitches that respond to FMN (see Example 3 and 6), SAM (see Example 7), guanine (see Example 6), and lysine (see Example 5).

Figure 40A:
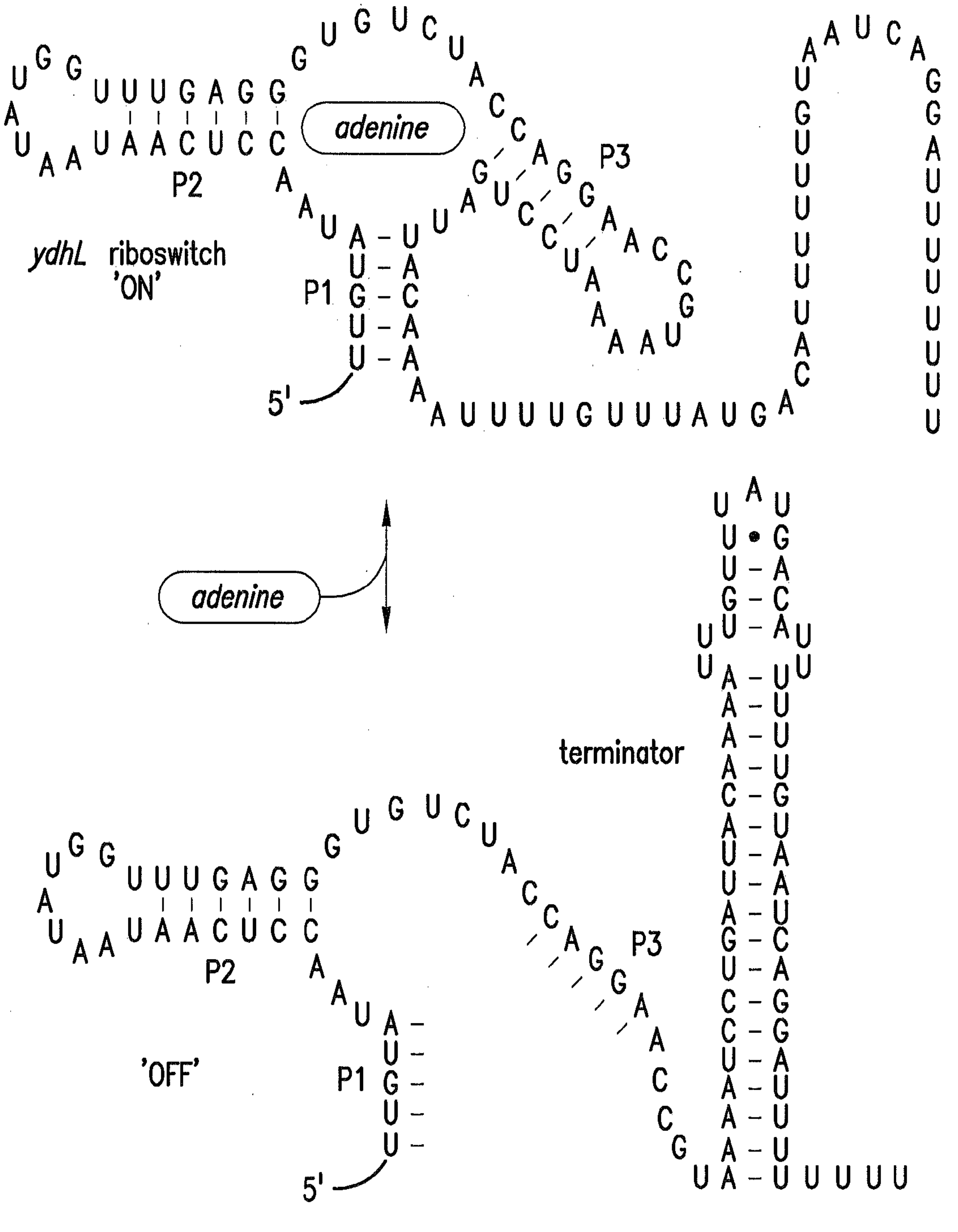
FIGS. 40A, 40B, 40C, 40D and 40E show a model for the genetic control of ydhL by an adenine riboswitch and its function as a gene-activating element.

The UTR sequence of the ydhL riboswitch eas examined to assess whether there is evidence of a transcription termination mechanism. Consistent with this possibility is the fact that the 5'-UTR of the ydhL mRNA can form a large hairpin, composed of as many as 22 base pairs, followed by a run of eight uridyl residues (FIG. 40A). This structural feature, which was also noted elsewhere recently (Johansen, L. E., et al., *J. Bacteriol.* 185, 5200-5209), is characteristic of an intrinsic terminator stem. In the absence of adenine, it was considered that the riboswitch can form this intrinsic terminator. If true, then the genetic control status for this riboswitch would default to this predicted 'OFF' state, which prevents gene expression by inducing transcription termination. In the presence of adenine, gene expression is expected to proceed because a substantial portion of the left shoulder of the terminator stem would be required to form stems P1 and P3 of the adenine aptamer domain. Since stems P1 and P2 are integral components of the adenine aptamer, ligand binding would establish a structure that precludes formation of the terminator stem.

Figure 40B:
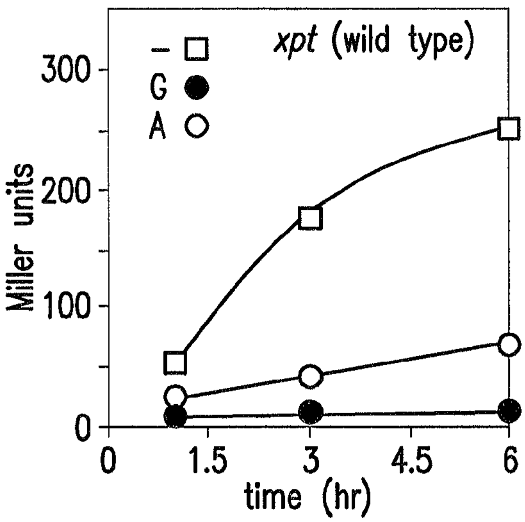

This mechanism for the ydhL riboswitch was assessed in vivo by generating reporter constructs wherein various forms of guanine- and adenine-specific riboswitches were integrated into the *B. subtilis* genome. As controls, two reporter constructs were prepared with either the wild-type xpt riboswitch, or the xpt variant with the C to U mutation at position 74. As expected, the wild-type xpt construct causes repression of β-galactosidase expression when presented with excess guanine in the culture medium (FIG. 40*b*). This finding is similar to those reported previously for function of the guanine riboswitch from xpt (see Example 6). Adenine also shows a modest (~4 fold) repression of reporter expression after a six-hour incubation. This latter effect is most likely due to the function of the PurR protein, which is known to provide modest down-regulation of transcription initiation in response to adenine at the xpt-pbuX promoter used in this construct (Cristiansen, L. C., et al., *J. Bacteriol.* 179, 2540-1550 (1997)).

Figure 40C:
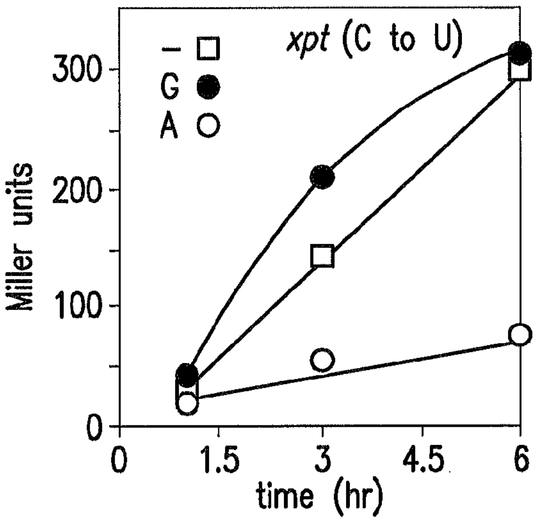

A near identical xpt construct carrying the C to U mutation causes a loss of regulation upon addition of guanine, but shows no change in the putative protein-dependent control due to adenine (FIG. 40C). These results are consistent with the observed loss of guanine binding in vitro when this mutation is made, but suggest that the resulting specificity change to adenine in vitro does not permit robust adenine-dependent genetic control in vivo. Most likely, the diminished expression upon addition of adenine again is due to the PurR protein.

Figure 40D:
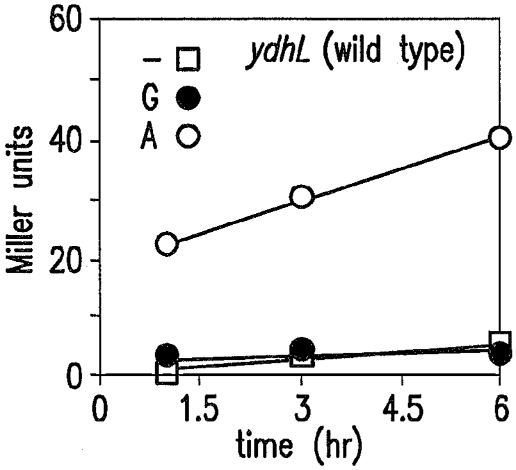
Figure 40E:
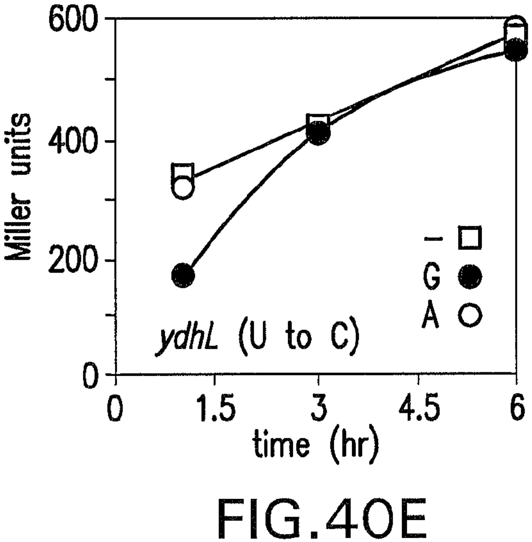
Figure 41L:
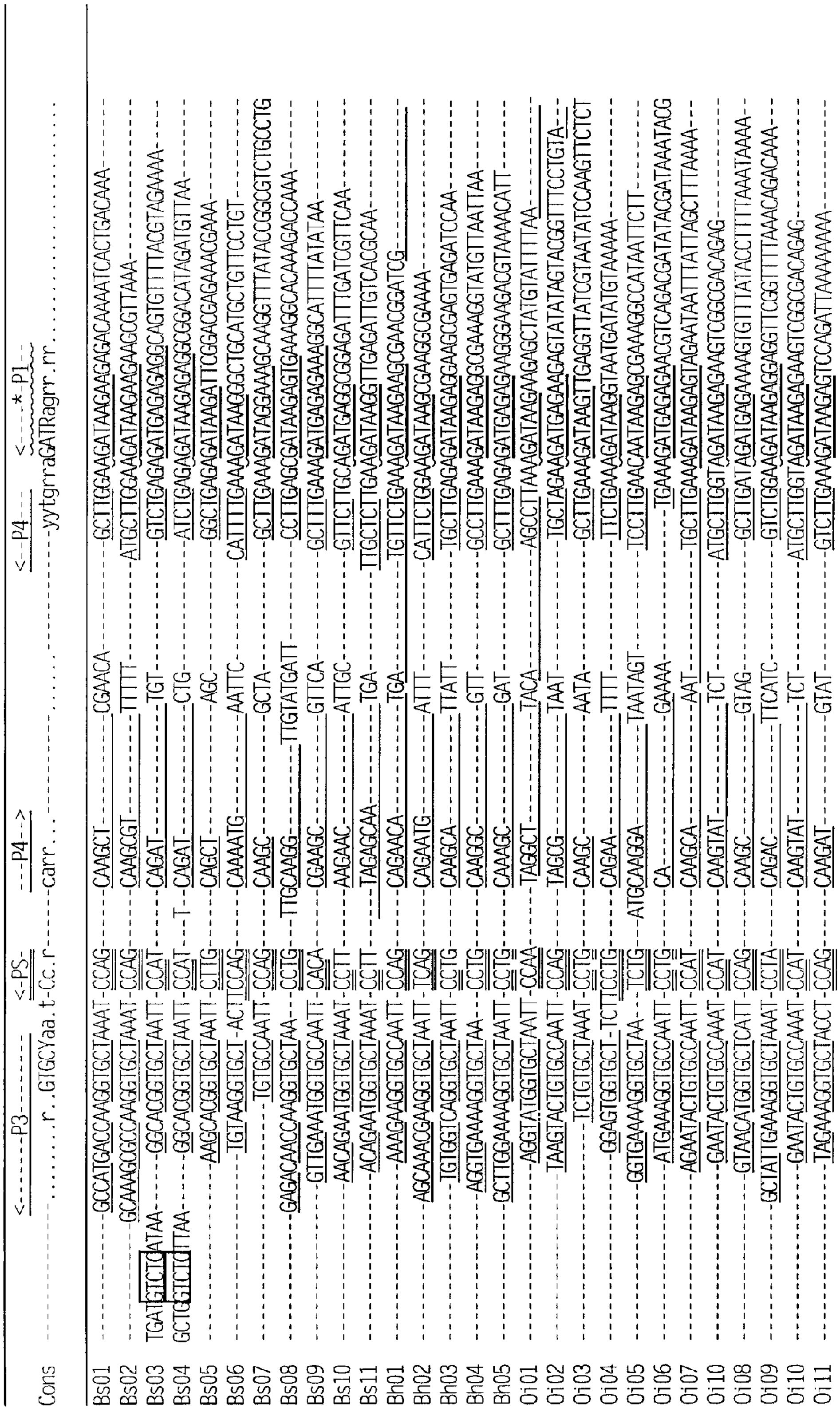
FIGS. 41A-41BA show the sequence and types of riboswitches Bs01, Bs02, Bs03, Bs04, Bs05, Bs06, Bs07, Bs08, Bs09, Bs10, Bs11, Bh01, Bh02, Bh03, Bh04, Bh05, Oi01, Oi02, Oi03, Oi04, Oi05, Oi06, Oi07, Oi10, Oi08, Oi09, Oi10, Oi11, Oi12, Oi13, Ca01, Ca02, Ca03, Ca04, Ca05, Ca06, Ca07, Cp01, Cp02, Lm01, Lm02, Lm03, Lm04, Lm05, Lm06, Lm07, Li01, Li02, Li03, Li04, Li05, Li06, Li07, Sa01, Sa02, Sa02, Sa04, Sc01, Ct01, Tt01, Tt02, Tt03, Fn01, Fn02, Dr01, Dr02, Xa01, Xc01, Se01, Se02, Gs01, Gs02, Ba01, Ba02, Ba03, Ba04, Ba05, Ba06, Ba07, Ba08, Ba09, Ba10, Ba11, Ba12, Ba13, Ba14, Ba15, Ba16, Ba17, Bc01, Bc02, Bc03, Bc04, Bc05, Bc06, Bc07, Bc08, Bc09, Bc10, Be11, Bc12, Bc13, Bc14, Bc15, Bc16, Bc17, Bc18, Atu01, Atu02, Atu03, Atu04, Atu05, Atu06, Bha01, Bha02, Bha03, Bha04, Bsu01, Bja01, Bja02, Bja03, Bja04, Bja05, Bme01, Bme02, Bme03, Bme04, Cer01, Cer02, CteOl, Cte02, Cte03, Cte04, Cte05, Cac01, Cac02, Cpe01, Cpe02, Cpe03, Cpe04, Eco01, Fnu01, Lig01, Lmo01, M1o01, M1o02, M1o03, M1o04, M1o05, M1o06, M1e01, Mtu01, Mtu02, Pae01, Pae02, Pae03, Pae04, Ppu01, Ppu02, Ppu03, Ppu04, Rso01, Sme01, Sme02, Sme03, Sme04, Sme05, Sco01, Sco02, Sco03, Sco04, Sco05, Sfl01, Son01, Son02, Sti01, Sti02, Tma01, Tte01, Tte02, Veh01, Vvu01, Xac01, Xax01, Ype01, Aca01, Avi01, Bfr01, Bmg01, Lma01, Pfr01, Rca01, Rca02, Rca03, Rsp01, Sbi01, SgiOl, Svi01, Zmo01, Zmo02, NC_002570.1/648448-648540, NC_002570.1/650317-650406, NC_002570.1/676483-676572, NC_002570.1/806882-806965, NC_002570.1/1593067-1592976, NC_000964.1/693955-694038, NC_000964.1/697886-697976, NC_000964.1/2319120-2319031, NC_000964.1/4004319-4004410, NC_003030.1/1002184-1002270, NC_003030.1/2904259-2904168, NC_003030.1/2824539-2824454, NC_003366.1/422828-422924, NC_003366.1/512410-512323, NC_003366.1/2617892-2617807, NC_003454.1/1645257-1645173, NC_002662.1/1159519-1159604, NC_003210.1/610773-610679, NC_003210.1/1958601-
Figure 41P:
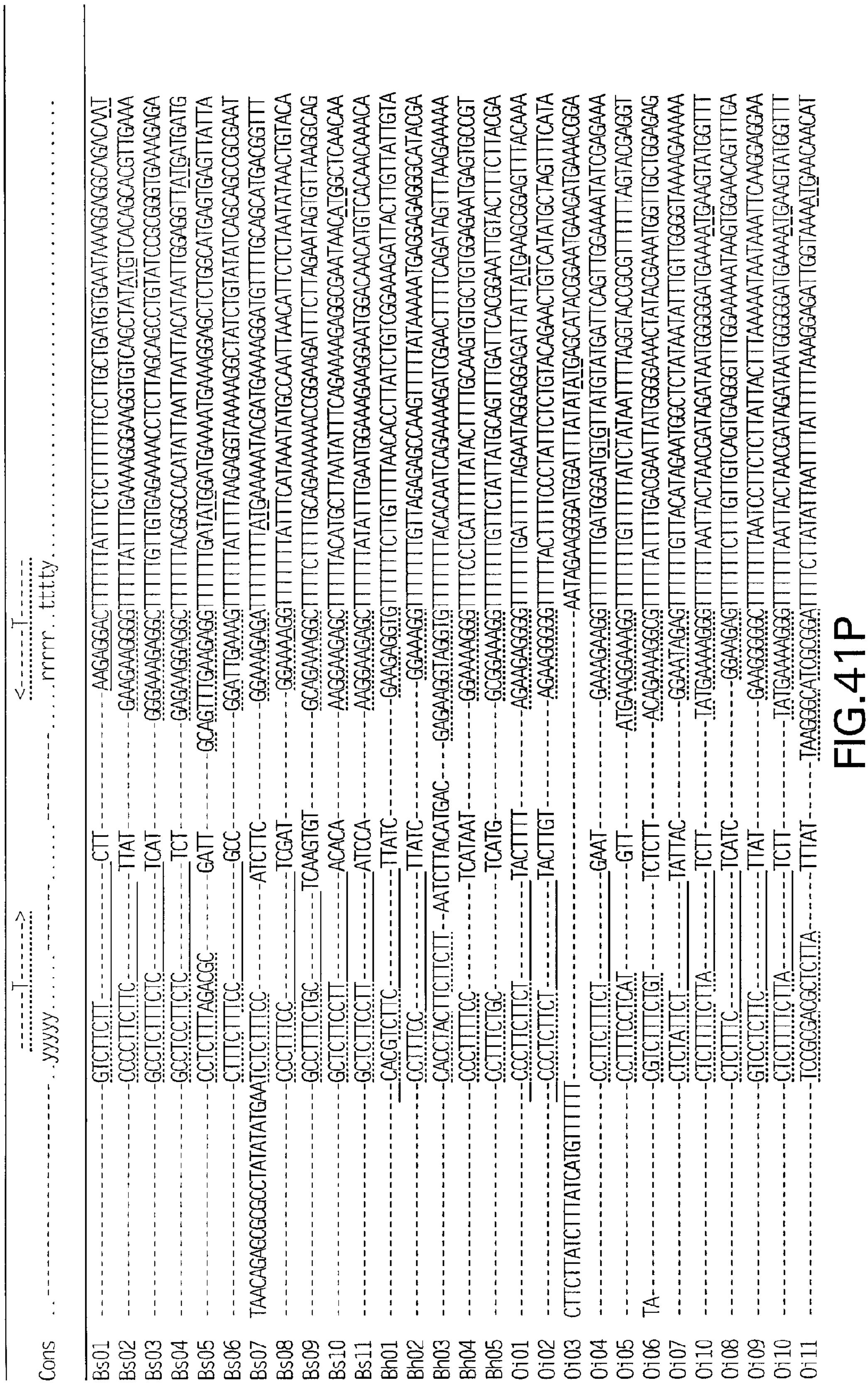
Figure 41A:
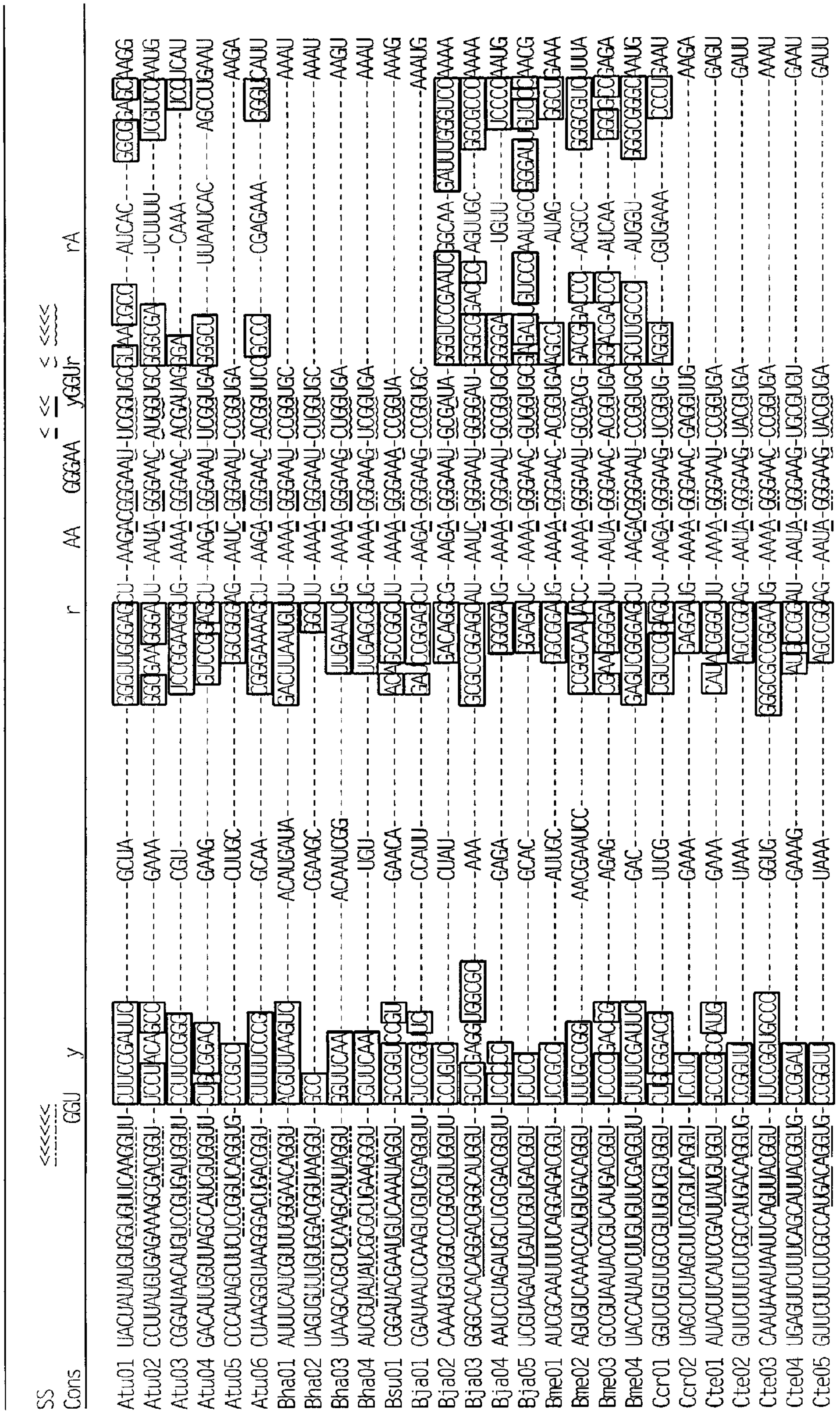
Figure 41A:
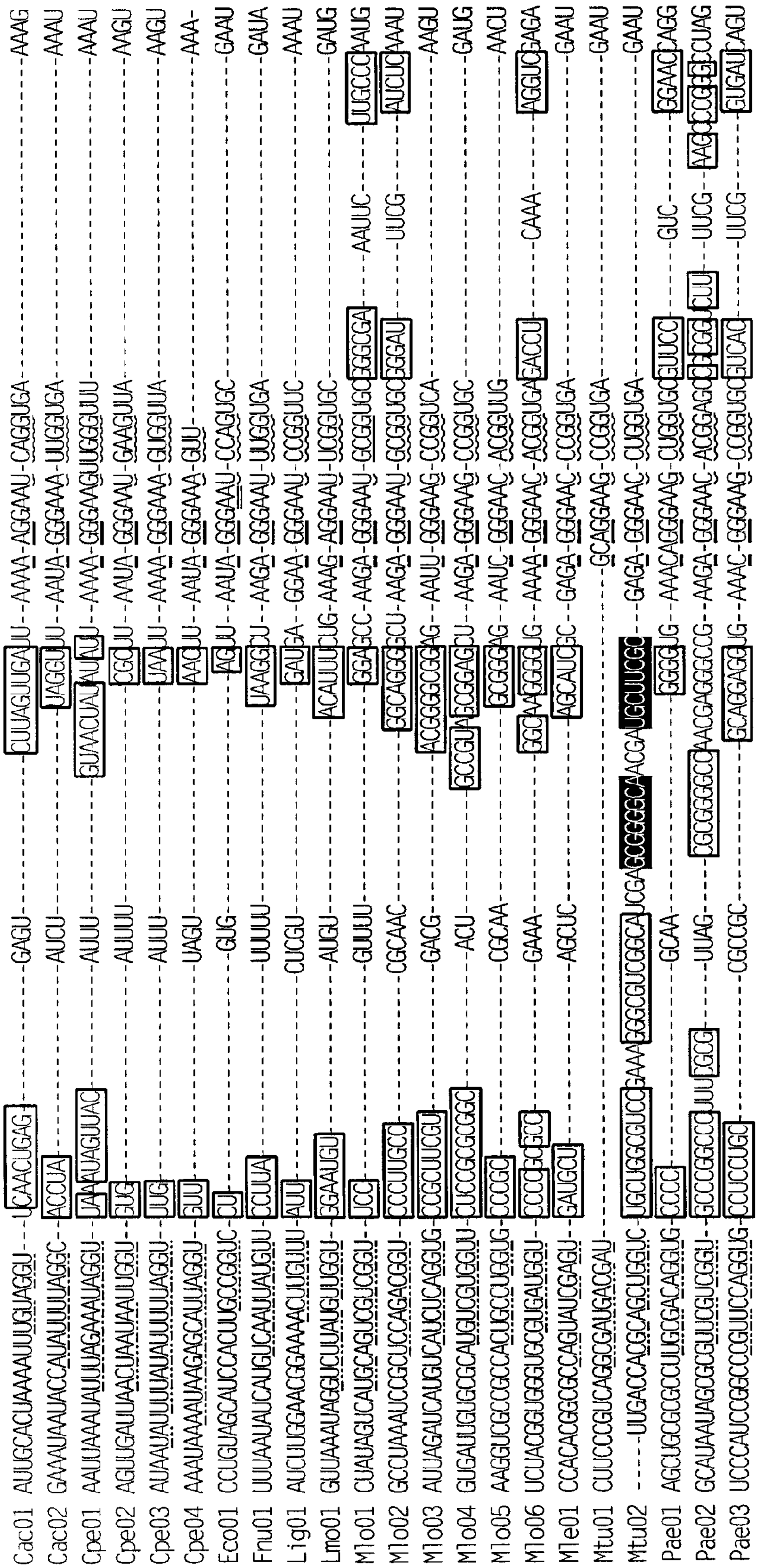
Figure 41A:
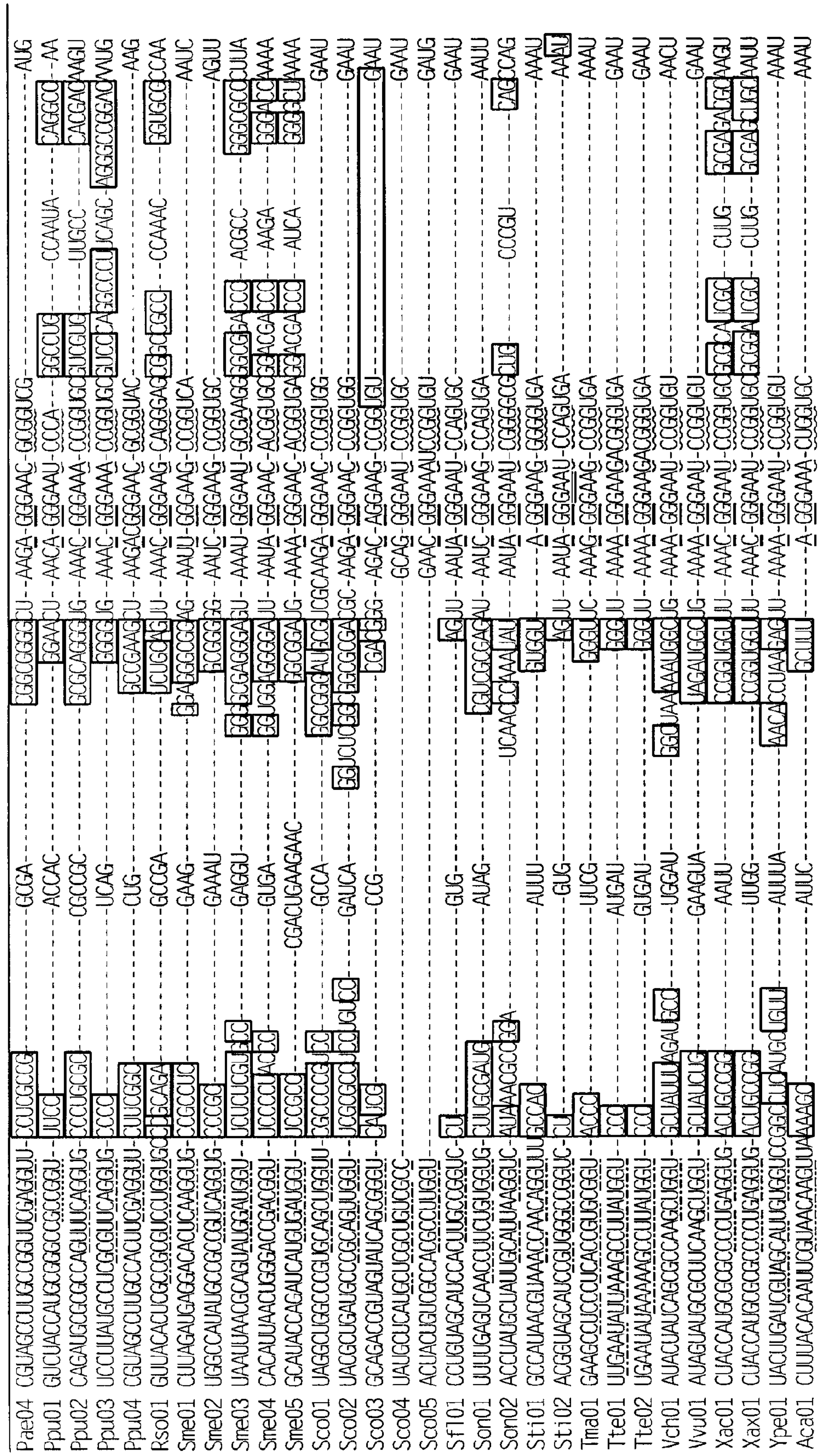
Figure 41A:
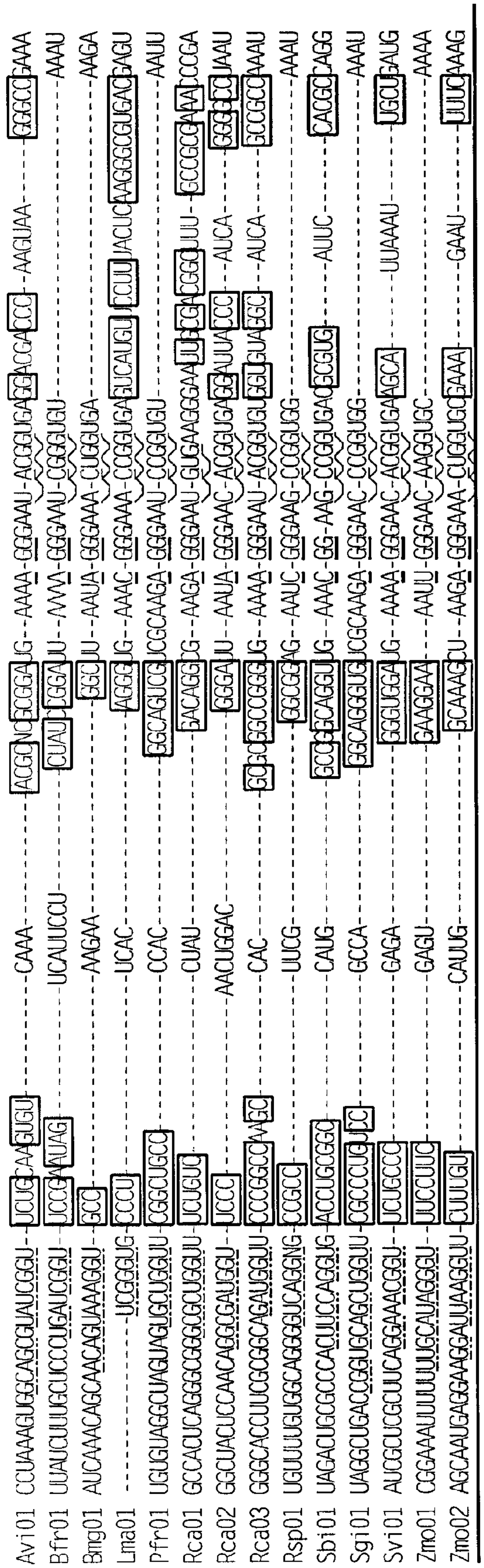
Figure 41A:
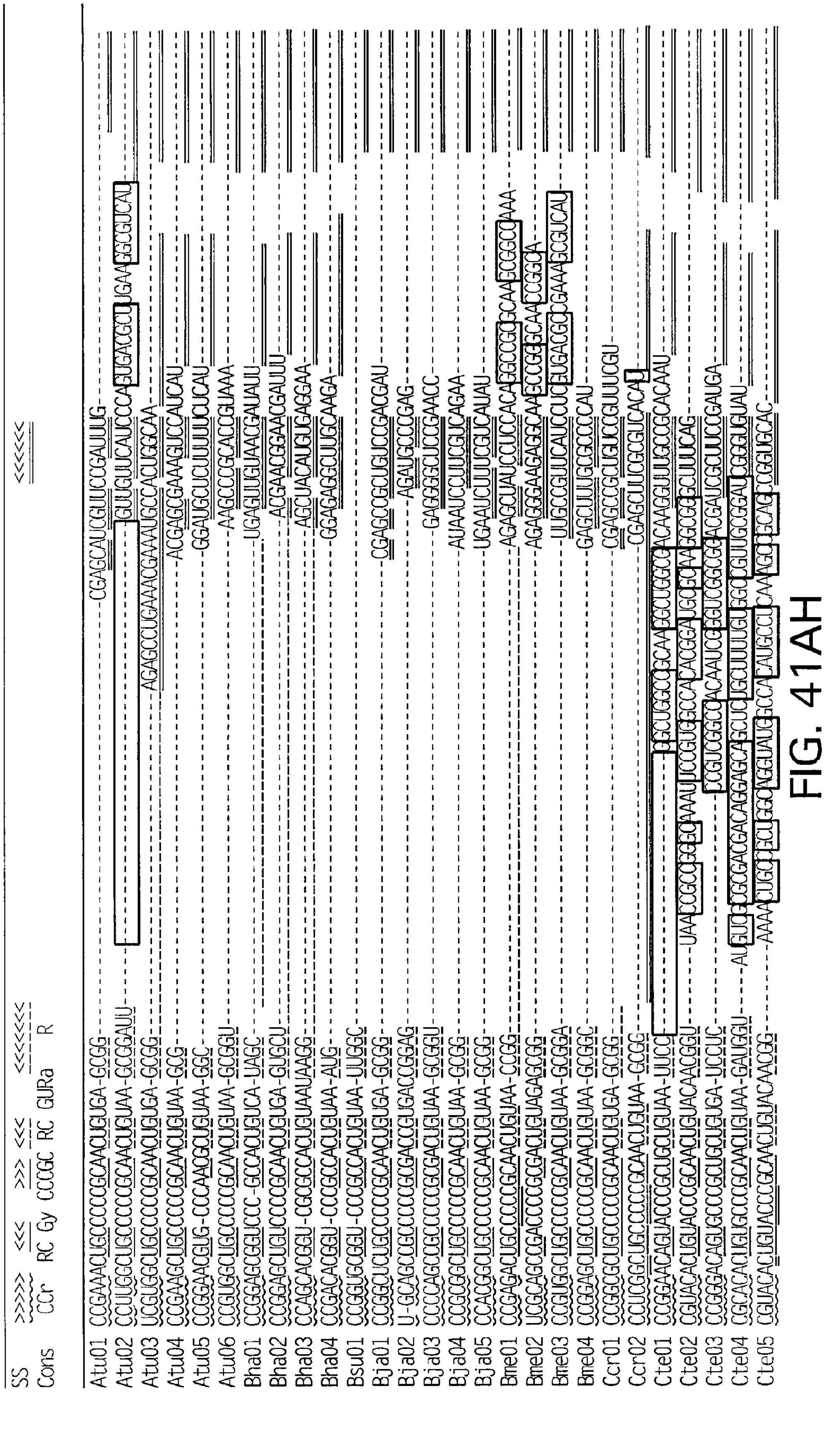
Figure 41A:
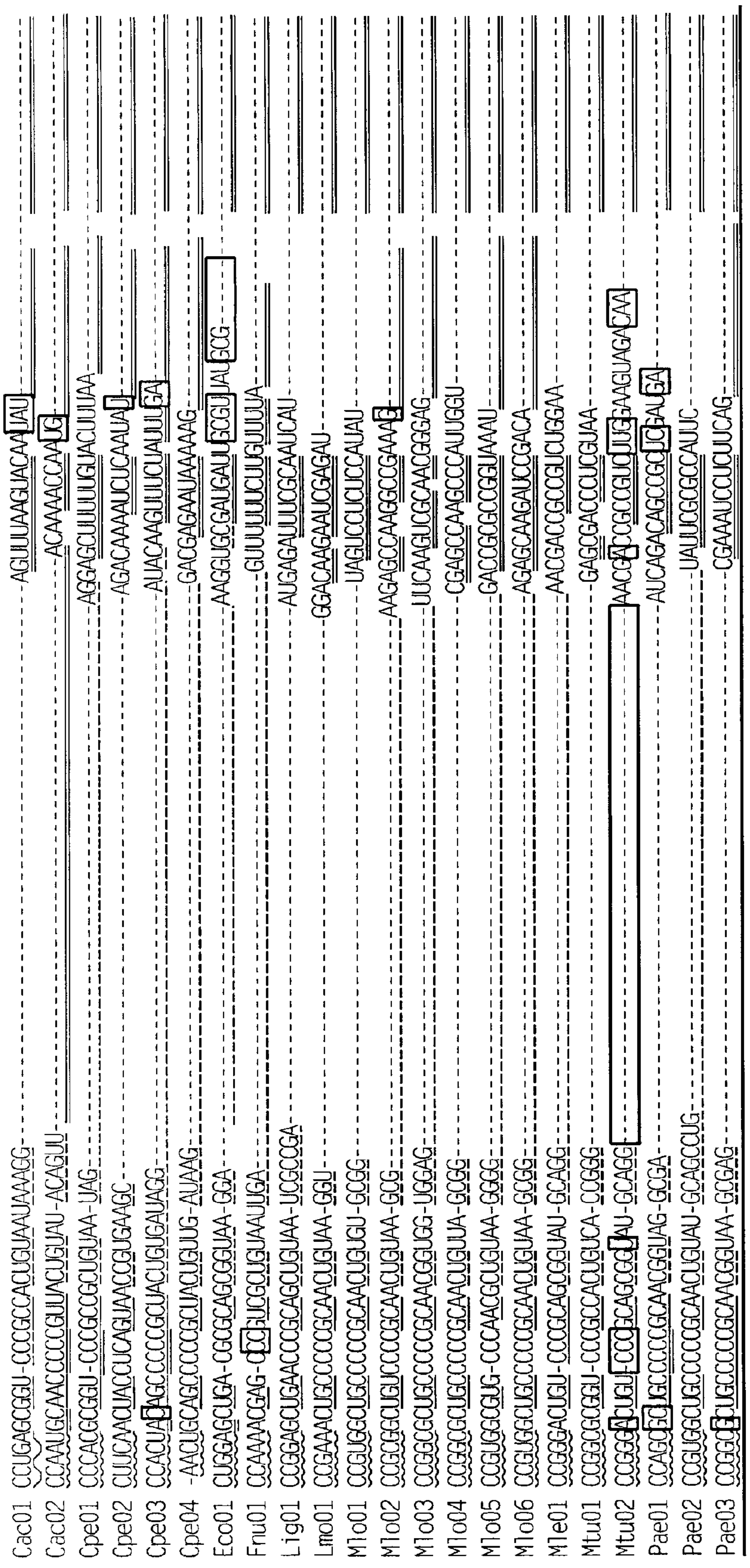
Figure 41A:
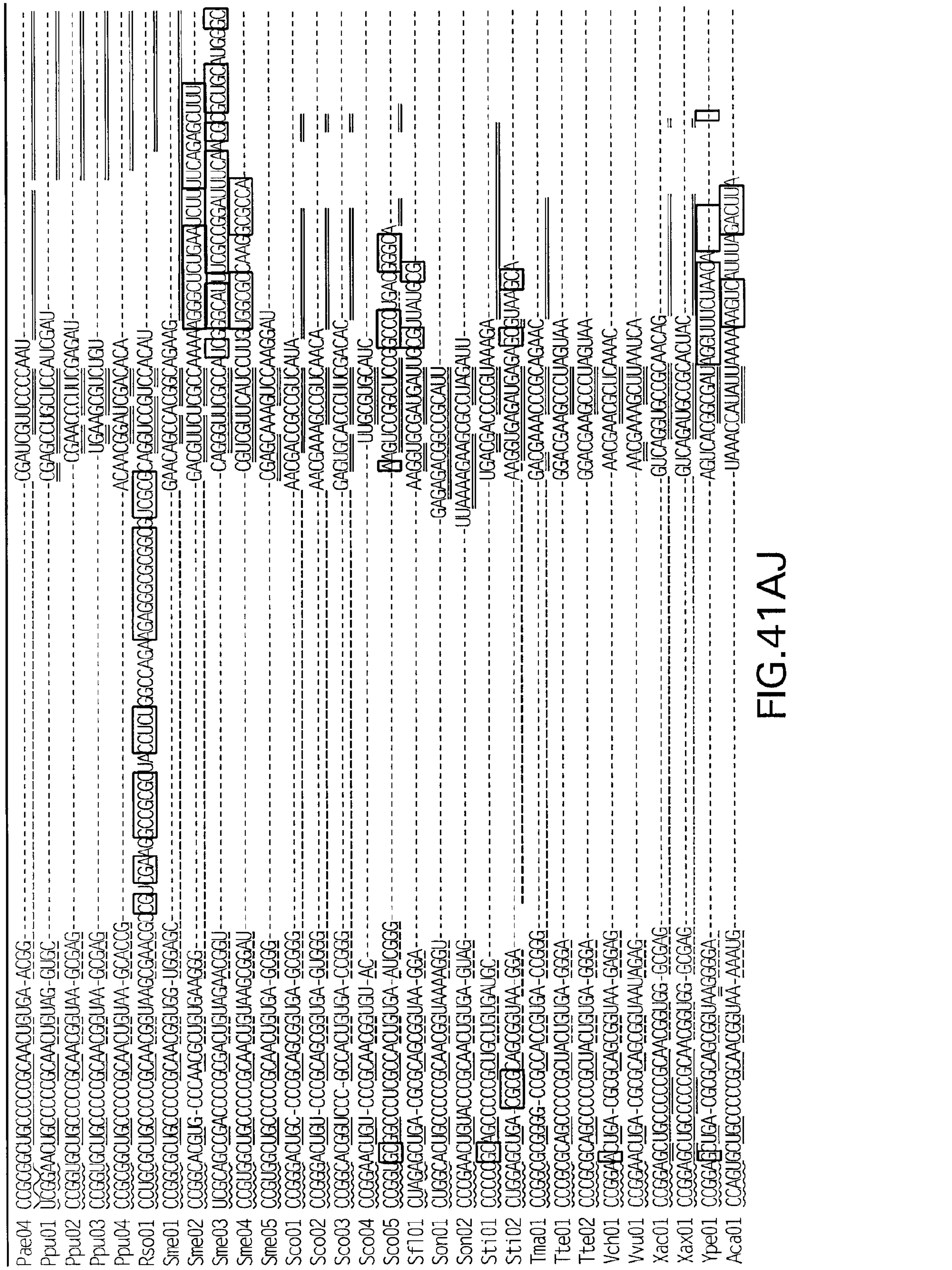
Figure 41A:
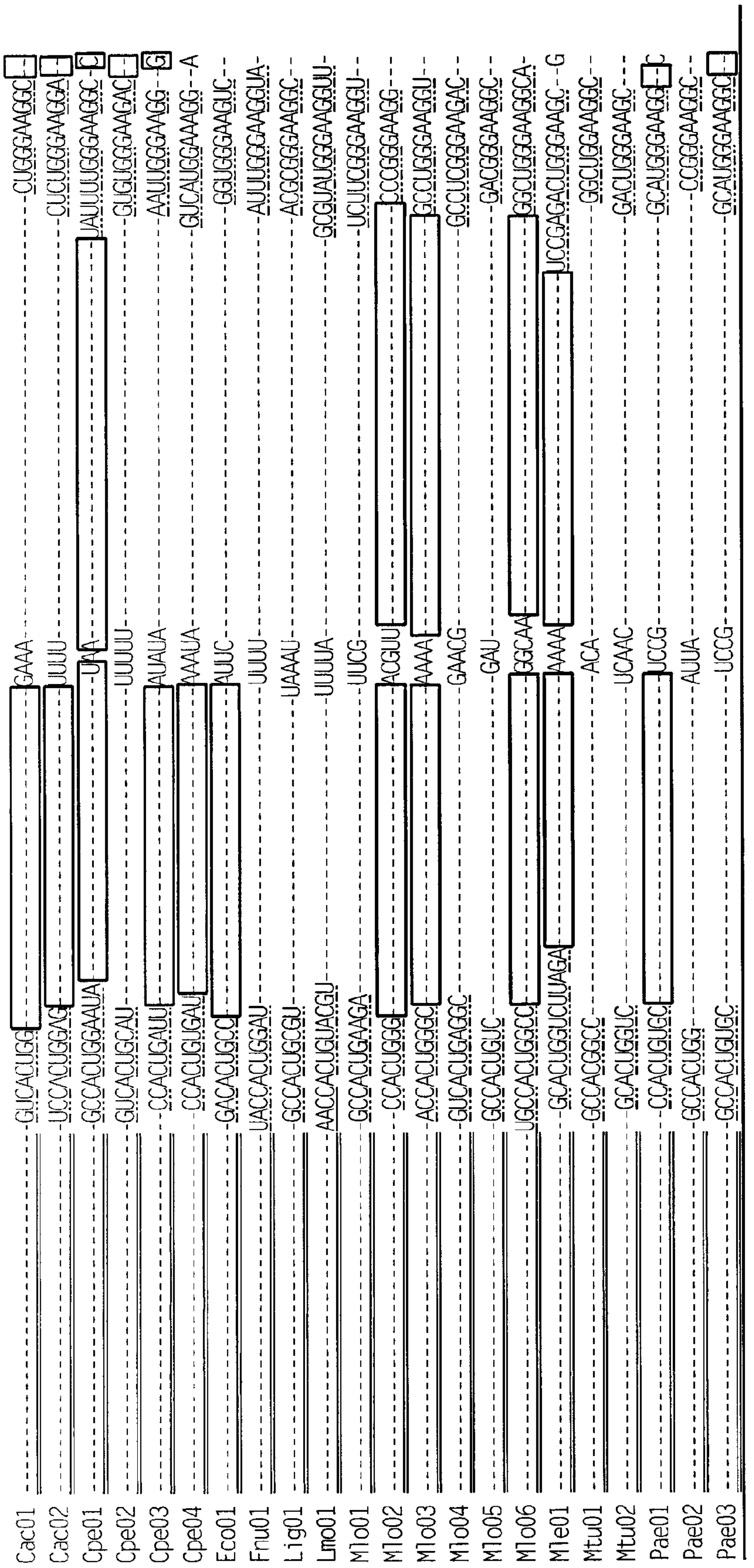
Figure 41A:
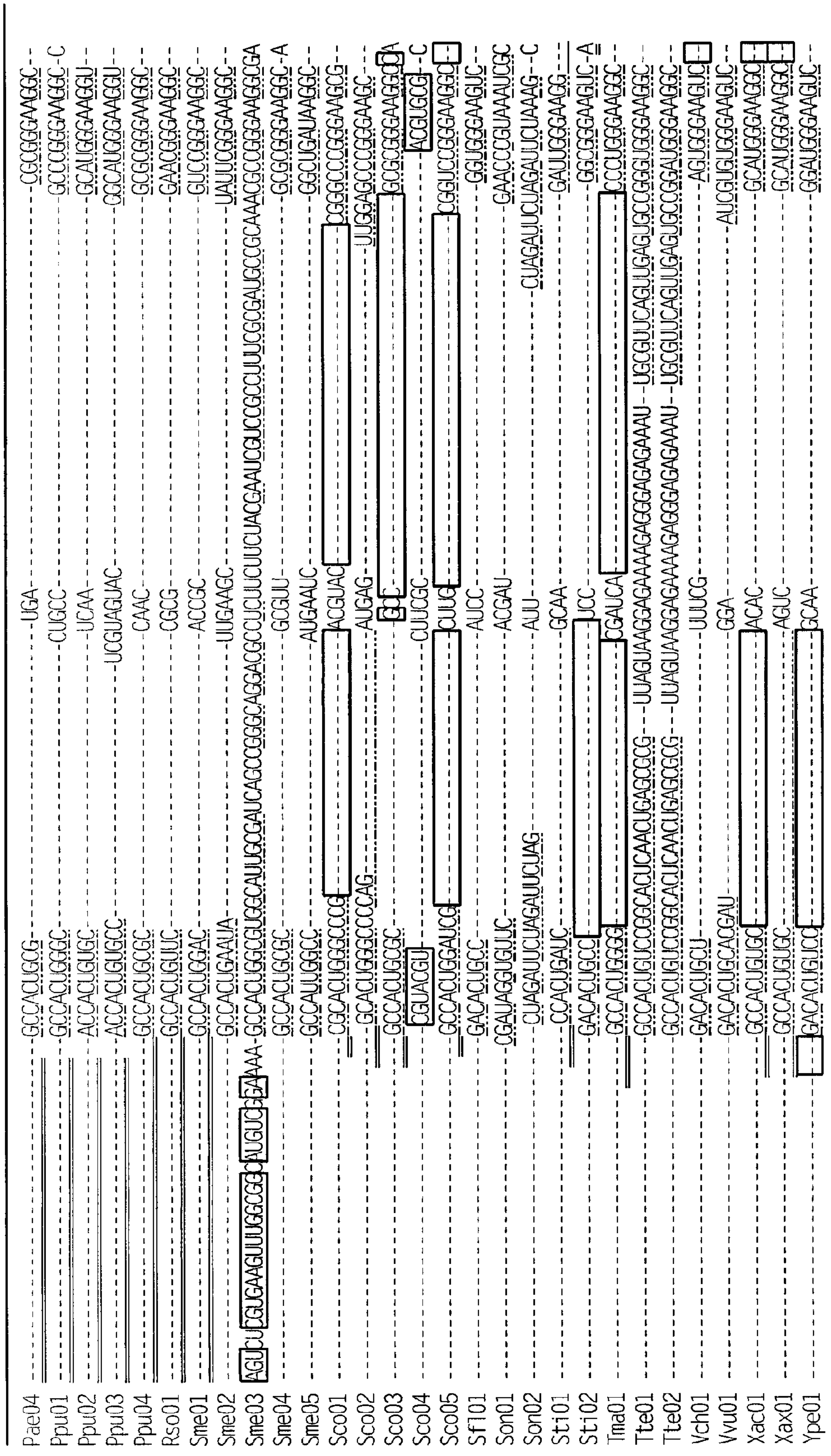
Figure 41A:
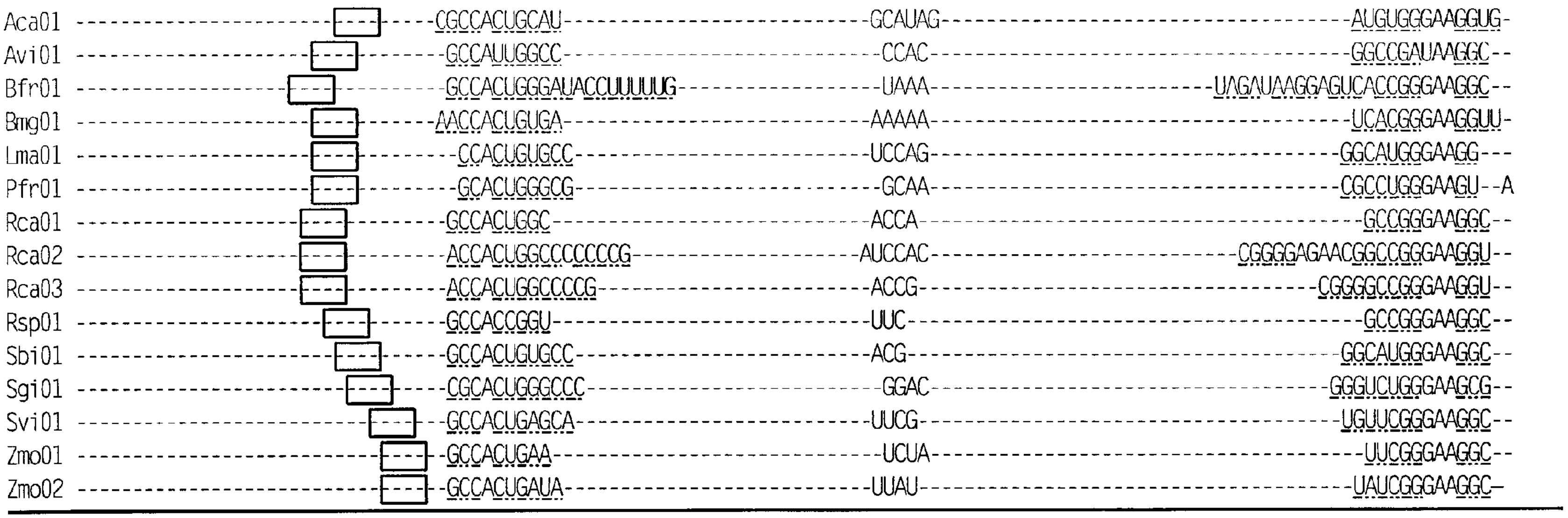
Figure 41A:
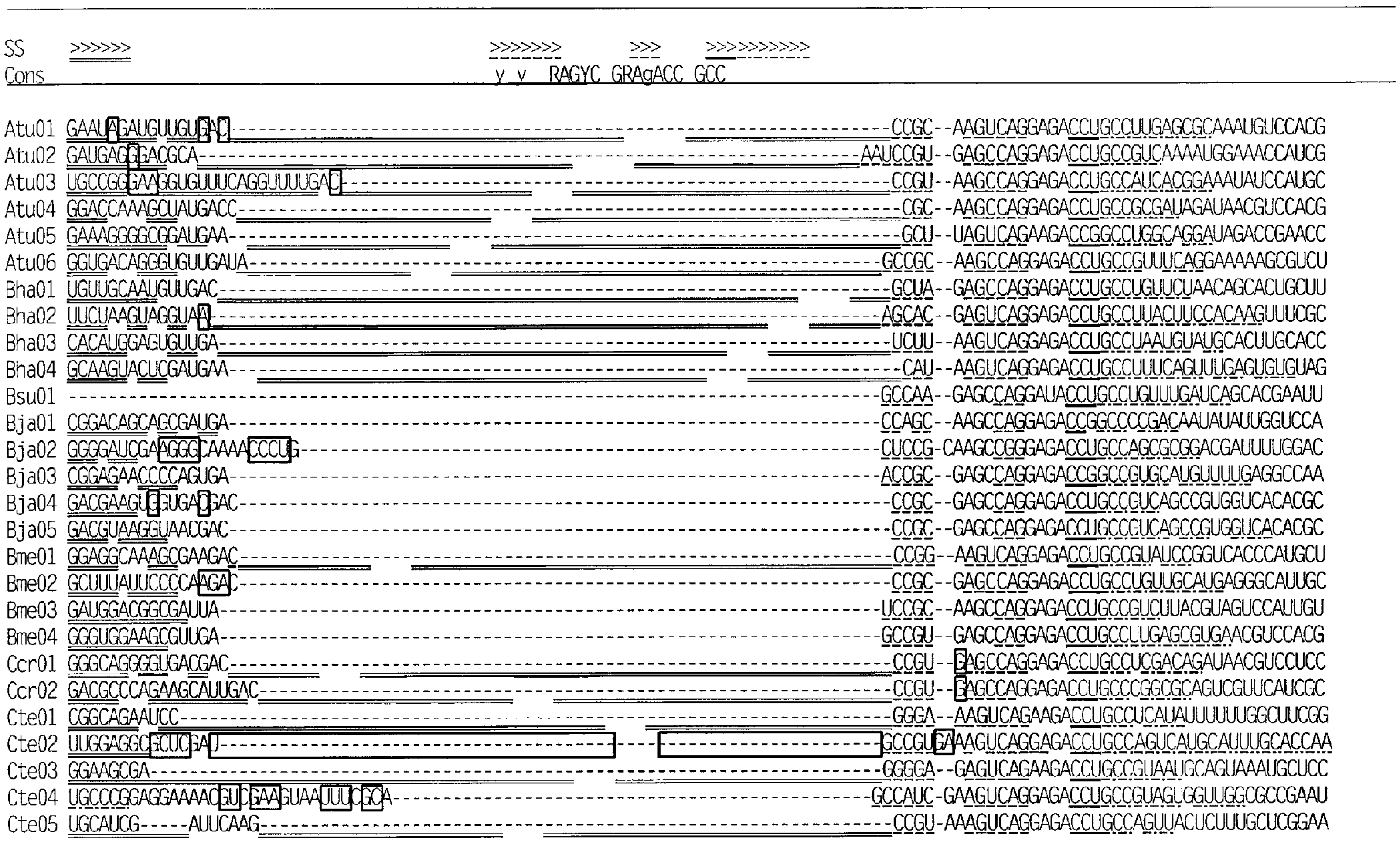
Figure 41A:
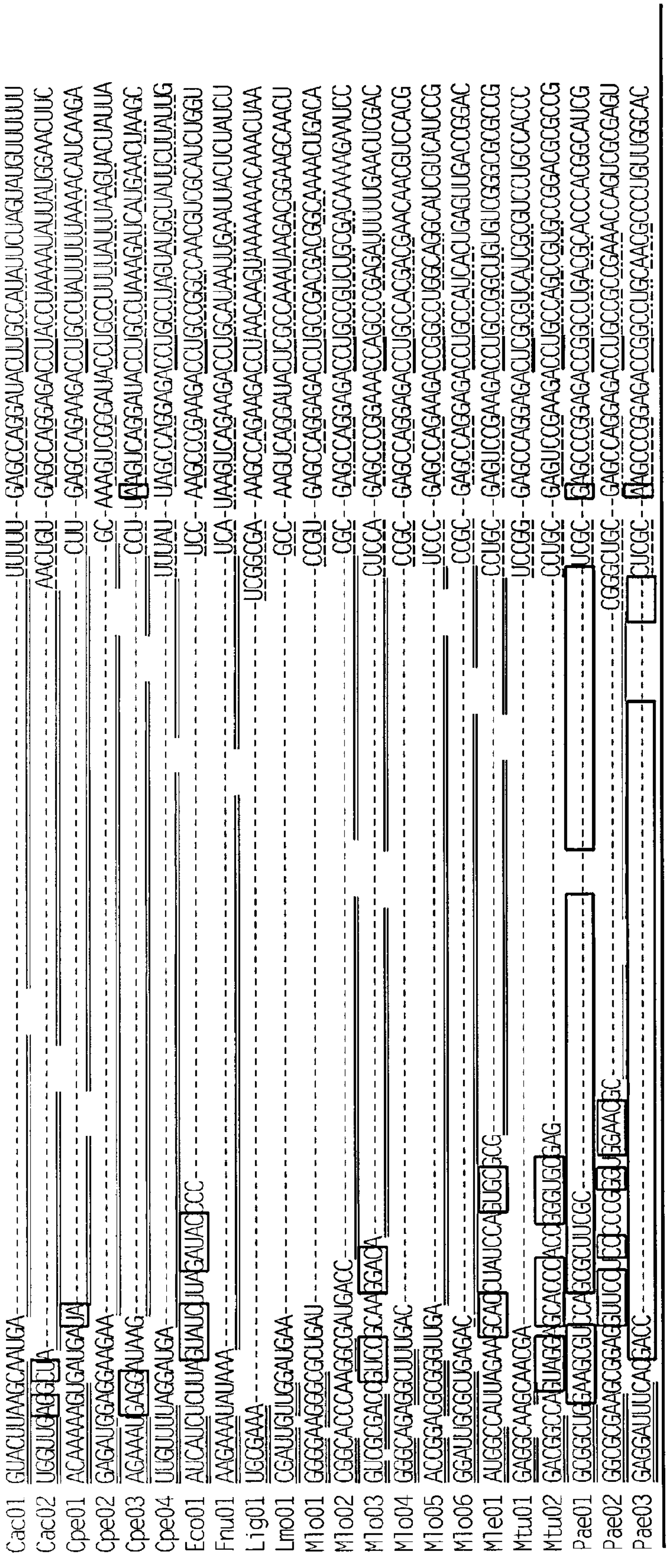
Figure 41A:
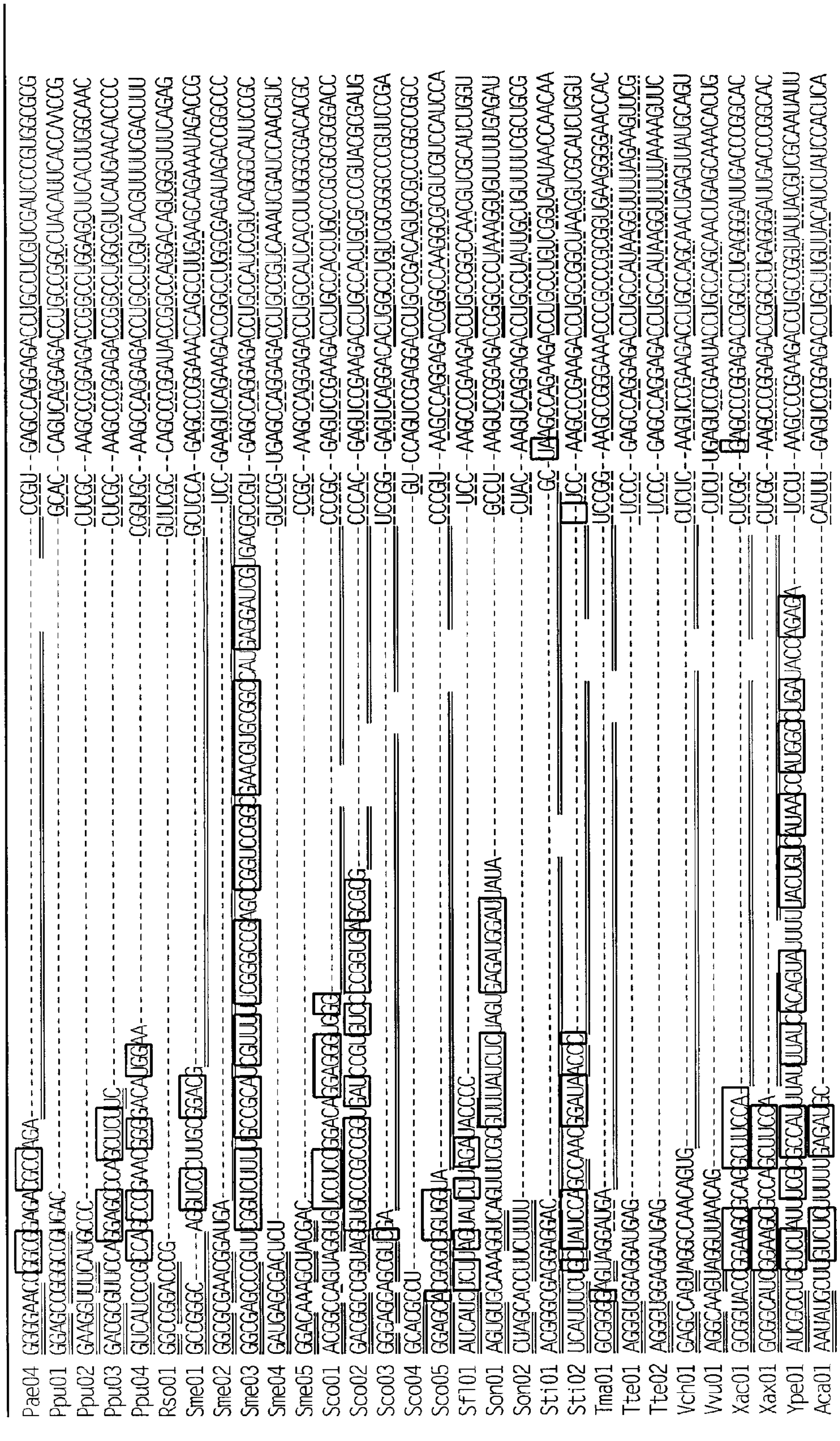

In contrast to the xpt riboswitch, the performance of the corresponding wild-type and mutant ydhL reporter constructs indicates that the latter is an adenine-dependent riboswitch with the opposite response to rising levels of ligand. Specifically, the wild-type ydhL construct exhibits very low β-galactosidase activity when assayed in the absence of ligand, or in the presence of guanine (FIG. 40D). However, a greater than 10-fold increase in gene expression occurs in response to added adenine. In addition, the single U to C mutation in the P1-P3 junction of the aptamer causes substantial (~100 fold) derepression regardless of what ligand is used (FIG. 40*e*). Although this seems counter to the model proposed for ydhL riboswitch function, it is important to note that this mutation indeed disrupts adenine binding, but it also causes a mismatch to occur in the terminator stem. If this mismatch is sufficiently destabilizing to the terminator stem, or if this mutation adversely affects the folding pathway for the riboswitch, then the default 'OFF' status for the genetic control element would be expected to change to default 'ON'. Therefore, the observed level of gene expression might be indicative of full activation of the ydhL gene when it's genetic control element is indifferent to the concentrations of purines in the cell.

2. Discussion i. The Structure and Evolution of Adenine Riboswitches

The sequence and biochemical similarities between guanine- and adenine-specific G box RNAs indicate that they are analogous in overall secondary and tertiary structure. The ease of interchanging ligand specificities of these aptamers by making single mutations to the xpt and ydhL aptamers suggests that such changes might occur with high frequency in natural populations. However, the fact that neither single-base variant of the xpt or ydhL riboswitches exhibits corresponding specificity changes in genetic control in vivo suggests that multiple mutations might be necessary to make a useful swap in riboswitch specificity.

It is important to note that the binding affinity of the resulting single-base xpt variant is not as robust for its new ligand. Specifically, the wild-type xpt RNA has an apparent $K_D$ for guanine of no poorer than 5 nM (FIG. 39*a*), while the C to U variant of this RNA exhibits an apparent $K_D$ for adenine of ~100 nM (FIG. 39*b*). In this case, although the mutation results in a substantial change in base discrimination between guanine and adenine, binding affinity for the matched ligand has been somewhat degraded. In contrast, the wild-type and mutant ydhL RNAs exhibit both specificity change and retention of binding affinity for the matched ligands (FIGS. 39C and 39D). However, the affinity for the U to C variant of 80 ydhL for guanine appears to be at least 10-fold poorer than that of 93 xpt.

Thus, accessory mutations that do not directly define ligand specificity but that further adjust the binding affinity might be necessary for G box RNAs to interconvert between guanine and adenine ligands in a biological setting. In this regard, it is interesting that the ydhL and xpt aptamers differ from each other at 23 positions (FIG. 35), with only one residing within an obviously critical position (C74 of xpt). Although some of these mutations might serve to fine-tune the binding affinity of the aptamers, many could be the result of neutral drift in the RNA sequence that is permitted because they retain the essential secondary-structure elements.

ii. Genetic Control and Function of the ydhL mRNA

Mutant strains of *B. subtilis* that resist the toxic effects of 2-fluoroadenine were reported recently (Johansen, L. E., et al., *J. Bacteriol.* 185, 5200-5209)). These mutations, which cause over-expression of the ydhL gene product, were mapped to the adenine riboswitch domain. In both instances, the changes (deletions) are expected to disrupt riboswitch function by eliminating a portion of the terminator stem or by eliminating both the terminator stem and portions of the adenine aptamer domain. In both instances, the variants preclude the riboswitch from adopting its default sate (transcription termination), which causes unmodulated activation of gene expression.

The protein product of the ydhL gene (also termed pbuE) has been proposed to be a purine efflux pump (Johansen, L. E., et al., *J. Bacteriol.* 185, 5200-5209)). Thus the resistance to 2-fluoroadenine conferred upon the cell by disruption of the adenine riboswitch from ydhL might be due to excretion of this toxic compound. In the natural genetic background, the presence of excess adenine within the cell most likely induces increased expression of the ydhL gene to produce the purine efflux protein. Higher levels of this protein then work to normalize the concentration of purines by pumping out of the cell one or more forms of this compound class.

iii. Riboswitch Mechanisms—Genetic Activation and Deactivation by Rising Metabolite Concentrations The adenine riboswitch from *B. subtilis* also is notable for its mechanism of action. In the majority of riboswitches examined to date, metabolite binding causes a lowering of gene expression. This occurs either by ligand-mediated formation of a terminator stem to prevent transcription of the complete mRNA, or by sequestering the Shine-Dalgarno sequence and precluding translation initiation. In most instances, the down-regulation of gene expression is expected, as a build-up of sufficient levels of a particular metabolite should logically provide a signal to turn off genes in that are involved in biosynthesis or import of the compound (Grundy, F. J. & Henkin, T. M. et al., *Frontiers Biosci.* 8, D20-31 (2003)).

The adenine riboswitch from ydhL (and presumably for the add riboswitches as well) belong to a group of genes whose functions would hint at the need for riboswitch activation in the presence of high concentrations of target compounds. In the case of ydhL, disposal of excess purines would seem to be an important capability given that certain purines such as guanine are insoluble at modest concentrations. Alternatively, there be no obvious need to express adenine deaminase if adenine concentrations were exceptionally low, and therefore we expect that the riboswitches from the add genes of *C. perfringens* and *V. vulnificus* might be activated by ligand binding as well. Interestingly, T box domains, which are 5'-UTR structures that control the expression of many aminoacyl-tRNA synthetases in *B. subtilis* and other Gram-positive organisms (Grundy, F. J., et al., *Proc. Natl. Acad. Sci. USA* 99, 11121-11126), also induce gene expression in response to rising concentrations of the target they sense. However, unlike the known metabolite-binding riboswitches, T box domains sense the biochemical precursor (non-aminoacylated tRNAs) to the products of the enzymes whose expression they control (Miller, J. H. A Short Course in Bacterial Genetics. Cold Spring Harbor Laboratory Press, Cold Spring Harbor, N.Y. (1992)).

Although we expect that riboswitches that induce gene activation in response to increasing metabolite will occur less frequently due to genetic necessity, there is no inherent structural flaws in RNA folding that would skew this distribution between gene-activating and gene-deactivating riboswitches. Whether the riboswitch responds to ligand binding by activating or repressing gene expression, the RNAs will exploit allosteric changes in secondary and/or tertiary structure that are based on the same principles of RNA folding. The only obligate difference between activating and repressing riboswitches is in the fine structure of the expression platform, whereas the aptamer domain can remain largely unchanged.

3. Methods i. Purine Analogs

Guanine, adenine, 2,6-diaminopurine, 2-aminopurine, hypoxanthine, xanthine, 1-methyladenine, purine, 6-methylaminopurine, $N^6$-$N^6$ dimethyladenine, 6-mercaptopurine, 3-methyladenine, guanine-8-$^3$H and adenine-2,8-$^3$H were purchased from Sigma. 6-cyanopurine and 8-azaadenine were obtained from Aldrich and 2-chloroadenine, 8-chloroadenine from Biolog Life Science Institute, Germany.

ii. DNA Oligonucleotides

Oligonucleotides were synthesized by the HHMI Keck Foundation Biotechnology Resource Center at Yale University, purified by denaturing polyacrylamide gel electrophoresis, and were eluted from the gel by crush-soaking in a buffer containing 10 mM Tris-HCl (pH 7.5 at 23° C.), 200 mM NaCl, and 1 mM EDTA. DNAs were precipitation with ethanol, resuspended in deionized water, and stored at −20° C. until use.

iii. In-Line Probing of RNA Constructs

RNA constructs were synthesized from the corresponding PCR DNA templates by transcription in vitro using T7 RNA polymerase, dephosphorylated, and 5'-end labeled with $^{32}$P as described in Example 6. In a typical in-line probing assay, 2 nM of labeled RNA were incubated in a buffer containing 20 mM $MgCl_2$, 50 mM Tris-HCl (pH 8.3 at 25° C.) and 100 mM KCl in the absence or presence of purine compounds as indicated for each experiment for 40 hrs at 25° C. Purine concentrations ranging from 1 nM to 10 μM were employed unless otherwise noted. At the end of each incubation, spontaneously cleaved products were separated on a denaturing (8 M urea) 10% PAGE, visualized using a PhosphorImager and quantitated using ImageQuaNT software (Molecular Dynamics).

iv. Equilibrium Dialysis

Equilibrium dialysis assays were conducted using a DispoEquilibrium Dialyzer (Harvard Biosciences), wherein chamber A and B are separated by a 5,000 MWCO membrane. Chamber A contained 30 μl of $^3$H-guanine or $^3$H-adenine at a concentration of 100 nM in a buffer containing 50 mM Tris-HCl (pH 8.5 at 25° C.), 20 mM $MgCl_2$, and 100 mM KCl. A 30 μl aliquot of the above mentioned buffer containing RNA at 3 μM concentration was delivered into chamber B. Equilibrations were allowed to proceed for 10 hrs at 25° C. Subsequently 5 μl was withdrawn from each chamber and quantitated by liquid scintillation counting.

v. Construction of xpt- and ydhL-lacZ Fusions

A DNA construct encompassing nucleotides −468 to +9 relative to translational start site of ydhL was PCR amplified from *B. subtilis* strain 1A40 (*Bacillus* Genetic Stock Center, Columbus, Ohio) with primers that introduced EcoR1-BamH1 restriction sites. The wild-type construct was cloned into pDG1661 at EcoR1-BamH1 restriction sites directly upstream of the lacZ reporter gene and sequenced to confirm its integrity. The resulting plasmid was used as a template for site-directed mutagenesis via the QuickChange site-directed mutagenesis kit (Stratagene) using the appropriate primer. Plasmid variants were integrated into the amyE locus of *B. subtilis* strain 1A40 and the transformants were confirmed as described in Example 6.

vi. In vivo Analysis of Riboswitch Function

Transformed *B. subtilis* cells were grown to mid log phase with constant shaking at 37° C. in minimal media containing 0.4% w/v glucose, 20 g/l $(NH_4)_2SO_4$, 25 g/l $K_2HPO_4$, 6 g/l $KH_2PO_4$, 1 g/l sodium citrate, 0.2 g/L $MgSO_4.7H_2O$, 0.2% glutamate, 5 μg/ml chloramphenicol, 50 μg/m L-tryptophan, 50 μg/ml L-lysine and 50 μg/ml L-methionine. Guanine or adenine was added to a final concentration of 0.1 mg/ml. Cells at mid exponential stage were harvested and resuspended in minimal media in the presence or absence of purines and grown for an additional time as indicated for each experiment, at which time 1 ml of cell culture was subjected to β-galactosidase activity assays using a variation of the method described by Miller (Miller, J. H. A Short Course in Bacterial Genetics. Cold Spring Harbor Laboratory Press, Cold Spring Harbor, N.Y. (1992)).

I. Example 9

Tables of Sequence Comparisons for the SAM, Cobalimin, Guanine, Adenine, and Lysine Riboswitches Discussed herein FIG. 41 shows sequence and types of riboswitches. The alignment of these sequences is as disclosed herein, regions disclosed in the other figures correspond to the same regions in FIG. 41.

Additional riboswitches were found based on published alignments and secondary structures (Grundy, F. J. & Henkin, T. M. The S box regulon: a new global transcription termination control system for methionine and cysteine biosynthesis genes in Gram-positive bacteria. *Mol. Microbiol.* 30, 737-749 (1998)) using the SequenceSniffer program. This program finds degenerate matches to RNA patterns defined by linked sequence motifs and base pairing constraints. In the alignments, base pairing regions have the identical underline styles or boxes and are labeled as in the corresponding figures discussed in Examples 1-8, with the addition of a putative pseudoknot marked PS. Predicted terminators (short dashed underline) and start codons (long dashed underline) are marked for some sequences. Positions for each sequence in the indicated Genbank record or unfinished genome contig are for the sequence column marked with a circle (•)—the fifth base in stem P1 that is 5' of the aptamer. Start is the offset from the column marked with an asterisk (*)—the sixth base in stem P1 that is 3' of the aptamer—to the start codon of the first gene in the operon. Genes were identified from COGNITOR (Tatusov, R. L., et al. The COG database: new developments in phylogenetic classification of proteins from complete genomes. *Nucleic Acids Res.* 29, 22-28 (2001)) and PFAM (Bateman, A., et al. The Pfam Protein Families Database. *Nucleic Acids Res.* 30, 276-280 (2002)) database matches to protein sequences annotated in the Genbank records. The standard names from these databases are used when possible (2011=COG2011; ????=no matches). Previous operon designations for B. subtilis are given in parentheses (Grundy, F. J. & Henkin, T. M. The S box regulon: a new global transcription termination control system for methionine and cysteine biosynthesis genes in Gram-positive bacteria. *Mol. Microbiol.* 30, 737-749 (1998)). A subset of sequences with <90% pairwise identity between the bases encompassed by stem P1 was selected for determining the consensus sequence. In the consensus sequence, lowercase and uppercase bases indicate >80% and >95% conservation at a position, respectively. Purine (R) and pyrimidine (Y) bases were assigned when no single base had >80% conservation.

(*) Sequence shares >90% identity with another sequence, and was excluded when determining the consensus.

(1) Very short hypothetical gene that may be a misannotated ORF.

(2) Possible S Box "pseudogene". The S Box is on the opposite strand 5' of the indicated operon.

It is understood that the disclosed method and compositions are not limited to the particular methodology, protocols, and reagents described as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a riboswitch" includes a plurality of such riboswitches, reference to "the riboswitch" is a reference to one or more riboswitches and equivalents thereof known to those skilled in the art, and so forth.

"Optional" or "optionally" means that the subsequently described event, circumstance, or material may or may not occur or be present, and that the description includes instances where the event, circumstance, or material occurs or is present and instances where it does not occur or is not present.

Ranges may be expressed herein as from "about" one particular value, and/or to "about" another particular value. When such a range is expressed, also specifically contemplated and considered disclosed is the range from the one particular value and/or to the other particular value unless the context specifically indicates otherwise. Similarly, when values are expressed as approximations, by use of the antecedent "about," it will be understood that the particular value forms another, specifically contemplated embodiment that should be considered disclosed unless the context specifically indicates otherwise. It will be further understood that the endpoints of each of the ranges are significant both in relation to the other endpoint, and independently of the other endpoint unless the context specifically indicates otherwise. Finally, it should be understood that all of the individual values and sub-ranges of values contained within an explicitly disclosed range are also specifically contemplated and should be considered disclosed unless the context specifically indicates otherwise. The foregoing applies regardless of whether in particular cases some or all of these embodiments are explicitly disclosed.

Unless defined otherwise, all technical and scientific terms used herein have the same meanings as commonly understood by one of skill in the art to which the disclosed method and compositions belong. Although any methods and materials similar or equivalent to those described herein can be used in the practice or testing of the present method and compositions, the particularly useful methods, devices, and materials are as described. Publications cited herein and the material for which they are cited are hereby specifically incorporated by reference. Nothing herein is to be construed as an admission that the present invention is not entitled to antedate such disclosure by virtue of prior invention. No admission is made that any reference constitutes prior art. The discussion of references states what their authors assert, and applicants reserve the right to challenge the accuracy and pertinency of the cited documents. It will be clearly understood that, although a number of publications are referred to herein, such reference does not constitute an admission that any of these documents forms part of the common general knowledge in the art.

Throughout the description and claims of this specification, the word "comprise" and variations of the word, such as "comprising" and "comprises," means "including but not limited to," and is not intended to exclude, for example, other additives, components, integers or steps.

Those skilled in the art will recognize, or be able to ascertain using no more than routine experimentation, many equivalents to the specific embodiments of the method and compositions described herein. Such equivalents are intended to be encompassed by the following claims.

We claim:

1. A method of inhibiting gene expression, the method comprising bringing into contact a compound and a cell, wherein the compound has the structure

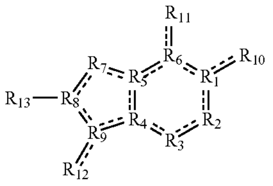

wherein, when the compound is bound to a guanine-responsive riboswitch, $R_7$ serves as a hydrogen bond acceptor, $R_{10}$ serves as a hydrogen bond donor, $R_{11}$ serves as a hydrogen bond acceptor, $R_{12}$ serves as a hydrogen bond donor, wherein $R_{13}$ is H, $H_2$ or is not present, wherein $R_1$, $R_3$, $R_4$, $R_5$, $R_6$, $R_8$, and $R_9$ are each independently C, N, O, or S, wherein $R_2$, is C, N, O, S, C—$NH_2$, C—NH—$CH_3$, N—$NH_2$, N—NH—$CH_3$, or C, N, O, or S substituted with a group that serves as a hydrogen bond donor, wherein ----- each independently represent a single or double bond, wherein the compound is not guanine, hypoxanthine, or xanthine, wherein the cell comprises a gene encoding an RNA comprising a guanine-responsive riboswitch, wherein the compound inhibits expression of the gene by binding to the guanine-responsive riboswitch.

2. The method of claim 1, wherein the cell is killed or growth of the cell is inhibited.

3. The method of claim 1, wherein the cell is a bacterial cell.

4. The method of claim 1, wherein the cell is in a patient.

5. The method of claim 1, wherein the cell is a bacterial cell, wherein the cell is in a patient.

6. The method of claim 1, wherein, when the compound is bound to a guanine-responsive riboswitch, $R_3$ serves as a hydrogen bond acceptor and $R_2$ serves as a hydrogen bond donor.

7. The method of claim 1, wherein $R_2$, is C—$NH_2$ or C—NH—$CH_3$.

8. The method of claim 1, wherein $R_2$, is C—$NH_2$.

9. The method of claim 1, wherein $R_2$, is C, N, O, or S substituted with a group that serves as a hydrogen bond donor.

10. The method of claim 1, wherein $R_2$, is C substituted with a group that serves as a hydrogen bond donor.

11. The method of claim 1, wherein $R_{10}$ is H, $H_2$ or is not present.

12. The method of claim 1, wherein $R_2$ is C=O.

13. The method of claim 1, wherein the riboswitch is a naturally occurring riboswitch, wherein the gene is a naturally occurring gene, and wherein the gene and riboswitch are not heterologous.

14. The method of claim 1, wherein the gene is essential to survival of the cell.

15. The method of claim 1, wherein the riboswitch comprises an aptamer domain and an expression platform domain, wherein the aptamer domain and the expression platform domain are heterologous.

16. The method of claim 1, wherein the riboswitch comprises an aptamer domain and an expression platform domain, wherein the aptamer domain comprises a P1 stem, wherein the P1 stem comprises an aptamer strand and a control strand, wherein the expression platform domain comprises a regulated strand, wherein the regulated strand, the control strand, or both have been designed to form a stem structure.

* * * * *